(12) United States Patent
McComas et al.

(10) Patent No.: US 9,265,773 B2
(45) Date of Patent: Feb. 23, 2016

(54) TETRACYCLIC HETEROCYCLE COMPOUNDS AND METHODS OF USE THEREOF FOR THE TREATMENT OF VIRAL DISEASES

(75) Inventors: Casey C. McComas, Phoenixville, PA (US); Nigel J. Liverton, Harleysville, PA (US); Joerg Habermann, Munich (DE); Uwe Koch, Dortmund (DE); Frank Narjes, Kullavik (SE); Peng Li, Shanghai (CN); Xuanjia Peng, Shanghai (CN); Richard Soll, San Diego, CA (US); Hao Wu, Shanghai (CN); Anandan Palani, Bridgewater, NJ (US); Shuwen He, Edison, NJ (US); Xing Dai, Cranford, NJ (US); Hong Liu, Hillsborough, NJ (US); Zhong Lai, East Brunswick, NJ (US); Clare London, Chatham, NJ (US); Dong Xiao, Warren, NJ (US); Nicolas Zorn, Fanwood, NJ (US); Ravi Nargund, East Brunswick, NJ (US)

(73) Assignees: Merck Sharp & Dohme Corp., Rahway, NJ (US); MSD Italia S.R.L., Rome (IT)

( * ) Notice: Subject to any disclaimer, the term of this patent is extended or adjusted under 35 U.S.C. 154(b) by 0 days.

(21) Appl. No.: 14/343,450

(22) PCT Filed: Aug. 20, 2012

(86) PCT No.: PCT/CN2012/001117
§ 371 (c)(1),
(2), (4) Date: Mar. 7, 2014

(87) PCT Pub. No.: WO2013/033971
PCT Pub. Date: Mar. 14, 2013

(65) Prior Publication Data
US 2014/0213571 A1    Jul. 31, 2014

(30) Foreign Application Priority Data
Sep. 8, 2011   (WO) ................ PCT/CN2011/079465

(51) Int. Cl.
| | |
|---|---|
| *A61K 31/553* | (2006.01) |
| *C07D 491/052* | (2006.01) |
| *A61K 31/519* | (2006.01) |
| *A61K 31/407* | (2006.01) |
| *C07D 498/22* | (2006.01) |
| *A61K 31/437* | (2006.01) |
| *C07D 491/147* | (2006.01) |
| *C07D 498/14* | (2006.01) |
| *C07D 498/04* | (2006.01) |
| *A61K 31/5365* | (2006.01) |
| *A61K 45/06* | (2006.01) |

(52) U.S. Cl.
CPC ............. *A61K 31/553* (2013.01); *A61K 31/407* (2013.01); *A61K 31/437* (2013.01); *A61K 31/519* (2013.01); *A61K 31/5365* (2013.01); *A61K 45/06* (2013.01); *C07D 491/052* (2013.01); *C07D 491/147* (2013.01); *C07D 498/04* (2013.01); *C07D 498/14* (2013.01); *C07D 498/22* (2013.01)

(58) Field of Classification Search
CPC ............... C07D 498/14; C07D 498/04; C07D 491/052; C07D 491/147; A61K 45/06; A61K 31/5365; A61K 31/553; A61K 31/407; A61K 31/519; A61K 31/437
USPC .......... 549/370; 514/210.02, 229.5, 257, 338, 514/211.09, 410; 548/421; 540/468; 544/89, 95; 546/64, 376.7
See application file for complete search history.

(56) References Cited

U.S. PATENT DOCUMENTS

| | | |
|---|---|---|
| 4,634,697 A | 1/1987 | Hamashima |
| 4,812,561 A | 3/1989 | Hamashima et al. |
| 4,933,443 A | 6/1990 | Hamashima et al. |

(Continued)

FOREIGN PATENT DOCUMENTS

| | | |
|---|---|---|
| CN | 1731993 | 2/2006 |
| WO | WO9814181 | 4/1998 |

(Continued)

OTHER PUBLICATIONS

Beaulieu et al, Inhibitors of the HCV NS5B polymerase: New hope for the treatment of hepatitis C infections, Current Opinions in Investigational Drugs, 2004, 5:838.

(Continued)

*Primary Examiner* — Samantha Shterengarts
*Assistant Examiner* — Matt Mauro
(74) *Attorney, Agent, or Firm* — Alysia A. Finnegan; Anna L. Cocuzzo

(57) ABSTRACT

The present invention relates to compounds of formula (I) that are useful as hepatitis C virus (HCV) NS5B polymerase inhibitors, the synthesis of such compounds, and the use of such compounds for inhibiting HCV NS5B polymerase activity, for treating or preventing HCV infections and for inhibiting HCV viral replication and/or viral production in a cell-based system.

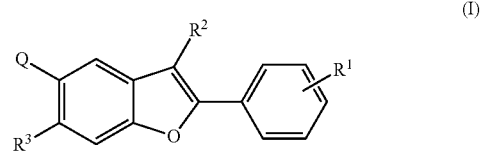

(I)

15 Claims, No Drawings

(56) References Cited

U.S. PATENT DOCUMENTS

| | | |
|---|---|---|
| 5,017,380 A | 5/1991 | Hamashima et al. |
| 6,767,991 B1 | 7/2004 | Llinas-Brunet et al. |
| 6,800,434 B2 | 10/2004 | Saksena et al. |
| 6,838,475 B2 | 1/2005 | Arasappan et al. |
| 6,846,802 B2 | 1/2005 | Chen et al. |
| 6,894,072 B2 | 5/2005 | Arasappan et al. |
| 6,911,428 B2 | 6/2005 | Zhu et al. |
| 6,914,122 B2 | 7/2005 | Venkatraman et al. |
| 7,012,066 B2 | 3/2006 | Saksena et al. |
| 7,169,760 B2 | 1/2007 | Saksena et al. |
| 7,173,057 B2 | 2/2007 | Chen et al. |
| 7,186,747 B2 | 3/2007 | Arasappan et al. |
| 7,192,957 B2 | 3/2007 | Venkatraman et al. |
| 7,205,330 B2 | 4/2007 | Bogen et al. |
| 7,244,271 B2 | 7/2007 | Lentz et al. |
| 7,253,160 B2 | 8/2007 | Njoroge et al. |
| 7,342,041 B2 | 3/2008 | Njoroge et al. |
| 7,425,576 B2 | 9/2008 | Arasappan et al. |
| 7,442,695 B2 | 10/2008 | Njoroge et al. |
| 7,449,447 B2 | 11/2008 | Chen et al. |
| 7,485,625 B2 | 2/2009 | Velazquez et al. |
| 7,494,988 B2 | 2/2009 | Perni et al. |
| 7,666,863 B2 | 2/2010 | Saha et al. |
| 2002/0068702 A1 | 6/2002 | Lim-Wilby et al. |
| 2002/0160962 A1 | 10/2002 | Saksena et al. |
| 2005/0119168 A1 | 6/2005 | Venkatraman et al. |
| 2005/0176648 A1 | 8/2005 | Saksena et al. |
| 2005/0209164 A1 | 9/2005 | Bogen et al. |
| 2005/0249702 A1 | 11/2005 | Njoroge et al. |
| 2007/0042968 A1 | 2/2007 | Bennett et al. |
| 2007/0274951 A1 | 11/2007 | Tong et al. |

FOREIGN PATENT DOCUMENTS

| | | |
|---|---|---|
| WO | WO9817679 | 4/1998 |
| WO | WO9822496 | 5/1998 |
| WO | WO9907734 | 2/1999 |
| WO | WO03006490 | 1/2003 |
| WO | WO03087092 | 10/2003 |
| WO | WO2004041201 | 5/2004 |
| WO | WO2004092161 | 10/2004 |
| WO | WO2005087731 | 9/2005 |
| WO | WO2008082484 | 7/2008 |
| WO | WO2008082488 | 7/2008 |
| WO | WO2008124148 | 10/2008 |
| WO | WO2008136815 | 11/2008 |
| WO | WO2009032116 | 3/2009 |
| WO | WO2009032123 | 3/2009 |
| WO | WO2009032124 | 3/2009 |
| WO | WO2009032125 | 3/2009 |
| WO | WO2009101022 | 8/2009 |
| WO | WO2010030592 | 3/2010 |
| WO | WO2011103063 | 8/2011 |
| WO | WO2011106340 | 9/2011 |
| WO | WO2011106992 | 9/2011 |
| WO | WO 2011106992 A1 * | 9/2011 |
| WO | WO2012142075 | 10/2012 |
| WO | WO2012142085 | 10/2012 |
| WO | WO2012142093 | 10/2012 |
| WO | WO2013033899 | 3/2013 |
| WO | WO2013033901 | 3/2013 |
| WO | WO2013034047 | 3/2013 |
| WO | WO2013034048 | 3/2013 |

OTHER PUBLICATIONS

Behrens et al., Identification and properties of the RNA-dependnt RNA polymerase of hepatitis C virus, EMBO. J., 1996, 15(1):12-22.

Bioworld Today, The Daily Biotechnology Newspaper, 1998, vol. 9(217), 1-5.

Carroll et al., Inhibition of Hepatitis C Virus RNA Replication by 2'-Modified Nucleoside Analogs, J. Biol. Chem. 2003, 278(14):11979-84.

Elzouki et al., Serine protease inhibitors in patients with chronic viral hepatitis, Journal of Hepatology, 1997, 27:42-48.

Ingallinella et al., Potent Peptide Inhibitors of Human Hepatitis C Virus NS3 Protease Are Obtained by Optimizing the Cleavage Products, Biochemistry, 1998, 37:8906-8914.

Landro et al., Mechanistic Role of an NS4A Peptide Cofactor with the Truncated NS3 Protease of Hepatitis C Virus: Elucidation of the NS4A Stimulatory Effect Via Kinetic Analysis and Inhibitor Mapping, Biochemistry, 1997, 31:9340-9348.

Llinas-Brunet et al., Peptide-based Inhibitors of the Hepatitis C Virus Serine Protease, Bioorganic & Medicinal Chemistry Letters, 1998, 8:1713-1718.

Martin et al., Affinity selection of a camelized VH domain antibody inhibitor of hepatitis C virus NS3 protease, Protein Engineering, 1997, 10(5):607-614.

Ni et al., Progress and Development of Small Molecule HCV Antivirals, Current Opinion in Drug Discovery and Development, 2004, 7(4):446.

Tan et al., Hepatitis C Therapeutics: Current Status and Emerging Strategies, Nature Reviews, 2002, 1:867-881.

* cited by examiner

TETRACYCLIC HETEROCYCLE COMPOUNDS AND METHODS OF USE THEREOF FOR THE TREATMENT OF VIRAL DISEASES

FIELD OF THE INVENTION

The present invention relates to novel Tetracyclic Heterocycle Compounds, compositions comprising at least one Tetracyclic Heterocycle Compound, and methods of using the Tetracyclic Heterocycle Compounds for treating or preventing HCV infection in a patient.

BACKGROUND OF THE INVENTION

Hepatitis C virus (HCV) infection is a major health problem that leads to chronic liver disease, such as cirrhosis and hepatocellular carcinoma, in a substantial number of infected individuals. Current treatments for HCV infection include immunotherapy with recombinant interferon-α alone or in combination with the nucleoside analog ribavirin.

Several virally-encoded enzymes are putative targets for therapeutic intervention, including a metalloprotease (NS2-3), a serine protease (NS3, amino acid residues 1-180), a helicase (NS3, full length), an NS3 protease cofactor (NS4A), a membrane protein (NS4B), a zinc metalloprotein (NS5A) and an RNA-dependent RNA polymerase (NS5B).

HCV NS5B polymerase is described, for example, in Behrens et al., *EMBO J.* 15(1) 12-22 (1996). Antagonists of NS5B activity are known to be inhibitors of HCV replication. See Carroll et al., *J. Biol. Chem.* 278(14) 11979-84 (2003).

There is a clear and long-felt need to develop effective therapeutics for treatment of HCV infection. Specifically, there is a need to develop compounds that selectively inhibit HCV viral replication and that would be useful for treating HCV-infected patients.

SUMMARY OF THE INVENTION

In one aspect, the present invention provides Compounds of Formula (I)

(I)

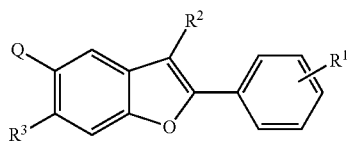

or a pharmaceutically acceptable salt thereof, wherein:

Q is:

(Q1)

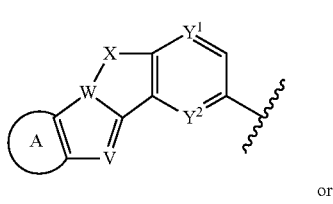

or (Q2)

A is phenyl, 5 or 6-membered heteroaryl, 5 to 7-membered monocyclic cycloalkyl or 5 to 7-membered heterocycloalkyl, each of which can be optionally substituted with up to four $R^5$ groups;

V is N or —C($R^4$)—;
W is N or —CH—;
X is —(CHR$^8$)$_n$—O—, —C(O)—O—,
$Y^1$ is N or —C($R^5$)—;
$Y^2$ is N or —C($R^5$)—;
Z is N, —C($R^5$)— or —C(O)—, such that when Z is —C(O)—, then the endocyclic double bond depicted in formula (Q2) between Z and $Y^1$ is understood to be a single bond;

$R^1$ represents up to 4 optional ring substituents, which can be the same or different, and are independently selected from halo, $C_1$-$C_6$ alkyl, $C_1$-$C_6$ haloalkyl, phenyl, 3 to 7-membered monocyclic cycloalkyl, —O—($C_1$-$C_6$ alkyl), —O—($C_1$-$C_6$ haloalkyl) and —CN;

$R^2$ is —C(O)N($R^6$)($R^7$) or —C(O)O—($C_1$-$C_6$ alkyl);
$R^3$ is H, 4- to 6-membered heterocycloalkyl, 5 or 6-membered heteroaryl, —N($R^{11}$)$_2$, halo, —CN, —N($R^{11}$)$_2$, —C(O)O—($C_1$-$C_6$ alkyl) or —N($R^9$)—S(O)$_n$—$R^{10}$, wherein said 5 or 6-membered heterocycloalkyl can optionally have one of its ring carbon atoms replaced with a carbonyl group;

$R^4$ is selected from H, halo, $C_1$-$C_6$ alkyl, 3 to 7-membered monocyclic cycloalkyl, $C_1$-$C_6$ haloalkyl, —O—($C_1$-$C_6$ alkyl), —C(OH)—C(O)OR$^{11}$ and —O—($C_1$-$C_6$ haloalkyl);

each occurrence of $R^5$ is independently selected from H, halo, $C_1$-$C_6$ alkyl, $C_1$-$C_6$ haloalkyl, —O—($C_1$-$C_6$ alkyl), —O—($C_1$-$C_6$ haloalkyl) and —CN, wherein said $C_1$-$C_6$ alkyl group can be optionally substituted with —OH or —N($R^{11}$)$_2$;

$R^6$ and $R^7$ are each independently selected from hydrogen, —C(O)$R^{11}$, —C(O)O$R^{11}$, —C(O)C(O)O$R^{11}$, $C_1$-$C_6$ alkyl, $C_1$-$C_6$ hydroxyalkyl, phenyl, 3 to 7-membered monocyclic cycloalkyl, 3 to 7-membered monocyclic heterocycloalkyl and 5 or 6-membered monocyclic heteroaryl;

each occurrence of $R^8$ is independently selected from H, halo, —OH, $C_1$-$C_6$ alkyl, $C_1$-$C_6$ hydroxyalkyl, phenyl, 5 or 6-membered monocyclic heteroaryl, —N($R^{11}$)$_2$, $C_1$-$C_6$ haloalkyl, —($C_1$-$C_3$ alkylene)$_p$-(3 to 7-membered monocyclic cycloalkyl), —($C_1$-$C_3$ alkylene)$_p$-O—($C_1$-$C_6$ alkyl), —($C_1$-$C_3$ alkylene)$_p$-N($R^{11}$)$_2$, —($C_1$-$C_3$ alkylene)-NHC(O)—($C_1$-$C_6$ alkyl), —($C_1$-$C_3$ alkylene)—OC(O)($C_1$-$C_6$ alkyl)NHC(O)O—($C_1$-$C_6$ alkyl), —($C_1$-$C_3$ alkylene)—OC(O)-(3 to 7-membered monocyclic heterocycloalkyl), —($C_1$-$C_3$ alkylene)—NHC(O)(3 to 7-membered monocyclic heterocycloalkyl), —CH(O—($C_1$-$C_6$ alkyl))$_2$, —O—($C_1$-$C_6$ haloalkyl), —C(O)OR$^{11}$, —C(O)N($R^{11}$)$_2$, —CH$_2$OC(O)CH(NH$_2$)—($C_1$-$C_6$ alkyl), —NHS(O)$_2$—($C_1$-$C_6$ alkyl), —CH$_2$NHCH($R^{11}$)C(O)OR$^{11}$, —NR$^{11}$—($C_1$-$C_3$ alkylene)-N($R^{11}$)$_2$, —NR$^{11}$—($C_1$-$C_3$ alkylene)-(3 to 7-membered monocyclic heterocycloalkyl), —NR$^{11}$—($C_1$-$C_6$ hydroxyalkyl) and —CN, or two $R^8$ groups and the common carbon atom to which they are attached, can join to form a spirocyclic ring selected from 3 to 7-membered monocyclic cycloalkyl and 3 to 7-membered monocyclic heterocycloalkyl;

$R^9$ is selected from H, $C_1$-$C_6$ alkyl, $C_1$-$C_6$ haloalkyl, $C_1$-$C_6$ hydroxyalkyl, benzyl, —($C_1$-$C_3$ alkylene)-(3 to 7-membered monocyclic cycloalkyl) and 3 to 7-membered monocyclic cycloalkyl, wherein said $C_1$-$C_6$ alkyl group can be optionally substituted with a group selected from —N($R^{11}$)$_2$, —O$R^{11}$, —COOH, —C(O)N($R^{11}$)$_2$, —S(O)$_2$N($R^{11}$)$_2$ and 3 to 7-membered monocyclic heterocycloalkyl and wherein the phenyl moiety of said benzyl group can be optionally substituted with a boronic acid group;

$R^{10}$ is selected from H, $C_1$-$C_6$ alkyl, $C_1$-$C_6$ haloalkyl, phenyl, 3 to 7-membered monocyclic cycloalkyl, 3 to 7-membered monocyclic heterocycloalkyl and 5 or 6-membered monocyclic heteroaryl, wherein said $C_1$-$C_6$ alkyl group can be optionally substituted with a group selected from —N($R^{11}$)$_2$, —O$R^{11}$, —COOH, —C(O)N($R^{11}$)$_2$, and —S(O)$_2$N($R^{11}$)$_2$;

each occurrence of $R^{11}$ is independently selected from H, $C_1$-$C_6$ alkyl, and 3 to 7-membered monocyclic cycloalkyl;

each occurrence of n is 1, 2 or 3; and each occurrence of p is 0 or 1.

The Compounds of Formula (I) (also referred to herein as the "Tetracyclic Heterocycle Compounds") and pharmaceutically acceptable salts thereof can be useful, for example, for inhibiting HCV viral replication or replicon activity, and for treating or preventing HCV infection in a patient. Without being bound by any specific theory, it is believed that the Tetracyclic Heterocycle Compounds inhibit HCV viral replication by inhibiting HCV NS5B.

Accordingly, the present invention provides methods for treating or preventing HCV infection in a patient, comprising administering to the patient an effective amount of at least one Tetracyclic Heterocycle Compound.

The details of the invention are set forth in the accompanying detailed description below.

Although any methods and materials similar to those described herein can be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention relates to novel Tetracyclic Heterocycle Compounds, compositions comprising at least one Tetracyclic Heterocycle Compound, and methods of using the Tetracyclic Heterocycle Compounds for treating or preventing HCV infection in a patient.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name and an ambiguity exists between the structure and the name, the structure is understood to predominate. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity or likelihood of one or more symptoms of the disease or condition. In another embodiment, the effective amount is a "therapeutically effective amount" for inhibition of HCV viral replication and/or HCV viral production. The term also includes herein the amount of active compound sufficient to inhibit HCV NS5B activity and thereby elicit the response being sought (i.e., an "inhibition effective amount"). When the active compound (i.e., active ingredient) is administered as the salt, references to the amount of active ingredient are to the free acid or free base form of the compound.

The term "preventing," as used herein with respect to an HCV viral infection or HCV-virus related disorder, refers to reducing the likelihood of HCV infection.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "$C_2$-$C_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —CH($CH_3$)$CH_2CH_2$—, —CH($CH_3$)— and —$CH_2$CH($CH_3$)$CH_2$—. In one embodiment, an alkylene group has from 1 to about 6 carbon atoms. In another embodiment, an alkylene group is branched. In another embodiment, an alkylene group is linear. In one embodiment, an alkylene group is —$CH_2$—. The term "$C_1$-$C_6$ alkylene" refers to an alkylene group having from 1 to 6 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. In one embodiment, an aryl group can be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "cycloalkyl," as used herein, refers to a non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group can be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

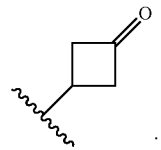 [SMILES: *C1CC(=O)C1]

The term "cycloalkenyl," as used herein, refers to a non-aromatic mono- or multicyclic ring system comprising from about 4 to about 10 ring carbon atoms and containing at least one endocyclic double bond. In one embodiment, a cycloalkenyl contains from about 4 to about 7 ring carbon atoms. In another embodiment, a cycloalkenyl contains 5 or 6 ring atoms. Non-limiting examples of monocyclic cycloalkenyls include cyclopentenyl, cyclohexenyl, cyclohepta-1,3-dienyl, and the like. A cycloalkenyl group can be optionally substituted with one or more "ring system substituents" which may be the same or different, and are as defined herein below. A ring carbon atom of a cycloalkyl group may be functionalized as a carbonyl group. In one embodiment, a cycloalkenyl group is cyclopentenyl. In another embodiment, a cycloalkenyl group is cyclohexenyl. The term "4 to 7-membered cycloalkenyl" refers to a cycloalkenyl group having from 4 to 7 ring carbon atoms. Unless otherwise indicated, a cycloalkenyl group is unsubstituted.

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms has been replaced with an —OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic and has 9 or 10 ring atoms. A heteroaryl group can be optionally substituted by one or more "ring system substituents" which may be the same or different, and are as defined herein below. A heteroaryl group is joined via a ring carbon atom, and any nitrogen atom of a heteroaryl can be optionally oxidized to the corresponding N-oxide. The term "heteroaryl" also encompasses a heteroaryl group, as defined above, which is fused to a benzene ring. The term "heteroaryl" also encompasses any fused polycyclic ring system containing at least one ring heteroatom selected from N, O and S, wherein at least one ring of the fused polycyclic ring system is aromatic. For example, the term "9 to 10-membered bicyclic heteroaryl" encompasses a non-aromatic 5 membered heterocyclic ring that is fused to a benzene or pyridyl ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered heteroaryl. In another embodiment, a heteroaryl group comprises a 5- to 6-membered heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group can be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 4 to about 7 ring atoms. In another embodiment, a heterocycloalkyl group is monocyclic has from about 5 to about 7 ring atoms. In another embodiment, a heterocycloalkyl group is bicyclic and has from about 7 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group can be optionally substituted by one or more "ring system substituents" which may be the same or different, and are as defined herein below. The nitrogen or sulfur atom of the heterocycloalkyl can be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone, silacyclopentane, silapyrrolidine and the like, and all isomers thereof. Non-limiting illustrative examples of a silyl-containing heterocycloalkyl group include:

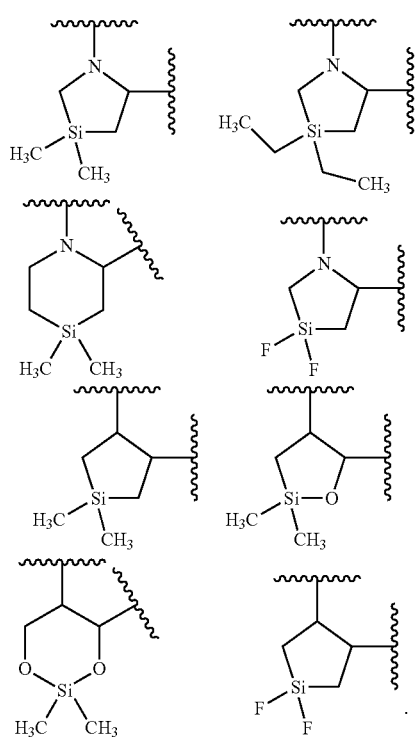

A ring carbon atom of a heterocycloalkyl group may be functionalized as a carbonyl group. Illustrative example of such heterocycloalkyl groups, include:

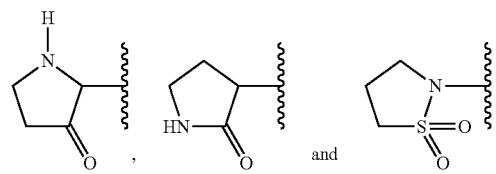

In one embodiment, a heterocycloalkyl group is a 5-membered monocyclic heterocycloalkyl. In another embodiment, a heterocycloalkyl group is a 6-membered monocyclic heterocycloalkyl. The term "3 to 7-membered monocyclic cycloalkyl" refers to a monocyclic heterocycloalkyl group having from 3 to 7 ring atoms. The term "4 to 7-membered monocyclic cycloalkyl" refers to a monocyclic heterocycloalkyl group having from 4 to 7 ring atoms. The term "5 to 7-membered monocyclic cycloalkyl" refers to a monocyclic heterocycloalkyl group having from 5 to 7 ring atoms. The term "7 to 11-membered bicyclic heterocycloalkyl" refers to a bicyclic heterocycloalkyl group having from 7 to 11 ring atoms. Unless otherwise indicated, an heterocycloalkyl group is unsubstituted.

The term "heterocycloalkenyl," as used herein, refers to a heterocycloalkyl group, as defined above, wherein the heterocycloalkyl group contains from 4 to 10 ring atoms, and at least one endocyclic carbon-carbon or carbon-nitrogen double bond. A heterocycloalkenyl group can be joined via a ring carbon or ring nitrogen atom. In one embodiment, a heterocycloalkenyl group has from 4 to 7 ring atoms. In another embodiment, a heterocycloalkenyl group is monocyclic and has 5 or 6 ring atoms. In another embodiment, a heterocycloalkenyl group is bicyclic. A heterocycloalkenyl group can optionally substituted by one or more ring system substituents, wherein "ring system substituent" is as defined above. The nitrogen or sulfur atom of the heterocycloalkenyl can be optionally oxidized to the corresponding N-oxide, S-oxide or S,S-dioxide. Non-limiting examples of heterocycloalkenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like and the like. A ring carbon atom of a heterocycloalkenyl group may be functionalized as a carbonyl group. In one embodiment, a heterocycloalkenyl group is a 5-membered heterocycloalkenyl. In another embodiment, a heterocycloalkenyl group is a 6-membered heterocycloalkenyl. The term "4 to 7-membered heterocycloalkenyl" refers to a heterocycloalkenyl group having from 4 to 7 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O-alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si(alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ can be the same or different and are independently selected from the group consisting of hydrogen, alkyl, aryl, cycloalkyl, and -alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

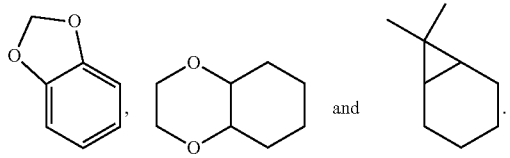

The term "silylalkyl," as used herein, refers to an alkyl group as defined above, wherein one or more of the alkyl group's hydrogen atoms has been replaced with a —Si(R$^x$)$_3$ group, wherein each occurrence of R$^x$ is independently a C$_1$-C$_6$ alkyl, phenyl or a 3- to 6-membered cycloalkyl group. In one embodiment, a silylalkyl group has from 1 to 6 carbon atoms. In another embodiment, a silyl alkyl group contains a —Si(CH$_3$)$_3$ moiety. Non-limiting examples of silylalkyl groups include —CH$_2$—Si(CH$_3$)$_3$ and —CH$_2$CH$_2$—Si(CH$_3$)$_3$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

When any substituent or variable (e.g., alkyl, R$^6$, R$^a$, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Tetracyclic Heterocycle Compound or a pharmaceutically acceptable salt or solvate of the compound. The transformation may occur by various mechanisms (e.g., by metabolic or chemical processes), such as, for example, through hydrolysis in blood.

For example, if a Tetracyclic Heterocycle Compound or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy)ethyl having from 4 to 9 carbon atoms, 1-methyl- 1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$) alkyl, and the like.

Similarly, if a Tetracyclic Heterocycle Compound contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkyl, α-amino($C_1$-$C_4$)alkylene-aryl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate), and the like.

If a Tetracyclic Heterocycle Compound incorporates an amine functional group, a prodrug can be formed by the replacement of a hydrogen atom in the amine group with a group such as, for example, R-carbonyl-, RO-carbonyl-, NRR'-carbonyl- wherein R and R' are each independently ($C_1$-$C_{10}$)alkyl, ($C_3$-$C_7$) cycloalkyl, benzyl, a natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl; carboxy ($C_1$-$C_6$)alkyl; amino($C_1$-$C_4$)alkyl or mono-N— or di-N,N—($C_1$-$C_6$)alkylaminoalkyl; —C(Y$^4$)Y$^5$ wherein Y$^4$ is H or methyl and Y$^5$ is mono-N— or di-N,N—($C_1$-$C_6$)alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$) alkyl) or amino); (2) sulfonate esters, such as alkyl- or aralkylsulfonyl (for example, methanesulfonyl); (3) amino acid esters (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$) acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates.

Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Tetracyclic Heterocycle Compounds can form salts which are also within the scope of this invention. Reference to a Tetracyclic Heterocycle Compound herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Tetracyclic Heterocycle Compound contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Tetracyclic Heterocycle Compound with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates (also known as tosylates) and the like. In one embodiment, a compound of formula (I) is present as its dihydrochloride salt. In another embodiment, a compound of formula (I) is present as its dimesylate salt. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures can be separated into their individual diastereomers on the basis of their physical chemical differences by methods well-known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Tetracyclic Heterocycle Compounds may be atropisomers (e.g., substituted biaryls) and are considered as part of this invention. Enantiomers can also be directly separated using chiral chromatographic techniques.

It is also possible that the Tetracyclic Heterocycle Compounds may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Tetracyclic Heterocycle Compound incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) can be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

Polymorphic forms of the Tetracyclic Heterocycle Compounds, and of the salts, solvates, hydrates, esters and prodrugs of the Tetracyclic Heterocycle Compounds, are intended to be included in the present invention.

The following abbreviations are used below and have the following meanings: Ac is acyl; BOC or Boc is tert-butyloxycarbonyl; (BPin)$_2$ is bis(pinacolato)diboron; CDI is N,N-carbonyl diimidazole; dba is dibenzylideneacetone; DMF is N,N-dimethylformamide; dppf is diphenylphosphinoferrocene; EtOAc is ethyl acetate; HPLC is high performance liquid chromatography; HRMS is high resolution mass spectrometry; KOAc is potassium acetate; LCMS is liquid chromatography/mass spectrometry; MeOH is methanol; Ms is mesyl (—SO$_2$CH$_3$); NCS is N-chlorosuccinimide; Pd/C is palladium on carbon; PdCl$_2$(dppf)$_2$ is [1,1'-bis(diphenylphosphino)ferrocene]dichloro palladium(II); petroleum ether is petroleum ether; PPA is polyphosphoric acid; PTSA is p-toluenesulfonic acid; TLC is thin-layer chromatography; and XPhos is 2-dicyclohexylphosphino-2',4',6'-triisopropylbiphenyl.

The Compounds of Formula (I)

The present invention provides Tetracyclic Heterocycle Compounds of Formula (I):

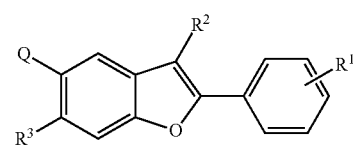

(I)

wherein Q, R$^1$, R$^2$ and R$^3$ are as defined above for the Compounds of Formula (I).

In one embodiment, Q is:

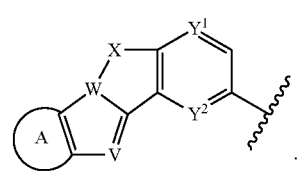

(Q1)

In another embodiment, Q is:

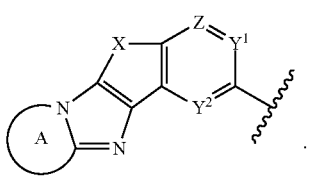

(Q2)

In one embodiment, each occurrence of $R^1$ is halo.

In another embodiment, $R^1$ represents a single halo substituent.

In another embodiment, $R^1$ represents a single F substituent.

In one embodiment, $R^2$ is —C(O)NH—($C_1$-$C_6$ alkyl).

In another embodiment, $R^2$ is —C(O)NH—$CH_3$.

In one embodiment, $R^3$ is —N($R^9$)—S(O)$_n$—$R^{10}$ wherein $R^9$ and $R^{10}$ are each independently $C_1$-$C_6$ alkyl.

In one embodiment, Q is Q1 and A is phenyl.
In another embodiment, Q is Q1 and A is pyridyl.
In one embodiment, Q is Q1 and V is —CH—.
In another embodiment, Q is Q1 and V is N.
In one embodiment, Q is Q1 and W is N.
In one embodiment, Q is Q1 and X is —$CHR^8$—O—.
In another embodiment, Q is Q1, X is —$CHR^8$—O— and $R^8$ is H, methyl or cyclopropyl.
In another embodiment, Q is Q1 and X is —$CH_2$—O—.
In still another embodiment, Q is Q1 and X is —$CH_2CH_2$—O—.
In another embodiment, Q is Q1 and X is —C(O)O—.
In one embodiment, Q is Q1 and $Y^1$ is —CH—.
In another embodiment, Q is Q1 and $Y^1$ is —N—.
In one embodiment, Q is Q1 and $Y^2$ is —CH—.
In another embodiment, Q is Q1 and $Y^2$ is —N—.
In one embodiment, Q is Q1, $Y^1$ is —CH— and $Y^2$ is —N—.
In another embodiment, Q is Q1, $Y^1$ is —N— and $Y^2$ is —CH—.
In one embodiment, Q is Q1 and Z is —CH—.
In another embodiment, Q is Q1 and Z is N.
In one embodiment, Q is Q1 and $Y^1$, $Y^2$ and Z are each —CH—.
In one embodiment, Q is Q1, A is phenyl and W is N.
In another embodiment, Q is Q1, A is phenyl, W is N, $Y^1$ is CH and $Y^2$ is CH.
In another embodiment, Q is Q1, A is phenyl, W is N, $Y^1$ is N and $Y^2$ is CH.
In another embodiment, Q is Q1, A is phenyl, W is N, $Y^1$ is CH and $Y^2$ is N.
In one embodiment, Q is Q1, A is pyridyl and W is N.
In another embodiment, Q is Q1, A is pyridyl, W is N, $Y^1$ is CH and $Y^2$ is CH.
In another embodiment, Q is Q1, A is pyridyl, W is N, $Y^1$ is N and $Y^2$ is CH.
In another embodiment, Q is Q1, A is pyridyl, W is N, $Y^1$ is CH and $Y^2$ is N.
In one embodiment, Q is Q2 and A is phenyl.
In another embodiment, Q is Q2 and A is pyridyl.
In one embodiment, Q is Q2 and X is —$CHR^8$—O—.
In another embodiment, Q is Q2, X is —$CHR^8$—O— and $R^8$ is H, methyl or cyclopropyl.
In another embodiment, Q is Q2 and X is —$CH_2$—O—.
In still another embodiment, Q is Q2 and X is —$CH_2CH_2$—O—.

In another embodiment, Q is Q2 and X is —C(O)O—.
In one embodiment, Q is Q2 and $Y^1$ is —CH—.
In another embodiment, Q is Q2 and $Y^1$ is —N—.
In one embodiment, Q is Q2 and $Y^2$ is —CH—.
In another embodiment, Q is Q2 and $Y^2$ is —N—.
In one embodiment, Q is Q2, $Y^1$ is —CH— and $Y^2$ is —N—.
In another embodiment, Q is Q2, $Y^1$ is —N— and $Y^2$ is —CH—.
In one embodiment, Q is Q2 and Z is —CH—.
In another embodiment, Q is Q2 and Z is N.
In one embodiment, Q is Q2 and $Y^1$, $Y^2$ and Z are each —CH—.
In another embodiment, Q is Q2, A is phenyl, Z is CH, $Y^1$ is CH and $Y^2$ is CH.
In another embodiment, Q is Q2, A is phenyl, Z is CH, $Y^1$ is N and $Y^2$ is CH.
In another embodiment, Q is Q2, A is phenyl, Z is CH, $Y^1$ is CH and $Y^2$ is N.
In another embodiment, Q is Q2, A is phenyl, and $Y^1$, $Y^2$ and Z are each CH.

In one embodiment, the compounds of formula (I) have the formula (Ia):

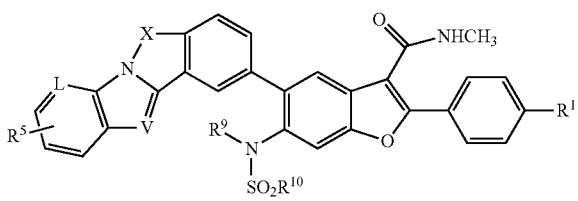

(Ia)

or a pharmaceutically acceptable salt thereof,
wherein:
  L is N or —CH—;
  V is N or —C($R^4$)—;
  X is —($CHR^8$)$_n$—O— or —C(O)—O—;
  $R^1$ is H, halo or $C_1$-$C_6$ alkyl;
  $R^4$ is H or halo;
  $R^5$ represents a single and optional halo substituent;
  $R^8$ is H, $C_1$-$C_6$ alkyl or 3 to 7-membered cycloalkyl;
  $R^9$ and $R^{10}$ are each $C_1$-$C_6$ alkyl; and
  n is 1 or 2.

In one embodiment, for the compounds of formula (Ia), V is —CH—.

In another embodiment, for the compounds of formula (Ia), V is N.

In one embodiment, for the compounds of formula (Ia), W is N.

In one embodiment, for the compounds of formula (Ia), X is —$CHR^8$—O—.

In another embodiment, for the compounds of formula (Ia), X is —$CHR^8$—O— and $R^8$ is H, methyl or cyclopropyl.

In another embodiment, for the compounds of formula (Ia), X is —$CH_2$—O—.

In still another embodiment, for the compounds of formula (Ia), X is —$CH_2CH_2$—O—.

In another embodiment, for the compounds of formula (Ia), X is —C(O)O—.

In one embodiment, for the compounds of formula (Ia):
L and V are each —CH— and X is —$CH_2$—O—.

In another embodiment, for the compounds of formula (Ia):
V is N or —C(R$^4$)—;
R$^1$ is F;
R$^4$ is H or Cl;
R$^5$ represents a single and optional F substituent;
R$^8$ is H, methyl or cyclopropyl; and
R$^9$ and R$^{10}$ are each methyl.

In one embodiment, the compounds of formula (I) have the formula (Ib):

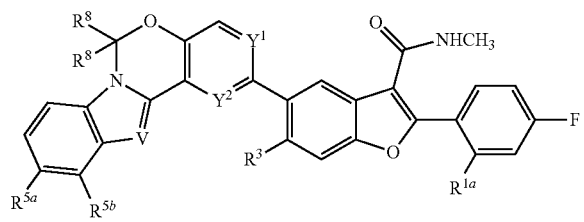

(Ib)

or a pharmaceutically acceptable salt thereof, wherein:
V is N or —CH—;
Y$^1$ is N or —C(R$^5$)—;
Y$^2$ is N or —CH—;
R$^{1a}$ is H or F;
R$^3$ is —N(CH$_3$)S(O)$_2$CH$_3$ or:

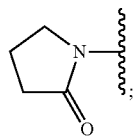 [SMILES: *N1CCCC1=O]

R$^5$ is H or —O—(C$_1$-C$_6$ alkyl);
R$^{5a}$ and R$^{5b}$ are each independently H or F; and
each occurrence of R$^8$ is H, or both R$^8$ groups, together with the common carbon atom to which they are attached, join to form a 4- to 6-membered monocyclic heterocycloalkyl group.

In one embodiment, for the compounds of formula (Ib), V is CH.

In another embodiment, for the compounds of formula (Ib), V is N.

In one embodiment, for the compounds of formula (Ib), Y$^1$ is CH and Y$^2$ is CH.

In another embodiment, for the compounds of formula (Ib), Y$^1$ is CH and Y$^2$ is N.

In another embodiment, for the compounds of formula (Ib), Y$^1$ is N and Y$^2$ is CH.

In another embodiment, for the compounds of formula (Ib), V is N.

In one embodiment, for the compounds of formula (Ib), R$^{1a}$ is H.

In another embodiment, for the compounds of formula (Ib), R$^3$ is —N(CH$_3$)S(O)$_2$CH$_3$.

In another embodiment, for the compounds of formula (Ib), R$^{1a}$ is H and R$^3$ is —N(CH$_3$)S(O)$_2$CH$_3$.

In another embodiment, for the compounds of formula (Ib), each occurrence of R$^8$ is H.

In one embodiment, for the compounds of formula (Ib), R$^{5a}$ is H and R$^{5b}$ is F.

In another embodiment, for the compounds of formula (Ib), R$^{5a}$ is F and R$^{5b}$ is H.

In one embodiment, for the compounds of formula (Ib), V is CH; R$^{1a}$ is H; R$^3$ is —N(CH$_3$)S(O)$_2$CH$_3$, and each occurrence of R$^8$ is H.

In one embodiment, the compound of formula (Ib) is:

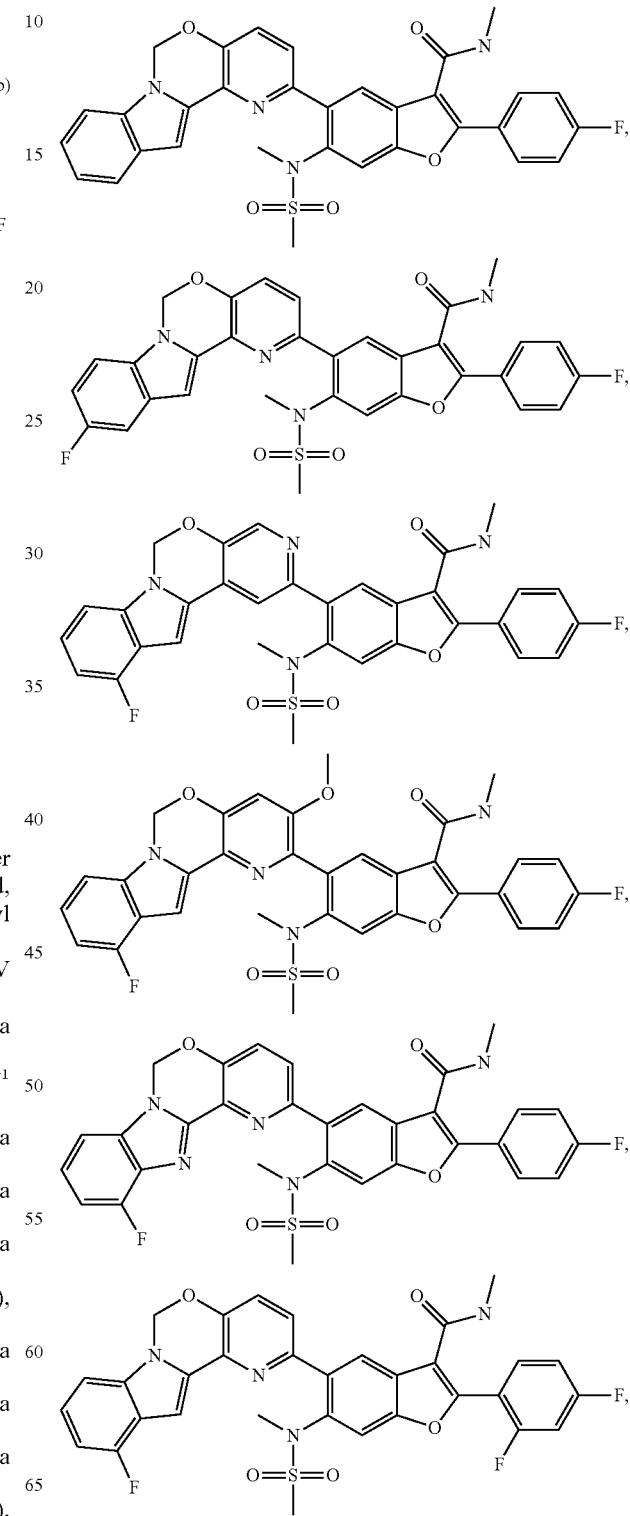

-continued

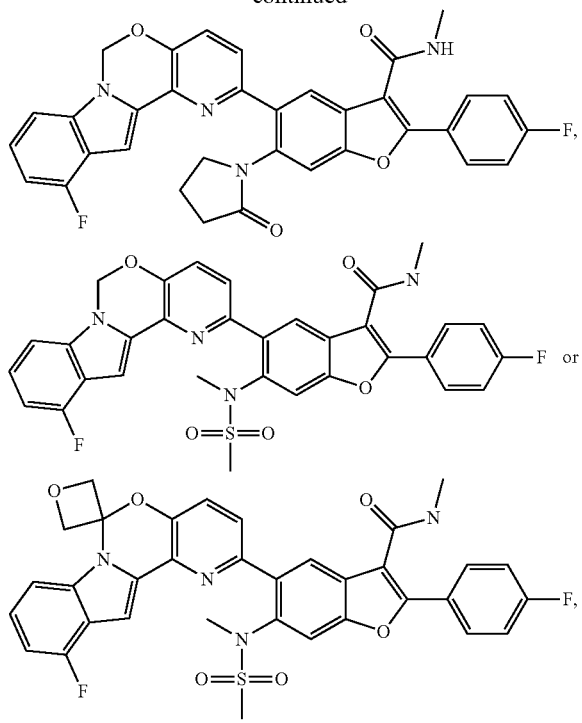

or a pharmaceutically acceptable salt thereof.

In one embodiment, for the Compounds of Formula (I), variables Q, $R^1$, $R^2$ and $R^3$ are selected independently of each other.

In another embodiment, the Compounds of Formula (I) are in substantially purified form.

In another embodiment of the invention, the compound of the invention is one of compounds 1-211, as depicted in the Examples below, or a pharmaceutically acceptable salt thereof.

Other embodiments of the present invention include the following:

(a) A pharmaceutical composition comprising an effective amount of a compound of formula (I) and a pharmaceutically acceptable carrier.

(b) The pharmaceutical composition of (a), further comprising a second therapeutic agent selected from the group consisting of HCV antiviral agents, immunomodulators, and anti-infective agents.

(c) The pharmaceutical composition of (b), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(d) A pharmaceutical combination that is (i) a compound of formula (I) and (ii) a second therapeutic agent selected from the group consisting of HCV antiviral agents, immunomodulators, and anti-infective agents; wherein the compound of formula (I) and the second therapeutic agent are each employed in an amount that renders the combination effective for inhibiting HCV NS5B activity, or for inhibiting HCV viral replication, or for treating HCV infection and/or reducing the likelihood or severity of symptoms of HCV infection.

(e) The combination of (d), wherein the HCV antiviral agents are one or more antiviral agents selected from the group consisting of direct inhibitors of HCV, including but not limited to NS3 and NS3/4A protease inhibitors, NS5A inhibitors and HCV NS5B polymerase inhibitors.

A use of a compound of formula (I) in the preparation of a medicament for inhibiting HCV NS5B activity in a subject in need thereof.

(g) A use of a compound of formula (I) in the preparation of a medicament for preventing and/or treating infection by HCV in a subject in need thereof.

(h) A method of treating HCV infection and/or reducing the likelihood or severity of symptoms of HCV infection in a subject in need thereof, which comprises administering to the subject an effective amount of a compound of formula (I).

(i) The method of (h), wherein the compound of formula (I) is administered in combination with an effective amount of at least one second therapeutic agent selected from the group consisting of HCV antiviral agents, immunomodulators, and anti-infective agents.

(j) The method of (i), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(k) A method of inhibiting HCV viral replication and/or HCV viral production in a cell-based system, which comprises administering to the subject an effective amount of a compound of formula (I) in combination with an effective amount of at least one second therapeutic agent selected from the group consisting of HCV antiviral agents, immunomodulators, and anti-infective agents.

(l) The method of (k), wherein the HCV antiviral agent is an antiviral selected from the group consisting of direct inhibitors of HCV, including but not limited to NS3 and NS3/4A protease inhibitors, NS5A inhibitors and HCV NS5B polymerase inhibitors.

(m) A method of inhibiting HCV NS5B activity in a subject in need thereof, which comprises administering to the subject the pharmaceutical composition of (a), (b), or (c) or the combination of (d) or (e).

(n) A method of treating HCV infection and/or reducing the likelihood or severity of symptoms of HCV infection in a subject in need thereof, which comprises administering to the subject the pharmaceutical composition of (a), (b), or (c) or the combination of (d) or (e).

The present invention also includes a compound of the present invention for use (i) in, (ii) as a medicament for, or (iii) in the preparation of a medicament for: (a) inhibiting HCV NS5B activity, or (b) inhibiting HCV viral replication, or (c) treating HCV infection and/or reducing the likelihood or severity of symptoms of HCV infection, or (d) use in medicine. In these uses, the compounds of the present invention can optionally be employed in combination with one or more second therapeutic agents selected from HCV antiviral agents, anti-infective agents, and immunomodulators.

In the embodiments of the compounds and salts provided above, it is to be understood that each embodiment may be combined with one or more other embodiments, to the extent that such a combination provides a stable compound or salt and is consistent with the description of the embodiments. It is further to be understood that the embodiments of compositions and methods provided as (a) through (n) above are understood to include all embodiments of the compounds and/or salts, including such embodiments as result from combinations of embodiments.

Additional embodiments of the invention include the pharmaceutical compositions, combinations, uses and methods set forth in (a) through (n) above, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1-5 below. Alternative synthetic pathways and analogous structures will be apparent to those skilled in the art of organic synthesis. All stereoisomers and tautomeric forms of the compounds are contemplated.

Some commercially available starting materials and intermediates used for the synthesis of the Compounds of Formula (I) are available which contain intact fused polycyclic tricyclic ring systems. These starting materials and intermediates are available from commercial suppliers such as Sigma-Aldrich (St. Louis, Mo.) and Acros Organics Co. (Fair Lawn, N.J.). Such starting materials and intermediates compounds are used as received.

Scheme 1 shows methods useful for making the compounds of formula F, which correspond to the Compounds of Formula (I), wherein A is phenyl; V is —CH—; W is N; X is —CH$_2$)$_n$—O—; Y and Z are each —CH—.

Scheme 1

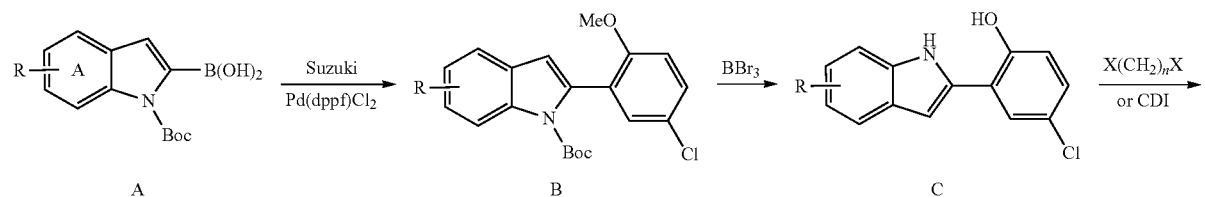

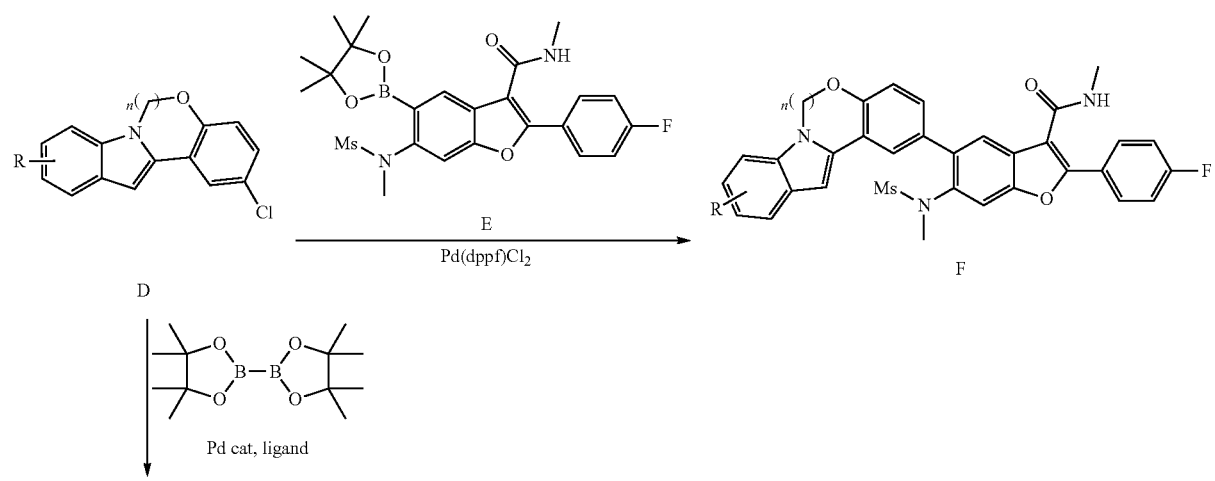

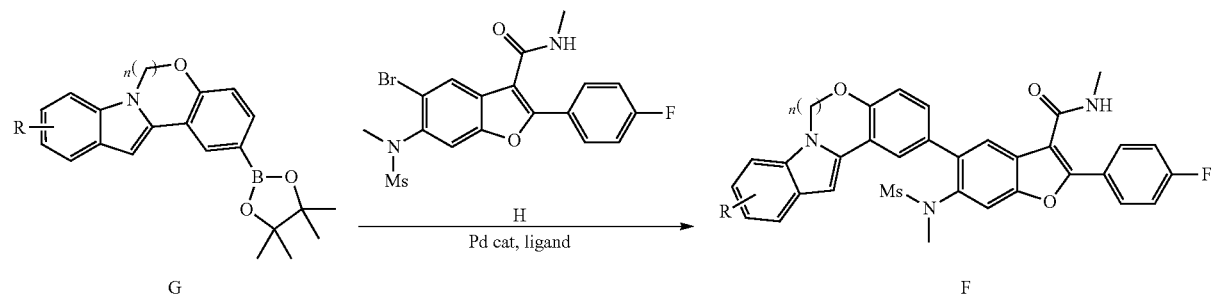

wherein Ms is mesyl (—SO$_2$CH$_3$).

This scheme describes the preparation of compounds with the general structure of F. Starting from compound A, which coupling with aromatic halides can afford compounds B. Compounds C are generated by deprotecting of methyl with BBr$_3$, and then the hydroxyl groups and the nitrogen of the left (aza-)indole in compounds C are cyclized with X(CH$_2$)$_n$X (X can be Cl, Br or I) or CDI to furnish compounds D. Transition metal mediated coupling of compounds D with compound E (made as described below in Scheme 4) provides the target compounds of general structure F. In some other cases, compounds D can be converted to corresponding boronic esters G in the presence of transition metal catalyst, and coupling of compounds G with compound H (described in previous patent) also can provides the target compounds of general structure F.

Scheme 2 show a method useful for making the compounds of formula M, which correspond to the Compounds of Formula (I), wherein A is phenyl; V is —CH—; W is N; X is —CH(cyclopropyl)-O—; Y and Z are each —CH—.

Scheme 2

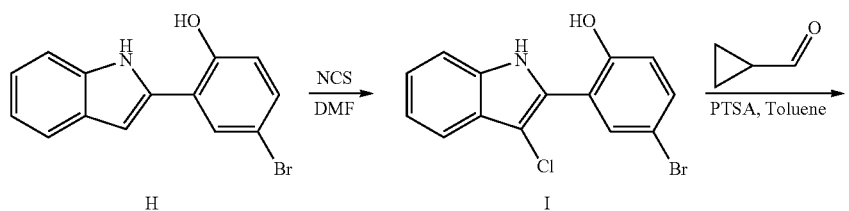

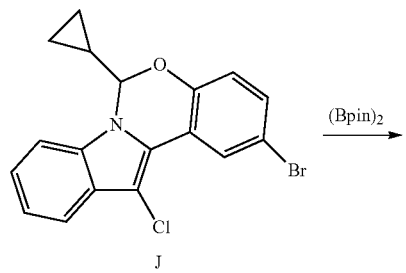

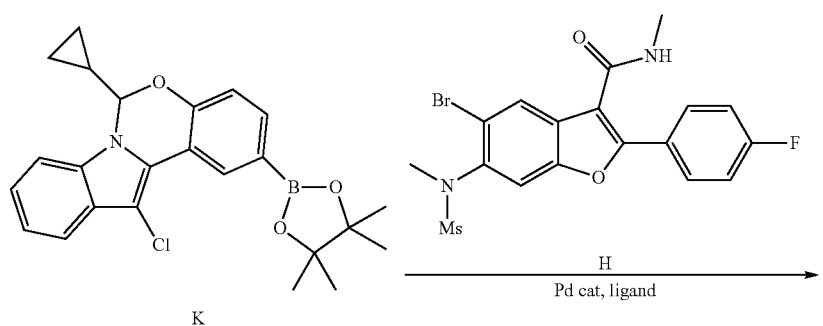

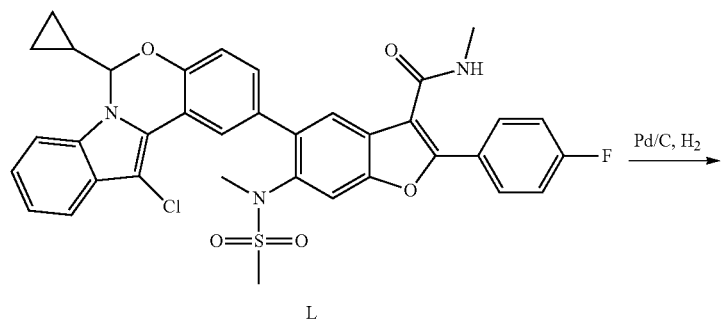

-continued

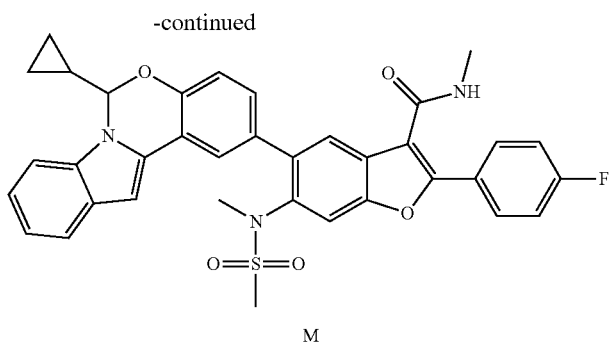

M

This scheme describes the preparation of compounds L and M. Starting from compound H (can be prepared using method for compounds C), which reacting with NCS can afford compound I. Compounds J is generated by cyclization with cyclopropanecarbaldehyde in the presence of PTSA. Compounds J can be converted to corresponding boronic esters K in the presence of transition metal catalyst, and coupling of compounds K with compound H provides the target compound L. Compounds L can be transferred to compound M by reduction of chlorine through catalytic hydrogenation.

Scheme 3 shows a method useful for making the compounds of formula Q, which correspond to the Compounds of Formula (I), wherein A is phenyl; V is N; W is N; X is —(CH$_2$)$_n$—O—; Y and Z are each —CH—.

Scheme 3

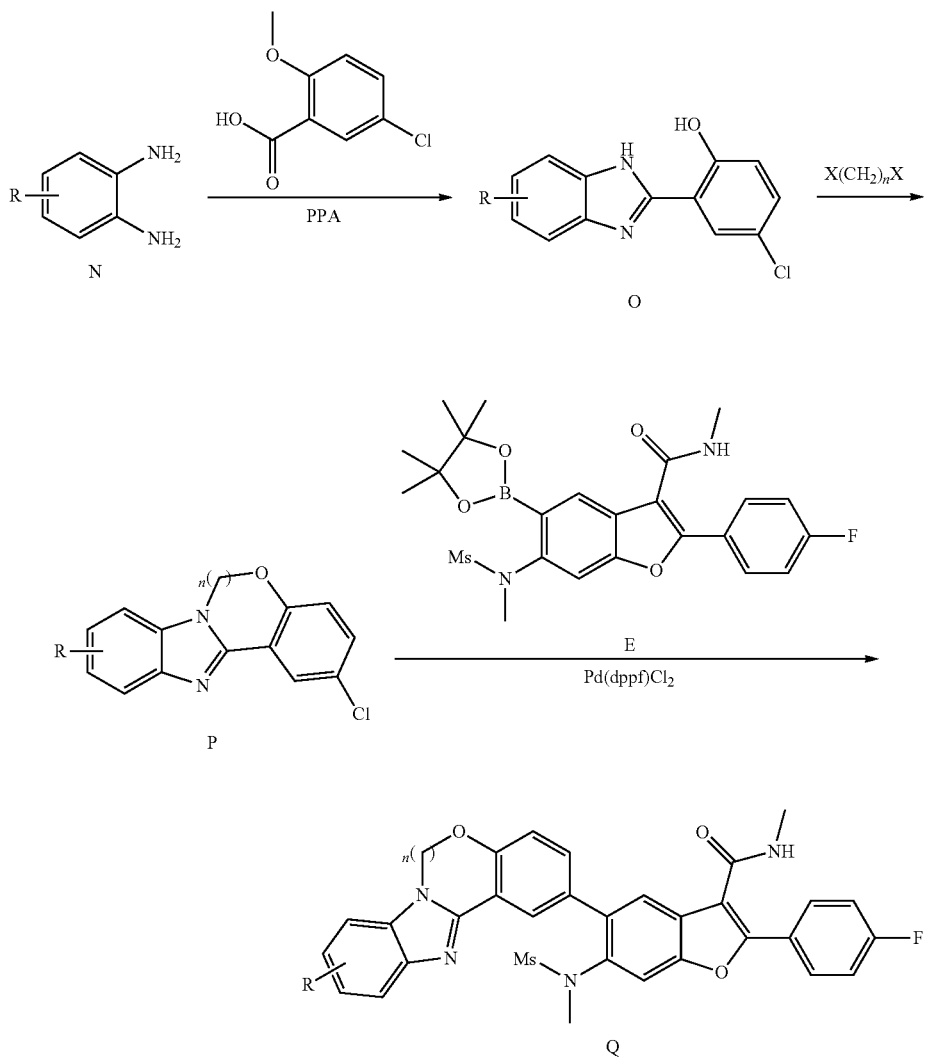

This scheme describes preparation of compounds with the general structure of Q. Starting from compound N, which reacting with 2-bromo-4-chloro-1-methoxybenzene can afford compounds O. Compounds O cyclized with X(CH$_2$)$_n$X (X can be Cl, Br or I) in the presence of base to furnish compounds P. Transition metal mediated coupling of compounds P with compound E provides the target compounds of general structure Q.

Scheme 4 shows a method useful for making compound E, which is a intermediate useful for making the Compounds of Formula (I).

Scheme 4

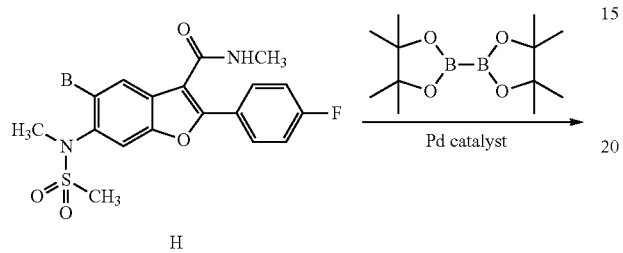

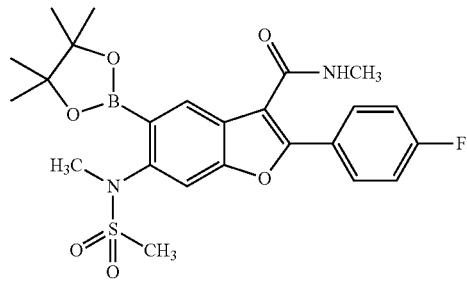

Intermediate boronic acid compound E can be made by reacting bromo-substitued benzofuran compound H with bis (pinacolato)diboron in the presence of an appropriate palladium catalyst.

Scheme 5 shows a method useful for making certain compounds of Formula (I). The cyclization was accomplished through an indoline intermediate.

Scheme 5

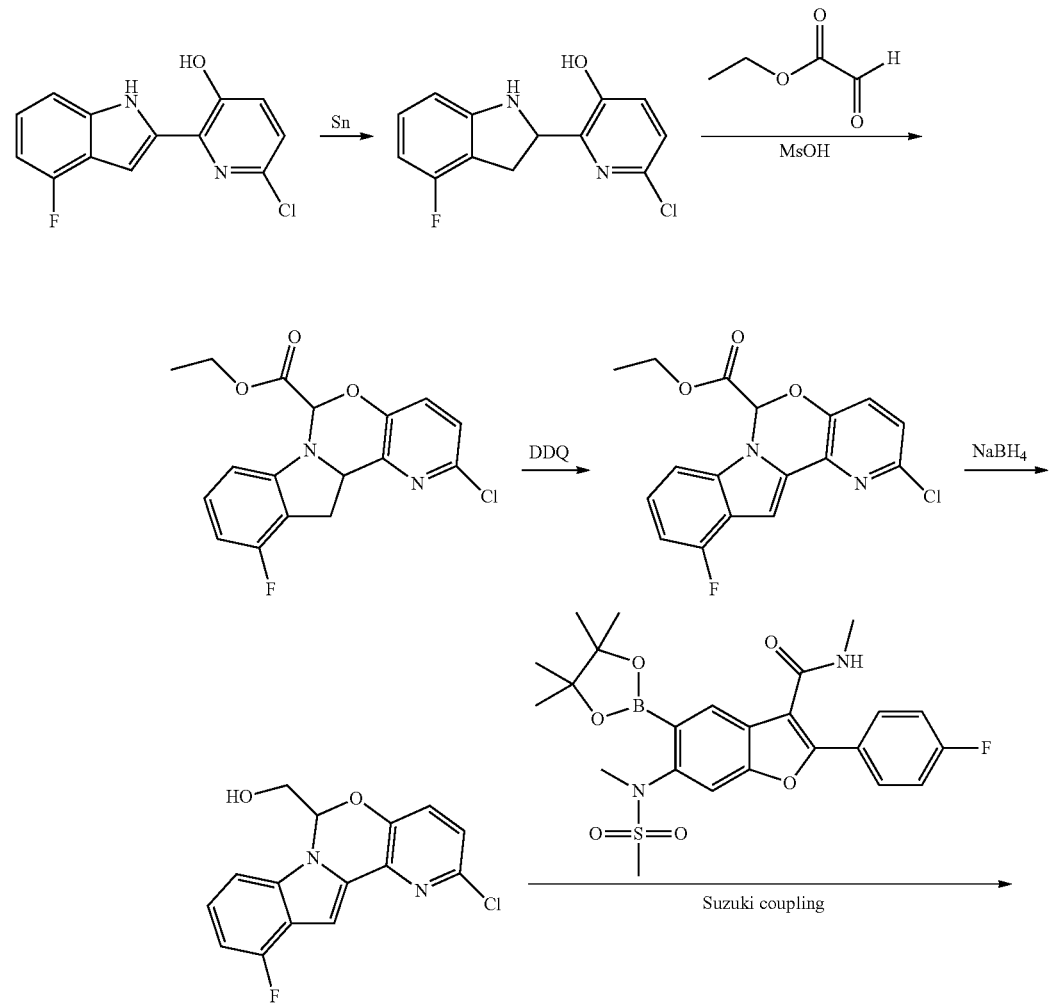

-continued

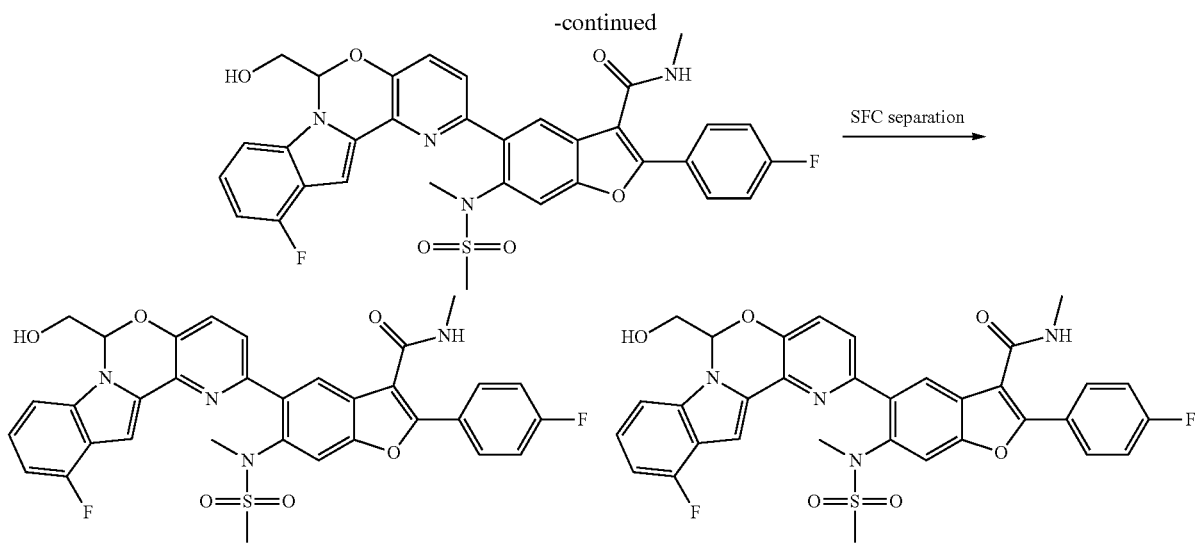

SFC separation

One skilled in the art of organic synthesis will recognize that the synthesis of compounds with multiple reactive functional groups, such as —OH and $NH_2$, may require protection of certain functional groups (i.e., derivatization for the purpose of chemical compatibility with a particular reaction condition). Suitable protecting groups for the various functional groups of these compounds and methods for their installation and removal are well-known in the art of organic chemistry. A summary of many of these methods can be found in Greene & Wuts, *Protecting Groups in Organic Synthesis*, John Wiley & Sons, $3^{rd}$ edition (1999).

One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

Compounds of formula F, M, Q and E may be further elaborated using methods that would be well-known to those skilled in the art of organic synthesis or, for example, the methods described in the Examples below, to make the full scope of the Compounds of Formula (I).

The starting materials used and the intermediates prepared using the methods set forth above in Schemes 1-5 may be isolated and purified if desired using conventional techniques, including but not limited to filtration, distillation, crystallization, chromatography and alike. Such materials can be characterized using conventional means, including physical constants and spectral data.

EXAMPLES

General Methods

The compounds described herein can be prepared according to the procedures of the following schemes and examples, using appropriate materials and are further exemplified by the following specific examples. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Mass spectra (MS) were measured by electrospray ion-mass spectroscopy (ESI). $^1H$ NMR spectra were recorded at 400-500 MHz. Compounds described herein were synthesized as a racemic mixture unless otherwise stated in the experimental procedures.

Example 1

Preparation of Compound 1

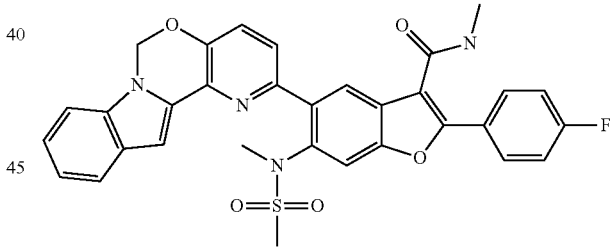

Step 1—Synthesis of 2,6-dichloropyridin-3-ol

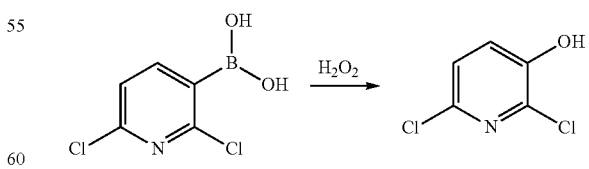

$H_2O_2$ (1.60 g, 47.12 mmol) was added slowly to the solution of compound 2,6-dichloropyridin-3-ylboronic acid (3 g, 15.71 mmol) in $CH_2Cl_2$ (30 mL) at 0° C. After stirred at room temperature for about 15 hours, the mixture was quenched with sat. $Na_2S_2O_3$ aqueous (50 mL) and adjusted to pH<7 with 1N HCl. The mixture was extracted with EtOAc (40 mL×3). The organic layer was washed with brine (100 mL), dried over Na₂SO₄, filtered and the solvent was concentrated in vacuo to provide 2,6-dichloropyridin-3-ol (2.34 g, yield: 91.4%). ¹H-NMR (CDCl₃, 400 MHz) δ 7.30 (d, J=8.4 Hz, 1H), 7.19 (d, J=8.4 Hz, 1H), 5.70 (br, 1H). MS (M+H)⁺: 164/166/168.

Step 2—Synthesis of
2,6-dichloro-3-methoxypyridine

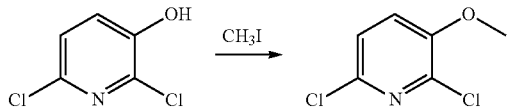

To a solution of 2,6-dichloropyridin-3-ol (16.3 g, 0.1 mol) and K₂CO₃ (41.4 g, 0.3 mol) in DMF (200 mL) were added MeI (21.3 g, 0.15 mol). The mixture was allowed to stir at 80° C. for 2 hours. The mixture was then diluted with water (200 mL) and extracted with EtOAc (200 mL×3). The organic layer was washed with brine (200 mL×3), dried over Na₂SO₄, filtered and the solvent was concentrated in vacuo to provide 2,6-dichloro-3-methoxypyridine (17.0 g, yield: 96.0%). ¹H-NMR (CDCl₃, 400 MHz) δ 7.12~7.18 (m, 2H), 3.86 (s, 3H). MS (M+H)⁺: 178/180/182.

Step 3—Synthesis of
2-(6-chloro-3-methoxypyridin-2-yl)-1H-indole

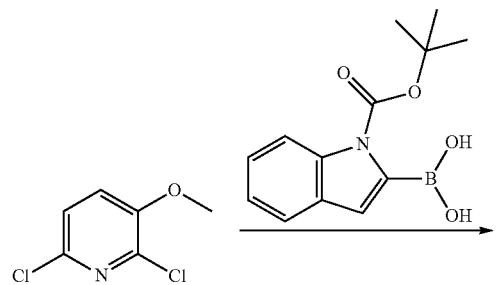

To a degassed solution of compound 2,6-dichloro-3-methoxypyridine (8.9 g, 0.05 mol), (1-(tert-butoxycarbonyl)-1H-indol-2-yl)boronic acid (13 g, 0.05 mol) and K₃PO₄ (31.8 g, 3.0 mol) in DMF (100 mL) was added Pd(dppf)Cl₂ (3.65 g, 5 mmol) under N₂. The mixture was heated at 60° C. for about 15 hours. The reaction mixture was cooled to room temperature, diluted with EtOAc and filtered. The filtrate was washed with H₂O, brine, dried over Na₂SO₄. After being concentrated in vacuo, the resulting resulting residue was purified using prep-HPLC to provide the desired product of 2-(6-chloro-3-methoxypyridin-2-yl)-1H-indole (9.0 g, yield: 69.8%). ¹H-NMR (CDCl₃, 400 MHz) δ 9.52 (s, 1H), 7.65 (d, J=7.6 Hz, 1H), 7.38~7.43 (m, 2H), 7.07~7.26 (m, 4H), 4.03 (s, 3H). MS (M+H)⁺: 259/261.

Step 4—Synthesis of
6-chloro-2-(1H-indol-2-yl)pyridin-3-ol

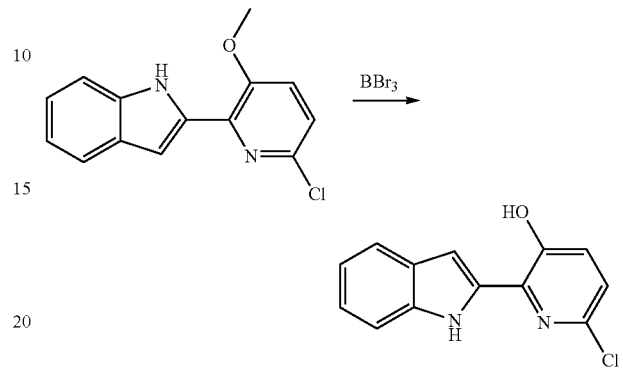

BBr₃ (0.4 mL, 0.39 mmol) was added to the solution of 2-(6-chloro-3-methoxypyridin-2-yl)-1H-indole (50 mg, 0.19 mmol) in CH₂Cl₂ (0.5 mL) at −78° C. under N₂. The mixture was allowed to stir at room temperature for 3 hours. The mixture was then quenched with CH₃OH (10 mL) at −78° C. After being concentrated in vacuo, the resulting resulting residue was purified using prep-TLC (petroleum ether:EtOAc=2.5:1) to provide 6-chloro-2-(1H-indol-2-yl)pyridin-3-ol (40 mg, yield: 85.1%), which was also prepared from 6-chloro-2-iodopyridin-3-ol and (1-(tert-butoxycarbonyl)-1H-indol-2-yl)boronic acid using similar procedure of step 3 of Example 1. ¹H-NMR (CDCl₃, 400 MHz) δ 10.09 (s, 1H), 9.72 (s, 1H), 7.50 (d, J=7.9 Hz, 1H), 7.17~7.32 (m, 3H), 7.08~7.14 (m, 1H), 6.87~6.96 (m, 2H). MS (M+H)⁺: 245/247.

Step 5—Synthesis of 2-chloro-6H-pyrido[2',3':5,6]
[1,3]oxazino[3,4-a]indole with/without 2-chloro-6,
11-dihydropyrido[2',3':5,6]pyrano[4,3-b]indole

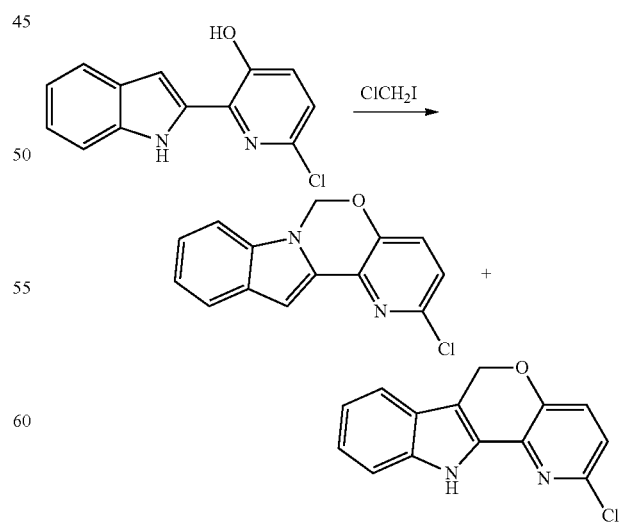

A solution of 6-chloro-2-(1H-indol-2-yl)pyridin-3-ol (500 mg, 3.05 mmol) in DMF (50 mL) was added dropwise to a mixture of chloroiodomethane (5.37 g, 30.5 mmol) and K₂CO₃ (1.26 g, 9.15 mmol) in DMF (50 mL) at 100° C. After addition, the mixture was diluted with water (100 mL) and extracted with EtOAc (50 mL*3). The organic layer was washed with brine (50 mL*3), dried over Na₂SO₄ and concentrated in vacuo. The resulting residue was purified using chromatography (petroleum ether:EtOAc=30:1) to provide the mixture of 2-chloro-6H-pyrido[2',3':5,6][1,3]oxazino[3,4-a]indole and 2-chloro-6,11-dihydropyrido[2',3':5,6]pyrano[4,3-b]indole (ratio=3:1, 80 mg, yield: 15.3%), which was further purified with prep-HPLC to provide both of the isomers. MS (M+H)⁺: 257/259.

mmol) in DMF (10 mL) was added dropwise. After addition, the mixture was allowed to stir for another 0.5 hours. The mixture was then diluted with water (100 mL) and extracted with EtOAc (100 mL*3). The organic layer was washed with brine (100 mL*3), dried over Na₂SO₄ and concentrated in vacuo. The resulting residue was purified using prep-TLC (petroleum ether:EtOAc=3:1) to provide the product 2-chloro-6H-pyrido[2',3':5,6][1,3]oxazino[3,4-a]indole (260 mg, yield: 50.7%). ¹H-NMR (CDCl₃, 400 MHz) δ 7.63 (d, J=8.0 Hz, 1H), 7.22~7.27 (m, 3H), 7.19 (d, J=2.4 Hz, 1H), 7.08~7.12 (m, 2H), 5.86 (s, 2H). MS (M+H)⁺: 257/259.

Step 6—Synthesis of 2-(4-fluorophenyl)-N-methyl-6-(N-methylmethylsulfonamido)-5-(6H-pyrido[2',3':5,6][1,3]oxazino[3,4-a]indol-2-yl)benzofuran-3-carboxamide (Compound 1)

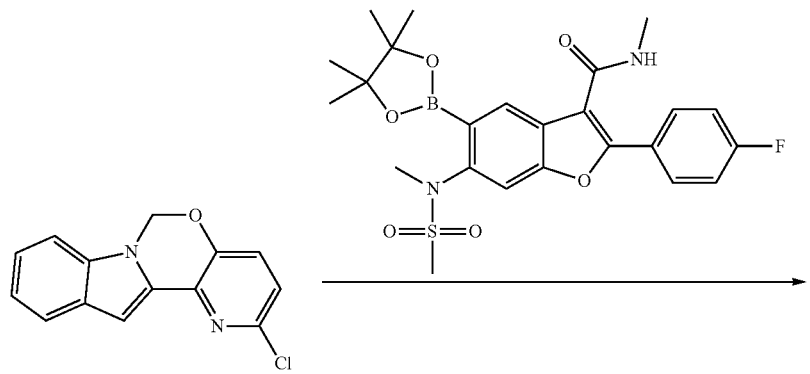

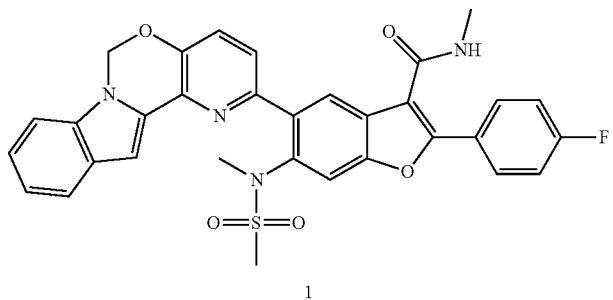

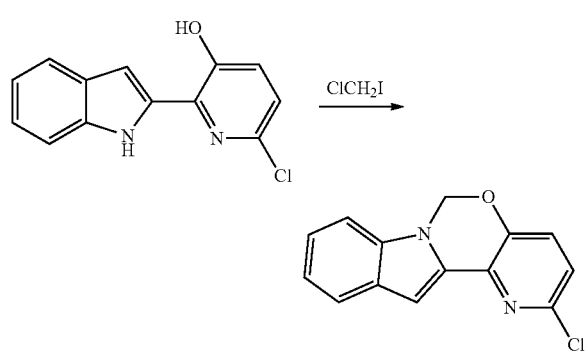

To a solution of 6-chloro-2-(1H-indol-2-yl)pyridin-3-ol (480 mg, 2.0 mmol) and K₂CO₃ (1.38 g, 10.0 mmol) in DMF (50 mL) stirring at 100° C., chloroiodomethane (386 mg, 2.2

To a degassed solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (502 mg, 1.0 mmol), 2-chloro-6H-pyrido[2',3':5,6][1,3]oxazino[3,4-a]indole (256 mg, 1.0 mmol) and K₃PO₄ (636 mg, 3.0 mmol) in dioxane:H₂O (1.5 mL:0.4 mL) was added Pd₂(dba)₃ (91 mg, 0.1 mmol) and X-Phos (91 mg, 0.2 mmol) under N₂. The mixture was heated to 110° C. for 3 hours. The reaction mixture was cooled to room temperature, diluted with EtOAc and filtered. The filtrate was washed with H₂O, brine, dried over Na₂SO₄. After being concentrated in vacuo, the resulting resulting residue was purified using prep-HPLC to provide the desired product of Compound 1 (275 mg, yield: 46.1%). ¹H-NMR (CDCl₃, 400 MHz) δ 7.88~7.94 (m, 3H), 7.61~7.63 (m, 2H), 7.40 (s, 2H), 7.09~7.28 (m, 6H), 5.94 (s, 2H), 5.86 (d, J=4.4 Hz, 1H), 3.29 (s, 3H), 2.92 (d, J=4.8 Hz, 3H), 2.65 (s, 3H). MS (M+H)⁺: 597.

Compounds 2-40, depicted in the table below, were prepared using the method described above and substituting the appropriate reactants and/or reagents.

| Compound No | Structure | NMR | MS (M + H)+ |
|---|---|---|---|
| 3 | 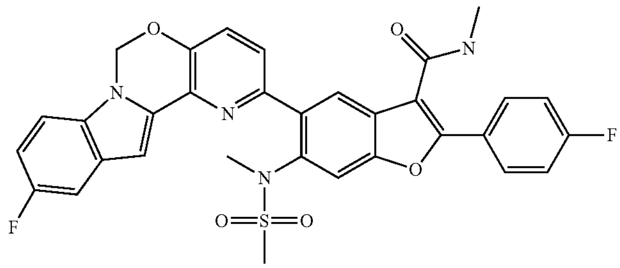 [SMILES: CNC(=O)c1c(-c2ccc(F)cc2)oc2cc(N(C)S(C)(=O)=O)c(-c3ccc4c(n3)-c3cc5cc(F)ccc5n3CO4)cc12] | $^1$H-NMR (CDCl$_3$, 400 MHz) δ 7.92~7.99 (m, 3H), 7.64 (s, 1H), 7.44~7.49 (m, 2H), 7.29~7.32 (m, 1H), 7.00~7.24 (m, 5H), 6.03 (d, J = 4.4 Hz, 1H), 5.95 (s, 2H), 3.33 (s, 3H), 2.97 (d, J = 4.8 Hz, 3H), 2.73 (s, 3H). | 615 |
| 4 | 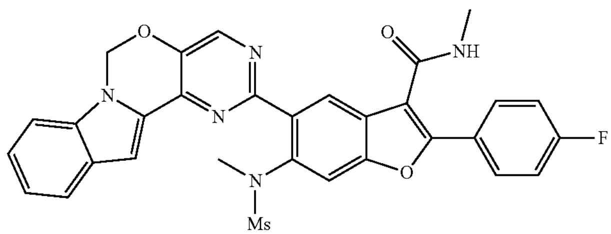 [SMILES: CNC(=O)c1c(-c2ccc(F)cc2)oc2cc(N(C)S(C)(=O)=O)c(-c3ncc4c(n3)-c3cc5ccccc5n3CO4)cc12] | $^1$H-NMR (CDCl$_3$, 400 MHz) δ 8.61 (s, 1H), 8.35 (s, 1H), 8.00~8.03 (m, 2H), 7.74 (t, J = 4.0 Hz, 2H), 7.41 (s, 1H), 7.37 (d, J = 4.8 Hz, 2H), 7.18~7.22 (m, 3H), 6.07 (s, 2H), 3.44 (s, 3H), 3.02 (s, 3H), 2.84 (s, 3H). | 598 |
| 5 | 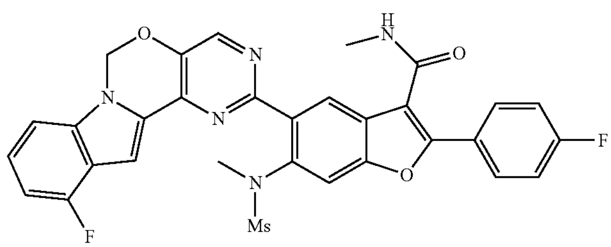 [SMILES: CNC(=O)c1c(-c2ccc(F)cc2)oc2cc(N(C)S(C)(=O)=O)c(-c3ncc4c(n3)-c3cc5c(F)cccc5n3CO4)cc12] | $^1$H-NMR (CDCl$_3$, 400 MHz) δ 8.65 (s, 1H), 8.36 (s, 1H), 8.01~8.04 (m, 2H), 7.72 (s, 1H), 7.48 (s, 1H), 7.13~7.23 (m, 4H), 6.89 (t, J = 8.0 Hz, 1H), 5.97~6.09 (br, 3H), 5.98 (d, J = 4.0 Hz, 1H), 3.48 (s, 3H), 3.04 (d, J = 5.2 Hz, 3H), 2.85 (s, 3H). | 616 |
| 6 | 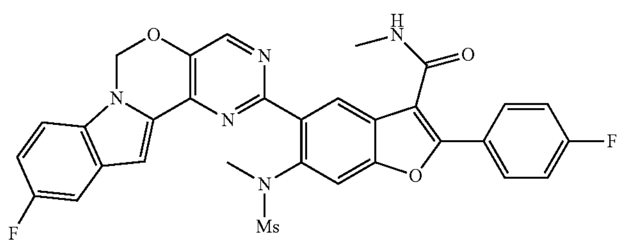 [SMILES: CNC(=O)c1c(-c2ccc(F)cc2)oc2cc(N(C)S(C)(=O)=O)c(-c3ncc4c(n3)-c3cc5cc(F)ccc5n3CO4)cc12] | $^1$H-NMR (CDCl$_3$, 400 MHz) δ 8.62 (s, 1H), 8.47 (s, 1H), 8.00~8.08 (m, 2H), 7.73 (s, 1H), 7.10~7.41 (m, 6H), 6.07 (s, 2H), 6.00 (d, J = 4.0 Hz, 1H), 3.45 (s, 3H), 3.04 (d, J = 4.8 Hz, 3H), 2.85 (s, 3H). | 616 |
| 7 | 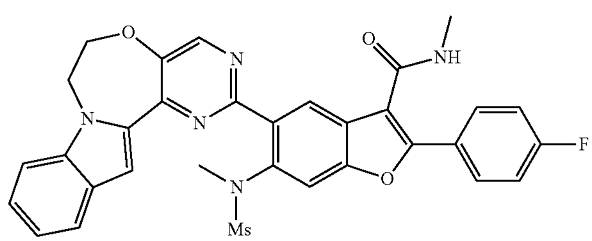 [SMILES: CNC(=O)c1c(-c2ccc(F)cc2)oc2cc(N(C)S(C)(=O)=O)c(-c3ncc4c(n3)-c3cc5ccccc5n3CCO4)cc12] | $^1$H-NMR (CDCl$_3$, 400 MHz) δ 8.59 (d, J = 1.2 Hz, 1H), 8.27 (s, 1H), 8.01~8.05 (m, 2H), 7.81 (s, 1H), 7.75 (s, 1H), 7.71 (d, J = 8.0 Hz, 1H), 7.34 (d, J = 2.4 Hz, 2H), 7.16~7.26 (m, 3H), 5.97 (d, J = 4.0 Hz, 1H), 4.67 (s, 4H), 3.41 (s, 3H), 3.03 (d, J = 1.2 Hz, 3H), 2.80 (s, 3H). | 612 |
| 8 | 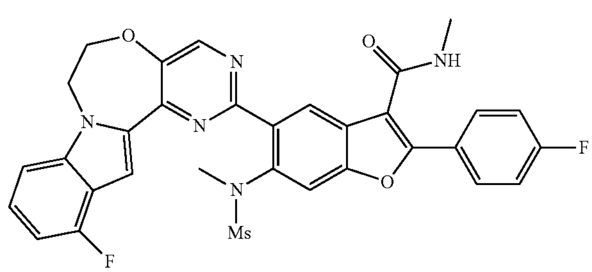 [SMILES: CNC(=O)c1c(-c2ccc(F)cc2)oc2cc(N(C)S(C)(=O)=O)c(-c3ncc4c(n3)-c3cc5c(F)cccc5n3CCO4)cc12] | $^1$H-NMR (DMSO-d6, 400 MHz) δ 8.74 (s, 1H), 8.62 (d, J = 4.0 Hz, 1H), 8.02~8.07 (m, 4H), 7.69 (s, 1H), 7.41~7.46 (m, 3H), 7.25~7.31 (m, 1H), 6.90~6.95 (m, 1H), 4.72~4.77 (m, 4H), 3.40 (s, 3H), 2.93 (s, 3H), 2.84 (d, J = 4.4 Hz, 3H). | 630 |

| Compound No | Structure | NMR | MS (M + H)+ |
|---|---|---|---|
| 9 | 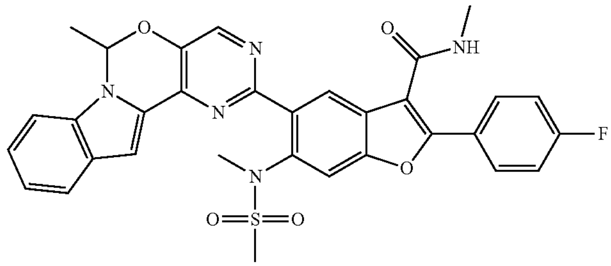 [SMILES: CNC(=O)c1c(-c2ccc(F)cc2)oc2cc(N(C)S(C)(=O)=O)c(-c3ncc4c(n3)-c3cc5ccccc5n3C(C)O4)cc12] | ¹H-NMR (CDCl₃, 400 MHz) δ 8.65 (s, 1H), 8.33 (s, 1H), 8.03~8.07 (m, 2H), 7.73~7.77 (m, 2H), 7.45 (s, 1H), 7.37~7.38 (m, 2H), 7.18~7.24 (m, 3H), 6.65~6.69 (m, 1H), 6.20 (s, 1H), 3.48 (s, 3H), 3.04 (d, J = 4.8 Hz, 3H), 2.83 (s, 3H), 1.71 (d, J = 5.6 Hz, 3H). | 612 |
| 10 | 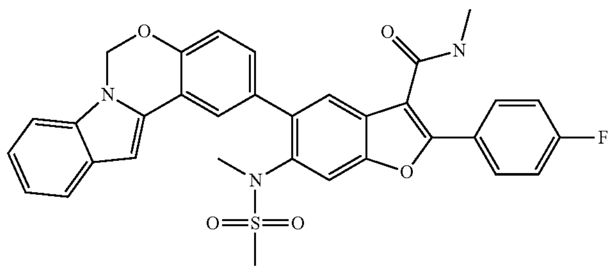 [SMILES: CNC(=O)c1c(-c2ccc(F)cc2)oc2cc(N(C)S(C)(=O)=O)c(-c3ccc4c(c3)-c3cc5ccccc5n3CO4)cc12] | ¹H-NMR (CDCl₃, 400 MHz) δ 7.96 (m, 2H), 7.85 (m, 2H), 7.64 (m, 2H), 7.31~7.36 (m, 2H), 7.17~7.25 (m, 5H), 6.86 (s, 1H), 5.96 (s, 2H), 5.88 (s, 1H), 3.15 (s, 3H), 3.00 (d, J = 5.2 Hz, 3H), 2.77 (s, 3H). | 596 |
| 11 | 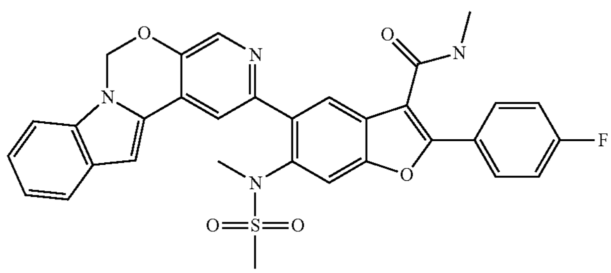 [SMILES: CNC(=O)c1c(-c2ccc(F)cc2)oc2cc(N(C)S(C)(=O)=O)c(-c3cc4c(cn3)OCn3c-4cc4ccccc43)cc12] | ¹H-NMR (Methanol-d4, 400 MHz) δ 8.51 (s, 1H), 8.24 (s, 1H), 8.04 (s, 1H), 7.92~7.95 (m, 3H), 7.71 (d, J = 8.0 Hz, 1H), 7.52 (d, J = 8.0 Hz, 1H), 7.42 (s, 1H), 7.37 (t, J = 8.0 Hz, 1H), 7.29 (t, J = 8.8 Hz, 1H), 7.20 (t, J = 8.0 Hz, 1H), 6.17 (s, 3H), 3.39 (s, 3H), 2.98 (s, 3H), 2.93 (s, 3H) | 597 |
| 12 | 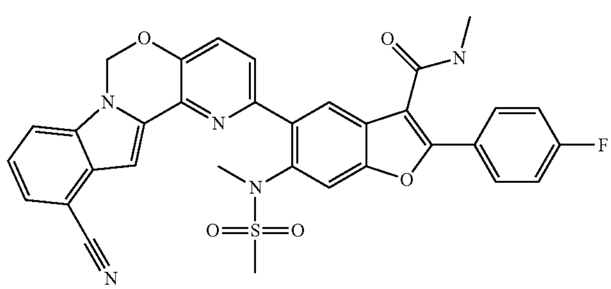 | ¹H-NMR (CDCl₃, 400 MHz) δ 8.04 (s, 1H), 7.65~7.99 (m, 2H), 7.65 (s, 1H), 7.52~7.59 (m, 4H), 7.21~7.37 (m, 2H), 7.19~7.23 (m, 2H), 6.06 (s, 3H), 3.34 (s, 3H), 3.01 (d, J = 5.2 Hz, 3H), 2.80 (s, 3H). | 622 |
| 13 | 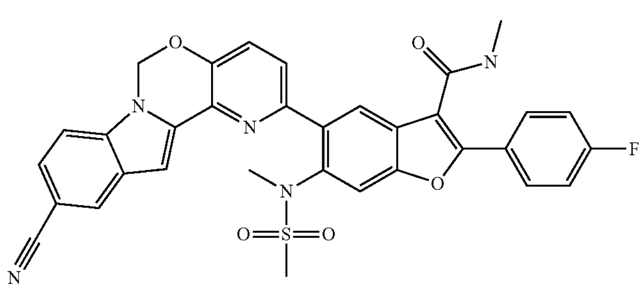 [SMILES: CNC(=O)c1c(-c2ccc(F)cc2)oc2cc(N(C)S(C)(=O)=O)c(-c3ccc4c(n3)-c3cc5cc(C#N)ccc5n3CO4)cc12] | ¹H-NMR (CDCl₃, 400 MHz) δ 8.05 (d, J = 9.2 Hz, 2H), 7.94~7.98 (m, 2H), 7.66 (s, 1H), 7.51~7.57 (m, 3H), 7.40 (d, J = 5.2 Hz, 1H), 7.20~7.24 (t, 3H), 6.04 (s, 2H), 5.94 (s, 1H), 3.36 (s, 3H), 2.99 (d, J = 5.2 Hz, 3H), 2.80 (s, 3H). | 622 |

| Compound No | Structure | NMR | MS (M + H)+ |
|---|---|---|---|
| 14 | 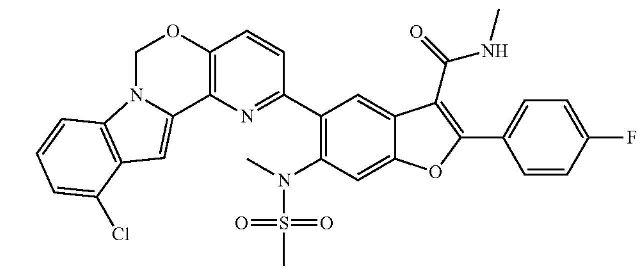 [SMILES: CNC(=O)c1c(-c2ccc(F)cc2)oc2cc(N(C)S(C)(=O)=O)c(-c3ccc4c(n3)-c3cc5c(Cl)cccc5n3CO4)cc12] | ¹H-NMR (CDCl₃, 400 MHz) δ 7.98~8.03 (m, 3H), 7.66 (s, 1H), 7.53~7.54 (m, 2H), 7.32 (s, 1H), 7.17~7.24 (m, 5H), 6.10 (br, 1H), 6.02 (s, 2H), 3.36 (s, 3H), 3.01 (d, J = 4.8 Hz, 3H), 2.79 (s, 3H). | 631 |
| 15 | 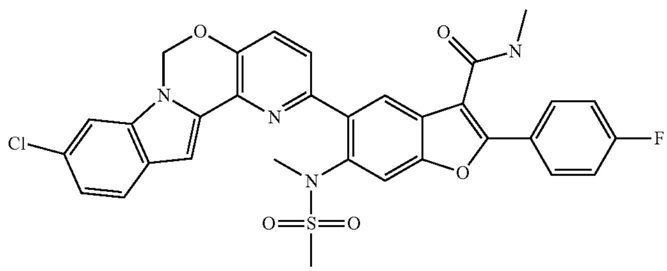 [SMILES: CNC(=O)c1c(-c2ccc(F)cc2)oc2cc(N(C)S(C)(=O)=O)c(-c3ccc4c(n3)-c3cc5ccc(Cl)cc5n3CO4)cc12] | ¹H-NMR (CDCl₃, 400 MHz) δ 8.03 (s, 1H), 7.99~7.95 (m, 2H), 7.67 (s, 1H), 7.61 (d, J = 8.4 Hz, 2H), 7.50 (s, 1H), 7.24 (m, 4H), 5.97 (s, 2H), 3.35 (s, 1H), 3.01 (d, J = 5.2 Hz, 3H), 2.76 (s, 3H). | 631 |
| 16 | 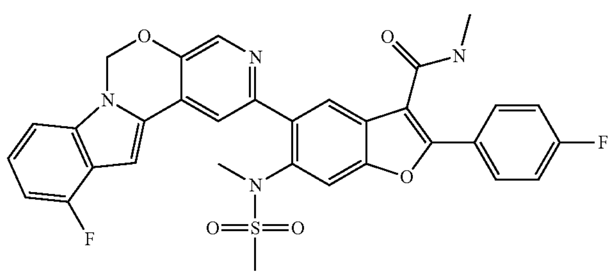 [SMILES: CNC(=O)c1c(-c2ccc(F)cc2)oc2cc(N(C)S(C)(=O)=O)c(-c3cc4c(cn3)OCn3c-4cc4c(F)cccc43)cc12] | ¹H-NMR (DMSO-d6, 400 MHz) δ 8.53~8.56 (m, 2H), 8.15 (s, 1H), 7.96~8.01 (m, 3H), 7.86 (s, 1H), 7.49 (d, J = 8.0 Hz, 1H), 7.39 (t, J = 8.8 Hz, 2H), 7.21~7.28 (m, 2H), 6.92 (dd, J = 10.0, 8.0 Hz, 1H), 6.24 (s, 2H), 3.21 (s, 3H), 3.00 (s, 3H), 2.79 (d, J = 4.8 Hz, 3H). | 615 |
| 17 | 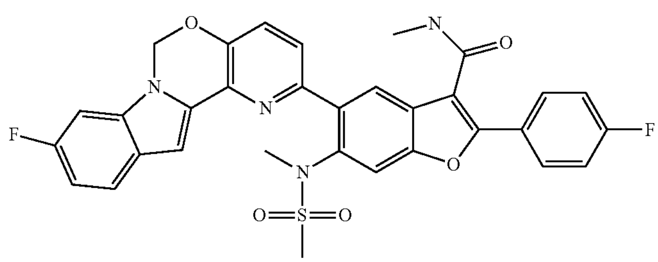 [SMILES: CNC(=O)c1c(-c2ccc(F)cc2)oc2cc(N(C)S(C)(=O)=O)c(-c3ccc4c(n3)-c3cc5ccc(F)cc5n3CO4)cc12] | ¹H-NMR (CDCl₃, 400 MHz) δ 8.02 (s, 1H), 7.95~7.98 (m, 2H), 7.68 (s, 1H), 7.59~7.62 (m, 1H), 7.48 (s, 2H), 7.19 (t, J = 8.0 Hz, 2H), 7.14 (s, 1H), 7.01 (d, J = 8 Hz, 1H), 6.94 (t, J = 8.0 Hz, 1H), 5.94 (br s, 3H), 3.35 (s, 3H), 3.00 (d, J = 4.0 Hz, 3H), 2.74 (s, 3H). | 615 |
| 18 | 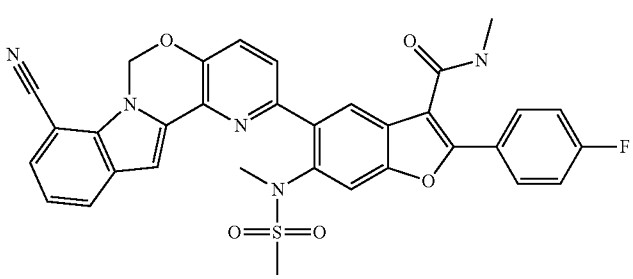 [SMILES: CNC(=O)c1c(-c2ccc(F)cc2)oc2cc(N(C)S(C)(=O)=O)c(-c3ccc4c(n3)-c3cc5cccc(C#N)c5n3CO4)cc12] | ¹H-NMR (CDCl₃, 400 MHz) δ 8.01 (s, 1H), 7.83~7.90 (m, 3H), 7.60 (s, 1H), 7.53 (d, J = 1.2 Hz, 1H), 7.44~7.49 (m, 2H), 7.12~7.16 (m, 4H), 6.38 (s, 2H), 5.91 (d, J = 4.8 Hz, 1H), 3.28 (s, 3H), 2.92 (d, J = 4.8 Hz, 3H), 2.71 (s, 3H). | 622 |

| Compound No | Structure | NMR | MS (M + H)+ |
|---|---|---|---|
| 19 | 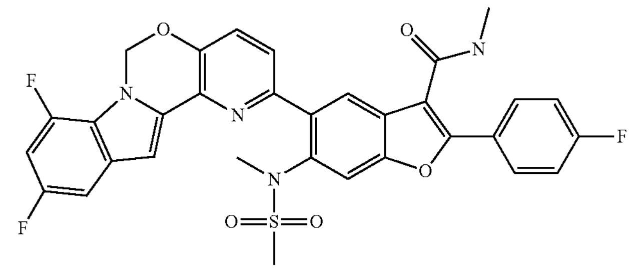 [SMILES: CNC(=O)c1c(-c2ccc(F)cc2)oc2cc(N(C)S(C)(=O)=O)c(-c3ccc4c(n3)-c3cc5cc(F)cc(F)c5n3CO4)cc12] | ¹H-NMR (CDCl₃, 400 MHz) δ 8.02 (s, 1H), 7.93~7.97 (m, 2H), 7.65 (s, 1H), 7.47~7.53 (m, 2H), 7.18~7.22 (m, 2H), 7.09~7.13 (m, 2H), 6.76~6.82 (m, 1H), 6.14 (s, 2H), 5.87 (br s, 1H), 3.33 (s, 3H), 2.98 (d, J = 4.8 Hz, 3H), 2.74 (s, 3H). | 633 |
| 20 | 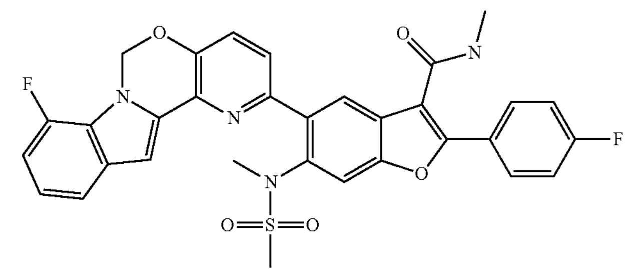 [SMILES: CNC(=O)c1c(-c2ccc(F)cc2)oc2cc(N(C)S(C)(=O)=O)c(-c3ccc4c(n3)-c3cc5cccc(F)c5n3CO4)cc12] | ¹H-NMR (CDCl₃, 400 MHz) δ 8.03 (s, 1H), 7.95~7.99 (m, 2H), 7.68 (s, 1H), 7.43~7.51 (m, 3H), 7.18~7.24 (m, 3H), 7.00~7.09 (m, 1H), 6.95~6.98 (m, 1H), 6.19 (s, 2H), 5.93 (br s, 1H), 3.36 (s, 3H), 3.00 (d, J = 4.8 Hz, 3H), 2.74 (s, 3H). | 615 |
| 21 | 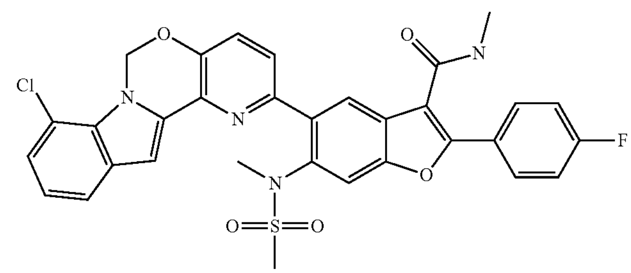 [SMILES: CNC(=O)c1c(-c2ccc(F)cc2)oc2cc(N(C)S(C)(=O)=O)c(-c3ccc4c(n3)-c3cc5cccc(Cl)c5n3CO4)cc12] | ¹H-NMR (CDCl₃, 400 MHz) δ 7.94 (d, J = 2.0 Hz, 1H), 7.91~7.93 (m, 2H), 7.64 (s, 1H), 7.54~7.56 (m, 1H), 7.44~7.49 (m, 2H), 7.16~7.24 (m, 4H), 7.05 (d, J = 8.0 Hz, 1H), 6.47 (s, 2H), 5.97 (br s, J = 4.0 Hz, 1H), 3.33 (s, 3H), 2.96 (d, J = 4.8 Hz, 3H), 2.71 (s, 3H). | 631 |
| 22 | 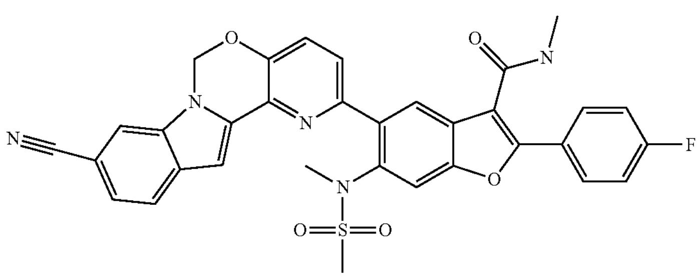 [SMILES: CNC(=O)c1c(-c2ccc(F)cc2)oc2cc(N(C)S(C)(=O)=O)c(-c3ccc4c(n3)-c3cc5ccc(C#N)cc5n3CO4)cc12] | ¹H-NMR (CDCl₃, 400 MHz) δ 8.54 (s, 1H), 8.24 (s, 1H), 7.98~8.02 (m, 3H), 7.80 (s, 2H), 7.61~7.69 (m, 3H), 7.32~7.45 (m, 2H), 7.21 (s, 1H), 6.25 (s, 2H), 3.24 (s, 3H), 2.92 (s, 3H), 2.78 (s, 3H). | 622 |
| 23 | 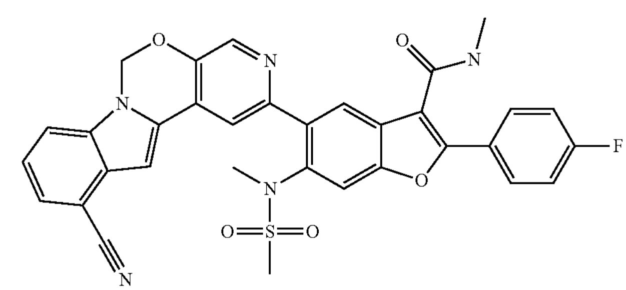 [SMILES: CNC(=O)c1c(-c2ccc(F)cc2)oc2cc(N(C)S(C)(=O)=O)c(-c3cc4c(cn3)OCn3c-4cc4c(C#N)cccc43)cc12] | ¹H-NMR (CDCl₃, 400 MHz) δ 8.77 (s, 1H), 8.24 (s, 1H) 8.09~8.05 (m, 3H), 7.62~7.58 (m, 3H), 7.42 (t, J = 8.0 Hz, 2H), 7.18 (t, J = 8.0 Hz, 2H), 6.82 (d, J = 16.0 Hz, 1H), 3.31 (s, 3H), 3.02 (d, J = 4.0 Hz, 3H), 2.96 (s, 3H). | 622 |

| Compound No | Structure | NMR | MS (M + H)+ |
|---|---|---|---|
| 24 | 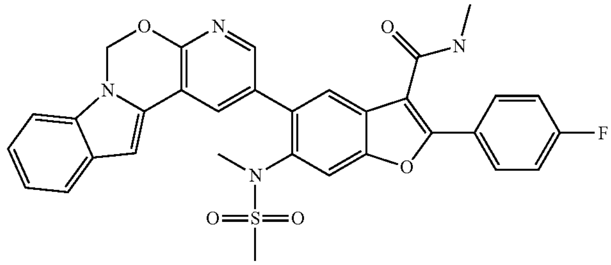 [SMILES: CNC(=O)c1c(-c2ccc(F)cc2)oc2cc(N(C)S(C)(=O)=O)c(-c3cnc4c(c3)-c3cc5ccccc5n3CO4)cc12] | ¹H-NMR (CDCl₃, 400 MHz) δ 8.17~8.18 (m, 2H), 7.85~7.89 (m, 3H), 7.58~7.60 (m, 2H), 7.08~7.28 (m, 5H), 6.89 (s, 1H), 6.08 (s, 2H), 5.79 (br s, 1H), 3.08 (s, 3H), 2.94 (d, J = 4.8 Hz, 3H), 2.83 (s, 3H). | 597 |
| 25 | 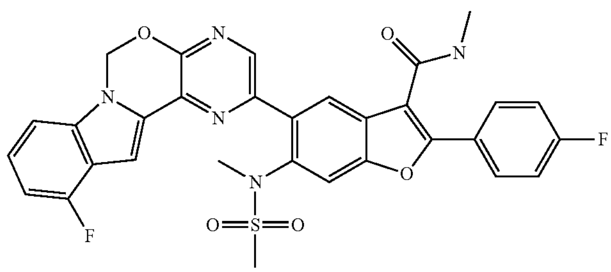 [SMILES: CNC(=O)c1c(-c2ccc(F)cc2)oc2cc(N(C)S(C)(=O)=O)c(-c3cnc4c(n3)-c3cc5c(F)cccc5n3CO4)cc12] | ¹H-NMR (DMSO-d6, 400 MHz) δ 8.34 (s, 1H), 8.05 (s, 1H), 7.89~7.92 (m, 2H), 7.64 (s, 1H), 7.29 (s, 1H), 7.14~7.23 (m, 2H), 7.07 (d, J = 8.4 Hz, 1H), 6.81 (t, J = 8.4 Hz, 1H), 6.14 (s, 2H), 5.81 (s, 1H), 5.23 (s, 1H), 3.34 (s, 3H), 2.95 (d, J = 4.8 Hz, 3H), 2.77 (s, 3H). | 616 |
| 26 | 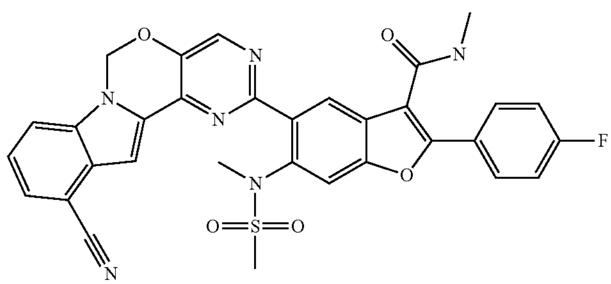 [SMILES: CNC(=O)c1c(-c2ccc(F)cc2)oc2cc(N(C)S(C)(=O)=O)c(-c3ncc4c(n3)-c3cc5c(C#N)cccc5n3CO4)cc12] | ¹H-NMR (CDCl₃, 400 MHz) δ 8.74 (s, 1H), 8.27 (s, 1H), 8.02 (dd, J = 5.2, 8.0 Hz, 2H), 7.67 (s, 1H), 7.60 (m, 3H), 7.43 (m, 1H), 7.20 (t, J = 8.4 Hz, 2H), 6.37 (br s, 1H), 6.13 (s, 2H), 3.53 (s, 3H), 3.02 (d, J = 4.4 Hz, 3H), 2.86 (s, 3H). | 623 |
| 27 | 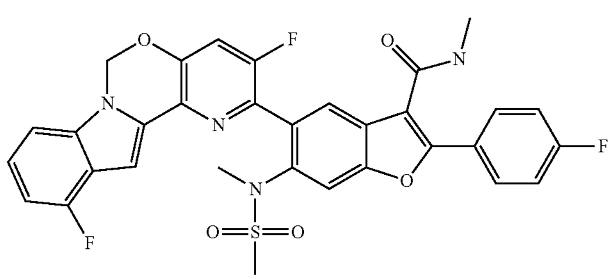 [SMILES: CNC(=O)c1c(-c2ccc(F)cc2)oc2cc(N(C)S(C)(=O)=O)c(-c3nc4c(cc3F)OCn3c-4cc4c(F)cccc43)cc12] | ¹H-NMR (CDCl₃, 400 MHz) δ 7.96~7.99 (m, 3H), 7.72 (s, 1H), 7.26~7.29 (m, 1H), 7.18~7.23 (m, 4H), 7.10 (d, J = 8.4 Hz, 1H), 6.84 (dd, J = 8.0, 10.0 Hz, 1H), 6.01 (s, 2H), 5.96 (brs, 1H), 3.37 (s, 3H), 3.00 (d, J = 4.8 Hz, 3H), 2.78 (s, 3H). | 633 |
| 28 | 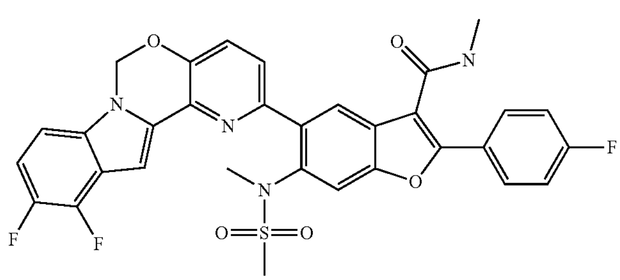 [SMILES: CNC(=O)c1c(-c2ccc(F)cc2)oc2cc(N(C)S(C)(=O)=O)c(-c3ccc4c(n3)-c3cc5c(F)c(F)ccc5n3CO4)cc12] | ¹H-NMR (CDCl₃, 400 MHz) δ 8.04 (s, 1H), 7.98 (d, J = 8.8 Hz, 2H), 7.67 (s, 1H), 7.49~7.52 (m, 2H), 7.20~7.24 (m, 3H), 7.11~7.14 (m, 1H), 7.01 (d, J = 8.8 Hz, 1H), 5.99 (s, 2H), 5.89 (bs, 1H), 3.38 (s, 3H), 3.00 (d, J = 4.8 Hz, 3H), 2.76 (s, 3H). | 633 |

| Compound No | Structure | NMR | MS (M + H)+ |
|---|---|---|---|
| 29 | 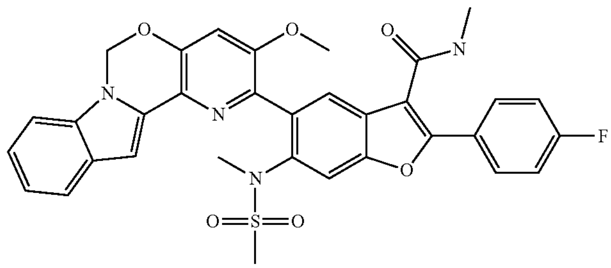 [SMILES: CNC(=O)c1c(-c2ccc(F)cc2)oc2cc(N(C)S(C)(=O)=O)c(-c3nc4c(cc3OC)OCn3c-4cc4ccccc43)cc12] | ¹H-NMR (CDCl₃, 400 MHz) δ 8.02~7.95 (m, 2H), 7.87 (s, 1H), 7.74 (s, 1H), 7.64 (d, J = 8.0 Hz, 1H), 7.31 (d, J = 8.0 Hz, 1H), 7.28~7.25 (m, 1H), 7.24~7.12 (m, 3H), 7.05 (s, 1H), 6.98 (s, 1H), 6.00 (s, 2H), 5.98 (d, J = 4.8 Hz, 1H), 3.83 (s, 3H), 3.24 (s, 3H), 2.97 (d, J = 4.8 Hz, 3H), 2.77 (s, 3H). | 627 |
| 30 | 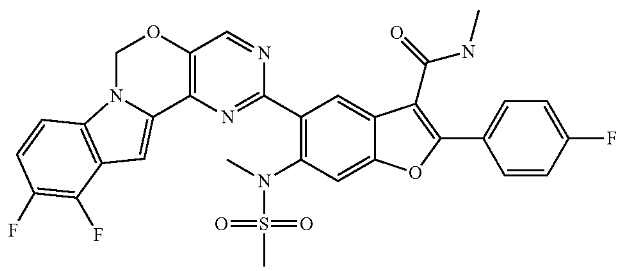 [SMILES: CNC(=O)c1c(-c2ccc(F)cc2)oc2cc(N(C)S(C)(=O)=O)c(-c3ncc4c(n3)-c3cc5c(F)c(F)ccc5n3CO4)cc12] | ¹H-NMR (CDCl₃, 400 MHz) δ 8.86 (s, 1H), 8.59 (d, J = 4.4 Hz, 1H), 8.07 (s, 1H), 8.04 (s, 1H), 7.98~8.01 (m, 2H), 7.54~7.57 (m, 1H), 7.39~7.44 (m, 4H), 6.35 (s, 2H), 3.40 (s, 3H), 2.93 (s, 3H), 2.82 (d, J = 4.8 Hz, 3H). | 634 |
| 31 | 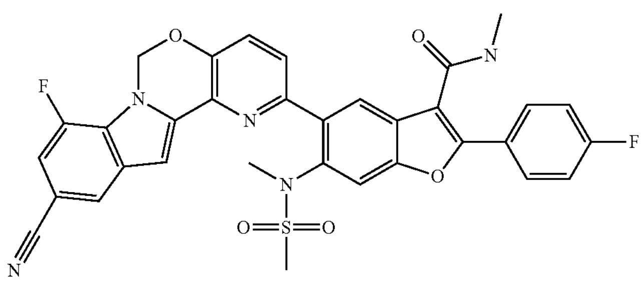 [SMILES: CNC(=O)c1c(-c2ccc(F)cc2)oc2cc(N(C)S(C)(=O)=O)c(-c3ccc4c(n3)-c3cc5cc(C#N)cc(F)c5n3CO4)cc12] | ¹H-NMR (DMSO-d6, 400 MHz) δ 8.55 (s, 1H), 7.97~8.08 (m, 4H), 7.82 (s, 1H), 7.72 (d, J = 8.0 Hz, 1H), 7.60~7.65 (m, 2H), 7.39 (t, J = 8.8 Hz, 2H), 7.28 (s, 1H), 6.30 (s, 2H), 3.27 (s, 3H), 2.93 (s, 3H), 2.79 (d, J = 4.4 Hz, 3H). | 640 |
| 32 | 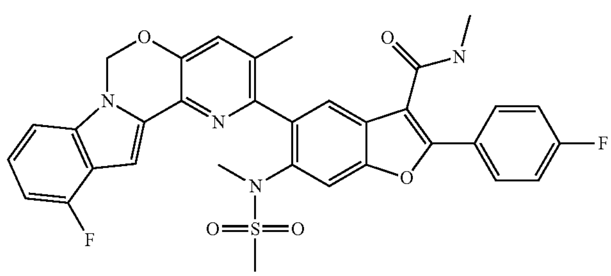 [SMILES: CNC(=O)c1c(-c2ccc(F)cc2)oc2cc(N(C)S(C)(=O)=O)c(-c3nc4c(cc3C)OCn3c-4cc4c(F)cccc43)cc12] | ¹H-NMR (CDCl₃, 400 MHz) δ 7.97 (d, J = 5.6 Hz, 2H), 7.80 (s, 1H), 7.71 (s, 1H), 7.35 (s, 1H), 7.23~7.18 (m, 3H), 7.11~7.09 (m, 2H), 6.83 (d, J = 8.0 Hz, 1H), 5.95 (s, 2H), 5.85 (d, J = 4.8 Hz, 1H), 3.29 (s, 3H), 2.97 (d, J = 4.8 Hz, 3H), 2.72 (s, 3H), 2.29 (s, 3H). | 629 |
| 33 | 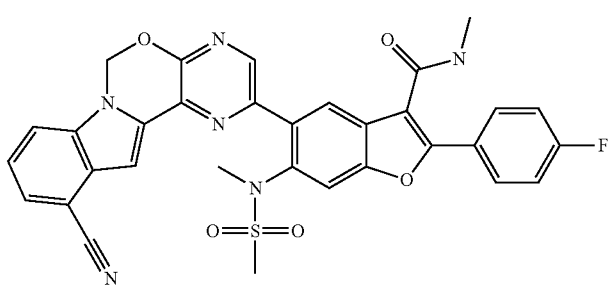 [SMILES: CNC(=O)c1c(-c2ccc(F)cc2)oc2cc(N(C)S(C)(=O)=O)c(-c3cnc4c(n3)-c3cc5c(C#N)cccc5n3CO4)cc12] | ¹H-NMR (CDCl₃, 400 MHz) δ 8.45 (s, 1H), 8.12 (s, 1H), 7.96 (t, J = 7.2 Hz, 2H), 7.68 (s, 1H), 7.55~7.60 (m, 2H), 7.45 (s, 1H), 7.38 (t, J = 8.0 Hz, 1H), 7.20~7.25 (m, 2H), 6.24 (s, 2H), 5.95 (s, 1H), 3.43 (s, 3H), 3.02 (d, J = 4.8 Hz, 3H), 2.86 (s, 3H). | 623 |

-continued

| Compound No | Structure | NMR | MS (M + H)+ |
|---|---|---|---|
| 34 | 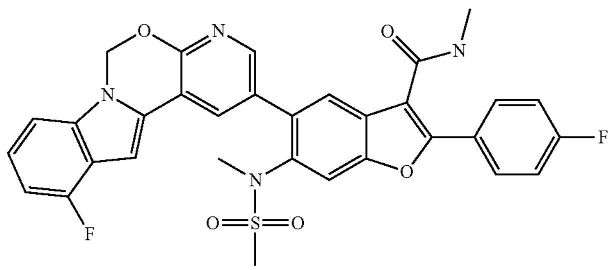 [SMILES: CNC(=O)c1c(-c2ccc(F)cc2)oc2cc(N(C)S(C)(=O)=O)c(-c3cnc4c(c3)-c3cc5c(F)cccc5n3CO4)cc12] | ¹H-NMR (CDCl₃, 400 MHz) δ 8.23~8.24 (m, 2H), 7.89~7.93 (m, 2H), 7.88 (s, 1H), 7.61 (s, 1H), 7.15~7.22 (m, 3H), 7.08 (d, J = 8.0 Hz, 1H), 6.99 (s, 1H), 6.80~6.85 (m, 1H), 6.09 (s, 2H), 5.95 (br s, 1H), 3.14 (s, 3H), 2.98 (d, J = 4.8 Hz, 3H), 2.89 (s, 3H). | 615 |
| 35 | 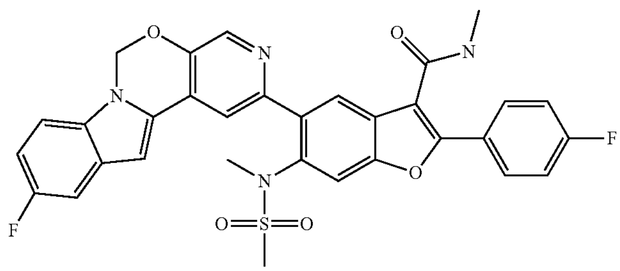 [SMILES: CNC(=O)c1c(-c2ccc(F)cc2)oc2cc(N(C)S(C)(=O)=O)c(-c3cc4c(cn3)OCn3c-4cc4cc(F)ccc43)cc12] | ¹H-NMR (CDCl₃, 400 MHz) δ 8.50 (s, 1H), 8.02 (s, 1H), 7.95~7.98 (m, 3H), 7.62 (s, 1H), 7.31~7.34 (m, 1H), 7.23~7.26 (m, 1H), 7.18 (t, J = 8.4 Hz, 2H), 7.02~7.07 (m, 2H), 5.97~6.00 (m, 3H), 3.16 (s, 3H), 2.99 (d, J = 4.8 Hz, 3H), 2.91 (s, 3H). | 615 |
| 36 | 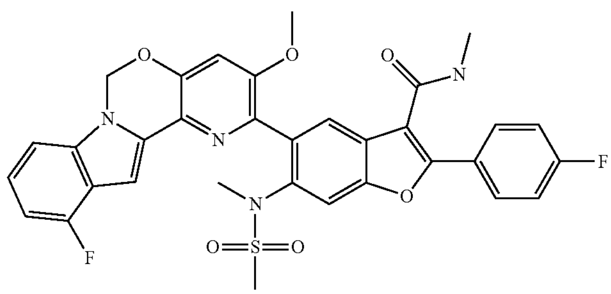 [SMILES: CNC(=O)c1c(-c2ccc(F)cc2)oc2cc(N(C)S(C)(=O)=O)c(-c3nc4c(cc3OC)OCn3c-4cc4c(F)cccc43)cc12] | ¹H-NMR (CDCl₃, 400 MHz) δ 7.95~8.02 (m, 2H), 7.88 (s, 1H), 7.74 (s, 1H), 7.14~7.21 (m, 3H), 7.09 (d, J = 8.0 Hz, 1H), 7.04~7.07 (m, 2H), 6.83 (q, J = 10.0 Hz, 8.0 Hz, 1H), 5.99 (s, 2H), 5.96 (d, J = 4.0 Hz, 1H), 3.83 (s, 3H), 3.26 (s, 3H), 2.97 (d, J = 4.8 Hz, 3H), 2.78 (s, 3H). | 645 |
| 37 | (Enantiomer 1, peak 1 on SFC) | ¹H-NMR (CDCl₃, 400 MHz) δ 7.99 (s, 1H), 7.93~7.96 (m, , 2H), 7.65 (s, 1H), 7.43~7.49 (m, 2H), 7.12~7.21 (m, 4H), 7.10 (d, J = 8.0 Hz, 1H), 6.83 (t, J = 8.4 Hz, 1H), 6.53~6.57 (m, 1H), 6.06 (d, J = 4.8 Hz, 1H), 3.38 (s, 3H), , 2.98 (d, J = 4.0 Hz, 3H), 2.68 (s, 3H), 1.66 (d, J = 5.6 Hz, 3H). | 629 |
| 38 | (Enantiomer 2, peak 2 on SFC) | ¹H-NMR (CDCl₃, 400 MHz) δ 7.99 (s, 1H), 7.93~7.96 (m, , 2H), 7.65 (s, 1H), 7.43~7.49 (m, 2H), 7.12~7.21 (m, 4H), 7.10 (d, J = 8.0 Hz, 1H), 6.83 (t, J = 8.4 Hz, 1H), 6.53~6.57 (m, 1H), 6.06 (d, J = 4.8 Hz, 1H), 3.38 (s, 3H), , 2.98 (d, J = 4.0 Hz, 3H), 2.68 (s, 3H), 1.66 (d, J = 5.6 Hz, 3H). | 629 |

| Compound No | Structure | NMR | MS (M + H)⁺ |
|---|---|---|---|
| 39 | 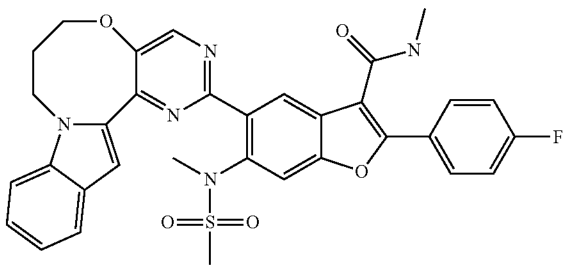 [SMILES: CNC(=O)c1c(-c2ccc(F)cc2)oc2cc(N(C)S(C)(=O)=O)c(-c3ncc4c(n3)-c3cc5ccccc5n3CCCO4)cc12] | ¹H-NMR (CDCl₃, 400 MHz) δ 8.49 (s, 1H), 8.23 (s, 1H), 7.99~8.03 (m, 2H), 7.72 (s, 1H), 7.16~7.20 (m, 2H), 6.94 (d, J = 2.0 Hz, 1H), 6.78 (s, 1H), 6.29 (t, J = 3.2 Hz, 1H), 6.04 (d, J = 4.4 Hz, 1H), 4.14~4.21 (m, 4H), 3.34 (s, 3H), 3.01 (d, J = 4.8 Hz, 3H), 2.79 (s, 3H), 2.06-2.08 (m, 2H). | 626 |
| 40 | 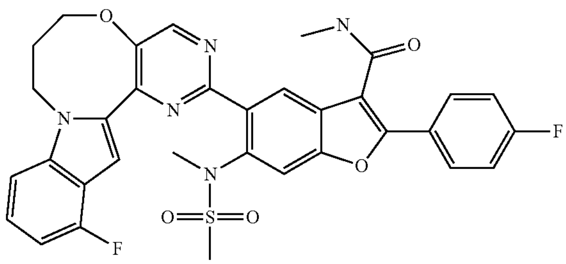 [SMILES: CNC(=O)c1c(-c2ccc(F)cc2)oc2cc(N(C)S(C)(=O)=O)c(-c3ncc4c(n3)-c3cc5c(F)cccc5n3CCCO4)cc12] | ¹H-NMR (Methanol-d4, 400 MHz) δ 8.64 (s, 1H), 8.16 (s, 1H), 7.97~8.00 (m, 2H), 7.88 (s, 1H), 7.36 (d, J = 8.4 Hz, 1H), 7.22~7.28 (m, 4H), 6.78~6.82 (m, 1H), 4.44 (t, J = 5.2 Hz, 2H), 4.19 (t, J = 5.2 Hz, 2H), 3.46 (s, 3H), 2.95 (s, 3H), 2.90 (s, 3H), 2.14~2.15 (m, 2H). | 644 |
Example 2
Preparation of Compound 41
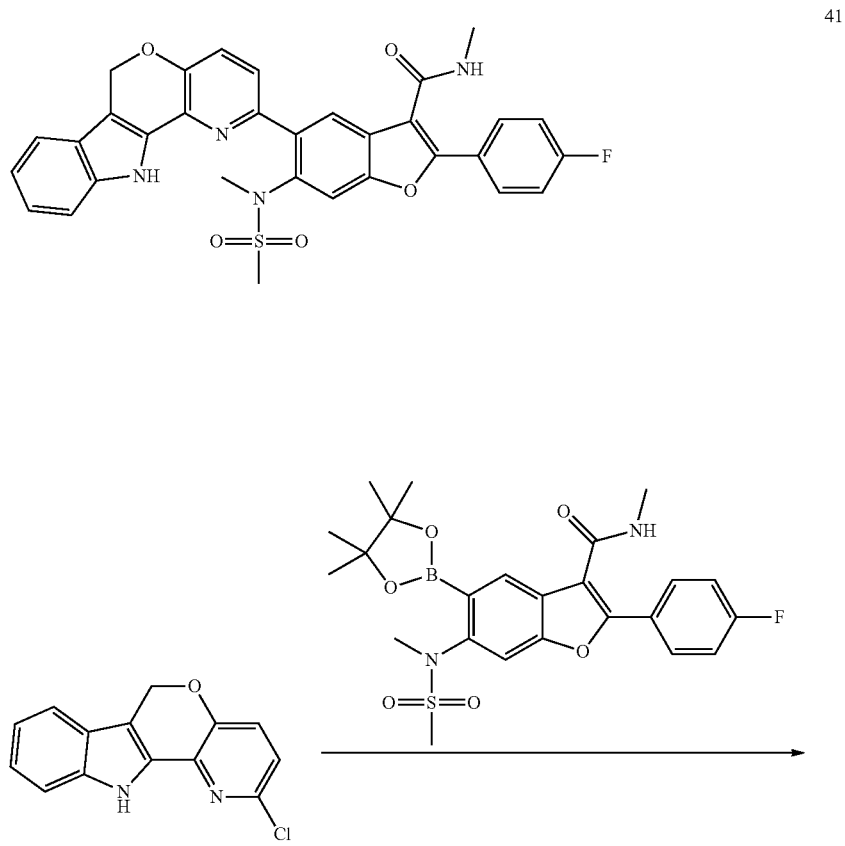

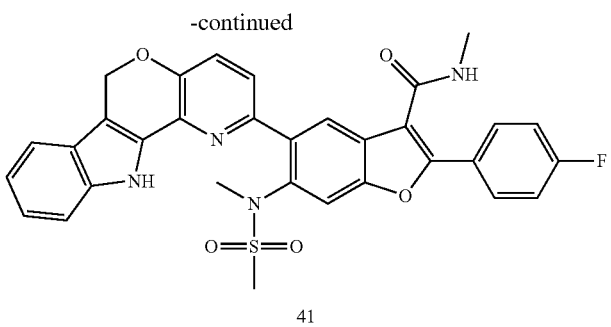

41

The procedure of compound 41 was similar to step 6 of Example 1, using 2-chloro-6,11-dihydropyrido[2',3':5,6]pyrano[4,3-b]indole obtained from step 5 of Example 1. $^1$H-NMR (CDCl$_3$, 400 MHz) δ 9.71 (s, 1H), 7.99 (s, 1H), 7.88-7.91 (m, 2H), 7.52 (m, 1H), 7.38 (d, J=8.4 Hz, 2H), 7.29 (d, J=8.4 Hz, 1H), 7.19 (s, 1H), 7.05-7.19 (m, 4H), 5.97 (s, 1H), 5.73 (s, 2H), 3.08 (s, 3H), 2.93 (d, J=5.2 Hz, 3H), 2.89 (s, 3H). MS (M+H)$^+$: 597.

Example 3

Preparation of Compound 42

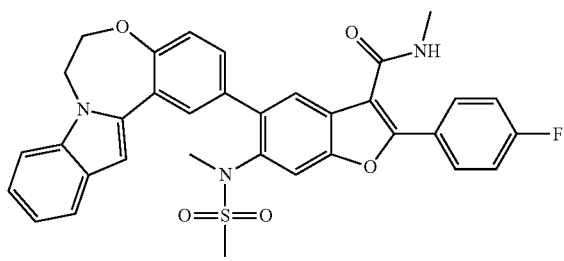

42

Step 1—Synthesis of 4-bromo-2-(1H-indol-2-yl)phenol

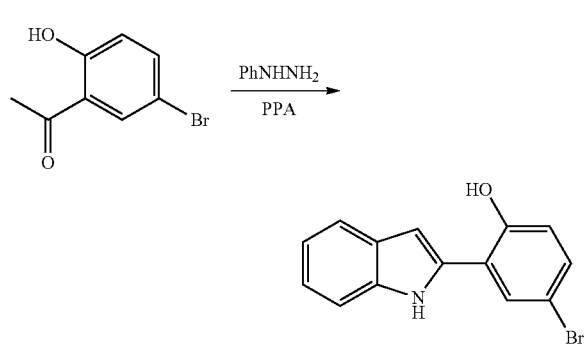

1-(5-bromo-2-hydroxyphenyl)ethanone (7.1 g, 33 mmol) and phenylhydrazine (4.3 g, 40 mmol) were stirred in 45 mL of dry ethanol. Acetic acid (27 drops) was added and the mixture was refluxed for 5 hours. After cooling to room temperature, the precipitates were collected by filtration to provide the crude product as a light yellow solid, which was stirred in 100 mL of xylene and 50 g of polyphosphoric acid at 85° C. for 8 hours. Water was added to the warm crude, and then the mixture was stirred for 10 minutes before poured into water and extracted with EtOAc. The organic layer was washed with water and brine, dried over Na$_2$SO$_4$, filtered, and concentrated in vacuo. Purification by flash chromatography on silica gel (petroleum ether:EtOAc=10:1) provided 4-bromo-2-(1H-indol-2-yl)phenol as a light yellow powder (2.1 g, 22.1%). $^1$H-NMR (CDCl$_3$, 400 MHz) δ 10.08 (s, 1H), 9.56 (s, 1H), 7.88 (s, 1H), 7.61 (d, J=8.0 Hz, 1H), 7.38 (d, J=8.0 Hz, 1H), 7.14~7.19 (m, 2H), 7.08 (t, J=7.2 Hz, 1H), 6.8~56.88 (m, 2H). MS (M+H)$^+$: 288/290.

Step 2—Synthesis of 2-(5-bromo-2-(2-bromoethoxy)phenyl)-1H-indole

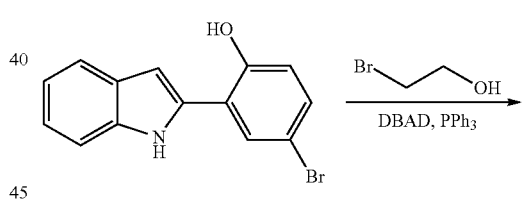

To a mixture of 4-bromo-2-(1H-indol-2-yl)phenol (1.44 g, 5 mmol) and 2-bromoethanol (1.12 g, 9 mmol) in 20 mL of THF was added DBAD (2.07 g, 9 mmol) followed by triphenylphosphine (2.36 g, 9 mmol) in portions at room temperature with stirring. After 1 hour, the reaction was concentrated to near dryness, and purified using flash column chromatography (hexane/EtOAc 30:1) to provide the crude product of 2-(5-bromo-2-(2-bromoethoxy)phenyl)-1H-indole (1.98 g, 100%). MS (M+H)+: 394/396/398.

Step 3—Synthesis of 2-bromo-6,7-dihydrobenzo[6,7][1,4]oxazepino[4,5-a]indole

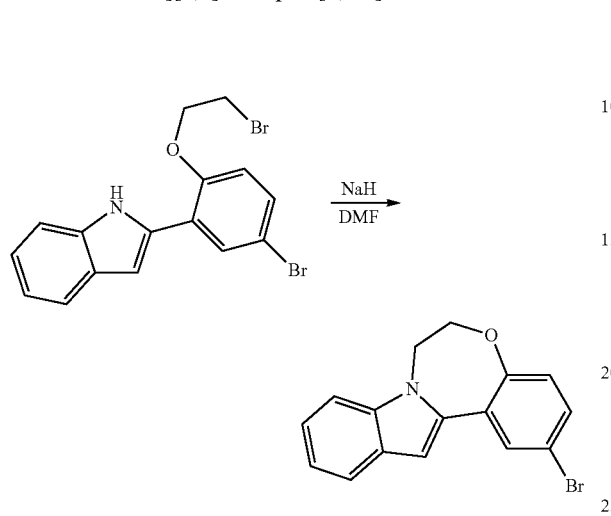

A solution of compound 2-(5-bromo-2-(2-bromoethoxy)phenyl)-1H-indole (1.97 g, 5 mmol) in 30 mL of DMF was cooled to 0° C. at N₂ atmosphere, NaH (600 mg, 15 mmol) was added at the same temperature. The reaction mixture was stirred at room temperature. After 8 hours, the reaction was quenched by water, extracted with EtOAc. The organic layer was washed with water and brine, dried over Na₂SO₄, filtered, and concentrated in vacuo. Purification by flash chromatography on silica gel (petroleum ether:EtOAc=50:1) provided 2-bromo-6,7-dihydrobenzo[6,7][1,4]oxazepino[4,5-a]indole as light yellow powder (0.8 g, 51%), which was also prepared from 4-bromo-2-(1H-indol-2-yl)phenol and 1,2-dibromoethane using similar method described in step 5 of Example 1. ¹H-NMR (CDCl₃, 400 MHz) δ 7.96 (s, 1H), 7.66 (d, J=7.6 Hz, 1H), 7.30~7.33 (m, 2H), 7.25~7.27 (m, 1H), 7.16 (t, J=6.8 Hz, 1H), 6.95 (d, J=8.8 Hz, 1H), 6.91 (s, 1H), 4.53~4.55 (m, 2H), 4.47~4.49 (m, 2H). MS (M+H)+: 314/316.

Step 4—Synthesis of 2-(4,4,5,5-tetramethyl-1,3,2-dioxaborolan-2-yl)-6,7-dihydrobenzo[6,7][1,4]oxazepino[4,5-a]indole

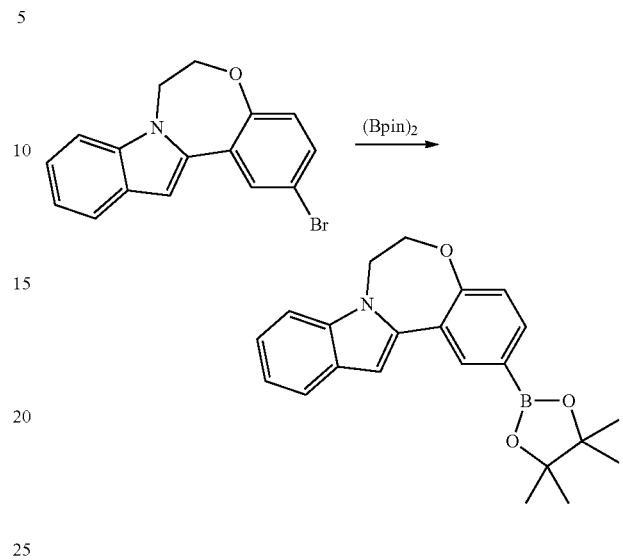

A mixture of 2-bromo-6,7-dihydrobenzo[6,7][1,4]oxazepino[4,5-a]indole (314 mg, 1 mmol), Bispinacolatodiboron (381 mg, 1.5 mmol), KOAc (393 mg, 4 mmol) and Pd(dppf)Cl₂ (73 mg, 0.1 mmol) in 10 mL of 1,4-dioxane was stirred at 90° C. for 8 h under N₂. The mixture was concentrated in vacuo to provide crude product, which was purified using silica gel column chromatography to provide 2-(4,4,5,5-tetramethyl-1,3,2-dioxaborolan-2-yl)-6,7-dihydrobenzo[6,7][1,4]oxazepino[4,5-a]indole (300 mg, yield: 83.1%). ¹H-NMR (CDCl₃, 400 MHz) δ 8.35 (s, 1H), 7.65~7.69 (m, 2H), 7.30 (d, J=8.4 Hz, 1H), 7.23 (t, J=7.2 Hz, 1H), 7.14 (t, J=7.2 Hz, 1H), 7.06~7.08 (m, 2H), 4.57 (t, J=4.2 Hz, 2H), 4.50 (t, J=4.2 Hz, 2H), 1.37 (s, 12H). MS (M+H)+: 362.

Step 5—Synthesis of 5-(6,7-dihydrobenzo[6,7][1,4]oxazepino[4,5-a]indol-2-yl)-2-(4-fluorophenyl)-N-methyl-6-(N-methylmethylsulfonamido)benzofuran-3-carboxamide (Compound 42)

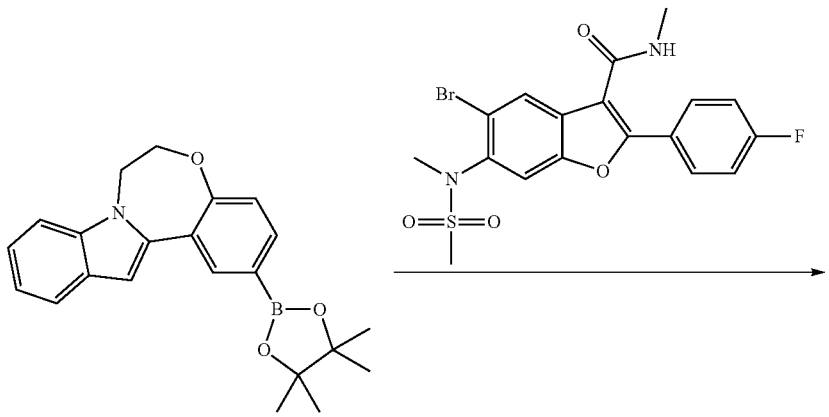

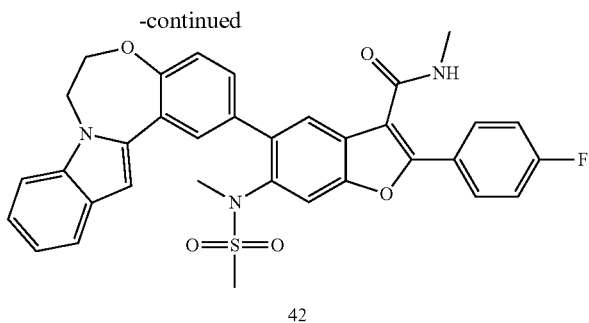

42

A mixture of compound 2-(4,4,5,5-tetramethyl-1,3,2-dioxaborolan-2-yl)-6,7-dihydrobenzo[6,7][1,4]oxazepino[4,5-a]indole (72 mg, 0.2 mmol), 5-bromo-2-(4-fluorophenyl)-N-methyl-6-(N-methylmethylsulfonamido)benzofuran-3-carboxamide (91 mg, 0.2 mmol), $K_3PO_4 \cdot 3H_2O$ (160 mg, 0.6 mmol) and Pd(dppf)Cl$_2$ (15 mg, 0.02 mmol) in 2 mL of DMF was stirred at 90° C. for 8 h under N$_2$, then the mixture was purified using prep-HPLC to provide Compound 42 (30 mg, yield: 24.9%). $^1$H-NMR (CDCl$_3$, 400 MHz) δ 7.92~7.97 (m, 3H), 7.81 (s, 1H), 7.63~7.65 (m, 2H), 7.33 (d, J=8.0 Hz, 2H), 7.12~7.25 (m, 5H), 6.97 (s, 1H), 6.00 (d, J=4.0 Hz, 1H), 4.62 (t, J=4.2 Hz, 2H), 4.54 (t, J=4.2 Hz, 2H), 3.18 (s, 3H), 3.00 (d, J=4.8 Hz, 3H), 2.72 (s, 3H). MS (M+H)$^+$: 610.

Example 4

Preparation of Compound 43

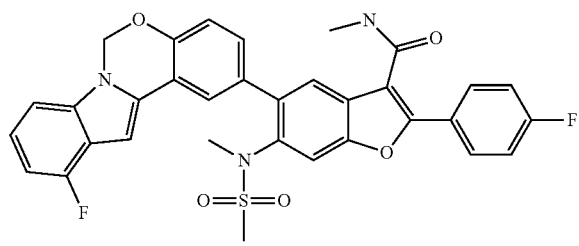

43

Step 1—Synthesis of ((5-chloro-2-methoxyphenyl)ethynyl)trimethylsilane

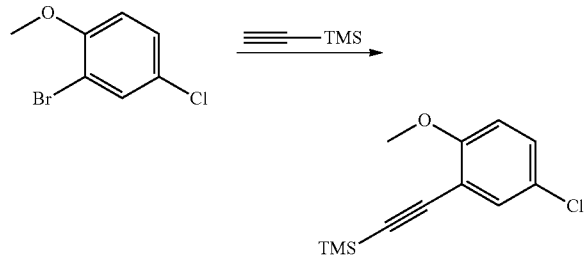

A mixture of 2-bromo-4-chloro-1-methoxybenzene (1 g, 4.5 mmol), CuI (43 mg, 0.23 mmol), Pd(PPh$_3$)$_2$Cl$_2$ (0.16 g, 0.23 mmol) in NEt$_3$ (10 mL) was degassed, Then ethynyltrimethylsilane (0.5 g, 5 mmol) was added to the solution, the mixture was stirred at 80° C. for 6 hours. Then the mixture was cooled to 25° C., and added to H$_2$O (50 mL). The mixture was extracted with ethyl acetate and washed with brine, dried over Na$_2$SO$_4$. After the combined organic layers were concentrated, the resulting residue was purified using prep-TLC (petroleum ether:EtOAc=10:1) to provide the product of ((5-chloro-2-methoxyphenyl)ethynyl)trimethylsilane (1 g, yield: 90%). $^1$H-NMR (CDCl$_3$, 400 MHz) δ 7.40 (s, 1H), 7.21~7.23 (m, 1H), 6.76~6.78 (d, J=9.2 Hz, 1H), 3.86 (s, 3H), 0.26 (s, 9H). MS (M+H)$^+$: 239/241

Step 2—Synthesis of 4-chloro-2-ethynyl-1-methoxybenzene

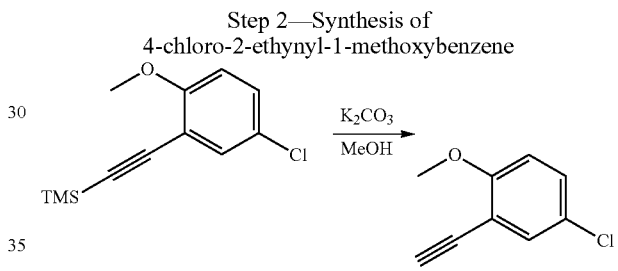

((5-chloro-2-methoxyphenyl)ethynyl)trimethylsilane (0.4 g, 1.7 mmol) was dissolved in MeOH (1 mL), K$_2$CO$_3$ (0.69 g, 5 mol) was added to it. Then the mixture was stirred at 25° C. for 1 hour, and added to H$_2$O (50 mL). The mixture was extracted with ethyl acetate and washed with brine, dried over Na$_2$SO$_4$. After the combined organic layers were concentrated, the resulting residue was purified using prep-TLC (petroleum ether:EtOAc=10:1) to provide the product of 4-chloro-2-ethynyl-1-methoxybenzene (0.25 g, yield: 80%). $^1$H-NMR (CDCl$_3$, 400 MHz) δ 7.43 (s, 1H), 7.28~7.29 (m, 1H), 6.81~6.85 (m, 1H), 3.89 (s, 3H), 3.34 (s, 1H). MS (M+H)$^+$: 167/169.

Step 3—Synthesis of 2-(5-chloro-2-methoxyphenyl)-4-fluoro-1H-indole

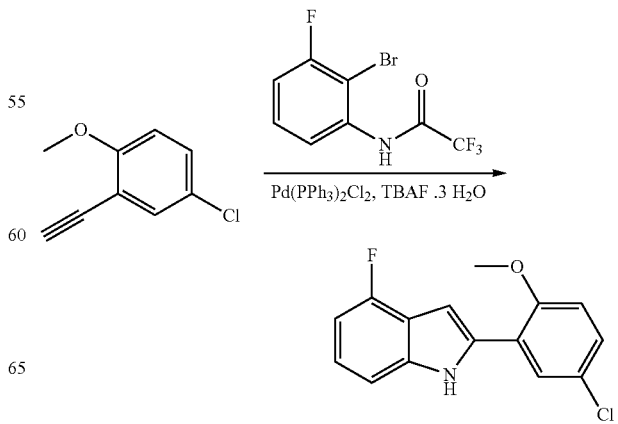

A mixture of 4-chloro-2-ethynyl-1-methoxybenzene (255 mg, 1.5 mmol), N-(2-bromo-3-fluorophenyl)-2,2,2-trifluoroacetamide (400 mg, 1.4 mmol), Pd(PPh$_3$)$_2$Cl$_2$ (30 mg, 0.04 mmol) was stirred in TBAF.3H$_2$O (1.43 g, 7 mmol) at 110° C. for 12 hours. The reaction mixture was cooled to 25° C. and added to water, then extracted with ethyl acetate and washed with brine, dried over Na$_2$SO$_4$. After concentrated, the crude product of 2-(5-chloro-2-methoxyphenyl)-4-fluoro-1H-indole (100 mg, yield: 20%) was obtained. MS (M+H)$^+$: 276/278.

Step 4—Synthesis of 4-chloro-2-(4-fluoro-1H-indol-2-yl)phenol

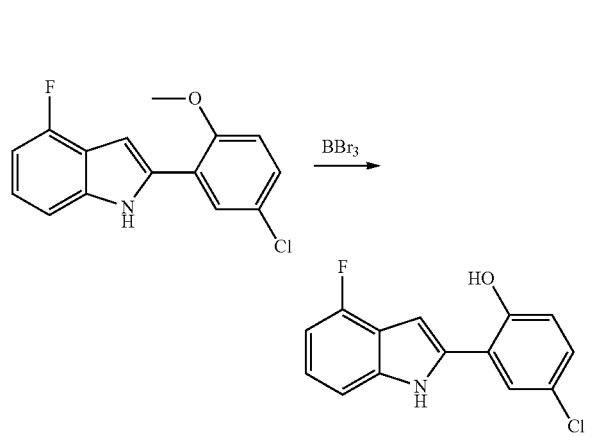

2-(5-chloro-2-methoxyphenyl)-4-fluoro-1H-indole (50 mg, 0.2 mmol) was dissolved in dichloromethane (1 mL), and then BBr$_3$ (150 mg, 0.6 mmol) was added at −78° C. The mixture was stirred at −78° C. for 1 hour, and then stirred at 25° C. for 12 hours. MeOH (1 mL) and H$_2$O (20 mL) were added to the solution. The mixture was extracted with ethyl acetate and washed with brine, dried over Na$_2$SO$_4$. After the combined organic layers were concentrated, the resulting residue was purified using prep-TLC (petroleum ether:EtOAc=5:1) to provide the product of 4-chloro-2-(4-fluoro-1H-indol-2-yl)phenol (10 mg, yield: 25%). $^1$H-NMR (CDCl$_3$, 400 MHz) δ 9.54 (s, 1H), 7.65 (s, 1H), 7.06~7.12 (m, 2H), 6.88 (s, 1H), 6.79~6.81 (m, 1H), 6.70~6.74 (m, 1H). MS (M+H)$^+$: 262/263.

Step 5—Synthesis of 2-chloro-11-fluoro-6H-benzo[5,6][1,3]oxazino[3,4-a]indole

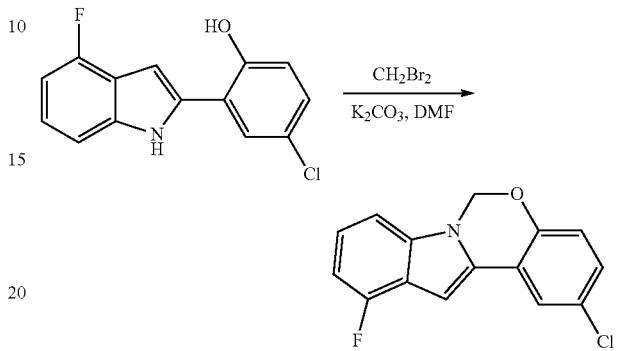

To a solution of 4-chloro-2-(4-fluoro-1H-indol-2-yl)phenol (40 mg, 0.15 mmol) in DMF (1 mL), K$_2$CO$_3$ (40 mg, 0.31 mmol) and CH$_2$Br$_2$ (53 mg, 0.31 mmol) were added at 25° C. The mixture was stirred at 80° C. for 2 hours, and cooled to 25° C. H$_2$O (50 mL) was added, then the mixture was extracted with ethyl acetate and washed with brine, dried over Na$_2$SO$_4$. After concentrated, the resulting residue was purified using prep-TLC (petroleum ether:EtOAc=10:1) to provide the product of 2-chloro-11-fluoro-6H-benzo[5,6][1,3]oxazino[3,4-a]indole (50 mg, yield: 45%). $^1$H-NMR (CDCl$_3$, 400 MHz) δ 7.68 (s, 1H), 7.14~7.23 (m, 2H), 7.03~7.09 (m, 2H), 6.90 (s, 1H), 6.81~6.86 (m, 1H), 5.88 (s, 2H). MS (M+H)$^+$: 274/276.

Step 6—Synthesis of 5-(11-fluoro-6H-benzo[5,6][1,3]oxazino[3,4-a]indol-2-yl)-2-(4-fluorophenyl)-N-methyl-6-(N-methylmethylsulfonamido)benzofuran-3-carboxamide (Compound 43)

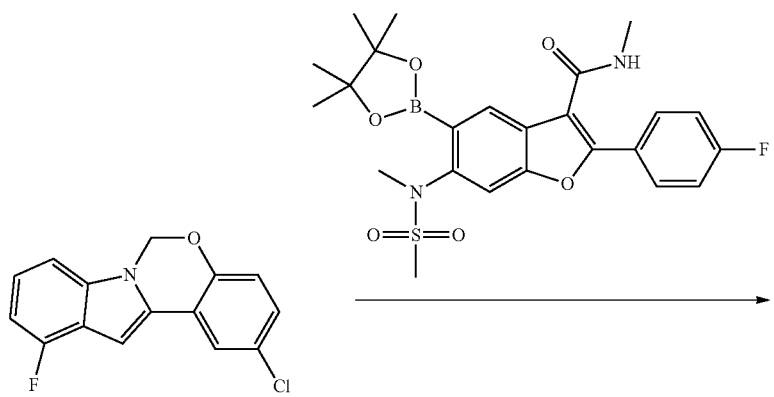

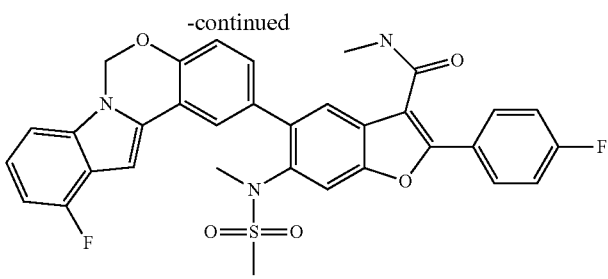

43

A mixture of 2-chloro-11-fluoro-6H-benzo[5,6][1,3]ox-azino[3,4-a]indole (30 mg, 0.11 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (55 mg, 0.11 mmol), $K_3PO_4 \cdot 3H_2O$ (88 mg, 0.33 mmol), $Pd_2(dba)_3$ (10 mg, 0.011 mmol), X-Phos (11 mg, 0.022 mmol) was stirred in dixane/$H_2O$ (5 mL, 4:1) at 110° C. for 12 hours. Then the mixture was cooled to 25° C., water was added to it. The mixture was extracted with ethyl acetate and washed with brine, dried over $Na_2SO_4$. After the combined organic layers were concentrated, the resulting residue was purified using prep-TLC (petroleum ether:EtOAc=3:1) to provide the product of Compound 43 (25 mg, yield: 40%). $^1$H-NMR (CDCl$_3$, 400 MHz) δ 9.94~7.97 (m, 2H), 7.83~7.86 (m, 2H), 7.62 (s, 1H), 7.37~7.40 (m, 1H), 7.09~7.24 (m, 5H), 6.93 (s, 1H), 6.80~6.85 (m, 1H), 5.95 (s, 2H), 5.85 (br, 1H), 3.16 (s, 3H), 3.00~3.01 (d, J=5.2 Hz, 3H), 2.78 (s, 3H). MS (M+H)$^+$: 614.

Compound 44, depicted in the table below, was prepared using the method described above and substituting the appropriate reagents and/or reactants.

Example 5

Preparation of Compound 45

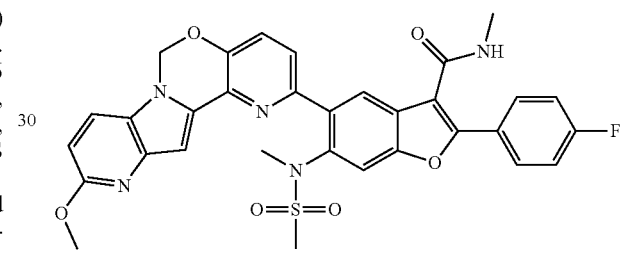

45

| Compound No | Structure | NMR | MS (M + H)$^+$ |
|---|---|---|---|
| 44 | ![structure] | $^1$H-NMR (DMSO-d6, 400 MHz) δ 8.67 (d, J = 2.8 Hz, 1H), 8.61 (d, J = 5.2 Hz, 2H), 8.11 (s, 1H), 8.03 (dd, J = 8.4, 5.6 Hz, 2H), 7.89 (s, 1H), 7.82 (d, J = 8.4 Hz, 1H), 7.75 (d, J = 8.8 Hz, 1H), 7.66 (t, J = 6.8 Hz, 1H), 7.44 (t, J = 8.8 Hz, 2H), 7.31 (s, 1H), 6.43 (s, 2H), 3.32 (s, 3H), 3.00 (s, 3H), 2.83 (d, J = 4.8 Hz, 3H). | 598 |

Step 1—Synthesis of tert-butyl 5-methoxy-1H-pyrrolo[3,2-b]pyridine-1-carboxylate

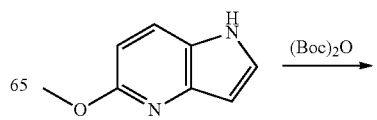

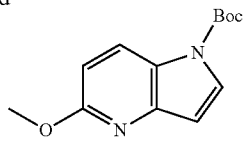

To 5-methoxy-1H-pyrrolo[3,2-b]pyridine (9 g, 60.8 mmol) in dichloromethane (200 mL) was added (Boc)$_2$O (9.2 g, 91.2 mmol), DMAP (1.34 g, 12.16 mmol) and Et$_3$N (7.37 g, 73 mmol) under N$_2$. The mixture was stirred at room temperature overnight. The reaction mixture was extracted with dichloromethane and washed with H$_2$O, brine, dried over Na$_2$SO$_4$. After concentrated, the crude product of tert-butyl 5-methoxy-1H-pyrrolo[3,2-b]pyridine-1-carboxylate (10 g, yield: 56%). $^1$H-NMR (CDCl$_3$, 400 MHz) δ 8.21 (s, 1H), 7.69 (s, 1H), 6.65 (d, J=9.2 Hz, 1H), 6.60 (d, J=7.6 Hz, 1H), 3.96 (s, 3H), 1.63 (s, 9H). MS (M+H)$^+$: 249.

Step 2—Synthesis of (1-(tert-butoxycarbonyl)-5-methoxy-1H-pyrrolo[3,2-b]pyridin-2-yl)boronic acid

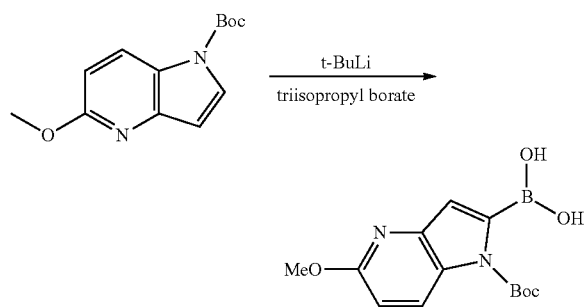

To a solution of tert-butyl 5-methoxy-1H-pyrrolo[3,2-b]pyridine-1-carboxylate (3 g, 12.08 mmol) in 40 mL of dry THF was added dropwise t-BuLi (1.16 g, 18.12 mmol) at −78° C. Then the solution was stirred at −78° C. for 1 hour. Then triisopropyl borate (4.55 g, 24.17 mmol) was added dropwise to the solution still at −78° C. The mixture was stirred at −78° C. for 2 hours and quenched the reaction with 1 M of HCl at low temperature to pH=3~4. After it was extracted with EtOAc, the combined organic phase was washed with brine, dried over Na$_2$SO$_4$. After concentrated, the resulting residue was purified using column (petroleum ether:ethyl acetate=3:1) to provide (1-(tert-butoxycarbonyl)-5-methoxy-1H-pyrrolo[3,2-b]pyridin-2-yl)boronic acid (1.3 g, yield: 37%). $^1$H-NMR (CDCl$_3$, 400 MHz) δ 8.10 (d, J=9.2 Hz, 1H), 7.46 (s, 1H), 6.88~6.84 (m, 2H), 6.70 (d, J=9.2 Hz, 1H), 3.98 (s, 3H), 1.71 (s, 9H). MS (M+H)$^+$: 293.

Step 3—Synthesis of tert-butyl 2-(6-chloro-3-hydroxypyridin-2-yl)-5-methoxy-1H-pyrrolo[3,2-b]pyridine-1-carboxylate

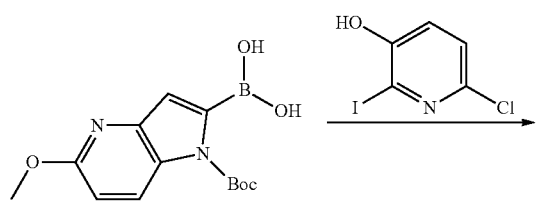

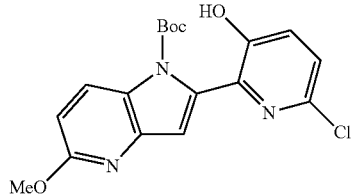

To a degassed solution of (1-(tert-butoxycarbonyl)-5-methoxy-1H-pyrrolo[3,2-b]pyridin-2-yl)boronic acid (500 mg, 1.17 mmol), NaHCO$_3$ (287 mg, 3.42 mmol) and 6-chloro-2-iodopyridin-3-ol (525 mg, 2.05 mmol) in 1,4-dioxane (10 mL) was added Pd(dppf)Cl$_2$ (10 mg) under N$_2$. The mixture was heated at 70° C. for 5 hours, concentrated in vacuo to remove 1,4-dioxane and extracted with EtOAc. After washed with brine and dried over Na$_2$SO$_4$, the solvent was removed by distillation. After concentrated, the crude product of tert-butyl 2-(6-chloro-3-hydroxypyridin-2-yl)-5-methoxy-1H-pyrrolo[3,2-b]pyridine-1-carboxylate (260 mg, yield: 40%). MS (M+H)$^+$: 376/378.

Step 4—Synthesis of 6-chloro-2-(5-methoxy-1H-pyrrolo[3,2-b]pyridin-2-yl)pyridin-3-ol

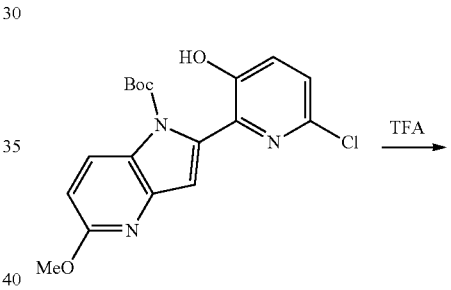

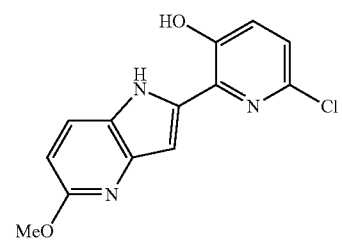

To a stirred solution of tert-butyl 2-(6-chloro-3-hydroxypyridin-2-yl)-5-methoxy-1H-pyrrolo[3,2-b]pyridine-1-carboxylate (260 mg, 0.69 mmol) in dichloromethane (6.0 mL) was added TFA (118 mg, 1.04 mmol). The mixture was stirred at room temperature for 8 hours. The mixture was diluted with H$_2$O and extract with EtOAc. The organics were washed with brine and dried over Na$_2$SO$_4$. After concentrated, the crude product of 6-chloro-2-(5-methoxy-1H-pyrrolo[3,2-b]pyridin-2-yl)pyridin-3-ol (128 mg, yield: 67%). MS (M+H)+: 276/278.

Step 5—Synthesis of 2-chloro-10-methoxy-6H-pyrido[2,3-e]pyrido[2',3':4,5]pyrrolo[1,2-c][1,3]oxazine

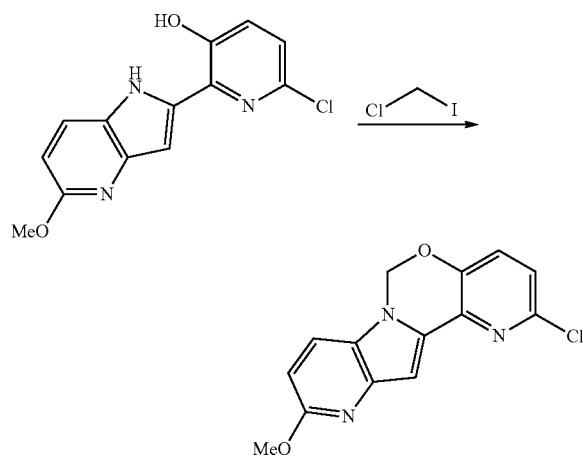

To a stirring solution of 6-chloro-2-(5-methoxy-1H-pyrrolo[3,2-b]pyridin-2-yl)pyridin-3-ol (200 mg, 0.727 mmol) and $Cs_2CO_3$ (472 mg, 1.45 mmol) in DMF (15 mL) was added chloroiodomethane (192 mg, 1.09 mmol) in DMF (2 mL) dropwise at 100° C. under $N_2$. The mixture was stirred at 100° C. for 1 hour. The mixture was diluted with $H_2O$ and extracted with EtOAc. The organics were washed with brine and dried over $Na_2SO_4$. After concentrated, the resulting residue was purified using Pre-TLC to provide 2-chloro-10-methoxy-6H-pyrido[2,3-e]pyrido[2',3':4,5]pyrrolo[1,2-c][1,3]oxazine (110 mg, yield: 52%). $^1$H-NMR (CDCl$_3$, 400 MHz) 7.44 (d, J=8.8 Hz, 1H), 7.26 (d, J=8.8 Hz, 1H), 7.16 (s, 1H), 7.10 (d, J=8.8 Hz, 1H), 6.63 (d, J=8.8 Hz, 1H), 5.81 (s, 2H), 3.95 (s, 3H). MS (M+H)+: 288/290.

Step 6—Synthesis of 2-(4-fluorophenyl)-5-(10-methoxy-6H-pyrido[2,3-e]pyrido[2',3':4,5]pyrrolo[1,2-c][1,3]oxazin-2-yl)-N-methyl-6-(N-methylmethylsulfonamido)benzofuran-3-carboxamide (Compound 45)

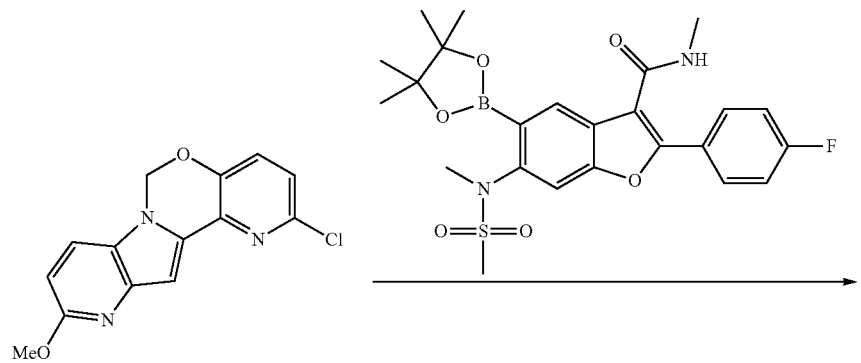

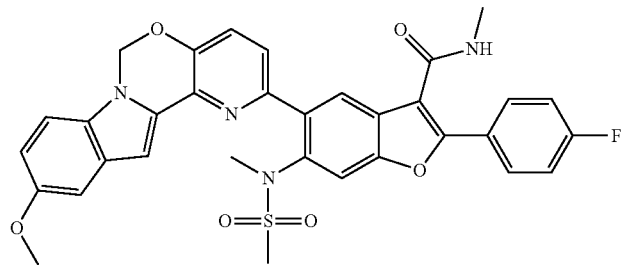

45

To a solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (100 mg, 0.199 mmol), 2-chloro-10-methoxy-6H-pyrido[2,3-e]pyrido[2',3': 4,5]pyrrolo[1,2-c][1,3]oxazine (64 mg, 0.18 mmol) and $K_3PO_4$ (104 mg, 0.398 mmol) in 3 mL of 1,4-dioxane and 0.2 mL of water were added $Pd_2(dba)_3$ (10 mg) and X-Phos (10 mg) under nitrogen. The reaction mixture was heated at 100° C. for 5 hours, concentrated and extracted with EtOAc. The combined organic phase was washed with brine, dried over $Na_2SO_4$ and concentrated to provide the compound 45 (30 mg, yield: 20%) through the prep-HPLC. $^1$H-NMR (CDCl$_3$, 400 MHz) δ 7.91 (s, 1H), 7.88 (d, J=5.6 Hz, 2H), 7.60 (s, 1H), 7.50 (d, J=8.0 Hz, 1H), 7.40 (s, 2H), 7.15~7.10 (m, 3H), 6.63 (d, J=8.8 Hz, 1H), 5.90 (s, 1H), 5.88 (s, 2H), 3.94 (s, 3H), 3.33 (s, 3H), 2.92 (d, J=4.8 Hz, 3H), 2.62 (s, 3H). MS (M+H)$^+$: 628.

Example 6

Preparation of Compound 46

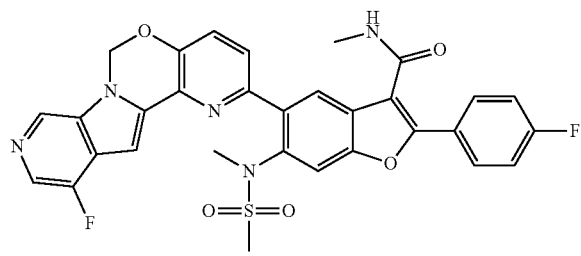

Step 1—Synthesis of 2-(3-(benzyloxy)-6-chloropyridin-2-yl)-4-fluoro-1H-pyrrolo[2,3-c]pyridine

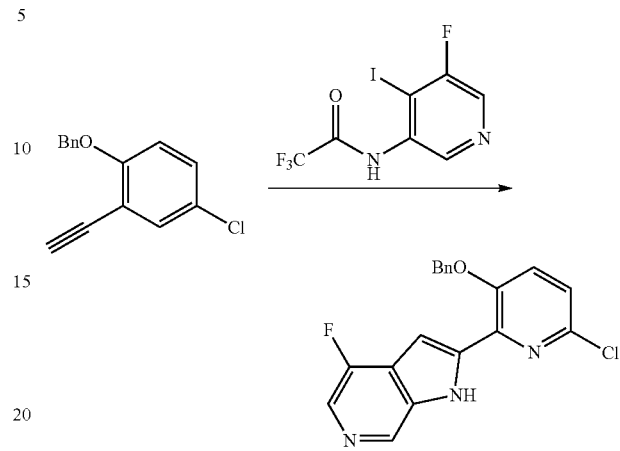

To a degassed solution of 2,2,2-trifluoro-N-(5-fluoro-4-iodopyridin-3-yl)acetamide (1 g, 2.99 mmol, prepared using similar method described in Example 4) and 3-(benzyloxy)-2-ethynyl-6-methylpyridine (735 mg, 3.29 mmol) in 1,4-dioxane (20 mL) was added PPh$_3$ (235 mg, 0.90 mmol), CuI (171 mg, 0.90 mmol) and $K_2CO_3$ (827 mg, 5.99 mmol) under $N_2$. The mixture was heated at 110° C. for 10 hours. The reaction mixture was cooled to room temperature and filtered. The filtrate was extract with EtOAc and washed with $H_2O$, brine, dried over $Na_2SO_4$. After concentrated, the resulting residue was purified using column (petroleum ether: EtOAc=5:1) to provide 2-(3-(benzyloxy)-6-chloropyridin-2-yl)-4-fluoro-1H-pyrrolo[2,3-c]pyridine (500 mg, yield: 25%). $^1$H-NMR (CDCl$_3$, 400 MHz) δ 9.94 (s, 1H), 8.64 (s, 1H), 8.09 (s, 1H), 7.48~7.41 (m, 6H), 7.32 (d, J=8.8 Hz, 1H), 7.25~7.18 (m, 1H), 5.31 (s, 2H). MS (M+H)$^+$: 354/356.

Step 2—Synthesis of 5-(5-(benzyloxy)-6-(4-fluoro-1H-pyrrolo[2,3-c]pyridin-2-yl)pyridin-2-yl)-2-(4-fluorophenyl)-N-methyl-6-(N-methylmethylsulfonamido)benzofuran-3-carboxamide

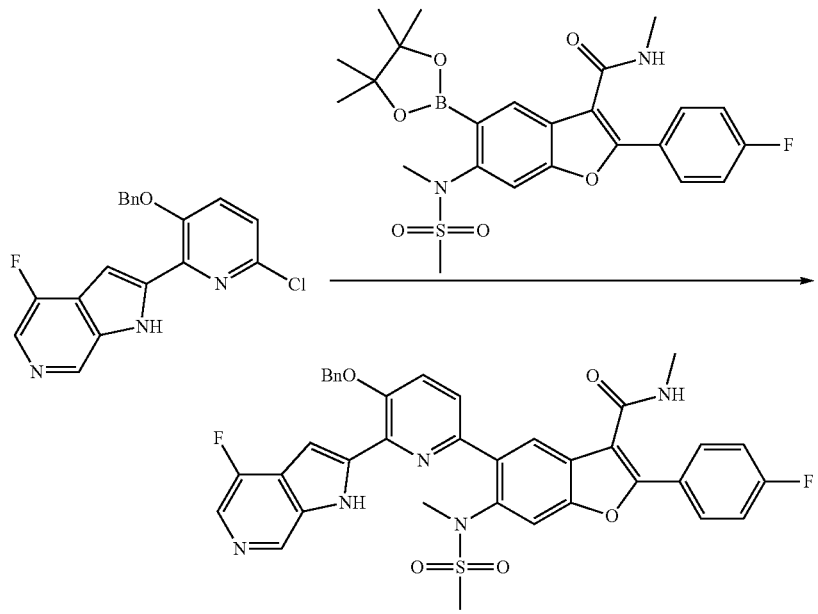

To a degassed solution of 2-(3-(benzyloxy)-6-chloropyridin-2-yl)-4-fluoro-1H-pyrrolo[2,3-c]pyridine (300 mg, 0.85 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (387 mg, 0.77 mmol) in 1,4-dioxane (5.0 mL) was added Pd$_2$(dba)$_3$ (10 mg), X-Phos (10 mg) and K$_3$PO$_4$ (452 mg, 1.70 mmol) under N$_2$. The mixture was heated at 100° C. for 3 hours. The reaction mixture was cooled to room temperature and filtered. The filtrate was washed with H$_2$O, brine, dried over Na$_2$SO$_4$. After it was concentrated, the resulting residue was purified using column (petroleum ether:EtOAc=2:1) to provide 5-(5-(benzyloxy)-6-(4-fluoro-1H-pyrrolo[2,3-c]pyridin-2-yl)pyridin-2-yl)-2-(4-fluorophenyl)-N-methyl-6-(N-methylmethylsulfonamido)benzofuran-3-carboxamide (165 mg, yield: 31%). $^1$H-NMR (CDCl$_3$, 400 MHz) δ 10.73 (s, 1H), 8.49 (s, 1H), 7.99 (d, J=8.0 Hz, 2H), 7.92 (dd, J=8.0, 8.0 Hz, 2H), 7.50~7.45 (m, 3H), 7.43~7.40 (m, 5H), 7.16 (t, J=8.0 Hz, 2H), 6.56 (s, 1H), 5.32 (s, 12H), 3.10 (s, 3H), 2.91 (d, J=4.0 Hz, 3H), 2.80 (s, 3H). MS (M+H)$^+$: 694.

Step 3—Synthesis of 5-(6-(4-fluoro-1H-pyrrolo[2,3-c]pyridin-2-yl)-5-hydroxypyridin-2-yl)-2-(4-fluorophenyl)-N-methyl-6-(N-methylmethylsulfonamido)benzofuran-3-carboxamide

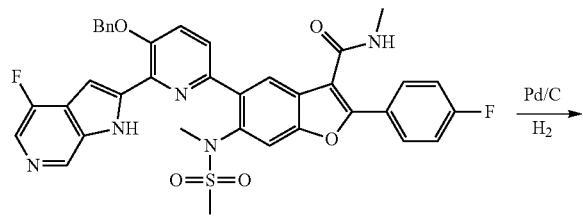

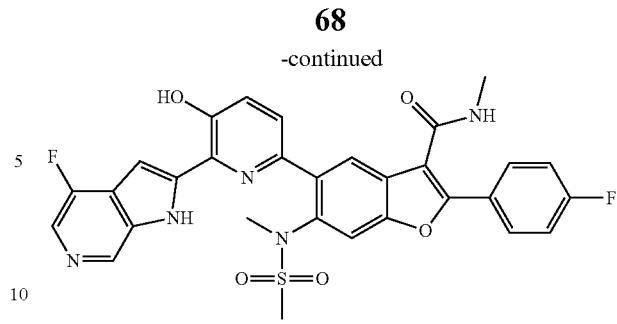

To a degassed solution of 5-(5-(benzyloxy)-6-(4-fluoro-1H-pyrrolo[2,3-c]pyridin-2-yl)pyridin-2-yl)-2-(4-fluorophenyl)-N-methyl-6-(N-methylmethylsulfonamido)benzofuran-3-carboxamide (150 mg, 0.22 mmol) was dissolved in THF (5 mL) and charged with 10% palladium on carbon (0.1 g). The mixture was hydrogenated at room temperature under hydrogen pressure for 4 hours. The reaction mixture was filtered and the filtrate was extract with EtOAc and washed with H$_2$O, brine, dried over Na$_2$SO$_4$. After concentrated, the resulting residue was purified using prep-TLC to provide 5-(6-(4-fluoro-1H-pyrrolo[2,3-c]pyridin-2-yl)-5-hydroxypyridin-2-yl)-2-(4-fluorophenyl)-N-methyl-6-(N-methylmethylsulfonamido)benzofuran-3-carboxamide (120 mg, yield: 92%). $^1$H-NMR (CDCl$_3$, 400 MHz) δ 12.00 (s, 1H), 11.17 (s, 1H), 8.67 (s, 1H), 8.52 (s, 1H), 8.01 (t, J=6.0 Hz, 3H), 7.91 (s, 1H), 7.52 (s, 2H), 7.41~7.35 (m, 3H), 3.19 (s, 3H), 2.95 (s, 3H), 2.80 (d, J=4.0 Hz, 3H). MS (M+H)$^+$: 604.

Step 4—Synthesis of 5-(11-fluoro-6H-pyrido[2,3-e]pyrido[4',3':4,5]pyrrolo[1,2-c][1,3]oxazin-2-yl)-2-(4-fluorophenyl)-N-methyl-6-(N-methylmethylsulfonamido)benzofuran-3-carboxamide (Compound 46)

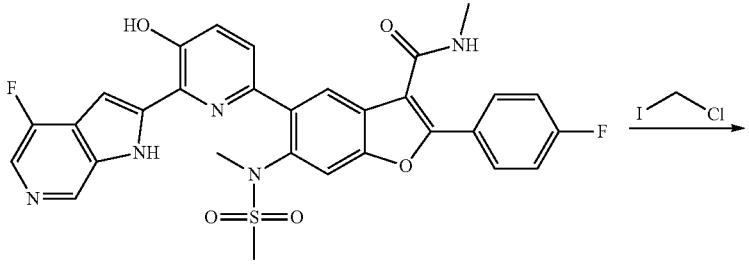

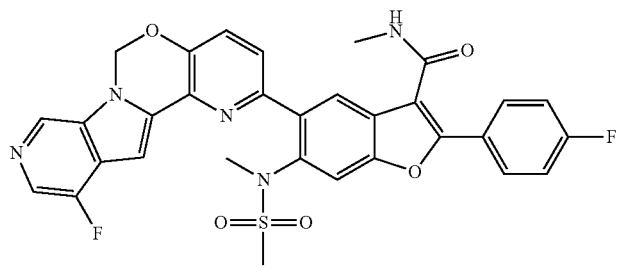

To a stirring solution of 5-(6-(4-fluoro-1H-pyrrolo[2,3-c]pyridin-2-yl)-5-hydroxypyridin-2-yl)-2-(4-fluorophenyl)-N-methyl-6-(N-methylmethylsulfonamido)benzofuran-3-carboxamide (100 mg, 0.17 mmol) and Cs$_2$CO$_3$ (108 mg, 0.33 mmol) in DMF (3 mL) was added chloroidomethane (35 mg, 0.2 mmol) dropwise at 100° C. under N$_2$. The mixture was heated for 8 hours. The mixture was diluted with H$_2$O and extracted with EtOAc. The organics were washed with brine and dried over Na$_2$SO$_4$. The crude product was purified using prep-HPLC to obtain the product of Compound 46 (30 mg, yield: 30%). $^1$H-NMR (CDCl$_3$, 400 MHz) δ 8.61 (s, 1H), 8.17 (s, 1H), 8.05 (s, 1H), 7.95 (t, J=6.0 Hz, 2H), 7.65 (s, 1H), 7.60 (d, J=8.4 Hz, 1H), 7.53 (d J=8.0 Hz, 1H), 7.25~7.19 (m, 3H), 6.10 (s, 2H), 5.99 (s, 1H), 3.37 (s, 3H), 3.00 (d, J=4.0 Hz, 3H), 2.80 (s, 3H). MS (M+H)$^+$: 616.

Compound 47, depicted in the table below, was prepared using the method described above and substituting the appropriate reagents and/or reactants.

NaH (4.90 g, 203.2 mmol) was added to a solution of 1H-pyrrolo[2,3-b]pyridine (20.0 g, 169.3 mmol) in dry DMF (200 mL) under N$_2$ protection. The mixture was stirred at 0° C. for 1 hour. Then SEMCl (42.2 g, 253.95 mmol) was added to the reaction mixture, and the mixture was stirred at 0° C. for 4 hours. After concentrated in vacuo to remove DMF, ice cold NH$_4$Cl (sat. aq.) was added and the mixture was extracted with EtOAc. The organic layer was washed with water, brine, dried over Na$_2$SO$_4$, filtered and the solvent was concentrated in vacuo under reduced pressure. The crude product was purified using column chromatography (petroleum ether:EtOAc=10:1) to provide the product of 1-((2-(trimethylsilyl)ethoxy)methyl)-1H-pyrrolo[2,3-b]pyridine (31.2 g, yield: 74%). $^1$H-NMR (CDCl$_3$, 400 MHz) δ 8.33 (dd, J=4.8 Hz, 1.6 Hz, 1H), 7.91 (dd, J=7.6 Hz, 1.6 Hz, 1H), 7.34 (d, J=3.6 Hz, 1H), 7.08 (dd, J=7.6 Hz, 4.8 Hz, 1H), 6.51 (d, J=3.6 Hz, 1H),

| Compound No | Structure | NMR | MS (M + H)$^+$ |
| --- | --- | --- | --- |
| 47 | 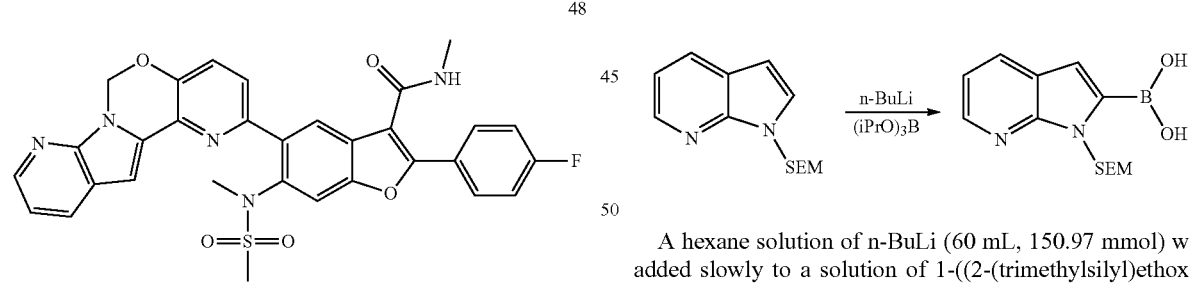 | $^1$H-NMR (CDCl$_3$, 400 MHz) δ 9.29 (s, 1H), 8.86 (s, 1H), 8.31 (s, 1H), 8.10 (d, J = 4.4 Hz, 1H), 7.87~7.90 (m, 2H), 7.54 (d, J = 8.0 Hz, 1H), 7.41 (s, 1H), 7.30~7.35 (m, 3H), 6.95~7.00 (m, 1H), 6.36 (s, 2H), 3.46 (s, 3H), 3.02 (s, 3H), 2.76 (d, J = 4.8 Hz, 3H). | 623 |

Example 7

Preparation of Compound 48

48

Step 1—Synthesis of 1-((2-(trimethylsilyl)ethoxy)methyl)-1H-pyrrolo[2,3-b]pyridine

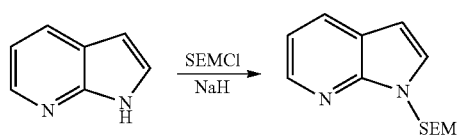

5.68 (s, 2H), 3.53 (t, J=8.4 Hz, 2H), 0.90 (t, J=8.4 Hz, 2H), –0.08 (s, 9H). MS (M+H)$^+$: 249.

Step 2—Synthesis of (1-((2-(trimethylsilyl)ethoxy)methyl)-1H-pyrrolo[2,3-b]pyridin-2-yl)boronic acid A hexane solution of n-BuLi (60 mL, 150.97 mmol) was added slowly to a solution of 1-((2-(trimethylsilyl)ethoxy)methyl)-1H-pyrrolo[2,3-b]pyridine (25.0 g, 100.65 mmol) in dry THF (200 mL) at –70° C. under N$_2$ protection. The mixture was stirred at –45° C. for 2 hour. After (i-PrO)$_3$B (30.29 g, 161.03 mmol) was added, the mixture was stirred overnight warming to RT. Then the reaction mixture was quenched with 1M aqueous HCl and extracted with EtOAc. The organic layer was washed with water, brine, dried over Na$_2$SO$_4$, filtered and the solvent was concentrated in vacuo under reduced pressure. The crude product was purified using column chromatography (petroleum ether:EtOAc=5:1) to provide the product of (1-((2-(trimethylsilyl)ethoxy)methyl)-1H-pyrrolo[2,3-b]pyridin-2-yl)boronic acid (14.4 g, yield: 49%). $^1$H-NMR (CDCl$_3$, 400 MHz) δ 8.49 (dd, J=4.8 Hz, 1.6 Hz, 1H), 8.07 (dd, J=8.0 Hz, 1.6 Hz, 1H), 7.21 (dd, J=8.0 Hz, 4.8 Hz, 1H), 6.92 (s, 1H), 6.02 (s, 2H), 3.74 (t, J=8.4 Hz, 2H), 1.08 (t, J=8.4 Hz, 2H), 0.04 (s, 9H). MS (M+H)⁺: 293.

Step 3—Synthesis of 6-chloro-2-(1-((2-(trimethylsilyl)ethoxy)methyl)-1H-pyrrolo[2,3-b]pyridin-2-yl)pyridin-3-ol

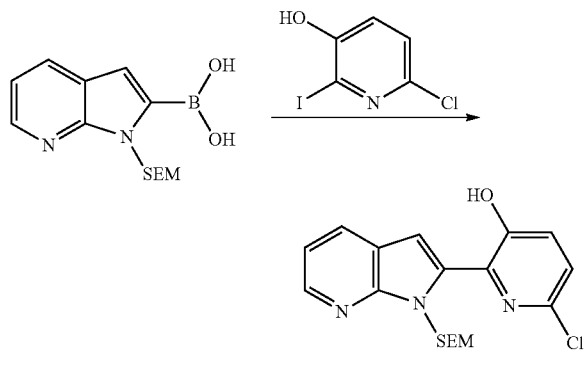

To a mixture of 6-chloro-2-iodopyridin-3-ol (8.39 g, 32.85 mmol), (1-((2-(trimethylsilyl)ethoxy)methyl)-1H-pyrrolo[2,3-b]pyridin-2-yl)boronic acid (8.00 g, 27.38 mmol) and K₃PO₄·3H₂O (22 mg, 82.13 mmol) in 1,4-dioxane (120 mL), Pd(dppf)Cl₂ (50 mg) was added under N₂ protection. After stirred overnight at 80° C., the reaction mixture was concentrated in vacuo, suspended in water and extracted with EtOAc. The organic layer was washed with brine, dried over Na₂SO₄ and concentrated in vacuo. The resulting residue was purified using column chromatography (petroleum ether:EtOAc=5:1) to provide the product of 6-chloro-2-(1-((2-(trimethylsilyl)ethoxy)methyl)-1H-pyrrolo[2,3-b]pyridin-2-yl)pyridin-3-ol (3.01 g, yield: 29%). ¹H-NMR (CDCl₃, 400 MHz) δ 8.40 (dd, J=4.8 Hz, 1.6 Hz, 1H), 7.96 (dd, J=8.0 Hz, 1.6 Hz, 1H), 7.39 (d, J=8.4 Hz, 1H), 7.30 (d, J=8.4 Hz, 1H), 7.17 (dd, J=8.0 Hz, 4.8 Hz, 1H), 6.82 (s, 1H), 5.85 (s, 2H), 3.65 (t, J=8.4 Hz, 2H), 0.89 (t, J=8.4 Hz, 2H), −0.08 (s, 9H). MS (M+H)⁺: 376/378.

Step 4—Synthesis of 6-chloro-2-(1H-pyrrolo[2,3-b]pyridin-2-yl)pyridin-3-ol

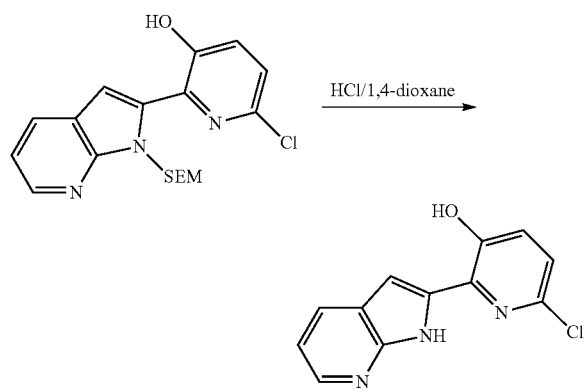

6-chloro-2-(1-((2-(trimethylsilyl)ethoxy)methyl)-1H-pyrrolo[2,3-b]pyridin-2-yl)pyridin-3-ol (320 mg, 1.10 mmol) was added to HCl/1,4-dioxane (15 mL), and the reaction mixture was heated to 100° C. and stirred for 10 hours. Then the mixture was concentrated in vacuo, diluted with EtOAc, washed with brine, dried over Na₂SO₄ and concentrated to provide the crude product of compound 5 (200 mg, yield: 74%), which was used for the next step without further purification. ¹H-NMR (DMSO-d₆, 400 MHz) δ 11.59 (s, 1H), 11.29 (br s, 1H), 8.26 (d, J=4.8 Hz, 1H), 8.01 (d, J=8.0 Hz, 1H), 7.49 (d, J=8.4 Hz, 1H), 7.30 (s, 1H), 7.27 (d, J=8.4 Hz, 1H), 7.07 (dd, J=8.0 Hz, 4.8 Hz, 1H). MS (M+H)⁺: 246/248.

Step 5—Synthesis of 2-chloro-6H-pyrido[2,3-e]pyrido[3',2':4,5]pyrrolo[1,2-c][1,3]oxazine

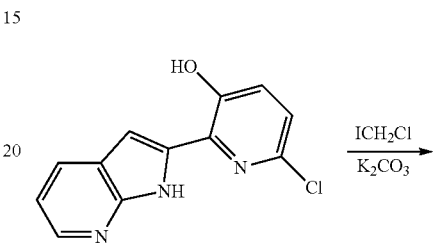

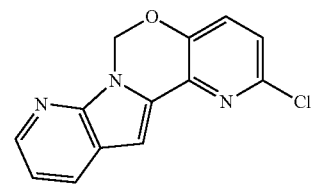

To a mixture of chloroiodomethane (2.01 g, 11.40 mmol), K₂CO₃ (338 mg, 2.44 mmol) in DMF (15 mL), 6-chloro-2-(1H-pyrrolo[2,3-b]pyridin-2-yl)pyridin-3-ol (200 mg, 0.81 mmol) in DMF (5 mL) was added dropwise at 100° C. under N₂ protection. After stirred at 100° C. for 2 hours, the reaction mixture was concentrated in vacuo, suspended in water and extracted with EtOAc. The organic layer was washed with brine, dried over Na₂SO₄ and concentrated in vacuo. The crude product was purified using prep-TLC (petroleum ether:EtOAc=8:1) to provide the product of 2-chloro-6H-pyrido[2,3-e]pyrido[3',2':4,5]pyrrolo[1,2-c][1,3]oxazine (20 mg, yield: 9%). ¹H-NMR (CDCl₃, 400 MHz) δ 8.35 (dd, J=4.8 Hz, 1.6 Hz, 1H), 7.99 (dd, J=8.0 Hz, 1.6 Hz, 1H), 7.36 (d, J=8.4 Hz, 1H), 7.21 (d, J=8.4 Hz, 1H), 7.16 (s, 1H), 7.13 (dd, J=8.0 Hz, 4.8 Hz, 1H), 6.14 (s, 2H). MS (M+H)⁺: 258/260.

Step 6—Synthesis of 2-(4-fluorophenyl)-N-methyl-6-(N-methylmethylsulfonamido)-5-(6H-pyrido[2,3-e]pyrido[3',2':4,5]pyrrolo[1,2-c][1,3]oxazin-2-yl)benzofuran-3-carboxamide (Compound 48)

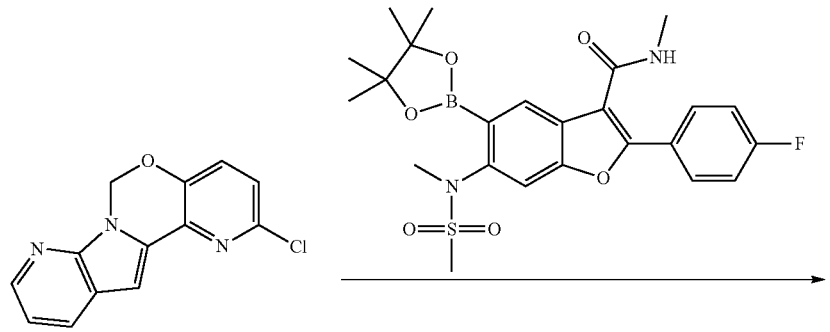

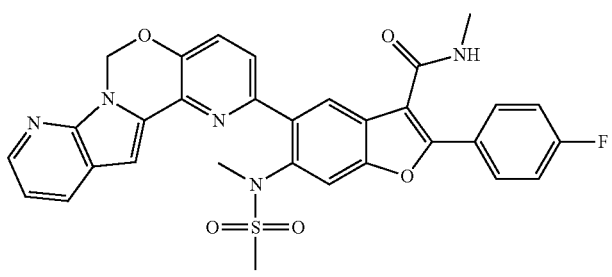

48

To a mixture of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (40 mg, 0.08 mmol), 2-chloro-6H-pyrido[2,3-e]pyrido[3',2':4,5]pyrrolo[1,2-c][1,3]oxazine (27 mg, 0.10 mmol) and $K_3PO_4 \cdot 3H_2O$ (64 mg, 0.24 mmol) in 1,4-dioxane/water (1.5 mL/0.2 mL), $Pd_2(dba)_3$ (5 mg), X-Phos (10 mg) were added under $N_2$ protection. After stirred overnight at 80° C., the reaction mixture was concentrated in vacuo, suspended in water and extracted with EtOAc. The organic layer was washed with brine, dried over $Na_2SO_4$ and concentrated in vacuo. The resulting residue was purified using prep-TLC (dichloromethane:MeOH=20:1) to provide the product of Compound 48 (30 mg, yield: 48%). $^1$H-NMR (CDCl$_3$, 400 MHz) δ 8.34~8.37 (m, 1H), 8.04 (s, 1H), 7.93~8.00 (m, 3H), 7.68 (s, 1H), 7.48~7.56 (m, 2H), 7.17~7.24 (m, 2H), 7.10~7.16 (m, 2H), 6.22 (s, 2H), 5.96 (br s, 1H), 3.53 (s, 3H), 3.00 (d, J=4.8 Hz, 3H), 2.76 (s, 3H). MS (M+H)$^+$: 598.

Compounds 49 and 50, depicted in the table below, were prepared using the method described above and substituting the appropriate reagents and/or reactants.

| Compound No | Structure | NMR | MS (M + H)$^+$ |
|---|---|---|---|
| 49 | 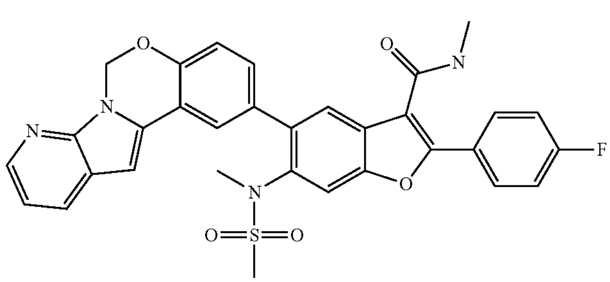 [SMILES: CNC(=O)c1c(-c2ccc(F)cc2)oc2cc(N(C)S(C)(=O)=O)c(-c3ccc4c(c3)-c3cc5cccnc5n3CO4)cc12] | $^1$H-NMR (CDCl$_3$, 400 MHz) δ 8.30 (d, J = 1.2 Hz, 1H), 7.87~7.97 (m, 5H), 7.61 (s, 1H), 7.73~7.77 (m, 1H), 7.18~7.24 (m, 3H), 7.08~7.12 (m, 1H), 6.80 (s, 1H), 6.16 (s, 2H), 5.87 (d, J = 4.4 Hz, 1H), 3.13 (s, 3H), 3.00 (d, J = 5.2 Hz, 3H), 2.82 (s, 3H). | 597 |

| Compound No | Structure | NMR | MS (M + H)+ |
|---|---|---|---|
| 50 | 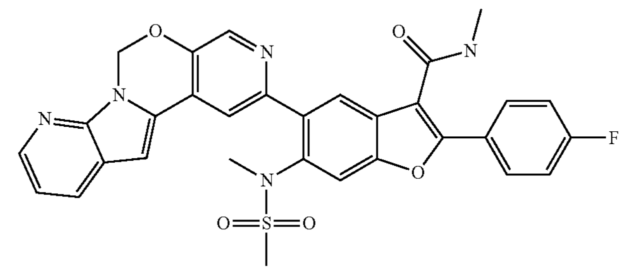 [SMILES: CNC(=O)c1c(-c2ccc(F)cc2)oc2cc(N(C)S(C)(=O)=O)c(-c3cc4c(cn3)OCn3c-4cc4cccnc43)cc12] | ¹H-NMR (CDCl₃, 400 MHz) δ 8.67 (s, 1H), 8.43 (dd, J = 4.8, 1.6 Hz, 1H), 8.27 (s, 1H), 8.11 (s, 1H), 8.10~8.03 (m, 3H), 7.63 (s, 1H), 7.25~7.15 (m, 4H), 6.64 (d, J = 2.8 Hz, 1H), 6.29 (s, 2H), 3.20 (s, 3H), 3.03 (d, J = 4.2 Hz, 3H), 3.02 (s, 3H). | 598 |

Example 8

Preparation of Compound 51

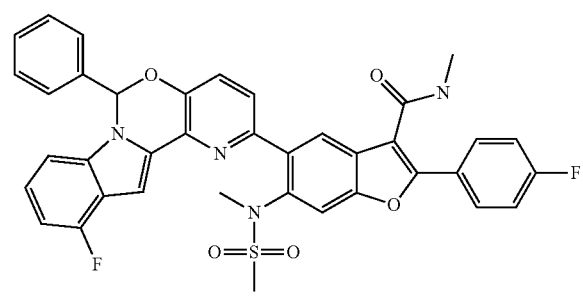

Step 1—Synthesis of 2-chloro-11-fluoro-6-phenyl-6H-pyrido[2',3':5,6][1,3]oxazino[3,4-a]indole

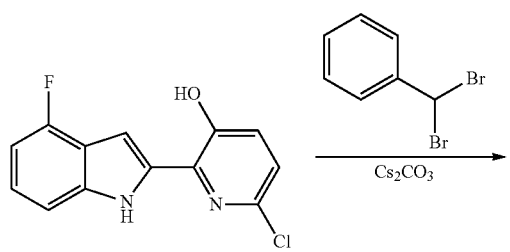

A solution of dibromotoluene (382 mg, 1.527 mmol, prepared using similar method described for Example 1) in DMF (2 mL) was added slowly to a mixture of compound 6-chloro-2-(4-fluoro-1H-indol-2-yl)pyridin-3-ol (200 mg, 0.763 mmol) and Cs₂CO₃ (746 mg, 2.289 mmol) in DMF (10 mL) at 100° C. After 10 min, the mixture was concentrated in vacuo. The resulting residue was diluted with water (50 mL) and extracted with ethyl acetate (25 mL×3). The organic layer was washed with brine (50 mL), dried over Na₂SO₄ and concentrated in vacuo. The resulting residue was purified using column chromatography (petroleum ether:ethyl acetate=50:1) to provide 2-chloro-11-fluoro-6-phenyl-6H-pyrido[2',3':5,6][1,3]oxazino[3,4-a]indole (187 mg, yield: 70.0%). ¹H-NMR (CDCl₃, 400 MHz) δ 7.43 (s, 1H), 7.23~7.35 (m, 3H), 7.18 (s, 1H), 7.10 (s, 1H), 7.03~7.08 (m, 4H), 6.79 (m, 1H), 6.65 (d, J=8.4 Hz, 1H). MS (M+H)⁺: 351/353.

Step 2—Synthesis of 5-(11-fluoro-6-phenyl-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (Compound 51)

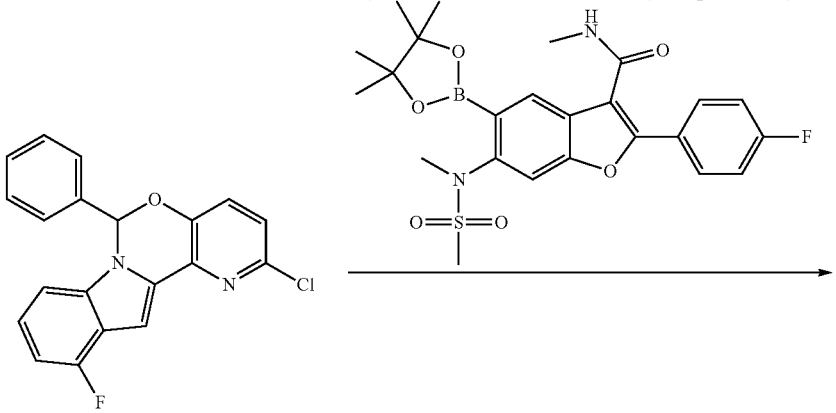

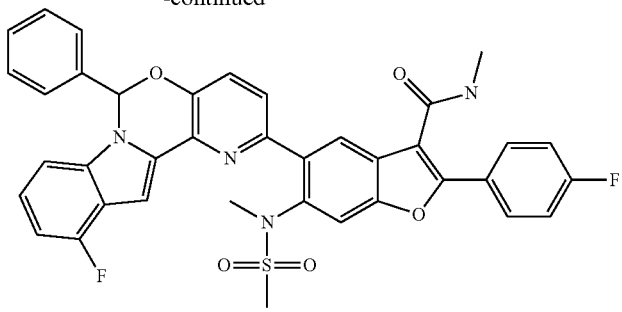

51

Compound 51 (45 mg, yield: 57.0%) was made using the method described in Example 1, Step $^1$H-NMR (CDCl$_3$, 400 MHz) δ 7.90~7.93 (m, 3H), 7.60 (s, 1H), 7.04~7.40 (m, 12H), 6.81~6.85 (m, 1H), 6.76 (d, J=8.4 Hz, 1H), 5.95 (br s, 1H), 3.34 (s, 3H), 2.94 (d, J=4.8 Hz, 3H), 2.30 (s, 3H). MS (M+H)$^+$: 691.

Example 9

Preparation of Compound 52

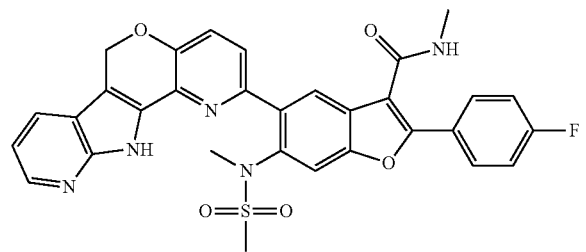

52

Step 1—Synthesis of 2-chloro-11-((2-(trimethylsilyl) ethoxy)methyl)-6,11-dihydropyrido[2',3':5,6]pyrano[4,3-b]-7-aza-indole

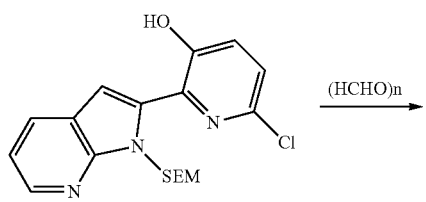

(HCHO)n

-continued

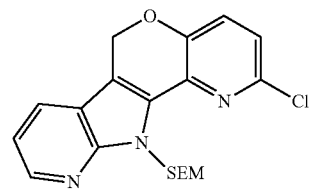

To a solution of mixture 6-chloro-2-(1-((2-(trimethylsilyl) ethoxy)methyl)-1H-pyrrolo[2,3-b]pyridin-2-yl)pyridin-3-ol (1.00 g, 2.66 mmol) and paraform (250 mg, 8.33 mmol) in 1,4-dioxane was added HCl/dioxane (4 M, 2 mL, 8.0 mmol). The reaction mixture was stirred at 70° C. for 3 hours. Then it was concentrated in vacuo, dissolved in EtOAc, washed with Na$_2$CO$_3$ (aq.), brine, dried over Na$_2$SO$_4$ and concentrated in vacuo. The resulting resulting residue was purified using column chromatography (petroleum ether:EtOAc=8:1) to provide the product of 2-chloro-11-((2-(trimethylsilyl) ethoxy)methyl)-6,11-dihydropyrido[2',3':5,6]pyrano[4,3-b]-7-aza-indole (150 mg, yield: 17%). $^1$H-NMR (CDCl$_3$, 400 MHz) δ 8.41 (dd, J=4.8 Hz, 1.6 Hz, 1H), 7.45 (dd, J=8.0, 1.6 Hz, 1H), 7.18~7.10 (m, 2H), 7.07 (d, J=8.8 Hz, 1H), 6.31 (s, 2H), 5.64 (s, 2H), 3.70 (t, J=8.4 Hz, 2H), 0.96 (t, J=8.4 Hz, 2H), −0.09 (s, 9H). MS (M+H)$^+$: 388/390.

Step 2—Synthesis of 2-(4-fluorophenyl)-N-methyl-6-(N-methylmethylsulfonamido)-5-(11-((2-(trimethylsilyl)ethoxy)methyl)-6,11-dihydropyrido[2',3':5,6]pyrano[4,3-b]-7-aza-indol-2-yl)benzofuran-3-carboxamide

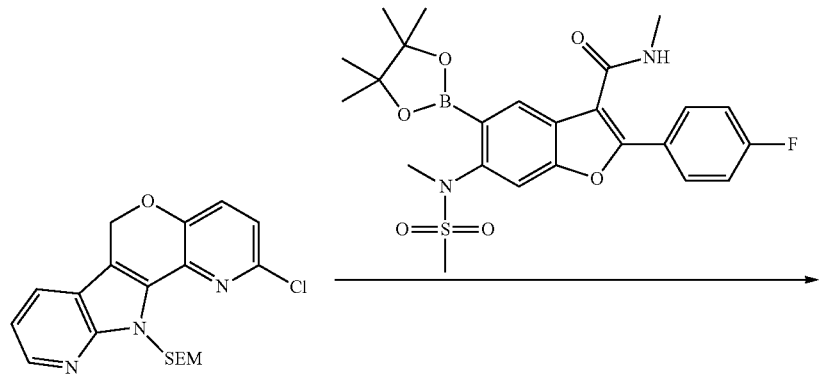

To a mixture of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (118 mg, 0.23 mmol), 2-chloro-11-((2-(trimethylsilyl)ethoxy)methyl)-6,11-dihydropyrido[2',3':5,6]pyrano[4,3-b]-7-aza-indole (100 mg, 0.26 mmol) and $K_3PO_4 \cdot 3H_2O$ (187 mg, 0.70 mmol) in 1,4-dioxane/$H_2O$ (2.0 mL/0.2 mL), $Pd_2(dba)_3$/X-Phos (10 mg/10 mg) was added under $N_2$ protection. The reaction mixture was stirred at 100° C. for 4 hours. Then it was concentrated in vacuo, suspended in water and extracted with EtOAc. The organic layer was washed with brine, dried over $Na_2SO_4$ and concentrated in vacuo. The resulting resulting residue was purified using prep-TLC (dichloromethane:MeOH=20:1) to provide the product 2-(4-fluorophenyl)-N-methyl-6-[methyl(methylsulfonyl)amino]-5-(11-{[2-(trimethylsilyl)ethoxy]methyl}-6,11-dihydropyrido[2'',3'':5',6']pyrano[3',4':4,5]pyrrolo[2,3-b]pyridin-2-yl)-1-benzofuran-3-carboxamide (80 mg, yield: 48%). $^1$H-NMR (CDCl$_3$, 400 MHz) δ 8.38 (d, J=1.6 Hz, 1H), 8.12 (s, 1H), 8.04~8.00 (m, 2H), 7.79 (dd, J=7.6, 1.6 Hz, 1H), 7.62 (s, 1H), 7.47 (d, J=8.4 Hz, 1H), 7.30 (d, J=8.4 Hz, 1H), 7.17~7.23 (m, 2H), 7.14 (dd, J=14.8, 8.0 Hz, 1H), 6.38 (s, 2H), 6.04 (d, J=3.2 Hz, 1H), 5.67 (s, 2H), 3.49 (t, J=8.4 Hz, 2H), 3.29 (s, 3H), 3.02 (d, J=5.2 Hz, 3H), 2.79 (s, 3H), 0.76 (t, J=8.4 Hz, 2H), 0.26 (s, 9H). MS (M+H)$^+$: 728.

Step 3—Synthesis of 5-(6,11-dihydropyrido[2'',3'':5',6']pyrano[3',4':4,5]pyrrolo[2,3-b]pyridin-2-yl)-2-(4-fluorophenyl)-N-methyl-6-[methyl(methylsulfonyl)amino]-1-benzofuran-3-carboxamide (Compound 52)

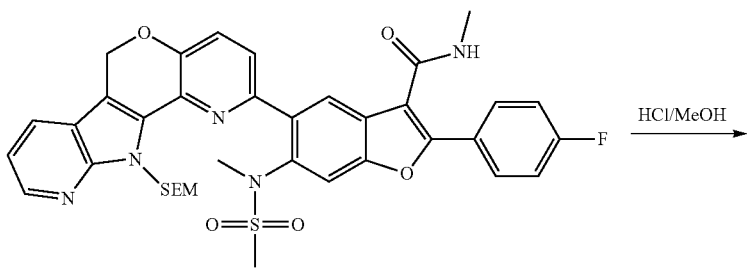

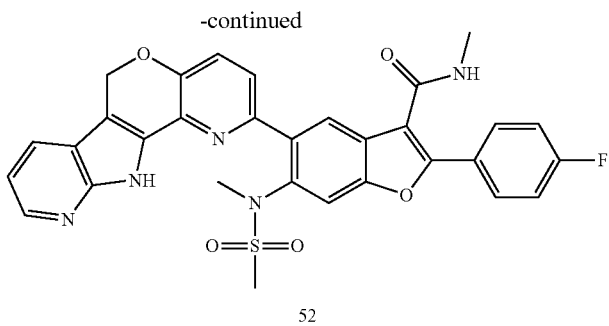

52

2-(4-fluorophenyl)-N-methyl-6-(N-methylmethylsulfonamido)-5-(11-((2-(trimethylsilyl)ethoxy)methyl)-6,11-dihydropyrido[2',3':5,6]pyrano[4,3-b]-7-aza-indol-2-yl)benzofuran-3-carboxamide (100 mg, 0.11 mmol) was added to HCl/dioxane (4 M, 10 mL), and the reaction mixture was stirred at 80° C. for 4 hours. Then the mixture was concentrated in vacuo, diluted with EtOAc, washed with brine, dried over $Na_2SO_4$ and concentrated in vacuo. The crude product was purified using prep-HPLC to provide the product of Compound 52 (30 mg, yield: 46%). $^1$H-NMR (DMSO-$d_6$, 400 MHz) δ 12.34 (br s, 1H), 8.52 (d, J=4.8 Hz, 1H), 8.27 (d, J=4.0 Hz, 1H), 8.04~7.95 (m, 3H), 7.93 (s, 1H), 7.50~7.38 (m, 4H), 7.13 (d, J=8.0 Hz, 1H), 5.75 (s, 2H), 3.27 (s, 3H), 2.99 (s, 3H), 2.84 (d, J=4.4 Hz, 3H). MS (M+H)$^+$: 598.

Example 10

Preparation of Compound 53

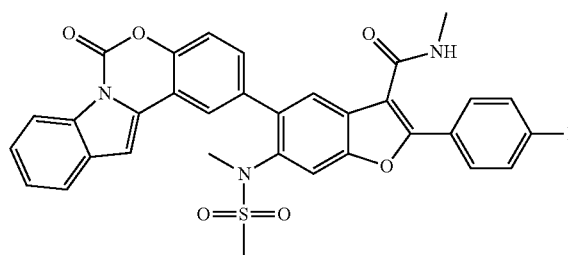

53

Step 1—Synthesis of 2-bromo-6H-benzo[5,6][1,3]oxazino[3,4-a]indol-6-one

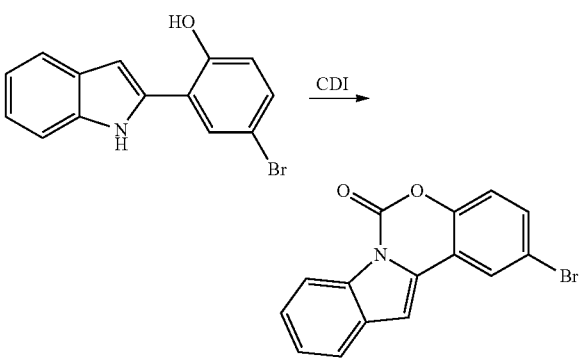

Carbonyldiimidazole (490 mg, 2 mmol) and DMAP (50 mg) were added to a solution of 4-bromo-2-(1H-indol-2-yl)phenol (576 mg, 2 mmol) in 20 mL of dichloromethane and the resulting mixture was stirred at room temperature overnight. The mixture was diluted with dichloromethane, washed with water and brine, dried over $Na_2SO_4$, filtered, and concentrated in vacuo. Purification by flash chromatography on silica gel (hexane/EtOAc 20:1) provided 2-bromo-6H-benzo[5,6][1,3]oxazino[3,4-a]indol-6-one as light yellow powder (500 mg, 79.6%). $^1$H-NMR (CDCl$_3$, 400 MHz) δ 8.49 (d, J=8.4 Hz, 1H), 7.96 (s, 1H), 7.70 (d, J=7.2 Hz, 1H), 7.41~7.53 (m, 3H), 7.22 (d, J=8.8 Hz, 1H), 7.07 (s, 1H). MS (M+H)$^+$: 314/316.

Step 2—Synthesis of 2-(4-fluorophenyl)-N-methyl-6-(N-methylmethylsulfonamido)-5-(6-oxo-6H-benzo[5,6][1,3]oxazino[3,4-a]indol-2-yl)benzofuran-3-carboxamide (Compound 53)

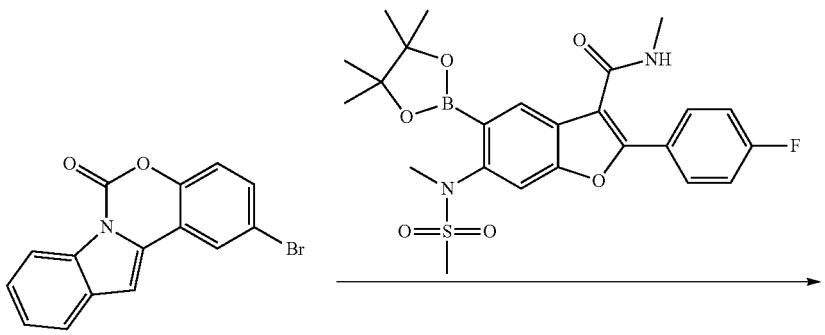

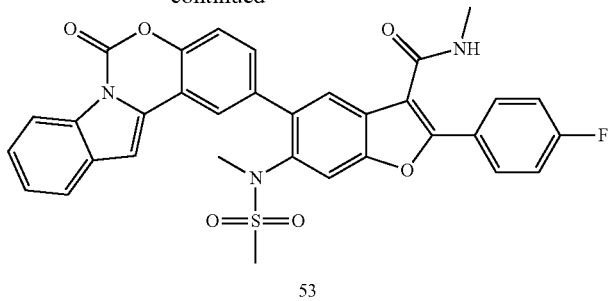

53

A mixture of 2-bromo-6H-benzo[5,6][1,3]oxazino[3,4-a]indol-6-one (47 mg, 0.15 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (51 mg, 0.1 mmol), K₃PO₄·3H₂O (80 mg, 0.3 mmol) and Pd(dppf)Cl₂ (7 mg, 0.01 mmol) in 2 mL of DMF was heated in a microwave reactor at 100° C. for 20 minutes, and then the mixture was purified using prep-HPLC to provide Compound 53 (2.7 mg, yield: 4.4%). ¹H-NMR (CDCl₃, 400 MHz) δ 8.52 (d, J=7.6 Hz, 1H), 8.07 (s, 1H), 7.92~7.96 (m, 3H), 7.70 (d, J=7.6 Hz, 1H), 7.62 (s, 1H), 7.41~7.54 (m, 4H), 7.21~7.23 (m, 2H), 7.12 (s, 1H), 5.89 (s, 1H), 3.11 (s, 3H), 3.00 (d, J=4.8 Hz, 3H), 2.88 (s, 3H). MS (M+H)⁺: 610.

Example 11

Preparation of Compound 54

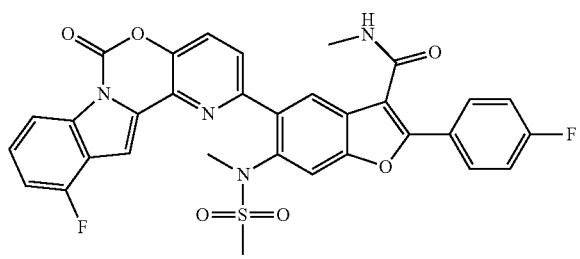

54

Step 1—Synthesis of 2-(3-(benzyloxy)-6-chloropyridin-2-yl)-4-fluoro-1H-indole

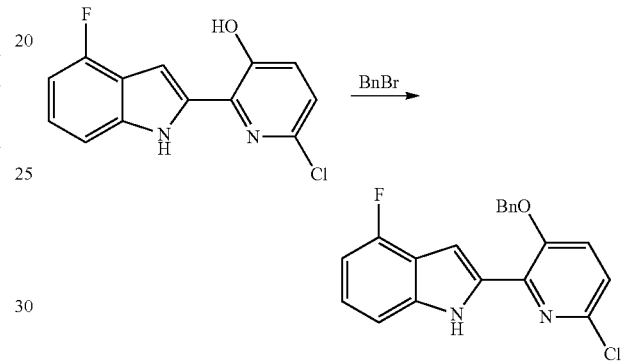

A mixture of 6-chloro-2-(4-fluoro-1H-indol-2-yl)pyridin-3-ol (100 mg, 0.38 mmol, prepared using similar method described in Example 1), BnBr (97 mg, 0.572 mmol) and K₂CO₃ (158 mg, 1.146 mmol) in DMF (1 mL) was stirred at room temperature overnight. The mixture was then concentrated in vacuo. The resulting resulting residue was diluted with water (15 mL) and extracted with ethyl acetate (10 mL×3). The organic layer was washed with brine (20 mL), dried over Na₂SO₄ and concentrated in vacuo. The resulting residue was purified using Prep-TLC (petroleum ether:EA=3:1) to provide 2-(3-(benzyloxy)-6-chloropyridin-2-yl)-4-fluoro-1H-indole (100 mg, yield: 74.6%). ¹H-NMR (CDCl₃, 400 MHz) δ 9.64 (s, 1H), 7.12~7.48 (m, 10H), 6.76 (t, J=8.8 Hz, 1H), 5.33 (s, 2H). MS (M+H)⁺: 353/355.

Step 2—Synthesis of 5-(5-(benzyloxy)-6-(4-fluoro-1H-indol-2-yl)pyridin-2-yl)-2-(4-fluorophenyl)-N-methyl-6-(N-methylmethylsulfonamido)benzofuran-3-carboxamide

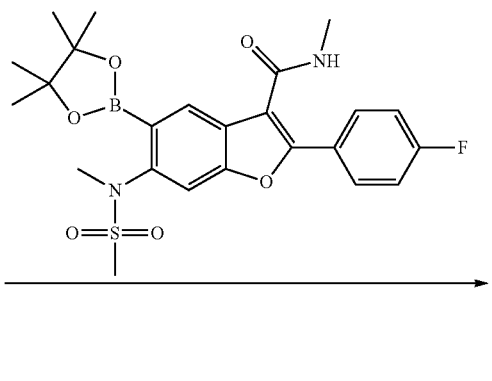

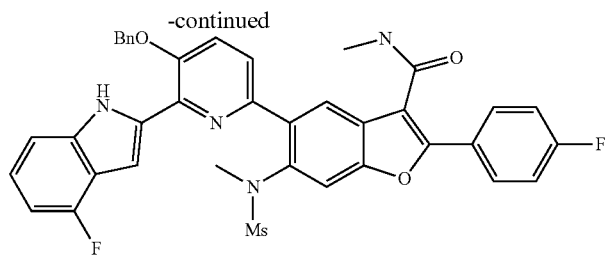

A mixture of 2-(3-(benzyloxy)-6-chloropyridin-2-yl)-4-fluoro-1H-indole (160 mg, 0.454 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (228 mg, 0.454 mmol), K$_3$PO$_4$·H$_2$O (362 mg, 1.362 mmol), Pd$_2$(dba)$_3$ (21 mg, 0.023 mmol) and X-Phos (22 mg, 0.046 mmol) in dioxane/H$_2$O (2 mL/0.4 mL) was stirred at 80° C. for 2 hours under N$_2$ atmosphere. The mixture was then diluted with water (50 mL) and extracted with ethyl acetate (30 mL×3). The organic layer was washed with brine (20 mL×3), dried over Na$_2$SO$_4$ and concentrated in vacuo. The resulting residue was purified using Prep-TLC (petroleum ether:EA=1:1) to provide 5-(5-(benzyloxy)-6-(4-fluoro-1H-indol-2-yl)pyridin-2-yl)-2-(4-fluorophenyl)-N-methyl-6-(N-methylmethylsulfonamido)benzofuran-3-carboxamide (120 mg, yield: 38.2%). $^1$H-NMR (CDCl$_3$, 400 MHz) δ 9.97 (s, 1H), 7.93 (s, 1H), 7.88~7.91 (m, 2H), 7.55 (s, 1H), 7.33~7.48 (m, 7H), 6.69~7.19 (m, 5H), 6.65~6.69 (m, 1H), 5.83 (d, J=4.4 Hz, 1H), 5.31 (s, 2H), 3.08 (s, 3H), 2.91 (d, J=4.8 Hz, 3H), 2.75 (s, 3H). MS (M+H)$^+$: 693.

Step 3—Synthesis of 5-(6-(4-fluoro-1H-indol-2-yl)-5-hydroxypyridin-2-yl)-2-(4-fluorophenyl)-N-methyl-6-(N-methylmethylsulfonamido)benzofuran-3-carboxamide

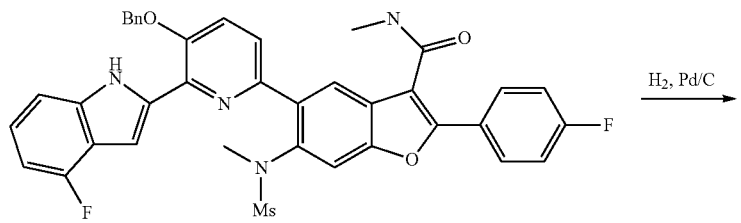

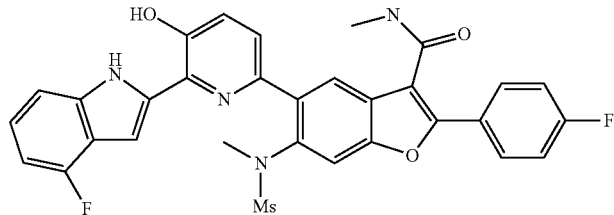

A mixture of 5-(5-(benzyloxy)-6-(4-fluoro-1H-indol-2-yl)pyridin-2-yl)-2-(4-fluorophenyl)-N-methyl-6-(N-methylmethylsulfonamido)benzofuran-3-carboxamide (120 mg, 0.173 mmol) and Pd/C (20 mg) in methanol (10 mL) was stirred under $H_2$ atmosphere at room temperature for 1 hour. The mixture was then filtered through Celite and concentrated to provide 5-(6-(4-fluoro-1H-indol-2-yl)-5-hydroxy-pyridin-2-yl)-2-(4-fluorophenyl)-N-methyl-6-(N-methylmethylsulfonamido)benzofuran-3-carboxamide (60 mg, yield: 57.7%). $^1$H-NMR (Methanol-$d_4$, 400 MHz) δ 7.95~8.00 (m, 4H), 7.80 (s, 1H), 7.37 (t, J=8.8 Hz, 2H), 7.22~7.30 (m, 4H), 6.64~6.69 (m, 1H), 3.23 (s, 3H), 2.94 (s, 3H), 2.90 (s, 3H). MS (M+H)$^+$: 603.

Step 4—Synthesis of 5-(11-fluoro-6-oxo-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (Compound 54)

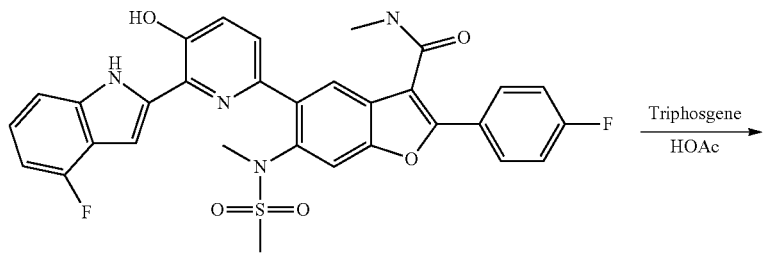

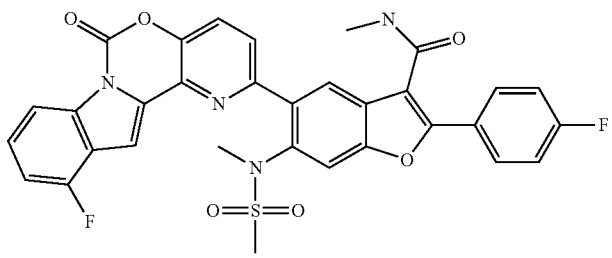

54

A mixture of 5-(6-(4-fluoro-1H-indol-2-yl)-5-hydroxypyridin-2-yl)-2-(4-fluorophenyl)-N-methyl-6-(N-methylmethylsulfonamido)benzofuran-3-carboxamide (60 mg, 0.100 mol) and triphosgene (59 mg, 0.199 mmol) in CH₃COOH (2 mL) was stirred at 100° C. for 2 hours. The mixture was then diluted with water (30 mL) and extracted with ethyl acetate (15 mL×3). The organic layer was washed with brine (30 mL), dried over Na₂SO₄ and concentrated in vacuo. The resulting residue was purified using Prep-HPLC to provide compound 54 (40 mg, yield: 63.5%). ¹H-NMR (DMSO-d₆, 400 MHz) δ 8.54 (d, J=4.8 Hz, 1H), 8.20 (d, J=8.0 Hz, 1H), 8.07 (s, 1H), 7.98~8.03 (m, 3H), 7.86 (s, 1H), 7.88 (d, J=8.4 Hz, 1H), 7.44~7.52 (m, 1H), 7.40 (t, J=8.8 Hz, 3H), 7.27 (t, J=8.8 Hz, 1H), 2.92 (s, 3H), 2.80 (d, J=4.4 Hz, 3H), 2.50 (s, 3H). MS (M+H)⁺: 629.

Example 12

Preparation of Compound 55

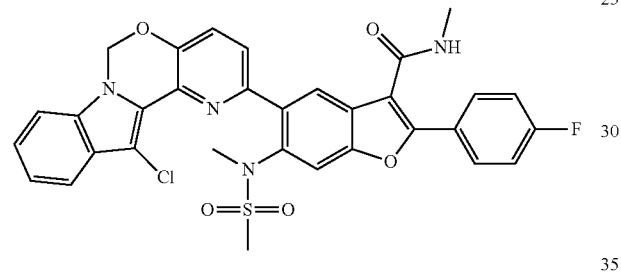

Step 1—Synthesis of 6-chloro-2-(3-chloro-1H-indol-2-yl)pyridin-3-ol

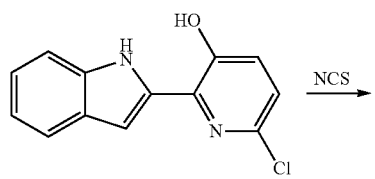

A mixture of 6-chloro-2-(1H-indol-2-yl)pyridin-3-ol (244 mg, 1 mmol, described in Example 1) and NCS (160 mg, 1.2 mmol) in Acetone (2 mL) was stirred at room temperature for 1 hour. The mixture was then concentrated and purified using prep-TLC (petroleum ether:EtOAc=2:1) to provide 6-chloro-2-(3-chloro-1H-indol-2-yl)pyridin-3-ol (180 mg, yield: 64.7%). ¹H-NMR (CDCl₃, 400 MHz) δ 9.03 (s, 1H), 7.61 (d, J=7.6 Hz, 1H), 7.15~7.36 (m, 5H), 6.20~6.40 (br s, 1H). MS (M+H)⁺: 279/281.

Step 2—Synthesis of 2,12-dichloro-6H-pyrido[2',3':5,6][1,3]oxazino[3,4-a]indole

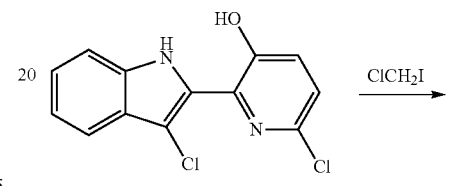

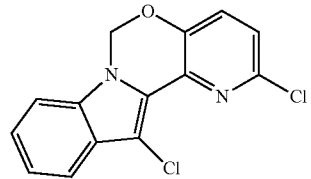

A solution of 6-chloro-2-(3-chloro-1H-indol-2-yl)pyridin-3-ol (128 mg, 0.46 mmol) and Cs₂CO₃ (452 mg, 1.39 mmol) in DMF (6 mL) was stirred at 100° C. (internal temperature), then chloroiodomethane (173 mg, 0.92 mmol) in DMF (1 mL) was added dropwise. After the reaction was completed according to TLC, the mixture was filtered and concentrated in vacuo. The resulting residue was purified using prep-TLC (petroleum ether:EtOAc=4:1) to provide 2,12-dichloro-6H-pyrido[2',3':5,6][1,3]oxazino[3,4-a]indole (100 mg, yield: 75.2%). ¹H-NMR (CDCl₃, 400 MHz) δ 7.65 (d, J=8.0 Hz, 1H), 7.11~7.31 (m, 5H), 5.82 (s, 2H). MS (M+H)⁺: 291/293.

Step 3—Synthesis of 5-(12-chloro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (Compound 55)

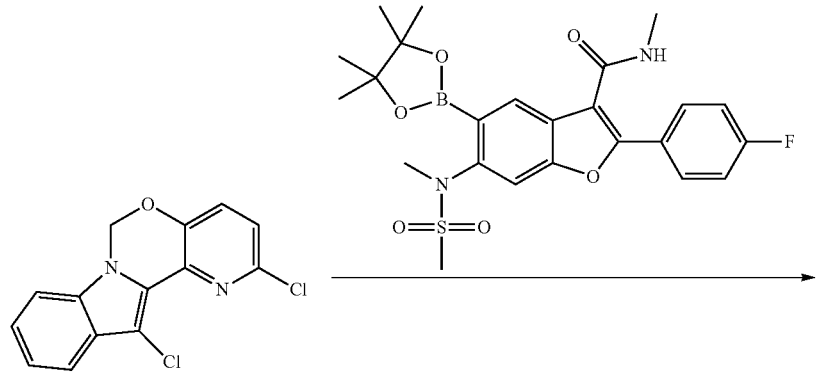

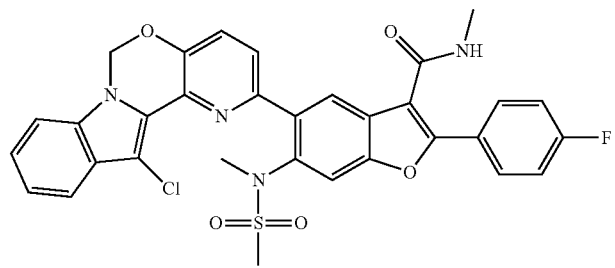

55

To a degassed solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (110 mg, 0.22 mmol), 2,12-dichloro-6H-pyrido[2',3':5,6][1,3]oxazino[3,4-a]indole (64 mg, 0.22 mmol) and $K_3PO_4$ (176 mg, 0.66 mmol) in dioxane/$H_2O$ (0.8 mL/0.2 mL) was added $Pd_2(dba)_3$ (10 mg, 0.01 mmol) and X-Phos (10 mg, 0.02 mmol) under $N_2$. The mixture was heated to 80° C. and then stirred for 1 hour. The reaction mixture was cooled to RT, diluted with EtOAc and filtered. The filtrate was washed with $H_2O$, brine, dried over $Na_2SO_4$. After concentrated, the resulting residue was purified using prep-TLC (petroleum ether:EtOAc=1:1) to provide the desired product of compound 55 (60 mg, yield: 43.2%). $^1$H-NMR (CDCl$_3$, 400 MHz) δ 8.13 (s, 1H), 7.94~7.98 (m, 2H), 7.65 (d, J=8.0 Hz, 1H), 7.58 (s, 1H), 7.53 (d, J=8.4 Hz, 1H), 7.42 (d, J=8.4 Hz, 1H), 7.28~7.31 (m, 2H), 7.11~7.20 (m, 3H), 5.85~5.95 (br s, 3H), 3.32 (s, 3H), 2.96 (d, J=4.8 Hz, 3H), 2.72 (s, 3H). MS (M+H)$^+$: 631.

Compounds 56 and 57, depicted in the table below, were prepared using similar method described above and substituting the appropriate reagents and/or reactants.

| Compound No | Structure | NMR | MS (M + H)$^+$ |
|---|---|---|---|
| 56 | 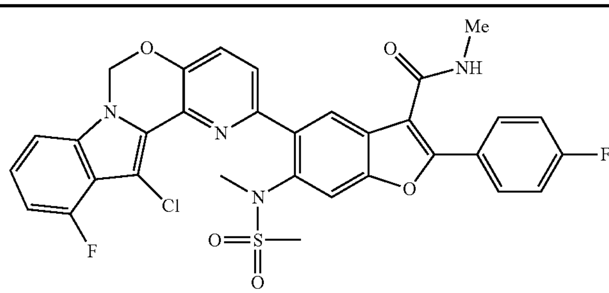 | $^1$H-NMR (CDCl$_3$, 400 MHz) 8.19 (s, 1H), 8.00~8.04 (m, 2H), 7.61~7.64 (m, 2H), 7.49 (d, J = 8.4 Hz, 1H), 7.18~7.24 (m, 3H), 7.10 (d, J = 8.4 Hz, 1H), 6.84~6.89 (m, 1H), 5.98 (s, 1H), 5.94 (s, 2H), 3.38 (s, 3H), 3.02 (d, J = 4.4 Hz, 3H), 2.80 (s, 3H). | 649 |

| Compound No | Structure | NMR | MS (M + H)+ |
|---|---|---|---|
| 57 | 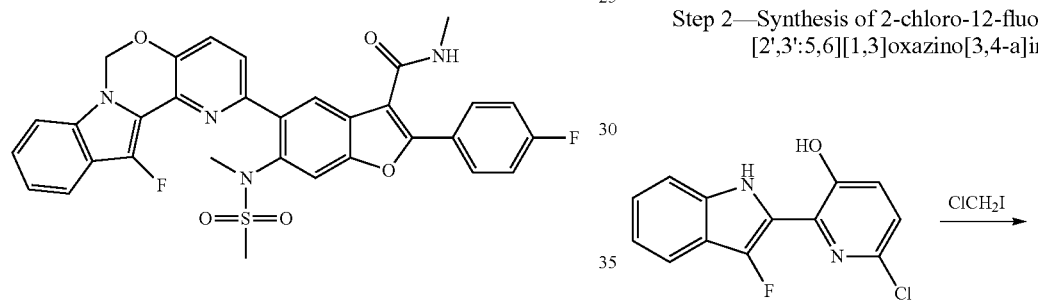 | 1H-NMR (CDCl3, 400 MHz) δ 8.18 (s, 1H), 7.99~8.03 (m, 2H), 7.61~7.64 (m, 2H), 7.49~7.52 (m, 1H), 7.18~7.24 (m, 5H), 6.08 (s, 1H), 5.95 (s, 2H), 3.39 (s, 3H) 3.03 (d, J = 4.4 Hz, 3H), 2.81 (s, 3H). | 665 |

Example 13

Preparation of Compound 58

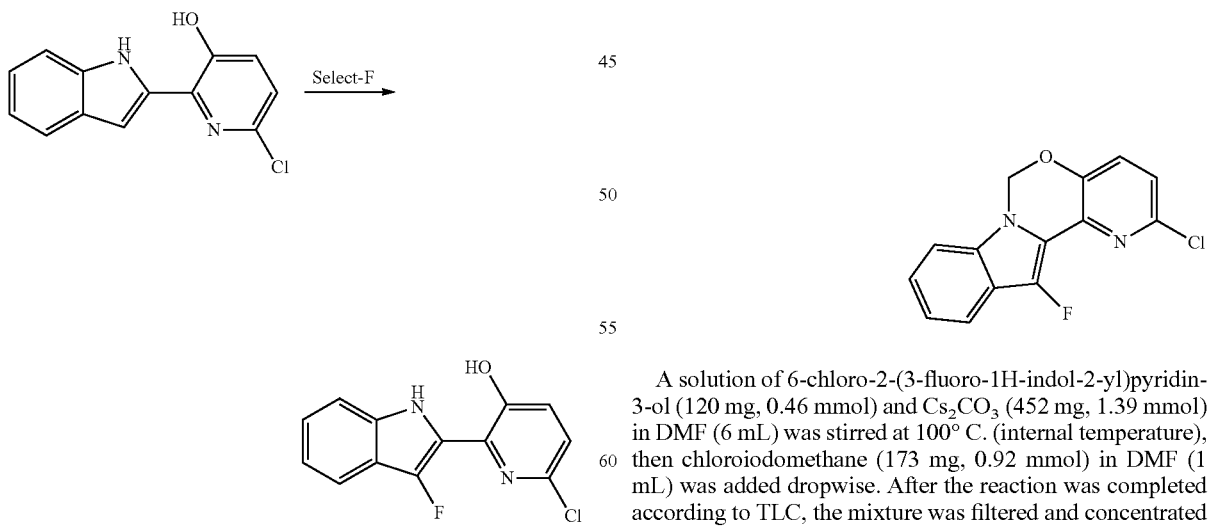

Step 1—Synthesis of 6-chloro-2-(3-fluoro-1H-indol-2-yl)pyridin-3-ol

A mixture of 6-chloro-2-(1H-indol-2-yl)pyridin-3-ol (244 mg, 1 mmol) and 1-(chloromethyl)-4-fluoro-1,4-diazoniabicyclo[2.2.2]octane tetrafluoroborate (425 mg, 1.2 mmol) in Acetone (2 mL) was stirred at room temperature for 1 hour. The mixture was then concentrated and purified using prep-TLC (petroleum ether:EtOAc=2:1) to provide desired product of 6-chloro-2-(3-fluoro-1H-indol-2-yl)pyridin-3-ol (120 mg, yield: 46.2%). 1H-NMR (Methanol-d4, 400 MHz) δ 7.55 (d, J=8.0 Hz, 1H), 7.39~7.44 (m, 1H), 7.25~7.34 (m, 1H), 6.97~7.20 (m, 3H). MS (M+H)+: 263/265.

Step 2—Synthesis of 2-chloro-12-fluoro-6H-pyrido[2',3':5,6][1,3]oxazino[3,4-a]indole A solution of 6-chloro-2-(3-fluoro-1H-indol-2-yl)pyridin-3-ol (120 mg, 0.46 mmol) and Cs2CO3 (452 mg, 1.39 mmol) in DMF (6 mL) was stirred at 100° C. (internal temperature), then chloroiodomethane (173 mg, 0.92 mmol) in DMF (1 mL) was added dropwise. After the reaction was completed according to TLC, the mixture was filtered and concentrated in vacuo. The resulting residue was purified using prep-TLC (petroleum ether:EtOAc=4:1) to provide 2-chloro-12-fluoro-6H-pyrido[2',3':5,6][1,3]oxazino[3,4-a]indole (60 mg, yield: 47.6%). 1H-NMR (CDCl3, 400 MHz) δ 7.63 (d, J=8.0 Hz, 2H), 7.06~7.28 (m, 4H), 5.76 (s, 2H). MS (M+H)+: 275/277.

Step 3—Synthesis of 5-(12-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (Compound 58)

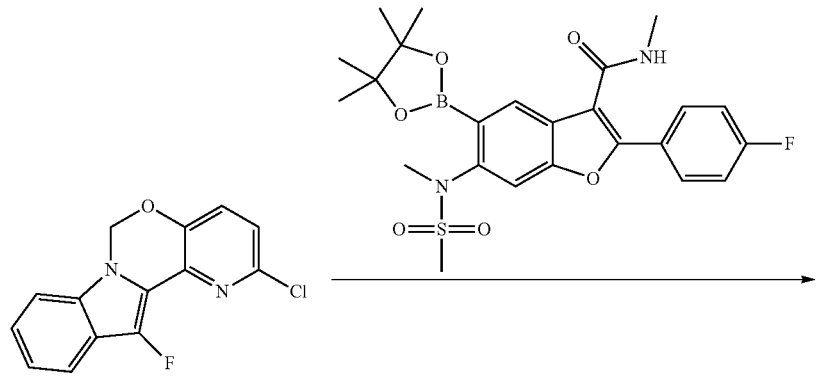

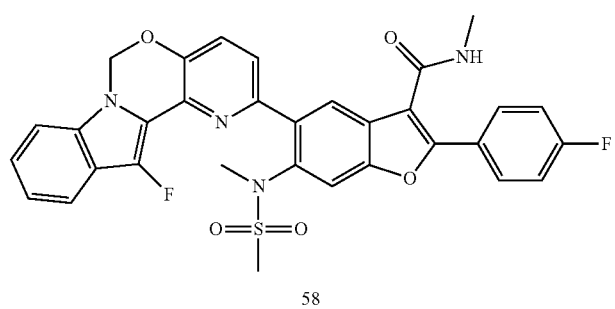

58

To a degassed solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (110 mg, 0.22 mmol), 2-chloro-12-fluoro-6H-pyrido[2',3':5,6][1,3]oxazino[3,4-a]indole (60 mg, 0.220 mmol) and $K_3PO_4$ (176 mg, 0.66 mmol) in dioxane/$H_2O$ (0.8 mL/0.2 mL) was added $Pd_2(dba)_3$ (10 mg, 0.01 mmol) and X-Phos (10 mg, 0.02 mmol) under $N_2$. The mixture was heated to 80° C. and then stirred for 1 hour. The reaction mixture was cooled to RT, diluted with EtOAc and filtered. The filtrate was washed with $H_2O$, brine, dried over $Na_2SO_4$. After concentrated, the resulting residue was purified using prep-TLC (petroleum ether:EtOAc=1:1) to provide the desired product of compound 58 (60 mg, yield: 44.4%). $^1$H-NMR (CDCl$_3$, 400 MHz) δ 7.94~8.00 (m, 3H), 7.66~7.68 (m, 2H), 7.46 (s, 2H), 7.29~7.35 (m, 2H), 7.19 (t, J=8.4 Hz, 3H), 6.02 (s, 1H), 5.91 (s, 2H), 3.39 (s, 3H), 2.98 (d, J=4.8 Hz, 3H), 2.70 (s, 3H). MS (M+H)$^+$: 615.

Compounds 59, depicted in the table below, were prepared using the method described above and substituting the appropriate reactants and/or reagents.

| Compound No | Structure | NMR | MS (M + H)$^+$ |
|---|---|---|---|
| 59 | 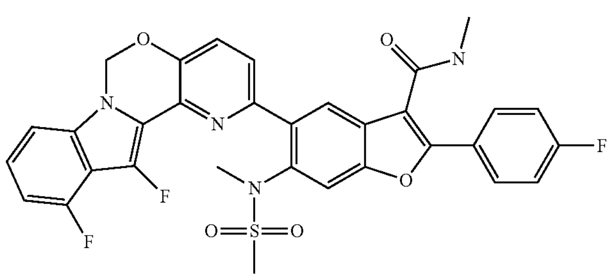 [SMILES: CNC(=O)c1c(-c2ccc(F)cc2)oc2cc(N(C)S(C)(=O)=O)c(-c3ccc4c(n3)-c3c(F)c5c(F)cccc5n3CO4)cc12] | $^1$H-NMR (CDCl$_3$, 400 MHz) 7.89~7.93 (m, 3H), 7.60 (s, 1H), 7.43 (s, 2H), 7.12~7.22 (m, 3H), 7.04 (d, J = 8.4 Hz, 1H), 6.78~6.82 (m, 1H), 6.21 (s, 1H), 5.86 (s, 2H), 3.36 (s, 3H), 2.92 (d, J = 4.8 Hz, 3H), 2.70 (s, 3H). | 633 |

Example 14

Preparation of Compound 60

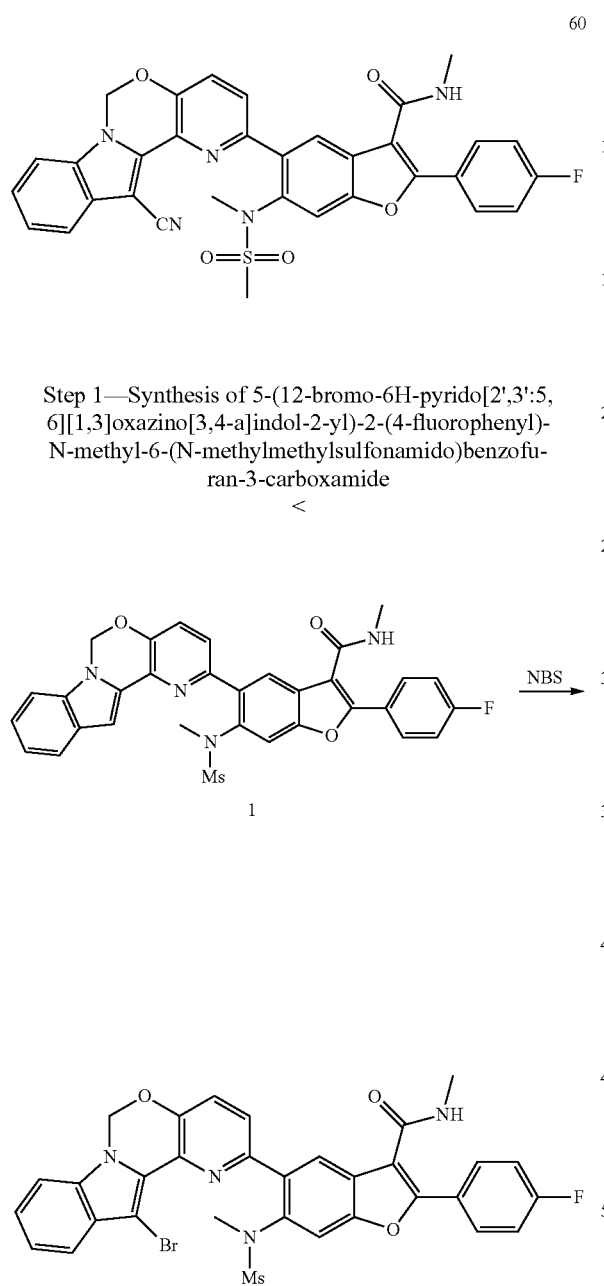

Step 1—Synthesis of 5-(12-bromo-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide NBS (33 mg, 0.19 mmol) was added to a solution of compound 1 (100 mg, 0.17 mmol, described in Example 1) in THF (1 mL). The mixture was stirred at room temperature for 1 hour and then purified using prep-TLC (petroleum ether:EtOAc=1:1) to provide 5-(12-bromo-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (100 mg, yield: 88.5%). $^1$H-NMR (CDCl$_3$, 400 MHz) δ 8.27 (s, 1H), 8.01~8.04 (m, 2H), 7.62~7.67 (m, 3H), 7.47 (d, J=8.8 Hz, 1H), 7.31~7.35 (m, 2H), 7.16~7.26 (m, 3H), 6.06 (br s, 1H), 5.97 (s, 2H), 3.36 (s, 3H), 3.02 (d, J=4.8 Hz, 3H), 2.80 (s, 3H). MS (M+H)$^+$: 675/677.

Step 2—Synthesis of 5-(12-cyano-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (Compound 60)

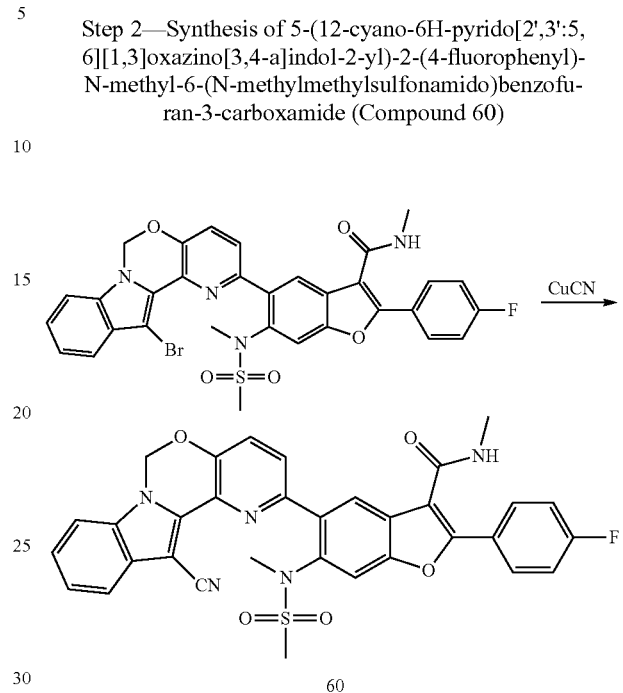

A mixture of 5-(12-bromo-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (50 mg, 0.07 mmol) and CuCN (14 mg, 0.15 mmol) in NMP (2 mL) was stirred at 180° C. for 2 h under microwave irradiate conditions. The mixture was then filtered through celite and diluted with water (20 mL). The mixture extracted with EtOAc (15 mL*3). The organic layer was washed with brine (15 mL*3), dried over Na$_2$SO$_4$ and concentrated in vacuo. The resulting residue was purified using prep-TLC (petroleum ether:EtOAc=2:3) to provide compound 60 (40 mg, yield: 87.0%). $^1$H-NMR (DMSO-d$_6$, 400 MHz) δ 8.48 (d, J=4.8 Hz, 1H), 7.98~8.06 (m, 4H), 7.71~7.80 (m, 4H), 7.31~7.44 (m, 4H), 6.36 (s, 2H), 3.39 (s, 3H), 2.94 (s, 3H), 2.80 (d, J=4.8 Hz, 3H). MS (M+H)$^+$: 622.

Example 15

Preparation of Compound 61

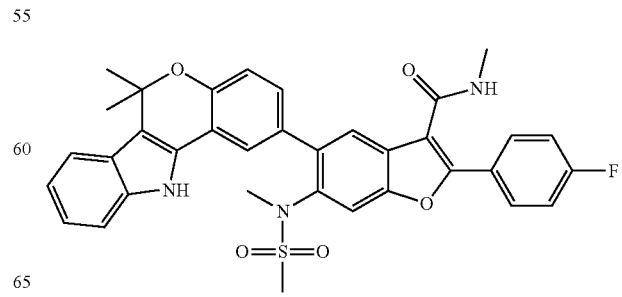

Step 1—Synthesis of 2-bromo-6,6-dimethyl-6,11-dihydrochromeno[4,3-b]indole

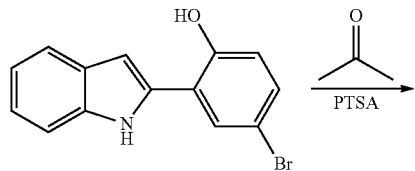

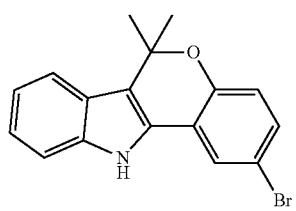

To the solution of 4-bromo-2-(1H-indol-2-yl)phenol (200 mg, 0.69 mmol) in acetone (5 mL) was added PTSA (26 mg, 0.14 mmol), it was stirred at 150° C. in a sealed tube. Then the solvent was removed and the crude product was purified using prep-TLC to provide the desired product of 2-bromo-6,6-dimethyl-6,11-dihydrochromeno[4,3-b]indole (180 mg, yield: 79.3%). MS (M+H)$^+$: 327/329.

Step 2—Synthesis of 6,6-dimethyl-2-(4,4,5,5-tetramethyl-1,3,2-dioxaborolan-2-yl)-6,11-dihydrochromeno[4,3-b]indole

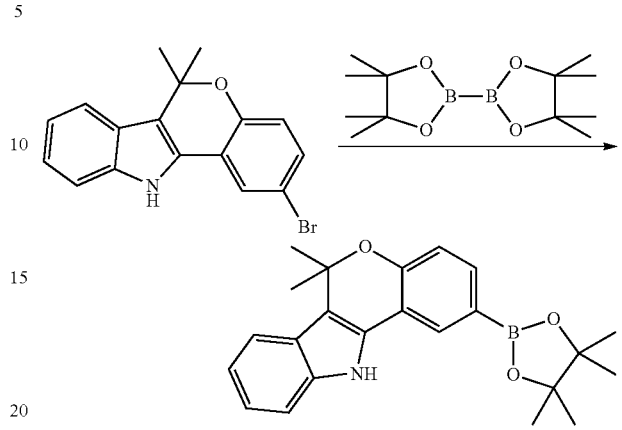

To a flask were added 2-bromo-6,6-dimethyl-6,11-dihydrochromeno[4,3-b]indole (100 mg, 0.30 mmol), (BPin)$_2$ (116 mg, 0.46 mmol), Pd(dppf)Cl$_2$ (10 mg), AcOK (74 mg, 0.76 mmol) and toluene (1.2 mL), it was stirred at 100° C. TLC showed the starting material was consumed completely. The solvent was removed and the crude product was purified using prep-TLC to provide the product of 6,6-dimethyl-2-(4,4,5,5-tetramethyl-1,3,2-dioxaborolan-2-yl)-6,11-dihydrochromeno[4,3-b]indole (80 mg, yield: 70.2%). $^1$H-NMR (CDCl$_3$, 400 MHz) δ 8.45 (s, 1H), 7.81 (s, 1H), 7.65 (d, J=7.6 Hz, 1H), 7.57 (d, J=8.0 Hz, 1H), 7.37 (d, J=8.0 Hz, 1H), 7.21~7.13 (m, 2H), 6.94 (d, J=8.0 Hz, 1H), 1.83 (s, 6H), 1.39 (s, 12H). MS (M+H)$^+$: 375.

Step 3—Synthesis of 5-(6,6-dimethyl-6,11-dihydrochromeno[4,3-b]indol-2-yl)-2-(4-fluorophenyl)-N-methyl-6-(N-methylmethylsulfonamido)benzofuran-3-carboxamide (Compound 61)

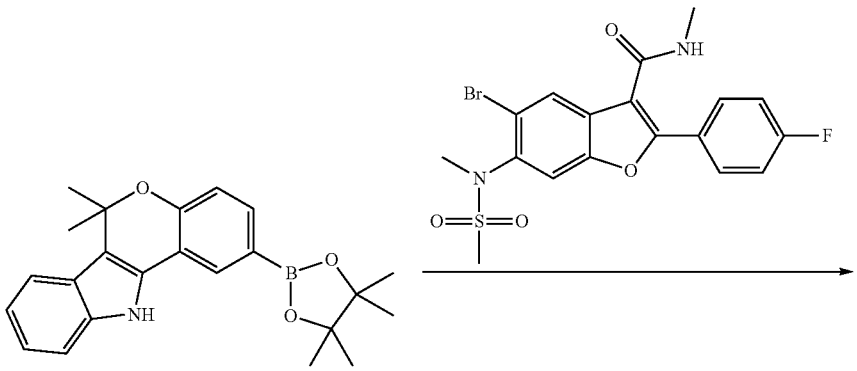

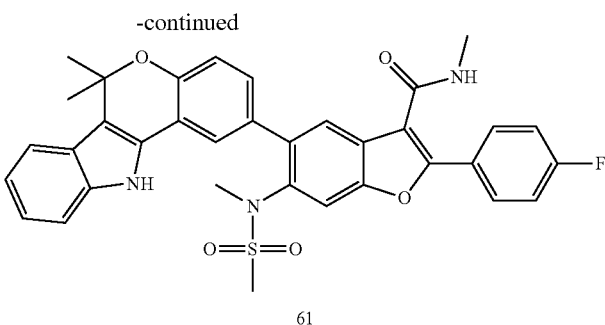

61

Compound 61 was made using the method described in step 6 of Example 1. $^1$H-NMR (CDCl$_3$, 400 MHz) δ 8.89 (s, 1H), 7.86 (d, J=5.2 Hz, 2H), 7.30 (d, J=2.4 Hz, 1H), 7.60 (s, 1H), 7.55 (d, J=8.0 Hz, 1H), 7.48 (s, 1H), 7.43 (d, J=8.0 Hz, 1H), 7.22~7.11 (m, 5H), 6.95 (d, J=4.4 Hz, 1H), 6.0 (s, 1H), 2.96 (t, J=8.8 Hz, 9H), 1.78 (s, 6H). MS (M+H)$^+$: 624.

Compounds 62, depicted in the table below, were prepared using the method described above and substituting the appropriate reactants and/or reagents.

| Compound No | Structure | NMR | MS (M + H)$^+$ |
|---|---|---|---|
| 62 | (structure shown) | 1H-NMR (Methanol-d4, 400 MHz) δ 8.49 (s, 1H), 8.48 (s, 1H), 7.95~7.91 (m, 2H), 7.83 (d, J = 7.6 Hz, 1H), 7.75 (d, J = 6.8 Hz, 1H), 7.66 (s, 2H), 7.39. (t, J = 8.4 Hz, 2H), 7.26~7.21 (m, 3H), 7.12~7.09 (m, 1H), 6.96~6.90 (m, 3H), 6.76 (d, J = 12.8 Hz, 1H), 3.20 (s, 3H), 2.91 (s, 3H), 2.77 (s, 3H). | 673 |

Example 16

Preparation of Compound 63

63

Step 1—Synthesis of 2-(5-bromo-2-methoxyphenyl)-1H-indole

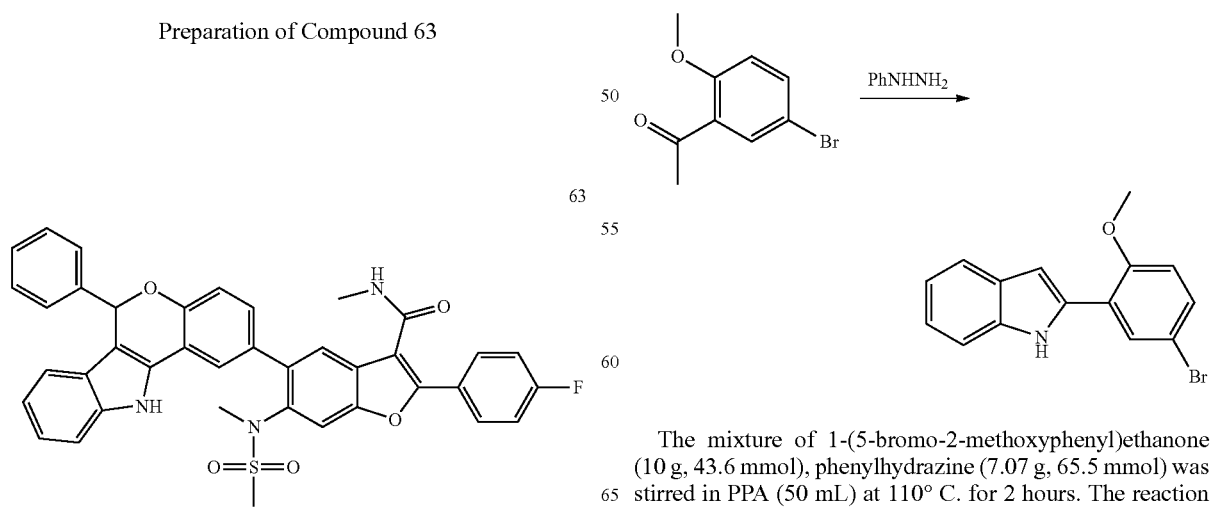

The mixture of 1-(5-bromo-2-methoxyphenyl)ethanone (10 g, 43.6 mmol), phenylhydrazine (7.07 g, 65.5 mmol) was stirred in PPA (50 mL) at 110° C. for 2 hours. The reaction mixture was added to water and basified to pH=7, then extracted with ethyl acetate and washed with brine, dried over Na₂SO₄. After concentrated, the resulting residue was purified using column chromatography to provide the product of 2-(5-bromo-2-methoxyphenyl)-1H-indole (10 g, yield: 71%). ¹H-NMR (CDCl₃, 400 MHz) δ 9.57 (s, 1H), 7.93 (d, J=2.4 Hz, 1H), 7.63 (d, J=8.0 Hz, 1H), 7.34~7.42 (m, 2H), 7.09~7.21 (m, 2H), 6.90 (d, J=8.8 Hz, 1H), 4.00 (s, 3H). MS (M+H)⁺: 302/304.

Step 2—Synthesis of 2-(2-methoxy-5-(4,4,5,5-tetramethyl-1,3,2-dioxaborolan-2-yl)phenyl)-1H-indole

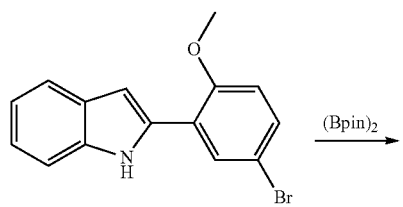

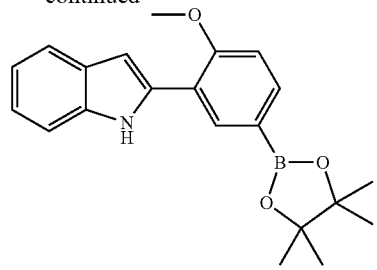

To a stirring solution of 2-(5-bromo-2-methoxyphenyl)-1H-indole (1.25 g, 3.90 mmol) in Toluene, KOAc (1.15 g, 11.7 mmol) and (Bpin)₂ (1.5 g, 5.86 mmol) were added, then Pd(dppf)Cl₂ (150 mg) was added under N₂ protection. The mixture was stirred at 90° C. for 3 hours. The mixture was concentrated in vacuo. The resulting residue was purified using column chromatography to provide the product of 2-(2-methoxy-5-(4,4,5,5-tetramethyl-1,3,2-dioxaborolan-2-yl)phenyl)-1H-indole (1.0 mg, yield: 77%). ¹H-NMR (CDCl₃, 400 MHz) δ 9.51 (s, 1H), 8.24 (d, J=1.6 Hz, 1H), 7.68~7.71 (m, 1H), 7.59 (d, J=7.6 Hz, 1H), 7.37 (d, J=8.0 Hz, 1H), 6.97~7.15 (m, 4H), 4.00 (s, 3H), 1.33 (s, 12H). MS (M+H)⁺: 350.

Step 3—Synthesis of 5-(3-(1H-indol-2-yl)-4-methoxyphenyl)-2-(4-fluorophenyl)-N-methyl-6-(N-methylmethylsulfonamido)benzofuran-3-carboxamide

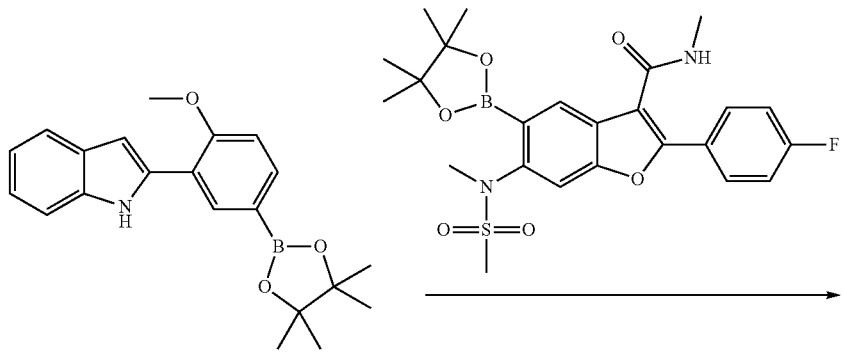

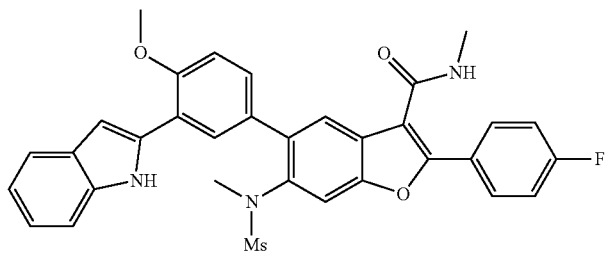

105

To a mixture of 2-(2-methoxy-5-(4,4,5,5-tetramethyl-1,3,2-dioxaborolan-2-yl)phenyl)-1H-indole (2.3 g, 6.59 mmol), (2.0 g, 4.39 mmol) and K$_3$PO$_4$·3H$_2$O (3.5 mg, 13.2 mmol) in DMF (20 mL), Pd(PPh$_3$)$_4$ (300 mg) was added under N$_2$ protection. The mixture was heated at 90° C. for 3 hours. Water was added, extracted with ethyl acetate and washed with brine, dried over Na$_2$SO$_4$. After concentrated, the resulting residue was purified using column chromatography to provide the product of 5-(3-(1H-indol-2-yl)-4-methoxyphenyl)-2-(4-fluorophenyl)-N-methyl-6-(N-methylmethylsulfonamido)benzofuran-3-carboxamide (800 mg, yield: 31%). $^1$H-NMR (CDCl$_3$, 400 MHz) δ 9.66 (s, 1H), 7.89~7.93 (m, 3H), 7.78 (s, 1H), 7.56 (d, J=7.2 Hz, 1H), 7.32~7.39 (m, 2H), 7.03~7.21 (m, 5H), 6.91 (d, J=1.2 Hz, 1H), 5.83 (d, J=4.8 Hz, 1H), 4.03 (s, 3H), 3.07 (s, 3H), 2.94 (d, J=4.8 Hz, 3H), 2.75 (s, 3H). MS (M+H)$^+$: 598.

Step 4—Synthesis of 2-(4-fluorophenyl)-5-(4-hydroxy-3-(1H-indol-2-yl)phenyl)-N-methyl-6-(N-methylmethylsulfonamido)benzofuran-3-carboxamide

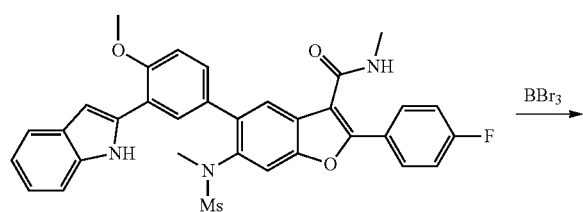

106

-continued

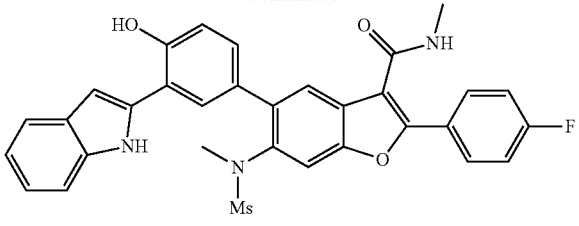

To a solution of 5-(3-(1H-indol-2-yl)-4-methoxyphenyl)-2-(4-fluorophenyl)-N-methyl-6-(N-methylmethylsulfonamido)benzofuran-3-carboxamide (100 g, 0.16 mmol) in dichloromethane (2 mL) was added dropwise BBr$_3$ (0.2 mL) at 0° C., Then warmed up to room temperature and stirred for 5 hours. Water was added, extracted with dichloromethane and washed with brine, dried over Na$_2$SO$_4$. After concentrated, the resulting residue was purified using Prep-TLC to provide the product of 2-(4-fluorophenyl)-5-(4-hydroxy-3-(1H-indol-2-yl)phenyl)-N-methyl-6-(N-methylmethylsulfonamido)benzofuran-3-carboxamide (30 mg, yield: 31%). $^1$H-NMR (CDCl$_3$, 400 MHz) δ 9.30 (s, 1H), 8.75 (s, 1H), 7.79~8.30 (m, 2H), 7.54 (d, J=7.6 Hz, 1H), 7.50 (s, 1H), 7.37 (d, J=1.6 Hz, 1H), 6.91~7.19 (m, 7H), 6.65 (d, J=1.2 Hz, 1H), 6.01 (d, J=4.4 Hz, 1H), 2.95 (d, J=4.8 Hz, 3H), 2.61 (s, 3H), 2.43 (s, 3H). MS (M+H)$^+$: 584.

Step 5—Synthesis of 2-(4-fluorophenyl)-N-methyl-6-(N-methylmethylsulfonamido)-5-(6-phenyl-6,11-dihydrochromeno[4,3-b]indol-2-yl)benzofuran-3-carboxamide (compound 63)

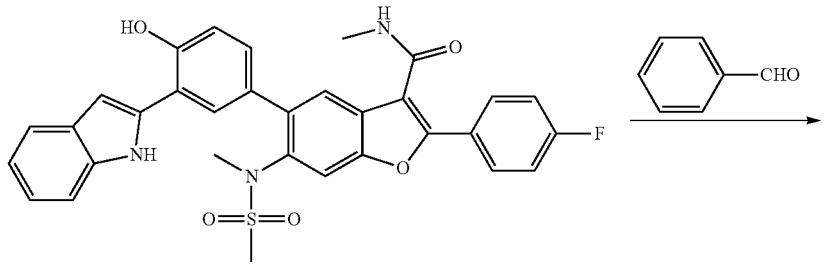

A mixture of 2-(4-fluorophenyl)-5-(4-hydroxy-3-(1H-indol-2-yl)phenyl)-N-methyl-6-(N-methylmethylsulfonamido)benzofuran-3-carboxamide (50 g, 0.08 mmol), PTSA (3.0 mg, 0.017 mmol), and benzaldehyde (42 mg, 0.41 mmol) in xylene (2 mL) was stirred at 130° C. for 2 h under microwave. Water was added, extracted with EtOAc, the organic layer was washed with brine, dried over $Na_2SO_4$. After concentrated, the resulting residue was purified using prep-TLC to provide the product of compound 63 (20 mg, yield: 38%). $^1$H-NMR (CDCl$_3$, 400 MHz) δ 8.96 (s, 1H), 7.88~7.92 (m, 2H), 7.76 (s, 1H), 7.65 (s, 1H), 7.50 (s, 1H), 7.32~7.47 (m, 6H), 7.14~7.17 (m, 4H), 6.96~6.99 (m, 2H), 6.86 (s, 1H), 6.55 (s, 1H), 5.91 (d, J=4.8 Hz, 1H), 3.02 (s, 3H), 2.98 (d, J=4.8 Hz, 3H), 2.94 (s, 3H). MS (M+H)$^+$: 672.

Compounds 64 and 65, depicted in the table below, were prepared using the method described above and substituting the appropriate reactants and/or reagents.

Step 1—Synthesis of 2-chloro-7-fluoro-6-(thiophen-2-yl)-6,11-dihydropyrido[2',3':5,6]pyrano[4,3-b]indole

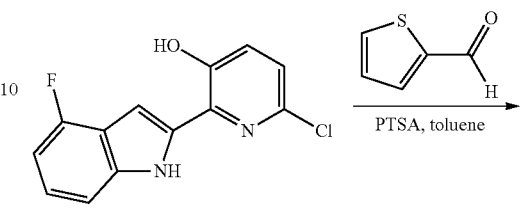

| Compound No | Structure | NMR | MS (M + H)$^+$ |
|---|---|---|---|
| 64 | 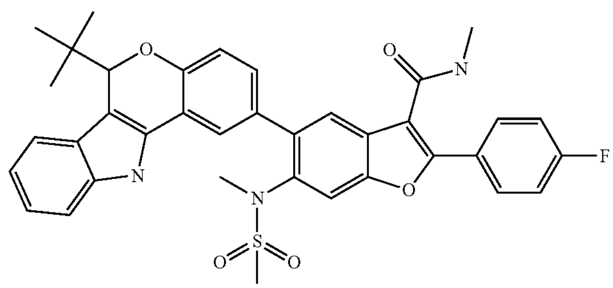 [SMILES: CNC(=O)c1c(-c2ccc(F)cc2)oc2cc(N(C)S(C)(=O)=O)c(-c3ccc4c(c3)-c3[nH]c5ccccc5c3C(C(C)(C)C)O4)cc12] | $^1$H-NMR (CDCl$_3$, 400 MHz) δ 8.95 (s, 1H), 7.46~7.88 (m, 7H), 7.11~7.22 (m, 5H), 6.95 (d, J = 8.4 Hz, 1H), 5.92~5.95 (m, 1H), 5.43 (s, 1H), 3.01 (d, J = 4.8 Hz, 3H), 2.96 (s, 3H), 2.92 (s, 3H). | 652 |
| 65 | 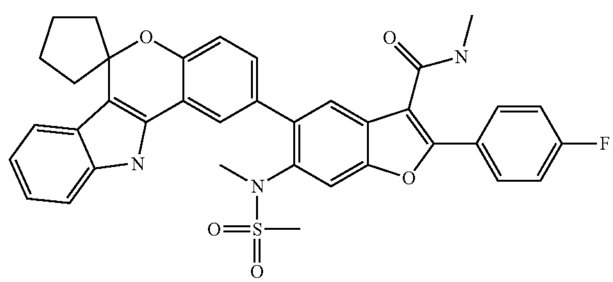 [SMILES: CNC(=O)c1c(-c2ccc(F)cc2)oc2cc(N(C)S(C)(=O)=O)c(-c3ccc4c(c3)-c3[nH]c5ccccc5c3C3(CCCC3)O4)cc12] | $^1$H-NMR (CDCl$_3$, 400 MHz) δ 9.95 (s, 1H), 7.80~7.83 (m, 2H), 7.64 (s, 1H), 7.41~7.50 (m, 4H), 7.12~7.20 (m, 3H), 7.07~7.11 (m, 2H), 6.87 (d, J = 8.0 Hz, 1H), 6.07~6.08 (m, 1H), 2.95 (d, J = 4.8 Hz, 3H), 2.92 (s, 6H), 2.13~2.16 (m, 4H), 2.00~2.02 (m, 2H), 1.82~1.86 (m, 2H). | 650 |

Example 17

Preparation of Compound 66

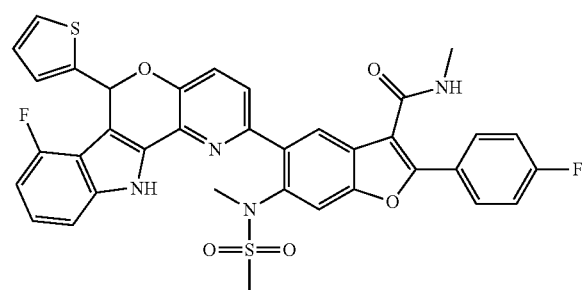

66

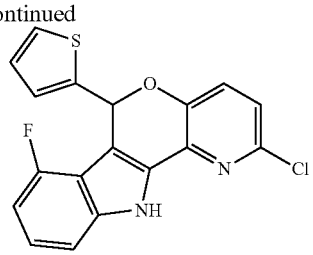

A mixture of compound 6-chloro-2-(4-fluoro-1H-indol-2-yl)pyridin-3-ol (60 mg, 0.224 mmol), thiophene-2-carbaldehyde (50 mg, 0.448 mmol) and PTSA (85 mg, 0.448 mmol) in toluene (1 mL) was stirred at 60° C. for 4 hours. The mixture was then diluted with water (20 mL) and extracted with EtOAc (15 mL*3). The organic layer was washed with brine (20 mL), dried over $Na_2SO_4$ and concentrated in vacuo. The resulting residue was purified using prep-TLC (petroleum ether:EtOAc=20:1) to provide 2-chloro-7-fluoro-6-(thiophen-2-yl)-6,11-dihydropyrido[2',3':5,6]pyrano[4,3-b]indole (40 mg, yield: 50.0%). $^1$H-NMR (CDCl$_3$, 400 MHz) δ

9.28 (s, 1H), 7.07~7.18 (m, 5H), 6.98 (d, J=8.4 Hz, 1H), 6.81~6.86 (m, 2H), 6.66~6.70 (m, 1H). MS (M+H)⁺: 357/359.

Step 2—Synthesis of 5-(7-fluoro-6-(thiophen-2-yl)-6,11-dihydropyrido[2',3':5,6]pyrano[4,3-b]indol-2-yl)-2-(4-fluorophenyl)-N-methyl-6-(N-methylmethylsulfonamido)benzofuran-3-carboxamide (Compound 66)

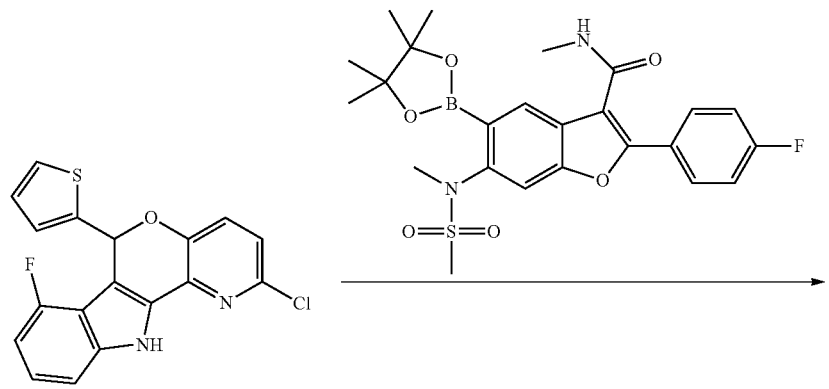

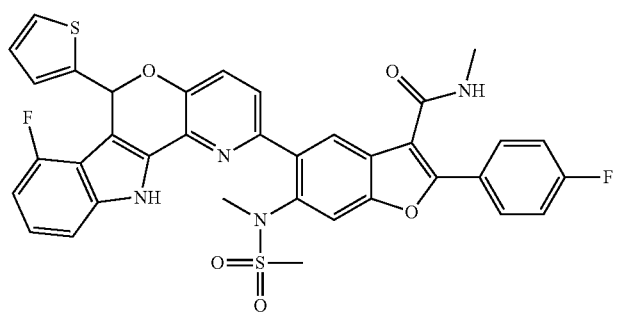

66

To a degassed solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (110 mg, 0.22 mmol), 2-chloro-7-fluoro-6-(thiophen-2-yl)-6,11-dihydropyrido[2',3':5,6]pyrano[4,3-b]indole (78 mg, 0.22 mmol) and $K_3PO_4$ (176 mg, 0.66 mmol) in dioxane/$H_2O$ (0.8 mL/0.2 mL) was added $Pd_2(dba)_3$ (10 mg, 0.011 mmol) and X-Phos (10 mg, 0.022 mmol) under $N_2$. The mixture was heated to 80° C. and then stirred for 1 hour. The reaction mixture was cooled to RT, diluted with EtOAc and filtered. The filtrate was washed with $H_2O$, brine, dried over $Na_2SO_4$. After concentrated, the resulting residue was purified using Prep-TLC (petroleum ether:EtOAc=1:1) to provide the desired product of compound 66 (65 mg, yield 42.7%). ¹H-NMR (CDCl₃, 400 MHz) δ 9.94 (s, 1H), 7.96 (s, 1H), 7.89~7.91 (m, 2H), 7.51 (s, 1H), 7.04~7.34 (m, 8H), 6.91 (s, 1H), 6.85 (t, J=4.0 Hz, 1H), 6.68 (t, J=9.2 Hz, 1H), 5.81 (br s, J=3.6 Hz, 1H), 3.02 (s, 3H), 2.93 (s, 6H). MS (M+H)⁺: 697.

Compound 67, depicted in the table below, was prepared using the method described above and substituting the appropriate reagents and/or reactants.

| Compound No | Structure | NMR | MS (M + H)+ |
|---|---|---|---|
| 67 | 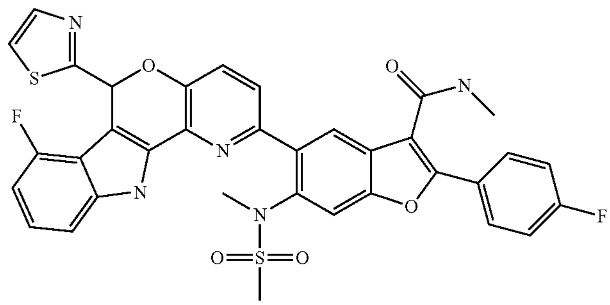 [SMILES: CNC(=O)c1c(-c2ccc(F)cc2)oc2cc(N(C)S(C)(=O)=O)c(-c3ccc4c(n3)-c3[nH]c5cccc(F)c5c3C(c3nccs3)O4)cc12] | 1H-NMR (CDCl3, 400 MHz) δ 10.09 (s, 1H), 7.96 (s, 1H), 7.85~7.89 (m, 2H), 7.75 (d, J = 3.2 Hz, 1H), 7.49 (s, 1H), 7.34 (d, J = 8.4 Hz, 1H), 7.05~7.26 (m, 7H), 6.67~6.72 (m, 1H), 5.87 (br s, J = 4.4 Hz, 1H), 3.02 (s, 3H), 2.91~2.95 (m, 6H). | 698 |

Example 18

Preparation of Compound 68

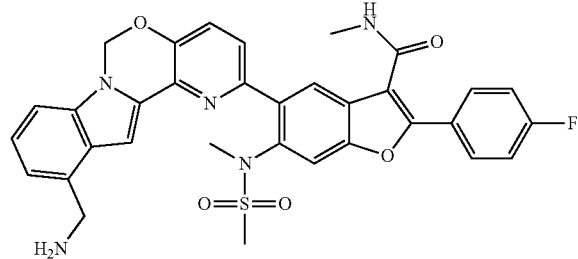 [SMILES: CNC(=O)c1c(-c2ccc(F)cc2)oc2cc(N(C)S(C)(=O)=O)c(-c3ccc4c(n3)-c3cc5c(CN)cccc5n3CO4)cc12]

To a solution of Compound 12 (150 mg, 0.24 mmol) in MeOH (15 mL) was added 0.5 mL of NH$_3$.H$_2$O and Raney Ni (30 mg). The mixture was degassed with H$_2$ (30 psi) and then stirred for 5 hours at room temperature. Then the mixture was filtered and the filtrate was concentrated in vacuo to provide the pure compound 68 (130 mg, yield: 86%) by prep-HPLC. 1H-NMR (Methanol-d4, 400 MHz) δ 7.90 (dd, J$_1$=5.6 Hz, J$_2$=8.4 Hz, 2H), 7.84 (d, J=12.4 Hz, 2H), 7.51 (s, 2H), 7.45 (d, J=8.4 Hz, 1H), 7.19~7.26 (m, 4H), 7.12 (d, J=7.2 Hz, 1H), 6.01 (s, 2H), 4.27 (s, 2H), 3.25 (d, J=4.8 Hz, 3H), 2.89 (s, 3H), 2.87 (s, 3H). MS (M+H)+: 626.

Compound 69, depicted in the table below, was prepared using the method described above and substituting the appropriate reagents and/or reactants.

| Compound No | Structure | NMR | MS (M + H)+ |
|---|---|---|---|
| 69 | 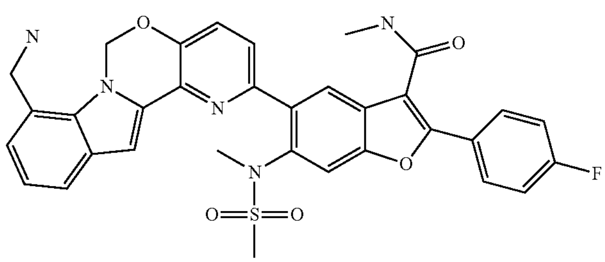 [SMILES: CNC(=O)c1c(-c2ccc(F)cc2)oc2cc(N(C)S(C)(=O)=O)c(-c3ccc4c(n3)-c3cc5cccc(CN)c5n3CO4)cc12] | 1H-NMR (CDCl3, 400 MHz) δ 7.94 (s, 1H), 7.89~7.93 (m, 2H), 7.62 (s, 1H), 7.54 (d, J = 8.0 Hz, 1H), 7.40 (s, 2H), 7.12~7.18 (m, 3H), 6.99~7.07 (m, 2H), 6.40 (s, 2H), 5.91 (s, 1H), 4.13 (s, 2H), 3.31 (s, 3H), 2.93 (d, J = 4.8 Hz, 3H), 2.62 (s, 3H). | 626 |

Example 19

Preparation of Compound 70

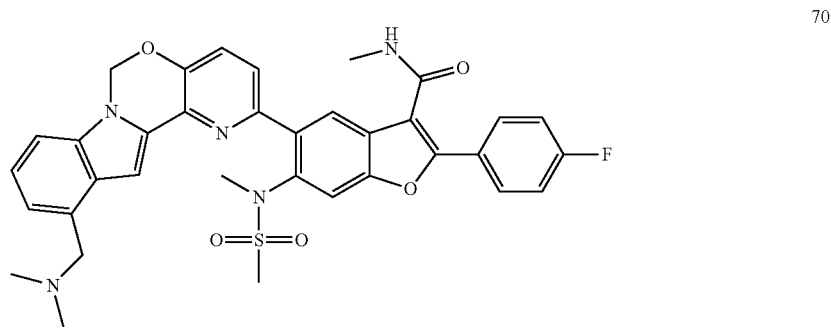

70

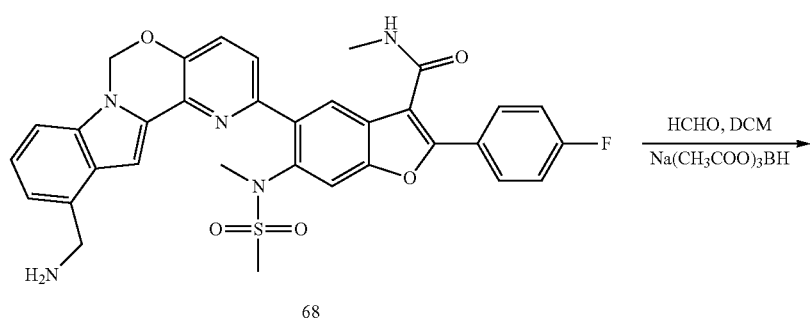

68

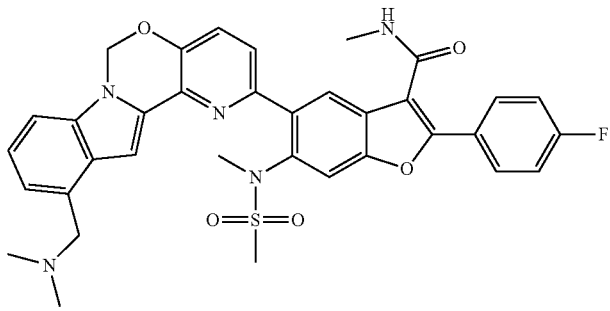

70

To a solution of compound 68 (50 mg, 0.08 mmol) in anhydrous dichloromethane (1 mL) was added HCHO (aq. in water, 0.5 mL) at room temperature. The mixture was stirred for 3 hours at room temperature, then Na(CH$_3$COO)$_3$BH (102 mg, 0.48 mmol) was added dropwise and the reaction mixture was stirred another 5 hours at room temperature. And then the mixture was quenched with water and extracted with dichloromethane. The organic phase was washed with brine, dried over Na$_2$SO$_4$, and concentrated to provide the compound 70 (30 mg, yield: 58%) by the prep-HPLC. $^1$H-NMR (Methanol-d4, 400 MHz) δ 7.88 (dd, J$_1$=5.6 Hz, J$_2$=8.8 Hz, 2H), 7.80 (d, J=18.4 Hz, 2H), 7.46 (s, 2H), 7.37 (d, J=8.0 Hz, 1H), 7.26 (s, 1H), 7.14~7.20 (m, 3H), 7.04 (d, J=7.2 Hz, 1H), 5.97 (s, 2H), 3.89 (s, 2H), 3.24 (d, J=6.4 Hz, 3H), 2.85 (s, 3H), 2.81 (s, 3H), 2.35 (s, 6H). MS (M+H)$^+$: 654.

Compound 71, depicted in the table below, was prepared using the method described above and substituting the appropriate reagents and/or reactants.

| Compound No | Structure | NMR | MS (M + H)+ |
|---|---|---|---|
| 71 | 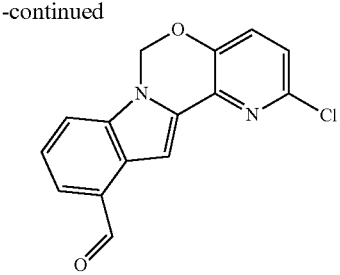 | ¹H-NMR (CDCl₃, 400 MHz) δ 7.92~7.95 (m, 3H), 7.76~7.78 (m, 1H), 7.60 (s, 1H), 7.51~7.58 (m, 2H), 7.40 (s, 1H), 7.15 (t, J = 8.4 Hz, 4H), 6.33 (d, J = 4.8 Hz, 1H), 6.19 (s, 2H), 4.59 (s, 2H), 3.29 (s, 3H), 2.96 (d, J = 4.8 Hz, 3H), 2.80 (s, 6H), 2.74 (s, 3H). | 654 |

Example 20

Preparation of Compound 72

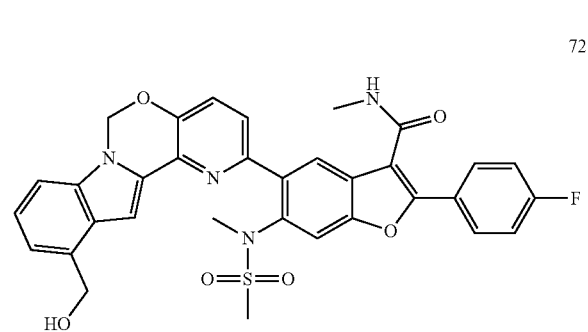 [SMILES: CNC(=O)c1c(-c2ccc(F)cc2)oc2cc(N(C)S(C)(=O)=O)c(-c3ccc4c(n3)-c3cc5c(CO)cccc5n3CO4)cc12]

Step 1—Synthesis of 2-chloro-6H-pyrido[2',3':5,6][1,3]oxazino[3,4-a]indole-11-carbaldehyde

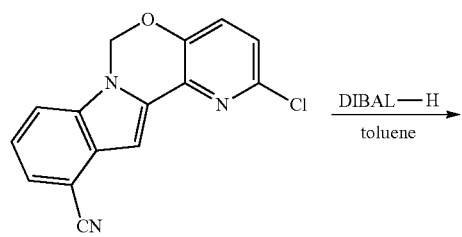

To a solution of 2-chloro-6H-pyrido[2',3':5,6][1,3]oxazino[3,4-a]indole-11-carbonitrile (500 mg, 1.77 mmol) in toluene (10 mL) was added DIBAL-H (505 mg, 3.55 mmol) in portion under nitrogen at −78° C. and then the mixture was stirred at −78° C. for 6 hours. The reaction mixture was quenched with ice water and extracted with EtOAc. Then the combined organic phase was washed with brine, dried over Na₂SO₄ and concentrated in vacuo to provide the 2-chloro-6H-pyrido[2',3':5,6][1,3]oxazino[3,4-a]indole-11-carbaldehyde (200 mg, yield: 40%) through the column chromatography (petroleum ether:EtOAc=5:1~2:1). ¹H-NMR (CDCl₃, 400 MHz) δ 10.29 (s, 1H), 8.03 (s, 1H), 7.69 (dd, J₁=0.8 Hz, J₂=7.2 Hz, 1H), 7.56 (d, J=8.4 Hz, 1H), 7.44 (t, J=8.0 Hz, 1H), 7.38 (d, J=8.4 Hz, 1H), 7.22 (d, J=8.4 Hz, 1H), 6.05 (s, 2H). MS (M+H)⁺: 285/287.

Step 2—Synthesis of 2-(4-fluorophenyl)-5-(11-formyl-6H-pyrido[2',3':5,6][1,3]oxazino[3,4-a]indol-2-yl)-N-methyl-6-(N-methylmethylsulfonamido)benzofuran-3-carboxamide

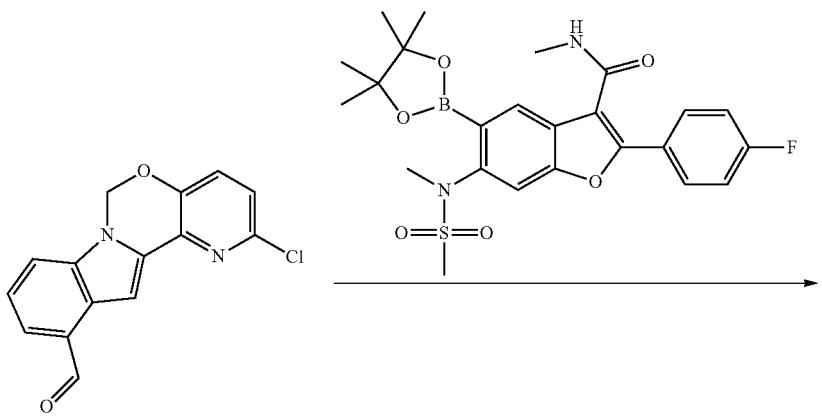

-continued

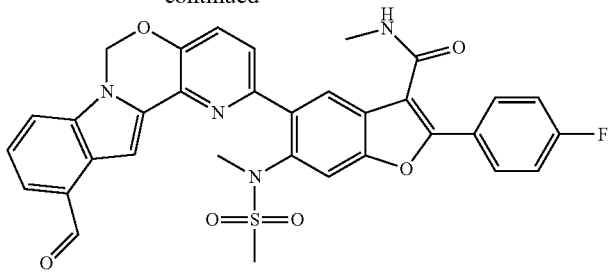

To a solution of 2-chloro-6H-pyrido[2',3':5,6][1,3]oxazino [3,4-a]indole-11-carbaldehyde (31 mg, 0.11 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (50 mg, 0.10 mmol) and $K_3PO_4.3H_2O$ (53 mg, 0.19 mmol) in 1,4-dioxane (1 mL) and water (0.2 mL) was added X-Phos (5 mg) and $Pd_2(dba)_3$ (5 mg) under nitrogen. The mixture was heated at 100° C. for 16 hours, and then filtered through the celite pad. The filtrate was extracted with EtOAc, then the combined organic phase was washed with brine, dried over $Na_2SO_4$ and concentrated in vacuo to provide the 2-(4-fluorophenyl)-5-(11-formyl-6H-pyrido[2',3':5,6][1,3]oxazino[3,4-a]indol-2-yl)-N-methyl-6-(N-methylmethylsulfonamido)benzofuran-3-carboxamide (50 mg, yield: 80%) by the prep-TLC (dichloromethane:MeOH=30:1). MS (M+H)+: 625.

Step 3—Synthesis of 2-(4-fluorophenyl)-5-(11-(hydroxymethyl)-6H-pyrido[2',3':5,6][1,3]oxazino[3,4-a]indol-2-yl)-N-methyl-6-(N-methylmethylsulfonamido)benzofuran-3-carboxamide (Compound 72)

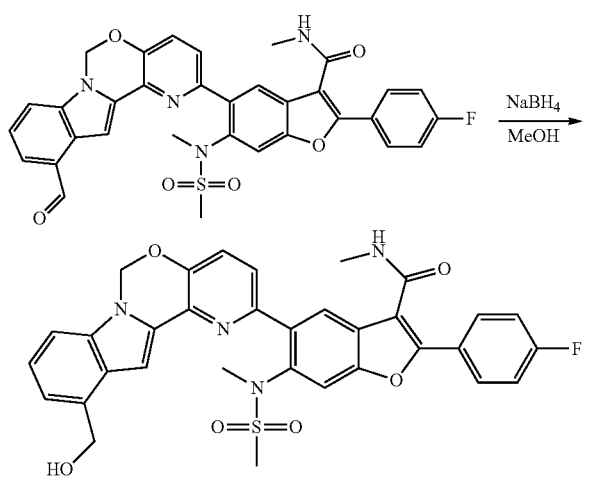

To a solution of 2-(4-fluorophenyl)-5-(11-formyl-6H-pyrido[2',3':5,6][1,3]oxazino[3,4-a]indol-2-yl)-N-methyl-6-(N-methylmethylsulfonamido)benzofuran-3-carboxamide (50 mg, 0.08 mmol) in MeOH (2 mL) was added $NaBH_4$ (12 mg, 0.32 mmol, diluted with 2 mL of MeOH) in portion under nitrogen at 0° C. and then the mixture was stirred at room temperature for 1 hour. The reaction mixture was quenched with water and extracted with dichloromethane. Then the combined organic phase was washed with brine, dried over $Na_2SO_4$ and concentrated in vacuo to provide the compound 72 (30 mg, yield: 60%) by the prep-HPLC. $^1$H-NMR ($CDCl_3$, 400 MHz) δ 7.95~7.99 (m, 3H), 7.63 (s, 1H), 7.47 (dd, $J_1$=8.4 Hz, $J_2$=14.8 Hz, 2H), 7.37 (s, 1H), 7.16~7.20 (m, 3H), 7.12 (t, J=8.0 Hz, 1H), 6.87 (d, J=7.6 Hz, 1H), 6.37 (brs, 1H), 5.93 (s, 2H), 4.81 (s, 2H), 3.31 (s, 3H), 2.87 (d, J=5.2 Hz, 3H), 2.79 (s, 3H). MS (M+H)+: 627.

Example 21

Preparation of Compound 73

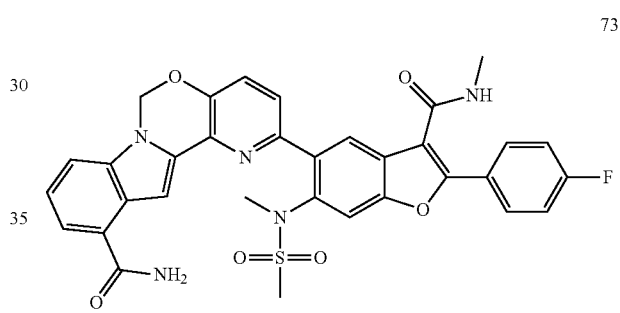

Step 1—Synthesis of methyl 2-chloro-6H-pyrido[2',3':5,6][1,3]oxazino[3,4-a]indole-11-carboxylate

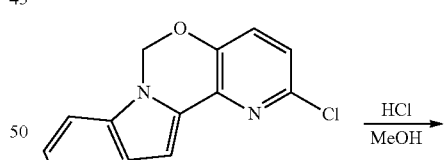

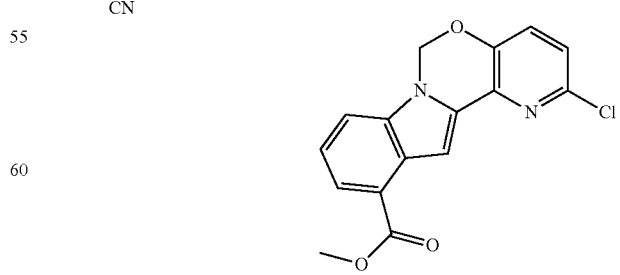

A mixture of 2-chloro-6H-pyrido[2',3':5,6][1,3]oxazino[3,4-a]indole-11-carbonitrile (300 mg, 1.06 mmol) in MeOH (4N HCl, 15 mL) was heated at 80° C. for overnight. The reaction mixture was concentrated in vacuo. The resulting residue was suspended in water and extracted with EtOAc. The organic layers was washed with brine (100 mL), dried over Na₂SO₄, filtered and concentrated in vacuo. The resulting residue was purified using column chromatography (petroleum ether:ethyl acetate=5:1) to provide product of methyl 2-chloro-6H-pyrido[2',3':5,6][1,3]oxazino[3,4-a]indole-11-carboxylate (120 mg, yield: 36%). ¹H-NMR (CDCl₃, 400 MHz) δ 7.98 (dd, J=7.2 Hz, 1.2 Hz, 1H), 7.85 (s, 1H), 7.50 (d, J=8.0 Hz, 1H), 7.33~7.38 (m, 2H), 7.21 (d, J=8.0 Hz, 1H), 5.97 (s, 2H), 4.03 (s, 3H). MS (M+H)⁺: 315/317.

Step 2—Synthesis of methyl 2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indole-11-carboxylate

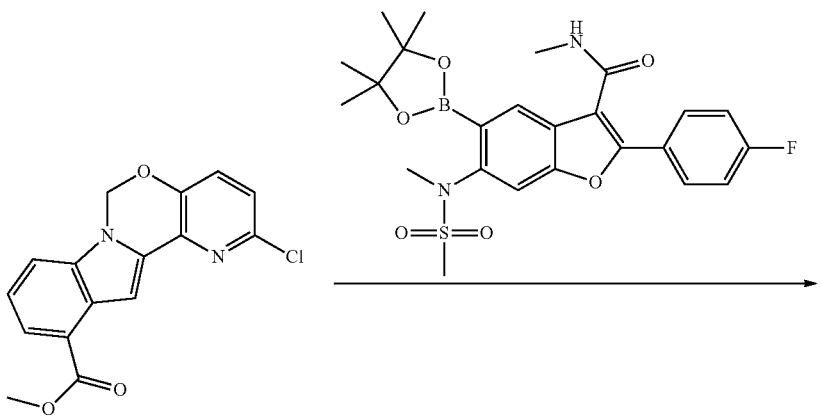

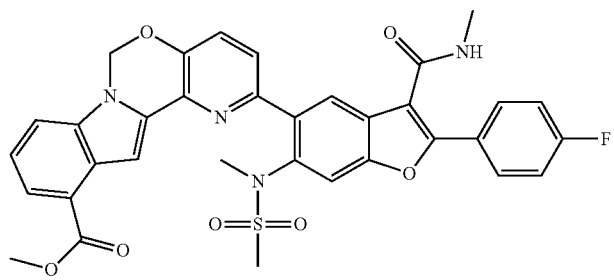

To a degassed solution of methyl 2-chloro-6H-pyrido[2',3':5,6][1,3]oxazino[3,4-a]indole-11-carboxylate (40 mg, 0.13 mmol) and 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (50 mg, 0.10 mmol) in 1,4-dioxane (3 mL), $Pd_2(dba)_3$ (10 mg), X-Phos (10 mg) and $K_3PO_4$ (60 mg, 0.23 mmol) were added under $N_2$. The mixture was heated to 100° C. for 2 hours. The reaction mixture was cooled to RT, filtered and washed with EtOAc. The filtrate was washed with $H_2O$, brine, dried over $Na_2SO_4$. After concentrated, the resulting residue was purified using column chromatography (dichloromethane:MeOH=100:1) to provide the product of methyl 2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indole-11-carboxylate (55 mg, yield: 84%). MS $(M+H)^+$: 655.

Step 3—Synthesis of 2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indole-11-carboxylic acid

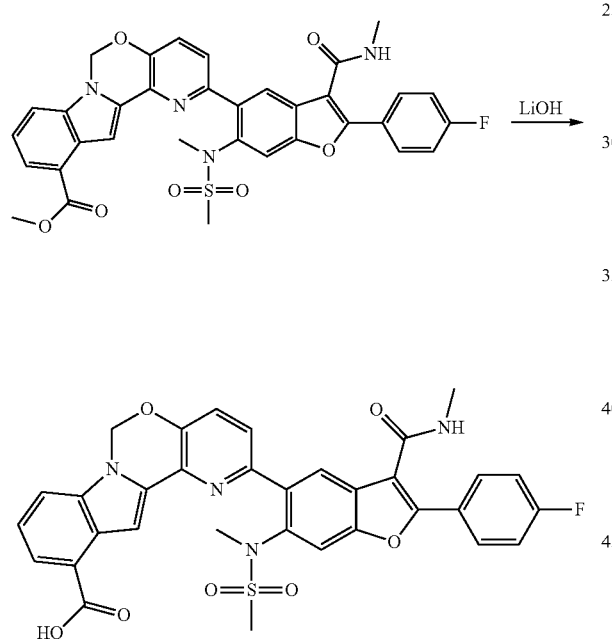

To a solution of methyl 2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indole-11-carboxylate (160 mg, 0.24 mmol) in dioxane (2 mL) and water (2 mL), $LiOH \cdot H_2O$ (30 mg, 0.71 mmol) was added and the mixture was heated to reflux for 2 hours. Then removed dioxane and the mixture was diluted with water, adjusted to pH=3~4 by 1 N HCl, and extracted with EtOAc. The combined organic phases were washed with brine, dried over $Na_2SO_4$, filtered and concentrated in vacuo. The resulting residue was purified using PTLC (dichloromethane:MeOH=20:1) to provide 2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indole-11-carboxylic acid (120 mg, yield: 76%). $^1$H-NMR (Methanol-d4, 400 MHz) δ 7.97~8.02 (m, 2H), 7.86~7.91 (m, 3H), 7.81 (s, 1H), 7.74 (d, J=8.4 Hz, 1H), 7.59 (s, 2H), 7.31~7.36 (m, 1H), 7.24~7.29 (m, 2H), 6.14 (s, 2H), 3.35 (s, 3H), 2.96 (s, 3H), 2.88 (s, 3H). MS $(M+H)^+$: 641.

Step 4—Synthesis of 2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indole-11-carboxamide (Compound 73)

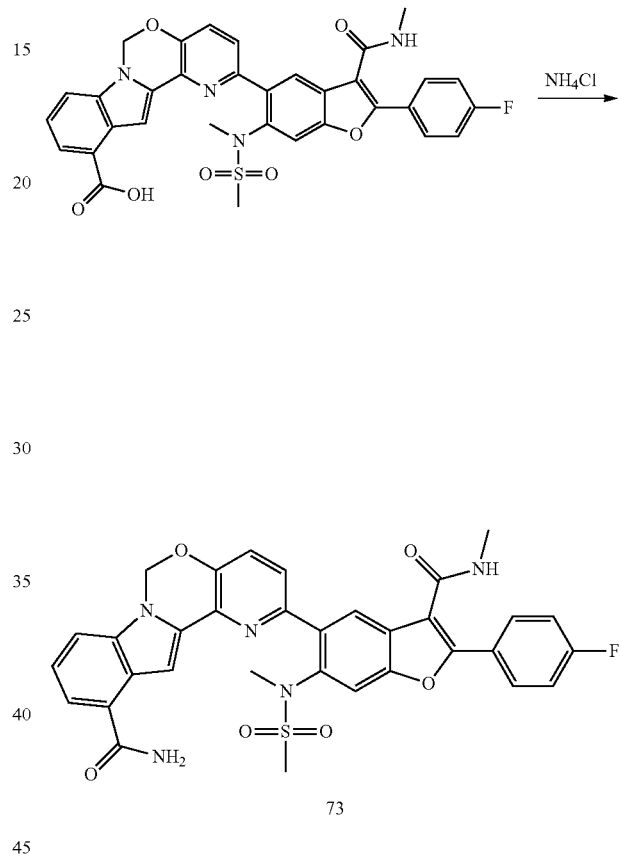

2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indole-11-carboxylic acid (80 mg, 0.13 mmol), HOBt (20 mg, 0.15 mmol) and EDCI (53 mg, 0.27 mmol) in DMF (5 mL) was allowed to stir at room temperature. After 30 minutes, ammonium chloride (20 mg, 0.15 mmol) and $Et_3N$ (140 mg, 1.3 mmol) were added to the mixture, and the mixture was allowed to stir overnight at room temperature. After the solvent was removed, $H_2O$ and $NaHCO_3$ (aq.) were added and the mixture was stirred at room temperature for 1 hour. After filtrated, the cake was washed with $H_2O$ and dried to provide compound 73 (40 mg, yield: 50%). $^1$H-NMR (CDCl$_3$, 400 MHz) δ 7.94~7.97 (m, 2H), 7.82~7.86 (m, 2H), 7.60~7.64 (m, 2H), 7.53~7.55 (m, 3H), 7.21~7.31 (m, 3H), 6.08 (s, 2H), 3.34 (s, 3H), 2.95 (d, J=4.8 Hz, 3H), 2.85 (s, 3H). MS $(M+H)^+$: 640.

Example 22
Preparation of Compound 74
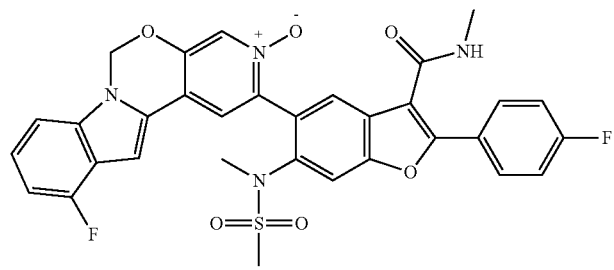
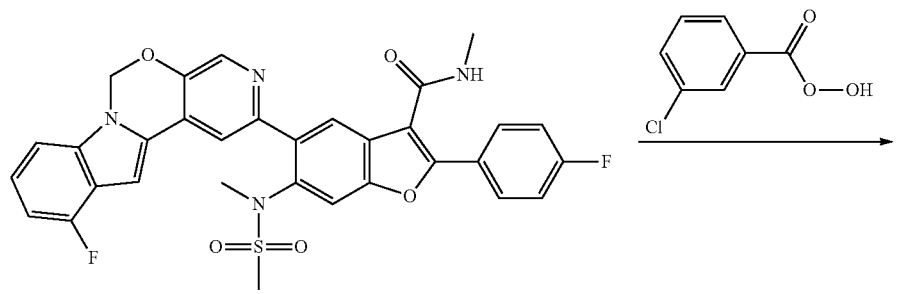
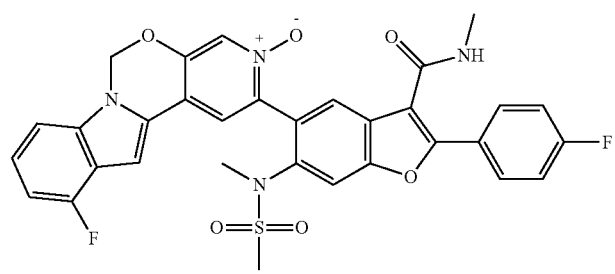

A mixture of Compound 16 (50 mg, 0.08 mmol) in dichloromethane (2 mL) was added 3-chlorobenzo peroxoic acid (50 mg, 0.27 mmol) at 0° C. The reaction mixture was stirred at 25° C. for 16 hours. Water was added and the mixture was extracted with ethyl acetate. The organic layer was washed with brine and dried over Na₂SO₄. After concentrated, the resulting residue was purified using prep-TLC (dichloromethane:EtOAc=5:1) to provide the product of compound 74 (10 mg, yield: 19%). ¹H-NMR (CDCl₃, 400 MHz) δ 8.11 (s, 1H), 7.98 (dd, J=8.8, 5.2 Hz, 2H), 7.92 (s, 1H), 7.76 (s, 1H), 7.64 (s, 1H), 7.20~7.24 (m, 3H), 7.10 (d, J=8.0 Hz, 1H), 7.01 (s, 1H), 6.86 (dd, J=10.0 Hz, 1H), 6.01 (s, 2H), 5.96 (s, 1H), 3.38 (s, 3H), 2.98 (d, J=4.8 Hz, 3H), 2.89 (s, 3H). MS (M+H)⁺: 631.

Example 23

Preparation of Compound 75

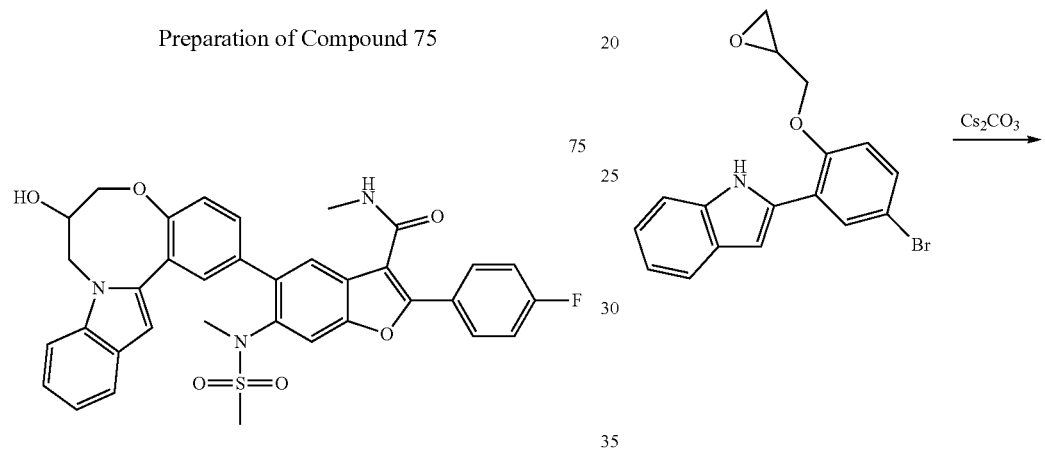

Step 1—Synthesis of 2-(5-bromo-2-(oxiran-2-ylmethoxy)phenyl)-1H-indole

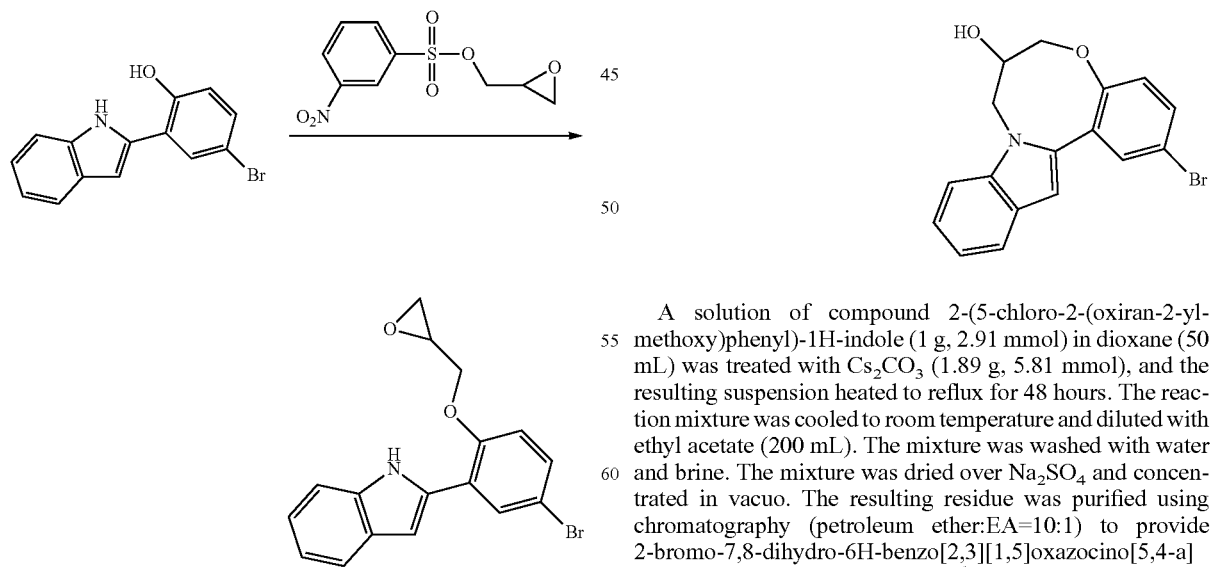

To a solution of compound 4-bromo-2-(1H-indol-2-yl)phenol (1 g, 3.48 mmol) in DMF (35 mL) was added CsF (1.59 g, 10.45 mmol) and oxiran-2-ylmethyl 3-nitrobenzenesulfonate (1.81 g, 6.97 mmol). The resulting mixture was stirred at room temperature overnight and then diluted with ethyl acetate and washed with water and brine. The crude product was purified using chromatography (petroleum ether:EA=14:1) to provide compound 2-(5-bromo-2-(oxiran-2-ylmethoxy)phenyl)-1H-indole (1 g, yield: 84.0%). ¹H-NMR (DMSO-d6, 400 MHz) δ 11.33 (s, 1H), 7.96 (d, J=2.4 Hz, 1H), 7.51 (d, J=7.6 Hz, 1H), 7.38~7.44 (m, 2H), 7.07~7.12 (m, 3H), 6.97 (t, J=7.2 Hz, 1H), 4.49~4.53 (m, 1H), 3.97~4.01 (m, 1H), 3.46~3.49 (m, 1H), 2.88 (t, J=4.4 Hz, 1H), 2.74~2.76 (m, 1H). MS (M+H)⁺: 344/346.

Step 3—Synthesis of 2-bromo-7,8-dihydro-6H-benzo[2,3][1,5]oxazocino[5,4-a]indol-7-ol A solution of compound 2-(5-chloro-2-(oxiran-2-ylmethoxy)phenyl)-1H-indole (1 g, 2.91 mmol) in dioxane (50 mL) was treated with Cs₂CO₃ (1.89 g, 5.81 mmol), and the resulting suspension heated to reflux for 48 hours. The reaction mixture was cooled to room temperature and diluted with ethyl acetate (200 mL). The mixture was washed with water and brine. The mixture was dried over Na₂SO₄ and concentrated in vacuo. The resulting residue was purified using chromatography (petroleum ether:EA=10:1) to provide 2-bromo-7,8-dihydro-6H-benzo[2,3][1,5]oxazocino[5,4-a]indol-7-ol (500 mg, yield: 50.0%). ¹H-NMR (DMSO-d6, 400 MHz) δ 7.40~7.55 (m, 4H), 7.13~7.18 (m, 2H), 7.04 (t, J=7.6 Hz, 1H), 6.66 (s, 1H), 5.43 (d, J=4.0 Hz, 1H), 3.78~4.24 (m, 4H). MS (M+H)⁺: 344/346.

Step 4—Synthesis of 2-(4-fluorophenyl)-5-(7-hydroxy-7,8-dihydro-6H-benzo[2,3][1,5]oxazocino[5,4-a]indol-2-yl)-N-methyl-6-(N-methylmethylsulfonamido)benzofuran-3-carboxamide (Compound 75)

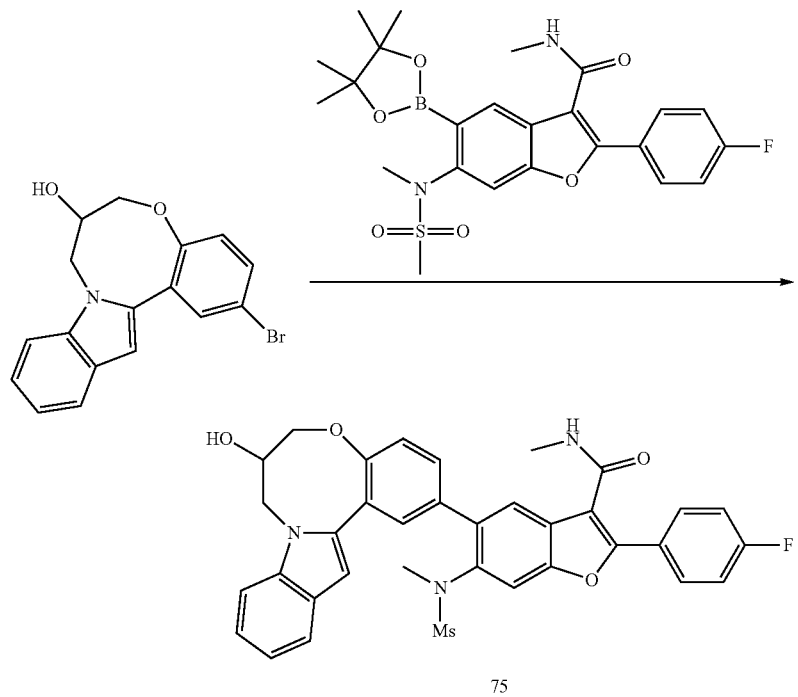

75

Compound 75 (40 mg, yield: 54.0%) was made using the method described in Example 1, Step X. $^1$H-NMR (CDCl$_3$, 400 MHz) δ 7.80~7.84 (m, 2H), 7.71 (s, 1H), 7.49~7.55 (m, 3H), 7.33~7.37 (m, 2H), 7.02~7.16 (m, 5H), 6.63 (s, 1H), 5.88 (d, J=5.2 Hz, 1H), 4.00~4.21 (m, 5H), 3.08 (s, 3H), 2.86 (d, J=4.8 Hz, 3H), 2.66 (s, 3H), 2.46~2.48 (m, 1H). MS (M+H)$^+$: 640.

Example 24

Preparation of Compound 76

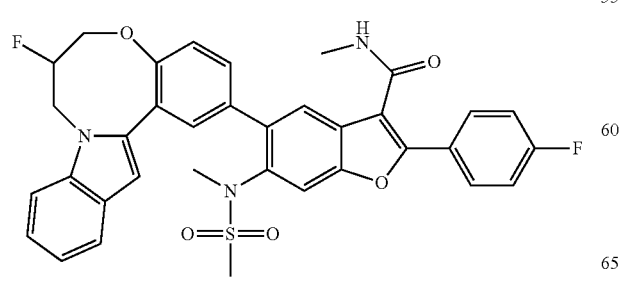

76

Step 1—Synthesis of 2-bromo-7-fluoro-7,8-dihydro-6H-benzo[2,3][1,5]oxazocino[5,4-a]indole

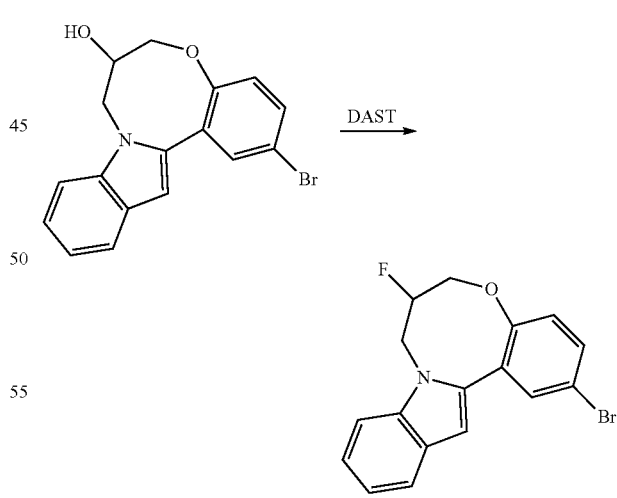

DAST (94 mg, 0.583 mmol) was added to a solution of 2-bromo-7,8-dihydro-6H-benzo[2,3][1,5]oxazocino[5,4-a]indol-7-ol (100 mg, 0.29 mmol) in CH$_2$Cl$_2$ (1 mL) under N$_2$ at −78° C. The mixture was stirred at room temperature for 2 hours. The mixture was then diluted with water (30 mL) and extracted with ethyl acetate (15 mL×3). The organic layer was washed with brine (20 mL×2), dried over Na$_2$SO$_4$ and concentrated in vacuo. The resulting residue was purified using p-TLC (petroleum ether:EA=10:1) to provide 2-bromo-7-fluoro-7,8-dihydro-6H-benzo[2,3][1,5]oxazocino[5,4-a]indole (40 mg, yield: 40.0%). MS (M+H)+: 346/348.

Step 2—Synthesis of 5-(7-fluoro-7,8-dihydro-6H-benzo[2,3][1,5]oxazocino[5,4-a]indol-2-yl)-2-(4-fluorophenyl)-N-methyl-6-(N-methylmethylsulfonamido)benzofuran-3-carboxamide (Compound 76)

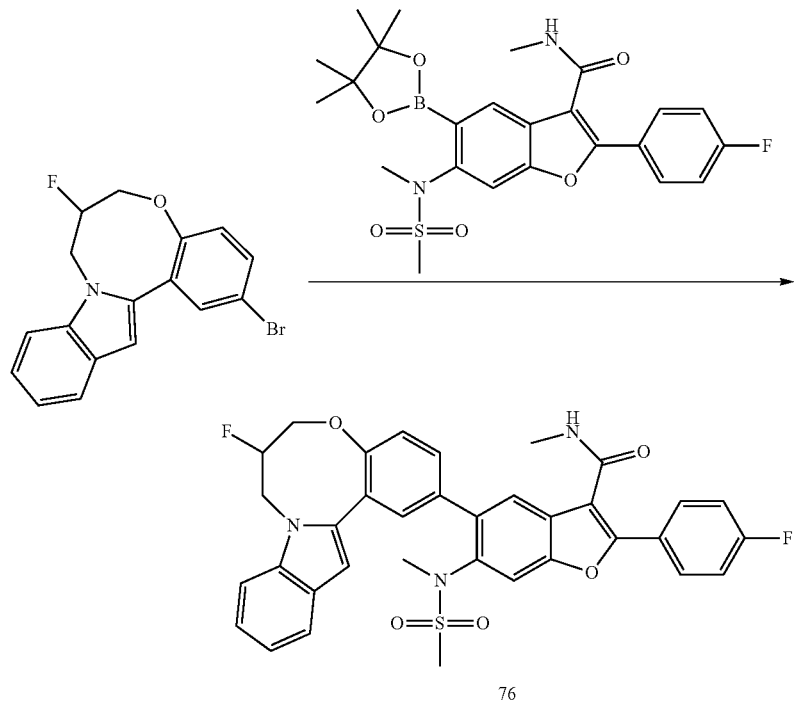

The procedure of compound 76 (40 mg, yield: 54.0%) was similar to that of Example 1. $^1$H-NMR (CDCl$_3$, 400 MHz) δ 7.84~7.85 (m, 2H), 7.74 (s, 1H), 7.52~7.57 (m, 3H), 7.36~7.39 (m, 2H), 7.06~7.21 (m, 5H), 6.68 (s, 1H), 5.83 (d, J=4.8 Hz, 1H), 4.80~4.91 (m, 1H), 4.37~4.50 (m, 2H), 4.04~4.26 (m, 2H), 3.11 (s, 3H), 2.89 (s, 3H), 2.69 (s, 3H). MS (M+H)+: 642.

Example 25

Preparation of Compound 77

Step 1—Synthesis of 2-bromo-6H-benzo[2,3][1,5]oxazocino[5,4-a]indol-7(8H)-one

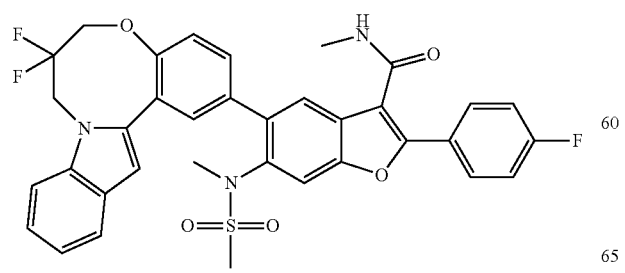

DMP (742 mg, 1.749 mmol) was added to the solution of 2-bromo-7,8-dihydro-6H-benzo[2,3][1,5]oxazocino[5,4-a]indol-7-ol (500 mg, 1.46 mmol) in CH$_2$Cl$_2$ (5 mL) at 0° C.

The mixture was stirred at room temperature overnight. The mixture was then diluted with saturated Na$_2$S$_2$O$_3$ and NaHCO$_3$ (30 mL, 30 mL). The mixture was extracted with ethyl acetate (20 mL×3). The organic layer was washed with brine (30 mL×3), dried over Na$_2$SO$_4$ and concentrated in vacuo. The resulting residue was purified using prep-TLC (petroleum ether:EA=3:1) to provide 2-bromo-6H-benzo[2,3][1,5]oxazocino[5,4-a]indol-7(8H)-one (350 mg, yield: 70.4%). $^1$H-NMR (CDCl$_3$, 400 MHz) δ 7.55~7.68 (m, 2H), 7.53 (t, J=6.0 Hz, 1H), 7.35~7.37 (m, 1H), 7.28~7.30 (m, 1H), 7.17~7.24 (m, 1H), 7.08 (t, J=8.4 Hz, 1H), 6.70 (d, J=0.8 Hz, 1H), 4.73 (s, 2H), 4.55 (s, 2H). MS (M+H)$^+$: 342/344.

Step 2—Synthesis of 2-bromo-7,7-difluoro-7,8-dihydro-6H-benzo[2,3][1,5]oxazocino[5,4-a]indole

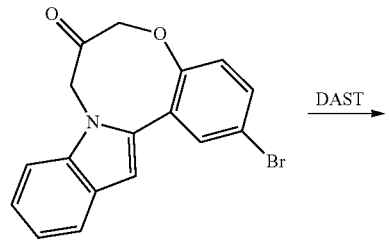

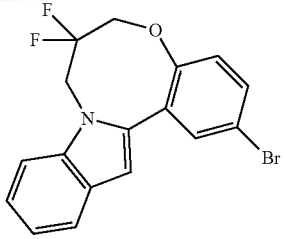

DAST (94 mg, 0.58 mmol) was added to a solution of 2-bromo-6H-benzo[2,3][1,5]oxazocino[5,4-a]indol-7(8H)-one (100 mg, 0.292 mmol) in CH$_2$Cl$_2$ (1 mL) under N$_2$ at −78° C. The mixture was stirred at room temperature for 2 hours. The mixture was then diluted with water (30 mL) and extracted with ethyl acetate (15 mL×3). The organic layer was washed with brine (20 mL×2), dried over Na$_2$SO$_4$ and concentrated in vacuo. The resulting residue was purified using prep-TLC (petroleum ether:EA=10:1) to provide 2-bromo-7,7-difluoro-7,8-dihydro-6H-benzo[2,3][1,5]oxazocino[5,4-a]indole (40 mg, yield: 37.7%). MS (M+H)$^+$: 364/366. $^1$H-NMR (CDCl$_3$, 400 MHz) δ 7.57~7.59 (m, 2H), 7.36~7.42 (m, 2H), 7.21~7.25 (m, 1H), 7.11 (t, J=7.2 Hz, 1H), 6.95 (d, J=8.8 Hz, 1H), 6.64 (s, 1H), 4.43 (t, J=7.2 Hz, 2H), 4.13 (t, J=10.4 Hz, 2H). MS (M+H)$^+$: 364/366.

Step 3—Synthesis of 5-(7,7-difluoro-7,8-dihydro-6H-benzo[2,3][1,5]oxazocino[5,4-a]indol-2-yl)-2-(4-fluorophenyl)-N-methyl-6-(N-methylmethylsulfonamido)benzofuran-3-carboxamide (Compound 77)

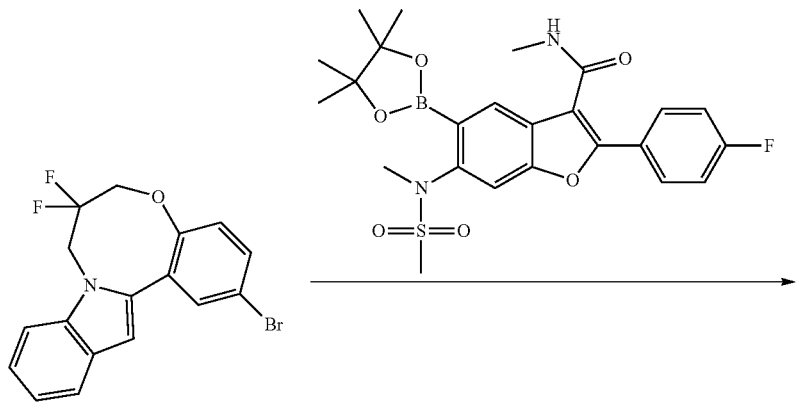

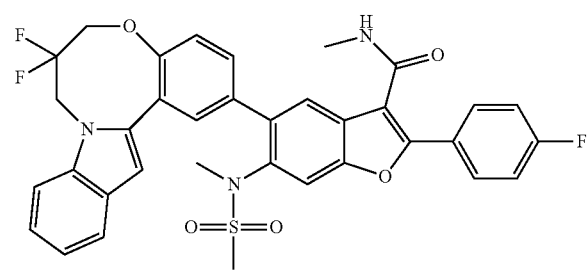

The procedure of compound 77 (40 mg, yield: 54.8%) was similar to that of Example 1. ¹H-NMR (CDCl₃, 400 MHz) δ 7.89~7.91 (m, 2H), 7.81 (s, 1H), 7.57~7.63 (m, 3H), 7.43~7.49 (m, 2H), 7.14~7.30 (m, 5H), 6.77 (s, 1H), 5.85 (d, J=4.4 Hz, 1H), 4.55 (t, J=10.8 Hz, 2H), 4.26 (t, J=10.8 Hz, 2H), 3.16 (s, 3H), 2.95 (d, J=6.0 Hz, 3H), 2.79 (s, 3H). MS (M+H)⁺: 660.

Example 26

Preparation of Compound 78

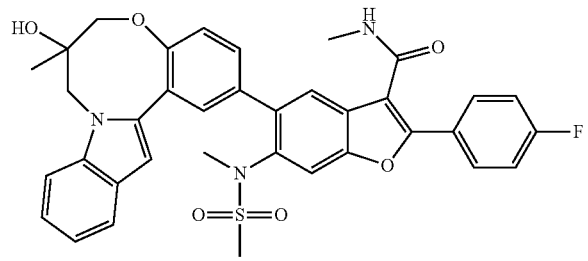

Step 1—Synthesis of 2-bromo-7-methyl-7,8-dihydro-6H-benzo[2,3][1,5]oxazocino[5,4-a]indol-7-ol

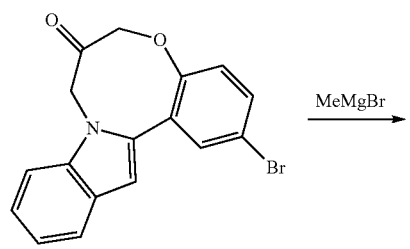

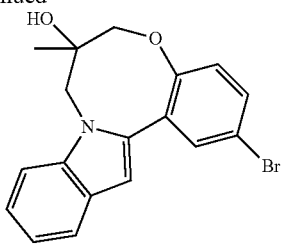

MgBrCH₃ (0.12 mL, 0.352 mmol) was added to the solution of 2-bromo-6H-benzo[2,3][1,5]oxazocino[5,4-a]indol-7(8H)-one (60 mg, 0.176 mmol) in THF (1 mL) at 0° C. under N₂. The mixture was stirred at room temperature for 30 minutes. The mixture was then quenched with saturated NH₄Cl (10 mL) and extracted with ethyl acetate (10 mL×3). The organic layer was washed with brine (20 mL), dried over Na₂SO₄ and concentrated in vacuo. The resulting residue was purified using p-TLC (petroleum ether:EA=3:1) to provide 2-bromo-7-methyl-7,8-dihydro-6H-benzo[2,3][1,5]oxazocino[5,4-a]indol-7-ol (30 mg, yield: 47.6%). ¹H-NMR (CDCl₃, 400 MHz) δ 7.56~7.59 (m, 2H), 7.36~7.40 (m, 2H), 7.18~7.22 (m, 1H), 7.08 (t, J=7.2 Hz, 1H), 6.93 (d, J=8.8 Hz, 1H), 6.61 (s, 1H), 3.81~4.15 (m, 4H), 2.34 (s, 1H), 1.24 (s, 3H). MS (M+H)⁺: 358/360.

Step 2—Synthesis of 2-(4-fluorophenyl)-5-(7-hydroxy-7-methyl-7,8-dihydro-6H-benzo[2,3][1,5]oxazocino[5,4-a]indol-2-yl)-N-methyl-6-(N-methylmethylsulfonamido)benzofuran-3-carboxamide (Compound 78)

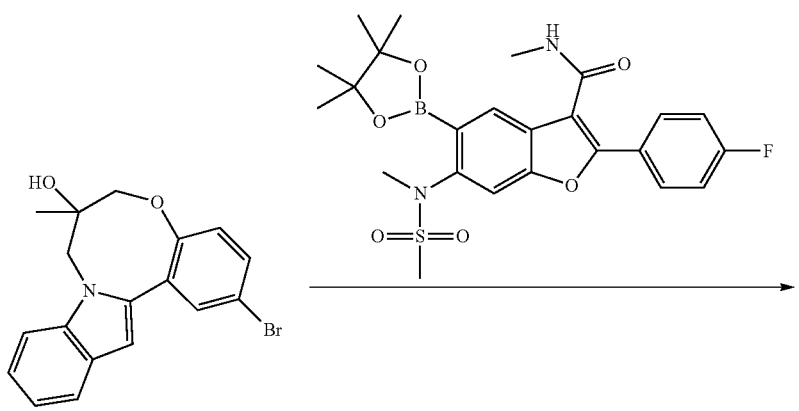

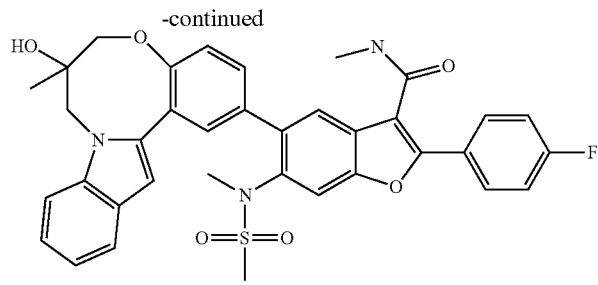

78

The procedure of compound 78 (30 mg, yield: 54.5%) was similar to step 6 of Example 1. $^1$H-NMR (CDCl$_3$, 400 MHz) δ 7.90~7.93 (m, 2H), 7.80 (s, 1H), 7.58~7.64 (m, 3H), 7.44~7.48 (m, 2H), 7.11~7.26 (m, 5H), 6.73 (s, 1H), 5.87 (d, J=5.2 Hz, 1H), 3.96~4.26 (m, 4H), 3.18 (s, 3H), 2.97 (d, J=4.8 Hz, 3H), 2.75 (s, 3H), 1.34 (s, 3H). MS (M+H)$^+$: 654.

Example 27

Preparation of Compound 79

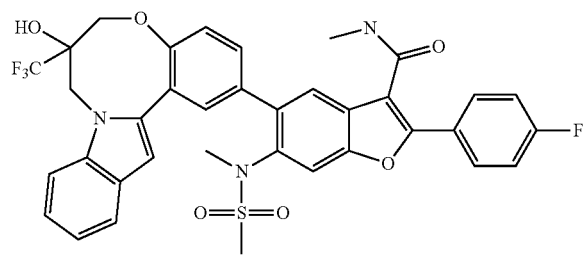 [SMILES: CNC(=O)c1c(-c2ccc(F)cc2)oc2cc(N(C)S(C)(=O)=O)c(-c3ccc4c(c3)-c3cc5ccccc5n3CC(O)(C(F)(F)F)CO4)cc12]

Step 1—Synthesis of 2-bromo-7-(trifluoromethyl)-7,8-dihydro-6H-benzo[2,3][1,5]oxazocino[5,4-a]indol-7-ol

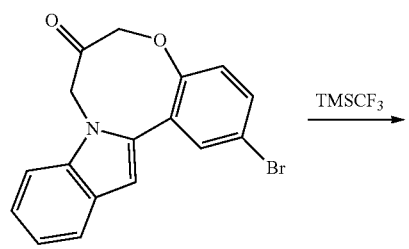

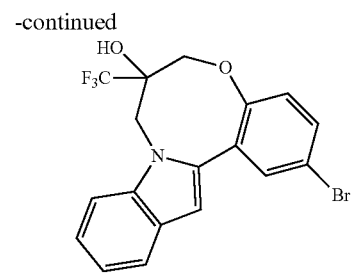

A mixture of 2-bromo-6H-benzo[2,3][1,5]oxazocino[5,4-a]indol-7(8H)-one (60 mg, 0.18 mmol), TMSCF$_3$ (275 mg, 0.194 mmol) and CsF (3 mg, 0.018 mmol) in DME (1 mL) was stirred at room temperature for 3 hours. The mixture was then diluted with TBAF (5 mL) and stirred for 1 hour at room temperature. The mixture was then diluted with water (25 mL) and extracted with ethyl acetate (20 mL×3). The organic layer was washed with brine (20 mL×2), dried over Na$_2$SO$_4$ and concentrated in vacuo. The resulting residue was purified using prep-TLC (petroleum ether:EA=3:1) to provide 2-bromo-7-(trifluoromethyl)-7,8-dihydro-6H-benzo[2,3][1,5]oxazocino[5,4-a]indol-7-ol (40 mg, yield: 55.6%). MS (M+H)$^+$: 412/414.

Step 2—Synthesis of 2-(4-fluorophenyl)-5-(7-hydroxy-7-(trifluoromethyl)-7,8-dihydro-6H-benzo[2,3][1,5]oxazocino[5,4-a]indol-2-yl)-N-methyl-6-(N-methylmethylsulfonamido)benzofuran-3-carboxamide (Compound 79)

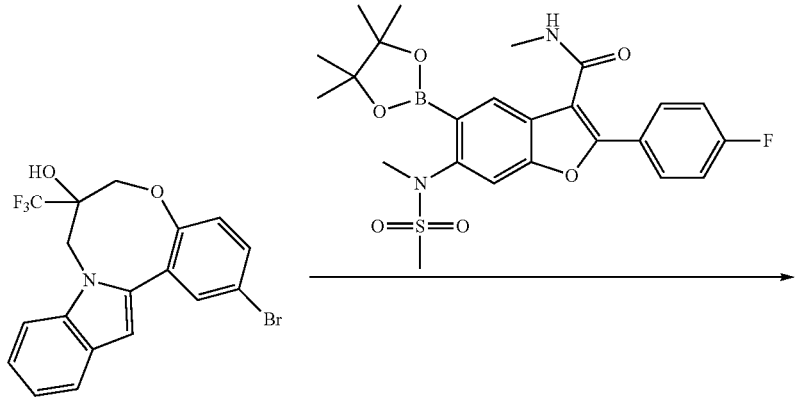

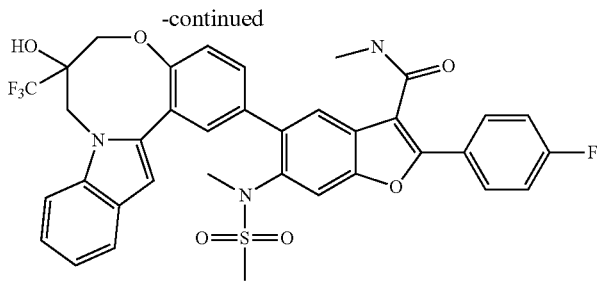

79

The procedure of compound 79 (30 mg, yield: 43.5%) was similar to that of Example 1. ¹H-NMR (CDCl₃, 400 MHz) δ 7.84~7.87 (m, 2H), 7.77 (s, 1H), 7.41~7.59 (m, 5H), 7.09~7.24 (m, 5H), 6.71 (s, 1H), 5.78 (d, J=5.2 Hz, 1H), 4.46~4.57 (m, 2H), 4.17~4.29 (m, 2H), 3.11 (s, 3H), 2.90 (d, J=5.2 Hz, 3H), 2.73 (s, 3H). MS (M+H)⁺: 708.

Example 28

Preparation of Compound 80

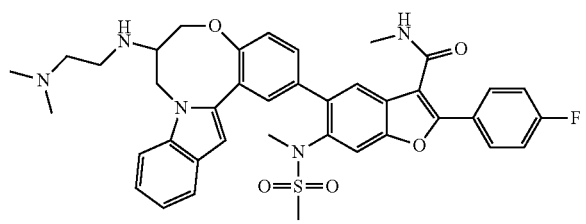

80

Step 1—Synthesis of N1-(2-bromo-7,8-dihydro-6H-benzo[2,3][1,5]oxazocino[5,4-a]indol-7-yl)-N2,N2-dimethylethane-1,2-diamine

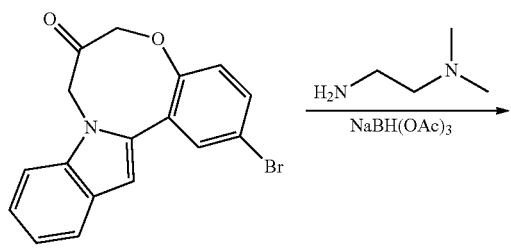

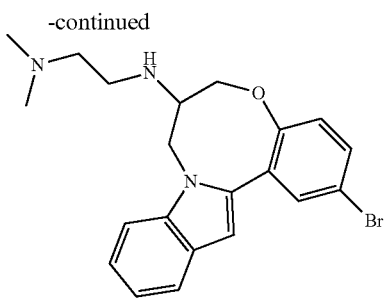

N',N'-dimethylethane-1,2-diamine (39 mg, 0.440 mmol) and CH₃COOH (26 mg, 0.440 mmol) were added to the mixture of 2-bromo-6H-benzo[2,3][1,5]oxazocino[5,4-a]indol-7(8H)-one (100 mg, 0.293 mmol) in 1,2-dichloroethane (2 mL). The mixture was stirred at room temperature for 20 minutes. Then NaBH(OAc)₃ (93 mg, 0.440 mmol) was added to the mixture. The mixture was stirred at room temperature for 2 hours. The mixture was then quenched with saturated NaHCO₃ (30 mL) and extracted with ethyl acetate (15 mL×3). The organic layer was washed with brine (20 mL), dried over Na₂SO₄ and concentrated in vacuo. The resulting residue was purified using p-TLC (dichloromethane: MeOH=1:1) to provide N1-(2-bromo-7,8-dihydro-6H-benzo [2,3][1,5]oxazocino[5,4-a]indol-7-yl)-N2,N2-dimethyl-ethane-1,2-diamine. ¹H-NMR (CDCl₃, 400 MHz) δ 7.51~7.56 (m, 2H), 7.42 (s, 1H), 7.29~7.32 (m, 1H), 7.16~7.18 (m, 1H), 7.06 (t, J=7.2 Hz, 1H), 6.85 (d, J=8.8 Hz, 1H), 6.56 (s, 1H), 3.86~4.32 (m, 4H), 2.81~3.03 (m, 5H), 2.59 (s, 6H). MS (M+H)⁺: 414/416.

Step 2—Synthesis of 5-(7-((2-(dimethylamino)ethyl) amino)-7,8-dihydro-6H-benzo[2,3][1,5]oxazocino[5, 4-a]indol-2-yl)-2-(4-fluorophenyl)-N-methyl-6-(N-methylmethylsulfonamido)benzofuran-3-carboxamide (Compound 80)

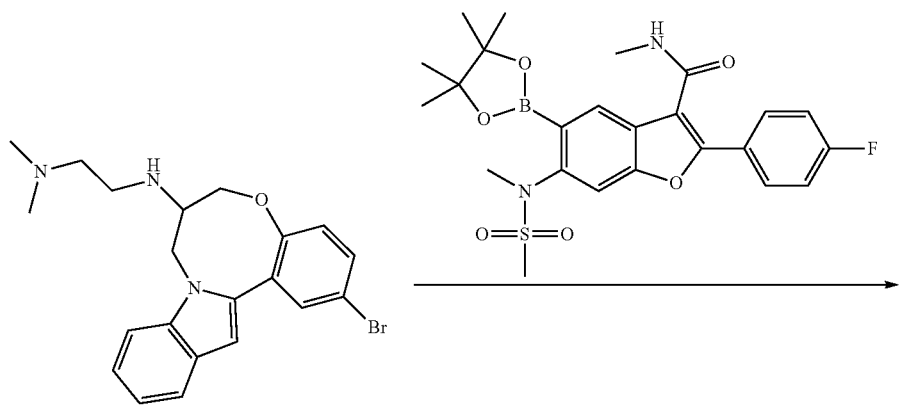

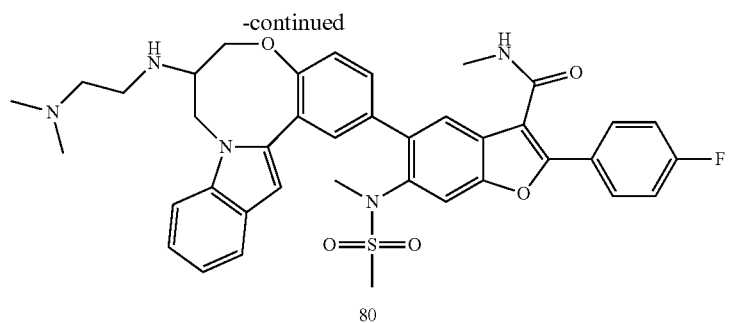

The procedure of compound 80 (50 mg, yield: 36.5%) was similar to that of Example 1. $^1$H-NMR (Methanol-d$_4$, 400 MHz) δ 7.90~7.94 (m, 2H), 7.78 (s, 1H), 7.64~7.68 (m, 2H), 7.56~7.59 (m, 2H), 7.44~7.47 (m, 1H), 7.16~7.26 (m, 4H), 7.10 (t, J=7.6 Hz, 1H), 6.82 (s, 1H), 4.75~4.90 (m, 1H), 4.07~4.38 (m, 3H), 3.64 (s, 3H), 3.53~3.54 (m, 2H), 3.14 (s, 3H), 2.90~2.98 (m, 2H). MS (M+H)$^+$: 710.

Compounds 81-86, depicted in the table below, were prepared using the method described above and substituting the appropriate reactants and/or reagents.

| Compound No | Structure | NMR | MS (M + H)$^+$ |
|---|---|---|---|
| 81 | 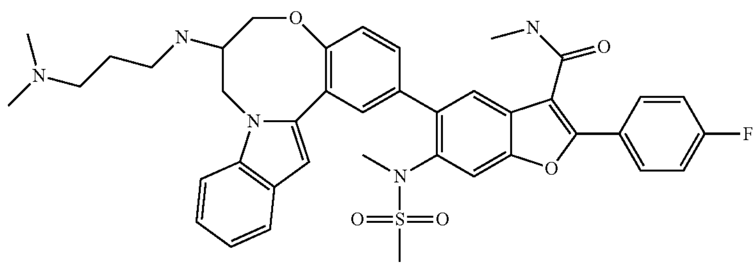 [SMILES: CNC(=O)c1c(-c2ccc(F)cc2)oc2cc(N(C)S(C)(=O)=O)c(-c3ccc4c(c3)-c3cc5ccccc5n3CC(NCCCN(C)C)CO4)cc12] | $^1$H-NMR (Methanol-d4, 400 MHz) δ 7.88~7.92 (m, 2H), 7.75 (s, 1H), 7.63~7.68 (m, 2H), 7.55 (d, J = 8.4 Hz, 2H), 7.43~7.46 (m, 1H), 7.16~7.24 (m, 4H), 7.09 (t, J = 7.6 Hz, 1H), 6.82 (s, 1H), 4.06~4.40 (m, 3H), 3.69 (d, J = 7.2 Hz, 1H), 3.25~3.38 (m, 5H), 3.12 (s, 3H), 2.91 (t, J = 8.4 Hz, 2H), 2.24 (d, J = 7.2 Hz, 2H). | 724 |
| 82 | 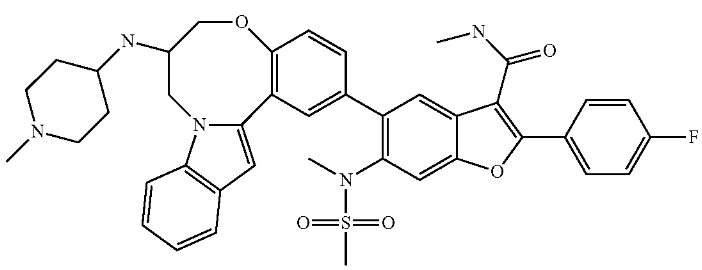 [SMILES: CNC(=O)c1c(-c2ccc(F)cc2)oc2cc(N(C)S(C)(=O)=O)c(-c3ccc4c(c3)-c3cc5ccccc5n3CC(NC3CCN(C)CC3)CO4)cc12] | $^1$H-NMR (CDCl$_3$, 400 MHz) δ 7.93~7.96 (m, 2H), 7.92 (s, 1H), 7.47~7.81 (m, 5H), 7.19~7.27 (m, 4H), 7.09~7.13 (m, 1H), 6.85 (s, 1H), 4.30~4.39 (m, 2H), 4.12~4.16 (m, 1H), 3.65~3.81 (m, 4H), 3.11~3.16 (m, 5H), 2.87~2.98 (m, 10H), 2.42~2.48 (m, 2H), 2.02~2.13 (m, 2H). | 736 |
| 83 | 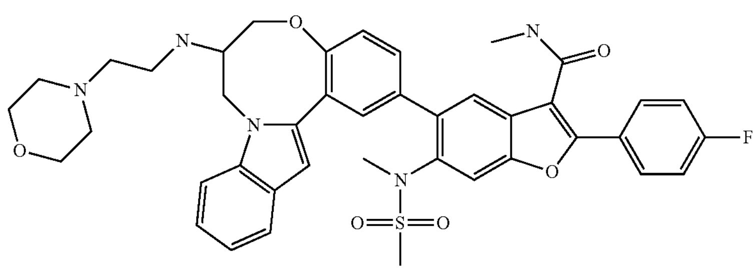 [SMILES: CNC(=O)c1c(-c2ccc(F)cc2)oc2cc(N(C)S(C)(=O)=O)c(-c3ccc4c(c3)-c3cc5ccccc5n3CC(NCCN3CCOCC3)CO4)cc12] | $^1$H-NMR (CDCl$_3$, 400 MHz) δ 7.89~7.91 (m, 2H), 7.88 (s, 1H), 7.57~7.78 (m, 3H), 7.40~7.45 (m, 2H), 7.23 (s, 1H), 7.02~7.18 (m, 4H), 6.70 (s, 1H), 5.93~6.15 (m, 1H), 4.48 (s, 1H), 3.94~4.12 (m, 3H), 3.73 (br, 3H), 2.32~3.42 (m, 20H). | 752 |
| 84 | 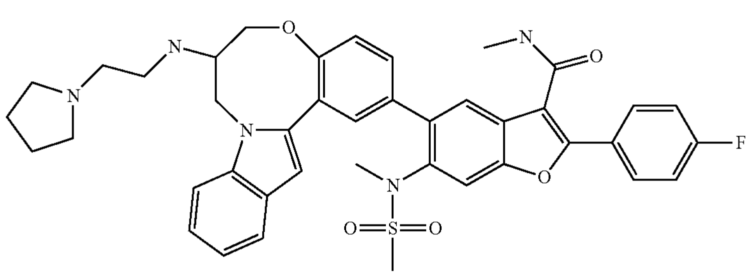 [SMILES: CNC(=O)c1c(-c2ccc(F)cc2)oc2cc(N(C)S(C)(=O)=O)c(-c3ccc4c(c3)-c3cc5ccccc5n3CC(NCCN3CCCC3)CO4)cc12] | $^1$H-NMR (CDCl$_3$, 400 MHz) δ 7.90 (s, 2H), 7.75 (s, 1H), 7.54~7.58 (m, 4H), 7.37~7.39 (m, 1H), 7.08~7.20 (m, 5H), 6.65 (s, 1H), 6.13 (s, 1H), 4.47~4.51 (m, 1H), 3.92~4.12 (m, 3H), 3.08~3.24 (m, 13H), 2.73~2.94 (m, 7H), 2.08 (s, 3H). | 736 |

| Compound No | Structure | NMR | MS (M + H)+ |
|---|---|---|---|
| 85 | 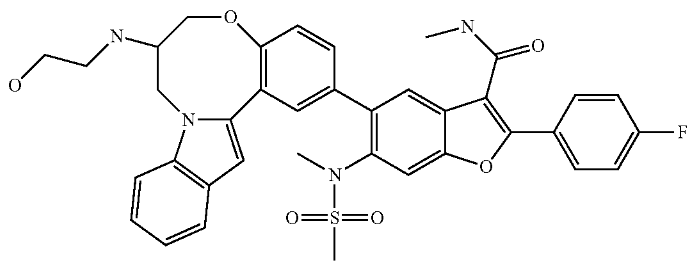 [SMILES: CNC(=O)c1c(-c2ccc(F)cc2)oc2cc(N(C)S(C)(=O)=O)c(-c3ccc4c(c3)-c3cc5ccccc5n3CC(NCCO)CO4)cc12] | $^1$H-NMR (CDCl$_3$, 400 MHz) δ 7.92~7.96 (m, 2H), 7.81 (s, 1H), 7.47~7.71 (m, 5H), 7.19~7.27 (m, 4H), 7.09~7.13 (m, 1H), 6.85 (s, 1H), 4.90~4.94 (m, 1H), 4.30~4.43 (m, 2H), 4.11~4.15 (m, 1H), 3.89~3.92 (m, 2H), 3.76~3.77 (m, 1H), 3.37~3.46 (m, 2H), 3.16 (s, 3H), 2.97 (s, 3H), 2.91~2.97 (m, 3H). | 683 |
| 86 | 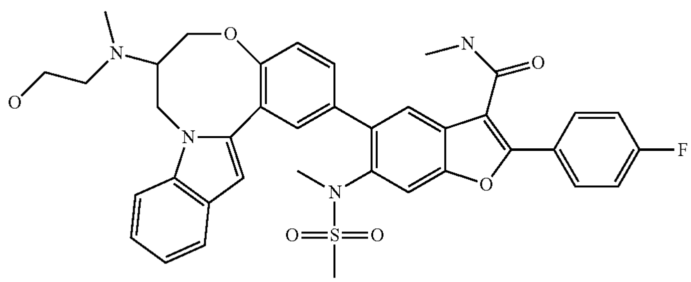 [SMILES: CNC(=O)c1c(-c2ccc(F)cc2)oc2cc(N(C)S(C)(=O)=O)c(-c3ccc4c(c3)-c3cc5ccccc5n3CC(N(C)CCO)CO4)cc12] | $^1$H-NMR (CDCl$_3$, 400 MHz) δ 7.93~7.96 (m, 2H), 7.82 (s, 1H), 7.48~7.73 (m, 5H), 7.10~7.28 (m, 5H), 6.87 (s, 1H), 4.98~5.01 (m, 1H), 4.49~4.61 (m, 2H), 4.15~4.19 (m, 1H), 3.77~3.98 (m, 3H), 3.58 (br, 2H), 2.92~3.18 (m, 12H). | 697 |

Example 29

Preparation of Compound 87 & 88

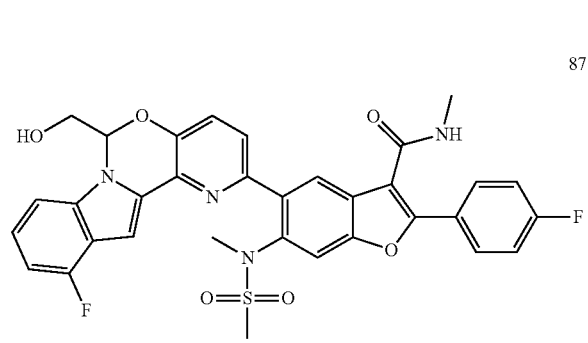

(Enantiomer 1, peak 1 on SFC)

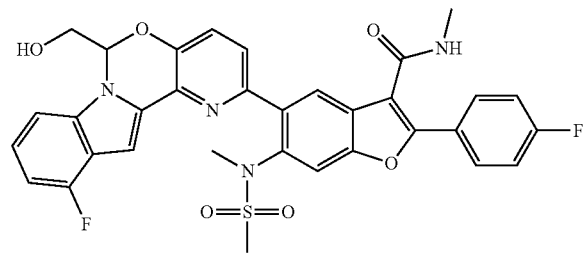

(Enantiomer 2, peak 2 on SFC)

Step 1—Synthesis of 6-chloro-2-(4-fluoroindolin-2-yl)pyridin-3-ol

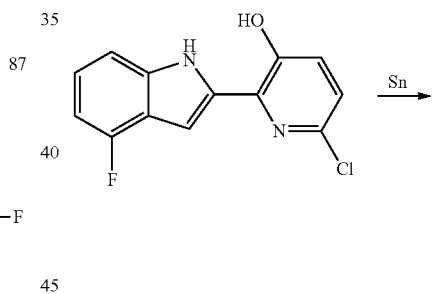

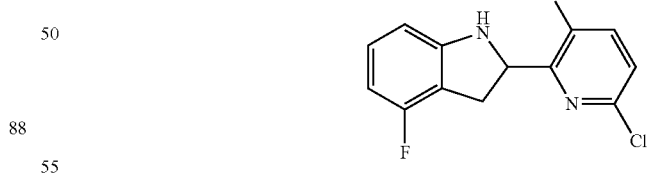

A mixture of 6-chloro-2-(4-fluoro-1H-indol-2-yl)pyridin-3-ol (10 g, 38 mmol) and metal Sn (23 g, 190 mmol) in CH$_3$CH$_2$OH/con. HCl (60 mL/40 mL) was stirred under reflux for 3 hours. The mixture was cooled to room temperature and adjusted to pH=7 by saturated NaOH and filtered though a Celit pad. The filtrate was extracted with EtOAc, washed by brine, dried over Na$_2$SO$_4$ and concentrated in vacuo. The resulting residue was purified using silica gel chromatography (petroleum ether:EtOAc=10:1) to get 6-chloro-2-(4-fluoroindolin-2-yl)pyridin-3-ol (8 g, yield: 80%). $^1$H-NMR (CDCl$_3$, 400 MHz) δ 9.86 (s, 1H), 7.10~7.20

(m, 3H), 6.33~6.91 (m, 2H), 5.15~5.21 (m, 1H), 4.61 (s, 1H), 3.65~3.71 (m, 1H), 3.04~3.11 (m, 1H). MS (M+H)+: 265.

Step 2—Synthesis of ethyl 2-chloro-11-fluoro-12,12a-dihydro-6H-pyrido[2',3':5,6][1,3]oxazino[3,4-a]indole-6-carboxylate

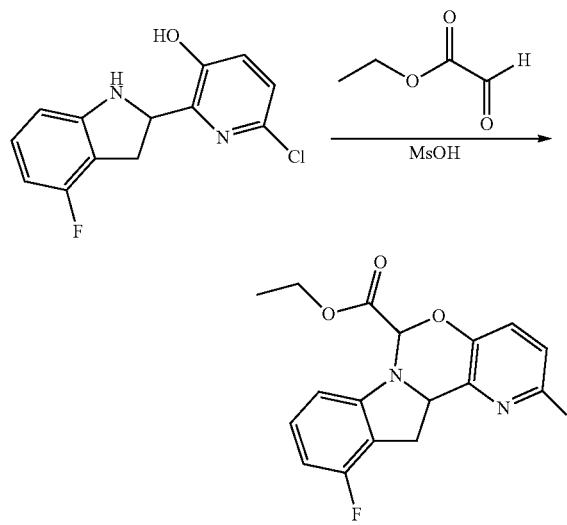

To a solution of 6-chloro-2-(4-fluoroindolin-2-yl)pyridin-3-ol (8.53 g, 32.31 mmol) and Glyoxylic acid ethyl ester (6.59 g, 64.59 mmol) in THF (80 mL), MsOH (0.31 g, 3.23 mmol) was added. The mixture was stirred at 50° C. for 2 hours. The mixture was diluted with water and extracted with EtOAc. The organic layer was washed with brine (30 mL), dried over Na$_2$SO$_4$ and concentrated in vacuo. The resulting residue was purified using column chromatography (petroleum ether:EtOAc=10:1) to provide ethyl 2-chloro-11-fluoro-12,12a-dihydro-6H-pyrido[2',3':5,6][1,3]oxazino[3,4-a]indole-6-carboxylate (10.2 g, yield: 90.3%). $^1$H-NMR (CDCl$_3$, 400 MHz) δ 7.04~7.13 (m, 3H), 6.63 (d, J=8.0 Hz, 1H), 6.55 (t, J=8.4 Hz, 1H), 6.03 (s, 1H), 5.09 (d, J=8.8 Hz, 1H), 4.22~4.34 (m, 2H), 3.73 (d, J=16.4 Hz, 1H), 3.44~3.51 (m, 1H), 1.29 (d, J=7.2 Hz, 3H). MS (M+H)+: 349.

Step 3—Synthesis of ethyl 2-chloro-11-fluoro-6H-pyrido[2',3':5,6][1,3]oxazino[3,4-a]indole-6-carboxylate

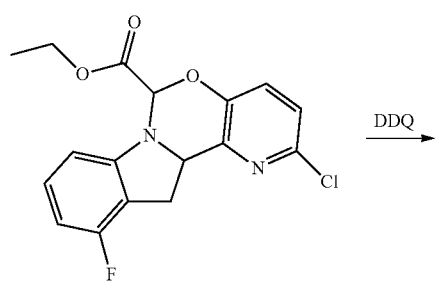

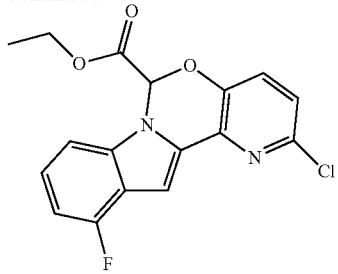

To a solution of ethyl 2-chloro-11-fluoro-12,12a-dihydro-6H-pyrido[2',3':5,6][1,3]oxazino[3,4-a]indole-6-carboxylate (10.22 g, 29.36 mmol) and DDQ (8.67 g, 38.17 mmol) in toluene (80 mL) was stirred at 80° C. for 2 hours. The mixture was then diluted with water (50 mL) and extracted with EtOAc (30 mL*3). The organic layer was washed with brine (30 mL), dried over Na$_2$SO$_4$ and concentrated in vacuo. The resulting residue was purified using column chromatography (petroleum ether:EtOAc=20:1) to provide ethyl 2-chloro-11-fluoro-6H-pyrido[2',3':5,6][1,3]oxazino[3,4-a]indole-6-carboxylate (8.64 g, yield: 85%), which was also prepared from 6-chloro-2-(4-fluoro-1H-indol-2-yl)pyridin-3-ol and methyl 2,2-dibromoacetate in the presence of base, such as DBU etc. $^1$H-NMR (CDCl$_3$, 400 MHz) δ 7.33 (d, J=8.4 Hz, 1H), 7.30 (s, 1H), 7.09~7.18 (m, 3H), 6.78~6.83 (m, 1H), 6.52 (s, 1H), 3.96~4.09 (m, 2H), 1.02 (t, J=7.2 Hz, 3H). MS (M+H)+: 347.

Step 4—Synthesis of (2-chloro-11-fluoro-6H-pyrido[2',3':5,6][1,3]oxazino[3,4-a]indol-6-yl)methanol

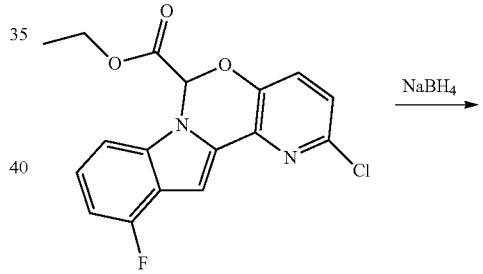

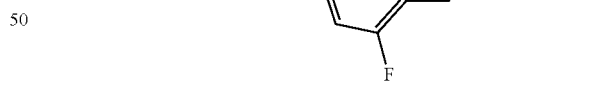

To a solution of ethyl 2-chloro-11-fluoro-6H-pyrido[2',3':5,6][1,3]oxazino[3,4-a]indole-6-carboxylate (3 g, 8.73 mmol) and NaBH$_4$ (1.58 g, 43.67 mmol) in CH$_3$OH/dichloromethane (30 mL/10 mL) was stirred at room temperature for 2 hours. The mixture was poured to H$_2$O and extracted with ethyl acetate. The organic layer was washed with brine, dried over Na$_2$SO$_4$ and concentrated in vacuo to provide (2-chloro-11-fluoro-6H-pyrido[2',3':5,6][1,3]oxazino[3,4-a]indol-6-yl)methanol (2.54 g, yield: 95.5%). $^1$H-NMR (DMSO-d6, 400 MHz) δ 7.60 (d, J=8.8 Hz, 1H), 7.46 (d, J=8.4 Hz, 1H), 7.41 (d, J=8.8 Hz, 1H), 7.22~7.28 (m, 1H), 7.08 (s, 1H), 6.94 (dd, J=10.4, 8.4 Hz, 1H), 6.78 (t, J=4.0 Hz, 1H), 5.29 (t, J=6.0 Hz, 1H), 3.71~3.78 (m, 1H), 3.61~3.67 (m, 1H). MS (M+H)+: 305.

Step 5—Synthesis of 5-(11-fluoro-6-(hydroxymethyl)-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide: enantiomer 1 and enantiomer 2 (Compound 87 and 88)

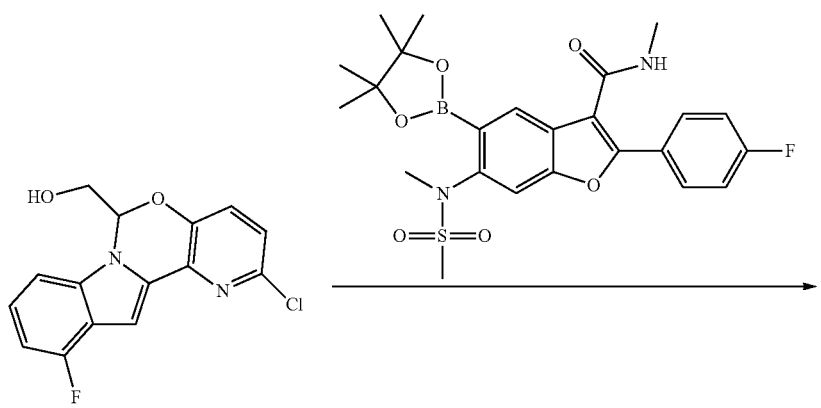

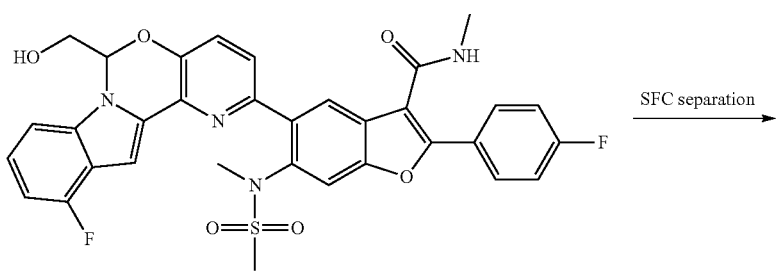

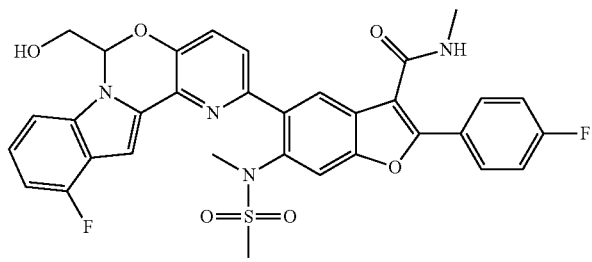

87 (Enantiomer 1, peak 1 on SFC)

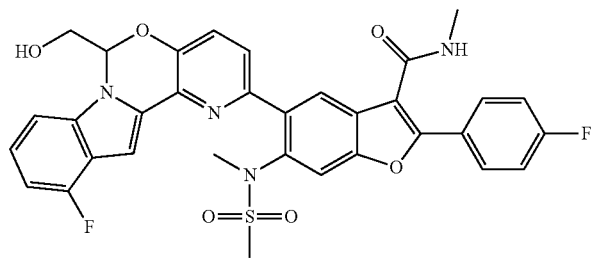

88 (Enantiomer 2, peak 2 on SFC)

The procedure of racemic 5-(11-fluoro-6-(hydroxymethyl)-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide was similar to step 6 of Example 1. And after SFC separation, two single enantiomers were obtained. Column: Chiralpak AD-3 50*4.6 mm I.D., 3 um Mobile phase:60% ethanol (0.05% DEA) in $CO_2$. Flow rate: 3 mL/min Wavelength: 220 nm. Compound 87: RT=0.541 min, Compound 88: RT=2.074 minutes.

Compound 87, enantiomer 1 (peak 1 on SFC), $^1$H-NMR (CDCl$_3$, 400 MHz) δ 8.02 (s, 1H), 7.93~7.97 (m, 2H), 7.65 (s, 1H), 7.45~7.48 (m, 2H), 7.15~7.22 (m, 5H), 6.82~6.87 (m, 1H), 6.43~6.46 (m, 1H), 5.95 (brs, 1H), 3.86~4.00 (m, 2H), 3.38 (s, 3H), 2.98 (d, J=4.8 Hz, 3H), 2.71 (s, 3H), 2.02 (brs, 1H), MS (M+H)$^+$: 645.

Compound 88, enantiomer 2 (peak 2 on SFC), $^1$H-NMR (CDCl$_3$, 400 MHz) δ 8.02 (s, 1H), 7.93~7.97 (m, 2H), 7.65 (s, 1H), 7.45~7.48 (m, 2H), 7.15~7.22 (m, 5H), 6.82~6.87 (m, 1H), 6.43~6.46 (m, 1H), 5.95 (brs, 1H), 3.86~4.00 (m, 2H), 3.38 (s, 3H), 2.98 (d, J=4.8 Hz, 3H), 2.71 (s, 3H), 2.02 (brs, 1H), MS (M+H)$^+$: 645.

Compounds 89-97, depicted in the table below, were prepared using the method described above and substituting the appropriate reactants and/or reagents.

| Compound No | Structure | NMR | MS (M + H)+ |
|---|---|---|---|
| 89 | 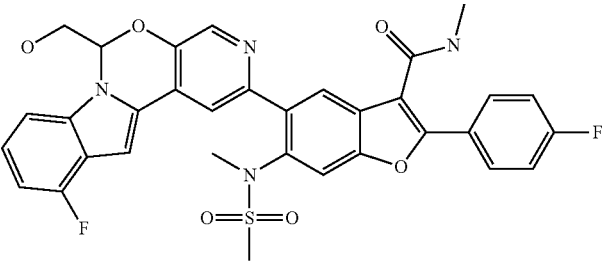<br>Enantiomer 1 | ¹H-NMR (CDCl₃, 400 MHz) δ 8.52 (s, 1H), 7.95~8.05 (m, 3H), 7.90 (s, 1H), 7.58 (s, 1H), 7.13~7.24 (m, 4H), 7.10 (s, 1H), 6.84 (t, J = 8.4 Hz, 1H), 6.46~6.49 (m, 1H), 6.21~6.24 (m, 1H), 3.87~3.93 (m, 1H), 3.68~3.73 (m, 1H), 3.19 (s, 3H), 2.93 (d, J = 4.4 Hz, 3H), 2.85 (s, 3H). | 645 |
| 90 | 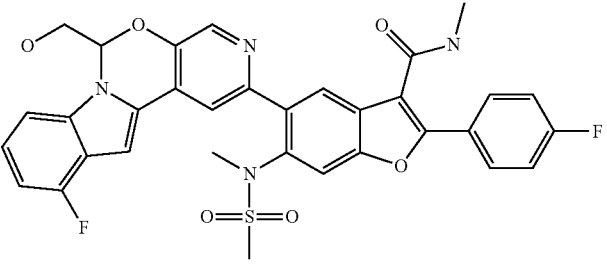<br>Enantiomer 2 | ¹H-NMR (CDCl₃, 400 MHz) δ 8.52 (s, 1H), 7.95~8.05 (m, 3H), 7.90 (s, 1H), 7.58 (s, 1H), 7.13~7.24 (m, 4H), 7.10 (s, 1H), 6.84 (t, J = 8.4 Hz, 1H), 6.46~6.49 (m, 1H), 6.21~6.24 (m, 1H), 3.87~3.93 (m, 1H), 3.68~3.73 (m, 1H), 3.19 (s, 3H), 2.93 (d, J = 4.4 Hz, 3H), 2.85 (s, 3H). | 645 |
| 91 | 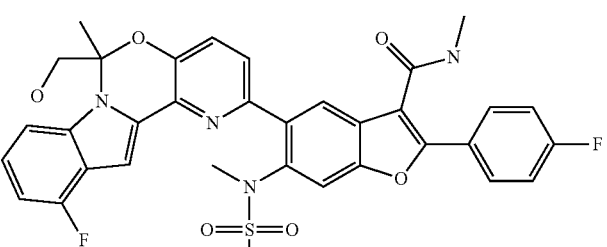<br>Enantiomer 1 | ¹H-NMR (CDCl₃, 400 MHz) δ 7.92~7.98 (m, 1H), 7.82~7.91 (m, 2H), 7.58 (s, 1H), 7.38 (s, 1H), 7.30~7.35 (m, 1H), 7.21~7.28 (m, 2H), 7.05~7.16 (m, 3H), 6.71~6.81 (m, 1H), 5.92 (d, J = 4.8 Hz, 1H), 4.09~4.18 (m, 1H), 3.90~4.00 (m, 1H), 3.31 (s, 3H), 2.89 (d, J = 5.2 Hz, 3H), 2.62 (s, 3H), 2.10~2.20 (m, 1H), 2.00 (s, 3H). | 659 |
| 92 | 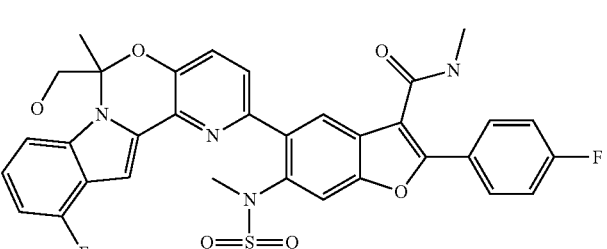<br>Enantiomer 2 | ¹H-NMR (CDCl₃, 400 MHz) δ 7.92~7.98 (m, 1H), 7.82~7.91 (m, 2H), 7.58 (s, 1H), 7.38 (s, 1H), 7.30~7.35 (m, 1H), 7.21~7.28 (m, 2H), 7.05~7.16 (m, 3H), 6.71~6.81 (m, 1H), 5.92 (d, J = 4.8 Hz, 1H), 4.09~4.18 (m, 1H), 3.90~4.00 (m, 1H), 3.31 (s, 3H), 2.89 (d, J = 5.2 Hz, 3H), 2.62 (s, 3H), 2.10~2.20 (m, 1H), 2.00 (s, 3H). | 659 |
| 93 | 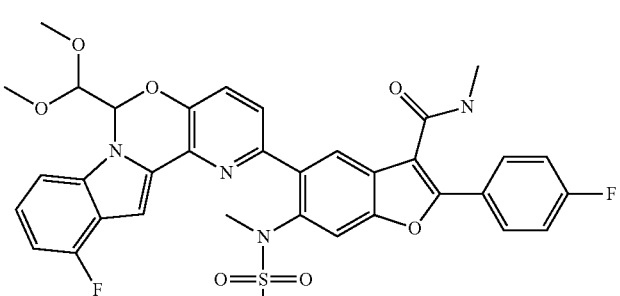 | ¹H-NMR (CDCl₃, 400 MHz) δ 8.04 (s, 1H), 7.90~7.99 (m, 2H), 7.66 (s, 1H), 7.48 (s, 2H), 7.13~7.25 (m, 5H), 6.79~6.88 (m, 1H), 6.21 (d, J = 5.6 Hz, 1H), 5.93 (br s, 1H), 4.49 (d, J = 5.6 Hz, 1H), 3.43 (s, 3H), 3.40 (s, 1H), 3.08 (s, 3H), 3.00 (d, J = 5.2 Hz, 3H), 2.71 (s, 3H). | 689 |

-continued

| Compound No | Structure | NMR | MS (M + H)+ |
|---|---|---|---|
| 94 | 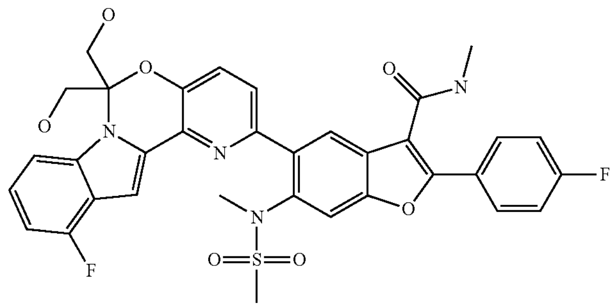 [SMILES: CNC(=O)c1c(-c2ccc(F)cc2)oc2cc(N(C)S(C)(=O)=O)c(-c3ccc4c(n3)-c3cc5c(F)cccc5n3C(CO)(CO)O4)cc12] | 1H-NMR (CDCl3, 400 MHz) δ 8.02 (s, 1H), 7.92 (dd, J = 5.2, 8.4 Hz, 2H), 7.62 (s, 1H), 7.34~7.45 (m, 3H), 7.29 (s, 1H), 7.11~7.24 (m, 3H), 6.81 (t, J = 8.8 Hz, 1H), 6.08 (br s, 1H), 4.27~4.37 (m, 2H), 4.15~4.25 (m, 2H), 3.35 (s, 3H), 2.93 (d, J = 5.2 Hz, 3H), 2.66~2.78 (m, 5H) | 675 |
| 95 | Enantiomer 1 | 1H-NMR (Methanol-d4, 400 MHz) δ 7.97~8.01 (m, 2H), 7.89 (s, 1H), 7.86 (s, 1H), 7.56 (s, 2H), 7.18~7.33 (m, 5H), 6.79~6.84 (m, 1H), 6.72 (t, J = 4.8 Hz, 1H), 3.78~3.83 (m, 1H), 3.65~3.69 (m, 1H), 3.35 (s, 3H), 3.20 (s, 3H), 2.95 (s, 3H), 2.85 (s, 3H). | 659 |
| 96 | Enantiomer 2 | 1H-NMR (Methanol-d4, 400 MHz) δ 7.97~8.01 (m, 2H), 7.89 (s, 1H), 7.86 (s, 1H), 7.56 (s, 2H), 7.18~7.33 (m, 5H), 6.79~6.84 (m, 1H), 6.72 (t, J = 4.8 Hz, 1H), 3.78~3.83 (m, 1H), 3.65~3.69 (m, 1H), 3.35 (s, 3H), 3.20 (s, 3H), 2.95 (s, 3H), 2.85 (s, 3H). | 659 |
| 97 | 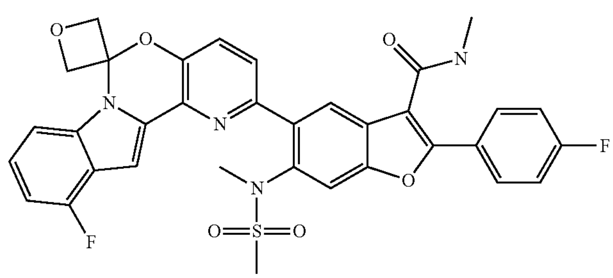 [SMILES: CNC(=O)c1c(-c2ccc(F)cc2)oc2cc(N(C)S(C)(=O)=O)c(-c3ccc4c(n3)-c3cc5c(F)cccc5n3C3(COC3)O4)cc12] | 1H-NMR (CDCl3, 400 MHz) δ 7.98 (s, 1H), 7.92~7.95 (m, 2H), 7.79 (d, J = 8.4 Hz, 1H), 7.63 (s, 1H), 7.48 (s, 2H), 7.32 (s, 1H), 7.23~7.29 (m, 1H), 7.19 (t, J = 8.4 Hz, 2H), 6.87~6.92 (m, 1H), 5.92 (br s, 1H), 5.48 (d, J = 8.4 Hz, 2H), 5.22 (d, J = 8.4 Hz, 2H), 3.35 (s, 3H), 2.96 (d, J = 4.8 Hz, 3H), 2.74 (s, 3H). | 657 |

Example 30

Preparation of Compound 98

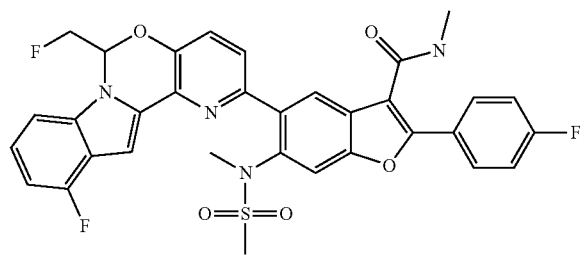

98

Step 1—Synthesis of 2-chloro-11-fluoro-6-(fluoromethyl)-6H-pyrido[2',3':5,6][1,3]oxazino[3,4-a]indole

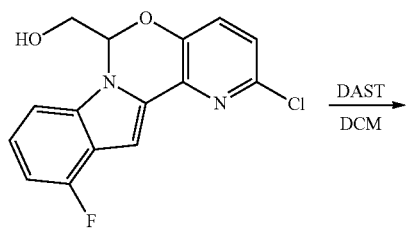

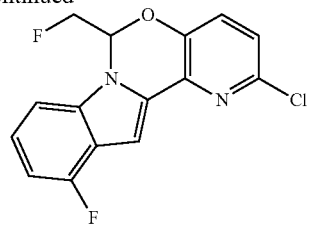

DAST (64 mg, 0.29 mmol) was added to a solution of (2-chloro-11-fluoro-6H-pyrido[2',3':5,6][1,3]oxazino[3,4-a]indol-6-yl)methanol (60 mg, 0.2 mmol) in $CH_2Cl_2$ (0.5 mL) at −78° C. under $N_2$. The mixture was stirred at −78° C. for 1 hour. The mixture was then heated to reflux and stirred for another 3 hours. The mixture was then diluted with water (30 mL) and extracted with $CH_2Cl_2$ (15 mL*3). The organic layer was washed with brine (20 mL), dried over $Na_2SO_4$ and concentrated in vacuo. The resulting residue was purified using prep-TLC (petroleum ether:EtOAc=4:1) to provide 2-chloro-11-fluoro-6-(fluoromethyl)-6H-pyrido[2',3':5,6][1,3]oxazino[3,4-a]indole (30 mg, yield: 50.0%). $^1$H-NMR (CDCl$_3$, 400 MHz) δ 7.29~7.33 (m, 2H), 7.13~7.20 (m, 2H), 7.03 (d, J=8.4 Hz, 1H), 6.78~6.83 (m, 1H), 6.46~6.51 (m, 1H), 4.35~4.63 (m, 2H). MS (M+H)$^+$: 307/309.

Step 2—Synthesis of 5-(11-fluoro-6-(fluoromethyl)-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (Compound 98)

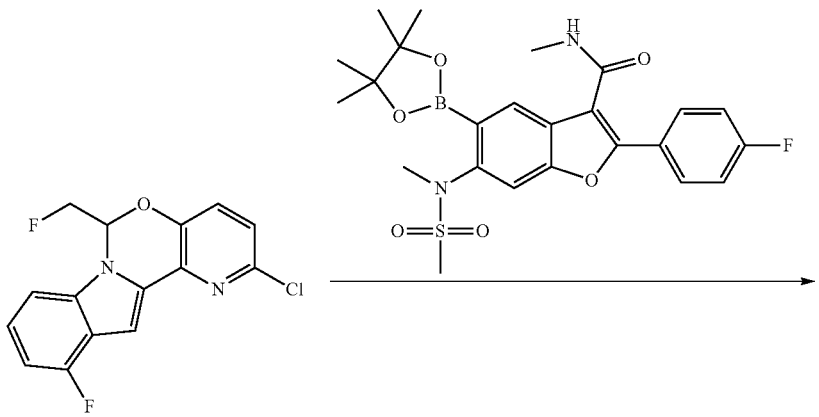

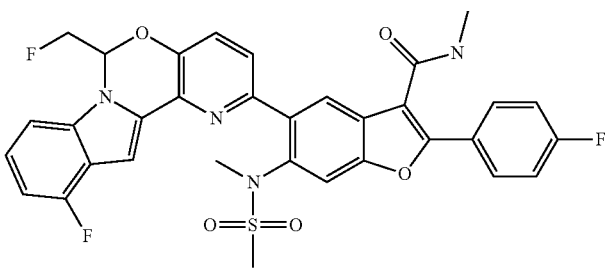

98

The procedure of Compound 98 (25 mg, yield 37.9%) was similar to step 6 of Example 1. ¹H-NMR (CDCl₃, 400 MHz) δ 7.96 (s, 1H), 7.88~7.91 (m, 2H), 7.60 (s, 1H), 7.45 (s, 2H), 7.13~7.18 (m, 4H), 7.06 (d, J=8.4 Hz, 1H), 6.81 (t, J=8.8 Hz, 1H), 6.51~6.56 (m, 1H), 5.82 (br s, 1H), 4.44~4.71 (m, 2H), 3.33 (s, 3H), 2.93 (d, J=4.8 Hz, 3H), 2.63 (s, 3H). MS (M+H)⁺: 647.

Example 31

Preparation of Compound 99 and Compound 100

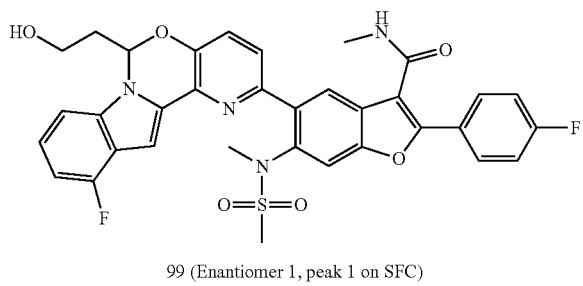

99 (Enantiomer 1, peak 1 on SFC)

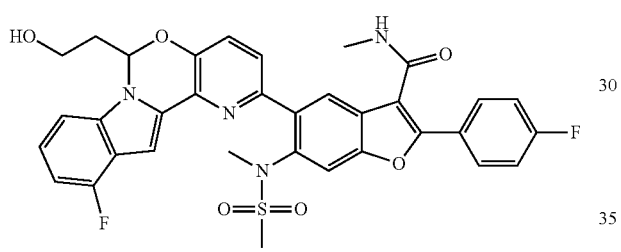

100 (Enantiomer 2, peak 2 on SFC)

Step 1—Synthesis of 6-(2-(benzyloxy)ethyl)-2-chloro-11-fluoro-12,12a-dihydro-6H-pyrido[2',3':5,6][1,3]oxazino[3,4-a]indole

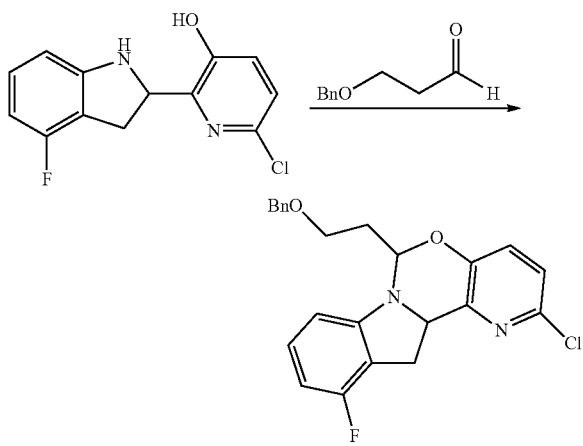

To a solution of 3-(benzyloxy)propanal (465 mg, 2.83 mmol) and 6-chloro-2-(4-fluoroindolin-2-yl)pyridin-3-ol (500 mg, 1.89 mmol) in MeCN (15 mL) was added TFA (10 mg, 0.09 mmol). The mixture was stirred at room temperature for 3 hours. The it was basified by NaHCO₃ (aq.), and then it was concentrated in vacuo, the resulting residue was purified using column chromatography (petroleum ether:EtOAc=10:1) to provide 6-(2-(benzyloxy)ethyl)-2-chloro-11-fluoro-12,12a-dihydro-6H-pyrido[2',3':5,6][1,3]oxazino[3,4-a]indole (540 mg, yield: 69%). ¹H-NMR (CDCl₃, 400 MHz) δ 7.28~7.38 (m, 5H), 7.04~7.10 (m, 2H), 6.95 (d, J=8.8 Hz, 1H), 6.60 (d, J=8.0 Hz, 1H), 6.50 (t, J=8.0 Hz, 1H), 5.93 (t, J=7.2 Hz, 1H), 5.02 (d, J=8.8 Hz, 1H), 4.55 (d, J=2.4 Hz, 1H), 3.62~3.71 (m, 3H), 3.40~3.48 (m, 1H), 2.19~2.27 (m, 2H). MS (M+H)⁺: 411.

Step 2—Synthesis of 6-(2-(benzyloxy)ethyl)-2-chloro-11-fluoro-6H-pyrido[2',3':5,6][1,3]oxazino[3,4-a]indole

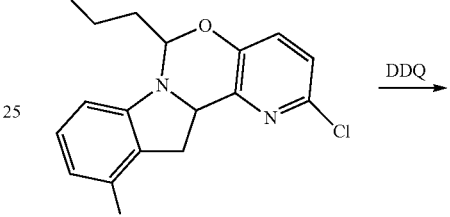

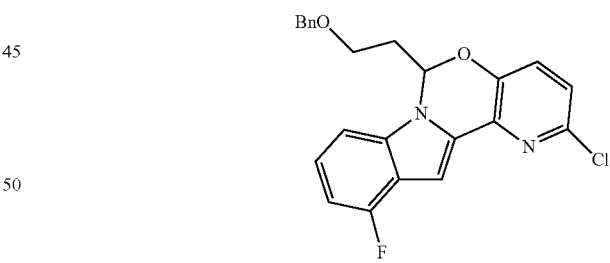

To a solution of 6-(2-(benzyloxy)ethyl)-2-chloro-11-fluoro-12,12a-dihydro-6H-pyrido[2',3':5,6][1,3]oxazino[3,4-a]indole (500 mg, 1.22 mmol) in toluene (7 mL) was added DDQ (552 mg, 2.43 mmol). The mixture was stirred at 80° C. for 2 hours. Then it was concentrated in vacuo, the resulting residue was purified using prep-HPLC to provide 6-(2-(benzyloxy)ethyl)-2-chloro-11-fluoro-6H-pyrido[2',3':5,6][1,3]oxazino[3,4-a]indole (44 mg, yield: 9%). ¹H-NMR (CDCl₃, 400 MHz) δ 7.32~7.43 (m, 5H), 7.22~7.28 (m, 1H), 7.11~7.20 (m, 3H), 6.80~6.86 (m, 1H), 6.65 (t, J=6.4 Hz, 1H), 4.48 (dd, J=8.0 Hz, 1H), 4.51 (d, J=12.0 Hz, 1H), 4.46 (d, J=12.0 Hz, 1H), 3.55~3.62 (m, 1H), 3.25~3.33 (m, 1H), 2.15~2.23 (m, 1H), 2.02~2.12 (m, 1H). MS (M+H)⁺: 409.

Step 3—Synthesis of 5-(6-(2-(benzyloxy)ethyl)-11-fluoro-6H-pyrido[2,3':5,6][1,3]oxazino[3,4-a]indol-2-yl)-2-(4-fluorophenyl)-N-methyl-6-(N-methylmethylsulfonamido)benzofuran-3-carboxamide

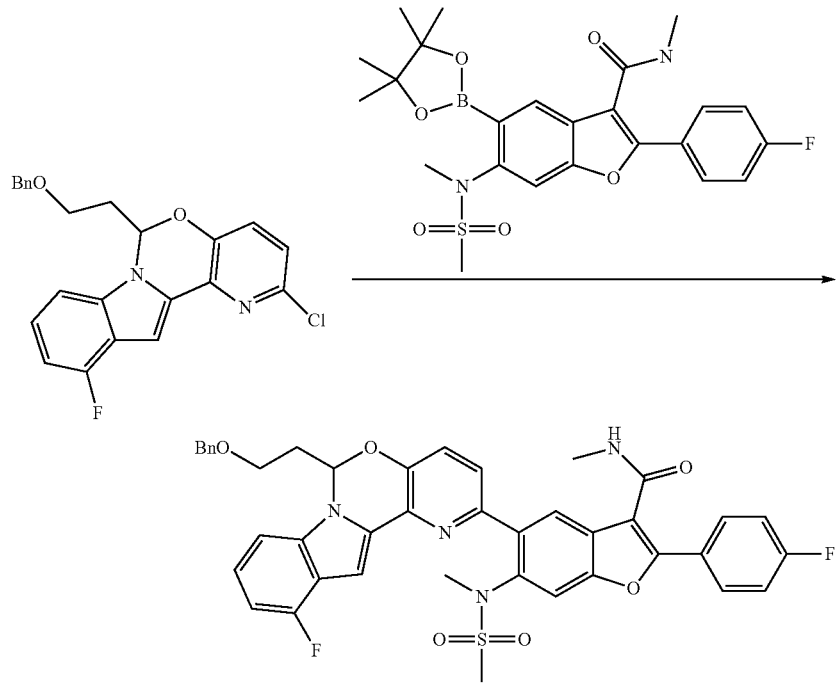

The procedure of racemic 5-(6-(2-(benzyloxy)ethyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (89 mg, yield: 79.0%) was similar to Example 1. $^1$H-NMR (CDCl$_3$, 400 MHz) δ 8.01 (s, 1H), 7.96 (dd, J=8.8, 5.6 Hz, 2H), 7.66 (s, 1H), 7.46~7.50 (m, 1H), 7.31~7.44 (m, 6H), 7.14~7.24 (m, 5H), 6.80~6.87 (m, 1H), 6.70 (t, J=6.4 Hz, 1H), 5.95 (br s, 1H), 4.47~4.57 (m, 2H), 3.62~3.69 (m, 1H), 3.31~3.42 (m, 4H), 2.99 (d, J=4.8 Hz, 3H), 2.70 (s, 3H), 2.20~2.30 (m, 1H), 2.08~2.18 (m, 1H). MS (M+H)$^+$: 749.

Step 4—Synthesis of 5-(11-fluoro-6-(2-hydroxyethyl)-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide
(Compound 99 and Compound 100)

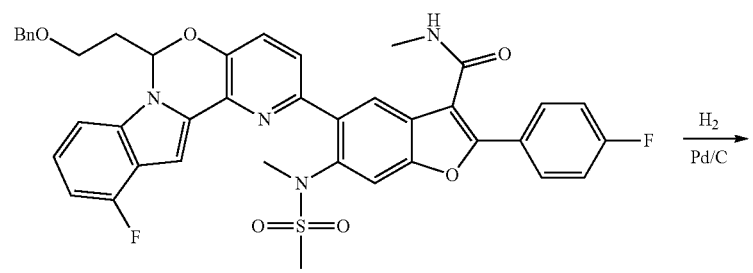

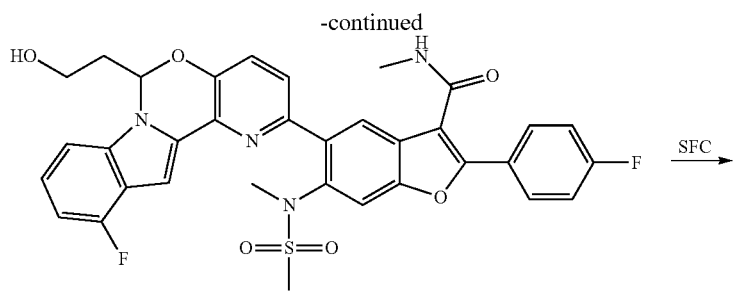

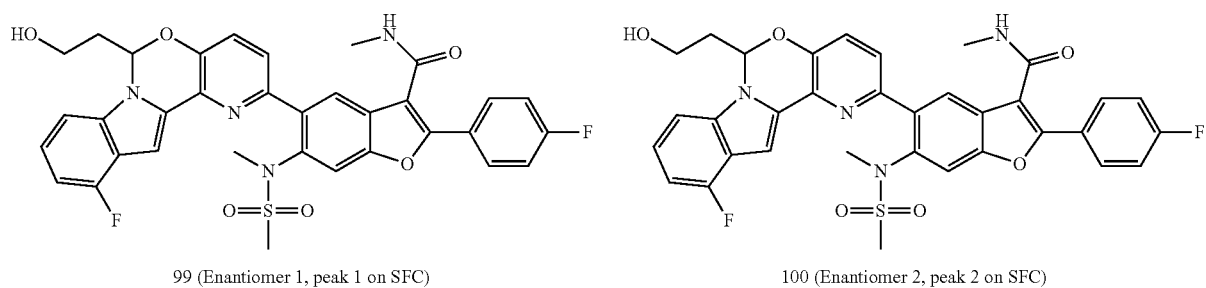

99 (Enantiomer 1, peak 1 on SFC)　　　100 (Enantiomer 2, peak 2 on SFC)

To a solution of 5-(6-(2-(benzyloxy)ethyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (85 mg, 0.11 mmol) in MeOH (3 mL) was added Pd/C (30 mg, 10%) under $H_2$ protection The mixture was stirred at room temperature overnight. The it was filtered to remove Pd/C, the filtrate was concentrated in vacuo, the resulting residue was purified using prep-TLC (dichloromethane:MeOH=20:1) to provide 5-(11-fluoro-6-(2-hydroxyethyl)-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (60 mg, yield: 85%). And after SFC separation, two enantiomers were obtained. Column: Chiralpak AD-3 50*4.6 mm I.D., 3 um Mobile phase: 60% ethanol (0.05% DEA) in CO2 Flow rate: 3 mL/min Wavelength: 220 nm. Compound 99: RT=0.529 min, Compound 100: RT=1.909 min Compound 99, enantiomer 1 (peak 1 on SFC), $^1$H-NMR (CDCl$_3$, 400 MHz) (CDCl$_3$, 400 MHz) δ 8.02 (s, 1H), 7.96 (dd, J=8.8, 5.6 Hz, 2H), 7.66 (s, 1H), 7.47 (q, J=8.8 Hz, 2H), 7.14~7.25 (m, 5H), 6.80~6.87 (m, 1H), 6.70 (dd, J=7.2, 5.2 Hz, 1H), 5.94 (br s, 1H), 3.83~3.91 (m, 1H), 3.62~3.71 (m, 1H), 3.39 (s, 3H), 3.00 (d, J=5.2 Hz, 3H), 2.72 (s, 3H), 2.16~2.26 (m, 1H), 2.01~2.12 (m, 1H), 1.79 (br. s., 1H). MS (M+H)$^+$: 659.

Compound 100, enantiomer 2 (peak 2 on SFC), $^1$H-NMR (CDCl$_3$, 400 MHz) (CDCl$_3$, 400 MHz) δ 8.02 (s, 1H), 7.96 (dd, J=8.8, 5.6 Hz, 2H), 7.66 (s, 1H), 7.47 (q, J=8.8 Hz, 2H), 7.14~7.25 (m, 5H), 6.80~6.87 (m, 1H), 6.70 (dd, J=7.2, 5.2 Hz, 1H), 5.94 (br s, 1H), 3.83~3.91 (m., 1H), 3.62~3.71 (m, 1H), 3.39 (s, 3H), 3.00 (d, J=5.2 Hz, 3H), 2.72 (s, 3H), 2.16~2.26 (m, 1H), 2.01~2.12 (m, 1H), 1.79 (br. s., 1H). MS (M+H)$^+$: 659.

Example 32

Preparation of Compound 101

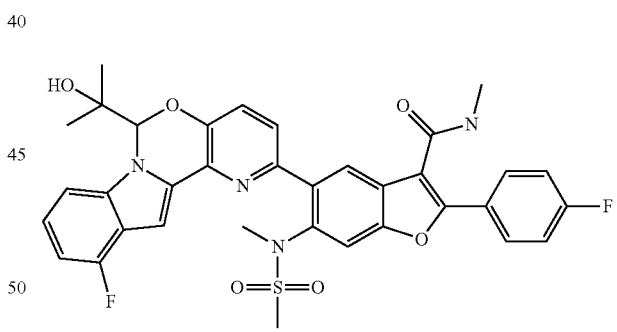

Step 1—Synthesis of 2-(2-chloro-11-fluoro-6H-pyrido[2',3':5,6][1,3]oxazino[3,4-a]indol-6-yl)propan-2-ol

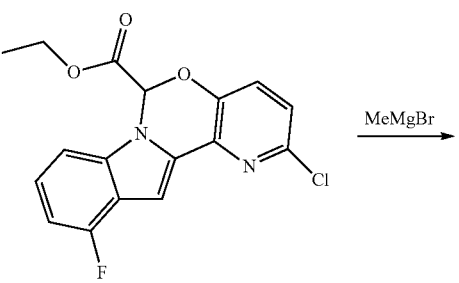

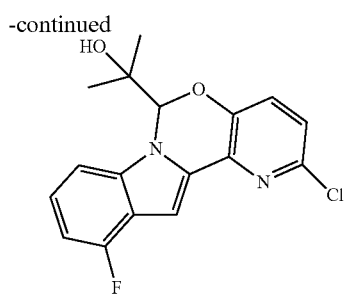

A mixture of ethyl 2-chloro-11-fluoro-6H-pyrido[2',3':5,6][1,3]oxazino[3,4-a]indole-6-carboxylate (120 mg, 0.33 mol) in THF (1 mL) was added MeMgBr (0.4 mL, 1.2 mmol) slowly at −78° C. under $N_2$ atmosphere. The mixture was stirred at −78° C. for 2 hours. After the reaction completed, the mixture was quenched with $NH_4Cl$ (aq., sat., 30 mL) at room temperature and extracted with EtOAc (20 mL*3). The organic layer was washed with brine (20 mL), dried over $Na_2SO_4$ and concentrated in vacuo. The resulting residue was purified using prep-TLC (petroleum ether:EtOAc=3:1) to provide 2-(2-chloro-11-fluoro-6H-pyrido[2',3':5,6][1,3]oxazino[3,4-a]indol-6-yl)propan-2-ol (70 mg, yield: 63.6%). $^1$H-NMR (CDCl$_3$, 400 MHz) δ 7.06~7.19 (m, 4H), 6.73~6.77 (m, 1H), 6.07 (s, 1H), 1.26 (s, 3H), 1.03 (s, 3H). MS (M+H)$^+$: 333.

Step 2—Synthesis of 5-(11-fluoro-6-(2-hydroxypropan-2-yl)-6H-pyrido[2',3',5,6][1,3]oxazino[3,4-a]indol-2-yl)-2-(4-fluorophenyl)-N-methyl-6-(N-methylmethylsulfonamido)benzofuran-3-carboxamide (Compound 101)

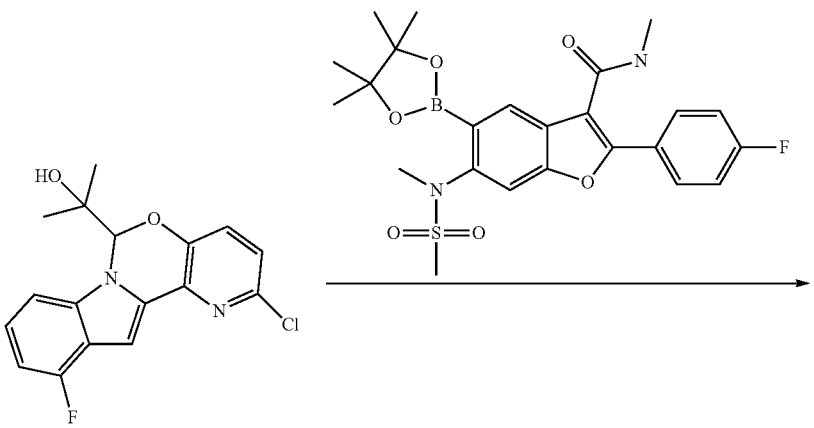

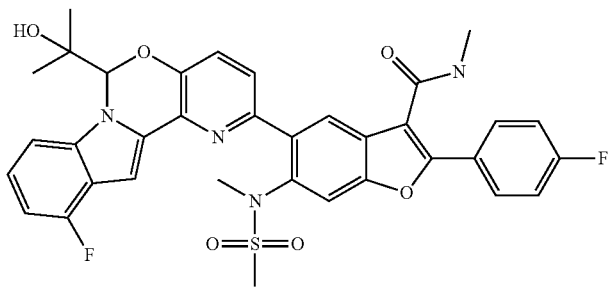 [SMILES: CNC(=O)c1c(-c2ccc(F)cc2)oc2cc(N(C)S(C)(=O)=O)c(-c3ccc4c(n3)-c3cc5c(F)cccc5n3C(C(C)(C)O)O4)cc12]

101

161

The procedure of Compound 101 (40 mg, yield: 50.0%) was similar to step 2 of Example 2. ¹H-NMR (CDCl₃, 400 MHz) δ 7.97 (s, 1H), 7.86~7.89 (m, 2H), 7.60 (s, 1H), 7.40 (d, J=8.4 Hz, 1H), 7.34 (d, J=8.4 Hz, 1H), 7.23 (d, J=10.0 Hz, 1H), 7.11~7.17 (m, 4H), 6.78~6.82 (m, 1H), 6.17 (s, 1H), 6.10 (br s, 1H), 3.34 (s, 3H), 2.91 (d, J=4.8 Hz, 3H), 2.65 (s, 3H), 1.86 (s, 1H), 1.33 (s, 3H), 1.15 (s, 3H). MS (M+H)⁺: 673.

Example 33

Preparation of Compound 102

162

Step 1—Synthesis of (2S)-(11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indol-6-yl)methyl 2-((tert-butoxycarbonyl)amino)-3-methylbutanoate

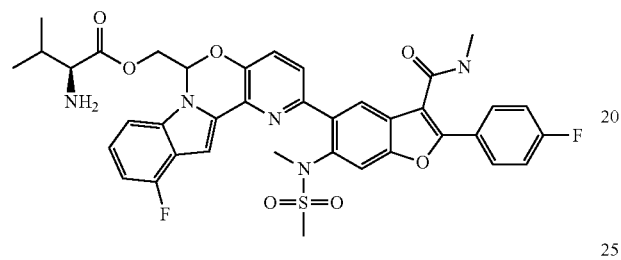

102

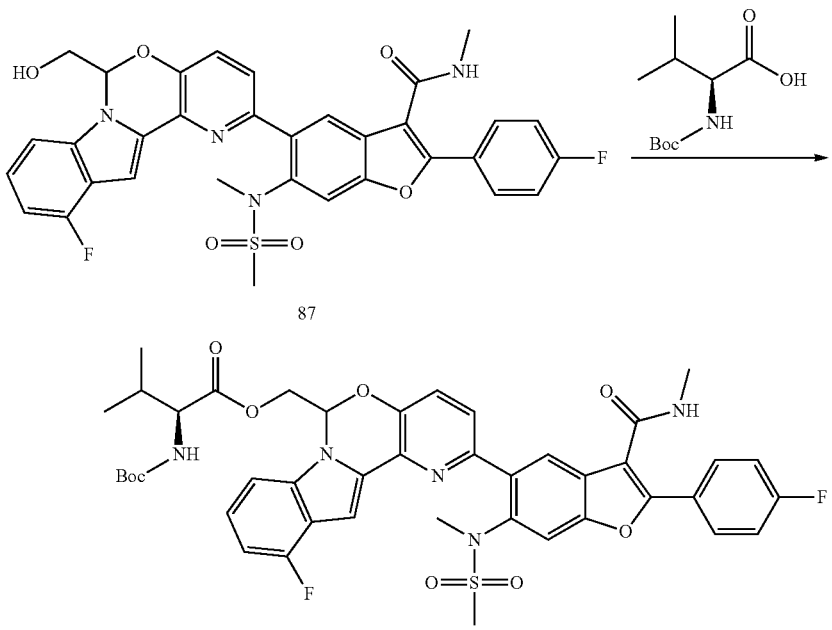 [SMILES: CNC(=O)c1c(-c2ccc(F)cc2)oc2cc(N(C)S(C)(=O)=O)c(-c3ccc4c(n3)-c3cc5c(F)cccc5n3C(CO)O4)cc12 ; CC(C)[C@H](NC(=O)OC(C)(C)C)C(=O)O ; CNC(=O)c1c(-c2ccc(F)cc2)oc2cc(N(C)S(C)(=O)=O)c(-c3ccc4c(n3)-c3cc5c(F)cccc5n3C(COC(=O)[C@@H](NC(=O)OC(C)(C)C)C(C)C)O4)cc12]

To a solution of 5-(11-fluoro-6-(hydroxymethyl)-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (30 mg, 0.05 mmol, Compound 87, single enantiomer) and N-Boc-L-Valine (20 mg, 0.09 mmol) in dichloromethane, EDCI (20 mg, 0.10 mmol), DMAP (8 mg, 0.06 mmol) and Et$_3$N (0.01 mL) were added. The reaction mixture was stirred at room temperature overnight. Then H$_2$O was added, and extracted with dichloromethane. The combined organic phases were washed with brine, dried over Na$_2$SO$_4$, filtered and concentrated in vacuo. The crude product was purified using prep-TLC (dichloromethane:MeOH=40:1) to provide (2S)-(11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indol-6-yl)methyl 2-((tert-butoxycarbonyl)amino)-3-methylbutanoate (30 mg, yield: 76%). $^1$H-NMR (CDCl$_3$, 400 MHz) δ 7.98~8.02 (m, 3H), 7.67 (s, 1H), 7.46~7.54 (m, 2H), 7.19~7.25 (m, 5H), 6.84~6.89 (m, 1H), 6.62~6.65 (m, 1H), 5.98 (br s, 1H), 4.91 (d, J=8.4 Hz, 1H), 4.42~4.48 (m, 1H), 4.30~4.35 (m, 1H), 4.18 (br s, 1H), 3.38 (s, 3H), 3.01 (d, J=4.8 Hz, 3H), 2.72 (s, 3H), 1.90~1.95 (m, 1H), 1.45 (s, 9H), 0.88 (d, J=6.4 Hz, 3H), 0.79 (d, J=6.4 Hz, 3H). MS (M+H)$^+$: 844.

Step 2—Synthesis of (S)—((S)-11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indol-6-yl)methyl 2-amino-3-methylbutanoate (Compound 102)

To a solution of (2S)-(11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indol-6-yl)methyl 2-((tert-butoxycarbonyl)amino)-3-methylbutanoate (30 mg, 0.04 mmol) in dichloromethane (2 mL), TFA (0.5 mL) was added. The mixture was stirred at room temperature overnight. The mixture was poured into sat NaHCO$_3$ solution (20 mL) and extracted with dichloromethane. The combined organic phase was dried over Na$_2$SO$_4$, filtered and concentrated in vacuo. The crude product was purified using prep-TLC (dichloromethane:MeOH=40:1) to provide the product Compound 102 (25 mg, yield: 94%). $^1$H-NMR (CDCl$_3$, 400 MHz) δ 8.03 (s, 1H), 7.95~7.99 (m, 2H), 7.66 (s, 1H), 7.53 (d, J=8.4 Hz, 1H), 7.46 (d, J=8.4 Hz, 1H), 7.19~7.25 (m, 5H), 6.84~6.89 (m, 1H), 6.63~6.66 (m, 1H), 5.95 (br s, 1H), 4.41~4.47 (m, 1H), 4.32~4.37 (m, 1H), 3.39 (s, 3H), 3.23 (d, J=5.2 Hz, 1H), 3.01 (d, J=4.8 Hz, 3H), 2.74 (s, 3H), 1.82~1.91 (m, 1H), 0.91 (d, J=6.8 Hz, 3H), 0.81 (d, J=6.8 Hz, 3H). MS (M+H)$^+$: 744.

Compounds 103-104, depicted in the table below, were prepared using the method described above and substituting the appropriate reactants and/or reagents.

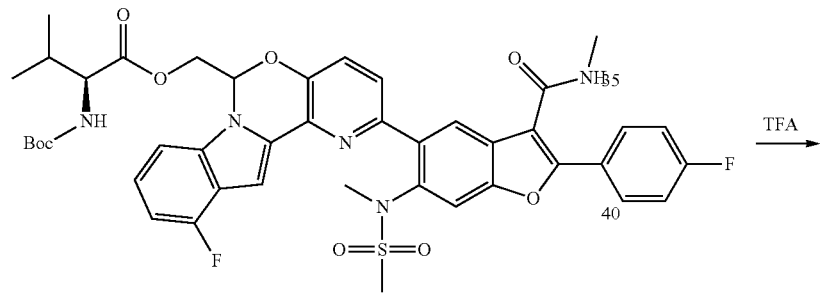

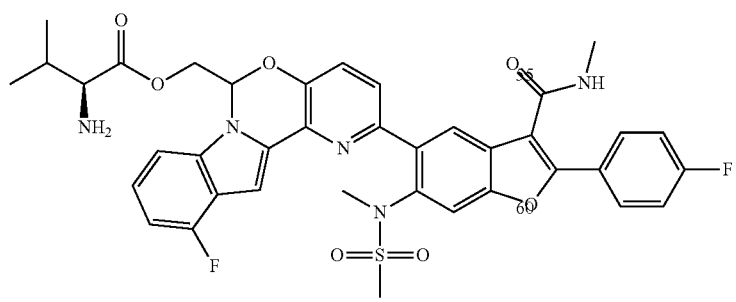

102

| Compound No | Structure | NMR | MS (M + H)+ |
|---|---|---|---|
| 103 | 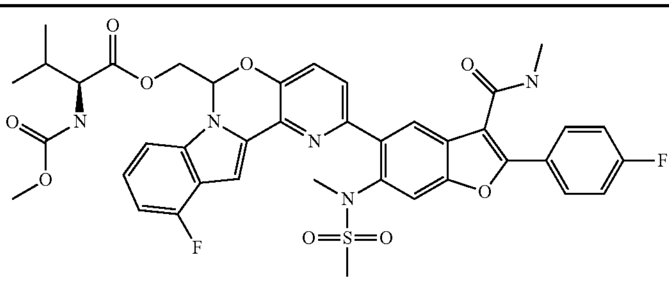 | ¹H-NMR (CDCl₃, 400 MHz) 8.05~7.91 (m, 3H), 7.67 (s, 1H), 7.56~7.50 (m, 1H), 7.49~7.43 (m, 1H), 7.25~7.15 (m, 4H), 6.91~6.83 (m, 1H), 6.64 (dd, J = 5.2, 6.8 Hz, 1H), 5.99 (d, J = 4.4 Hz, 1H), 5.04 (d, J = 8.4 Hz, 1H), 4.51~4.41 (m, 1H), 4.35 (dd, J = 4.8, 11.2 Hz, 1H), 4.23 (dd, J = 4.4, 8.4 Hz, 1H), 3.68 (s, 3H), 3.39 (s, 3H), 3.01 (d, J = 4.8 Hz, 3H), 2.73 (s, 3H), 2.00~1.90 (m, 1H), 0.89 (d, J = 6.8 Hz, 3H), 0.79 (d, J = 6.4 Hz, 3H). | 802 |
| 104 | Chiral | ¹H-NMR (CDCl₃, 400 MHz) δ 1.69~1.97 (m, 4H), 2.69~2.78 (d, J = 12.4 Hz, 3H), 2.98~3.08 (d, J = 4.4 Hz, 3H), 3.38~3.56 (m, 5H), 3.67~3.76 (m, 3H), 4.27~4.41 (m, 2H), 4.43~4.52 (m, 1H), 5.95~6.05 (d, J = 13.2 Hz, 1H), 6.59~6.66 (m, 1H), 6.81~6.89 (m, 1H), 7.20~7.29 (m, 5H), 7.43~7.55 (m, 2H), 7.68 (s, 1H), 7.95~8.09 (m, 3H). | 800 |

Example 34

Preparation of Compound 105 and 106

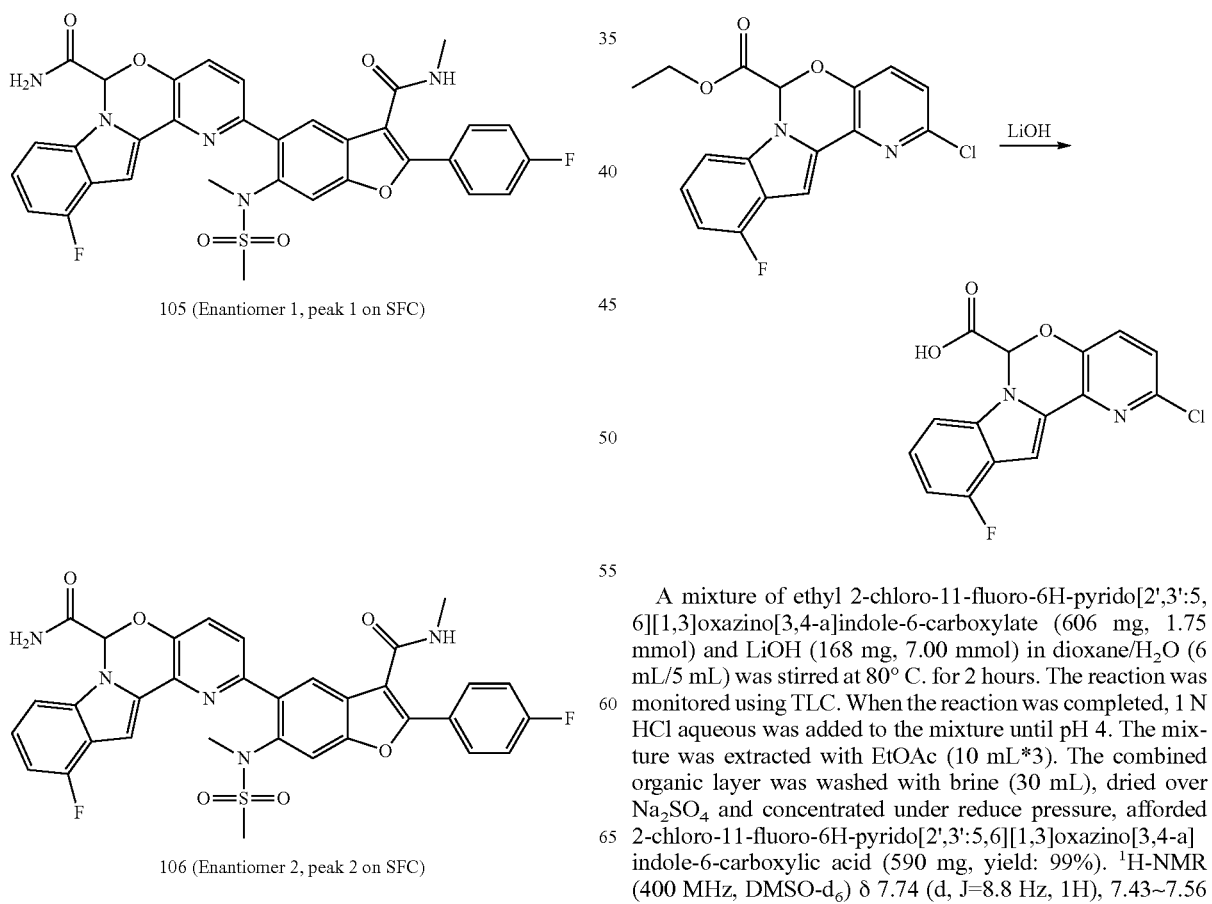

105 (Enantiomer 1, peak 1 on SFC)

106 (Enantiomer 2, peak 2 on SFC)

Step 1—Synthesis of 2-chloro-11-fluoro-6H-pyrido[2',3':5,6][1,3]oxazino[3,4-a]indole-6-carboxylic acid A mixture of ethyl 2-chloro-11-fluoro-6H-pyrido[2',3':5,6][1,3]oxazino[3,4-a]indole-6-carboxylate (606 mg, 1.75 mmol) and LiOH (168 mg, 7.00 mmol) in dioxane/H₂O (6 mL/5 mL) was stirred at 80° C. for 2 hours. The reaction was monitored using TLC. When the reaction was completed, 1 N HCl aqueous was added to the mixture until pH 4. The mixture was extracted with EtOAc (10 mL*3). The combined organic layer was washed with brine (30 mL), dried over Na₂SO₄ and concentrated under reduce pressure, afforded 2-chloro-11-fluoro-6H-pyrido[2',3':5,6][1,3]oxazino[3,4-a]indole-6-carboxylic acid (590 mg, yield: 99%). ¹H-NMR (400 MHz, DMSO-d₆) δ 7.74 (d, J=8.8 Hz, 1H), 7.43~7.56

(m, 2H), 7.37 (s, 1H), 7.25~7.34 (m, 1H), 7.15 (s, 1H), 6.92~7.02 (m, 1H). MS (M+H)+: 319.

Step 2—Synthesis of 2-chloro-11-fluoro-6H-pyrido [2',3':5,6][1,3]oxazino[3,4-a]indole-6-carboxamide

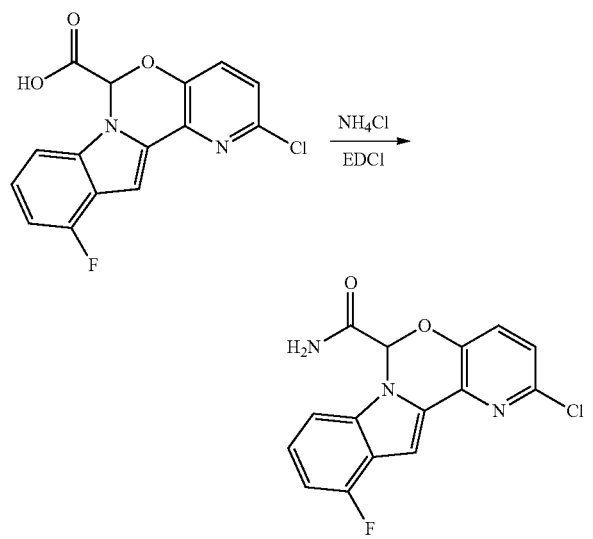

A mixture of 2-chloro-11-fluoro-6H-pyrido[2',3':5,6][1,3] oxazino[3,4-a]indole-6-carboxylic acid (60 mg, 0.19 mmol), NH$_4$Cl (20 mg, 0.38 mmol), HOBT (38 mg, 0.28 mmol), EDCI (54 mg, 0.28 mmol) and triethylamine (76 mg, 0.75 mmol) in DMF (1 mL) was stirred at room temperature overnight under N$_2$ atmosphere. The mixture was then diluted with water (30 mL) and extracted with EtOAc (20 mL×3). The organic layer was washed with brine (30 mL×3), dried over Na$_2$SO$_4$ and concentrated in vacuo. The resulting residue was purified using column chromatography (dichloromethane:MeOH=30:1) to provide 2-chloro-11-fluoro-6H-pyrido[2',3':5,6][1,3]oxazino[3,4-a]indole-6-carboxamide (20 mg, yield: 33.3%). $^1$H-NMR (Methanol-d$_4$, 400 MHz) δ 7.54 (d, J=8.4 Hz, 1H), 7.28~7.31 (m, 2H), 7.20~7.24 (m, 2H), 6.90 (s, 1H), 6.82~6.84 (m, 1H). MS (M+H)+: 318.

Step 3—Synthesis of 11-fluoro-2-(2-(4-fluorophenyl)-3-(methylcarbamoyl)-6-(N-methylmethylsulfonamido)benzofuran-5-yl)-6H-pyrido[2',3':5,6][1,3] oxazino[3,4-a]indole-6-carboxamide: two enantiomers (Compound 105 and 106)

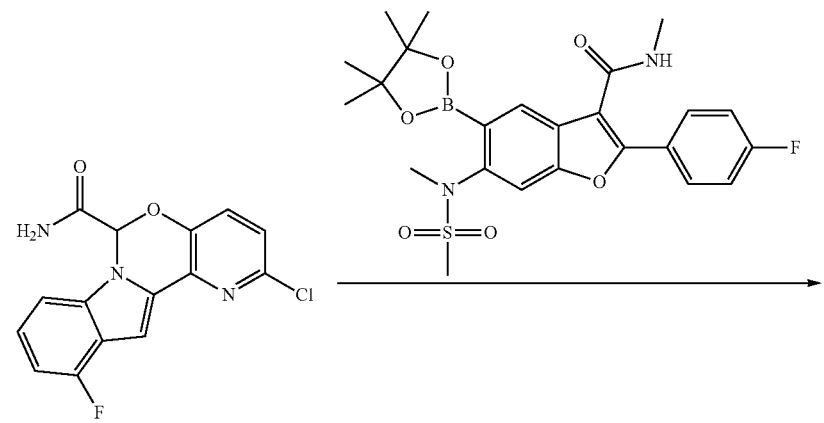

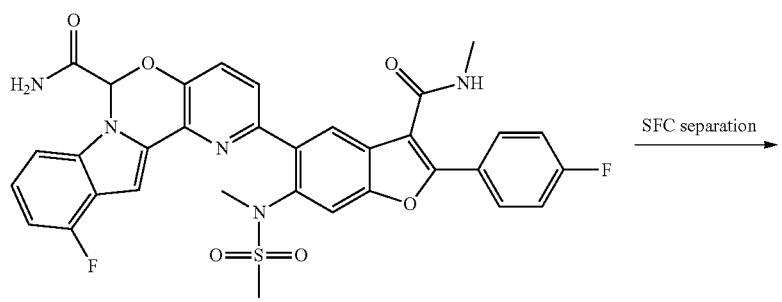

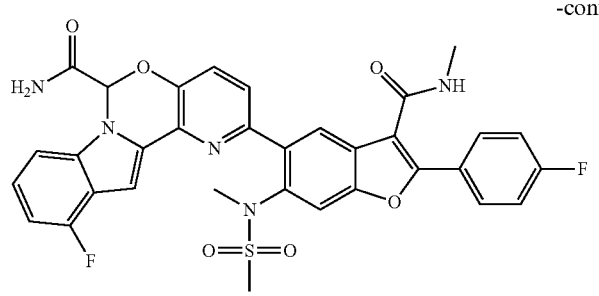

105 (Enantiomer 1, peak 1 on SFC)

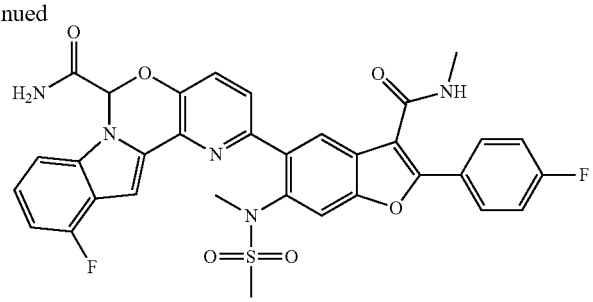

106 (Enantiomer 2, peak 2 on SFC)

The procedure of racemic 11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indole-6-carboxamide was similar to step 6 of Example 1. And after SFC separation, Compound 105 and 106 were obtained. Column: Chiralpak AS-H 150×4.6 mm I.D., 5 um Mobile phase: methanol (0.05% DEA) in $CO_2$ fromS % to 40%. Flow rate: 3 mL/min Wavelength: 220 nm. Compound 105: RT=5.010 min, Compound 106: RT=6.066 min Compound 105, enantiomer 1 (peak 1 on SFC), $^1$H-NMR (DMSO-$d_6$, 400 MHz) δ 8.55 (s, 1H), 8.13 (s, 1H), 7.81~8.01 (m, 3H), 7.81 (s, 1H), 7.68~7.74 (m, 2H), 7.57 (d, J=8.4 Hz, 1H), 7.47 (d, J=8.8 Hz, 1H), 7.39 (t, J=8.8 Hz, 2H), 7.20~7.25 (m, 1H), 7.08 (d, J=5.6 Hz, 2H), 6.89~6.94 (m, 1H), 3.28 (s, 3H), 2.80~2.82 (m, 6H). MS (M+H)$^+$: 658.

Compound 106, enantiomer 2 (peak 2 on SFC), $^1$H-NMR (DMSO-$d_6$, 400 MHz) δ 8.55 (s, 1H), 8.13 (s, 1H), 7.81~8.01 (m, 3H), 7.81 (s, 1H), 7.68~7.74 (m, 2H), 7.57 (d, J=8.4 Hz, 1H), 7.47 (d, J=8.8 Hz, 1H), 7.39 (t, J=8.8 Hz, 2H), 7.20~7.25 (m, 1H), 7.08 (d, J=5.6 Hz, 2H), 6.89~6.94 (m, 1H), 3.28 (s, 3H), 2.80~2.82 (m, 6H). MS (M+H)$^+$: 658.

Compounds 107-113, depicted in the table below, were prepared using the method described in Example 8 and substituting the appropriate reagents and/or reactants.

| Compound No | Structure | NMR | MS (M + H)$^+$ |
|---|---|---|---|
| 107 | 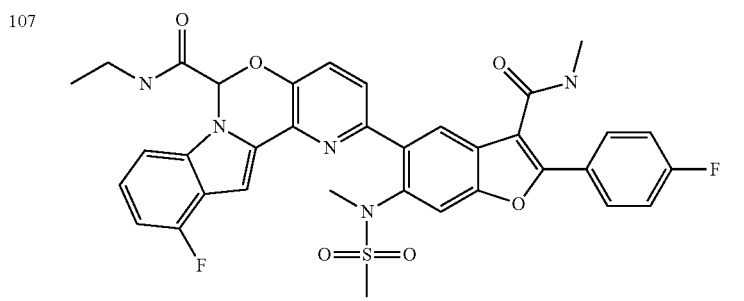<br>(Enantiomer 1, peak 1 on SFC) | $^1$H-NMR (DMSO-$d_6$, 400 MHz) δ 8.78 (br s, 1H), 8.55 (d, J = 4.4 Hz, 1H), 8.00 (br s, 3H), 7.82 (s, 1H), 7.67 (d, J = 8.0 Hz, 1H), 7.57 (d, J = 8.0 Hz, 1H), 7.34~7.48 (m, 3H), 7.20~7.27 (m, 1H), 7.09 (s, 1H), 7.04 (s, 1H), 6.89~6.96 (m, 1H), 3.27 (s, 3H), 3.02 (q, J = 7.2 Hz, 2H), 2.70~2.93 (m, 6H), 0.94 (t, J = 7.2 Hz, 3H). | 686 |
| 108 | 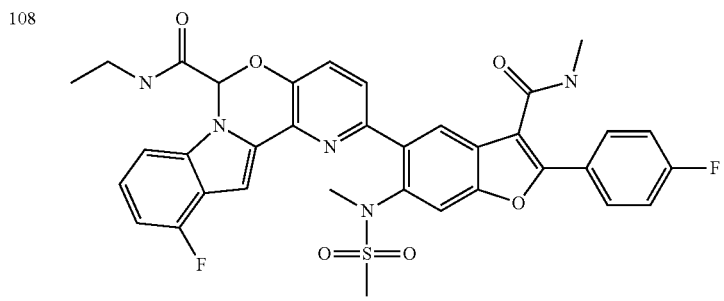<br>(Enantiomer 2, peak 2 on SFC) | $^1$H-NMR (DMSO-$d_6$, 400 MHz) δ 8.78 (br s, 1H), 8.55 (d, J = 4.4 Hz, 1H), 8.00 (br s, 3H), 7.82 (s, 1H), 7.67 (d, J = 8.0 Hz, 1H), 7.57 (d, J = 8.0 Hz, 1H), 7.34~7.48 (m, 3H), 7.20~7.27 (m, 1H), 7.09 (s, 1H), 7.04 (s, 1H), 6.89~6.96 (m, 1H), 3.27 (s, 3H), 3.02 (q, J = 7.2 Hz, 2H), 2.70~2.93 (m, 6H), 0.94 (t, J = 7.2 Hz, 3H), | 686 |

-continued

| Compound No | Structure | NMR | MS (M + H)+ |
|---|---|---|---|
| 109 | (Enantiomer 1, peak 1 on SFC) | ¹H-NMR (CDCl₃, 400 MHz) δ 7.97 (s, 1H), 7.87~7.91 (m, 2H), 7.58 (s, 1H), 7.43~7.48 (m, 2H), 7.23 (s, 1H), 7.10~7.17 (m, 4H), 6.81 (t, J = 8.8 Hz, 1H), 6.51 (s, 1H), 5.86 (br s, 1H), 5.79 (br s, 1H), 3.32 (s, 3H), 2.93 (d, J = 4.8 Hz, 3H), 2.67 (d, J = 4.4 Hz, 3H), 2.63 (s, 3H). | 672 |
| 110 | (Enantiomer 2, peak 2 on SFC) | ¹H-NMR (Methanol-d₄, 400 MHz) δ 7.93~7.96 (m, 2H), 7.83 (s, 1H), 7.79 (s, 1H), 7.52~7.59 (m, 2H), 7.17~7.26 (m, 5H), 6.80~6.86 (m, 2H), 3.29 (s, 3H), 2.94 (s, 3H), 2.75 (s, 3H), 2.67 (s, 3H). | 672 |
| 111 | 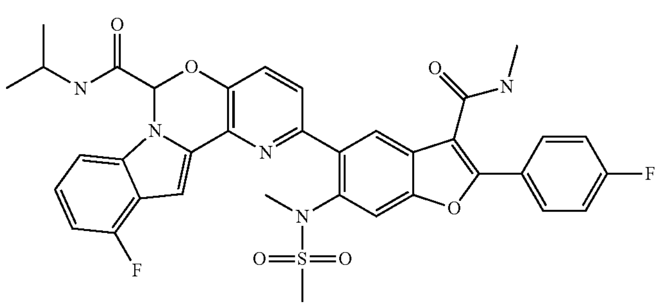 [SMILES: CNC(=O)c1c(-c2ccc(F)cc2)oc2cc(N(C)S(C)(=O)=O)c(-c3ccc4c(n3)-c3cc5c(F)cccc5n3C(C(=O)NC(C)C)O4)cc12] | ¹H-NMR (DMSO-d₆, 400 MHz) δ 8.67 (d, J = 8.0 Hz, 1H), 8.53 (d, J = 4.4 Hz, 1H), 7.99~8.02 (m, 3H), 7.82 (s, 1H), 7.66 (d, J = 8.4 Hz, 1H), 7.55 (d, J = 8.4 Hz, 1H), 7.37~7.45 (m, 3H), 7.20~7.25 (m, 1H), 7.09 (s, 1H), 6.97 (s, 1H), 6.90~6.94 (m, 1H), 3.64~3.73 (m, 1H), 3.26 (s, 3H), 2.84 (s, 3H), 2.80 (d, J = 4.4 Hz, 3H), 0.98 (d, J = 6.8 Hz, 6H). | 700 |
| 112 | 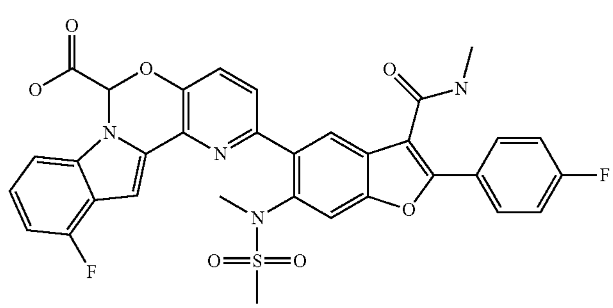 [SMILES: CNC(=O)c1c(-c2ccc(F)cc2)oc2cc(N(C)S(C)(=O)=O)c(-c3ccc4c(n3)-c3cc5c(F)cccc5n3C(C(=O)O)O4)cc12] | ¹H-NMR (CDCl3, 400 MHz) δ 7.89~7.93 (m, 2H), 7.67 (br s, 1H), 7.49 (d, J = 8.4 Hz, 1H), 7.32~7.35 (m, 1H), 7.25~7.27 (m, 1H), 7.14 (s, 1H), 7.02~7.09 (m, 4H), 6.92~6.96 (m, 1H), 6.67-6.72 (m, 1H), 6.46 (s, 1H), 5.59 (br s, 1H), 3.02 (s, 3H), 2.82 (br s, 3H), 2.57 (s, 3H). | 659 |

| Compound No | Structure | NMR | MS (M + H)+ |
|---|---|---|---|
| 113 | 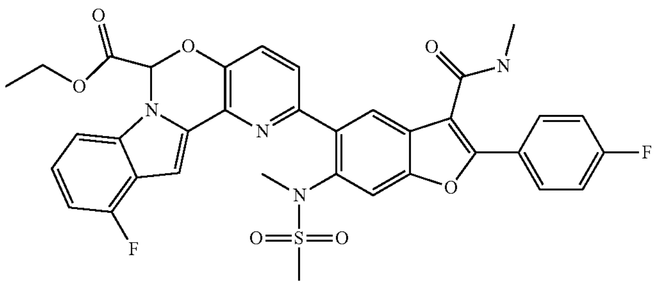 [SMILES: CCOC(=O)C1Oc2ccc(-c3cc4c(C(=O)NC)c(-c5ccc(F)cc5)oc4cc3N(C)S(C)(=O)=O)nc2-c2cc3c(F)cccc3n21] | ¹H-NMR (CDCl₃, 400 MHz) δ 7.99 (s, 1H), 7.92~7.98 (m, 2H), 7.66 (s, 1H), 7.46~7.54 (m, 2H), 7.16~7.26 (m, 4H), 6.87 (dd, J = 8.0, 1.6 Hz, 1H), 6.94 (s, 1H), 5.95 (br s, 1H), 4.05~4.16 (m, 2H), 3.38 (s, 3H), 3.00 (d, J = 4.8 Hz, 3H), 2.86 (s, 3H), 1.13 (t, J = 7.2 Hz, 3H) | 687 |

Example 35

Preparation of Compound 114 and 115

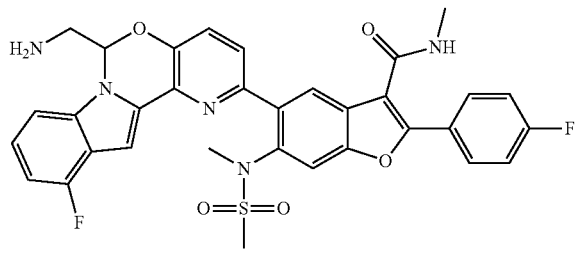

114 (Enantiomer 1, peak 1 on SFC)

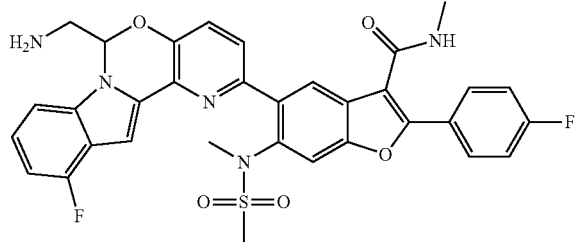

115 (Enantiomer 2, peak 2 on SFC)

Step 1—Synthesis of (2-chloro-11-fluoro-6H-pyrido[2',3':5,6][1,3]oxazino[3,4-a]indol-6-yl)methyl methanesulfonate

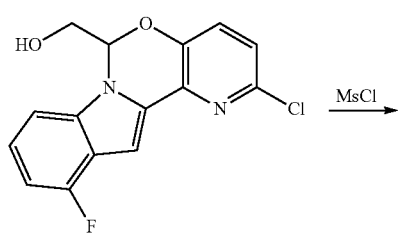

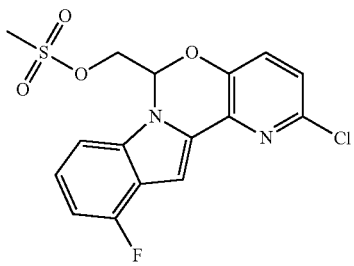

To a solution of (2-chloro-11-fluoro-6H-pyrido[2',3':5,6][1,3]oxazino[3,4-a]indol-6-yl)methanol (1.00 g, 3.29 mmol) in dry pyridine (10 mL) at room temperature was added dropwise MsCl (1.23 g, 10.74 mmol) at 0° C. Then the reaction mixture was stirred at room temperature for 2 hours under N₂ protection. The reaction was poured into water and filtered. The filter cake was washed with water and dried to provide (2-chloro-11-fluoro-6H-pyrido[2',3':5,6][1,3]oxazino[3,4-a]indol-6-yl)methyl methanesulfonate (1.20 g, yield: 90.1%). ¹H-NMR (DMSO-d6, 400 MHz) δ 7.37~7.51 (m, 2H), 7.28~7.33 (m, 2H), 7.18~7.24 (d, J=8.4 Hz, 1H), 6.9-6.98 (m, 1H), 6.65~6.72 (m, 1H), 4.46~4.53 (m, 1H), 4.31~4.38 (m, 1H), 2.90 (s, 3H). MS (M+H)⁺: 383.

Step 2—Synthesis of 6-(azidomethyl)-2-chloro-11-fluoro-6H-pyrido[2',3':5,6][1,3]oxazino[3,4-a]indole

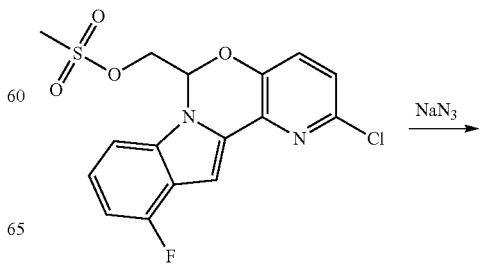

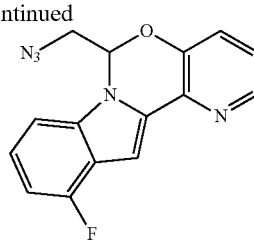

To a solution of (2-chloro-11-fluoro-6H-pyrido[2',3':5,6][1,3]oxazino[3,4-a]indol-6-yl)methyl methanesulfonate (5 g, 13.08 mmol) in DMF (50 mL), NaN₃ (4.18 g, 39.25 mmol) was added at room temperature. The mixture was stirred at 60° C. for 6 hours under N₂ protection. After H₂O was added, the mixture was extracted with EtOAc (20 mL*3). The combined organic phases were washed with water and brine, dried over Na₂SO₄ and concentrated to provide 6-(azidomethyl)-2-chloro-11-fluoro-6H-pyrido[2',3':5,6][1,3]oxazino[3,4-a]indole (4.2 g, yield: 97.4%). The crude product was used in the next step without purification. ¹H-NMR (CDCl₃, 400 MHz) δ 3.62~3.71 (m, 1H), 3.72~3.81 (m, 1H), 5.28~5.34 (t, J=5.6 Hz, 1H), 6.76~6.83 (t, J=4.4 Hz, 1H), 6.92~7.00 (m, 1H), 7.05~7.13 (s, 1H), 7.23~7.31 (m, 1H), 7.39~7.51 (m, 2H), 7.57~7.67 (d, J=8.8 Hz, 1H). MS (M+H)⁺: 330.

Step 3—Synthesis of 5-(6-(azidomethyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide

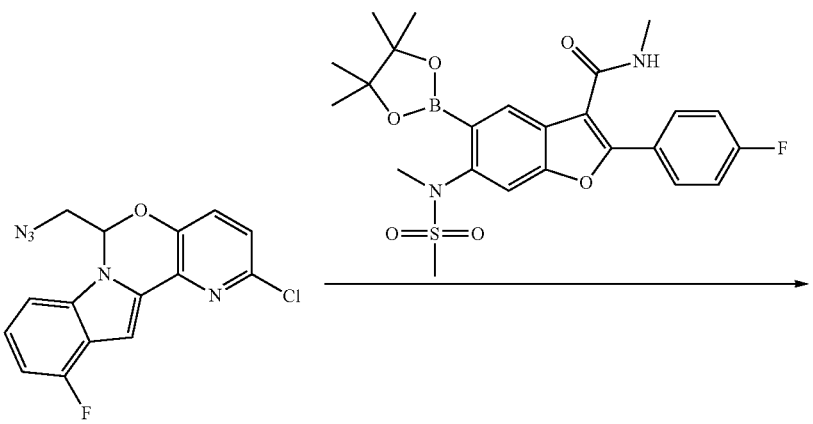

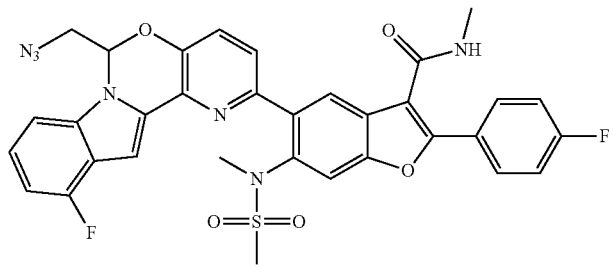

To a mixture of 6-(azidomethyl)-2-chloro-11-fluoro-6H-pyrido[2',3':5,6][1,3]oxazino[3,4-a]indole (1.4 g, 4.25 mmol), 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (1.8 g, 3.73 mmol) and K$_3$PO$_4$.3H$_2$O (3.4 g, 12.75 mmol) in Dioxane/water (10 mL/1 mL), Pd$_2$(dba)$_3$ (195 mg, 0.21 mmol) and X-Phos (200 mg, 0.42 mmol) were added. The reaction mixture was stirred at 90° C. for 2 hours under N$_2$ protection. Then cooled to room temperature and added EtOAc, then filtered through a Celite pad. The combined organic phase was washed with water and brine, dried over Na$_2$SO$_4$. The solvent was concentrated in vacuo giving 5-(6-(azidomethyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide. The crude product was used in the next step without purification. $^1$H-NMR (CDCl$_3$, 400 MHz) δ 2.73 (s, 3H), 2.97~3.03 (d, J=4.8 Hz, 3H), 3.04~3.15 (d, J=10.8 Hz, 1H), 3.20~3.32 (m, 1H), 3.40 (s, 3H), 5.93~6.02 (m, 1H), 6.33~6.40 (m, 1H), 6.81~6.89 (m, 1H), 7.14~7.26 (m, 5H), 7.45~7.53 (m, 2H), 7.67 (s, 1H), 7.93~8.01 (m, 2H), 8.03 (s, 1H). MS (M+H)$^+$: 670.

Step 4—Synthesis of (S)-5-(6-(aminomethyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide: two enantiomers (Compound 114 and 115)

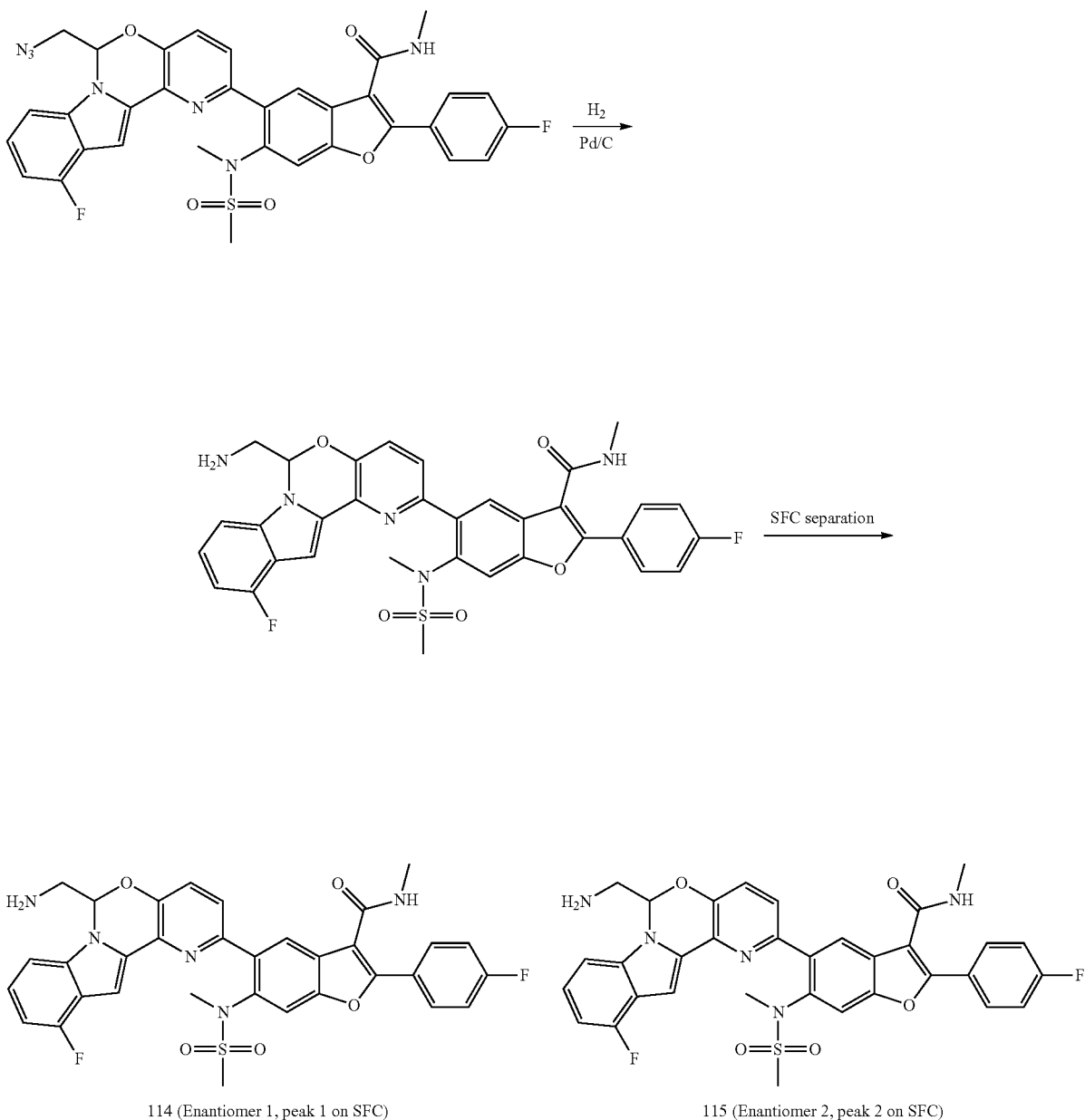

114 (Enantiomer 1, peak 1 on SFC)    115 (Enantiomer 2, peak 2 on SFC)

To a solution of 5-(6-(azidomethyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (2.8 g, 4.1 mmol) in MeOH (25 mL) at room temperature, 5% wet Pd/C (300 mg) was added and stirred under hydrogen atmosphere (30 psi) overnight. The reaction mixture was filtered. The filtrate was concentrated and the resulting residue was purified using silica gel column chromatography (dichloromethane:MeOH=20:1) to provide racemic 5-(6-(aminomethyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (1.5 g, yield: 62.5%). And after SFC separation, Compound 114 and 115 were obtained. Column: Chiralpak AD-3 50*4.6 mm I.D., 3 um Mobile phase:60% ethanol (0.05% DEA) in $CO_2$. Flow rate: 3 mL/min Wavelength: 220 nm. Compound 114: RT=0.605 min, Compound 115: RT=1.393 minutes.

Compound 114, enantiomer 1 (peak 1 on SFC), $^1$H-NMR (CDCl$_3$, 400 MHz) δ 8.03 (s, 1H), 7.93~8.01 (m, 2H), 7.67 (s, 1H), 7.45~7.53 (m, 2H), 7.14~7.26 (m, 5H), 6.81~6.89 (m, 1H), 6.33~6.40 (m, 1H), 5.93~6.02 (m, 1H), 3.40 (s, 3H), 3.20~3.32 (m, 1H), 3.04~3.15 (d, J=10.8 Hz, 1H), 2.97~3.03 (d, J=4.8 Hz, 3H), 2.73 (s, 3H), MS (M+H)$^+$: 644.

Compound 115, enantiomer 1 (peak 1 on SFC), $^1$H-NMR (CDCl$_3$, 400 MHz) δ 8.03 (s, 1H), 7.93~8.01 (m, 2H), 7.67 (s, 1H), 7.45~7.53 (m, 2H), 7.14~7.26 (m, 5H), 6.81~6.89 (m, 1H), 6.33~6.40 (m, 1H), 5.93~6.02 (m, 1H), 3.40 (s, 3H), 3.20~3.32 (m, 1H), 3.04~3.15 (d, J=10.8 Hz, 1H), 2.97~3.03 (d, J=4.8 Hz, 3H), 2.73 (s, 3H), MS (M+H)$^+$: 644.

Example 36

Preparation of Compound 116

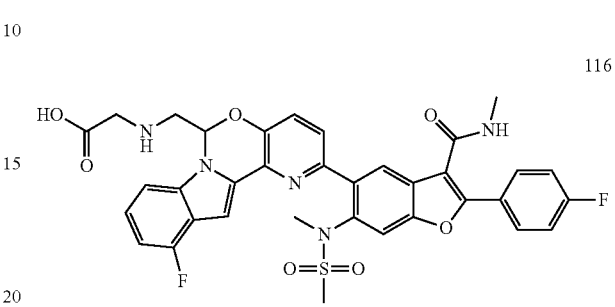

Step 1—Synthesis of ethyl 2-(((11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indol-6-yl)methyl)amino)acetate

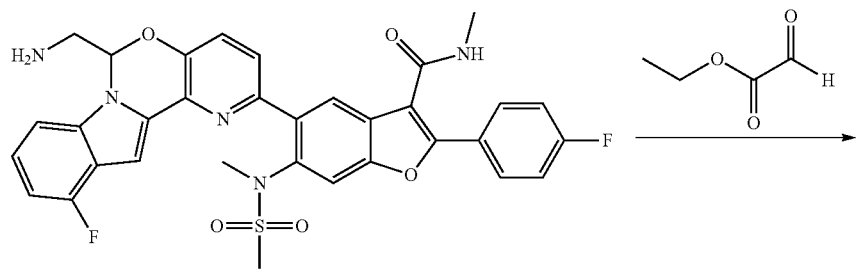

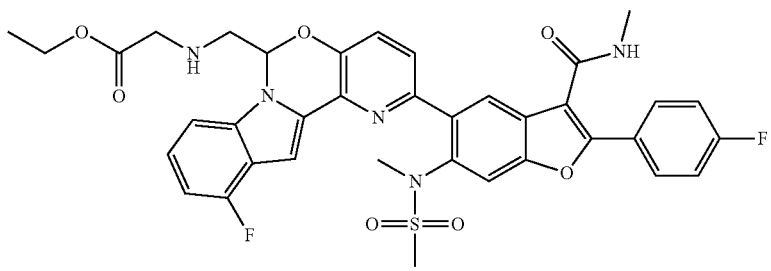

To a solution of 5-(6-(aminomethyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (200 mg, 0.31 mmol) and ethyl 2-oxoacetate (64 mg, 0.62 mmol) in CH$_2$Cl$_2$ (4 mL) was added acetic acid (4 mg, 0.06 mmol). The mixture was stirred at room temperature for 1 hour, and then NaBH(AcO)$_3$ (144 mg, 0.68 mmol) added to the mixture. After stirring overnight, the mixture diluted with CH$_2$Cl$_2$, washed with brine, dried over Na$_2$SO$_4$ and concentrated in vacuo. The resulting residue was purified using prep-HPLC give the product of ethyl 2-(((11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indol-6-yl)methyl)amino)acetate (45 mg, yield: 20%). $^1$H-NMR (CDCl$_3$, 400 MHz) δ 8.01 (s, 1H), 7.96 (dd, J=8.4, 5.2 Hz, 2H), 7.67 (s, 1H), 7.50 (s, 2H), 7.13~7.25 (m, 5H), 6.84 (dd, J=9.2, 8.0 Hz, 1H), 6.50 (dd, J=7.6, 3.6 Hz, 1H), 5.99 (br s, 1H), 4.12 (q, J=7.2 Hz, 2H), 3.29~3.44 (m, 5H), 3.20 (dd, J=12.8, 8.4 Hz, 1H), 3.00 (d, J=4.8 Hz, 3H), 2.86~2.96 (m, 1H), 2.67 (s, 3H), 1.22 (t, J=7.2 Hz, 3H). MS (M+H)$^+$: 730.

Step 2—Synthesis of 2-(((11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indol-6-yl)methyl)amino)acetic acid (Compound 116)

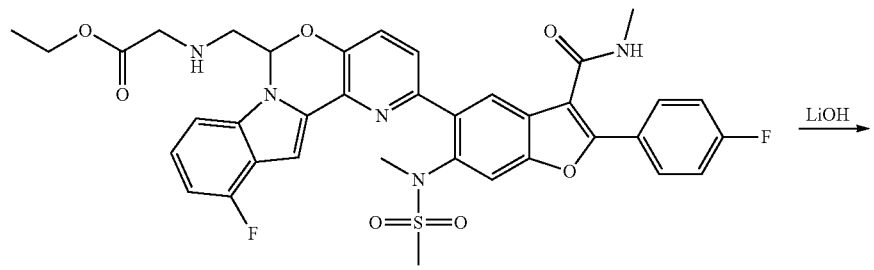

LiOH

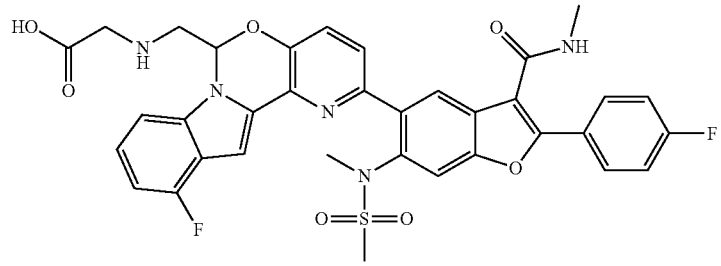

116

To a solution of ethyl 2-(((11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indol-6-yl)methyl)amino)acetate (35 mg, 0.048 mmol) in 1,4-dioxane/H$_2$O (3.0 mL/0.5 mL) was added LiOH.H$_2$O (20 mg, 0.45 mmol). The mixture was stirred at room temperature overnight. Then it was concentrated in vacuo, neutralized with HCl (aq. 5%), extracted with EtOAc. The organic layer was washed with brine, dried over Na$_2$SO$_4$ and concentrated to provide Compound 116 (30 mg, yield: 91%). $^1$H-NMR (DMSO-d$_6$, 400 MHz) δ 8.58 (d, J=4.8 Hz, 1H), 8.00~8.07 (m, 2H), 7.85 (s, 1H), 7.69 (d, J=8.8 Hz, 1H), 7.61 (d, J=8.4 Hz, 1H), 7.52 (d, J=8.4 Hz, 1H), 7.43 (t, J=8.8 Hz, 2H), 7.20~7.29 (m, 1H), 7.09 (s, 1H), 6.89~6.97 (m, 1H), 6.85 (br. s, 1H), 3.19 (s, 3H), 3.07 (m, 2H), 2.88 (s, 3H), 2.83 (s, 3H). MS (M+H)$^+$: 702.

Compounds 117-120, depicted in the table below, were prepared using the method described above and substituting the appropriate reactants and/or reagents.

| Compound No | Structure | NMR | MS (M + H)$^+$ |
|---|---|---|---|
| 117 | 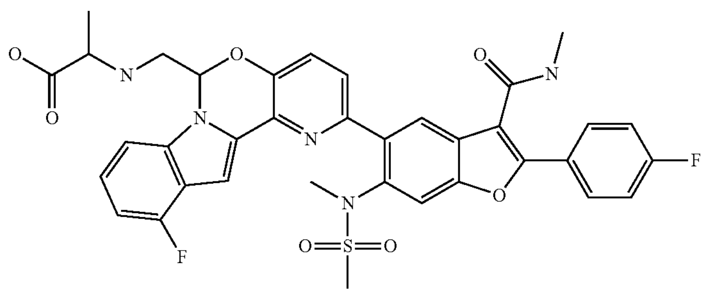 [SMILES: CNC(=O)c1c(-c2ccc(F)cc2)oc2cc(N(C)S(C)(=O)=O)c(-c3ccc4c(n3)-c3cc5c(F)cccc5n3C(CNC(C)C(=O)O)O4)cc12] | $^1$H-NMR (Methanol-d4, 400 MHz) δ 7.99 (dd, J = 8.4, 5.2 Hz, 2H), 7.89 (d, J = 1.6 Hz, 1H), 7.84 (d, J = 3.2 Hz, 1H), 7.61~7.70 (m, 1H), 7.54~7.61 (m, 1H), 7.31~7.41 (m, 1H), 7.17~7.30 (m, 4H), 6.82 (t, J = 9.2 Hz, 1H), 6.64~6.78 (m, 1H), 3.64~3.73 (m, 1H), 3.36 (s, 3H), 3.07~3.27 (m, 2H), 2.97 (s, 3H), 2.81~2.87 (m, 3H), 1.28 (d, J = 6.5 Hz, 3H). | 716 |
| 118 | 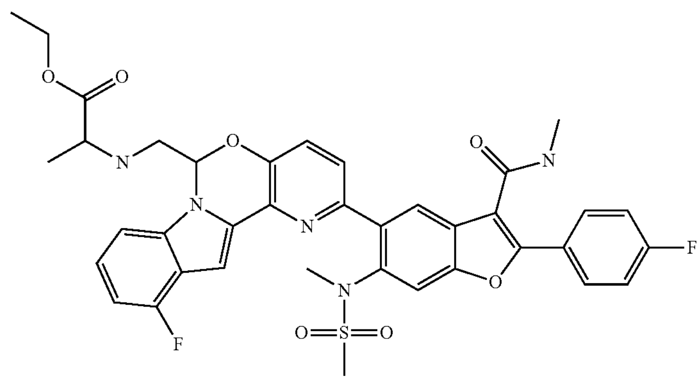 [SMILES: CCOC(=O)C(C)NCC1Oc2ccc(-c3cc4c(C(=O)NC)c(-c5ccc(F)cc5)oc4cc3N(C)S(C)(=O)=O)nc2-c2cc3c(F)cccc3n21] | $^1$H-NMR (CDCl$_3$, 400 MHz) δ 8.01 (s, 1H), 7.96 (dd, J = 8.0, 5.6 Hz, 2H), 7.67 (d, J = 5.2 Hz, 1H), 7.43~7.57 (m, 2H), 7.14~7.29 (m, 5H), 6.80~6.87 (m, 1H), 6.43~6.53 (m, 1H), 5.97 (br s, 1H), 3.99~4.16 (m, 2H), 3.38 (s, 3H), 3.35~3.45 (m, 1H), 3.12~3.24 (m, 1H), 2.96~3.08 (m, 4H), 2.62~2.77 (m, 4H), 1.15~1.28 (m, 6H). | 744 |
| 119 | 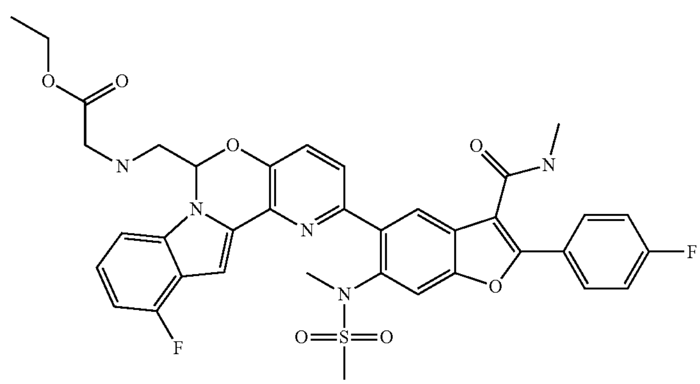 [SMILES: CCOC(=O)CNCC1Oc2ccc(-c3cc4c(C(=O)NC)c(-c5ccc(F)cc5)oc4cc3N(C)S(C)(=O)=O)nc2-c2cc3c(F)cccc3n21] | $^1$H-NMR (CDCl$_3$, 400 MHz) δ 8.01 (s, 1H), 7.96 (dd, J = 8.4, 5.2 Hz, 2H), 7.67 (s, 1H), 7.50 (s, 2H), 7.13~7.25 (m, 5H), 6.84 (dd, J = 9.2, 8.0 Hz, 1H), 6.50 (dd, J = 7.6, 3.6 Hz, 1H), 5.99 (br s, 1H), 4.12 (q, J = 7.2 Hz, 2H), 3.29~3.44 (m, 5H), 3.20 (dd, J = 12.8, 8.4 Hz, 1H), 3.00 (d, J = 4.8 Hz, 3H), 2.86~2.96 (m, 1H), 2.67 (s, 3H), 1.22 (t, J = 7.2 Hz, 3H). | 730 |
| 120 | 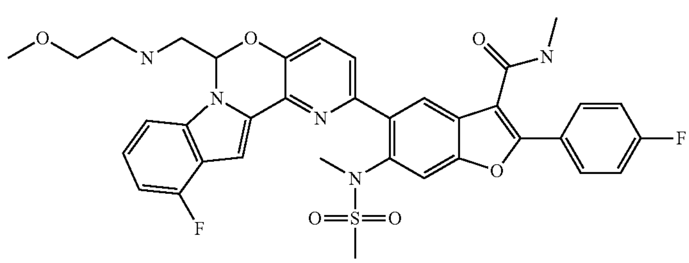 [SMILES: CNC(=O)c1c(-c2ccc(F)cc2)oc2cc(N(C)S(C)(=O)=O)c(-c3ccc4c(n3)-c3cc5c(F)cccc5n3C(CNCCOC)O4)cc12] | $^1$H-NMR (CDCl$_3$, 400 MHz) 8.01 (s, 1H), 7.95 (dd, J = 5.6, 8.8 Hz, 2H), 7.65 (s, 1H), 7.49 (s, 2H), 7.16~7.24 (m, 5H), 6.79~6.88 (m, 1H), 6.55 (dd, J = 3.2, 8.0 Hz, 1H), 6.01 (d, J = 4.8 Hz, 1H), 3.44 (t, J = 4.8 Hz, 2H), 3.39 (s, 3H), 3.33 (s, 3H), 3.17 (dd, J = 8.6, 13.2 Hz, 1H), 2.99 (d, J = 5.2 Hz, 3H), 2.92~2.97 (m, 1H), 2.74~2.86 (m, 2H), 2.70 (s, 3H), 2.09 (br. s, 1H). | 702 |

Example 37
Preparation of Compound 121 and 122
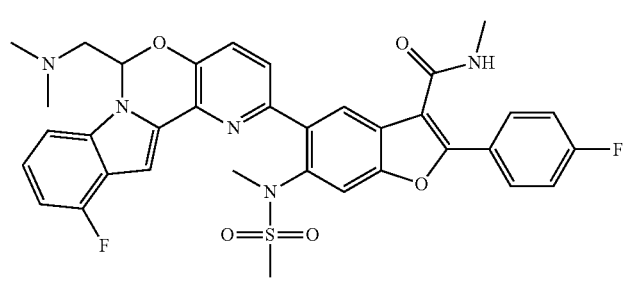
121
(Enantiomer 1, peak 1 on SFC)
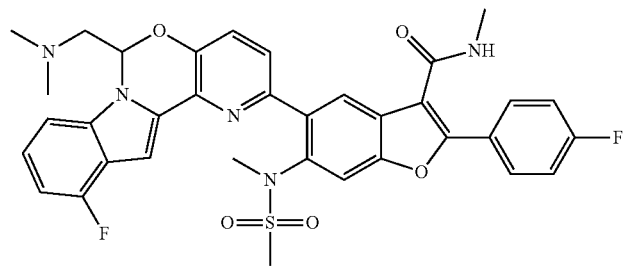
122
(Enantiomer 2, peak 2 on SFC)
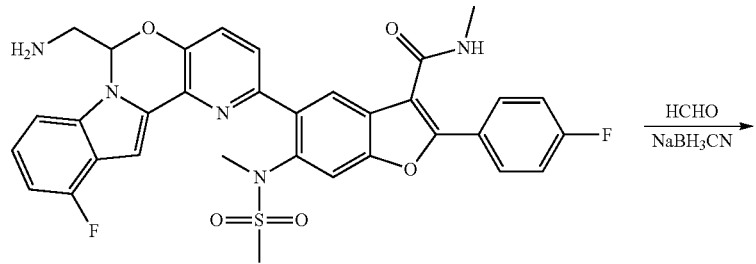
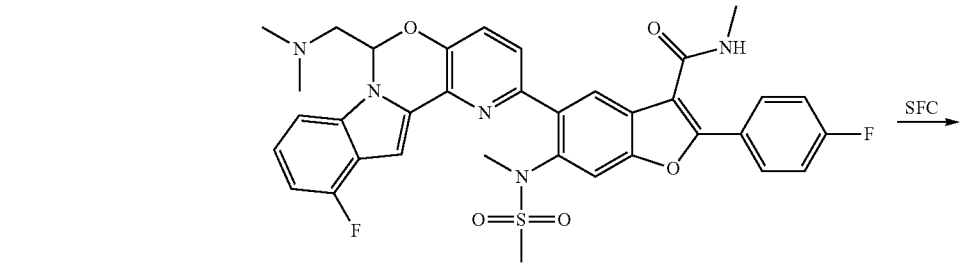
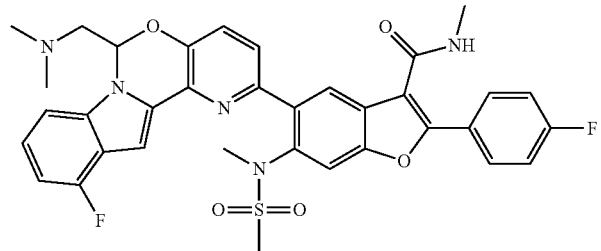
121 (Enantiomer 1, peak 1 on SFC)
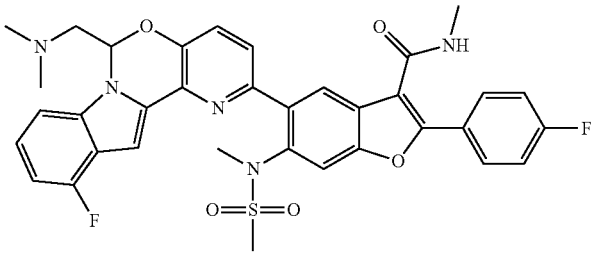
122 (Enantiomer 2, peak 2 on SFC)

A mixture of 5-(6-(aminomethyl)-11-fluoro-6H-pyrido[2', 3':5,6][1,3]oxazino[3,4-a]indol-2-yl)-2-(4-fluorophenyl)-N-methyl-6-(N-methylmethylsulfonamido)benzofuran-3-carboxamide (200 mg, 0.31 mmol), and 30% formaldehyde (1 mL), AcOH (0.1 mL) and NaBH₃CN (96 mg, 1.55 mmol) in MeOH (2 mL) was stirred at room temperature for 2 hours under N₂ protection. Then quenched with water and extracted with EtOAc (10 mL*3). The combined organic layer was washed with brine (30 mL), dried over Na₂SO₄ and concentrated in vacuo. The resulting residue was purified using prep-TLC (dichloromethane:MeOH=20:1) to provide 5-(6-((dimethylamino)methyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (100 mg, yield: 48%). And after SFC separation, two enantiomers were obtained. Column: Chiralpak AD-3 50*4.6 mm I.D., 3 um Mobile phase:60% ethanol (0.05% DEA) in CO₂. Flow rate: 3 mL/min Wavelength: 220 nm. Compound 121: RT=0.865 min, Compound 122: RT=4.536 minutes.

Compound 121, enantiomer 1 (peak 1 on SFC), ¹H-NMR (CDCl₃, 400 MHz) δ8.05 (s, 1H), 7.92~8.01 (m, 2H), 7.68 (s, 1H), 7.51 (s, 2H), 7.12~7.26 (m, 5H), 6.82~6.91 (m, 1H), 6.51~6.62 (m, 1H), 5.90~5.96 (m, 1H), 3.42 (s, 3H), 3.02 (d, J=4.8 Hz, 3H), 2.85~2.93 (m, 1H), 2.70 (s, 3H), 2.55~2.63 (m, 1H), 2.28~2.45 (m, 6H). MS (M+H)⁺: 672.

Compound 122, enantiomer 2 (peak 2 on SFC), ¹H-NMR (CDCl₃, 400 MHz) δ8.05 (s, 1H), 7.92~8.01 (m, 2H), 7.68 (s, 1H), 7.51 (s, 2H), 7.12~7.26 (m, 5H), 6.82~6.91 (m, 1H), 6.51~6.62 (m, 1H), 5.90~5.96 (m, 1H), 3.42 (s, 3H), 3.02 (d, J=4.8 Hz, 3H), 2.85~2.93 (m, 1H), 2.70 (s, 3H), 2.55~2.63 (m, 1H), 2.28~2.45 (m, 6H). MS (M+H)⁺: 672.

Example 38

Preparation of Compound 123

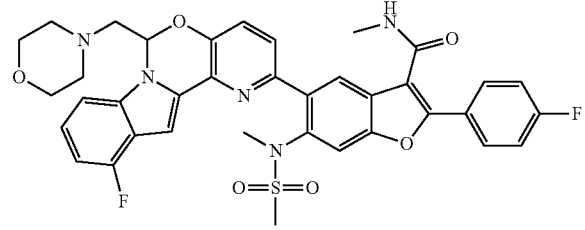

Step 1—Synthesis of 2-chloro-11-fluoro-6H-pyrido[2',3':5,6][1,3]oxazino[3,4-a]indole-6-carboxylic acid

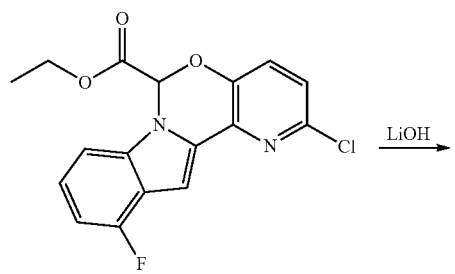

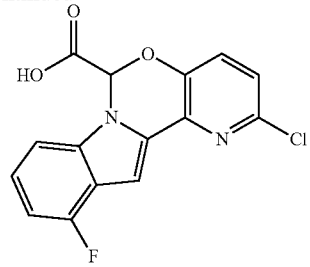

A mixture of ethyl 2-chloro-11-fluoro-6H-pyrido[2',3':5, 6][1,3]oxazino[3,4-a]indole-6-carboxylate (606 mg, 1.75 mmol) and LiOH (168 mg, 7.00 mmol) in dioxane/H₂O (6 mL/5 mL) was stirred at 80° C. for 2 hours. The reaction was monitored using TLC. When the reaction was completed, the mixture was adjusted to pH 4-5 with 1 N HCl aqueous. The mixture was extracted with EtOAc (10 mL*3). The combined organic layer was washed with brine (30 mL), dried over Na₂SO₄ and concentrated under reduce pressure, afforded the desired product of 2-chloro-11-fluoro-6H-pyrido[2',3':5,6][1,3]oxazino[3,4-a]indole-6-carboxylic acid (crude: 590 mg, yield: 99%). ¹H-NMR (400 MHz, DMSO-d6) δ 7.74 (d, J=8.6 Hz, 1H), 7.56~7.43 (m, 2H), 7.37 (s, 1H), 7.34~7.25 (m, 1H), 7.15 (s, 1H), 7.02~6.92 (m, 1H). MS (M+H)⁺: 319.

Step 2—Synthesis of (2-chloro-11-fluoro-6H-pyrido[2',3':5,6][1,3]oxazino[3,4-a]indol-6-yl)(morpholino)methanone

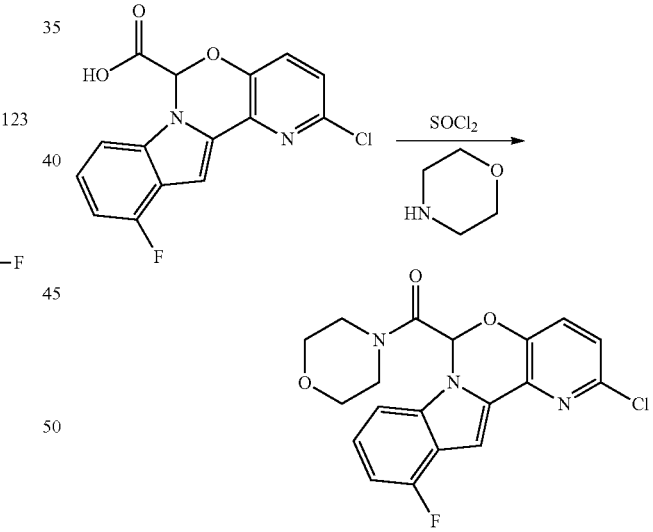

A solution of 2-chloro-11-fluoro-6H-pyrido[2',3':5,6][1,3]oxazino[3,4-a]indole-6-carboxylic acid (300 mg, 0.94 mmol) in SOCl₂ (5 mL) was reflux for 2.0 hours, then concentrated the solution and afforded to the residue. A mixture of the residue, Et₃N (0.2 mL) and morpholine (250 mg, 2.87 mmol) in dichloromethane (5 mL) was stirred at room temperature for overnight. Then the mixture was diluted with water (30 mL) and extracted with EtOAc (10 mL*3). The combined organic layer was washed with brine (30 mL), dried over Na₂SO₄ and concentrated in vacuo. The resulting residue was purified using prep-TLC (petroleum ether:EtOAc=1:1) to provide (2-chloro-11-fluoro-6H-pyrido[2',3':5,6][1,3]oxazino[3,4-a]indol-6-yl)(morpholino)methanone (120 mg, yield: 32.9%). ¹H-NMR (CDCl₃, 400 MHz) δ7.37~7.47 (s, 1H), 7.24 (d, J=4.4, 1H), 7.11~7.20 (m, 2H), 6.94 (d, J=8.4 Hz, 1H), 6.79~6.86 (m, 1H), 6.70~6.75 (m, 1H), 3.79~3.90 (m, 2H), 3.62~3.73 (m, 3.51~3.59 (m, 1H), 3.36~3.45 (m, 1H). MS (M+H)⁺: 388.

Step 3—Synthesis of 2-chloro-11-fluoro-6-(morpholinomethyl)-6H-pyrido[2',3':5,6][1,3]oxazino[3,4-a]indole

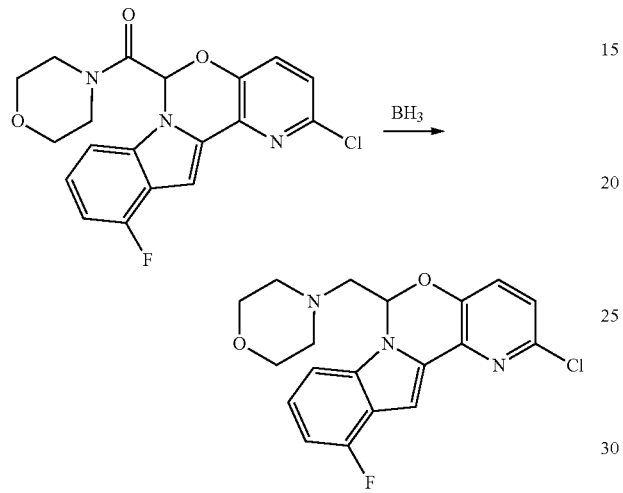

To a solution of (2-chloro-11-fluoro-6H-pyrido[2',3':5,6][1,3]oxazino[3,4-a]indol-6-yl)(morpholino)methanone (60 mg, 0.16 mmol) in THF (2 mL) was added to BH₃·SMe₂ (1 mL, 1 mmol) at 0° C. After being stirred for overnight, MeOH and water was added, the mixture was extracted with EtOAc (10 mL*3). The combined organic layer was washed with brine, dried over Na₂SO₄ and concentrated in vacuo. The resulting residue was purified using prep-TLC (petroleum ether:EtOAc=2:1) to provide 2-chloro-11-fluoro-6-(morpholinomethyl)-6H-pyrido[2',3':5,6][1,3]oxazino[3,4-a]indole (50 mg, yield: 86.2%). ¹H-NMR (CDCl₃, 400 MHz) δ 7.28~7.34 (m, 1H), 7.22~7.26 (m, 1H), 7.13~7.22 (m, 2H), 7.09 (d, J=8.4, 1H), 6.79~6.86 (m, 1H), 6.43 (t, J=4.8 Hz, 1H), 3.45~3.53 (m, 2H), 3.34~3.43 (m, 2H), 2.80~2.88 (m, 1H), 2.63~2.70 (m, 1H), 2.30~2.39 (m, 2H), 2.21~2.29 (m, 2H). MS (M+H)⁺: 374.

Step 4—Synthesis of 5-(11-fluoro-6-(morpholinomethyl)-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (Compound 123)

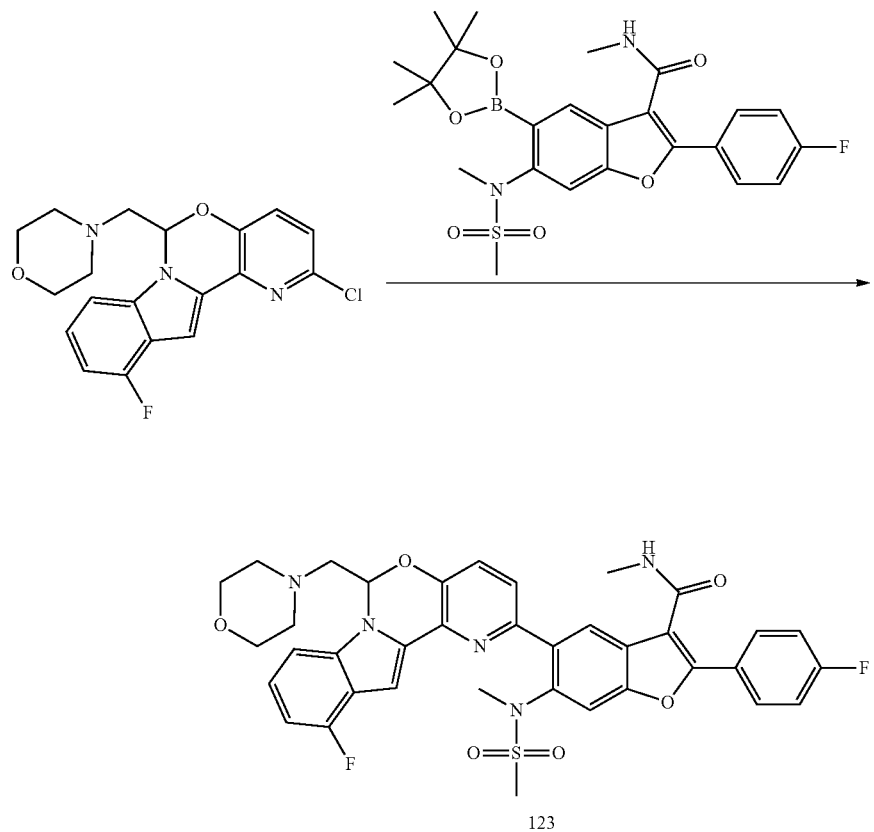

123

The procedure of Compound 123 (35 mg, yield: 40%) was similar to step 2 of Example 2. ¹H-NMR (CDCl₃, 400 MHz) δ 8.05 (s, 1H), 7.91~8.01 (m, 2H), 7.67 (s, 1H), 7.48~7.54 (d, J=8.4 Hz, 1H), 7.39~7.47 (m, 1H), 7.13~7.26 (m, 5H), 6.81~6.89 (m, 1H), 6.51 (d, J=4.5 Hz, 1H), 5.90~6.00 (m, 1H), 3.52~3.60 (m, 2H), 3.34~3.51 (m, 5H), 3.00 (d, J=4.8 Hz, 3H), 2.88~2.95 (m, 1H), 2.67~2.82 (m, 4H), 2.39~2.49 (m, 2H), 2.27~2.37 (m, 2H). MS (M+H)⁺: 714.
Example 39
Preparation of Compound 124
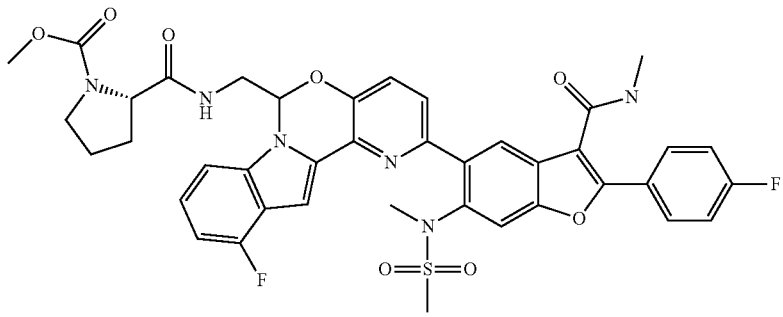
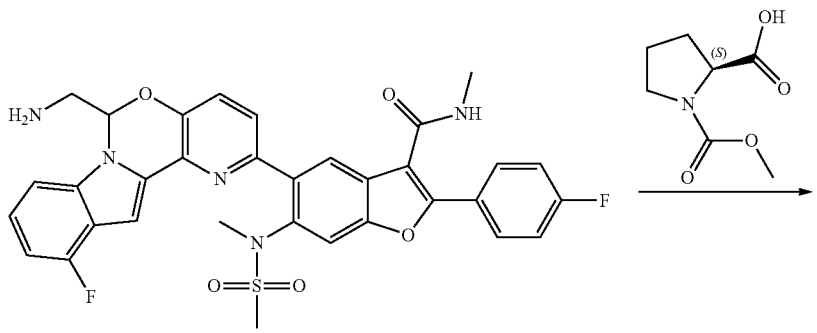
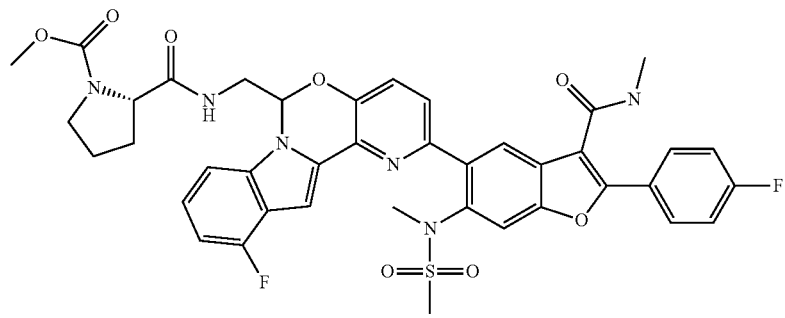
124

A mixture of 5-(6-(aminomethyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (70 mg, 0.11 mmol), (S)-1-(methoxycarbonyl)pyrrolidine-2-carboxylic acid (38 mg, 0.22 mmol), EDCI (12 mg, 0.27 mmol), DMAP (40 mg, 0.33 mmol) and triethylamine (33 mg, 0.33 mmol) in CH$_2$Cl$_2$ (2 mL) was stirred at room temperature overnight. The mixture was then purified using Prep-TLC(CH$_2$Cl$_2$:EtOAc=1:1) to provide (2S)-methyl 2-(((11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indol-6-yl)methyl)carbamoyl)pyrrolidine-1-carboxylate (60 mg, yield: 69.0%). $^1$H-NMR (CDCl$_3$, 400 MHz) δ 7.86~8.05 (m, 3H), 7.28~7.69 (m, 4H), 7.16~7.27 (m, 5H), 6.85 (d, J=9.2 Hz, 1H), 6.60 (dd, J=5.2, 7.2 Hz, 1H), 5.98~6.25 (m, 1H), 4.31 (br. s, 1H), 3.65 (br. s, 5H), 3.39 (s, 5H), 2.97 (d, J=3.2 Hz, 3H), 2.72 (br. s, 3H), 1.90~2.49 (m, 2H), 1.63~1.79 (m, 2H). MS (M+H)$^+$: 799.

Compounds 125-127, depicted in the table below, were prepared using the method described above and substituting the appropriate reactants and/or reagents.

| Compound No | Structure | NMR | MS (M + H)$^+$ |
|---|---|---|---|
| 125 | 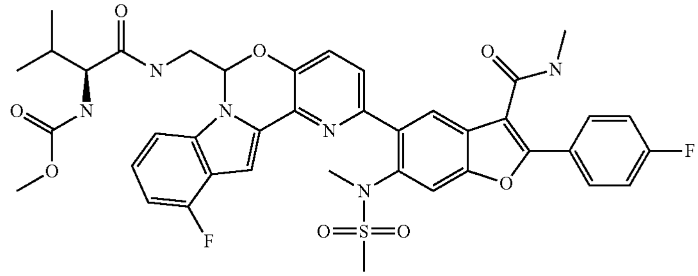 [SMILES: CNC(=O)c1c(-c2ccc(F)cc2)oc2cc(N(C)S(C)(=O)=O)c(-c3ccc4c(n3)-c3cc5c(F)cccc5n3C(CNC(=O)[C@@H](NC(=O)OC)C(C)C)O4)cc12] | $^1$H-NMR (CDCl$_3$, 400 MHz) δ 7.91 (br. s, 3H), 7.34~7.60 (m, 3H), 7.15~7.26 (m, 5H), 6.76~6.89 (m, 2H), 6.55 (d, J = 4.4 Hz, 1H), 6.27~6.49 (m, 1H), 5.27~5.44 (m, 1H), 3.94~4.06 (m, 1H), 3.71~3.83 (m, 1H), 3.63 (br. s, 3H), 3.36 (s, 4H), 2.90 (br. s, 3H), 2.70 (br. s, 3H), 1.99~2.19 (m, 1H), 0.86~0.98 (m, 6H). | 801 |
| 126 | 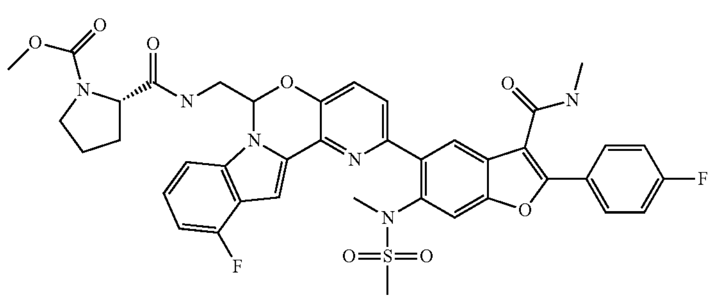 [SMILES: CNC(=O)c1c(-c2ccc(F)cc2)oc2cc(N(C)S(C)(=O)=O)c(-c3ccc4c(n3)-c3cc5c(F)cccc5n3C(CNC(=O)[C@@H]3CCCN3C(=O)OC)O4)cc12] | $^1$H-NMR (CDCl$_3$, 400 MHz) δ 7.86~8.05 (m, 3H), 7.28~7.69 (m, 4H), 7.16~7.27 (m, 5H), 6.85 (d, J = 9.2 Hz, 1H), 6.60 (dd, J = 5.2, 7.2 Hz, 1H), 5.98~6.25 (m, 1H), 4.31 (br. s, 1H), 3.65 (br. s, 5H), 3.39 (s, 5H), 2.97 (d, J = 3.2 Hz, 3H), 2.72 (br. s., 3H), 1.90~2.49 (m, 2H), 1.63~1.79 (m, 2H). | 799 |
| 127 | 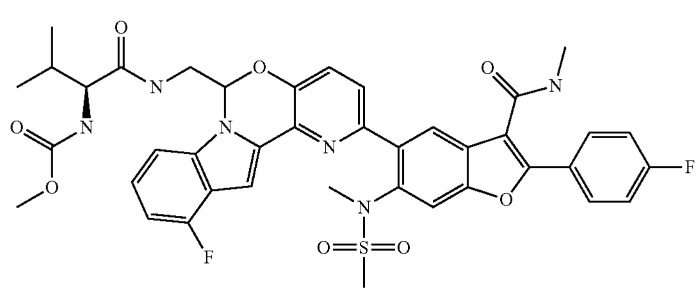 [SMILES: CNC(=O)c1c(-c2ccc(F)cc2)oc2cc(N(C)S(C)(=O)=O)c(-c3ccc4c(n3)-c3cc5c(F)cccc5n3C(CNC(=O)[C@@H](NC(=O)OC)C(C)C)O4)cc12] | $^1$H-NMR (CDCl$_3$, 400 MHz) δ 7.96 (s, 1H), 7.88 (d, J = 3.2 Hz, 2H), 7.55 (s, 1H), 7.38 (d, J = 17.6 Hz, 2H), 7.04~7.18 (m, 5H), 6.76 (t, J = 8.4 Hz, 1H), 6.40~6.54 (m, 2H), 5.97~6.08 (m, 1H), 5.18 (d, J = 8.0 Hz, 1H), 3.87 (t, J = 7.2 Hz, 1H), 3.61 (s, 3H), 3.38~3.58 (m, 2H), 3.32 (s, 3H), 2.91 (d, J = 5.2 Hz, 3H), 2.72 (s, 3H), 2.03~2.18 (m, 1H), 0.90 (dd, J = 19.2, 6.8 Hz, 6H). | 801 |

Example 40

Preparation of Compound 128

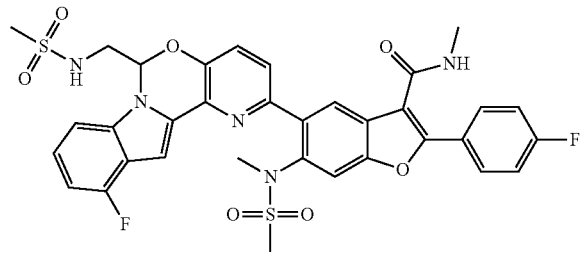

128

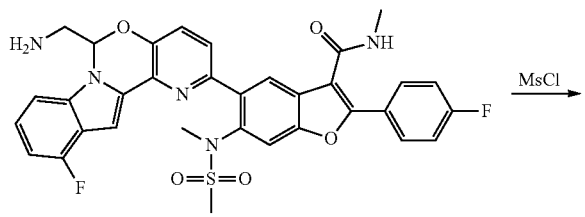

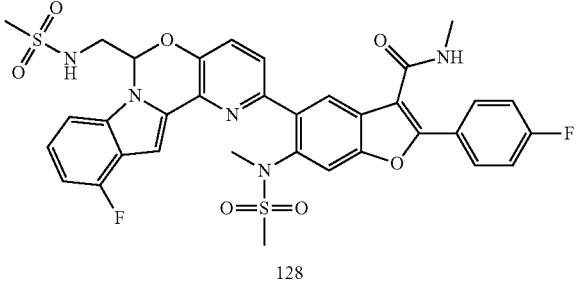

128

A mixture of 5-(6-(aminomethyl)-11-fluoro-6H-pyrido[2', 3':5,6][1,3]oxazino[3,4-a]indol-2-yl)-2-(4-fluorophenyl)-N-methyl-6-(N-methylmethylsulfonamido)benzofuran-3-carboxamide (50 mg, 0.08 mmol), and Et$_3$N (11 mg, 0.12 mmol) in dichloromethane (1 mL) was stirred at room temperature under N$_2$ protection. Then MsCl (11 mg, 0.09 mmol) was added and the solution was stirred at room temperature for overnight. Then the mixture was diluted with water (50 mL) and extracted with EtOAc (10 mL*3). The combined organic layer was washed with brine (30 mL), dried over Na$_2$SO$_4$ and concentrated in vacuo. The resulting residue was purified using prep-TLC (dichloromethane:MeOH=15:1) to provide 5-(11-fluoro-6-(methylsulfonamidomethyl)-6H-pyrido[2', 3':5,6][1,3]oxazino[3,4-a]indol-2-yl)-2-(4-fluorophenyl)-N-methyl-6-(N-methylmethylsulfonamido)benzofuran-3-carboxamide (20 mg, yield: 35.7%). $^1$H-NMR (400 MHz, DMSO-d$_6$) δ 8.55 (d, J=4.8 Hz, 1H), 7.83 (s, 1H), 7.96~8.06 (m, 3H), 7.65~7.70 (m, 1H), 7.59~7.63 (m, 1H), 7.57 (t, J=6.4 Hz, 1H), 7.37~7.44 (m, 3H), 7.24~7.30 (m, 1H), 7.10 (s, 1H), 6.91~6.97 (m, 1H), 6.77 (dd, J=6.8 Hz, 4.4 Hz, 1H), 3.37 (dd, J=14.0, 7.2 Hz, 2H), 3.29 (br s, 3H), 2.89 (s, 3H), 2.77~2.87 (m, 6H). MS (M+H)$^+$: 722.

Example 41

Preparation of Compound 129 and 130

129

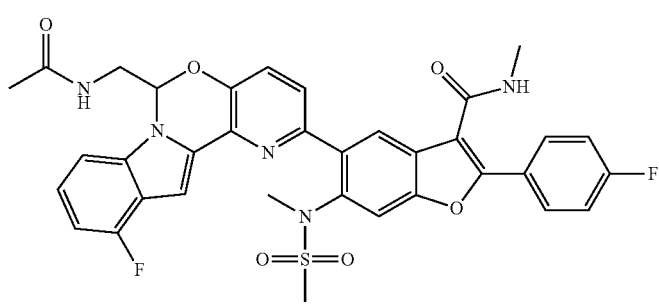

(Enantiomer 1, peak 1 on SFC)

130

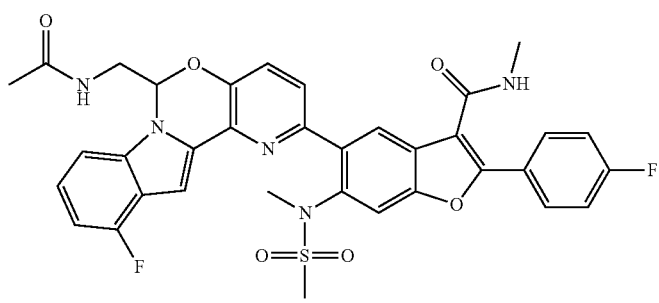

(Enantiomer 2, peak 2 on SFC)

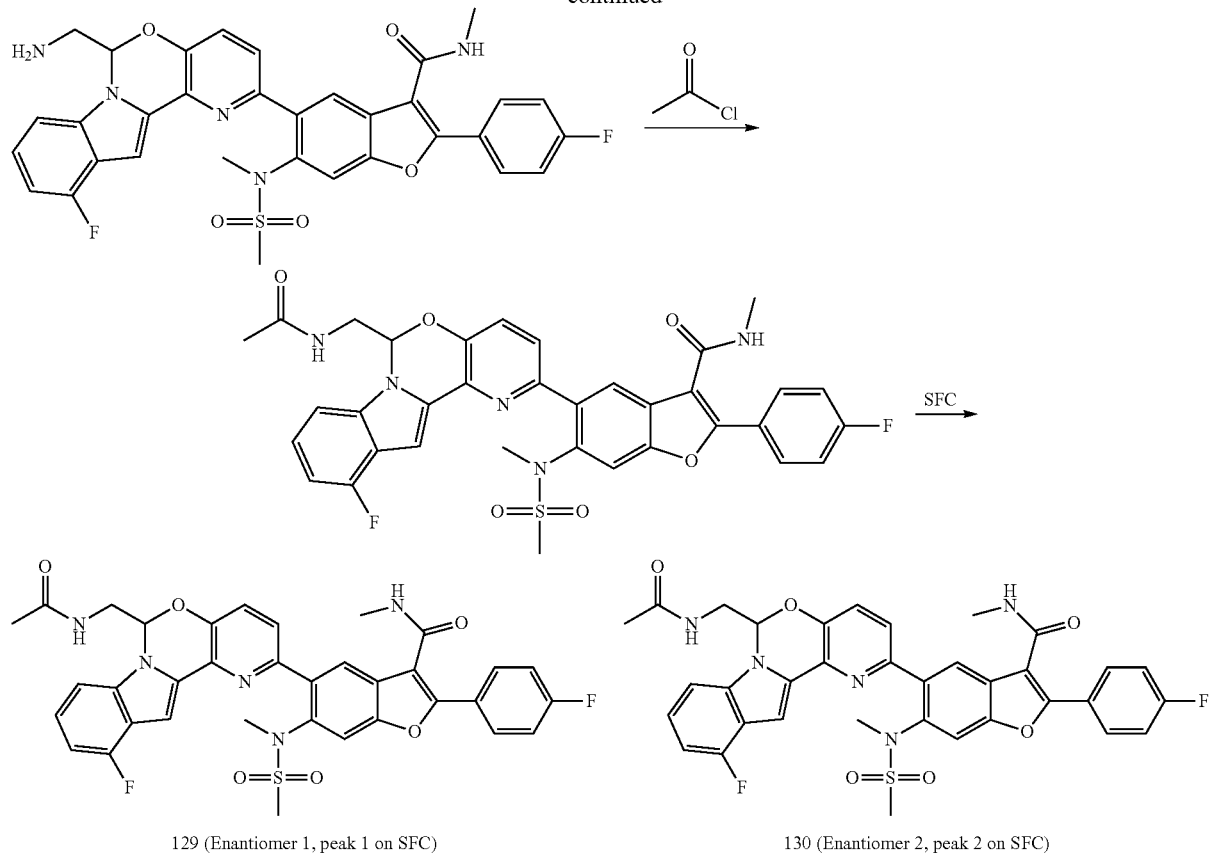

129 (Enantiomer 1, peak 1 on SFC)

130 (Enantiomer 2, peak 2 on SFC)

A mixture of 5-(6-(aminomethyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (50 mg, 0.08 mmol), and pyridine (11 mg, 0.14 mmol) in dichloromethane (1 mL) was stirred at room temperature under $N_2$ protection. Then acetyl chloride (11 mg, 0.14 mmol) was added and the solution was stirred at room temperature for 1.5 hours. Then the mixture was diluted with water (50 mL) and extracted with EtOAc (10 mL*3). The combined organic layer was washed with brine (30 mL), dried over $Na_2SO_4$ and concentrated in vacuo. The resulting residue was purified using prep-TLC (dichloromethane:MeOH=10:1) to provide 546-(acetamidomethyl)-11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (30 mg, yield: 56.3%). And after SFC separation, two enantiomers were obtained. Column: Chiralpak AD-3 50*4.6 mm I.D., 3 um. Mobile phase: 60% ethanol (0.05% DEA) in $CO_2$. Flow rate: 3 mL/min. Wavelength: 220 nm. Compound 129: RT=0.449 min, Compound 130: RT=1.264 minutes.

Compound 129, enantiomer 1 (peak 1 on SFC), $^1$H-NMR (CDCl$_3$, 400 MHz) δ8.05 (s, 1H), 7.85~7.95 (m, 2H), 7.62 (s, 1H), 7.39~7.49 (m, 2H), 7.10~7.26 (m, 5H), 6.82 (t, J=8.4 Hz, 1H), 6.60 (t, J=5.2 Hz, 1H), 6.12 (d, J=3.6 Hz, 1H), 5.96~6.04 (m, 1H), 3.52~3.65 (m, 2H), 3.38 (s, 3H), 2.93 (d, J=4.4 Hz, 3H), 2.69~2.80 (m, 3H), 1.91 (s, 3H). MS (M+H)$^+$: 686.

Compound 130, enantiomer 2 (peak 2 on SFC), $^1$H-NMR (CDCl$_3$, 400 MHz) δ8.05 (s, 1H), 7.85~7.95 (m, 2H), 7.62 (s, 1H), 7.39~7.49 (m, 2H), 7.10~7.26 (m, 5H), 6.82 (t, J=8.4 Hz, 1H), 6.60 (t, J=5.2 Hz, 1H), 6.12 (d, J=3.6 Hz, 1H), 5.96~6.04 (m, 1H), 3.52~3.65 (m, 2H), 3.38 (s, 3H), 2.93 (d, J=4.4 Hz, 3H), 2.69~2.80 (m, 3H), 1.91 (s, 3H). MS (M+H)$^+$: 686.

Example 42

Preparation of Compound 131

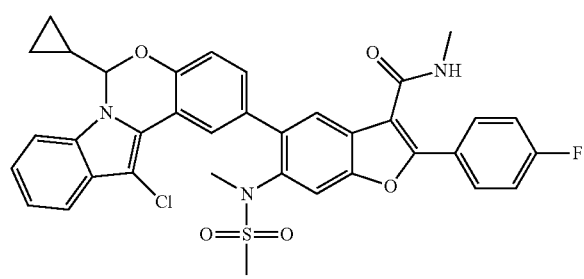

131

Step 1—Synthesis of 4-bromo-2-(3-chloro-1H-indol-2-yl)phenol

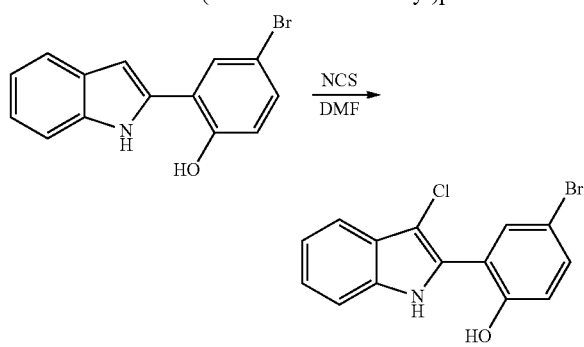

To a solution of 4-bromo-2-(1H-indol-2-yl)phenol (100 mg, 0.35 mmol) in DMF (1 mL) was added NCS (46 mg, 0.35 mmol), it was allowed to stir at room temperature until LCMS showed the starting material was consumed completely. The reaction solution was extracted with EtOAc, and the combined organic layers were washed with H₂O (3×10 mL), brine and dried over Na₂SO₄. The solvent was removed and the crude product was purified using prep-TLC to provide the desired product of 4-bromo-2-(3-chloro-1H-indol-2-yl)phenol (110 mg, yield: 98.2%). ¹H-NMR (CDCl₃, 400 MHz) δ 9.25 (s, 1H), 7.80 (d, J=2.4 Hz, 1H), 7.64 (d, J=8.0 Hz, 1H), 7.40~7.43 (m, 1H), 7.20~7.30 (m, 2H), 7.12 (t, J=4.0 Hz, 1H), 6.86 (t, J=6.0 Hz, 1H), 5.93 (s, 1H). MS (M+H)⁺: 322/324.

Step 2—Synthesis of 2-bromo-12-chloro-6-cyclopropyl-6H-benzo[5,6][1,3]oxazino[3,4-a]indole

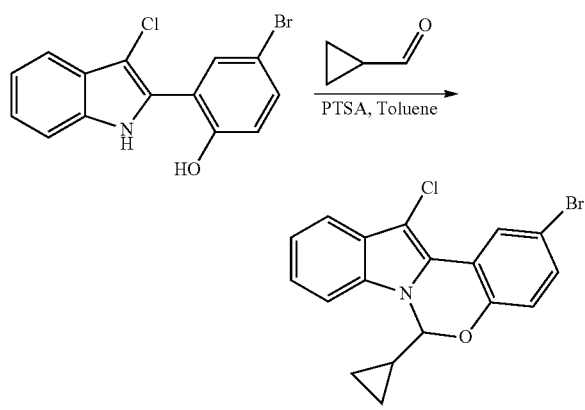

Cyclopropanecarbaldehyde (70 mg, 1.0 mmol) and PTSA (17 mg, 0.1 mmol) were added to a solution of 4-bromo-2-(3-chloro-1H-indol-2-yl)phenol (110 mg, 0.34 mmol) in toluene (2 mL). The mixture was allowed to stir at 110° C. for about 15 hours. The reaction solution was extracted by EtOAc, and the combined organic layers were washed with H₂O (3×10 mL), brine and dried over Na₂SO₄. The solvent was removed and the crude product was Purified using prep-TLC to provide the desired product of 2-bromo-12-chloro-6-cyclopropyl-6H-benzo[5,6][1,3]oxazino[3,4-a]indole (40 mg, yield: 31.3%). ¹H-NMR (CDCl₃, 400 MHz) δ 8.42 (m, 1H), 7.63 (t, J=0.4 Hz, 1H), 7.30~7.35 (m, 2H), 7.15~7.24 (m, 2H), 6.93 (m, 1H), 5.62 (d, J=0.8 Hz, 1H), 1.36~1.45 (m, 1H), 0.50~0.56 (m, 4H). MS (M+H)⁺: 374/376.

Step 3—Synthesis of 12-chloro-6-cyclopropyl-2-(4,4,5,5-tetramethyl-1,3,2-dioxaborolan-2-yl)-6H-benzo[5,6][1,3]oxazino[3,4-a]indole

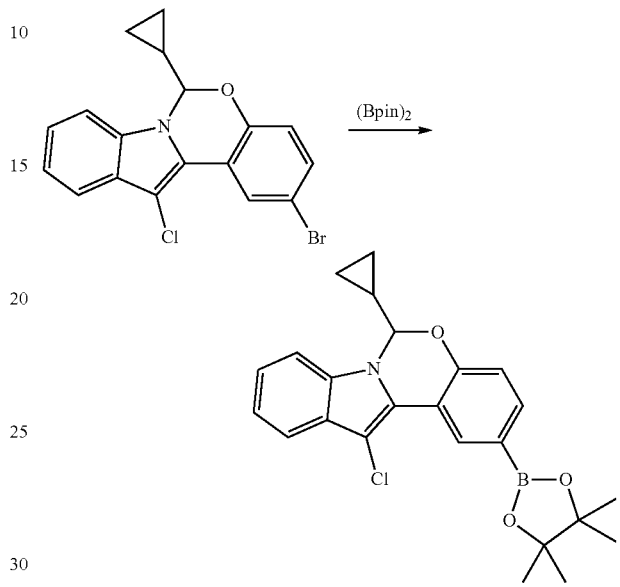

To a degassed solution of 2-bromo-12-chloro-6-cyclopropyl-6H-benzo[5,6][1,3]oxazino[3,4-a]indole (40 mg, 0.11 mmol) and pinacol diborane (56 mg, 0.22 mmol) in dry DMF (1.5 mL) were added Pd(dppf)Cl₂(10 mg) and KOAc (49 mg, 0.50 mmol) under N₂. The mixture was heated to 90° C. and stirred for about 15 hours. The reaction mixture was cooled to room temperature and filtered. The filtrate was washed with H₂O, brine, dried over Na₂SO₄. After being concentrated in vacuo, the resulting resulting residue was purified using column chromatography eluted with petroleum ether: EtOAc=4:1 to provide 12-chloro-6-cyclopropyl-2-(4,4,5,5-tetramethyl-1,3,2-dioxaborolan-2-yl)-6H-benzo[5,6][1,3]oxazino[3,4-a]indole (40 mg, yield: 88.3%). MS (M+H)⁺: 422.

Step 4—Synthesis of 5-(12-chloro-6-cyclopropyl-6H-benzo[5,6][1,3]oxazino[3,4-a]indol-2-yl)-2-(4-fluorophenyl)-N-methyl-6-(N-methylmethylsulfonamido)benzofuran-3-carboxamide (Compound 131)

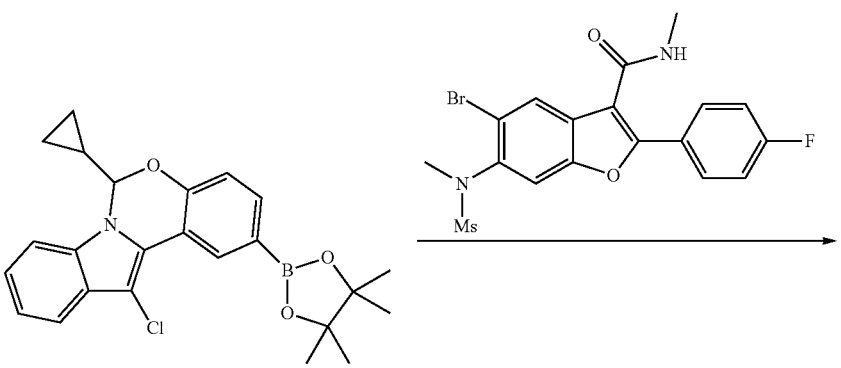

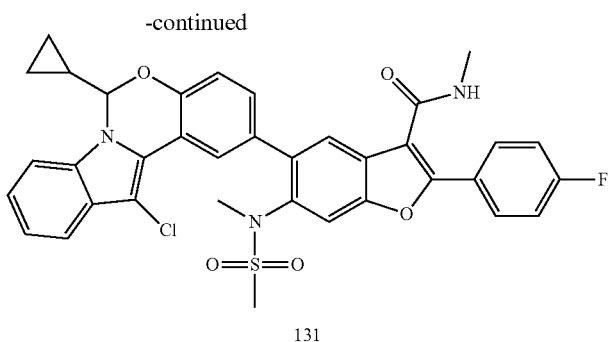

131

A mixture of 12-chloro-6-cyclopropyl-2-(4,4,5,5-tetramethyl-1,3,2-dioxaborolan-2-yl)-6H-benzo[5,6][1,3]oxazino[3,4-a]indole (40 mg, 0.10 mmol), 5-bromo-2-(4-fluorophenyl)-N-methyl-6-(N-methylmethylsulfonamido)benzofuran-3-carboxamide (45 mg, 0.10 mmol), $K_3PO_4 \cdot 3H_2O$ (80 mg, 0.30 mmol) and $Pd(dppf)Cl_2$ (7 mg, 0.01 mmol) in 2 mL of DMF was heated in a sealed tube under microwave condition at 100° C. for 20 minutes, and then the mixture was purified using prep-HPLC to provide Compound 131 (35 mg, yield: 55.1%). $^1$H-NMR (CDCl$_3$, 400 MHz) δ 8.39 (s, 1H), 7.96~7.93 (t, J=8.0 Hz, 2H), 7.85 (s, 1H), 7.64 (d, J=6.8 Hz, 2H), 7.40 (d, J=4.4 Hz, 2H), 7.30 (d, J=7.2 Hz, 1H), 7.23~7.20 (m, 4H), 5.94 (s, 1H), 5.77 (d, J=7.2 Hz, 1H), 3.29 (s, 3H), 3.00 (d, J=4.8 Hz, 3H), 2.62 (s, 3H), 1.55~1.50 (m, 1H), 0.66~0.60 (m, 4H). MS (M+H)$^+$: 670.

Example 43

Preparation of Compound 132

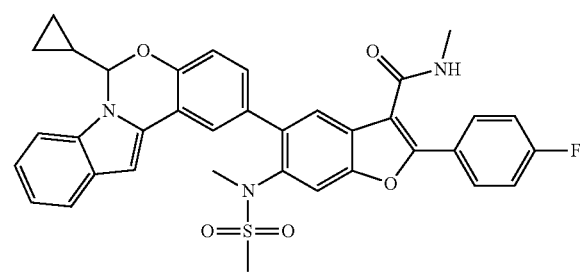

132

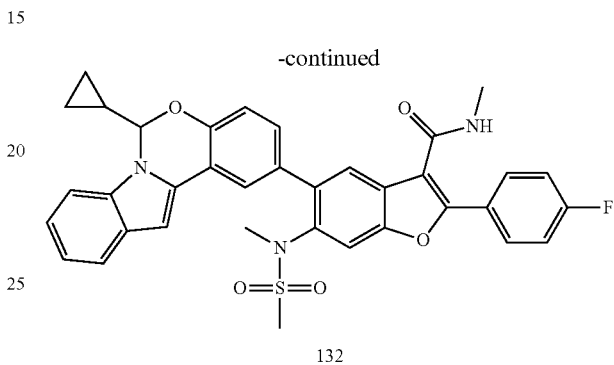

132

Pd/C (10 mg) was added to a solution of Compound 131 (20 mg, 0.03 mmol) in MeOH (5 mL). The mixture was allowed to stir under H2 atmosphere (50 psi) for about 15 hours. After filtrated and concentrated, the mixture was purified using prep-HPLC to provide Compound 132 (10 mg, yield: 52.6%). $^1$H-NMR (CDCl$_3$, 400 MHz) δ 7.92~7.94 (m, 2H), 7.84 (s, 1H), 7.80 (d, J=2.0 Hz, 1H), 7.63 (d, J=10.8 Hz, 2H), 7.42 (d, J=8.0 Hz, 1H), 7.31~7.34 (m, 1H), 7.11~7.24 (m, 5H), 6.85 (s, 1H), 5.94 (d, J=4.8 Hz, 1H), 5.81 (d, J=7.2 Hz, 1H), 3.16 (s, 3H), 2.98 (d, J=5.2 Hz, 3H), 2.71 (s, 3H), 1.50~1.58 (m, 1H), 0.57~0.66 (m, 4H). MS (M+H)$^+$: 636.

Example 44

Preparation of Compound 133

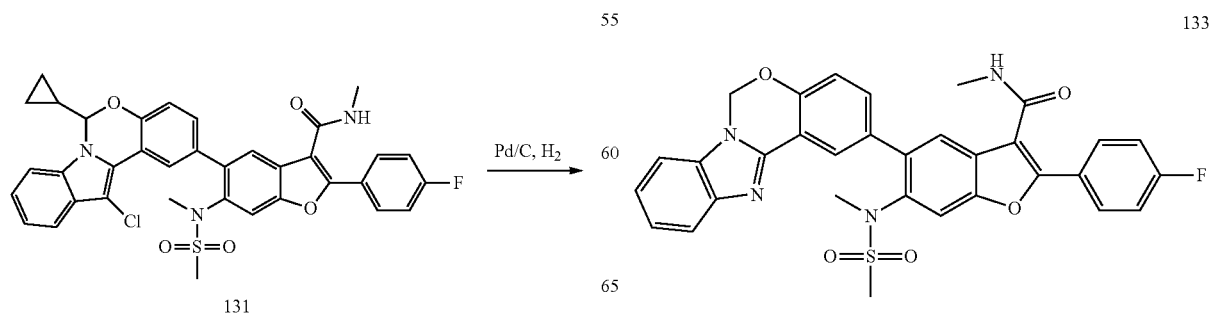

Step 1—Synthesis of 2-(1H-benzo[d]imidazol-2-yl)-4-chlorophenol

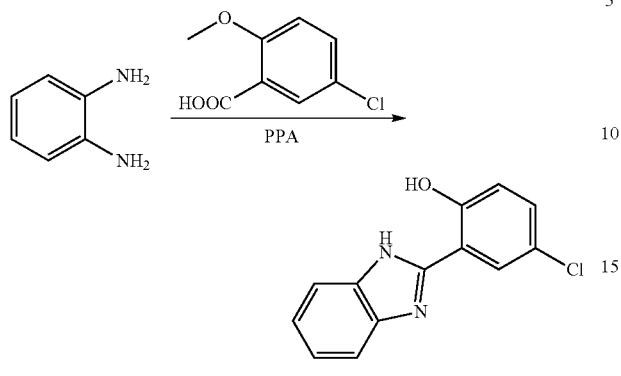

A mixture of benzene-1,2-diamine (500 mg, 4.6 mmol), 5-chloro-2-methoxy-benzoic acid (1.3 g, 6.9 mmol) in PPA (30 mL) was allowed to stir at 200° C. for 5 hours. The mixture was poured to ice and neutralized with KOH. The mixture was extracted with ethyl acetate. The organic layer was washed with brine and dried over Na$_2$SO$_4$. The organic phase was concentrated to provide 2-(1H-benzo[d]imidazol-2-yl)-4-chlorophenol (300 mg, yield: 27%). $^1$H-NMR (DMSO-d$_6$, 400 MHz) δ 8.20 (d, J=2.5 Hz, 1H), 7.73~7.70 (m, 2H), 7.44 (dd, J=8.8, 2.6 Hz, 1H), 7.34~7.32 (m, 2H), 7.10 (d, J=8.8 Hz, 1H). MS (M+H)$^+$: 245.

Step 2—Synthesis of 2-chloro-6H-benzo[e]benzo[4,5]imidazo[1,2-c][1,3]oxazine

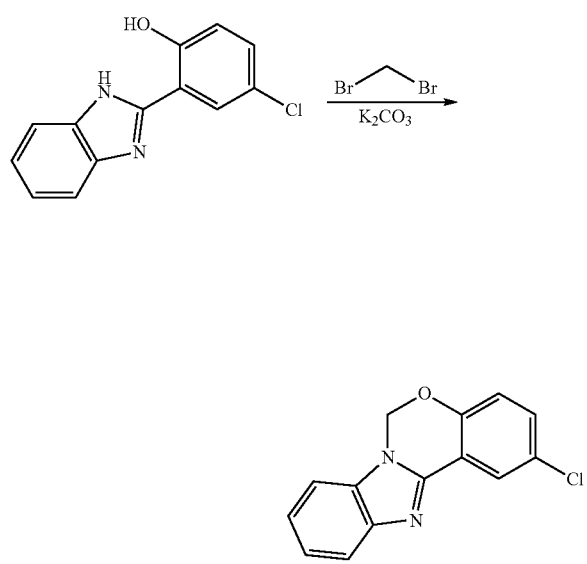

A mixture of 2-(1H-benzo[d]imidazol-2-yl)-4-chlorophenol (80 mg, 0.33 mmol), dibromo-methane (341 mg, 1.96 mmol), K$_2$CO$_3$ (137 mg, 0.99 mmol) in DMF (6 mL) was allowed to stir at 80° C. for 12 hours. Water (20 mL) was added and the mixture was extracted with ethyl acetate. The organic layer was washed with brine and dried over Na$_2$SO$_4$. After being concentrated in vacuo, the resulting resulting residue was purified using prep-HPLC to provide 2-chloro-6H-benzo[e]benzo[4,5]imidazo[1,2-c][1,3]oxazine (30 mg, yield: 36%). $^1$H-NMR (Methanol-d4, 400 MHz) δ 8.07 (d, J=2.1 Hz, 1H), 7.83~7.81 (m, 1H), 7.78~7.75 (m, 1H), 7.63 (dd, J=8.8, 2.2 Hz, 1H), 7.54~7.52 (m, 2H), 7.30 (d, J=8.8 Hz, 1H), 6.33 (s, 2H). MS (M+H)$^+$: 257.

Step 3—Synthesis of 5-(6H-benzo[e]benzo[4,5]imidazo[1,2-c][1,3]oxazin-2-yl)-2-(4-fluorophenyl)-N-methyl-6-(N-methylmethylsulfonamido)benzofuran-3-carboxamide (Compound 133)

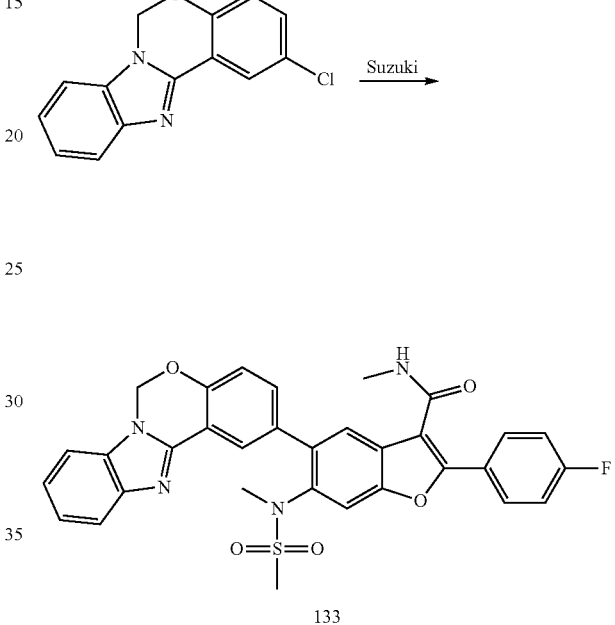

To a degassed solution of 2-(4-fluorophenyl)-N-methyl-6-(N-methylmethylsulfonamido)-5-(3-(4,4,5,5-tetramethyl-1,3,2-dioxaborolan-2-yl)phenyl)benzofuran-3-carboxamide (117 mg, 0.23 mmol) and 2-chloro-6H-benzo[e]benzo[4,5]imidazo[1,2-c][1,3]oxazine (60 mg, 0.23 mmol) in dioxane:H$_2$O (2 mL:0.5 mL) was added Pd$_2$(dba)$_3$ (21 mg, 0.02 mmol), X-Phos (22 mg, 0.05 mmol) and K$_3$PO$_4$ (184 mg, 0.69 mmol) under N$_2$. The mixture was heated to 100° C. and stirred for about 15 hours. The reaction mixture was cooled to room temperature and filtered. The filtrate was washed with H$_2$O, brine, dried over Na$_2$SO$_4$. After being concentrated in vacuo, the resulting resulting residue was purified using prep-HPLC to provide the product of Compound 133 (30 mg, yield: 22%). $^1$H-NMR (DMSO-d$_6$, 400 MHz) δ 8.59 (d, J=4.4 Hz, 1H), 8.14 (d, J=1.9 Hz, 1H), 8.08~8.05 (m, 3H), 7.77~7.72 (m, 2H), 7.69 (s, 1H), 7.63 (dd, J=8.7, 2.0 Hz, 1H), 7.46 (t, J=8.7 Hz, 2H), 7.37~7.30 (m, 3H), 6.38 (s, 2H), 3.21 (s, 3H), 3.05 (s, 3H), 2.87 (d, J=4.4 Hz, 3H). MS (M+H)$^+$: 597.

Compound 134-140, depicted in the table below, was prepared using the method described above and substituting the appropriate reagents and/or reactants.

| Compound No | Structure | NMR | MS (M + H)+ |
|---|---|---|---|
| 134 | 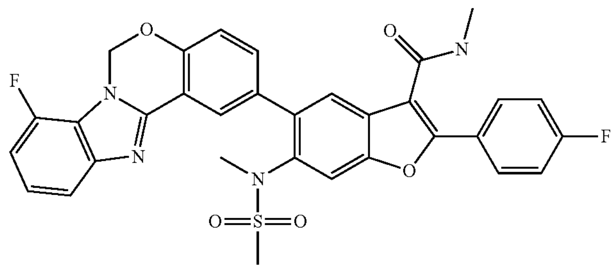 [SMILES: CNC(=O)c1c(-c2ccc(F)cc2)oc2cc(N(C)S(C)(=O)=O)c(-c3ccc4c(c3)-c3nc5cccc(F)c5n3CO4)cc12] | ¹H-NMR (DMSO-d6, 400 MHz) δ 8.60 (d, J = 4.5 Hz, 1H), 8.15 (d, J = 2.1 Hz, 1H), 8.09~8.05 (m, 3H), 7.69 (s, 1H), 7.66 (dd, J = 8.5, 2.1 Hz, 1H), 7.61 (d, J = 7.8 Hz, 1H), 7.46 (t, J = 8.8 Hz, 2H), 7.37 (d, J = 8.5 Hz, 1H), 7.33~7.27 (m, 1H), 7.24~7.19 (m, 1H), 6.41 (s, 2H), 3.21 (s, 3H), 3.06 (s, 3H), 2.86 (d, J = 4.5 Hz, 3H). | 615 |
| 135 | 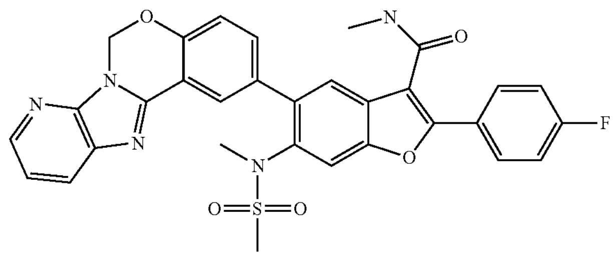 [SMILES: CNC(=O)c1c(-c2ccc(F)cc2)oc2cc(N(C)S(C)(=O)=O)c(-c3ccc4c(c3)-c3nc5cccnc5n3CO4)cc12] | ¹H-NMR (DMSO-d6, 400 MHz) δ 8.56 (d, J = 4.8 Hz, 1H), 8.38 (dd, J = 4.8, 1.2 Hz, 1H), 8.13~8.16 (m, 2H), 8.06 (s, 1H), 8.01~8.05 (m, 2H), 7.63~7.65 (m, 2H), 7.43 (t, J = 8.8 Hz, 2H), 7.34~7.37 (m, 2H), 6.34 (s, 2H), 3.17 (s, 3H), 3.02 (s, 3H), 2.83 (d, J = 4.8 Hz, 3H). | 598 |
| 136 | 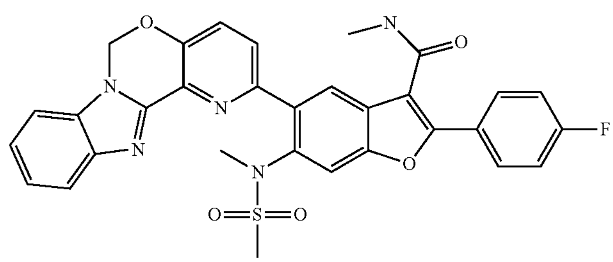 [SMILES: CNC(=O)c1c(-c2ccc(F)cc2)oc2cc(N(C)S(C)(=O)=O)c(-c3ccc4c(n3)-c3nc5ccccc5n3CO4)cc12] | ¹H-NMR (CDCl₃, 400 MHz) δ 8.07 (s, 1H), 7.96~8.00 (m, 2H), 7.75~7.82 (m, 2H), 7.51~7.54 (m, 2H), 7.35~7.37 (m, 2H), 7.27~7.32 (m, 1H), 7.11~7.17 (m, 2H), 6.93 (br s, 1H), 6.12 (s, 2H), 3.17 (s, 3H), 3.05 (d, J = 4.8 Hz, 3H), 2.97 (s, 3H). | 598 |
| 137 | 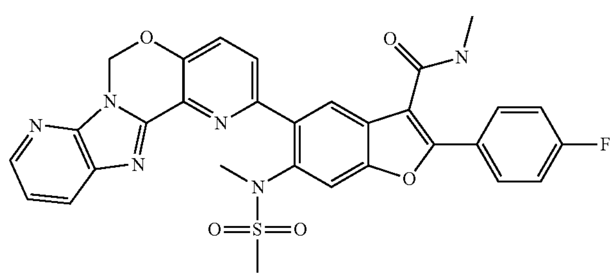 | ¹H-NMR (CDCl₃, 400 MHz) δ 8.39~8.41 (m, 1H), 8.04~8.08 (m, 2H), 7.92~7.96 (m, 2H), 7.77 (d, J = 4.4 Hz, 1H), 7.55~7.58 (m, 2H), 7.25~7.29 (m, 1H), 7.11~7.16 (m, 2H), 6.73 (br s, 1H), 6.27 (s, 2H), 3.19 (s, 3H), 3.04 (d, J = 4.8 Hz, 3H), 2.97 (s, 3H). | 599 |
| 138 | 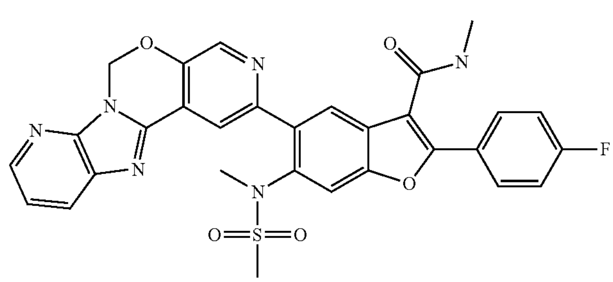 [SMILES: CNC(=O)c1c(-c2ccc(F)cc2)oc2cc(N(C)S(C)(=O)=O)c(-c3cc4c(cn3)OCn3c-4nc4cccnc43)cc12] | ¹H-NMR (CDCl₃, 400 MHz) δ 8.64 (s, 1H), 8.44~8.45 (m, 1H), 8.26 (s, 1H), 8.13 (d, J = 8.0 Hz, 1H), 8.03 (s, 1H), 7.97~8.00 (m, 2H), 7.69 (s, 1H), 7.32~7.35 (m, 1H), 7.19 (t, J = 8.0 Hz, 2H), 6.32 (s, 2H), 6.03 (s, 1H), 3.30 (s, 3H), 3.01 (d, J = 4.0 Hz, 3H), 2.86 (s, 3H). | 599 |

-continued

| Compound No | Structure | NMR | MS (M + H)+ |
|---|---|---|---|
| 139 | 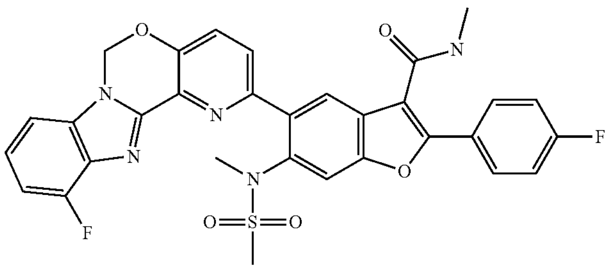 [SMILES: CNC(=O)c1c(-c2ccc(F)cc2)oc2cc(N(C)S(C)(=O)=O)c(-c3ccc4c(n3)-c3nc5c(F)cccc5n3CO4)cc12] | ¹H-NMR (CDCl₃, 400 MHz) δ 7.97 (s, 1H), 7.87~7.90 (m, 2H), 7.69 (d, J = 8.8 Hz, 1H), 7.47 (d, J = 8.8 Hz, 2H), 7.21~7.24 (m, 1H), 7.06~7.09 (m, 3H), 6.93 (t, J = 8.0 Hz, 1H), 6.58 (s, 1H), 6.06 (s, 2H), 3.12 (s, 3H), 3.00 (d, J = 4.8 Hz, 3H), 2.94 (s, 3H). | 616 |
| 140 | 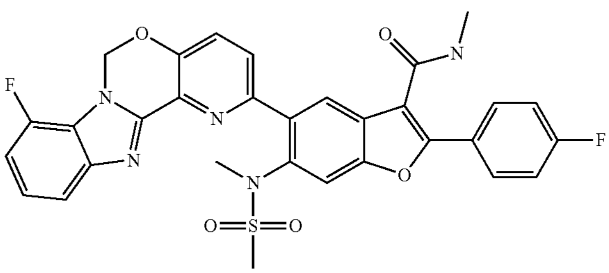 [SMILES: CNC(=O)c1c(-c2ccc(F)cc2)oc2cc(N(C)S(C)(=O)=O)c(-c3ccc4c(n3)-c3nc5cccc(F)c5n3CO4)cc12] | ¹H-NMR (CDCl₃, 400 MHz) δ 8.03 (s, 1H), 7.97~8.00 (m, 2H), 7.74~7.76 (m, 1H), 7.56~7.64 (m, 3H), 7.16~7.21 (m, 3H), 7.04~7.08 (m, 1H), 6.31 (s, 2H), 6.10~6.16 (m, 1H), 3.22 (s, 3H), 3.00 (d, J = 5.2 Hz, 3H), 2.96 (s, 3H). | 616 |

Example 45

Preparation of Compound 141

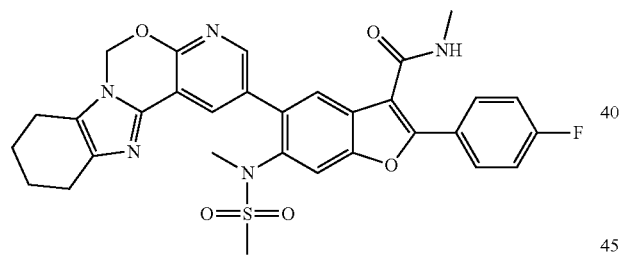

141

Step 1—Synthesis of 5-bromo-2-methoxynicotinamide

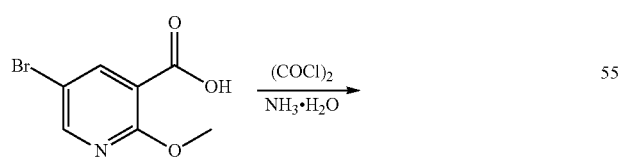

To a solution of 5-bromo-2-methoxynicotinic acid (5 g, 22 mmol) in dichloromethane (75 mL) was treated with Oxalyl dichloride (10 ml) by dropwise at 0° C., then the mixture was stirred at R.T. for 4 hours. A mixture of Ice-NH₃.H₂O was poured into the react solution within an ice-bath and stirred at 0° C. for more 10 min and filtered, the filter cake was dried to provide 5-bromo-2-methoxynicotinamide (4.7 g, yield: 94.4%). ¹HNMR (400 MHz, CDCl₃) δ 8.45 (d, J=2.4 Hz, 1H), 8.20 (d, J=2.4 Hz, 1H), 7.78 (br, 2H), 3.94 (s, 3H). MS (M+H)⁺: 231/233.

Step 2—Synthesis of methyl 5-bromo-2-methoxynicotinimidate

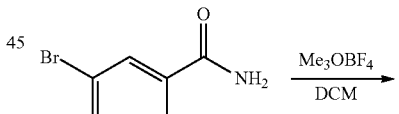

To a solution of 5-bromo-2-methoxynicotinamide (4.7 g, 0.02 mol) in dichloromethane (100 mL) was added Trimethyl-oxonium tetrafluoro borate (4.6 g, 0.02 mol) at room temperature. The mixture was stirred at room for 12 hours. The solvent was moved off and the resulting residue was washed with dichloromethane (50 mL*2), then dry to provide methyl 5-bromo-2-methoxynicotinimidate (6.1 g, yield 91%). ¹HNMR (400 MHz, D₂O) δ 8.46 (m, 2H), 4.22 (s, 3H), 4.02 (s, 3H), 1.93 (s, 2H). MS (M+H)⁺: 333/335.

Step 3—Synthesis of trans-2-(5-bromo-2-methoxy-pyridin-3-yl)-3a,4,5,6,7,7a-hexahydro-1H-benzo[d]imidazole

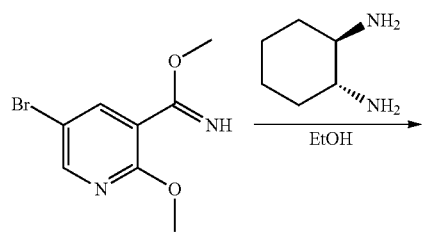

To a solution of methyl 5-bromo-2-methoxynicotinimidate (6.1 g, 18.5 mmol) in EtOH (100 mL) was added trans-Cyclohexane-1,2-diamine (2.1 g, 18.5 mmol) at room temperature, the mixture was stirred at 80° C. for 12 hours. The solvent was removed and the resulting residue was washed with dichloromethane (50 mL*2), then dry to provide trans-2-(5-bromo-2-methoxypyridin-3-yl)-3a,4,5,6,7,7a-hexahydro-1H-benzo[d]imidazole (4 g, yield 70.2%). ¹HNMR (400 MHz, CDCl₃) δ 8.56 (d, J=2.4 Hz, 1H), 8.43 (s, J=2.4 Hz, 1H), 4.14 (s, 3H), 3.51~3.53 (m, 2H), 2.45~2.49 (m, 2H), 1.91~1.93 (m, 2H), 1.61~1.63 (m, 2H), 1.36~1.41 (m, 2H), 1.25 (s, 1H). MS (M+H)⁺: 310/312.

Step 4—Synthesis of 2-(5-bromo-2-methoxypyridin-3-yl)-4,5,6,7-tetrahydro-1H-benzo[d]imidazole

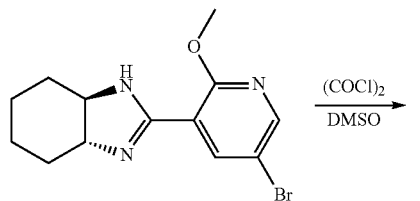

To a solution of Oxalyl dichloride (10 ml) in dichloromethane (10 mL), was treated with DMSO (2 mL) in dichloromethane (10 mL) by dropwise at −78° C., the solution was stirred at −78° C. for another 10 min, then trans-2-(5-bromo-2-methoxypyridin-3-yl)-3a,4,5,6,7,7a-hexahydro-1H-benzo[d]imidazole (1 g, 3.3 mmol) was added in one portion under N₂ protection. The react solution was stirred at −60° C. for 30 min, triethylamine is added over 5 min and the mixture was stirred at R.T. overnight. The resulting solution was treated with ice-cold 1 M hydrochloric acid solution (10 mL), the two phases are separated, the aqueous phase was extracted with dichloromethane (2*30 mL), and the combined organic phases was washed with pH 7 aqueous phosphate buffer (2*20 mL), then dried with anhydrous sodium sulfate and concentrated under reduced pressure to provide 2-(5-bromo-2-methoxypyridin-3-yl)-4,5,6,7-tetrahydro-1H-benzo[d]imidazole (0.78 g, yield 78.8%) as a solid. ¹HNMR (400 MHz, DMSO) δ 14.5 (br, 1H), 8.78 (d, J=2 Hz, 1H), 8.50 (d, J=2 Hz, 1H), 4.04 (s, 3H), 3.15 (s, 4H), 2.66 (s, 4H). MS (M+H)⁺: 310/312. MS (M+H)⁺: 308/310.

Step 5—Synthesis of 5-bromo-3-(4,5,6,7-tetrahydro-1H-benzo[d]imidazol-2-yl)pyridin-2-ol

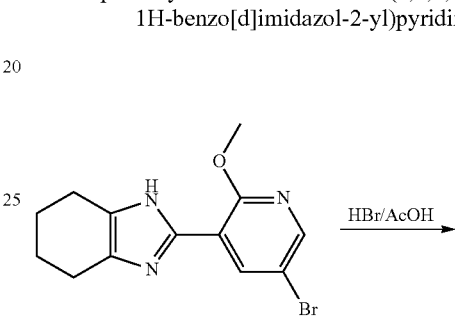

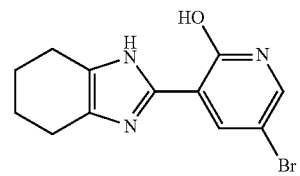

To a solution of 2-(5-bromo-2-methoxypyridin-3-yl)-4,5,6,7-tetrahydro-1H-benzo[d]imidazole (0.8 g, 2.6 mmol) in HBr/AcOH (10 mL), was heated to 100° C. for 12 hours. The solvent was removed off and the resulting residue was washed with dichloromethane (2*20 mL), then dry to provide 5-bromo-3-(4,5,6,7-tetrahydro-1H-benzo[d]imidazol-2-yl)pyridin-2-ol (1 g, yield 100%) as a solid. ¹HNMR (400 MHz, DMSO) δ 13.87 (br, 2H), 8.40 (d, J=2.7 Hz, 1H), 8.03 (d, J=2.7 Hz, 1H), 2.61 (s, 4H), 1.76 (s, 4H). MS (M+H)⁺: 294/296.

Step 6—Synthesis of 2-bromo-8,9,10,11-tetrahydro-6H-benzo[4,5]imidazo[1,2-c]pyrido[3,2-e][1,3]oxazine

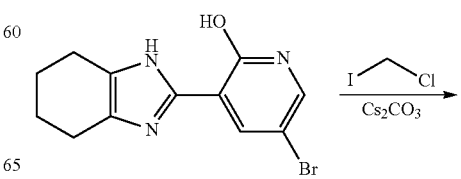

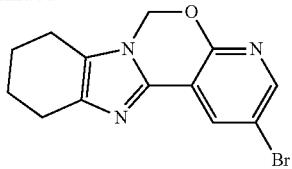

To a solution of 5-bromo-3-(4,5,6,7-tetrahydro-1H-benzo[d]imidazol-2-yl)pyridin-2-ol (0.3 g, 1.02 mmol) and Cesium carbonate (0.663 g, 2.04 mmol) in DMF (10 mL), was heated to 100° C. Then chloroiodomethane (215 mg, 1.22 mmol) was added by dropwise, the react mixture was stirred at 100° C. for 30 minutes. The solvent was removed off and the resulting residue was purified using flash column (petroleum ether:EtOAc 3:1) to provide 2-bromo-8,9,10,11-tetrahydro-6H-benzo[4,5]imidazo[1,2-c]pyrido[3,2-e][1,3]oxazine (50 mg, yield 16%) as a solid. $^1$HNMR (400 MHz, CDCl$_3$): δ=8.30 (d, J=2.4 Hz, 1H), 8.20 (d, J=2.4 Hz, 1H), 5.87 (s, 2H), 2.66~2.68 (m, 2H), 2.58~2.61 (m, 2H), 1.87~1.88 (m, 4H). MS (M+H)$^+$: 306/308.

Step 7—Synthesis of 2-(4-fluorophenyl)-N-methyl-6-(N-methylmethylsulfonamido)-5-(8,9,10,11-tetrahydro-6H-benzo[4,5]imidazo[1,2-c]pyrido[3,2-e][1,3]oxazin-2-yl)benzofuran-3-carboxamide
(Compound 141)

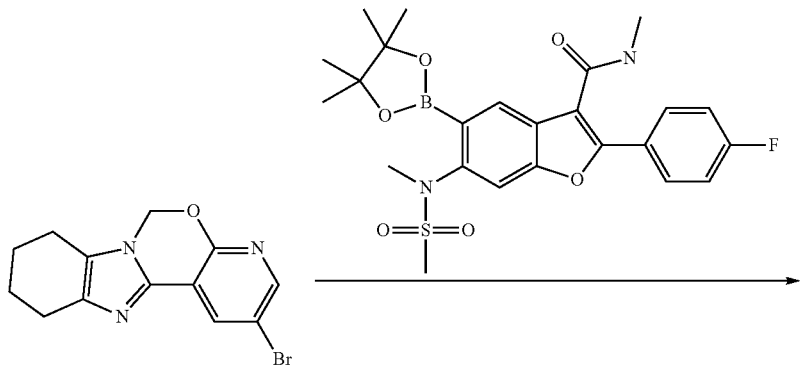

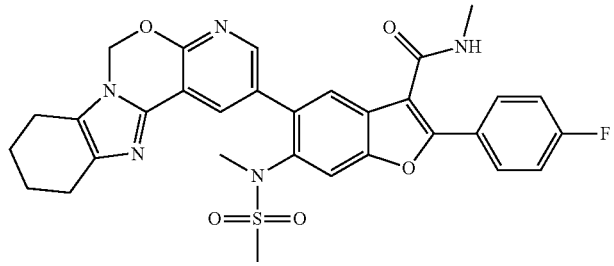

141

The procedure of Compound 141 (80 mg, yield: 44.4%) was similar to Example 1. ¹HNMR (400 MHz, CDCl₃) δ 8.82 (s, 1H), 8.55 (s, 1H), 8.04~8.08 (m, 2H), 7.93 (s, 1H), 7.59 (s, 1H), 7.45 (br, 1H), 7.16~7.20 (m, 2H), 6.07 (s, 2H), 3.32 (s, 3H), 3.04 (d, J=4.8 Hz, 3H), 2.90 (s, 3H), 2.83 (s, 2H) 2.69 (s, 2H), 1.95~1.96 (m, 4H). MS (M+H)⁺: 602.

Example 46

Preparation of Compound 142

142

Step 1—Synthesis of 2-(5-bromo-2-methoxyphenyl)imidazo[1,2-a]pyridine

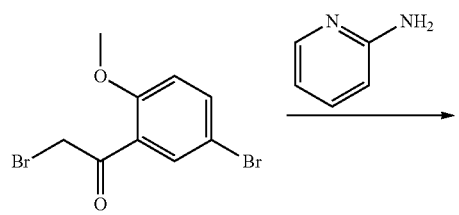

To a mixture of 2-bromo-1-(5-bromo-2-methoxyphenyl) ethanone (500 mg, 1.6 mmol) in EtOH (5 mL), pyridin-2-amine (153 mg, 1.6 mmol) was added. The mixture was stirred at 80° C. for 12 hours, and then cooled to 25° C. After filtrated, the solid was dried in vacuo to provide 2-(5-bromo-2-methoxyphenyl)imidazo[1,2-a]pyridine (30 mg, yield: 5%). ¹H-NMR(CDCl₃, 400 MHz) δ 8.54 (s, 1H), 8.18 (s, 1H), 8.12~8.13 (m, 1H), 7.62~7.64 (m, 1H), 7.37~7.40 (m, 1H), 7.16~7.21 (m, 1H), 6.86~6.88 (m, 1H), 6.76~6.79 (m, 1H), 3.98 (s, 3H). MS (M+H)⁺: 303/305.

Step 2—Synthesis of 2-(5-bromo-2-methoxyphenyl) imidazo[1,2-a]pyridine-3-carbaldehyde

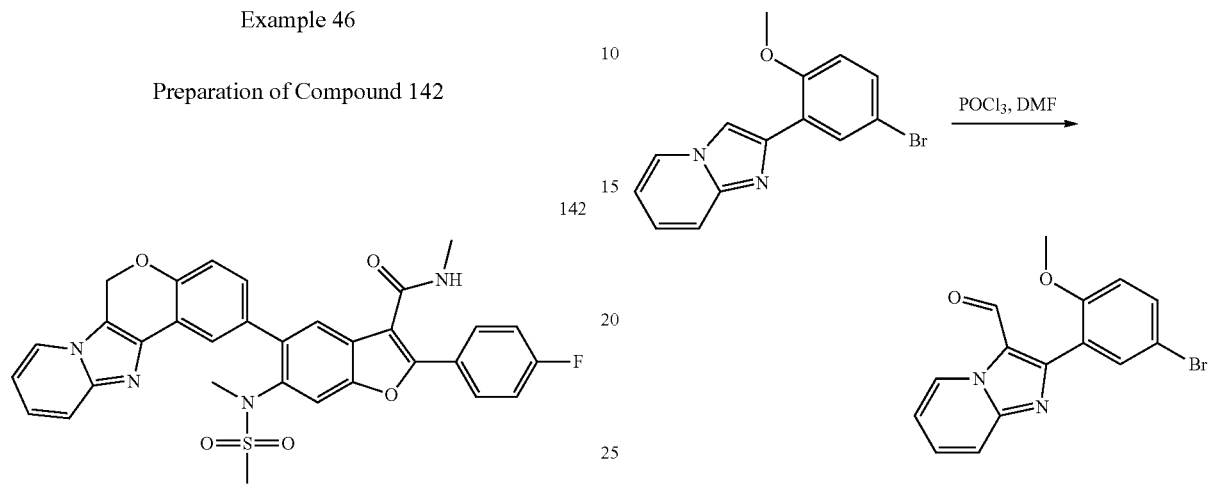

POCl₃ (0.39 g, 2.5 mmol) was added to DMF (0.43 g, 6 mmol) by dropwise at 0° C. Then 2-(5-bromo-2-methoxyphenyl)imidazo[1,2-a]pyridine (0.1 g, 0.33 mmol) in DMF (3 mL) was added. Then warmed to 25° C. and heated to 120° C. and stirred for 30 minutes and at 80° C. for 2 hours and then cooled to 25° C. H₂O (20 mL) was added and extracted with EtOAc (3*50 mL), washed by aq NaHCO₃ (3*50 mL) and brine (50 mL). After concentrated, the resulting residue was purified using prep-TLC (petroleum ether:EtOAc=3:1) to provide 2-(5-bromo-2-methoxyphenyl)imidazo[1,2-a]pyridine-3-carbaldehyde (100 mg, yield: 90%). ¹H-NMR (CDCl₃, 400 MHz) δ 9.85 (s, 1H), 9.60 (s, 1H), 7.77~7.81 (m, 2H), 7.54~7.58 (m, 2H), 7.12~7.15 (m, 1H), 6.92~6.94 (m, 1H), 3.82 (s, 3H). MS (M+H)⁺: 331/333.

Step 3—Synthesis of 2-(5-bromo-2-hydroxyphenyl) imidazo[1,2-a]pyridine-3-carbaldehyde

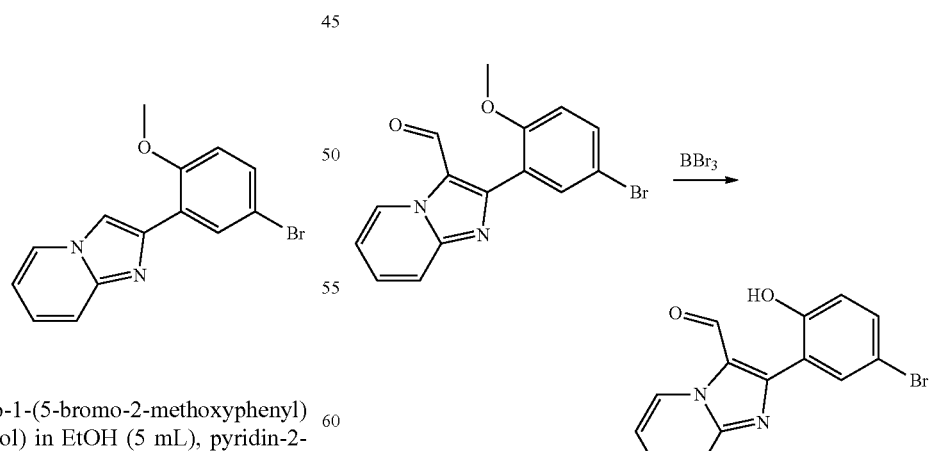

2-(5-bromo-2-methoxyphenyl)imidazo[1,2-a]pyridine-3-carbaldehyde (0.1 g, 3 mmol) was dissolved in dichloromethane (0.5 mL) at −78° C. BBr₃ (1 mL) was added by dropwise stirred for 2 hours at that temperature. Then warmed to 25° C. and stirred for 10 hours. H₂O (20 mL) was added by dropwise at −78° C. and extracted with EtOAc (3*50 mL), washed by aq NaHCO₃ (3*50 mL) and brine (50 mL). After concentrated, the resulting residue was purified using Prep-TLC (petroleum ether:EtOAc=3:1) to provide 2-(5-bromo-2-hydroxyphenyl)imidazo[1,2-a]pyridine-3-carbaldehyde (40 mg, yield: 48%). ¹H-NMR (CDCl₃, 400 MHz) δ 10.29 (s, 1H), 9.76 (s, 1H), 7.78~7.79 (m, 2H), 7.65~7.69 (m, 1H), 7.46~7.48 (m, 1H), 7.20~7.22 (m, 1H), 7.00~7.02 (m, 1H). MS (M+H)⁺: 317/319.

Step 4—Synthesis of 4-bromo-2-(3-(hydroxymethyl)imidazo[1,2-a]pyridin-2-yl)phenol

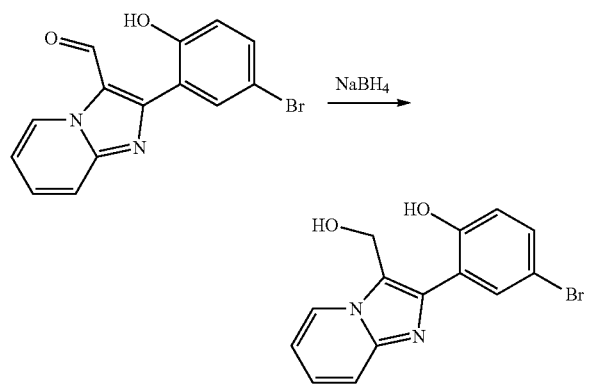

2-(5-bromo-2-hydroxyphenyl)imidazo[1,2-a]pyridine-3-carbaldehyde (0.19 g, 0.63 mmol) was dissolved in MeOH (2 mL) at 0° C. NaBH₄ (0.072 g, 1.9 mmol) was added portionwise. After addition, the mixture was stirred at 25° C. for 30 minutes, and then H₂O (20 mL) was added by dropwise. Extracted with EtOAc (3*50 mL), washed by brine (50 mL). After concentrated, the resulting residue was purified using Prep-TLC (petroleum ether:EtOAc=3:1) to provide 4-bromo-2-(3-(hydroxymethyl)imidazo[1,2-a]pyridin-2-yl)phenol (150 mg, yield: 85%). ¹H-NMR (CDCl₃, 400 MHz) δ 8.33~8.35 (m, 1H), 7.72 (s, 1H), 7.62~7.64 (m, 1H), 7.31~7.37 (m, 2H), 6.92~7.01 (m, 2H), 5.20 (s, 2H). MS (M+H)⁺: 319/321.

Step 5—Synthesis of 2-bromo-6H-chromeno[4',3':4,5]imidazo[1,2-a]pyridine

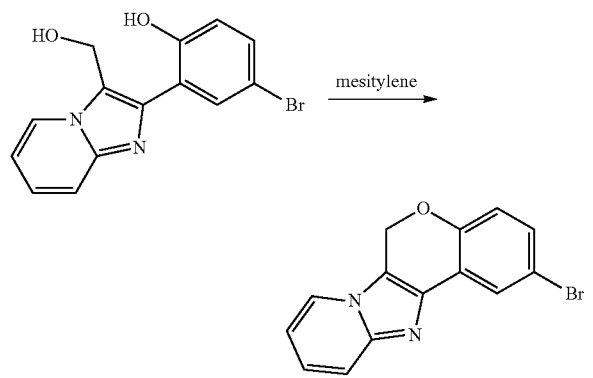

4-bromo-2-(3-(hydroxymethyl)imidazo[1,2-a]pyridin-2-yl)phenol (0.2 g, 0.06 mmol) was dissolved in mesitylene (1 mL). The mixture was stirred at 170° C. for 6 hours, and then cooled to 25° C. H₂O (20 mL) was added and extracted with EtOAc (3*50 mL), washed by brine (50 mL). After concentrated, the resulting residue was purified using Prep-TLC (petroleum ether:EtOAc=1:1) to provide 2-bromo-6H-chromeno[4',3':4,5]imidazo[1,2-a]pyridine (100 mg, yield: 53.0%). ¹H-NMR (CDCl₃, 400 MHz) δ 7.98~7.99 (m, 1H), 7.74~7.76 (m, 1H), 7.66~7.68 (m, 1H), 7.21~7.28 (m, 2H), 6.82~6.90 (m, 2H), 5.70 (s, 2H). MS (M+H)⁺: 301/303.

Step 6—Synthesis of 5-(6H-chromeno[4',3':4,5]imidazo[1,2-a]pyridin-2-yl)-2-(4-fluorophenyl)-N-methyl-6-(N-methylmethylsulfonamido)benzofuran-3-carboxamide (Compound 142)

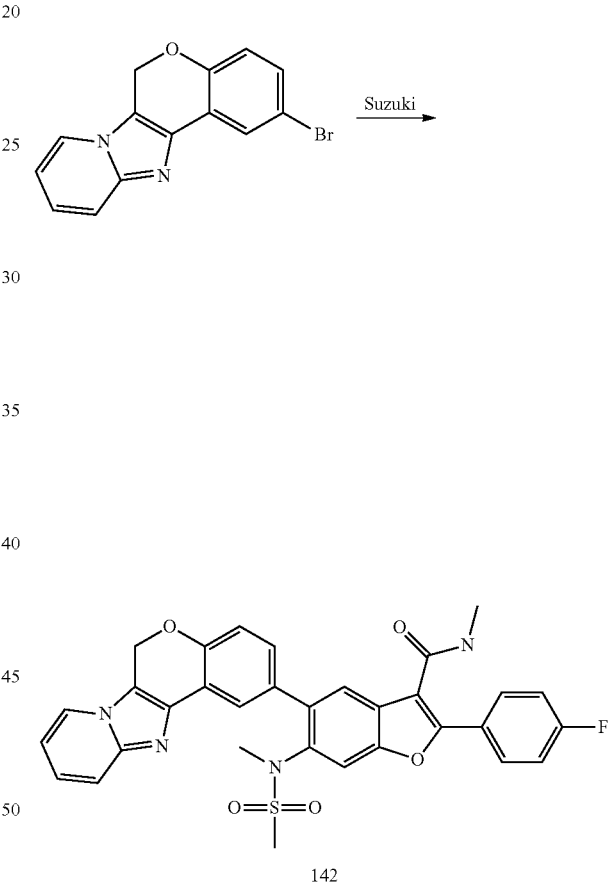

The procedure of Compound 142 (30 mg, yield: 45%) was similar to Example 1. ¹H-NMR (Methanol-d4, 400 MHz) δ 8.64~8.66 (m, 1H), 7.96~8.02 (m, 4H), 7.89 (s, 1H), 7.76 (s, 1H), 7.71 (s, 1H), 7.51~7.58 (m, 2H), 7.28~7.32 (m, 2H), 7.17~7.19 (m, 1H), 5.89 (s, 2H), 3.23 (s, 3H), 2.94~2.97 (m, 6H). MS (M+H)⁺: 597.

Compound 143, depicted in the table below, were prepared using the method described above and substituting the appropriate reactants and/or reagents.

| Compound No | Structure | NMR | MS (M + H)+ |
|---|---|---|---|
| 143 | 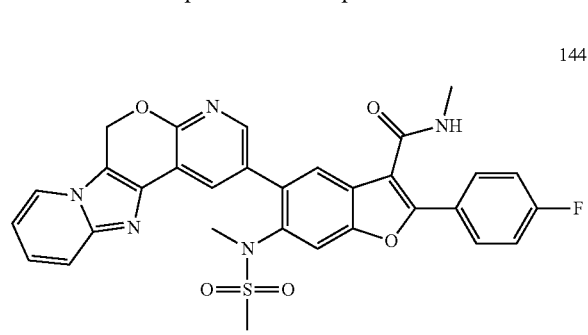 | ¹H-NMR (CDCl₃, 400 MHz) δ 8.19~8.23 (m, 1H), 7.99~8.05 (m, 4H), 7.83 (s, 1H), 7.51~7.56 (m, 3H), 7.15~7.19 (m, 2H), 7.04~7.06 (m, 1H), 6.89 (br s, 1H), 5.67 (s, 2H), 3.25 (s, 3H), 2.99~3.01 (m, 3H), 2.82 (s, 3H). | 615 |

Example 47

Preparation of Compound 144

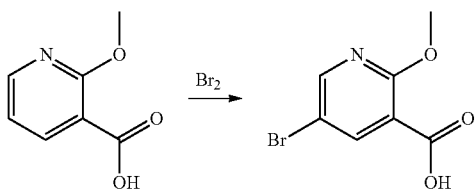

144

Step 1—Synthesis of 5-bromo-2-methoxynicotinic acid

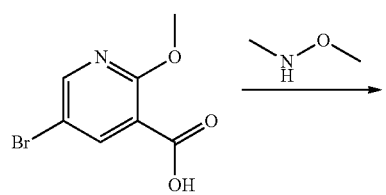

To a solution of 2-methoxynicotinic acid (20 g, 130.60 mmol) in H₂O (1500 mL), Br₂ (20 mL, 375.45 mmol) was added at room temperature. The mixture was stirred at room temperature overnight. The reaction mixture was filtered, washed with water and dried to provide 5-bromo-2-methoxynicotinic acid (25 g, yield: 82%). ¹H-NMR (DMSO, 400 MHz) δ 13.33 (br s, 1H), 8.47 (d, J=2.4 Hz, 1H), 8.21 (d, J=2.4 Hz, 1H), 3.90 (s, 3H). MS (M+H)⁺: 232/234.

Step 2—Synthesis of 5-bromo-N,2-dimethoxy-N-methylnicotinamide

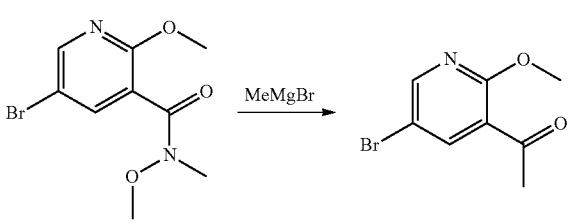

-continued

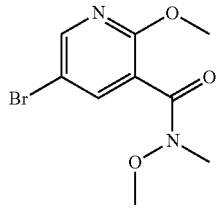

To a solution of 5-bromo-2-methoxynicotinic acid (15.0 g, 64.65 mmol) in anhydrous DMF (150 mL), HOBT (9.0 g, 66.61 mmol) and EDCI (25.0 g, 130.41 mmol) were added. The reaction mixture was stirred at room temperature for 2 hour. And then MeNHOMe.HCl (20.0 g, 205.04 mmol) and Et₃N (60 mL, 415.06 mmol) was added to the mixture. The mixture was stirred at 20° C. overnight. The reaction mixture was concentrated in vacuo. Then H₂O was added, and extracted with EtOAc. The combined organic phases were washed with brine, dried over Na₂SO₄, filtered and concentrated in vacuo. The crude product was purified using column chromatography (eluted with petroleum ether:EtOAc=2:1) to provide 5-bromo-N,2-dimethoxy-N-methylnicotinamide (16.5 g, yield: 92%). ¹H-NMR (CDCl₃, 400 MHz) δ 8.23 (d, J=2.4 Hz, 1H), 7.68 (d, J=2.4 Hz, 1H), 3.95 (s, 3H), 3.53 (s, 3H), 3.33 (s, 3H). MS (M+H)⁺: 275/277.

Step 3—Synthesis of 1-(5-bromo-2-methoxypyridin-3-yl)ethanone

To a solution of 5-bromo-N,2-dimethoxy-N-methylnicotinamide (5.0 g, 18.18 mmol) in THF (50 mL), MeMgBr (10 mL, 30.0 mmol) was added dropwise at −78° C. The reaction mixture was stirred at 20° C. overnight. Then the reaction mixture was added to NH₄Cl solution. The mixture was extracted with EtOAc. The combined organic phases were washed with brine, dried over Na₂SO₄, filtered and concentrated in vacuo. The crude product was purified using column chromatography (eluted with petroleum ether:EtOAc=10:1)

to provide 1-(5-bromo-2-methoxypyridin-3-yl)ethanone (3.0 g, yield: 71%). ¹H-NMR (CDCl₃, 400 MHz) δ 8.33 (d, J=2.4 Hz, 1H), 8.19 (d, J=2.4 Hz, 1H), 4.03 (s, 3H), 2.63 (s, 3H). MS (M+H)⁺: 230/232

Step 4—Synthesis of
2-bromo-1-(5-bromo-2-hydroxypyridin-3-yl)ethanone

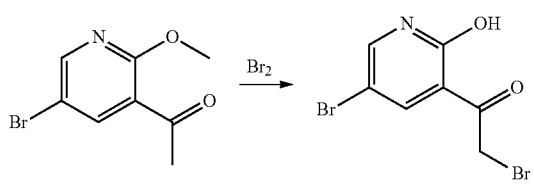

To a solution of 1-(5-bromo-2-methoxypyridin-3-yl)ethanone (2.0 g, 8.69 mmol) in HBr (20 mL, HOAc solution), Br₂ (1.4 g, 8.76 mmol) was added dropwise at room temperature. The reaction mixture was stirred at room temperature for 5 hours. Then the reaction mixture was filtered to collect the HBr salt. The solid was suspended with Na₂CO₃ solution, extracted with EtOAc. The combined organic phases were washed with brine, dried over Na₂SO₄, filtered and concentrated in vacuo to provide 2-bromo-1-(5-bromo-2-hydroxypyridin-3-yl)ethanone (2.0 g, yield: 74%). ¹H-NMR (DMSO, 400 MHz) δ 12.83 (br s, 1H), 8.11~8.13 (m, 2H), 4.85 (s, 2H). MS (M+H)⁺: 295.

Step 5—Synthesis of
5-bromo-3-(imidazo[1,2-a]pyridin-2-yl)pyridin-2-ol

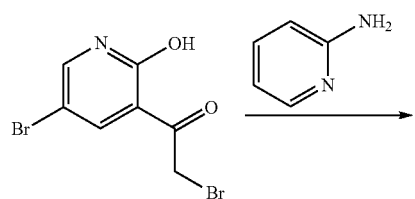

A mixture of 2-bromo-1-(5-bromo-2-hydroxypyridin-3-yl)ethanone (300 mg, 1.02 mmol) and 2-aminopyridine (100 mg, 1.06 mmol) in EtOH (10 mL) was stirred at reflux overnight. The reaction mixture was cooled and filtered to provide 5-bromo-3-(imidazo[1,2-a]pyridin-2-yl)pyridin-2-ol (200 mg, yield: 67%). ¹H-NMR (DMSO, 400 MHz) δ 12.75 (br s, 1H), 9.02 (s, 1H), 8.94 (d, J=6.8 Hz, 1H), 8.42 (d, J=2.8 Hz, 1H), 7.89~7.96 (m, 3H), 7.45 (d, J=4.8 Hz, 1H). MS (M+H)⁺: 290/292.

Step 6—Synthesis of 2-(5-bromo-2-chloropyridin-3-yl)imidazo[1,2-a]pyridine-3-carbaldehyde

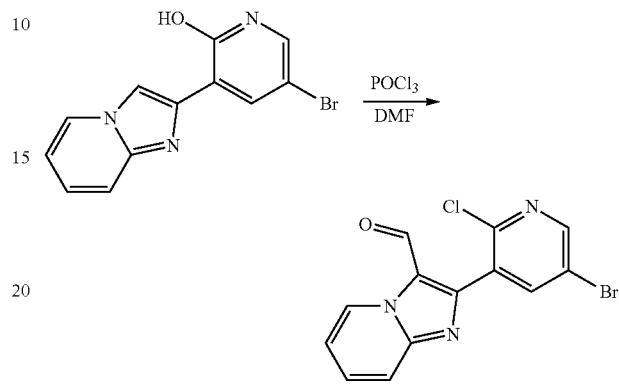

A solution of 5-bromo-3-(imidazo[1,2-a]pyridin-2-yl)pyridin-2-ol (500 mg, 1.72 mmol) in POCl₃ (10 mL) was stirred at 100° C. overnight. Then DMF (10 mL) was added dropwise. The reaction mixture was stirred at 100° C. for 3 hours. The reaction mixture was concentrated in vacuo. The resulting residue was suspended with water, and saturated aqueous NaHCO₃ solution was added until the solution was at pH 7. The mixture was extracted with EtOAc. The combined organic phases were washed with brine, dried over Na₂SO₄, filtered and concentrated in vacuo. The crude product was purified using column chromatography (eluted with dichloromethane:MeOH=50:1) to provide 2-(5-bromo-2-chloropyridin-3-yl)imidazo[1,2-a]pyridine-3-carbaldehyde (300 mg, yield: 51%). ¹H-NMR (CDCl₃, 400 MHz) δ 9.87 (s, 1H), 9.62 (d, J=7.2 Hz, 1H), 8.61 (d, J=2.4 Hz, 1H), 8.12 (d, J=2.4 Hz, 1H), 7.84 (d, J=9.2 Hz, 1H), 7.63~7.67 (m, 1H), 7.21~7.24 (m, 2H). MS (M+H)⁺: 336/338.

Step 7—Synthesis of (2-(5-bromo-2-chloropyridin-3-yl)imidazo[1,2-a]pyridin-3-yl)methanol

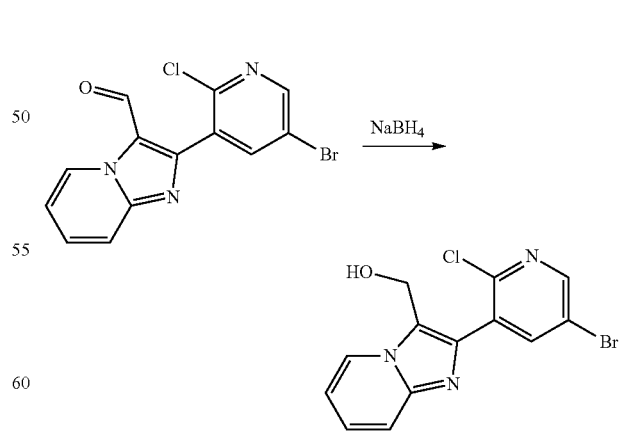

To a solution of 2-(5-bromo-2-chloropyridin-3-yl)imidazo[1,2-a]pyridine-3-carbaldehyde (100 mg, 0.29 mmol) in MeOH (5 mL), NaBH₄ (20 mg, 0.53 mmol) was added at 0° C. The reaction mixture was stirred at room temperature for 30 minutes. The reaction mixture was added water and extracted with EtOAc. The organic layer was washed with brine, dried over $Na_2SO_4$ and concentrated in vacuo. The resulting residue was purified using PTLC (eluted with dichloromethane:MeOH=30:1) to provide (2-(5-bromo-2-chloropyridin-3-yl)imidazo[1,2-a]pyridin-3-yl)methanol (30 mg, yield: 29%). $^1$H-NMR (DMSO, 400 MHz) δ 8.66 (d, J=2.4 Hz, 1H), 8.49 (d, J=6.8 Hz, 1H), 8.25 (d, J=2.4 Hz, 1H), 7.64 (d, J=9.2 Hz, 1H), 7.35~7.40 (m, 1H), 7.03~7.07 (m, 1H), 5.33 (t, J=5.2 Hz, 1H), 4.75 (d, J=5.2 Hz, 2H). MS $(M+H)^+$: 338/340.

Step 8—Synthesis of 2-bromo-4-aza-6H-chromeno[4',3':4,5]imidazo[1,2-a]pyridine

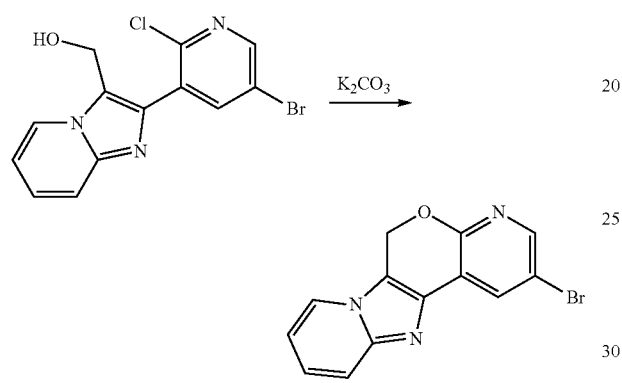

To a solution of (2-(5-bromo-2-chloropyridin-3-yl)imidazo[1,2-a]pyridin-3-yl)methanol (20 mg, 0.06 mmol) in DMF (2 mL), $K_2CO_3$ (20 mg, 0.14 mmol) was stirred at 100° C. overnight. The reaction mixture was concentrated in vacuo. The resulting residue was suspended with water and extracted with EtOAc. The combined organic phases were washed with brine, dried over $Na_2SO_4$, filtered and concentrated in vacuo. The crude product was purified using PTLC (eluted with dichloromethane:MeOH=50:1) to provide 2-bromo-4-aza-6H-chromeno[4',3':4,5]imidazo[1,2-a]pyridine (7 mg, yield: 39%). $^1$H-NMR (CDCl$_3$, 400 MHz) δ 8.23 (d, J=2.4 Hz, 1H), 8.13 (d, J=2.4 Hz, 1H), 7.75 (d, J=6.8 Hz, 1H), 7.66 (d, J=9.2 Hz, 1H), 7.27~7.30 (m, 1H), 6.90~6.95 (m, 1H), 5.93 (s, 2H). MS $(M+H)^+$: 302/304.

Step 9—Synthesis of 2-(4-fluorophenyl)-N-methyl-6-[methyl(methylsulfonyl)amino]-5-(6H pyrido[1",2":1',2']imidazo[4',5':4,5]pyrano[2,3-b]pyridin-2-yl)-1-benzofuran-3-carboxamide (Compound 144)

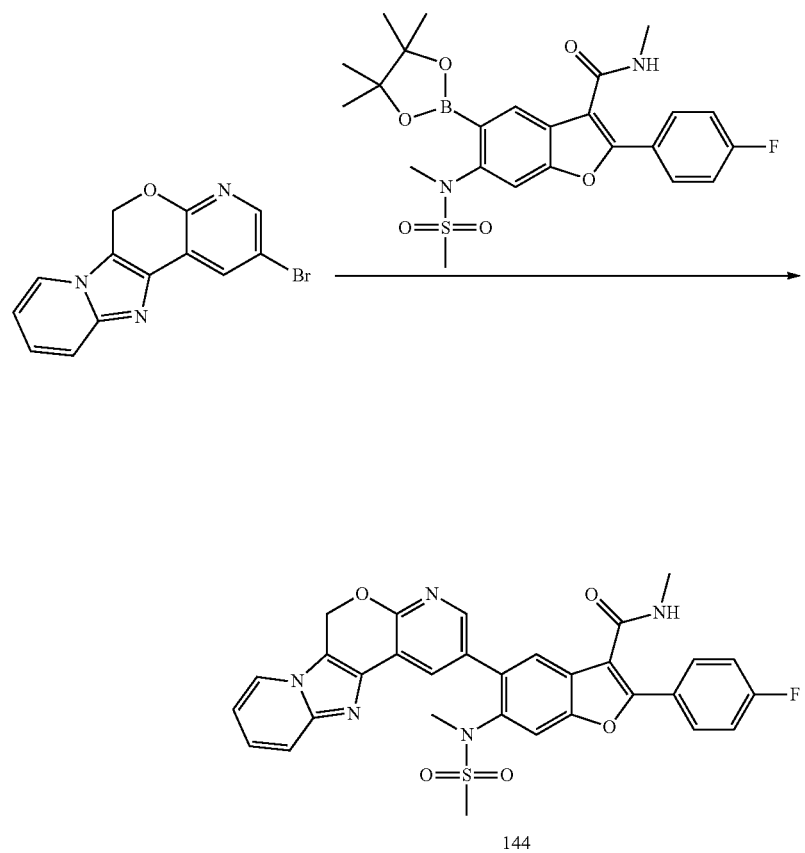

144

The procedure of Compound 144 (30 mg, yield: 45%) was similar to Example 1. ¹H-NMR (CDCl₃, 400 MHz) δ 8.21 (d, J=2.0 Hz, 1H), 8.14 (d, J=2.0 Hz, 1H), 7.94~7.98 (m, 2H), 7.83 (s, 1H), 7.77 (d, J=6.8 Hz, 1H), 7.62~7.65 (m, 2H), 7.16~7.27 (m, 3H), 6.90~6.94 (m, 1H), 6.14 (br s, 1H), 5.96 (s, 2H), 3.22 (s, 3H), 3.03 (d, J=4.8 Hz, 3H), 2.78 (s, 3H). MS (M+H)⁺: 598.

Example 48

Preparation of Compound 145

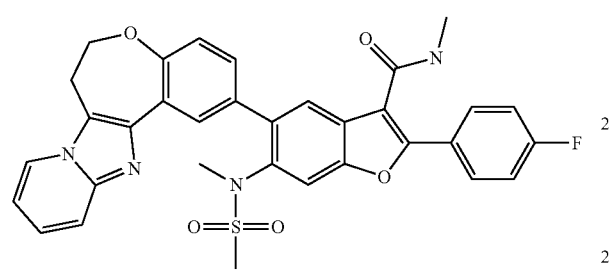

Step 1—Synthesis of 4,7-dibromo-3,4-dihydrobenzo[b]oxepin-5(2H)-one

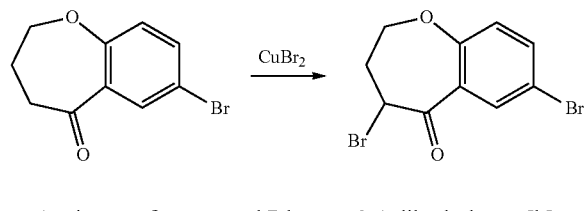

A mixture of compound 7-bromo-3,4-dihydrobenzo[b]oxepin-5(2H)-one (100 mg, 0.415 mmol) and CuBr₂ (93 mg, 0.415 mmol) in ethyl acetate/CHCl₃ (1 mL/1 mL) was stirred at 70-80° C. under N₂ overnight. The mixture was then purified using prep-TLC (petroleum ether:ethyl acetate=10:1) to provide compound 4,7-dibromo-3,4-dihydrobenzo[b]oxepin-5(2H)-one (58 mg, yield: 44.4%). MS (M+H)⁺: 319/321/323.

Step 2—Synthesis of 2-bromo-6,7-dihydrobenzo[2',3']oxepino[4',5':4,5]imidazo[1,2-a]pyridine

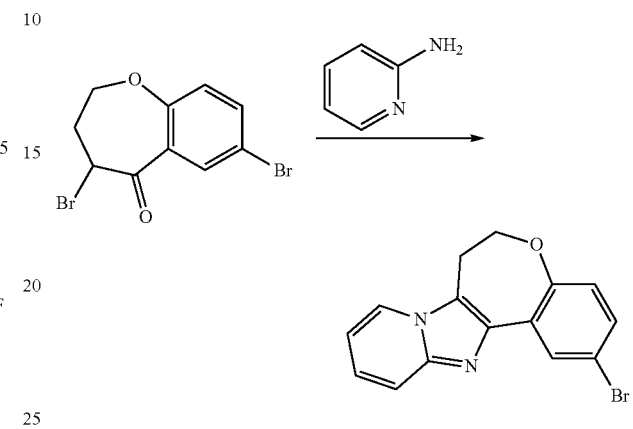

A mixture of compound 4,7-dibromo-3,4-dihydrobenzo[b]oxepin-5(2H)-one (330 mg, 1.031 mmol) and pyridin-2-amine (97 mg, 1.031 mmol) was stirred at 60° C. for 3 hours. The mixture was then purified using chromatography (petroleum ether:ethyl acetate=3:1) to provide 2-bromo-6,7-dihydrobenzo[2',3']oxepino[4',3':4,5]imidazo[1,2-a]pyridine (40 mg, yield: 12.3%). ¹H-NMR (CDCl₃, 400 MHz) δ 8.54 (d, J=2.8 Hz, 1H), 7.78 (d, J=6.8 Hz, 1H), 7.58 (d, J=9.2 Hz, 1H), 7.14~7.24 (m, 2H), 6.78~6.88 (m, 2H), 4.42 (d, J=5.2 Hz, 2H), 3.21 (d, J=5.2 Hz, 2H). MS (M+H)⁺: 315/317.

Step 3—Synthesis of 5-(6,7-dihydrobenzo[2',3']oxepino[4',5':4,5]imidazo[1,2-a]pyridin-2-yl)-2-(4-fluorophenyl)-N-methyl-6-(N-methylmethylsulfonamido)benzofuran-3-carboxamide (Compound 145)

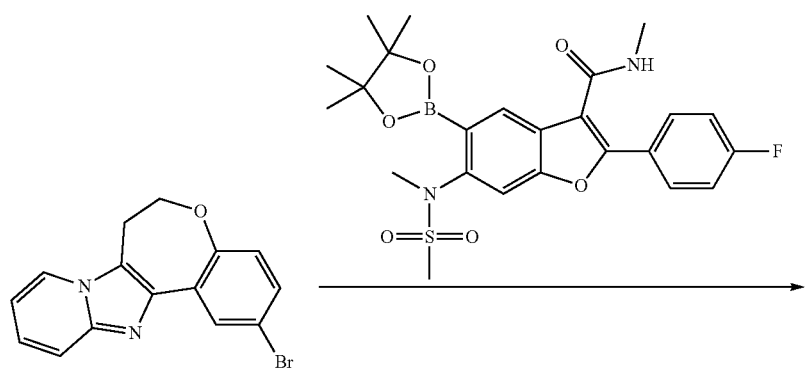

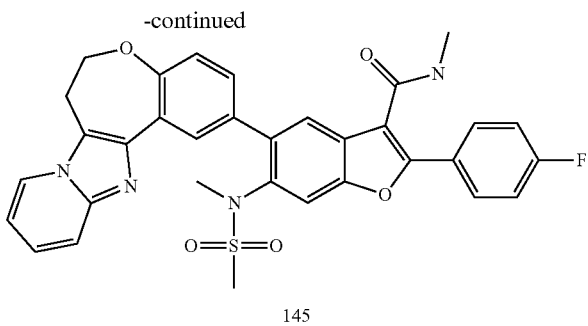

145

The procedure of compound 145 (50 mg, yield: 64.9%) was similar to that of Example 1. ¹H-NMR (DMSO-d₆, 400 MHz) δ 8.62 (s, 1H), 8.50 (d, J=2.4 Hz, 1H), 8.36 (d, J=6.8 Hz, 1H), 8.06~8.09 (m, 2H), 8.02 (s, 1H), 7.66 (t, J=4.4 Hz, 2H), 7.48 (t, J=8.8 Hz, 2H), 7.33~7.43 (m, 2H), 7.17 (d, J=8.4 Hz, 1H), 7.03 (t, J=6.8 Hz, 1H), 4.56 (t, J=5.0 Hz, 2H), 3.44 (t, J=5.0 Hz, 2H), 3.17 (s, 3H), 3.01 (s, 3H), 2.87 (d, J=4.8 Hz, 3H). MS (M+H)⁺: 611.

Example 49

Preparation of Compound 146

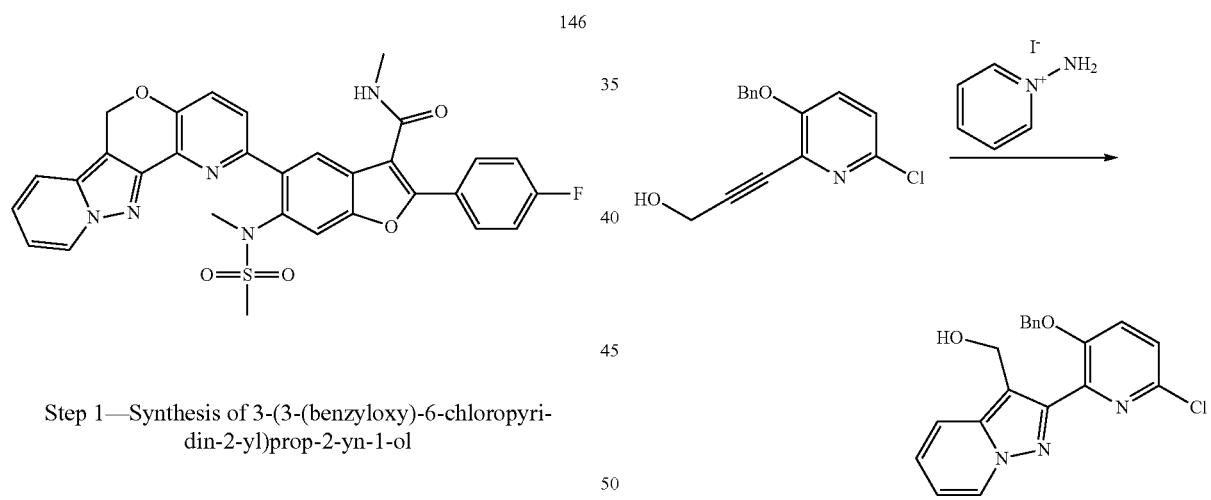

146

Step 1—Synthesis of 3-(3-(benzyloxy)-6-chloropyridin-2-yl)prop-2-yn-1-ol

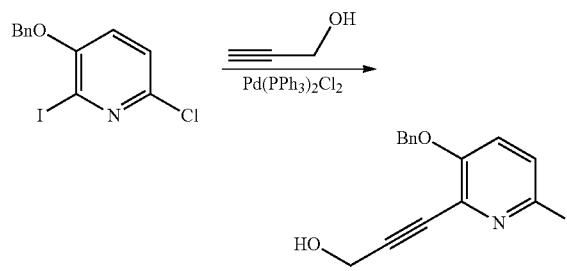

A mixture of compound 3-(benzyloxy)-6-chloro-2-iodopyridine (2.5 g, 7.2 mmol), prop-2-yn-1-ol (443 mg, 7.9 mmol), Pd(PPh₃)₂Cl₂ (280 mg, 0.4 mmol) and CuI (76 mg, 0.4 mmol) in Et₃N (25 mL) was stirred at room temperature for 6 hours. Water (50 mL) was added and the mixture was extracted with dichloromethane. The organic layer was washed with brine and dried over Na₂SO₄. After concentrated, the resulting residue was purified using column chromatography (petroleum ether:ethyl acetate=2:1) to provide the product of compound 3-(3-(benzyloxy)-6-chloropyridin-2-yl)prop-2-yn-1-ol (1.8 g, yield: 90%). ¹H-NMR (CDCl₃, 400 MHz) δ 7.42~7.33 (m, 5H), 7.17 (s, 2H), 5.18 (s, 2H), 4.54 (s, 2H). MS (M+H)⁺: 274/276.

Step 2—Synthesis of (2-(3-(benzyloxy)-6-chloropyridin-2-yl)pyrazolo[1,5-a]pyridin-3-yl)methanol A mixture of compound 3-(3-(benzyloxy)-6-chloropyridin-2-yl)prop-2-yn-1-ol (1.9 g, 6.9 mmol), 1-aminopyridinium iodide (2.3 g, 10.4 mmol) and DBU (2.2 g, 14 mmol) in MeCN (15 mL) was stirred at 80° C. for 2 hours. Water (15 mL) was added and the mixture was extracted with ethyl acetate. The organic layer was washed with brine and dried over Na₂SO₄. After concentrated, the resulting residue was purified using column chromatography (petroleum ether: ethyl acetate=1:1) to provide the product of compound (2-(3-(benzyloxy)-6-chloropyridin-2-yl)pyrazolo[1,5-a]pyridin-3-yl)methanol (1.2 g, yield: 47%). ¹H-NMR (CDCl₃, 400 MHz) δ 8.42 (d, J=8.0 Hz, 1H), 7.58 (d, J=8.0 Hz, 1H), 7.37 (d, J=8.0 Hz, 1H), 7.29~7.22 (m, 3H), 7.21~7.17 (m, 3H), 7.02 (t, J=8.0 Hz, 1H), 6.76 (dt, J=1.6, 8.0 Hz, 1H), 5.09 (s, 2H), 4.77 (d, J=6.4 Hz, 2H). MS (M+H)⁺: 366/368.

Step 3—Synthesis of 5-(5-(benzyloxy)-6-(3-(hydroxymethyl)pyrazolo[1,5-a]pyridin-2-yl)pyridin-2-yl)-2-(4-fluorophenyl)-N-methyl-6-(N-methylmethylsulfonamido)benzofuran-3-carboxamide

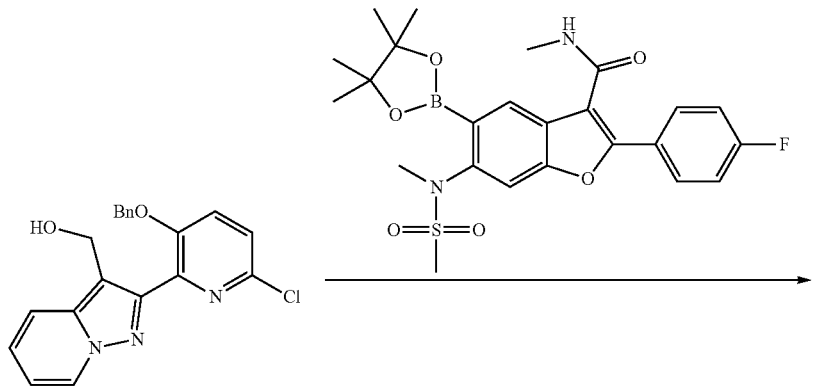

To a degassed solution of 2-(4-fluorophenyl)-N-methyl-6-(N-methylmethylsulfonamido)-5-(3-(4,4,5,5-tetramethyl-1,3,2-dioxaborolan-2-yl)phenyl)benzofuran-3-carboxamide (452 mg, 0.90 mmol) and compound (2-(3-(benzyloxy)-6-chloropyridin-2-yl)pyrazolo[1,5-a]pyridin-3-yl)methanol (300 mg, 0.82 mmol) in dioxane/H$_2$O (5 mL/1 mL) was added Pd$_2$(dba)$_3$ (90 mg, 0.1 mmol), X-Phos (95 mg, 0.2 mmol) and K$_3$PO$_4$ (1.2 g, 2.4 mmol) under N$_2$. After stirred at 100° C. overnight, the reaction mixture was cooled to room temperature and filtered. The filtrate was washed with brine and dried over Na$_2$SO$_4$. After concentrated, the resulting residue was purified using column chromatography (petroleum ether: ethyl acetate=1:2) to provide the product of compound 5-(5-(benzyloxy)-6-(3-(hydroxymethyl)pyrazolo[1,5-a]pyridin-2-yl)pyridin-2-yl)-2-(4-fluorophenyl)-N-methyl-6-(N-methylmethylsulfonamido)benzofuran-3-carboxamide (300 mg, yield: 53%). $^1$H-NMR (Methanol-d4, 400 MHz) δ 8.47 (d, J=8.8 Hz, 1H), 8.00 (dd, J=5.2, 8.8 Hz, 2H), 7.76 (d, J=8.8 Hz, 1H), 7.68 (d, J=9.2 Hz, 1H), 7.63 (d, J=8.4 Hz, 1H), 7.30~7.24 (m, 7H), 7.16~7.11 (m, 1H), 7.13 (dt, J=0.8, 6.8 Hz, 1H), 5.22 (s, 2H), 4.74 (s, 2H), 3.29 (s, 3H), 2.93 (s, 3H), 2.89 (s, 3H). MS (M+H)$^+$: 706.

Step 4—Synthesis of 2-(4-fluorophenyl)-5-(5-hydroxy-6-(3-(hydroxymethyl)pyrazolo[1,5-a]pyridin-2-yl)pyridin-2-yl)-N-methyl-6-(N-methylmethylsulfonamido)benzofuran-3-carboxamide

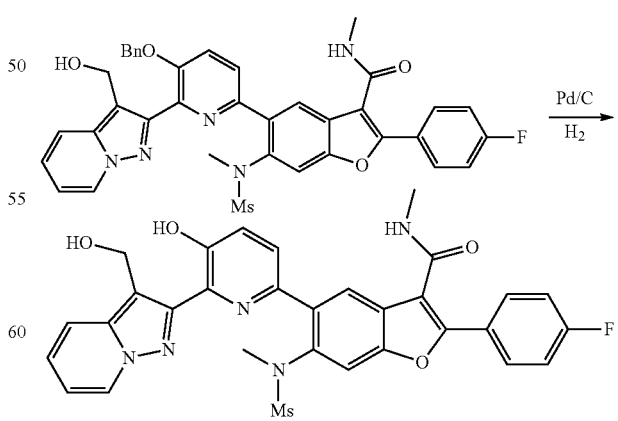

A mixture of compound 5-(5-(benzyloxy)-6-(3-(hydroxymethyl)pyrazolo[1,5-a]pyridin-2-yl)pyridin-2-yl)-2-(4-fluorophenyl)-N-methyl-6-(N-methylmethylsulfonamido)benzofuran-3-carboxamide (250 mg, 0.35 mmol) and

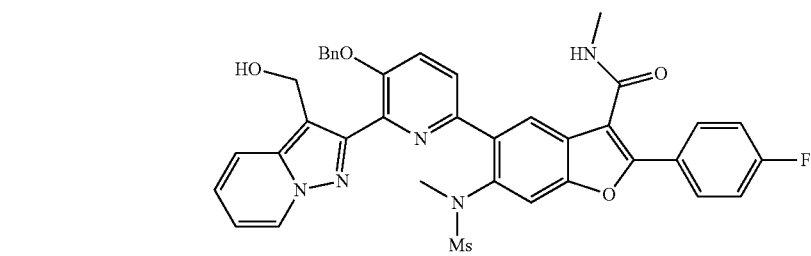

Pd/C (20 mg) in MeOH (2 mL) was stirred at room temperature under $H_2$ for 2 hours. The mixture was filtered and the filtrate was concentrated in vacuo. The resulting residue was purified using prep-TLC (EA:MeOH=20:1) to provide the product of compound 2-(4-fluorophenyl)-5-(5-hydroxy-6-(3-(hydroxymethyl)pyrazolo[1,5-a]pyridin-2-yl)pyridin-2-yl)-N-methyl-6-(N-methylmethylsulfonamido)benzofuran-3-carboxamide (100 mg, yield: 46%). $^1$H-NMR (Methanol-d4, 400 MHz) δ 8.50 (d, J=6.8 Hz, 1H), 7.98 (dd, J=5.2, 8.4 Hz, 2H), 7.84 (s, 2H), 7.78 (d, J=9.2 Hz, 1H), 7.51 (d, J=8.4 Hz, 1H), 7.45 (d, J=8.4 Hz, 1H), 7.29~7.23 (m, 3H), 6.93 (t, J=6.8 Hz, 1H), 4.77 (s, 2H), 3.26 (s, 3H), 2.93 (s, 3H), 2.90 (s, 3H). MS (M+H)$^+$: 616.

Step 5—Synthesis of 2-(4-fluorophenyl)-N-methyl-5-(1-aza-6H-chromeno[4',3':3,4]pyrazolo[1,5-a]pyridin-2-yl)-6-(N-methylmethylsulfonamido)benzofuran-3-carboxamide (Compound 146)

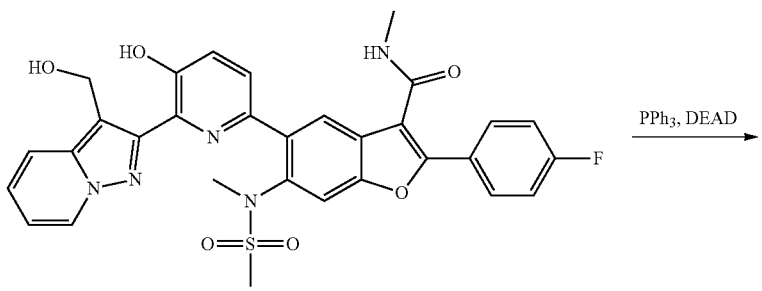

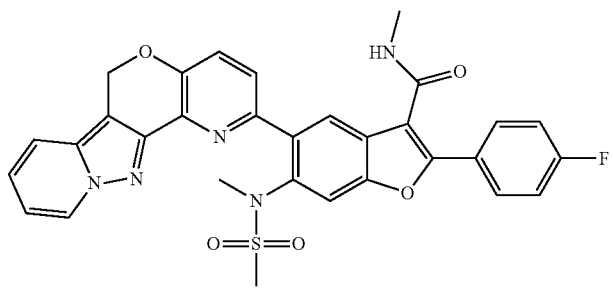

146

A solution of DEAD (158 mg, 0.91 mmol) and PPh₃ (341 mg, 1.3 mmol) in THF (1 mL) was added dropwise to a solution of compound 2-(4-fluorophenyl)-5-(5-hydroxy-6-(3-(hydroxymethyl)pyrazolo[1,5-a]pyridin-2-yl)pyridin-2-yl)-N-methyl-6-(N-methylmethylsulfonamido)benzofuran-3-carboxamide (80 mg, 0.13 mmol) in THF (1 mL) at 0° C. The reaction mixture was stirred at room temperature for 12 hours. The mixture was concentrated and the resulting residue was purified using prep-HPLC to provide the product of 146 (30 mg, yield: 39%). ¹H-NMR (DMSO, 400 MHz) δ 8.81 (d, J=6.8 Hz, 1H), 8.68 (d, J=4.8 Hz, 1H), 8.18 (d, J=8.8 Hz, 1H), 8.07~8.03 (m, 3H), 7.98 (s, 1H), 7.46~7.42 (m, 5H), 7.04 (t, J=6.8 Hz, 1H), 5.65 (s, 2H), 3.25 (s, 3H), 2.99 (s, 3H), 2.85 (d, J=4.4 Hz, 3H). MS (M+H)⁺: 598.

Example 50

Preparation of Compound 147

147

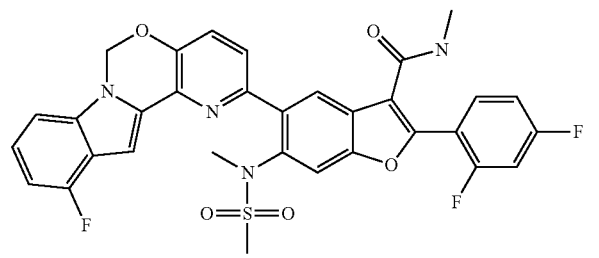

Step 1—Synthesis of ethyl 6-amino-5-bromo-2-(2,4-difluorophenyl)benzofuran-3-carboxylate

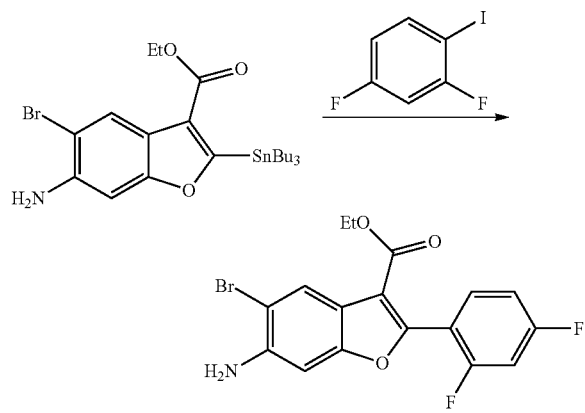

2,4-difluoro-1-iodobenzene (2.09 g, 8.72 mmol) and Pd(PPh₃)₄ (20 mg) were added into a solution of ethyl 6-amino-5-bromo-2-(tributylstannyl)benzofuran-3-carboxylate (5 g, 8.72 mmol, prepared from ethyl 6-amino-5-bromobenzofuran-3-carboxylate with LDA and Bu₃SnCl) in toluene (10 mL) under N₂, then the mixture was stirred at 60° C. overnight. The reaction mixture was cooled to room temperature and filtered. The filtrate was washed with H₂O, brine, dried over Na₂SO₄. After concentrated, the resulting residue was purified using column chromatography (petroleum ether: EtOAc=6:1) to provide the product of ethyl 6-amino-5-bromo-2-(2,4-difluorophenyl)benzofuran-3-carboxylate (310 mg, yield: 9%). ¹H-NMR (CDCl₃, 400 MHz) δ 8.10 (s, 1H), 7.66 (d, J=8.0 Hz, 1H), 6.95~7.01 (m, 2H), 6.92 (d, J=8.0 Hz, 1H), 4.37 (q, J=7.6 Hz, 2H), 1.33 (t, J=7.6 Hz, 3H). MS (M+H)⁺: 396/398.

Step 2—Synthesis of ethyl 5-bromo-2-(2,4-difluorophenyl)-6-(methylsulfonamido)benzofuran-3-carboxylate

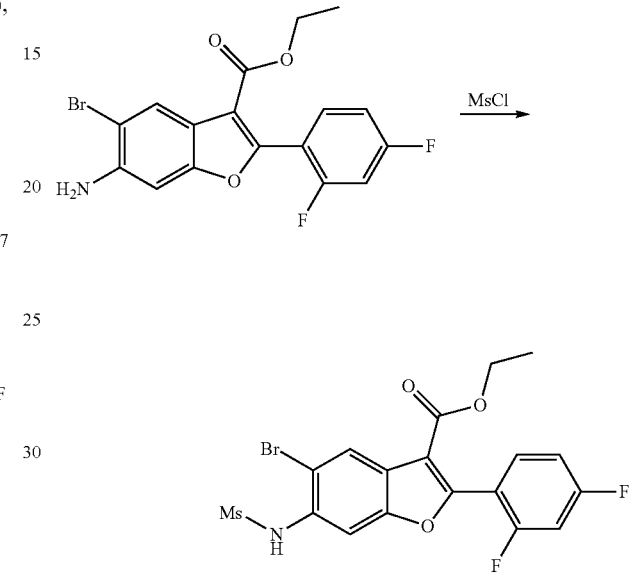

To a solution of ethyl 6-amino-5-bromo-2-(2,4-difluorophenyl)benzofuran-3-carboxylate (310 mg, 0.78 mmol) and pyridine (185 mg, 2.35 mmol) in dichloromethane (10 mL) was added dropwise methanesulfonyl chloride (179 mg, 1.56 mmol) at 0° C., then the mixture was stirred at 25° C. overnight. 10% HCl (aq) was added, then the mixture was extracted with dichloromethane (30 mL*3), dried over Na₂SO₄, and concentrated to provide ethyl 5-bromo-2-(2,4-difluorophenyl)-6-(methylsulfonamido)benzofuran-3-carboxylate (350 mg, yield: 94%). ¹H-NMR (CDCl₃, 400 MHz) δ 8.32 (s, 1H), 7.91 (s, 1H), 7.64~7.90 (m, 1H), 7.06 (d, J=3.0 Hz, 1H), 7.03 (d, J=3.0 Hz, 1H), 6.88 (s, 1H), 4.38 (q, J=7.2 Hz, 2H), 3.02 (s, 3H), 1.33 (t, J=7.6 Hz, 3H). MS (M+H)⁺: 474/476.

Step 3—Synthesis of 5-bromo-2-(2,4-difluorophenyl)-6-(methylsulfonamido)benzofuran-3-carboxylic acid

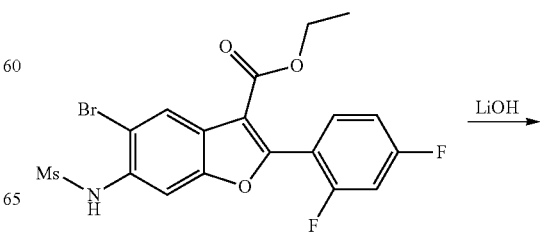

233

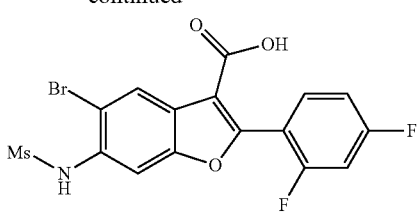

To a solution of ethyl 5-bromo-2-(2,4-difluorophenyl)-6-(methylsulfonamido)benzofuran-3-carboxylate (653 mg, 1.38 mmol) in 1,4-Dioxane (10 mL) and H₂O (1 mL) was added LiOH (289 mg, 6.88 mmol), then the mixture was stirred at 110° C. After 3 hours, 10% HCl (aq) was added until pH reach 4. The mixture was extracted with EtOAc. The organic layer was dried over Na₂SO₄ and concentrated to provide 5-bromo-2-(2,4-difluorophenyl)-6-(methylsulfonamido)benzofuran-3-carboxylic acid (440 mg, yield: 65%). ¹H-NMR (CDCl₃, 400 MHz) δ 8.38 (s, 1H), 7.94 (s, 1H), 7.66~7.94 (m, 1H), 7.08 (d, J=3.0 Hz, 1H), 6.91 (s, 1H), 3.04 (s, 3H). MS (M+H)⁺: 446/448.

Step 4—Synthesis of 5-bromo-2-(2,4-difluorophenyl)-N-methyl-6-(methylsulfonamido)benzofuran-3-carboxamide

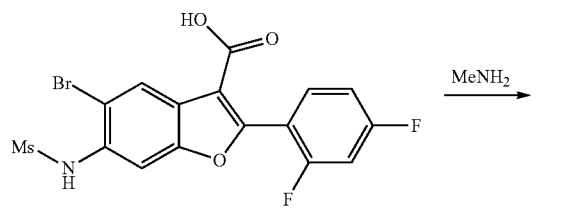

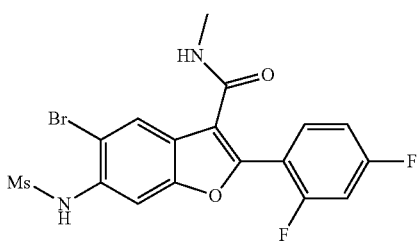

A solution of 5-bromo-2-(2,4-difluorophenyl)-6-(methylsulfonamido)benzofuran-3-carboxylic acid (440 mg, 0.99 mmol), HOBT (199 mg, 1.48 mmol) and EDCI (283 mg, 1.48 mmol) in dry DMF (10 mL) was stirred at 25° C. After 2 hours, Et₃N (299 mg, 2.96 mmol) and MeNH₂ (200 mg, 2.96 mmol) was added to the mixture and then stirred overnight. The solvent was removed by vacuum, the mixture was washed with H₂O (20 mL) and extract with EtOAc (40 mL*3), dried over Na₂SO₄, After concentrated, the resulting residue was purified using column chromatography (dichloromethane:EtOAc=2:1) to provide 5-bromo-2-(2,4-difluorophenyl)-N-methyl-6-(methylsulfonamido)benzofuran-3-carboxamide (400 mg, yield: 88%). ¹H-NMR (DMSO-d6, 400 MHz) δ 9.61 (s, 1H), 8.19 (d, J=3.6 Hz, 1H), 7.97 (s, 1H), 7.80~7.86 (m, 1H), 7.73 (s, 1H), 7.44~7.50 (m, 1H), 7.27~7.31 (m, 1H), 3.02 (s, 3H), 2.75 (d, J=4.8 Hz, 3H). MS (M+H)⁺: 459/461.

Step 5—Synthesis of 5-bromo-2-(2,4-difluorophenyl)-N-methyl-6-(N-methylmethylsulfonamido)benzofuran-3-carboxamide

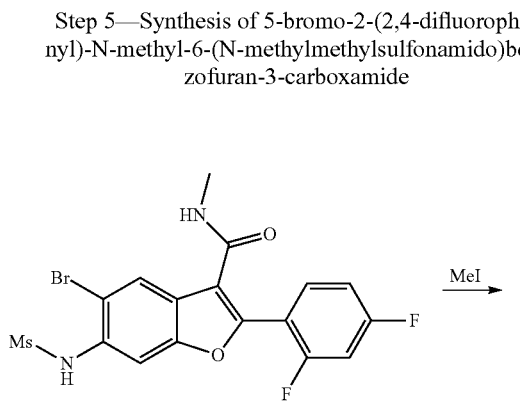

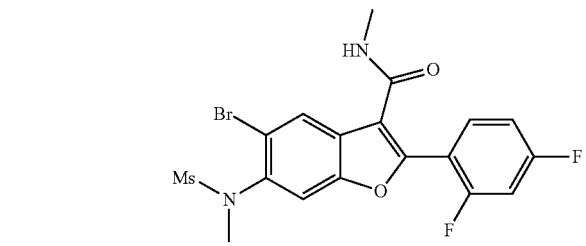

To a solution of 5-bromo-2-(2,4-difluorophenyl)-N-methyl-6-(methylsulfonamido)benzofuran-3-carboxamide (653 mg, 1.38 mmol), K₂CO₃ (406 mg, 2.94 mmol) in DMF (10 mL) was added MeI (519 mg, 3.66 mmol), then the mixture was stirred at 80° C. After 3 hours, the solvent was removed by vacuum, the mixture was washed with H₂O (20 mL) and extract with dichloromethane (50 mL*3), dried over Na₂SO₄ and concentrated to provide 5-bromo-2-(2,4-difluorophenyl)-N-methyl-6-(N-methylmethylsulfonamido)benzofuran-3-carboxamide (118 mg, yield: 25%). ¹H-NMR (CDCl₃, 400 MHz) 8.24 (s, 1H), 7.69~7.75 (m, 2H), 7.05~7.10 (m, 1H), 6.98~7.03 (m, 1H), 5.64 (d, J=3.0 Hz, 1H), 3.09 (s, 3H), 2.97 (s, 3H), 2.95 (s, 3H). MS (M+H)⁺: 473/475.

Step 6—Synthesis of 2-(2,4-difluorophenyl)-N-methyl-6-(N-methylmethylsulfonamido)-5-(4,4,5,5-tetramethyl-1,3,2-dioxaborolan-2-yl)benzofuran-3-carboxamide

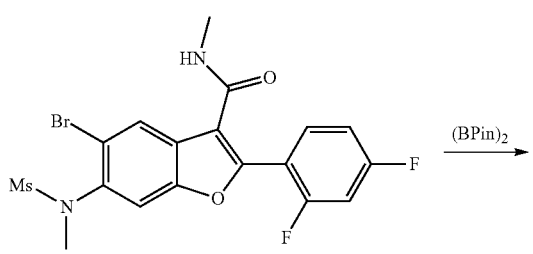

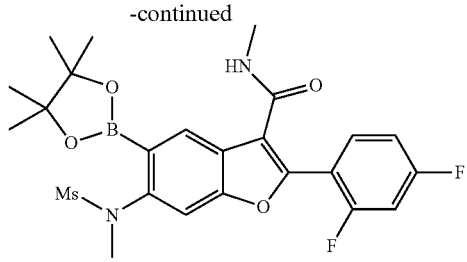

To a degassed solution of 5-bromo-2-(2,4-difluorophenyl)-N-methyl-6-(N-methylmethylsulfonamido)benzofuran-3-carboxamide (400 mg, 0.85 mmol), (Bpin)$_2$ (1 g, 4.23 mmol), KOAc (249 mg, 2.54 mmol) in 1,4-Dioxane (5 mL) and H$_2$O (1 mL) was added Pd(dppf)Cl$_2$ (5 mg), then the mixture was stirred at 130° C. After 3 hours, the solvent was removed by vacuum, and the mixture was washed with H$_2$O (20 mL), extract with dichloromethane (50 mL*3), dried over Na$_2$SO$_4$. After concentrated, the resulting residue was purified using column chromatography (petroleum ether:EtOAc=2:1) to provide 2-(2,4-difluorophenyl)-N-methyl-6-(N-methylmethylsulfonamido)-5-(4,4,5,5-tetramethyl-1,3,2-dioxaborolan-2-yl)benzofuran-3-carboxamide (240 mg, yield: 54%). $^1$H-NMR (CDCl$_3$, 400 MHz) 8.26 (s, 1H), 7.73 (d, J=6.8 Hz, 1H), 7.56 (s, 1H), 7.05 (t, J=6.8 Hz, 1H), 6.96 (q, J=6.8 Hz, 1H), 5.96 (s, 1H), 3.33 (s, 3H), 2.97 (s, 3H), 2.93 (s, 3H), 1.20 (s, 12H). MS (M+H)$^+$: 521.

Step 7—Synthesis of 2-(2,4-difluorophenyl)-5-(11-fluoro-6H-pyrido[2',3':5,6][1,3]oxazino[3,4-a]indol-2-yl)-N-methyl-6-(N-methylmethylsulfonamido)benzofuran-3-carboxamide (Compound 147)

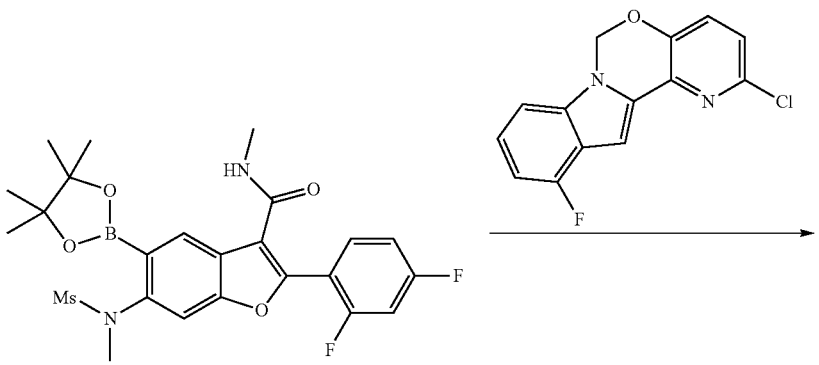

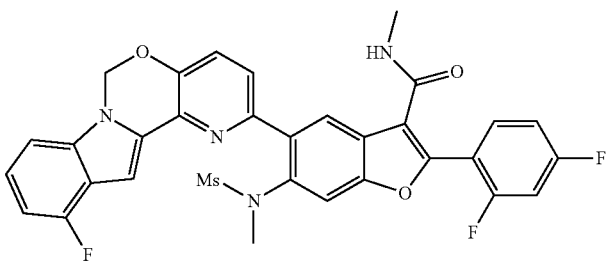

147

The procedure of Compound 147 (30 mg, yield: 25%) was similar to step 6 of Example 1. ¹H-NMR (CDCl₃, 400 MHz) δ 8.12 (s, 1H), 7.76~7.81 (m, 1H), 7.70 (s, 1H), 7.48~7.52 (m, 2H), 7.23~7.46 (m, 2H), 7.19~7.24 (m, 2H), 7.71 (t, J=7.2 Hz, 1H), 6.99 (t, J=7.6 Hz, 1H), 6.83 (s, 2H), 5.75 (d, J=7.2 Hz, 1H), 3.39 (s, 3H), 2.96 (d, J=4.8 Hz, 3H), 2.74 (s, 3H). MS (M+H)⁺: 633.

Compounds 148-149, depicted in the table below, were prepared using the method described above and substituting the appropriate reactants and/or reagents.

| Compound No | Structure | NMR | MS (M + H)⁺ |
|---|---|---|---|
| 148 | 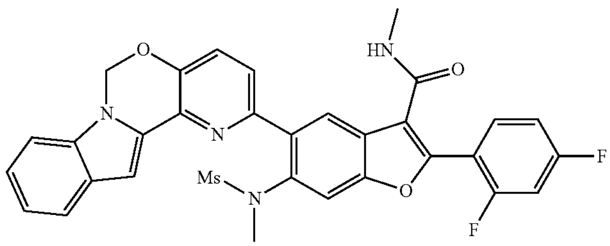 [SMILES: CNC(=O)c1c(-c2ccc(F)cc2F)oc2cc(N(C)S(C)(=O)=O)c(-c3ccc4c(n3)-c3cc5ccccc5n3CO4)cc12] | ¹H-NMR (CDCl₃, 400 MHz) δ 8.12 (s, 1H), 7.73~7.84 (m, 1H), 7.71 (t, J = 7.2 Hz, 2H), 7.51 (s, 2H), 7.31~7.51 (m, 2H), 7.13~7.22 (m, 2H), 7.13 (t, J = 7.2 Hz, 1H), 7.03~7.09 (m, 1H), 6.05 (s, 2H), 5.78 (s, 1H), 3.40 (s, 3H), 2.99 (d, J = 4.8 Hz, 3H), 2.74 (s, 3H). | 615 |
| 149 | 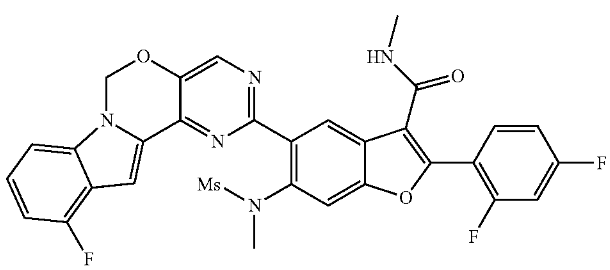 [SMILES: CNC(=O)c1c(-c2ccc(F)cc2F)oc2cc(N(C)S(C)(=O)=O)c(-c3ncc4c(n3)-c3cc5c(F)cccc5n3CO4)cc12] | ¹H-NMR (CDCl₃, 400 MHz) δ 8.60 (s, 1H), 8.28 (s, 1H), 7.75~7.81 (m, 1H), 7.67 (s, 1H), 7.44 (s, 1H), 7.05~7.13 (m, 1H), 7.04 (t, J = 7.2 Hz, 1H), 6.88~7.98 (m, 1H), 7.82~7.87 (m, 2H), 6.05 (s, 2H), 5.27 (s, 1H), 3.46 (s, 3H), 2.97 (d, J = 4.8 Hz, 3H), 2.82 (s, 3H). | 634 |

Example 51

Preparation of Compound 150

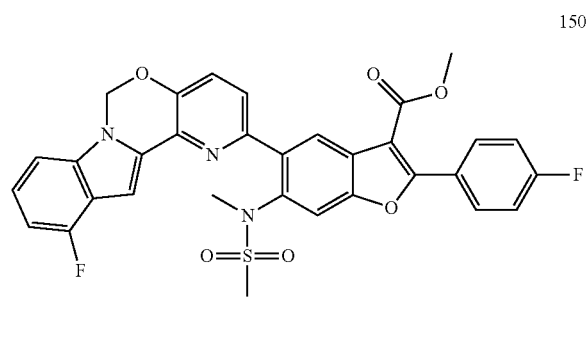 [SMILES: COC(=O)c1c(-c2ccc(F)cc2)oc2cc(N(C)S(C)(=O)=O)c(-c3ccc4c(n3)-c3cc5c(F)cccc5n3CO4)cc12]

Step 1—Synthesis of methyl 5-bromo-2-(4-fluorophenyl)-6-(methylsulfonamido)benzofuran-3-carboxylate

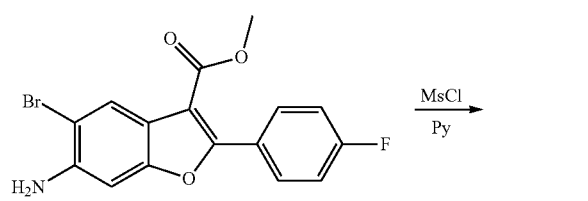

MsCl (4.8 g, 41.2 mmol) was added to a solution of methyl 6-amino-5-bromo-2-(4-fluorophenyl)benzofuran-3-carboxylate (5.0 g, 13.4 mmol) and pyridine (5.4 g, 68.7 mL) in dry dichloromethane (50 mL) at 0° C. After stirred overnight at room temperature, the mixture was diluted with water, and extracted with dichloromethane. The organic layer was washed with brine, dried over $Na_2SO_4$, filtered and concentrated in vacuo. The resulting residue was purified using column chromatography to provide methyl 5-bromo-2-(4-fluorophenyl)-6-(methylsulfonamido)benzofuran-3-carboxylate (5.3 g, yield: 83%). $^1$H-NMR (400 MHz, CDCl$_3$) δ 8.21 (s, 1H), 7.99~8.03 (m, 2H), 7.83 (s, 1H), 7.11~7.16 (m, 2H), 6.82 (br s, 1H), 3.90 (s, 3H), 2.96 (s, 3H). MS (M+H)$^+$: 442/444.

Step 2—Synthesis of methyl 5-bromo-2-(4-fluorophenyl)-6-(N-methylmethylsulfonamido)benzofuran-3-carboxylate

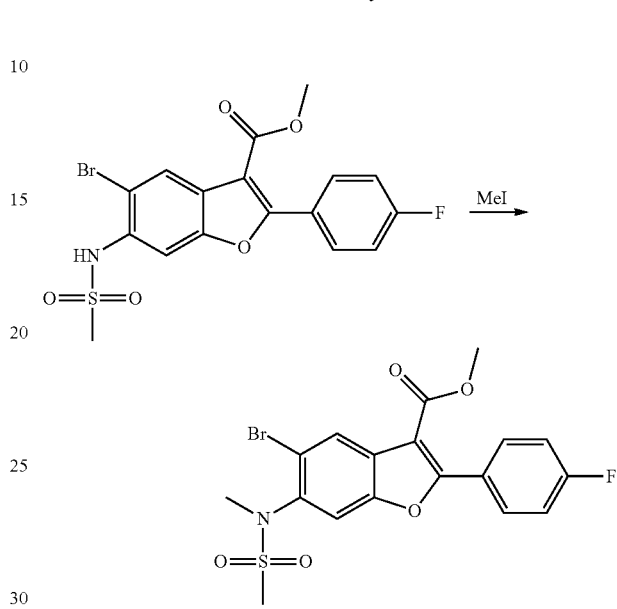

The procedure of methyl 5-bromo-2-(4-fluorophenyl)-6-(N-methylmethylsulfonamido)benzofuran-3-carboxylate (5 g, yield: 93%) was similar to step 5 of Example 3. $^1$H-NMR (400 MHz, CDCl$_3$) δ 8.32 (s, 1H), 8.05~8.09 (m, 2H), 7.72 (s, 1H), 7.17~7.22 (m, 2H), 3.96 (s, 3H), 3.35 (s, 3H), 3.10 (s, 3H). MS (M+H)$^+$: 456/458.

Step 3—Synthesis of methyl 2-(4-fluorophenyl)-6-(N-methylmethylsulfonamido)-5-(4,4,5,5-tetramethyl-1,3,2-dioxaborolan-2-yl)benzofuran-3-carboxylate

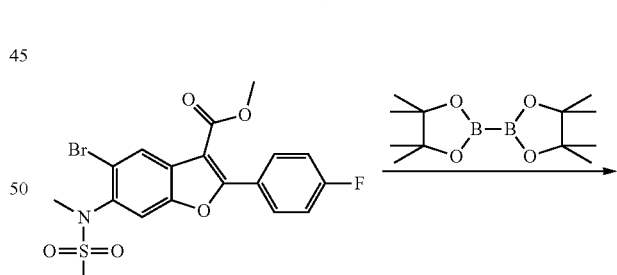

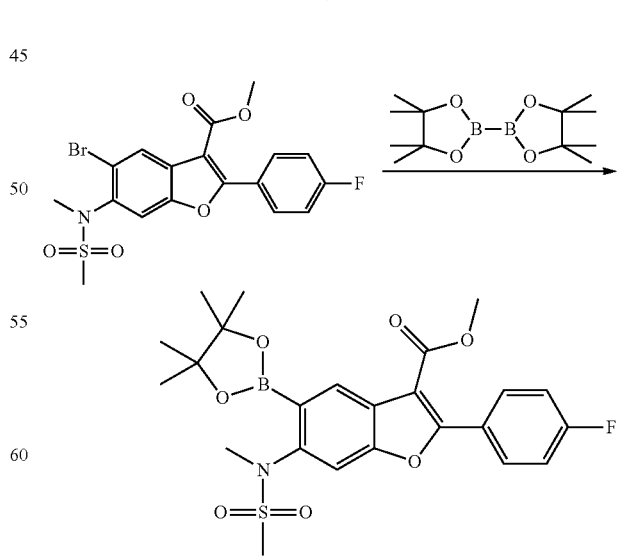

To a $N_2$ degassed solution of methyl 5-bromo-2-(4-fluorophenyl)-6-(N-methylmethylsulfonamido)benzofuran-3- carboxylate (4.0 g, 8.8 mmol), KOAc (2.5 g, 26.3 mmol) and dis(pinacolato)diboron (6.7 g, 26.3 mmol) in dioxane (150 mL), Pd(dppf)Cl₂ (600 mg, 0.88 mmol) was added. The reaction mixture was stirred at 100° C. for 3 hours, and then filtered through a Celite pad. The filtrate was concentrated in vacuo, and the resulting residue was purified using column chromatography (petroleum ether:EtOAc=15:1) to provide methyl 2-(4-fluorophenyl)-6-(N-methylmethylsulfonamido)-5-(4,4,5,5-tetramethyl-1,3,2-dioxaborolan-2-yl)benzofuran-3-carboxylate (2.6 g, yield: 60%). ¹H-NMR (CDCl₃, 400 MHz) δ 8.47 (s, 1H), 8.05~8.06 (m, 2H), 7.60 (s, 1H), 7.18~725 (m, 2H), 4.00 (s, 3H), 3.38 (s, 3H), 2.97 (s, 3H), 1.39 (s, 12H). MS (M+H)⁺: 504.

Step 4—Synthesis of methyl 5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxylate (Compound 150)

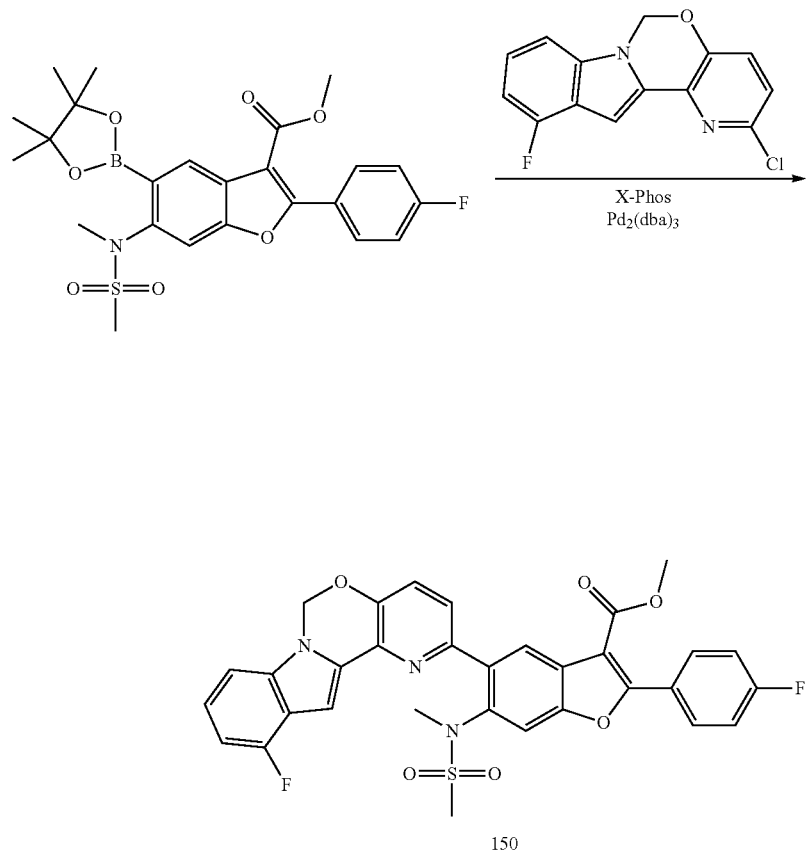

150

The procedure of Compound 150 (2.6 g, yield: 53%) was similar to step 6 of Example 1. $^1$H-NMR (CDCl$_3$, 400 MHz) δ 8.15 (s, 1H), 8.00~8.04 (m, 2H), 7.61 (s, 1H), 7.43~7.44 (m, 2H), 7.12~7.18 (m, 4H), 7.03 (d, J=8.8 Hz, 1H), 6.75~6.79 (m, 1H), 5.92 (s, 2H), 3.86 (s, 3H), 3.31 (s, 1H), 2.67 (s, 3H). MS (M+H)$^+$: 616.

Example 52

Preparation of Compound 151

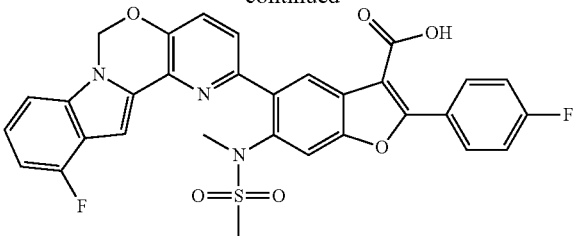

To a solution of methyl 5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxylate (60 mg, 0.10 mmol) in dioxane/H$_2$O (11 mL/5 mL) was added LiOH.H$_2$O (12.3 mg, 0.30 mol), and the mixture was stirred at 100° C. for 2 hours. After concentrated, the resulting residue was dissolved in H$_2$O, 1 N HCl was added until pH reached 3, and the mixture was extracted with EtOAc. The organic layer was washed with brine, dried over Na$_2$SO$_4$ and filtered. The solvent was removed by distillation to provide 5-(11-fluoro-6H-pyrido[2',3':5,6][1,3]oxazino[3,4-a]indol-2-yl)-2-(4-fluorophenyl)-6-(N-methylmethylsulfonamido) benzofuran-3-carboxylic acid (41 mg, yield: 70%). $^1$H-NMR (DMSO-d6, 400 MHz) δ 13.36 (s, 1H), 8.26 (s, 1H), 8.13~8.16 (m, 2H), 8.09 (s, 1H), 7.71 (d, J=8.4 Hz, 1H), 7.61 (d, J=8.4 Hz, 1H), 7.52 (d, J=8.4 Hz, 1H), 7.42~7.46 (m, 2H), 7.25~7.27 (m, 1H), 7.09 (s, 1H), 6.92~6.96 (m, 1H), 6.28 (s, 2H), 3.30 (s, 3H), 2.98 (d, 3H). MS (M+H)$^+$: 602.

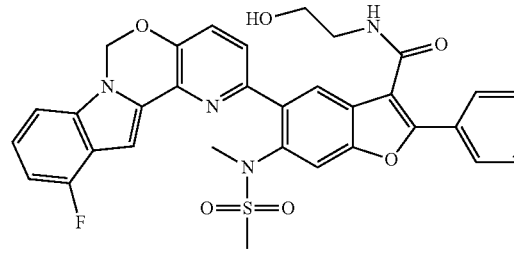

Step 1—Synthesis of 5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxylic acid

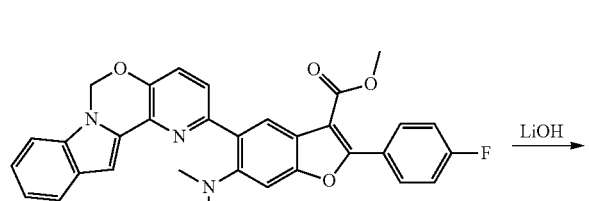

Step 2—Synthesis of 5-(11-fluoro-6H-pyrido[2',3':5,6][1,3]oxazino[3,4-a]indol-2-yl)-2-(4-fluorophenyl)-N-(2-hydroxyethyl)-6-(N-methylmethylsulfonamido)benzofuran-3-carboxamide (Compound 151)

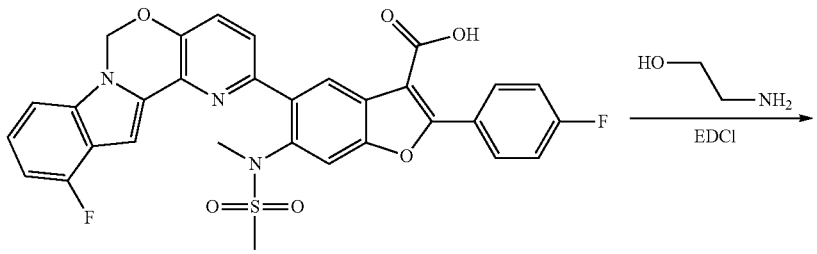

The procedure of Compound 151 (48 mg, yield: 73%) was similar to step 2 of Example 8. ¹H-NMR (CDCl₃, 400 MHz) 8.09 (s, 1H), 7.98~8.02 (m, 2H), 7.68 (s, 1H), 7.48~7.54 (m, 2H), 7.19~7.25 (m, 4H), 7.12 (d, J=8.4 Hz, 1H), 6.83~6.88 (m, 1H), 6.38 (s, 1H), 6.01 (s, 2H), 3.82 (t, J=4.4 Hz, 2H), 3.64 (t, J=4.4 Hz, 2H), 3.39 (s, 3H), 2.75 (s, 3H). MS (M+H)⁺: 645.

Compounds 152-158, depicted in the table below, were prepared using the method described above and substituting the appropriate reactants and/or reagents.

| Compound No | Structure | NMR | MS (M + H)⁺ |
|---|---|---|---|
| 152 | 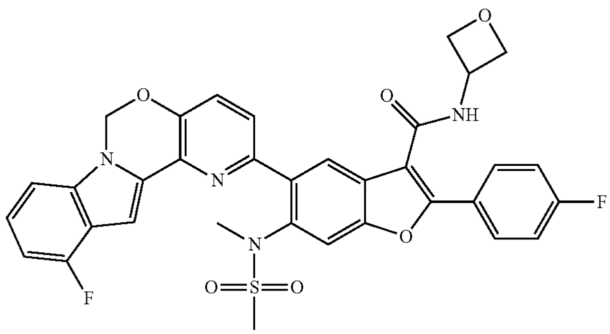 [SMILES: CN(c1cc2oc(-c3ccc(F)cc3)c(C(=O)NC3COC3)c2cc1-c1ccc2c(n1)-c1cc3c(F)cccc3n1CO2)S(C)(=O)=O] | ¹H-NMR (CDCl₃, 400 MHz) 7.95 (s, 1H), 7.84~7.88 (m, 2H), 7.59 (s, 1H), 7.40~7.50 (m, 2H), 7.11~7.18 (m, 4H), 7.03 (d, J = 8.4 Hz, 1H), 6.74~6.79 (m, 1H), 6.50~6.52 (m, 1H), 5.91 (s, 2H), 5.16~5.22 (m, 1H), 4.86~4.89 (m, 2H), 4.38~4.42 (m, 2H), 3.29 (s, 3H), 2.64 (s, 3H). | 657 |
| 153 | 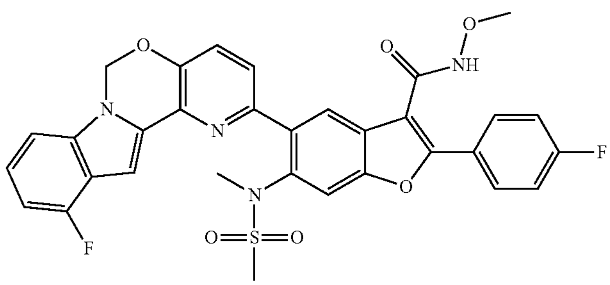 [SMILES: CONC(=O)c1c(-c2ccc(F)cc2)oc2cc(N(C)S(C)(=O)=O)c(-c3ccc4c(n3)-c3cc5c(F)cccc5n3CO4)cc12] | ¹H-NMR (CDCl₃, 400 MHz) 8.62 (s, 1H), 7.95~7.99 (m, 2H), 7.67 (s, 1H), 7.48~7.50 (m, 2H), 7.18~7.24 (m, 4H), 7.12 (d, J = 8.4 Hz, 1H), 6.84~6.88 (m, 1H), 6.01 (s, 2H), 3.90 (s, 3H), 3.35 (s, 3H), 2.75 (s, 3H). | 631 |
| 154 | 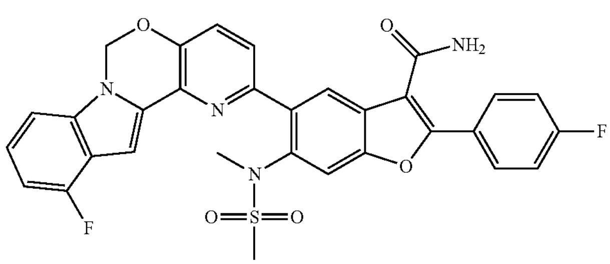 [SMILES: CN(c1cc2oc(-c3ccc(F)cc3)c(C(N)=O)c2cc1-c1ccc2c(n1)-c1cc3c(F)cccc3n1CO2)S(C)(=O)=O] | ¹H-NMR (CDCl₃, 400 MHz) 8.14 (s, 1H), 7.98~8.02 (m, 2H), 7.69 (s, 1H), 7.48~7.53 (m, 2H), 7.21~7.26 (m, 4H), 7.12 (d, J = 8.4 Hz, 1H), 6.83~6.87 (m, 1H), 6.01 (s, 2H), 5.75~5.86 (m, 2H), 3.39 (s, 3H), 2.74 (s, 3H). | 601 |
| 155 | 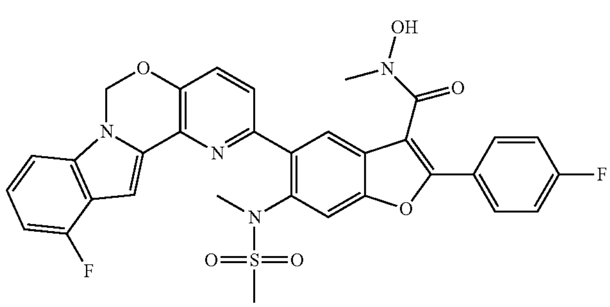 [SMILES: CN(O)C(=O)c1c(-c2ccc(F)cc2)oc2cc(N(C)S(C)(=O)=O)c(-c3ccc4c(n3)-c3cc5c(F)cccc5n3CO4)cc12] | ¹H-NMR (Methanol-d4, 400 MHz) 7.93~7.97 (m, 3H), 7.89 (s, 1H), 7.59 (s, 2H), 7.21~7.33 (m, 5H), 6.80~6.84 (m, 1H), 6.11 (s, 2H), 3.48 (m, 3H), 3.34 (s, 3H), 2.91 (s, 3H). | 631 |

-continued

| Compound No | Structure | NMR | MS (M + H)+ |
|---|---|---|---|
| 156 | 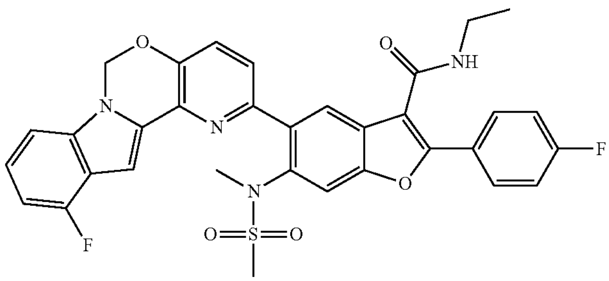 [SMILES: CCNC(=O)c1c(-c2ccc(F)cc2)oc2cc(N(C)S(C)(=O)=O)c(-c3ccc4c(n3)-c3cc5c(F)cccc5n3CO4)cc12] | ¹H-NMR (CDCl₃, 400 MHz) δ 8.03 (s, 1H), 7.94~7.99 (m, 2H), 7.66 (s, 1H), 7.46~7.52 (m, 2H), 7.10~7.23 (m, 4H), 6.82-6.87 (m, 1H), 6.00 (s, 2H), 5.93 (br s, 1H), 3.46~3.54 (m, 2H), 3.38 (s, 3H), 2.74 (s, 3H), 1.21 t, J = 7.2 Hz, 3H). | 629 |
| 157 | 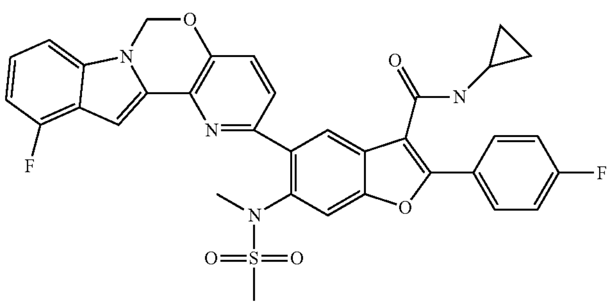 [SMILES: CN(c1cc2oc(-c3ccc(F)cc3)c(C(=O)NC3CC3)c2cc1-c1ccc2c(n1)-c1cc3c(F)cccc3n1CO2)S(C)(=O)=O] | ¹H-NMR (CDCl₃, 400 MHz) δ 8.04 (s, 1H), 7.94~7.98 (m, 2H), 7.67 (s, 1H), 7.50 (d, J = 2.4 Hz, 2H), 7.19~7.24 (m, 4H), 7.12 (d, J = 8.4 Hz, 1H), 6.83~6.87 (m, 1H), 6.01 (s, 2H), 5.99 (brs, 1H), 3.38 (s, 3H), 2.90-2.93 (m, 1H), 2.74 (d, J = 5.2 Hz, 3H), 0.66~0.72 (m, 2H), 0.50~0.59(m, 2H). | 641 |
| 158 | 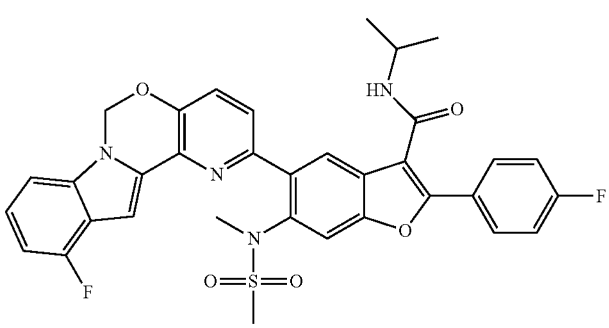 [SMILES: CC(C)NC(=O)c1c(-c2ccc(F)cc2)oc2cc(N(C)S(C)(=O)=O)c(-c3ccc4c(n3)-c3cc5c(F)cccc5n3CO4)cc12] | ¹H-NMR (CDCl₃, 400 MHz) δ 8.03 (s, 1H), 7.94~7.97 (m, 2H), 7.66 (s, 1H), 7.46~7.51 (m, 2H), 7.17~7.22 (m, 4H), 7.09~7.11 (m, 1H), 6.81~6.86 (m, 1H), 5.98 (s, 2H), 5.79 (d, J = 8.0 Hz, 1H), 4.30~4.38 (m, 1H), 3.38 (s, 3H), 2.74 (s, 3H), 1.22 (s, 3H), 1.21 (s, 3H). | 643 |

Example 53
Preparation of Compound 159

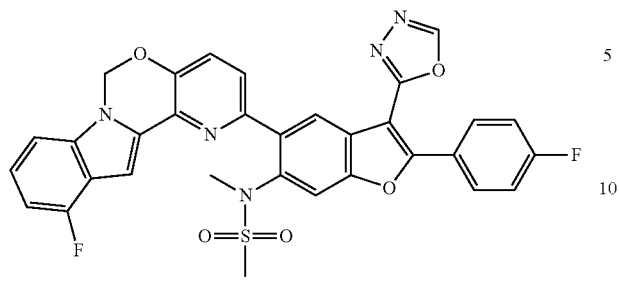

Step 1—Synthesis of N-(5-(11-fluoro-6H-pyrido[2', 3':5,6][1,3]oxazino[3,4-a]indol-2-yl)-2-(4-fluorophenyl)-3-(hydrazinecarbonyl)benzofuran-6-yl)-N-methylmethanesulfonamide

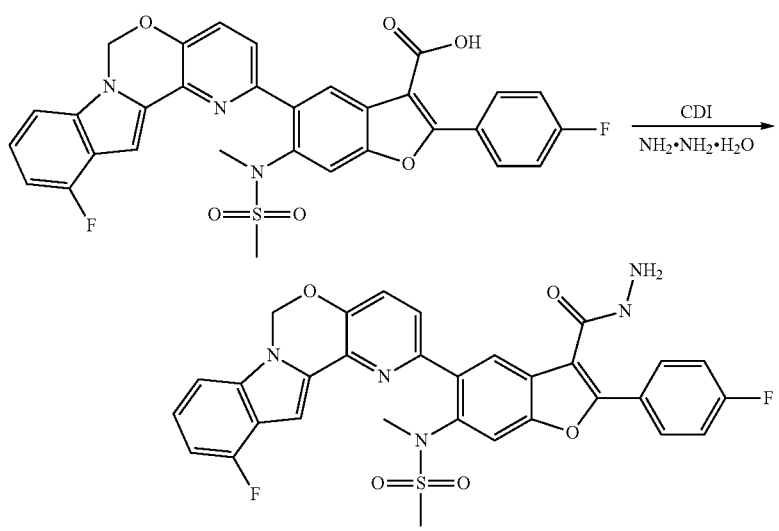

To a solution of 5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxylic acid (50 mg, 0.08 mmol) in THF (10 mL) was added CDI (172 mg, 0.67 mmol). After 1 hour, $NH_2 \cdot NH_2 \cdot H_2O$ (12 mg, 0.25 mmol) was added to the reaction mixture. Then the mixture was stirred at 25° C. for 2 hours. After the solvent was removed by vacuum, the resulting residue was purified using prep-TLC (dichloromethane:MeOH=10:1) to provide N-(5-(11-fluoro-6H-pyrido[2',3':5,6][1,3]oxazino[3,4-a]indol-2-yl)-2-(4-fluorophenyl)-3-(hydrazinecarbonyl)benzofuran-6-yl)-N-methylmethanesulfonamide (30 mg, yield: 59%). $^1$H-NMR (CDCl$_3$, 400 MHz) δ 8.01 (s, 1H), 7.95~7.98 (m, 2H), 7.69 (s, 1H), 7.50 (s, 2H), 7.19~7.24 (m, 4H), 7.11~7.15 (m, 2H), 6.83~6.85 (m, 1H), 6.01 (s, 2H), 4.14 (s, 2H), 3.37 (s, 3H), 2.75 (s, 3H). MS (M+H)$^+$: 616.

Step 2—Synthesis of N-(5-(11-fluoro-6H-pyrido[2',3':5,6][1,3]oxazino[3,4-a]indol-2-yl)-2-(4-fluorophenyl)-3-(1,3,4-oxadiazol-2-yl)benzofuran-6-yl)-N-methylmethanesulfonamide (Compound 159)

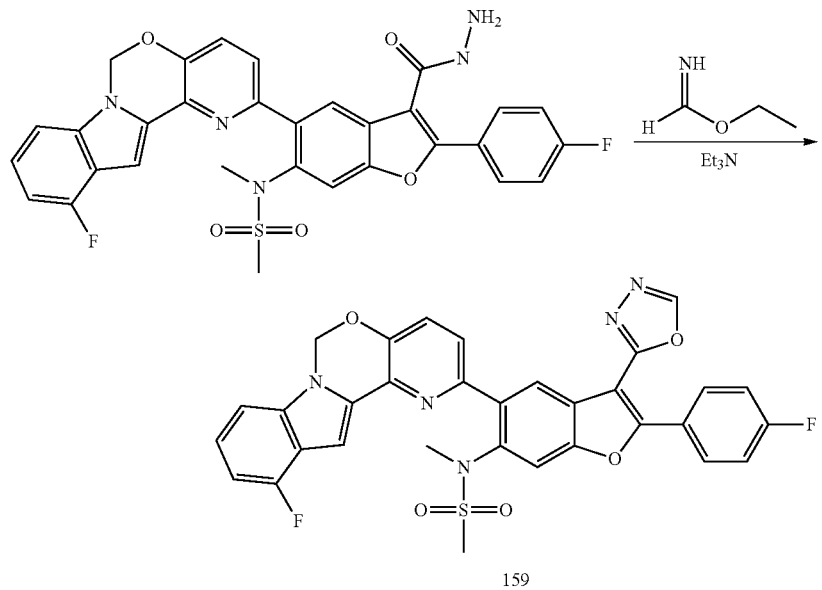

159

To a solution of N-(5-(11-fluoro-6H-pyrido[2',3':5,6][1,3]oxazino[3,4-a]indol-2-yl)-2-(4-fluorophenyl)-3-(hydrazinecarbonyl)benzofuran-6-yl)-N-methylmethanesulfonamide (20 mg, 0.03 mmol) and Et$_3$N (1 mL) in MeCN (5 mL) was added ethyl formimidate (6 mg, 0.05 mmol). Then the mixture was stirred at 110° C. for 2 hours. After the solvent was removed by vacuum, the resulting residue was purified using prep-HPLC to provide Compound 159 (10 mg, yield: 40%). $^1$H-NMR (CDCl$_3$, 400 MHz) δ 9.01 (s, 1H), 8.35 (s, 1H), 8.10 (t, J=2.8 Hz, 2H), 7.89 (s, 1H), 7.48 (t, J=2.8 Hz, 2H), 7.15~7.23 (m, 4H), 7.07 (s, 1H), 6.78 (t, J=2.8 Hz, 1H), 5.98 (s, 2H), 3.29 (s, 3H), 2.89 (s, 3H). MS (M+H)$^+$: 626.

Example 54

Preparation of Compound 160

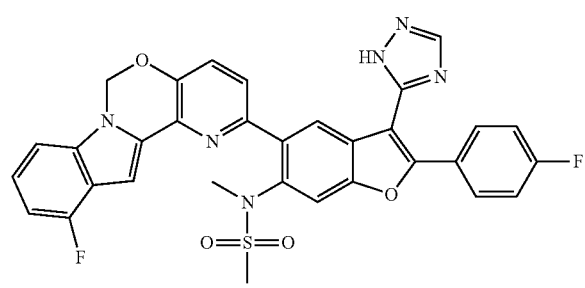

160

Step 1—Synthesis of 5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxamide

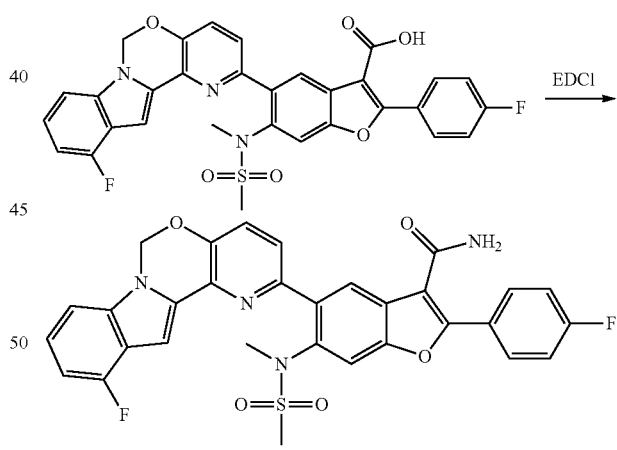

5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxylic acid (200 mg, 0.33 mmol), HOBT (50 mg, 0.37 mmol) and EDCI (140 mg, 0.73 mmol) were dissolved in dry DMF (5 mL). The resulting solution was stirred for 2 hours. And then NH$_4$Cl (100 mg, 1.87 mmol) and Et$_3$N (0.5 mL) were added to the mixture. The mixture was stirred at room temperature overnight. Then H$_2$O was added, and extracted with EtOAc. The combined organic phases were washed with brine, dried over Na$_2$SO$_4$, filtered and concentrated in vacuo. The crude product was purified using column chromatography (dichloromethane:

MeOH=40:1) to provide 5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxamide (180 mg, yield: 90%). $^1$H-NMR (CDCl$_3$, 400 MHz) δ 8.14 (s, 1H), 7.98~8.03 (m, 2H), 7.69 (s, 1H), 7.48~7.54 (m, 2H), 7.19~7.24 (m, 4H), 7.12 (d, J=8.4 Hz, 1H), 6.83~6.88 (m, 1H), 6.01 (s, 2H), 5.70~5.86 (m, 2H), 3.39 (s, 3H), 2.74 (s, 3H). MS (M+H)$^+$: 601.

Step 2—Synthesis of (Z)—N-((dimethylamino)methylene)-5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxamide

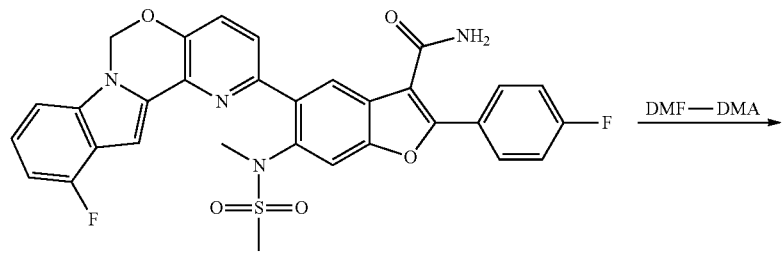

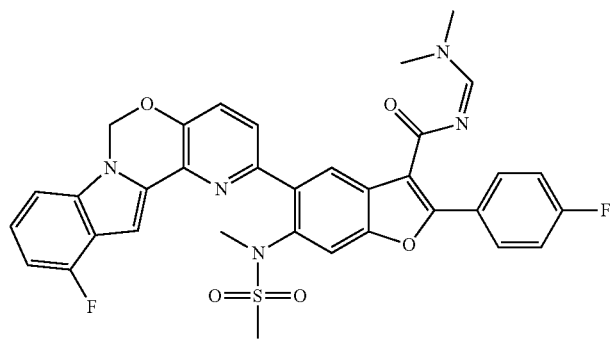

To a solution of 5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxamide (80 mg, 0.13 mmol) in DMF-DMA (2 mL) was stirred at 120° C. for 2 hour. The reaction mixture was concentrated in vacuo and the resulting residue was used to the next step without further purification. $^1$H-NMR (CDCl$_3$, 400 MHz) δ 8.66 (s, 2H), 8.10~8.15 (m, 2H), 7.63 (s, 1H), 7.58 (d, J=8.4 Hz, 1H), 7.48

(d, J=8.4 Hz, 1H), 7.10~7.24 (m, 5H), 6.82~6.87 (m, 1H), 6.00 (s, 2H), 3.38 (s, 3H), 3.16 (s, 3H), 3.08 (s, 3H), 2.78 (s, 3H). MS (M+H)+: 656.

Step 3—Synthesis of N-(5-(11-fluoro-6H-pyrido[2', 3':5,6][1,3]oxazino[3,4-a]indol-2-yl)-2-(4-fluorophenyl)-3-(1H-1,2,4-triazol-5-yl)benzofuran-6-yl)-N-methylmethanesulfonamide (Compound 160)

mL) was added Hydrazine hydrate (0.1 mL). The reaction mixture was stirred at 120° C. for 3 hour. The reaction mixture was concentrated in vacuo and the resulting residue was purified using prep-HPLC to provide compound 160 (40 mg, yield: 52%). ¹H-NMR (CDCl₃, 400 MHz) δ 13.20 (br s, 1H), 8.52 (s, 1H), 7.94~7.98 (m, 2H), 7.92 (s, 1H), 7.54 (s, 1H), 7.41 (d, J=8.4 Hz, 1H), 7.31~7.34 (m, 2H), 7.08~7.14 (m, 1H), 7.01~7.05 (m, 2H), 6.96 (d, J=8.4 Hz, 1H), 6.67~6.72 (m, 1H), 5.71 (s, 2H), 3.38 (s, 3H), 2.80 (s, 3H). MS (M+H)+: 625.

Example 55

Preparation of Compound 161

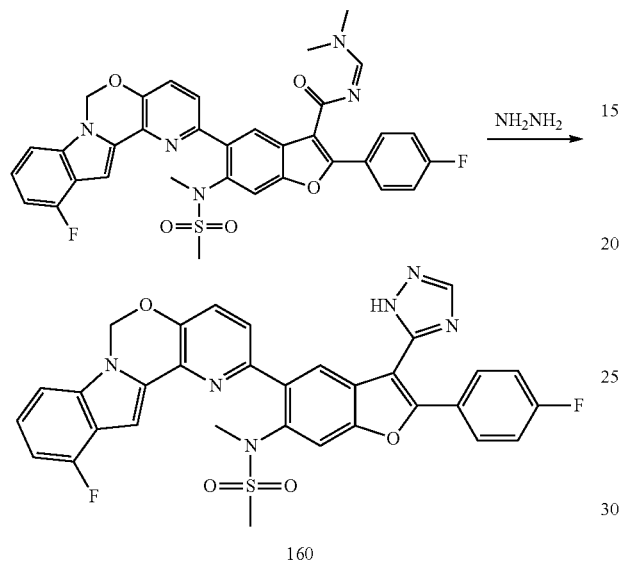

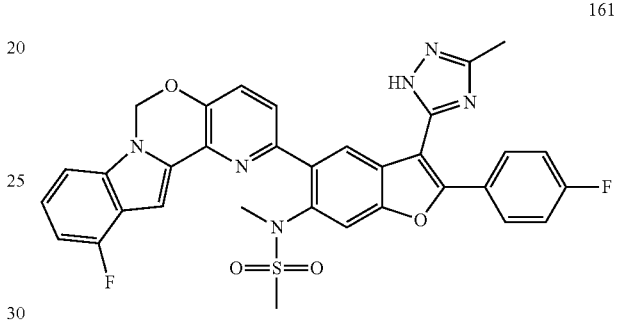

To a solution of (Z)—N-((dimethylamino)methylene)-5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxamide (80 mg, 0.12 mmol) in HOAc (2

Step 1—Synthesis of (Z)—N-(1-(dimethylamino)ethylidene)-5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxamide

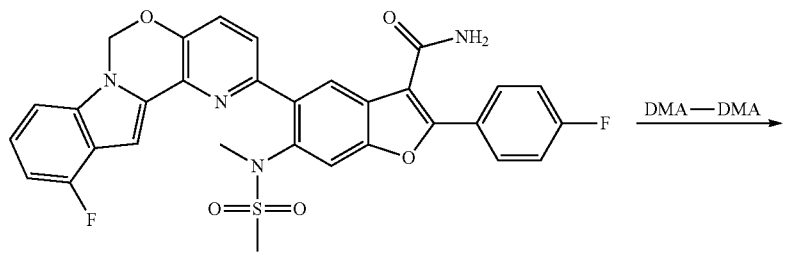

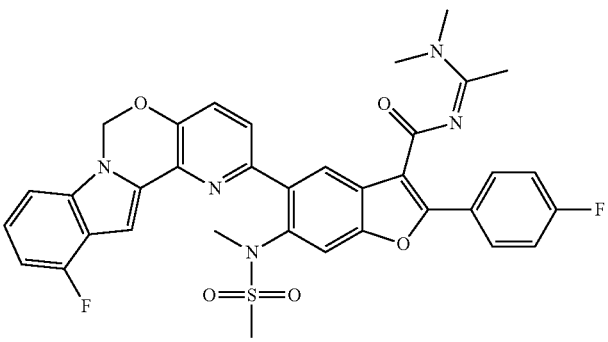

To a solution of 5-(11-fluoro-6H-pyrido[2',3':5,6][1,3]ox-azino[3,4-a]indol-2-yl)-2-(4-fluorophenyl)-6-(N-methylmethylsulfonamido)benzofuran-3-carboxamide (100 mg, 0.17 mmol) in DMA-DMA (2 mL) was stirred at 120° C. for 2 hour. The reaction mixture was concentrated in vacuo and the resulting residue was used to the next step without further purification.

Step 2—Synthesis of N-(5-(11-fluoro-6H-pyrido[2', 3':5,6][1,3]oxazino[3,4-a]indol-2-yl)-2-(4-fluorophenyl)-3-(3-methyl-1H-1,2,4-triazol-5-yl)benzofuran-6-yl)-N-methylmethanesulfonamide (Compound 161)

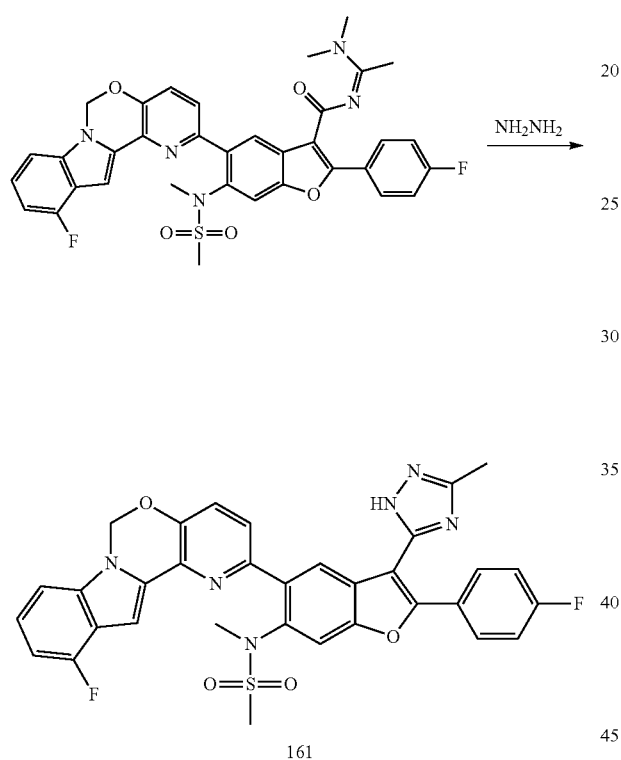

161

To a solution of (Z)—N-(1-(dimethylamino)ethylidene)-5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carboxamide (110 mg, 0.16 mmol) in HOAc (2 mL) was added Hydrazine hydrate (0.15 mL). The reaction mixture was stirred at 120° C. for 3 hour. The reaction mixture was concentrated in vacuo and the resulting residue was purified using prep-HPLC to provide compound 161 (50 mg, yield: 47%). $^1$H-NMR (CDCl$_3$, 400 MHz) δ 11.86 (br s, 1H), 8.21 (s, 1H), 8.01 (br s, 2H), 7.61 (s, 1H), 7.45 (d, J=8.0 Hz, 1H), 7.35 (d, J=8.0 Hz, 1H), 7.17 (s, 2H), 7.04~7.08 (m, 3H), 6.78~6.83 (m, 1H), 5.90 (s, 2H), 3.36 (s, 3H), 2.76 (s, 3H), 2.35 (s, 3H). MS (M+H)$^+$: 639.

Example 56

Preparation of Compound 162

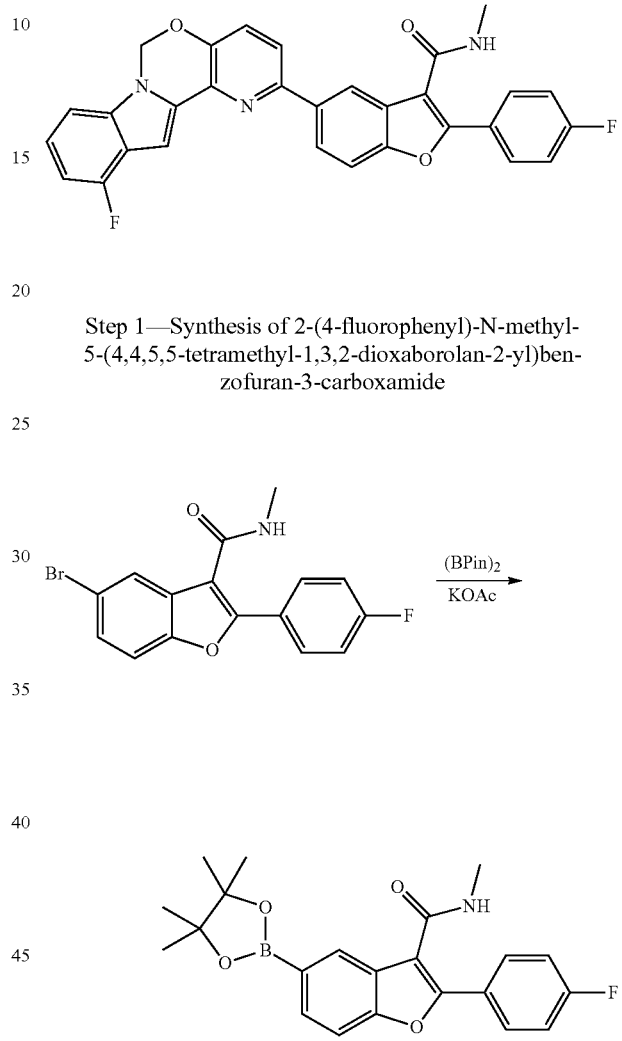

Step 1—Synthesis of 2-(4-fluorophenyl)-N-methyl-5-(4,4,5,5-tetramethyl-1,3,2-dioxaborolan-2-yl)benzofuran-3-carboxamide To a degassed solution of 5-bromo-2-(4-fluorophenyl)-N-methylbenzofuran-3-carboxamide (500 mg, 1.44 mmol), KOAc (423 mg, 4.31 mmol) and (BPin)$_2$ (730 mg, 2.87 mmol) in 1,4-dioxane (8 mL) was added Pd(dppf)Cl$_2$ (30 mg) under N$_2$ protection. The mixture was stirred at 140° C. for 6 hours. The mixture was filtered through a celite pad, and the resulting residue was concentrated to provide crude product. The resulting residue was purified using column chromatography (petroleum ether:EtOAc=3:1) to provide 2-(4-fluorophenyl)-N-methyl-5-(4,4,5,5-tetramethyl-1,3,2-dioxaborolan-2-yl)benzofuran-3-carboxamide (500 mg, yield: 88%). $^1$H-NMR (CDCl$_3$, 400 MHz) δ 8.19 (s, 1H), 7.96~8.00 (m, 2H), 7.77~7.79 (dd, J=8.4 Hz, 1H), 7.48 (d, J=7.6 Hz, 1H), 7.11~7.16 (m, 2H), 5.95 (s, 1H), 3.02~3.04 (d, J=4.8 Hz, 3H), 1.35 (s, 12H). MS (M+H)$^+$: 396.

Step 2—Synthesis of 5-(11-fluoro-6H-pyrido[2',3':5,6][1,3]oxazino[3,4-a]indol-2-yl)-2-(4-fluorophenyl)-N-methylbenzofuran-3-carboxamide (Compound 162)

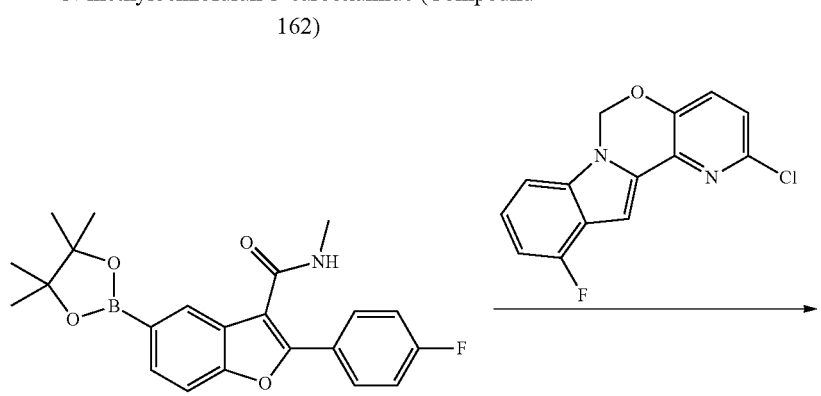

162

The procedure of Compound 162 (10 mg, yield: 10.5%) was similar to step 6 of Example 1. $^1$H-NMR (DMSO-$d_6$, 400 MHz) δ 8.56 (d, J=4.4 Hz, 1H), 8.31 (s, 1H), 8.20 (d, J=10.0 Hz, 1H), 7.95~7.99 (m, 3H), 7.76 (d, J=8.8 Hz, 1H), 7.67 (d, J=8.8 Hz, 1H), 7.48 (d, J=8.0 Hz, 1H), 7.35~7.39 (t, J=8.8 Hz, 2H), 7.20 (s, 2H), 6.89~6.93 (dd, J=10 Hz, 1H), 6.22 (s, 2H), 2.86 (d, J=4.4 Hz, 3H). MS (M+H)$^+$: 508.

Example 57

Preparation of Compound 163

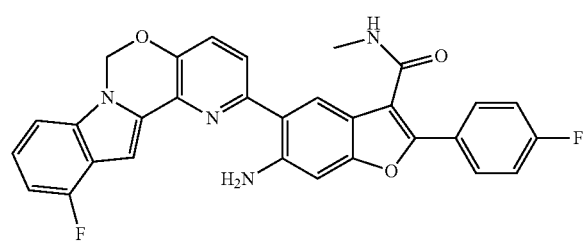

163

Step 1—Synthesis of 6-amino-2-(4-fluorophenyl)-N-methyl-5-(4,4,5,5-tetramethyl-1,3,2-dioxaborolan-2-yl)benzofuran-3-carboxamide

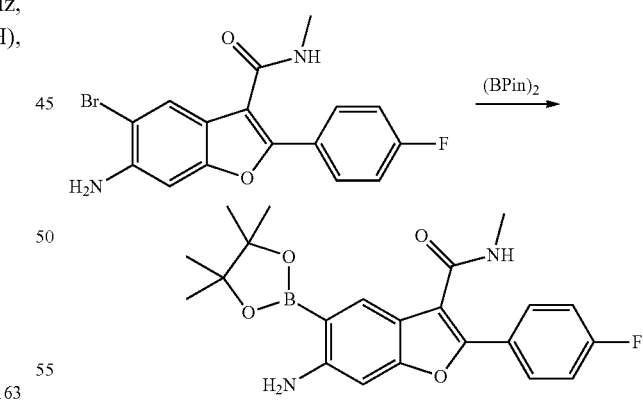

To a degassed solution of 6-amino-5-bromo-2-(4-fluorophenyl)-N-methylbenzofuran-3-carboxamide (8 g, 22.03 mmol), KOAc (4.32 g, 44.06 mmol) and (BPin)$_2$ (27.97 g, 110.14 mmol) in 1,4-dioxane (100 mL) was added Pd(dppf)Cl$_2$ (0.8 g) under N$_2$ protection. The mixture was stirred at 140° C. for 6 hours. The mixture was filtered through a celite pad, and the resulting residue was concentrated to provide crude product. The resulting residue was purified using column chromatography (petroleum ether:EtOAc=3:1) to provide 6-amino-2-(4-fluorophenyl)-N-methyl-5-(4,4,5,5-tetramethyl-1,3,2-dioxaborolan-2-yl)benzofuran-3-carboxamide (6 g, yield: 66%). $^1$H-NMR (CDCl$_3$, 400 MHz) δ 7.90~7.95 (m, 3H), 7.10 (t, J=8.8 Hz, 2H), 6.67 (s, 1H), 5.98 (s, 1H), 3.00 (d, J=4.4 Hz, 3H), 1.23 (s, 12H). MS (M+H)$^+$: 411.

Step 2—Synthesis of 6-amino-5-(11-fluoro-6H-pyrido[2',3':5,6][1,3]oxazino[3,4-a]indol-2-yl)-2-(4-fluorophenyl)-N-methylbenzofuran-3-carboxamide (Compound 163)

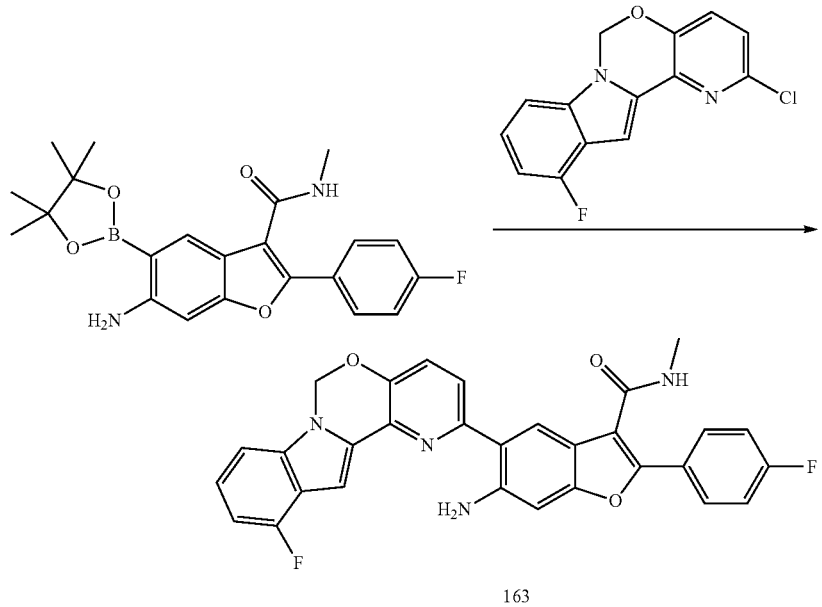

163

The procedure of Compound 163 (2.4 g, yield: 63%) was similar to step 6 of Example 1. $^1$H-NMR (CDCl$_3$, 400 MHz) δ 7.94 (s, 1H), 7.87~7.90 (m, 2H), 6.65 (d, J=8.8 Hz, 1H), 7.51 (t, J=8.8 Hz, 1H), 7.24 (d, J=7.6 Hz, 1H), 7.11~7.21 (m, 3H), 6.84~6.90 (m, 2H), 6.00 (s, 1H), 5.90 (s, 2H), 3.00 (d, J=4.8 Hz, 3H). MS (M+H)$^+$: 523.

Example 58

Preparation of Compound 164

164

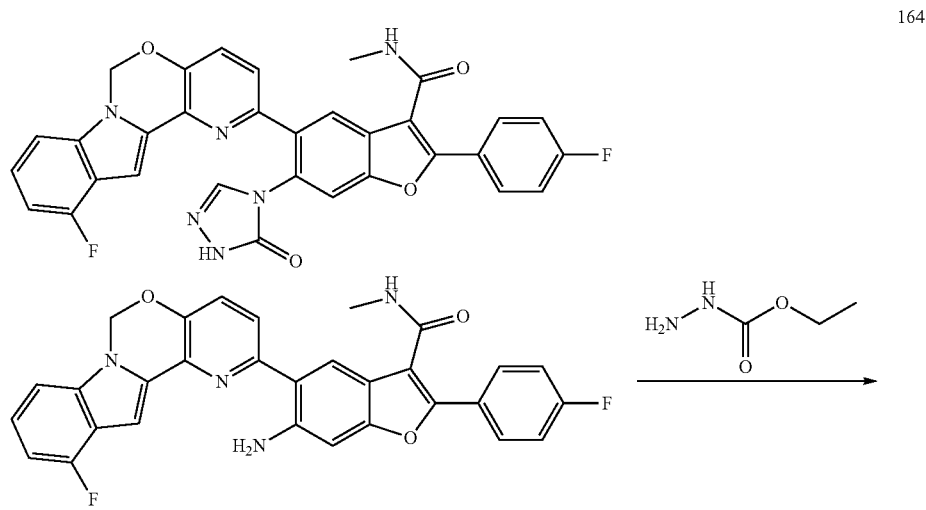

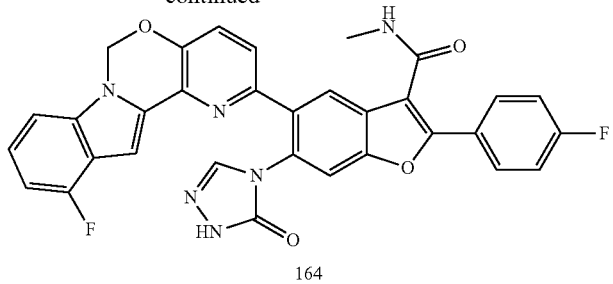

164

To a solution of 6-amino-5-(11-fluoro-6H-pyrido[2',3':5,6][1,3]oxazino[3,4-a]indol-2-yl)-2-(4-fluorophenyl)-N-methylbenzofuran-3-carboxamide (200 mg, 0.38 mmol), ethyl hydrazinecarboxylate (42 mg, 0.40 mmol) and trimethoxymethane (204 mg, 1.92 mmol) in 10 mL of methanol was added PTSA (6 mg, 0.04 mmol) and the mixture was heated at 100° C. for 6 hours. Then the solution was cooled to room temperature and to this mixture sodium methanolate was added before this reaction mixture was heated at reflux for another 16 hours. The pH of the reaction system was adjusted to 1 with concentrated HCl and then the mixture was filtered to get a yellow solid. Finally the desired Compound 164 (40 mg, yield: 18%) was obtained by the prep-HPLC. $^1$H-NMR (Methanol-d4, 400 MHz) δ 7.80~8.01 (m, 5H), 7.57 (s, 2H), 7.06~7.30 (m, 5H), 6.78~6.82 (m, 1H), 6.05 (s, 2H), 2.97 (s, 3H). MS (M+H)$^+$: 591.

Example 59

Preparation of Compound 165

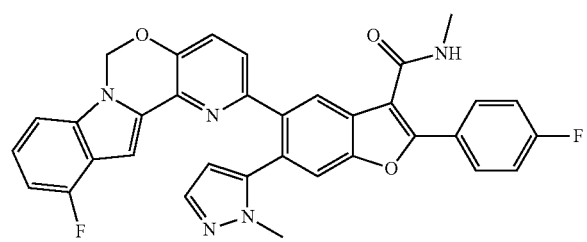

165

Step 1—Synthesis of 5-(11-fluoro-6H-pyrido[2',3':5,6][1,3]oxazino[3,4-a]indol-2-yl)-2-(4-fluorophenyl)-6-iodo-N-methylbenzofuran-3-carboxamide

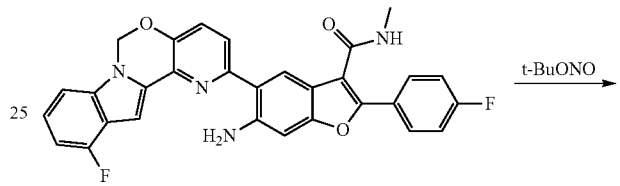

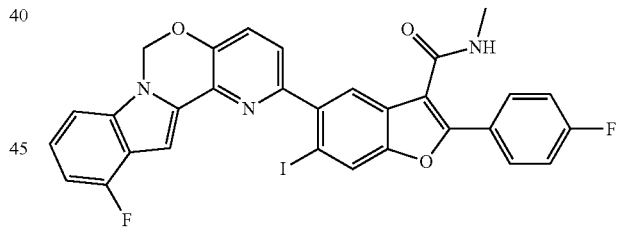

To a mixture of 6-amino-5-(11-fluoro-6H-pyrido[2',3':5,6][1,3]oxazino[3,4-a]indol-2-yl)-2-(4-fluorophenyl)-N-methylbenzofuran-3-carboxamide (500 mg, 0.96 mmol), CuI (182 mg, 0.96 mmol), KI (238 mg, 1.44 mmol) in acetonitrile (5 mL) was added t-BuONO (168 mg, 1.44 mmol) at 0° C. under N$_2$ protection. The mixture was stirred at 80° C. for 4 hours. The mixture was filtered through a celite pad, and the resulting residue was concentrated to provide crude product. The crude product was purified using column chromatography (petroleum ether:EtOAc=1:1) to provide 5-(11-fluoro-6H-pyrido[2',3':5,6][1,3]oxazino[3,4-a]indol-2-yl)-2-(4-fluorophenyl)-6-iodo-N-methylbenzofuran-3-carboxamide (170 mg, yield: 28%). $^1$H-NMR (CDCl$_3$, 400 MHz) δ 8.15 (s, 1H), 7.94~8.00 (m, 3H), 7.47 (d, J=8.4 Hz, 1H), 7.41 (d, J=8.4 Hz, 1H), 7.37 (s, 1H), 7.20 (t, J=8.8 Hz, 5H), 6.80~6.87 (m, 1H), 6.02 (s, 2H), 3.00 (d, J=4.8 Hz, 3H). MS (M+H)$^+$: 634.

Step 2—Synthesis of 5-(11-fluoro-6H-pyrido[2',3':5,6][1,3]oxazino[3,4-a]indol-2-yl)-2-(4-fluorophenyl)-N-methyl-6-(1-methyl-1H-pyrazol-5-yl)benzofuran-3-carboxamide (Compound 165)

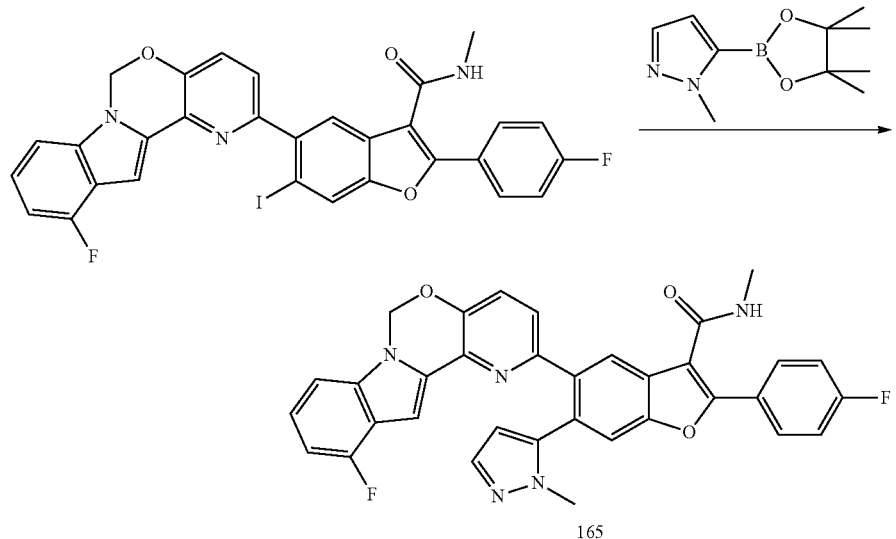

165

To a degassed solution of 5-(11-fluoro-6H-pyrido[2',3':5,6][1,3]oxazino[3,4-a]indol-2-yl)-2-(4-fluorophenyl)-6-iodo-N-methylbenzofuran-3-carboxamide (100 mg, 0.16 mmol), 1-methyl-5-(4,4,5,5-tetramethyl-1,3,2-dioxaborolan-2-yl)-1H-pyrazole (100 mg, 0.48 mmol) and $K_3PO_4 \cdot 3H_2O$ (60 mg, 0.45 mmol) in DMF (2 mL) was added Pd(dppf)Cl$_2$ (20 mg) under N$_2$ protection. The reaction mixture was stirred at 100° C. for 16 hours. The mixture was filtered through a celite pad, and the resulting residue was concentrated to provide crude product. The resulting residue was purified using column chromatography (petroleum ether:EtOAc=1:2) to provide the product of Compound 165 (15 mg, yield: 16%). $^1$H-NMR (CDCl$_3$, 400 MHz) δ 8.12 (s, 1H), 7.95 (dd, J=8.4, 6.0 Hz, 2H), 7.51 (s, 1H), 7.42 (s, 1H), 7.15 (t, J=8.8 Hz, 5H), 7.02 (d, J=8.0 Hz, 1H), 6.87 (d, J=8.4 Hz, 1H), 6.78 (t, J=8.8 Hz, 1H), 6.24 (s, 1H), 5.96 (s, 1H), 5.88 (s, 2H), 3.38 (s, 3H), 3.00 (d, J=5.2 Hz, 3H). MS (M+H)$^+$: 588.

Compounds 166-167, depicted in the table below, were prepared using the method described above and substituting the appropriate reactants and/or reagents.

| Compound No | Structure | NMR | MS (M + H)$^+$ |
|---|---|---|---|
| 166 | 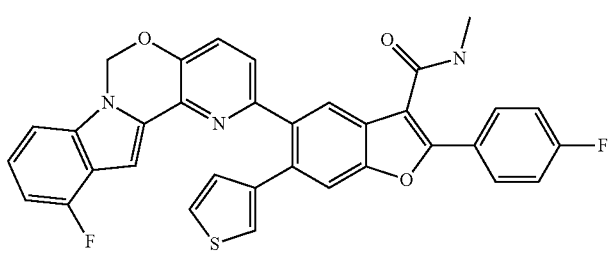 | $^1$H-NMR (CDCl$_3$, 400 MHz) δ 8.01 (d, J = 5.6 Hz, 2H), 7.90 (s, 1H), 7.57 (s, 1H), 7.23 (d, J = 8.0 Hz, 2H), 7.04~7.17 (m, 7H), 6.86 (d, J = 8.8 Hz, 1H), 6.75~6.84 (m, 2H), 5.91 (s, 2H), 2.98 (d, J = 4.0 Hz, 3H). | 590 |
| 167 | 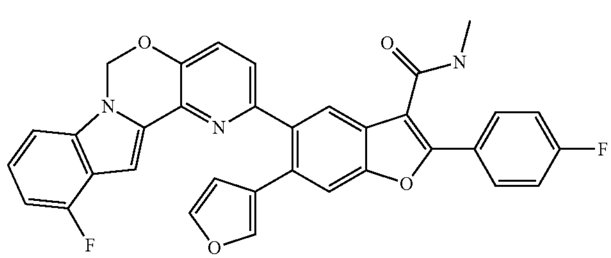 [SMILES: CNC(=O)c1c(-c2ccc(F)cc2)oc2cc(-c3ccoc3)c(-c3ccc4c(n3)-c3cc5c(F)cccc5n3CO4)cc12] | $^1$H-NMR (CDCl$_3$, 400 MHz) δ 7.97 (s, 2H), 7.92 (s, 1H), 7.54 (s, 1H), 7.23 (d, J = 8.8 Hz, 3H), 7.05~7.13 (m, 5H), 6.78 (s, 1H), 6.15 (s, 1H), 5.92~5.97 (m, 3H), 2.96 (s, 3H). | 574 |

Example 60

Preparation of Compound 168

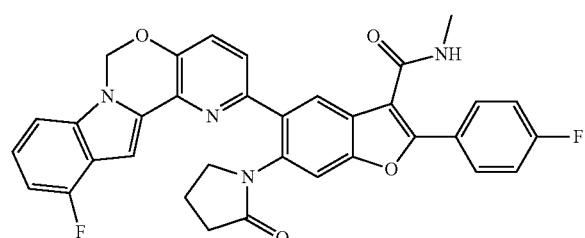

Step 1—Synthesis of ethyl 5-bromo-2-(4-fluorophenyl)-6-(2-oxopyrrolidin-1-yl)benzofuran-3-carboxylate

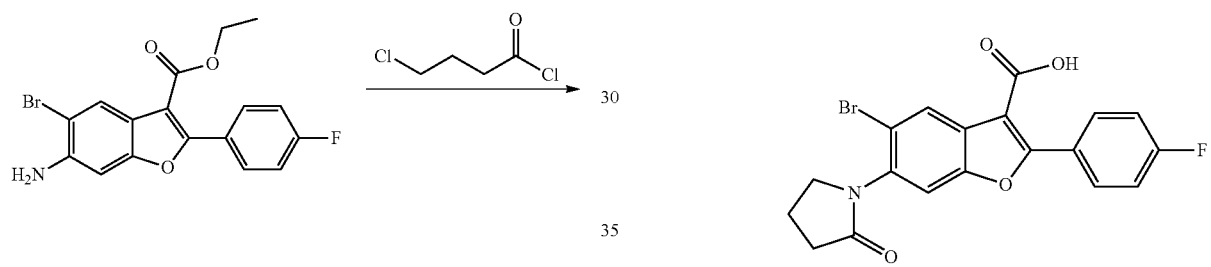

4-chlorobutanoyl chloride (670 mg, 4.76 mmol) was added dropwise to a 0° C. solution of ethyl 6-amino-5-bromo-2-(4-fluorophenyl)benzofuran-3-carboxylate and Et$_3$N (1.0 mL) in CH$_2$Cl$_2$ (10 mL) under N$_2$ atmosphere. The resulting reaction was allowed to stir at room temperature for 16 hours, then the reaction mixture was concentrated in vacuo. The resulting resulting residue was dissolved in CH$_3$CN (10 mL), and then K$_2$CO$_3$ (658 mg, 4.76 mmol) and KI (263 mg, 1.59 mmol) was added and the mixture was heated to reflux and allowed to stir at this temperature for 16 hours. After being cooled to room temperature, the mixture was diluted with water and extracted with EtOAc. The organic extract was washed with brine, dried over Na$_2$SO$_4$, filtered and concentrated in vacuo. The residue obtained was purified using column chromatography (eluted with petroleum ether:EtOAc=2:1) to provide ethyl 5-bromo-2-(4-fluorophenyl)-6-(2-oxopyrrolidin-1-yl) benzofuran-3-carboxylate (280 mg, yield: 40%). $^1$H-NMR (CDCl$_3$, 400 MHz) δ 8.32 (s, 1H), 8.04~8.07 (m, 2H), 7.48 (s, 1H), 7.17~7.21 (m, 2H), 4.42~4.43 (m, 2H), 3.82~3.86 (m, 2H), 2.61~2.65 (m, 2H), 2.27~2.31 (m, 2H), 1.40~1.44 (m, 3H). MS (M+H)$^+$: 446/448.

Step 2—Synthesis of 5-bromo-2-(4-fluorophenyl)-6-(2-oxopyrrolidin-1-yl)benzofuran-3-carboxylic acid

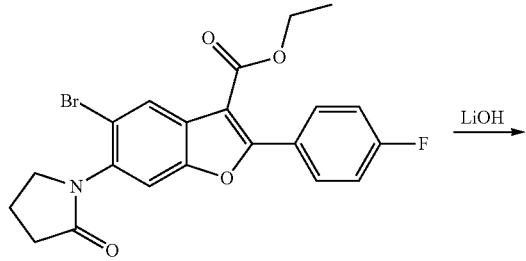

A solution of ethyl 5-bromo-2-(4-fluorophenyl)-6-(2-oxopyrrolidin-1-yl)benzofuran-3-carboxylate (2.5 g, 5.8 mmol) and LiOH (0.5 g, 21.0 mmol) in dioxane (30 mL) and water (10 mL) was allowed to stir at 90° C. for 1 hour. The mixture was cooled to room temperature and extracted with dichloromethane, the organic extract was washed with brine, dried over Na$_2$SO$_4$ and concentrated to provide 5-bromo-2-(4-fluorophenyl)-6-(2-oxopyrrolidin-1-yl)benzofuran-3-carboxylic acid (2.2 g, yield: 91%). $^1$H-NMR (CDCl$_3$, 400 MHz) δ 8.08 (s, 1H), 7.81~7.84 (m, 2H), 7.34 (s, 1H), 6.89~6.93 (m, 2H), 3.79~3.82 (m, 2H), 2.66~2.70 (m, 2H), 2.26~2.31 (m, 2H). MS (M+H)$^+$: 418/420.

Step 3—Synthesis of 5-bromo-2-(4-fluorophenyl)-N-methyl-6-(2-oxopyrrolidin-1-yl)benzofuran-3-carboxamide

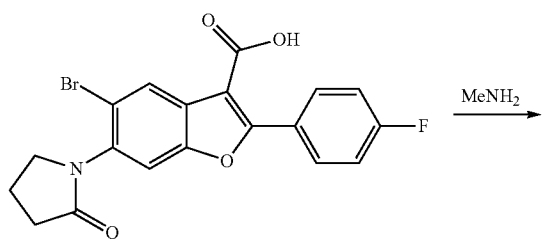

-continued

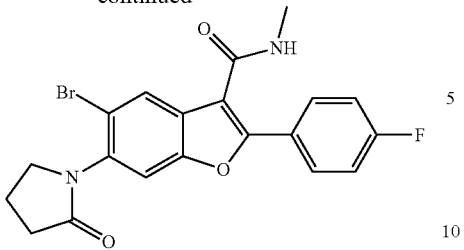

A solution of 5-bromo-2-(4-fluorophenyl)-6-(2-oxopyrrolidin-1-yl)benzofuran-3-carboxylic acid (280 mg, 0.67 mmol), HOBT (150 mg, 1.11 mmol) and EDCI (280 mg, 1.47 mmol) in dry DMF (2 mL) was allowed to stir at room temperature for 1 hour. Then $Et_3N$ (0.2 mL) and $CH_3NH_2$ (HCl salt, 100 mg, 1.48 mmol) was added to the mixture, and the reaction was allowed to stir for about 15 hours. After being concentrated in vacuo, water was added and the mixture was extracted with ethyl acetate. The organic extract was washed with brine, dried and concentrated in vacuo and the resulting resulting residue was purified using column chromatography (eluted with petroleum ether:EtOAc=1:1) to provide 5-bromo-2-(4-fluorophenyl-N-methyl-6-(2-oxopyrrolidin-1-yl)benzofuran-3-carboxamide (220 mg, yield: 73%), which was also prepared from 6-amino-5-bromo-2-(4-fluorophenyl)-N-methylbenzofuran-3-carboxamide and 4-chlorobutanoyl chloride using the method described in step 1 above. $^1$H-NMR (CDCl$_3$, 400 MHz) δ 7.94 (s, 1H), 7.82~7.86 (m, 2H), 7.32 (s, 1H), 7.09~7.14 (m, 2H), 6.29 (s, 1H), 3.75~3.78 (m, 2H), 2.97 (d, J=4.8 Hz, 3H), 2.56~2.60 (m, 2H), 2.24~2.26 (m, 2H). MS (M+H)$^+$: 431/433.

Step 4—Synthesis of 2-(4-fluorophenyl)-N-methyl-6-(2-oxopyrrolidin-1-yl)-5-(4,4,5,5-tetramethyl-1,3,2-dioxaborolan-2-yl)benzofuran-3-carboxamide

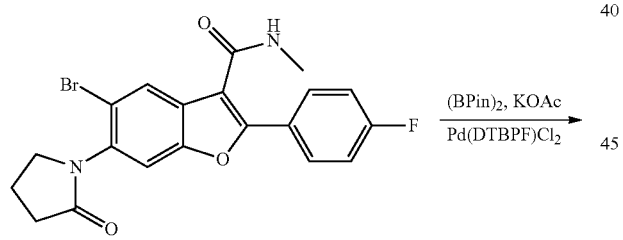

To a solution of 5-bromo-2-(4-fluorophenyl)-N-methyl-6-(2-oxopyrrolidin-1-yl)benzofuran-3-carboxamide (500 mg, 1.16 mmol) and (Bpin)$_2$ (900 mg, 3.54 mmol) in THF (15 mL), KOAc (400 mg, 4.08 mmol), Pd(dtbpf)Cl$_2$ (80 mg, 0.12 mmol) were added under $N_2$ protection. The mixture was heated at 70° C. for 1 hour. The mixture was added dichloromethane and MeOH. The mixture was filtered through a Celit pad. The filtrate was dried and concentrated in vacuo. The resulting residue was purified using column chromatography (dichloromethane:MeOH=80:1) to provide 2-(4-fluorophenyl)-N-methyl-6-(2-oxopyrrolidin-1-yl)-5-(4,4,5,5-tetramethyl-1,3,2-dioxaborolan-2-yl)benzofuran-3-carboxamide (230 mg, yield: 41.5%). $^1$H-NMR (CDCl$_3$, 400 MHz) δ 8.03~8.07 (m, 3H), 7.12~7.18 (m, 2H), 7.04 (s, 1H), 6.17 (br s, 1H), 4.06 (t, J=7.2 Hz, 2H), 3.05 (d, J=4.8 Hz, 3H), 2.92 (t, J=8.0 Hz, 2H), 2.27~2.35 (m, 2H), 1.36 (s, 12H). MS (M+H)$^+$: 479.

Step 5—Synthesis of 5-(11-fluoro-6H-pyrido[2',3':5,6][1,3]oxazino[3,4-a]indol-2-yl)-2-(4-fluorophenyl)-N-methyl-6-(2-oxopyrrolidin-1-yl)benzofuran-3-carboxamide (Compound 168)

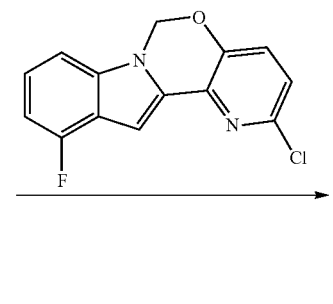

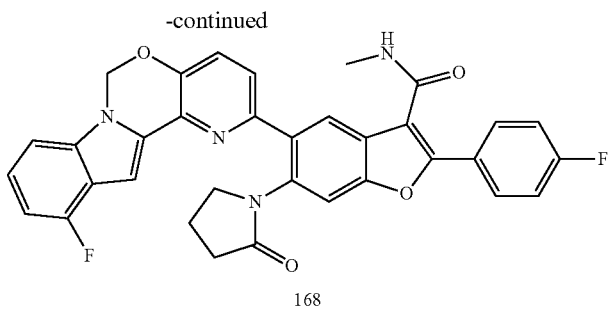

168

The procedure of Compound 168 (30 mg, yield: 45%) was similar to step 6 of Example 1. ¹H-NMR (CDCl₃, 400 MHz) δ 7.97 (s, 1H), 7.89~7.93 (m, 2H), 7.44 (s, 1H), 7.40~7.42 (m, 2H), 7.11~7.19 (m, 4H), 7.04~7.07 (m, 1H), 6.77~6.82 (m, 1H), 5.92 (s, 2H), 5.85 (br s, 1H), 3.83 (t, J=7.2 Hz, 2H), 2.95 (d, J=4.8 Hz, 3H), 2.26 (t, J=8.0 Hz, 2H), 2.01~2.06 (m, 2H). MS (M+H)⁺: 591.

Method II for Preparation of Compound 168

Step 1—Synthesis of 11-fluoro-2-(trimethylstannyl)-6H-pyrido[2',3':5,6][1,3]oxazino[3,4-a]indole

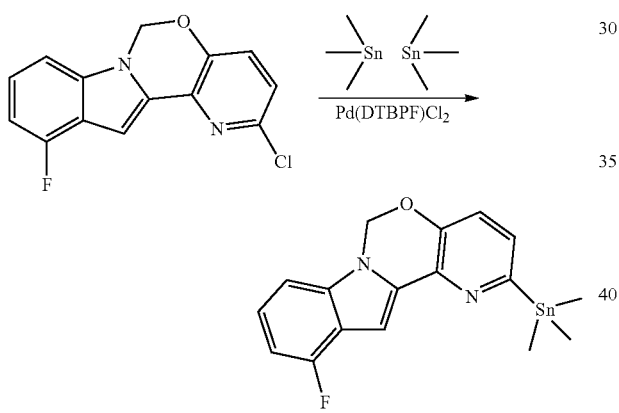

To a degassed solution of 2-chloro-11-fluoro-6H-pyrido[2',3':5,6][1,3]oxazino[3,4-a]indole (3.0 g, 10.92 mmol) in Toluene (80 mL), (Me₃Sn)₂ (5.4 g, 16.40 mmol) and Pd(DTBPF)Cl₂ (250 mg, 0.41 mmol) were added. The reaction mixture was stirred at 100° C. for 3.5 hours. The reaction mixture was filtered through a Celit pad. The filtrate was concentrated in vacuo and purified using aluminum oxide column chromatography (petroleum ether:EtOAc=30:1) to provide 11-fluoro-2-(trimethylstannyl)-6H-pyrido[2',3':5,6][1,3]oxazino[3,4-a]indole (3.7 g, yield 84%). ¹H-NMR (CDCl₃, 400 MHz) δ 7.35~7.31 (m, 2H), 7.26~7.16 (m, 2H), 7.08 (d, J=8.4 Hz, 1H), 6.84 (dd, J=8.4 Hz, 1H), 5.91 (s, 2H), 0.45~0.31 (m, 9H).

Step 2—Synthesis of 5-(11-fluoro-6H-pyrido[2',3':5,6][1,3]oxazino[3,4-a]indol-2-yl)-2-(4-fluorophenyl)-N-methyl-6-(2-oxopyrrolidin-1-yl)benzofuran-3-carboxamide (Compound 168)

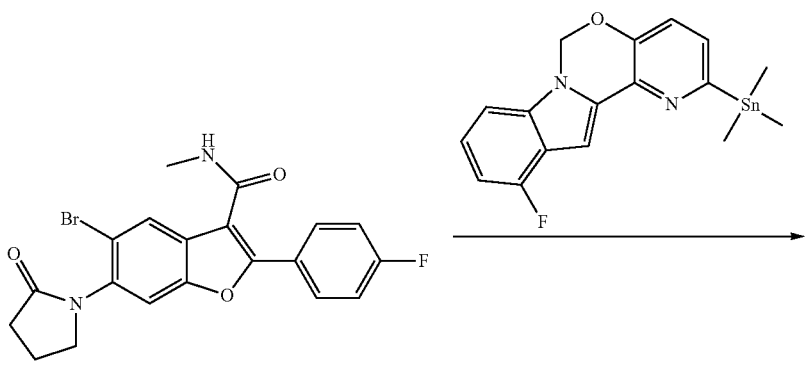

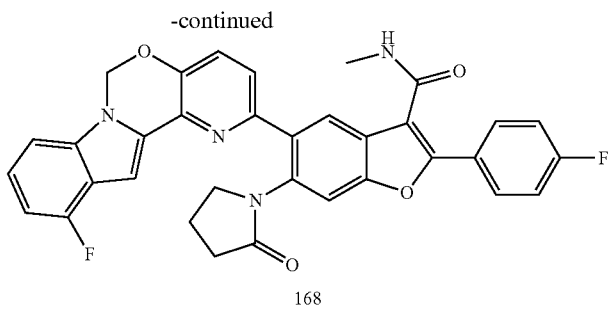

168

To a solution of 11-fluoro-2-(trimethylstannyl)-6H-pyrido[2',3':5,6][1,3]oxazino[3,4-a]indole (60 mg, 0.14 mmol), 5-bromo-2-(4-fluorophenyl)-N-methyl-6-(2-oxopyrrolidin-1-yl)benzofuran-3-carboxamide (50 mg, 0.11 mmol) in DMF (4 mL), Pd(PPh$_3$)$_4$ was added. The reaction mixture was stirred at 100° C. overnight. The reaction mixture was filtered through a Celit pad. The filtrate was concentrated in vacuo. The resulting residue was suspended in water, extracted with EtOAc. The organic layer was washed with brine, dried over Na$_2$SO$_4$ and concentrated in vacuo. The resulting residue was purified using prep-HPLC to provide 5-(11-fluoro-6H-pyrido[2',3':5,6][1,3]oxazino[3,4-a]indol-2-yl)-2-(4-fluorophenyl)-N-methyl-6-(2-oxopyrrolidin-1-yl)benzofuran-3-carboxamide (20 mg, yield: 29.2%). $^1$H-NMR (CDCl$_3$, 400 MHz) δ 7.97 (s, 1H), 7.89~7.93 (m, 2H), 7.44 (s, 1H), 7.40~7.42 (m, 2H), 7.11~7.19 (m, 4H), 7.05 (d, J=8.8 Hz, 1H), 6.77~6.82 (m, 1H), 5.92 (s, 2H), 5.85 (br s, 1H), 3.83 (t, J=7.2 Hz, 2H), 2.95 (d, J=4.8 Hz, 3H), 2.26 (t, J=8.4 Hz, 2H), 2.00~2.06 (m, 2H). MS (M+H)$^+$: 591.

Compounds 169-170, depicted in the table below, were prepared using method II described above and substituting the appropriate reagents and/or reactants.

| Compound No | Structure | NMR | MS (M + H)$^+$ |
|---|---|---|---|
| 169 | 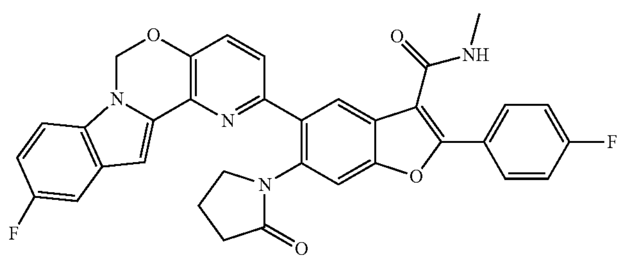 [SMILES: CNC(=O)c1c(-c2ccc(F)cc2)oc2cc(N3CCCC3=O)c(-c3ccc4c(n3)-c3cc5cc(F)ccc5n3CO4)cc12] | $^1$H-NMR (CDCl$_3$, 400 MHz) δ 7.90~7.93 (m, 3H), 7.60 (s, 1H), 7.04~7.40 (m, 12H), 6.81~6.85 (m, 1H), 6.76 (d, J = 8.4 Hz, 1H), 5.95 (br s, 1H), 3.34 (s, 3H), 2.94 (d, J = 4.8 Hz, 3H), 2.30 (s, 3H). | 591 |
| 170 | 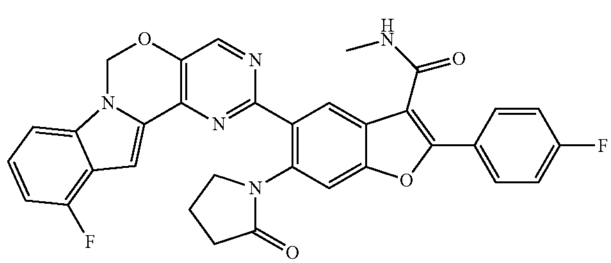 [SMILES: CNC(=O)c1c(-c2ccc(F)cc2)oc2cc(N3CCCC3=O)c(-c3ncc4c(n3)-c3cc5c(F)cccc5n3CO4)cc12] | $^1$H-NMR (CDCl$_3$, 400 MHz) δ 8.62 (s, 1H), 8.43 (s, 1H), 8.02~8.07 (m, 2H), 7.48 (s, 1H), 7.40 (s, 1H), 7.27~7.32 (m, 1H), 7.13~7.21 (m, 3H), 6.87~6.92 (m, 1H), 6.15 (br s, 1H), 6.04 (s, 2H), 4.09 (t, J = 6.4 Hz, 2H), 3.06 (d, J = 4.8 Hz, 3H), 2.37 (t, J = 8.0 Hz, 2H), 2.22~2.29 (m, 2H). | 592 |

Example 61

Preparation of Compound 171

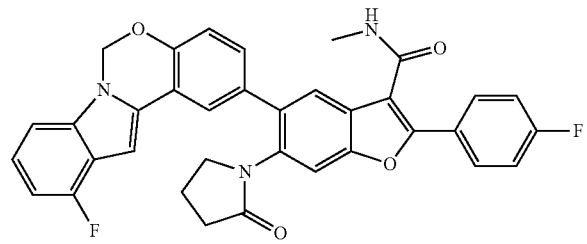
171

Step 1—Synthesis of 11-fluoro-2-(4,4,5,5-tetramethyl-1,3,2-dioxaborolan-2-yl)-6H-benzo[5,6][1,3]oxazino[3,4-a]indole

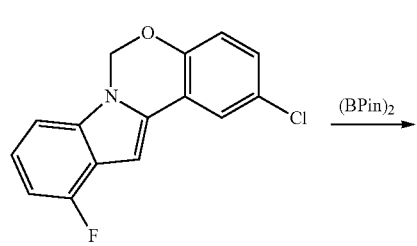

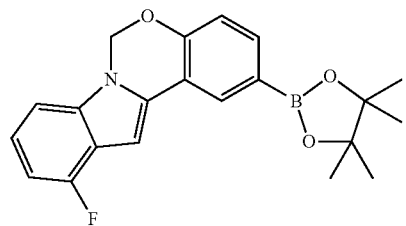

The procedure of 11-fluoro-2-(4,4,5,5-tetramethyl-1,3,2-dioxaborolan-2-yl)-6H-benzo[5,6][1,3]oxazino[3,4-a]indole was similar to step 4 of Example 3, using 2-chloro-11-fluoro-6H-benzo[5,6][1,3]oxazino[3,4-a]indole described in Example 4. MS (M+H)$^+$: 366.

Step 2—Synthesis of 5-(11-fluoro-6H-benzo[5,6][1,3]oxazino[3,4-a]indol-2-yl)-2-(4-fluorophenyl)-N-methyl-6-(2-oxopyrrolidin-1-yl)benzofuran-3-carboxamide (Compound 171)

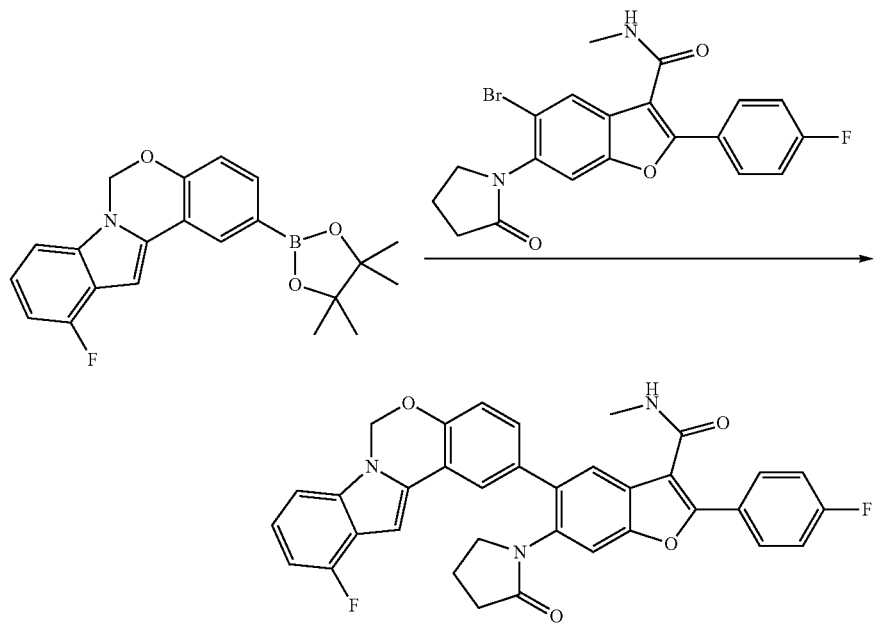
171

The procedure of Compound 171 was similar to step 5 of Example 3 using 11-fluoro-2-(4,4,5,5-tetramethyl-1,3,2-dioxaborolan-2-yl)-6H-benzo[5,6][1,3]oxazino[3,4-a]indole and 5-bromo-2-(4-fluorophenyl)-N-methyl-6-(2-oxopyrrolidin-1-yl)benzofuran-3-carboxamide described in Example 60. $^1$H-NMR (CDCl$_3$, 400 MHz) δ 7.93~7.97 (m, 2H), 7.86 (s, 1H), 7.77~7.78 (m, 1H), 7.51 (s, 1H), 7.31~7.34 (m, 1H), 7.08~7.22 (m, 5H), 6.91 (s, 1H), 6.80~6.85 (m, 1H), 5.93 (s, 3H), 3.32~3.35 (m, 2H), 2.99~3.00 (m, 3H), 2.45~2.49 (m, 2H), 1.88~1.96 (m, 2H). MS (M+H)$^+$: 590.

Example 62

Preparation of Compound 172

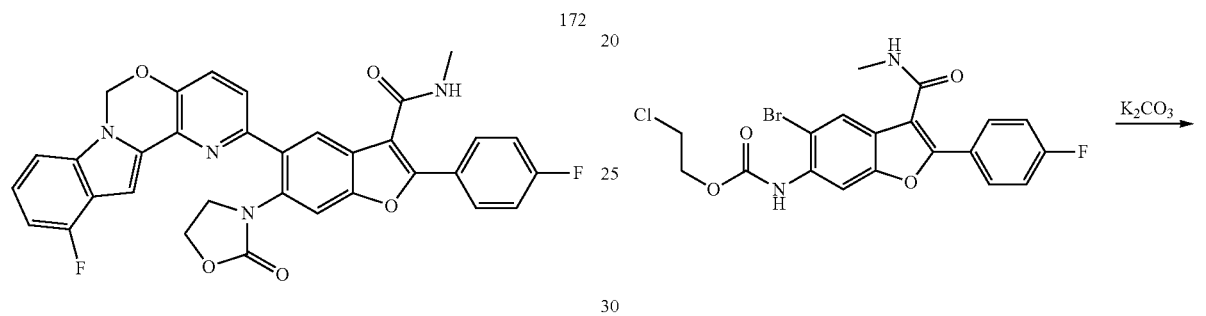

Step 1—Synthesis of 2-chloroethyl (5-bromo-2-(4-fluorophenyl)-3-(methylcarbamoyl)benzofuran-6-yl)carbamate

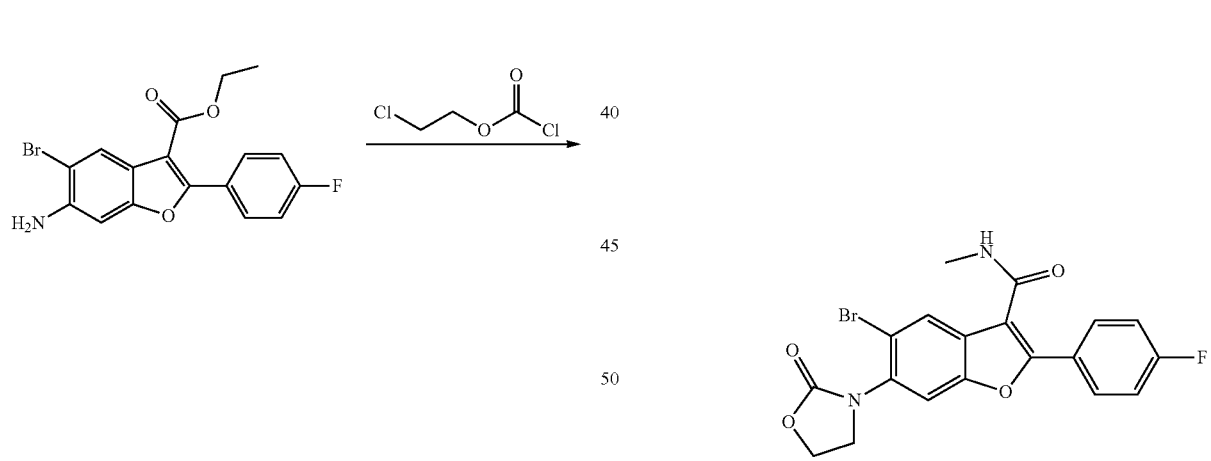

2-chloroethyl carbonochloridate (189 mg, 0.83 mmol) was added to a solution of ethyl 6-amino-5-bromo-2-(4-fluorophenyl)benzofuran-3-carboxylate (200 mg, 0.55 mmol) and C$_5$H$_5$N (131 mg) in CH$_2$Cl$_2$ (3 mL), and then the mixture was stirred at room temperature under N$_2$ for 12 hours. The mixture was concentrated in vacuo. The resulting residue was extracted with EtOAc and concentrated to obtain the ethyl 2-chloroethyl (5-bromo-2-(4-fluorophenyl)-3-(methylcarbamoyl)benzofuran-6-yl)carbamate (158 mg, yield: 61%). $^1$H-NMR (CDCl$_3$, 400 MHz) δ 8.38 (s, 1H), 8.04 (s, 1H), 7.87~7.91 (m, 2H), 7.38 (s, 1H), 7.19~7.21 (m, 2H), 5.79 (s, 1H), 4.46~4.49 (m, 2H), 3.76~3.79 (m, 2H), 2.99 (d, J=4.8 Hz, 3H). MS (M+H)$^+$: 469/471.

Step 2—Synthesis of 5-bromo-2-(4-fluorophenyl)-N-methyl-6-(2-oxooxazolidin-3-yl)benzofuran-3-carboxamide

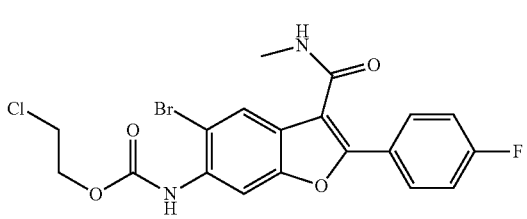

2-chloroethyl (5-bromo-2-(4-fluorophenyl)-3-(methylcarbamoyl)benzofuran-6-yl)carbamate (1.00 g, 2.10 mmol) was added to a mixture of KI (0.40 g, 2.10 mmol) and K$_2$CO$_3$ (0.75 g, 6.30 mmol) in DMF (20 mL) and the mixture was stirred under N$_2$ protection at 110° C. for 2 hours. After concentrated in vacuo, the resulting residue was washed with water and EtOAc to provide 5-bromo-2-(4-fluorophenyl)-N-methyl-6-(2-oxooxazolidin-3-yl)benzofuran-3-carboxamide (408 mg, yield: 45%). $^1$H-NMR (CDCl$_3$, 400 MHz) δ 7.58 (s, 1H), 7.51 (m, 2H), 7.19 (s, 1H), 7.11~7.13 (d, J=8.0 Hz, 1H), 6.83~6.88 (m, 1H), 4.37~7.41 (m, 2H), 4.12~4.14 (m, 2H), 3.00 (d, J=4.8 Hz, 3H). MS (M+H)$^+$: 433/435.

Step 3—Synthesis of 5-(11-fluoro-6H-pyrido[2',3':5,6][1,3]oxazino[3,4-a]indol-2-yl)-2-(4-fluorophenyl)-N-methyl-6-(2-oxooxazolidin-3-yl)benzofuran-3-carboxamide (Compound 172)
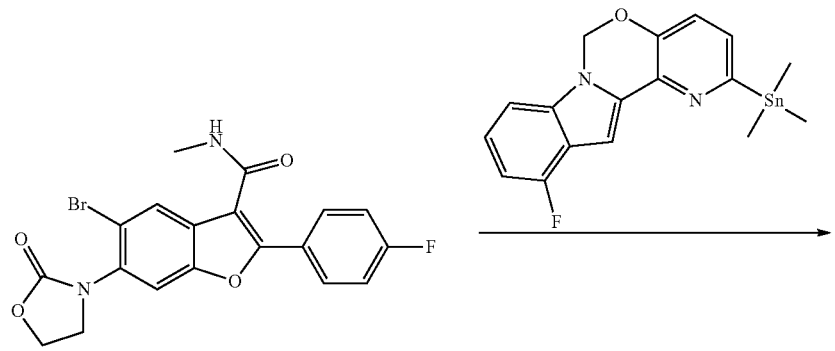
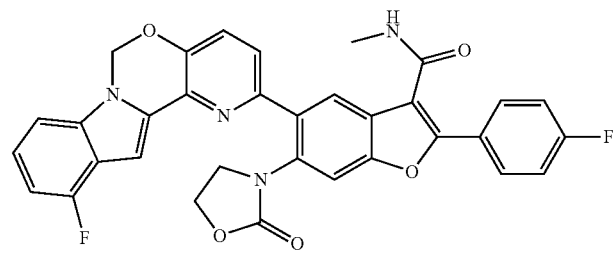
172

Pd₂(dba)₃ (10 mg, 0.01 mmol) and X-Phos (11 mg, 0.02 mmol) was added to the mixture of 5-bromo-2-(4-fluorophenyl)-N-methyl-6-(2-oxooxazolidin-3-yl)benzofuran-3-carboxamide (100 mg, 0.23 mmol), 11-fluoro-2-(trimethylstannyl)-6H-pyrido[2',3':5,6][1,3]oxazino[3,4-a]indole (140 mg, 0.35 mmol) in dioxane/H₂O (4 mL/0.2 mL) under N₂. Then the reaction mixture was heated to 100° C. for 1 hour and filtered. The resulting residue was extracted with EtOAc. The combined organic phase was dried over Na₂SO₄ and concentrated in vacuo. The resulting residue was purified using prep-TLC (petroleum ether:EtOAc=1:2) to provide 5-(11-fluoro-6H-pyrido[2',3':5,6][1,3]oxazino[3,4-a]indol-2-yl)-2-(4-fluorophenyl)-N-methyl-6-(2-oxooxazolidin-3-yl)benzofuran-3-carboxamide (32 mg, yield: 24%). ¹H-NMR (CDCl₃, 400 MHz) δ 8.01 (s, 1H), 7.94~7.98 (m, 2H), 7.58 (s, 1H), 7.51 (m, 2H), 7.19~7.23 (m, 4H), 7.11~7.13 (d, J=8.0 Hz, 1H), 6.83~6.88 (m, 1H), 6.12 (s, 1H), 6.00 (s, 2H), 4.37~7.41 (m, 2H), 4.12~4.14 (m, 2H), 3.00 (d, J=4.8 Hz, 3H). MS (M+H)⁺: 593.

Example 63

Preparation of Compound 173

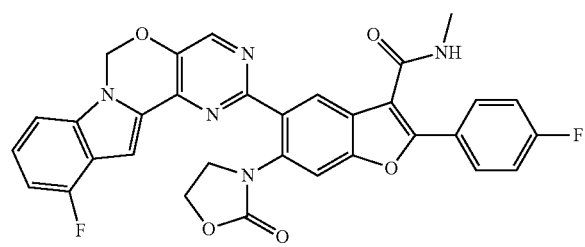

173

Step 1—Synthesis of 2-(4-fluorophenyl)-N-methyl-6-(2-oxooxazolidin-3-yl)-5-(4,4,5,5-tetramethyl-1,3,2-dioxaborolan-2-yl)benzofuran-3-carboxamide

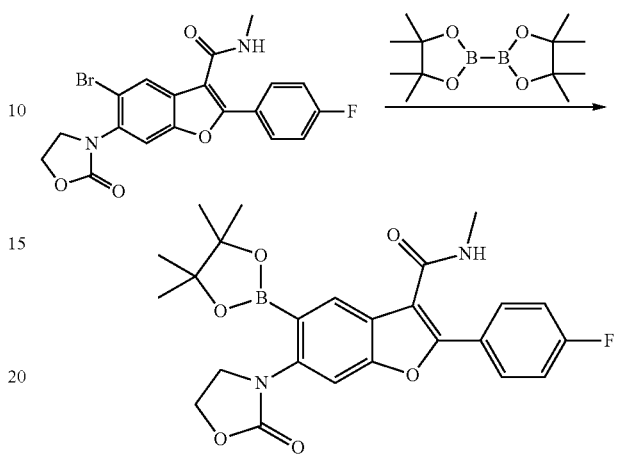

To a N₂ degassed solution of 5-bromo-2-(4-fluorophenyl)-N-methyl-6-(2-oxooxazolidin-3-yl)benzofuran-3-carboxamide (500 mg, 1.2 mmol), KOAc (352 mg, 3.6 mmol) and dis(pinacolato)diboron (913 mg, 3.6 mmol) in THF (10 mL), Pd(dppf)Cl₂ (67 mg, 0.12 mmol) was added. The reaction mixture was stirred at 100° C. for 1 hour, and then filtered through a celite pad. The filtrate was concentrated in vacuo, and the resulting residue was purified using column chromatography (petroleum ether:EtOAc=15:1) to provide 2-(4-fluorophenyl)-N-methyl-6-(2-oxooxazolidin-3-yl)-5-(4,4,5,5-tetramethyl-1,3,2-dioxaborolan-2-yl)benzofuran-3-carboxamide (397 mg, yield: 69%). ¹H-NMR (CDCl₃, 400 MHz) δ 7.58 (s, 1H), 7.50~7.53 (m, 3H), 7.19 (s, 1H), 7.11~7.13 (d, J=8.0 Hz, 1H), 6.83~6.88 (m, 1H), 4.39 (t, J=4.4 Hz, 2H), 4.13 (t, J=4.4 Hz, 2H), 3.00 (d, J=4.8 Hz, 3H), 1.39 (s, 12H). MS (M+H)⁺: 481.

Step 2—Synthesis of 5-(11-fluoro-6H-pyrimido[4',3':5,6][1,3]oxazino[3,4-a]indol-2-yl)-2-(4-fluorophenyl)-N-methyl-6-(2-oxooxazolidin-3-yl)benzofuran-3-carboxamide (Compound 173)

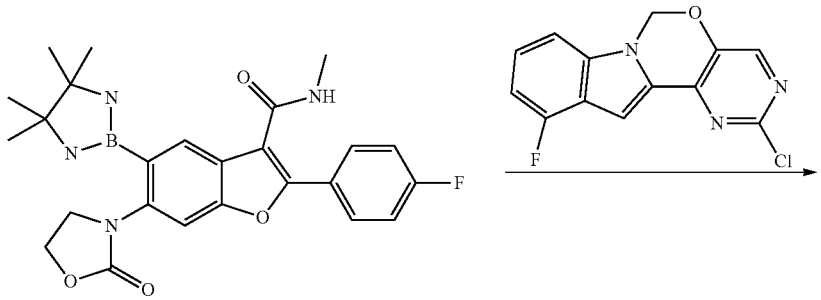

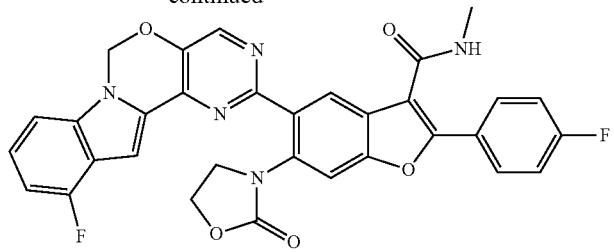

173

Pd$_2$(dba)$_3$ (14 mg, 0.015 mmol) and X-Phos (14 mg, 0.03 mmol) was added to the mixture of 2-(4-fluorophenyl)-N-methyl-6-(2-oxooxazolidin-3-yl)-5-(4,4,5,5-tetramethyl-1,3,2-dioxaborolan-2-yl)benzofuran-3-carboxamide (73 mg, 0.15 mmol), 2-chloro-11-fluoro-6H-pyrimido[4',3':5,6][1,3]oxazino[3,4-a]indole (50 mg, 0.18 mmol) and K$_3$PO$_4$.3H$_2$O (121 mg, 0.45 mmol) in dioxane/H$_2$O (3 mL/0.5 mL) under N$_2$. Then the reaction mixture was heated to 100° C. for 1 hour and filtered. The mixture was extracted with EtOAc. The combined organic phase was washed with brine, dried over Na$_2$SO$_4$ and concentrated in vacuo. The resulting residue was purified using chromatography (petroleum ether:EtOAc=1:2) to provide 5-(11-fluoro-6H-pyrimido[4',3':5,6][1,3]oxazino[3,4-a]indol-2-yl)-2-(4-fluorophenyl)-N-methyl-6-(2-oxooxazolidin-3-yl)benzofuran-3-carboxamide (43 mg, yield: 42%). $^1$H-NMR (CDCl$_3$, 400 MHz) δ 8.63 (s, 1H), 8.55 (s, 1H), 8.00~8.04 (m, 2H), 7.56 (s, 1H), 7.46 (s, 1H), 7.32~7.35 (m, 1H), 7.15~7.20 (m, 3H), 6.87~6.91 (m, 1H), 6.03 (s, 2H), 5.97~6.00 (m, 1H), 4.54 (t, 2H), 4.24 (t, 2H), 3.06 (d, J=4.8 Hz, 3H). MS (M+H)$^+$: 594.

Compound 174, depicted in the table below, was prepared using the method described above and substituting the appropriate reagents and/or reactants.

| Compound No | Structure | NMR | MS (M + H)$^+$ |
|---|---|---|---|
| 174 | (structure shown) | $^1$H-NMR (CDCl$_3$, 400 MHz) δ 8.03 (s, 1H), 7.94~8.97 (m, 2H), 7.60 (s, 1H), 7.44~7.49 (m, 2H), 7.32~7.35 (m, 1H), 7.21~7.24 (m, 3H), 7.14 (s, 1H), 7.02~7.08 (m, 1H), 6.01 (s, 1H), 5.97~6.00 (m, 2H), 4.35 (t, J = 4.8 Hz, 2H), 4.02 (t, J = 4.8 Hz, 2H), 2.99 (d, J = 4.8 Hz, 3H). | 593 |

Example 64
Preparation of Compound 175
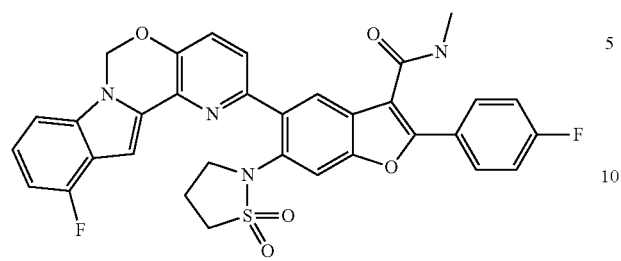
Step 1—Synthesis of 6-(3-chloropropylsulfonamido)-5-(11-fluoro-6H-pyrido[2',3':5,6][1,3]oxazino[3,4-a]indol-2-yl)-2-(4-fluorophenyl)-N-methylbenzofuran-3-carboxamide
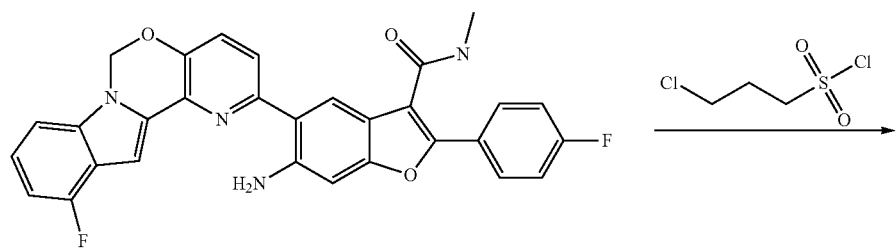
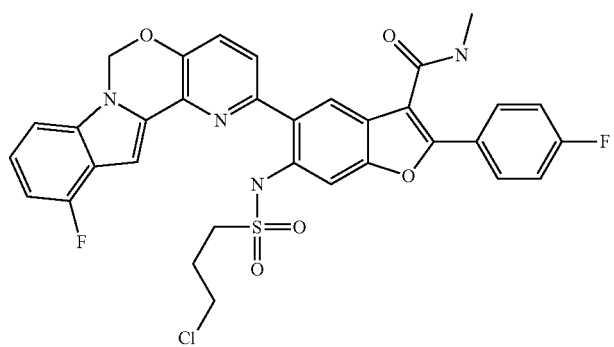

To a solution of 6-amino-5-(11-fluoro-6H-pyrido[2',3':5,6][1,3]oxazino[3,4-a]indol-2-yl)-2-(4-fluorophenyl)-N-methylbenzofuran-3-carboxamide (70 mg, 0.13 mmol) and Et$_3$N (0.1 mL) in CH$_2$Cl$_2$ (2 mL) was added 3-chloropropane-1-sulfonyl chloride (140 mg, 0.92 mmol) dropwise at 0° C. The reaction mixture was stirred at 12° C. for 16 hours. The reaction mixture was concentrated to provide 6-(3-chloropropylsulfonamido)-5-(11-fluoro-6H-pyrido[2',3':5,6][1,3]oxazino[3,4-a]indol-2-yl)-2-(4-fluorophenyl)-N-methylbenzofuran-3-carboxamide (90 mg, yield: 100%), which was used directly in the next step without further purification.

Step 2—Synthesis of 6-(1,1-dioxidoisothiazolidin-2-yl)-5-(11-fluoro-6H-pyrido[2',3':5,6][1,3]oxazino[3,4-a]indol-2-yl)-2-(4-fluorophenyl)-N-methylbenzofuran-3-carboxamide (Compound 175)

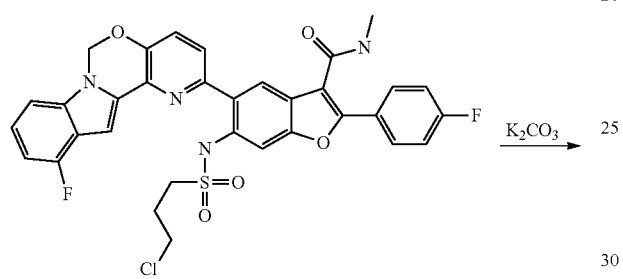

A solution of 6-(3-chloropropylsulfonamido)-5-(11-fluoro-6H-pyrido[2',3':5,6][1,3]oxazino[3,4-a]indol-2-yl)-2-(4-fluorophenyl)-N-methylbenzofuran-3-carboxamide (90 mg, 0.15 mmol) and K$_2$CO$_3$ (63 mg, 0.45 mmol) in CH$_3$CN (3 mL) was refluxed for 16 hours. The reaction mixture was added water and extracted with EtOAc. The organic layer was washed with brine, dried over Na$_2$SO$_4$ and concentrated in vacuo. The resulting residue was purified using prep-HPLC to provide compound 175 (20 mg, yield: 20%). $^1$H-NMR (CDCl$_3$, 400 MHz) δ 7.98 (s, 1H), 7.89~7.92 (m, 2H), 7.83 (s, 1H), 7.59 (d, J=8.8 Hz, 1H), 7.39 (d, J=8.8 Hz, 1H), 7.10~7.19 (m, 4H), 7.04~7.06 (m, 1H), 6.76~6.81 (m, 1H), 5.93 (s, 2H), 5.88~5.90 (br s, 1H), 3.63~3.66 (m, 2H), 3.07~3.11 (m, 2H), 2.93 (d, J=4.8 Hz, 3H), 2.25~2.29 (m, 2H). MS (M+H)$^+$: 627.

Example 65

Preparation of Compound 176

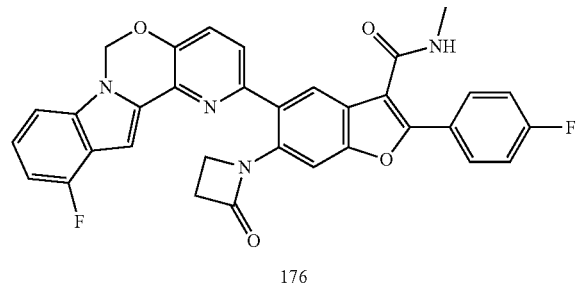

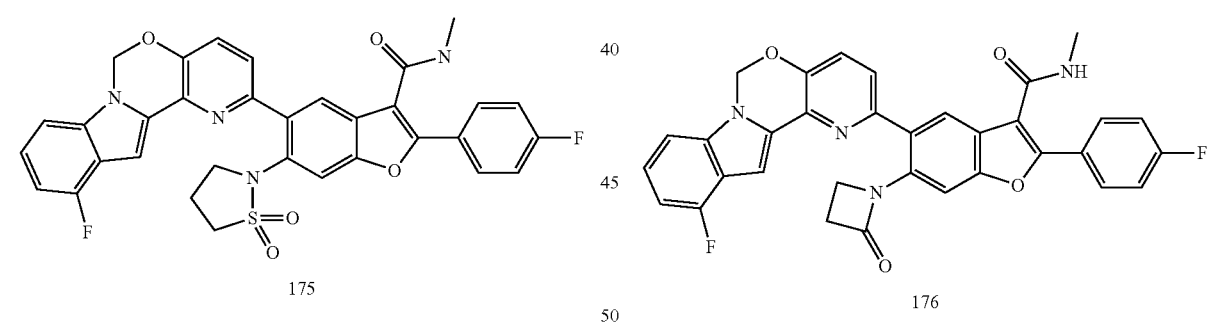

To a solution of 5-(11-fluoro-6H-pyrido[2',3':5,6][1,3]oxazino[3,4-a]indol-2-yl)-2-(4-fluorophenyl)-6-iodo-N-methylbenzofuran-3-carboxamide (50 mg, 0.08 mmol), azetidin-2-one (17 mg, 0.23 mmol) and K$_2$CO$_3$ (22 mg, 0.16 mmol) in 1 mL of 1,4-dioxane was added CuI (10 mg) and N,N'-dimethylcyclohexane-1,2-diamine (10 mg) in seal tube. The mixture was heated at 100° C. for 10 hours, concentrated and extracted with EtOAc. The combined organic phase was washed with brine, dried over Na$_2$SO$_4$ and concentrated to provide compound 176 (10 mg, yield: 22%) through the prep-TLC. $^1$H-NMR (CDCl$_3$, 400 MHz) δ 8.01 (s, 1H), 7.89 (d, J=5.6 Hz, 2H), 7.79 (s, 1H), 7.41 (d, J=8.4 Hz, 1H), 7.35 (d, J=8.0 Hz, 1H), 7.23 (s, 1H), 7.17~7.10 (m, 3H), 7.05 (d, J=8 Hz, 1H), 6.78 (d, J=8.0 Hz, 1H), 5.94 (s, 2H), 5.85 (d, J=4.0

Hz, 1H), 3.25 (t, J=4.4 Hz, 2H), 2.92 (d, J=4.8 Hz, 3H), 2.89 ((t, J=4.4 Hz, 2H). MS (M+H)⁺: 577.
Example 66
Preparation of Compound 177
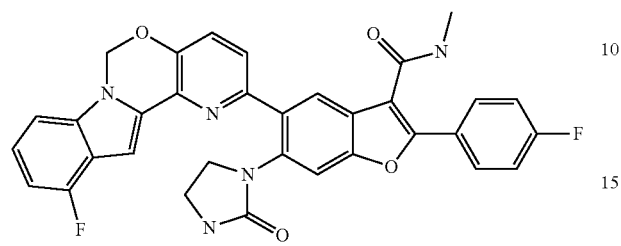
177
Step 1—Synthesis of 6-(3-(2-chloroethyl)ureido)-5-(11-fluoro-6H-pyrido[2',3':5,6][1,3]oxazino[3,4-a]indol-2-yl)-2-(4-fluorophenyl)-N-methylbenzofuran-3-carboxamide
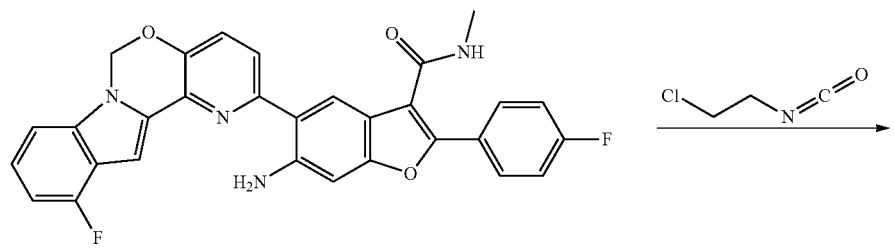
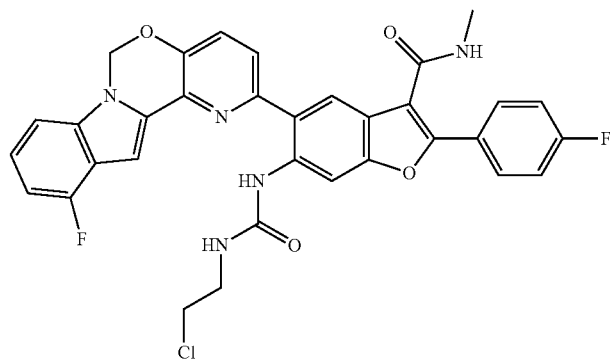

To a solution of 6-amino-5-(11-fluoro-6H-pyrido[2',3':5,6][1,3]oxazino[3,4-a]indol-2-yl)-2-(4-fluorophenyl)-N-methylbenzofuran-3-carboxamide (100 mg, 0.19 mmol) in THF, 1-chloro-2-isocyanatoethane (60 mg, 0.57 mmol) was added at 80° C. Then the reaction mixture was stirred at room temperature overnight. The mixture was extracted with EtOAc, washed with brine, dried and concentrated to provide 6-(3-(2-chloroethyl)ureido)-5-(11-fluoro-6H-pyrido[2',3':5,6][1,3]oxazino[3,4-a]indol-2-yl)-2-(4-fluorophenyl)-N-methylbenzofuran-3-carboxamide (80 mg, yield: 66.5%) without further purification. MS (M+H)$^+$: 628.

Step 2—Synthesis of 5-(11-fluoro-6H-pyrido[2',3':5,6][1,3]oxazino[3,4-a]indol-2-yl)-2-(4-fluorophenyl)-N-methyl-6-(2-oxoimidazohdin-1-yl)benzofuran-3-carboxamide

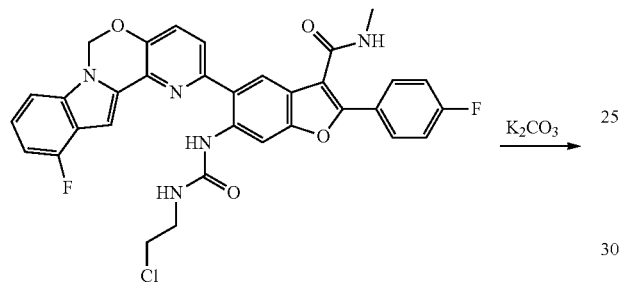

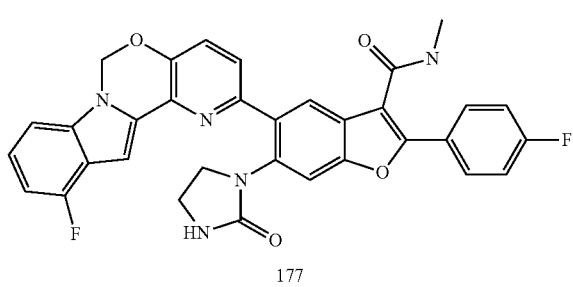

177

To a solution of 6-(3-(2-chloroethyl)ureido)-5-(11-fluoro-6H-pyrido[2',3':5,6][1,3]oxazino[3,4-a]indol-2-yl)-2-(4-fluorophenyl)-N-methylbenzofuran-3-carboxamide (80 mg, 0.13 mmol) in CH$_3$CN (2 mL), K$_2$CO$_3$ (50 mg, 0.36 mmol) was stirred reflux overnight. The reaction mixture was concentrated in vacuo. The resulting residue was suspended with water and extracted with EtOAc. The combined organic phases were washed with brine, dried over Na$_2$SO$_4$, filtered and concentrated in vacuo. The crude product was purified using PTLC (eluted with dichloromethane:MeOH=50:1) to provide compound 177 (20 mg, yield: 26.6%). $^1$H-NMR (DMSO-d$_6$, 400 MHz) δ 8.56 (d, J=4.8 Hz, 1H), 8.02 (dd, J=8.8 Hz, J$_2$=5.6 Hz, 2H), 7.81 (s, 1H), 7.77 (s, 1H), 7.68 (d, J=8.4 Hz, 1H), 7.57 (d, J=8.8 Hz, 1H), 7.51 (d, J=8.4 Hz, 1H), 7.41 (t, J=8.8 Hz, 2H), 7.23~7.28 (m, 1H), 7.10 (s, 1H), 6.94 (dd, J$_1$=J$_2$=8.0 Hz, 1H), 6.54 (s, 1H), 6.25 (s, 2H), 3.84 (t, J=8.4 Hz, 2H), 3.32 (t, J=8.4 Hz, 2H), 2.83 (s, 3H). MS (M+H)$^+$: 592.

Example 67

Preparation of Compound 178

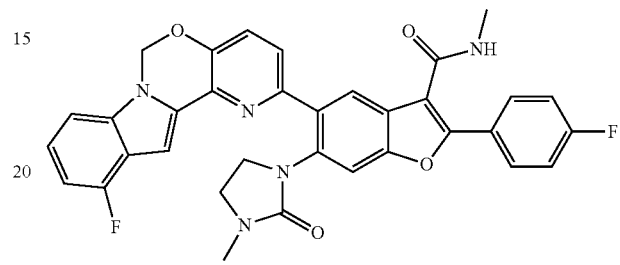

178

Step 1—Synthesis of 1-(2-chloroethyl)-3-methylurea

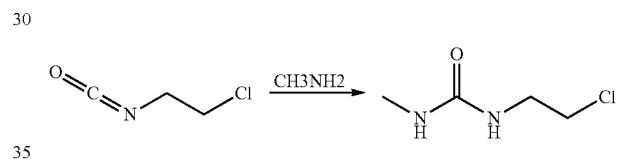

To a solution of 1-chloro-2-isocyanatoethane (5 g, 47 mmol) in THF (120 mL) was added 2M CH$_3$NH$_2$ (38 mL) in THF at 0° C. The reaction mixture was stirred at room temperature overnight, concentrated in vacuo to provide 1-(2-chloroethyl)-3-methylurea (6 g, yield: 92%) and used to the next step without purified. $^1$H-NMR (CDCl$_3$, 400 MHz) δ 5.48 (s, 1H), 5.21 (s, 1H), 3.56~3.59 (m, 2H), 3.47~3.52 (m, 2H), 2.74 (s, 3H). MS (M+H)$^+$: 137.

Step 2—Synthesis of 1-methylimidazolidin-2-one

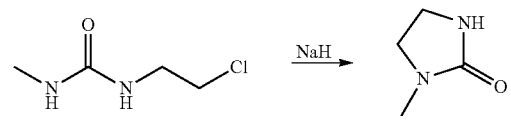

To a solution of 1-(2-chloroethyl)-3-methylurea (3 g, 22 mmol) was dissolved in THF (80 mL) and to the resulting solution was added NaH (2.2 g, 55 mmol). The reaction mixture was stirred at room temperature under N$_2$ for 18 hours, quenched with MeOH, filtrated, the filtrate was dried with Na$_2$SO$_4$, concentrated in vacuo to provide 1-methylimidazolidin-2-one (1.5 g, yield: 68%). MS (M+H)$^+$: 101.

Step 3—Synthesis of 5-(11-fluoro-6H-pyrido[2',3':5,6][1,3]oxazino[3,4-a]indol-2-yl)-2-(4-fluorophenyl)-N-methyl-6-(3-methyl-2-oxoimidazolidin-1-yl)benzofuran-3-carboxamide (Compound 178)

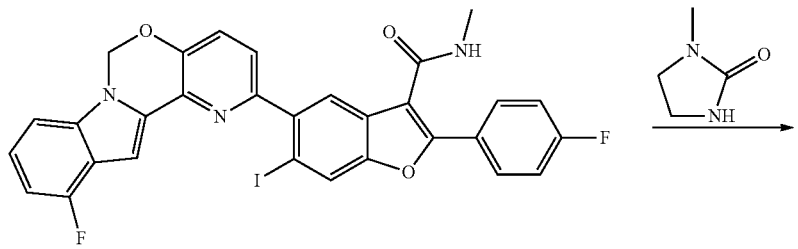

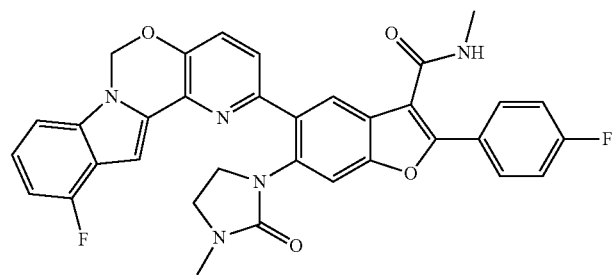

178

To a solution of 5-(11-fluoro-6H-pyrido[2',3':5,6][1,3]oxazino[3,4-a]indol-2-yl)-2-(4-fluorophenyl)-6-iodo-N-methylbenzofuran-3-carboxamide (200 mg, 0.3 mmol), 1-methylimidazolidin-2-one (63 mg, 0.6 mmol) and $Cs_2CO_3$ (206 mg, 0.6 mmol) in 1,4-dioxane (5 mL) was added (1R,2R)—$N^1,N^2$-dimethylcyclohexane-1,2-diamine (20 mg) and CuI (20 mg) under nitrogen. The reaction mixture was heated at 100° C. overnight in seal tube, concentrated in vacuo to remove 1,4-dioxane and purified to provide compound 178 (20 mg, yield: 10%) through the prep-HPLC. $^1$H-NMR (CDCl$_3$, 400 MHz) δ 7.90~7.95 (m, 3H), 7.49 (s, 1H), 7.45 (d, J=8.4 Hz, 1H), 7.38 (d, J=8.4 Hz, 1H), 7.04~7.14 (m, 4H), 7.76~7.81 (m, 1H), 6.76~6.81 (m, 1H), 5.91 (s, 2H), 5.85 (brs, 1H), 3.62~3.66 (m, 2H), 3.26~3.30 (m, 2H), 2.94 (d, J=4.8 Hz, 3H), 2.68 (s, 3H). MS (M+H)$^+$: 606.

Example 68

Preparation of Compound 179

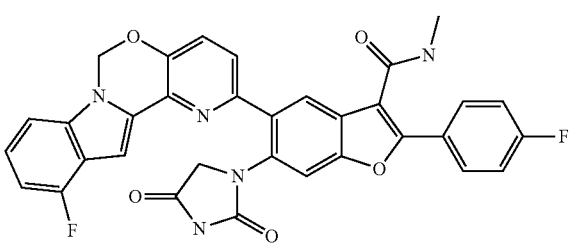

179

Step 1—Synthesis of 6-(3-(2-chloroacetyl)ureido)-5-(11-fluoro-6H-pyrido[2',3':5,6][1,3]oxazino[3,4-a]indol-2-yl)-2-(4-fluorophenyl)-N-methylbenzofuran-3-carboxamide

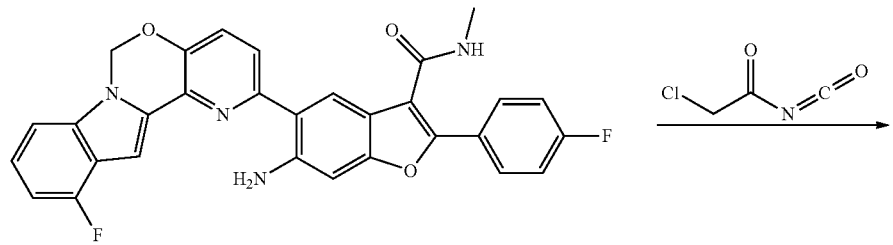

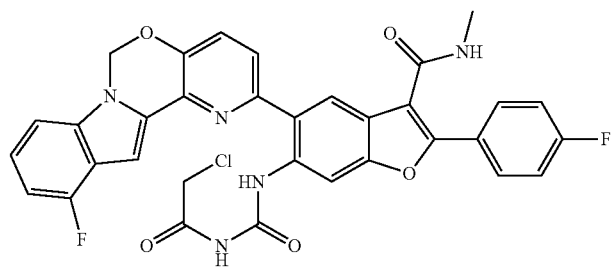

To a solution of 6-amino-5-(11-fluoro-6H-pyrido[2',3':5,6][1,3]oxazino[3,4-a]indol-2-yl)-2-(4-fluorophenyl)-N-methylbenzofuran-3-carboxamide (200 mg, 0.38 mmol) in THF (15 mL) was added a solution of 2-chloroacetyl isocyanate (100 mg, 0.78 mmol) in THF (1 mL) dropwise under nitrogen. The mixture was stirred at room temperature overnight. The solvent was removed under reduced pressure, the resulting residue was obtained 6-(3-(2-chloroacetyl)ureido)-5-(11-fluoro-6H-pyrido[2',3':5,6][1,3]oxazino[3,4-a]indol-2-yl)-2-(4-fluorophenyl)-N-methylbenzofuran-3-carboxamide (203 mg, yield: 81%) without further purification. MS (M+H)$^+$: 642.

Step 2—Synthesis of 6-(2,4-dioxoimidazolidin-1-yl)-5-(11-fluoro-6H-pyrido[2',3':5,6][1,3]oxazino[3,4-a]indol-2-yl)-2-(4-fluorophenyl)-N-methylbenzofuran-3-carboxamide (Compound 179)

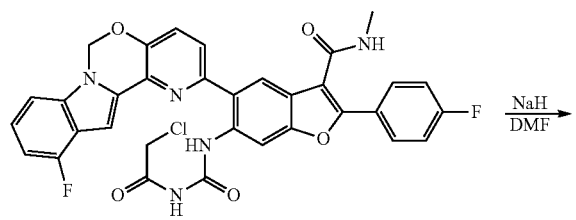

-continued

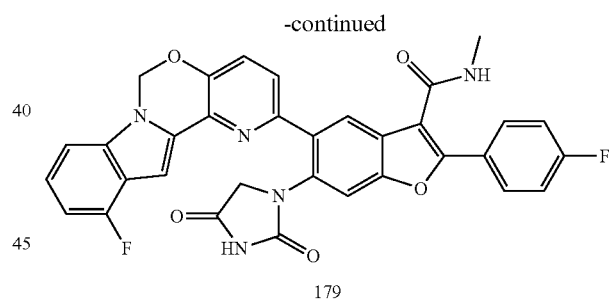

179

To a solution of 6-(3-(2-chloroacetyl)ureido)-5-(11-fluoro-6H-pyrido[2',3':5,6][1,3]oxazino[3,4-a]indol-2-yl)-2-(4-fluorophenyl)-N-methylbenzofuran-3-carboxamide (140 mg, 0.22 mmol) in DMF (10 mL) was added NaH (26 mg, 0.65 mmol) at 0° C. The mixture was stirred at 0° C. for 30 minutes. The reaction was quenched with saturated aqueous NH$_4$Cl, and the solvent was removed under reduced pressure. The resulting residue was diluted with water and extracted CH$_2$Cl$_2$/MeOH (10:1). The organic layers were washed with brine, dried over Na$_2$SO$_4$, and concentrated to provide the crude. The crude was purified using prep-HPLC to obtained compound 179 (65 mg yield: 50%). $^1$H-NMR (CDCl$_3$, 400 MHz) δ 8.08 (s, 1H), 7.95 (t, J=7.2 Hz, 2H), 7.63 (s, 1H), 7.57 (s, 1H), 7.49 (d, J=8.4 Hz, 1H), 7.41 (d, J=8.4 Hz, 1H), 7.22 (d, J=8.8 Hz, 2H), 7.20 (s, 1H), 7.07 (d, J=6.4 Hz, 2H), 6.84 (t, J=8.8 Hz, 1H), 6.55 (d, J=4.4 Hz, 1H), 5.92 (s, 2H), 4.32 (s, 2H), 3.00 (d, J=4.8 Hz, 3H). MS (M+H)+: 606.

Example 69

Preparation of Compound 180

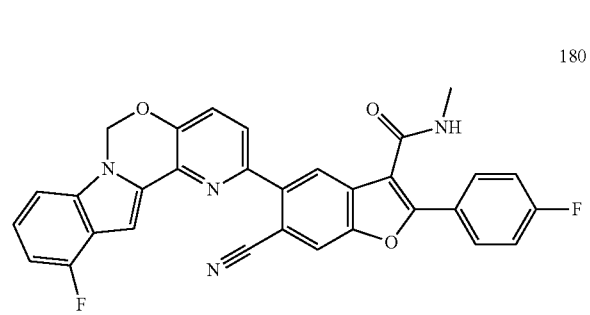

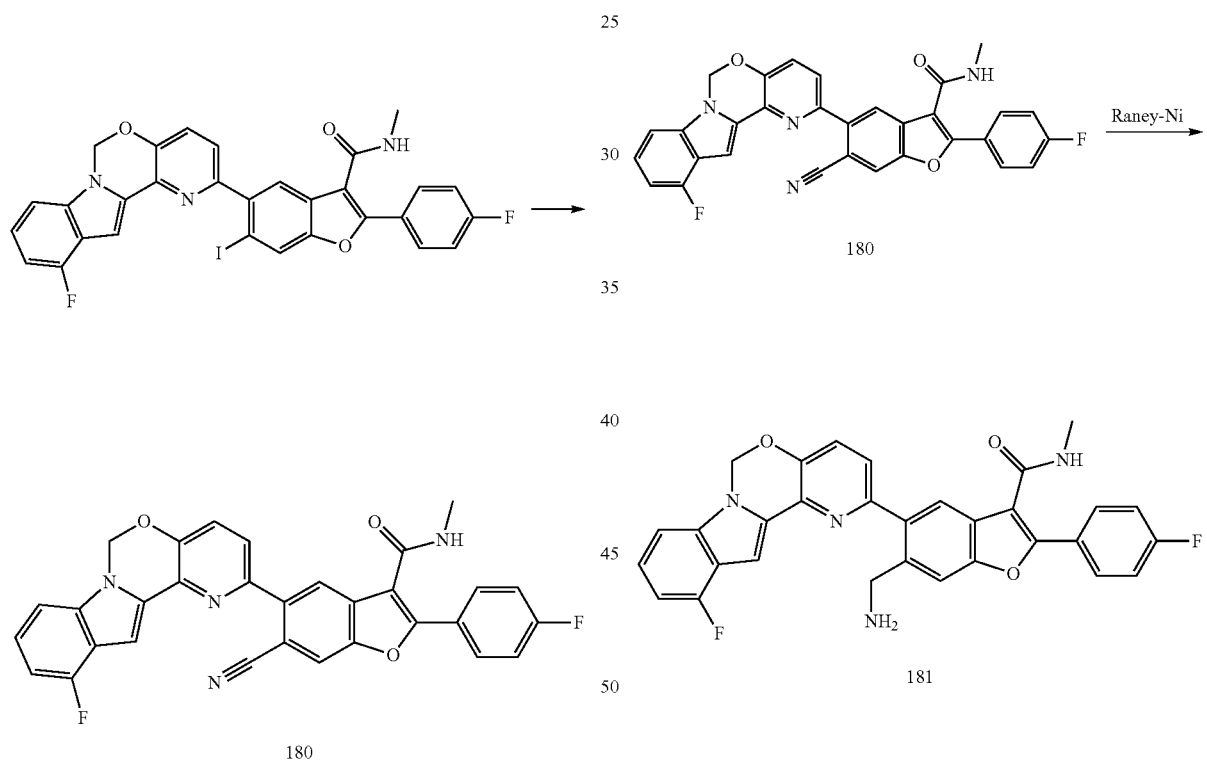

To a degassed solution of 5-(11-fluoro-6H-pyrido[2',3':5,6][1,3]oxazino[3,4-a]indol-2-yl)-2-(4-fluorophenyl)-6-iodo-N-methylbenzofuran-3-carboxamide (150 mg, 0.24 mmol) and Zn(CN)₂ (28 mg, 0.24 mmol) in DMSO (3.0 mL) were added Pd(PPh₃)₄(20 mg) under N₂. The mixture was heated at 100° C. for 3 hours. The reaction mixture was cooled to room temperature and added water. Then the suspension was filtered, the collection was purified using the prep-HPLC to provide compound 180 (50 mg, yield: 40%). ¹H-NMR (DMSO, 400 MHz) δ 8.60 (s, 1H), 8.42 (s, 1H), 8.10 (s, 1H), 8.00 (t, J=4.4 Hz, 2H), 7.90 (d, J=8.4 Hz, 1H), 7.76 (d, J=8.8 Hz, 1H), 7.48 (d, J=8.4 Hz, 1H), 7.41 (t, J=8.8 Hz, 2H), 7.23 (d, J=7.6 Hz, 1H), 7.18 (s, 1H), 6.91 (t, J=8.8 Hz, 1H), 6.27 (s, 2H). 2.82 (s, 3H). MS (M+H)+: 533.

Example 70

Preparation of Compound 181

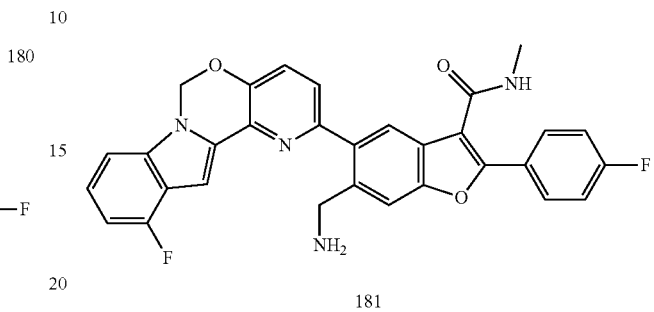

A solution of 6-cyano-5-(11-fluoro-6H-pyrido[2',3':5,6][1,3]oxazino[3,4-a]indol-2-yl)-2-(4-fluorophenyl)-N-methylbenzofuran-3-carboxamide (50 mg, 0.09 mmol) and Raney-Ni (10 mg) in dichloromethane/MeOH (10 mL, V/V=3:1) was hydrogenated at room temperature under hydrogen for 10 hours. After filtered, the filtrate was concentrated to provide the crude product. The crude product was purified using the prep-HPLC to provide compound 181 (10 mg, yield: 20%). ¹H-NMR (DMSO, 400 MHz) δ 8.55 (d, J=5.2 Hz, 1H), 8.04 (t, J=7.6 Hz, 2H), 7.99 (s, 1H), 7.84 (s, 1H), 7.81 (s, 1H), 7.77 (d, J=8.4 Hz, 1H), 7.60 (t, J=8.4 Hz, 1H), 7.54 (d, J=8.4 Hz, 2H), 7.42 (t, J=8.8 Hz, 2H), 7.31 (s, 1H), 7.29 (m, 1H), 6.95 (t, J=8.8 Hz, 1H), 6.29 (s, 2H), 4.18 (s, 2H), 2.85 (d, J=4.4 Hz, 3H). MS (M+H)+: 537.

Example 71

Preparation of Compound 182

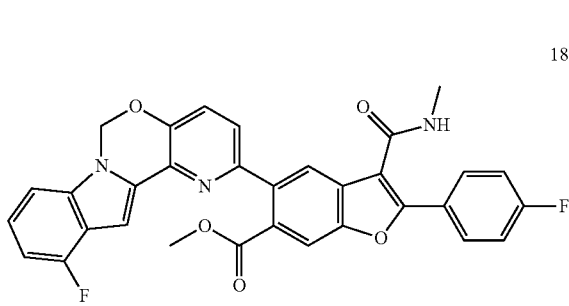

182

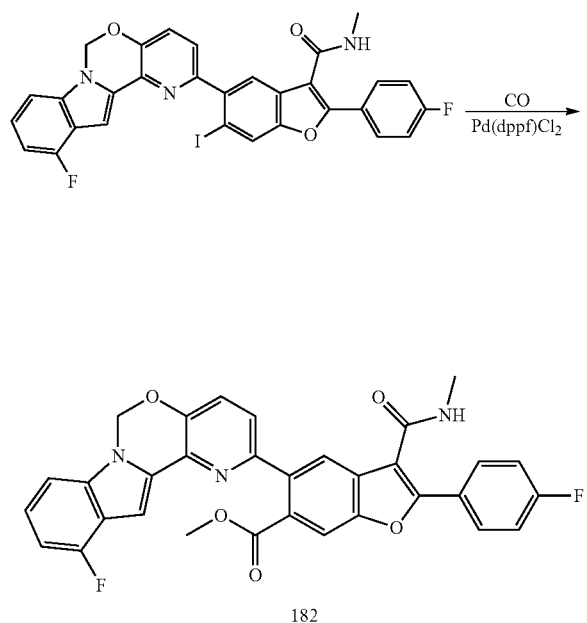

To a solution of 5-(11-fluoro-6H-pyrido[2',3':5,6][1,3]oxazino[3,4-a]indol-2-yl)-2-(4-fluorophenyl)-6-iodo-N-methylbenzofuran-3-carboxamide (100 mg, 0.15 mmol) and Et₃N (36 mg, 0.36 mmol) in DMSO (5 mL) and MeOH (2 mL) was added Pd(dppf)Cl₂ (10 mg). The reaction mixture was stirred under CO atmosphere (30 psi) at 80° C. for 10 hours, concentrated and extracted with EtOAc. The combined organic phase was washed with brine, dried over Na₂SO₄ and concentrated to provide the compound 182 (30 mg, yield: 36%) through the prep-HPLC. ¹H-NMR (DMSO, 400 MHz) δ 8.56 (d, J=4.0 Hz, 1H), 8.03~8.01 (m, 2H), 7.93 (s, 1H), 7.78 (d, J=8.8 Hz, 1H), 7.71 (d, J=8.4 Hz, 1H), 7.49 (d, J=8.4 Hz, 1H), 7.40 (t, J=8.8 Hz, 2H), 7.24 (d, J=8.0 Hz, 1H), 6.97 (s, 1H), 6.92 (t, J=8.8 Hz, 1H), 6.24 (s, 2H), 5.73 (s, 1H), 3.58 (s, 3H), 2.83 (d, J=4.5 Hz, 3H). MS (M+H)+: 566.

Example 72

Preparation of Compound 183

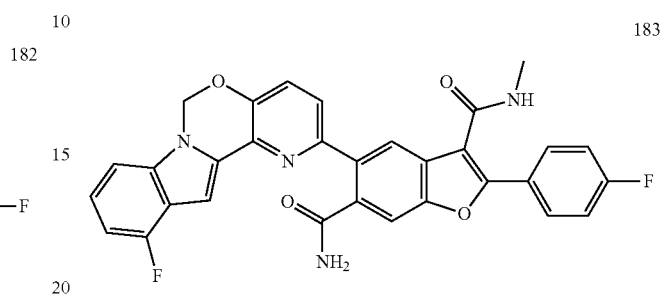

183

Step 1—Synthesis of 5-(11-fluoro-6H-pyrido[2',3':5,6][1,3]oxazino[3,4-a]indol-2-yl)-2-(4-fluorophenyl)-3-(methylcarbamoyl)benzofuran-6-carboxylic acid

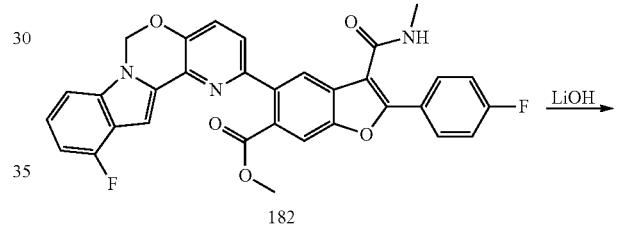

The procedure of 5-(11-fluoro-6H-pyrido[2',3':5,6][1,3]oxazino[3,4-a]indol-2-yl)-2-(4-fluorophenyl)-3-(methylcarbamoyl)benzofuran-6-carboxylic acid (30 mg, yield: 45%) was similar to step 1 of Example 38. MS (M+H)+: 552.

Step 2—Synthesis of 5-(11-fluoro-6H-pyrido[2',3':5,6][1,3]oxazino[3,4-a]indol-2-yl)-2-(4-fluorophenyl)-N3-methylbenzofuran-3,6-dicarboxamide (Compound 183)

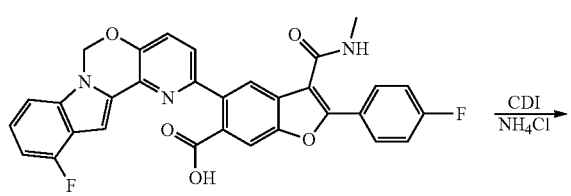

-continued

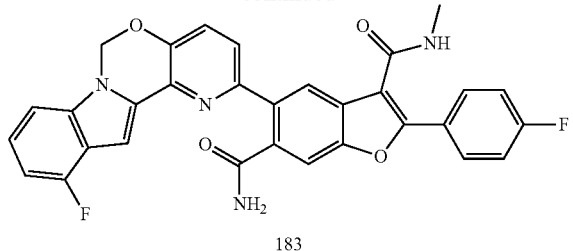

183

To a degassed solution of 5-(11-fluoro-6H-pyrido[2',3':5,6][1,3]oxazino[3,4-a]indol-2-yl)-2-(4-fluorophenyl)-3-(methylcarbamoyl)benzofuran-6-carboxylic acid (50 mg, 0.09 mmol), EDCI (25 mg, 0.13 mmol), HOBT (20 mg, 0.13 mmol), NH$_4$Cl (24 mg, 0.45 mmol) and Et$_3$N (45 mg, 0.45 mmol) in THF (3 mL) was stirred at room temperature for 2 hours under N$_2$. The reaction mixture was extracted with EtOAc and washed with water, brine and dried over Na$_2$SO$_4$. After concentrated, the crude product was purified using prep-HPLC to provide compound 183 (20 mg, yield: 40%). $^1$H-NMR (DMSO, 400 MHz) δ 8.50 (d, J=5.2 Hz, 1H), 7.98~7.99 (m, 2H), 7.92 (s, 1H), 7.81 (s, 1H), 7.76 (s, 1H), 7.63 (d, J=4.0 Hz, 1H), 7.56 (d, J=8.4 Hz, 1H), 7.43~7.47 (m, 2H), 7.37 (t, J=8.8 Hz, 2H), 7.18~7.21 (m, 1H), 7.05 (s, 1H), 6.89 (t, J=9.2 Hz, 1H), 6.20 (s, 2H), 2.80 (d, J=4.8 Hz, 3H). MS (M+H)$^+$: 551.

Example 73

Preparation of Compound 184

184

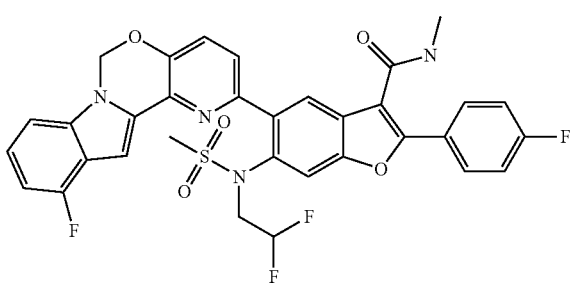

Step 1—Synthesis of 2,2-difluoroethyl 4-methylbenzenesulfonate

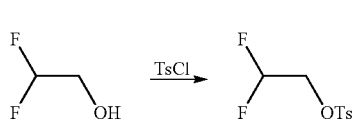

To a solution of compound 2,2-difluoroethanol (1 g, 12.2 mmol) in CH$_2$Cl$_2$ (15 mL) was added TsCl (3.5 g, 18.3 mmol) at 0° C. The mixture was stirred at room temperature overnight. Then aqueous HCl was added to the mixture to adjusted the mixture to pH<7 and the mixture was separated. The aqueous phase was extracted with EtOAc and the combined organic phases was washed with brine, dried over Na$_2$SO$_4$ and concentrated in vacuo. The resulting residue was purified using column chromatography (petroleum ether:EtOAc=15:1) to provide 2,2-difluoroethyl 4-methylbenzenesulfonate. (2.5 g, yield: 86.8%). $^1$H-NMR (CDCl$_3$, 400 MHz) δ 7.78 (d, J=8.0 Hz, 2H), 7.35 (d, J=8.0 Hz, 2H), 5.75~6.04 (m, 1H), 4.10~4.18 (m, 2H), 2.44 (s, 3H). MS (M+H)$^+$: 267.

Step 2—Synthesis of 5-bromo-6-(N-(2,2-difluoroethyl)methylsulfonamido)-2-(4-fluorophenyl)-N-methylbenzofuran-3-carboxamide

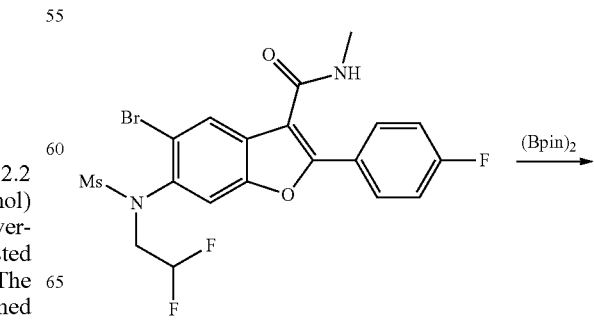

A mixture of compound 2,2-difluoroethyl 4-methylbenzenesulfonate (0.3 g, 1.25 mmol), 5-bromo-6-(N-(2,2-difluoroethyl)methylsulfonamido)-2-(4-fluorophenyl)-N-methylbenzofuran-3-carboxamide (0.55 g, 1.25 mmol), K$_2$CO$_3$ (0.35 g, 2.5 mmol) and KI (0.25 g, 0.15 mmol) in DMF (10 mL) was stirred at 80° C. under reflux for 2 hours. The mixture was concentrated in vacuo and the resulting residue was washed by H$_2$O and filtered to provide 5-bromo-6-(N-(2,2-difluoroethyl)methylsulfonamido)-2-(4-fluorophenyl)-N-methylbenzofuran-3-carboxamide (440 mg, yield: 70.2%). $^1$H-NMR (CDCl$_3$, 400 MHz) δ 8.18 (s, 1H), 7.86~7.89 (m, 2H), 7.66~7.72 (m, 1H), 7.18~7.22 (m, 2H), 5.92~6.23 (m, 1H), 5.78 (s, 1H), 4.12~4.32 (m, 1H), 3.71~3.89 (m, 1H), 3.09 (s, 3H), 2.98 (d, J=4.8 Hz, 3H). MS (M+H)$^+$: 505/507.

Step 3—Synthesis of 6-(N-(2,2-difluoroethyl)methylsulfonamido)-2-(4-fluorophenyl)-N-methyl-5-(4,4,5,5-tetramethyl-1,3,2-dioxaborolan-2-yl)benzofuran-3-carboxamide 303
-continued

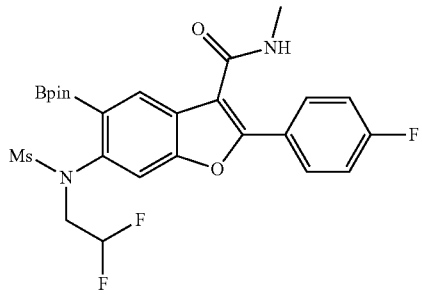

To a solution of 5-bromo-6-(N-(2,2-difluoroethyl)methylsulfonamido)-2-(4-fluorophenyl)-N-methylbenzofuran-3-carboxamide (2 g, 4 mmol), (Bpin)₂ (3 g, 6 mmol) and KOAc (1.2 g, 6 mmol) in dioxane/H₂O (100/10 mL) was added Pd(dppf)Cl₂ (0.4 g, 0.3 mmol) under N₂. The mixture was stirred at 80° C. under reflux for 4 hours. Then it was filtered and extracted with EtOAc. The combined organic phase was washed with brine, dried over Na₂SO₄ and concentrated in vacuo. The resulting residue was purified using flash gel chromatography (petroleum ether:EtOAc=4:1) to provide 6-(N-(2,2-difluoroethyl)methylsulfonamido)-2-(4-fluorophenyl)-N-methyl-5-(4,4,5,5-tetramethyl-1,3,2-dioxaborolan-2-yl)benzofuran-3-carboxamide (1.63 g, yield: 74.0%). ¹H-NMR (CDCl₃, 400 MHz) δ 8.32 (s, 1H), 7.93 (m, 2H), 7.60 (s, 1H), 7.17 (t, J=8.4 Hz, 2H), 5.92~5.98 (m, 1H), 4.20~4.31 (m, 1H), 3.77 (br s, 1H), 3.02 (d, J=4.8 Hz, 3H), 2.98 (s, 3H), 1.36 (s, 12H). MS (M+H)⁺: 553.

Step 4—Synthesis of 6-(N-(2,2-difluoroethyl)methylsulfonamido)-5-(11-fluoro-6H-pyrido[2',3':5,6][1,3]oxazino[3,4-a]indol-2-yl)-2-(4-fluorophenyl)-N-methylbenzofuran-3-carboxamide (Compound 184)

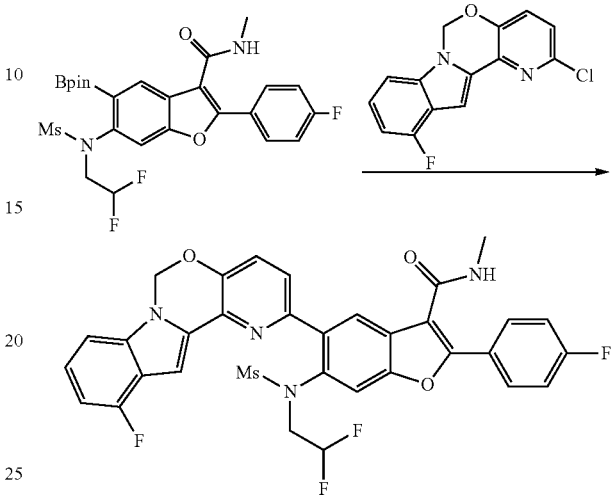

The procedure of Compound 184 (150 mg, yield: 62.5%) was similar to step 6 of Example 1. ¹H-NMR (CDCl₃, 400 MHz) δ 8.01 (s, 1H), 7.91~7.95 (m, 2H), 7.73 (s, 1H), 7.50 (s, 2H), 7.16~7.23 (m, 4H), 7.09~7.11 (m, 1H), 6.82~6.86 (m, 1H), 5.86~6.23 (m, 4H), 4.05~4.16 (m, 2H), 2.97 (d, J=4.8 Hz, 3H), 2.86 (s, 3H). MS (M+H)⁺: 665.

Compounds 185-204, depicted in the table below, were prepared using the method described above and substituting the appropriate reactants and/or reagents. For some compounds, such as Compound 204, mesylation and alkylation were conducted as the last two steps using compound 163.

| Compound No | Structure | NMR | MS (M + H)⁺ |
|---|---|---|---|
| 185 | 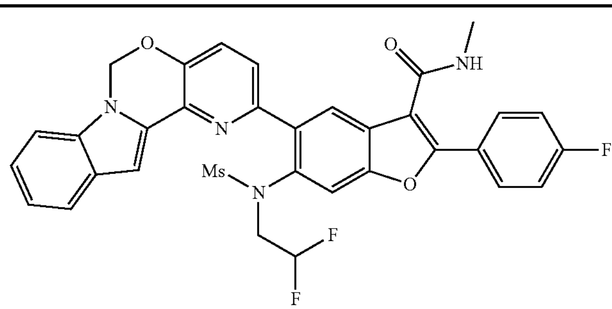 | ¹H-NMR (CDCl₃, 400 MHz) δ 8.01 (s, 1H), 7.91~7.93 (m, 2H), 7.69~7.74 (m, 2H), 7.48 (s, 2H), 7.28~7.34 (m, 2H), 7.15~7.23 (m, 3H), 7.11 (s, 1H), 5.96~6.26 (m, 3H), 5.85~5.86 (m, 1H), 4.05~4.11 (m, 2H), 2.97 (d, J = 4.8 Hz, 3H), 2.80 (s, 3H). | 647 |
| 186 | 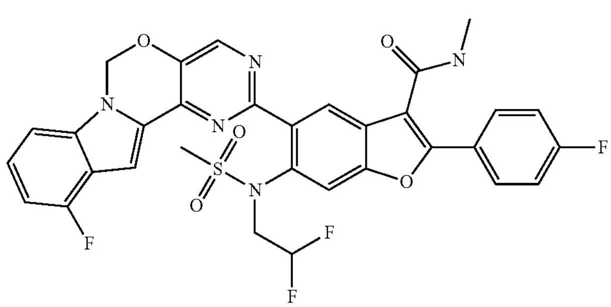 [SMILES: CNC(=O)c1c(-c2ccc(F)cc2)oc2cc(N(CC(F)F)S(C)(=O)=O)c(-c3ncc4c(n3)-c3cc5c(F)cccc5n3CO4)cc12] | ¹H-NMR (DMSO-d₆, 400 MHz) δ 8.84 (s, 1H), 8.60 (s, 1H), 8.23 (s, 1H), 7.94~8.00 (m, 3H), 7.52~7.55 (m, 1H), 7.29~7.42 (m, 4H), 6.94~6.99 (m, 1H), 6.28~6.42 (m, 3H), 4.31~4.34 (m, 1H), 4.06~4.09 (m, 1H), 2.98 (s, 3H), 2.81 (d, J = 4.4 Hz, 3H). | 666 |

-continued

| Compound No | Structure | NMR | MS (M + H)+ |
|---|---|---|---|
| 187 | 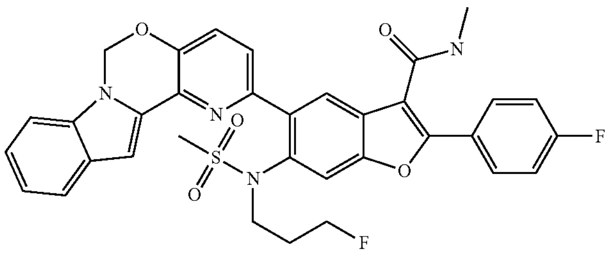 [SMILES: CNC(=O)c1c(-c2ccc(F)cc2)oc2cc(N(CCCF)S(C)(=O)=O)c(-c3ccc4c(n3)-c3cc5ccccc5n3CO4)cc12] | ¹H-NMR (CDCl₃, 400 MHz) δ 7.95~7.99 (m, 3H), 7.71 (t, J = 4.0 Hz, 2H), 7.50 (s, 2H), 7.29~7.36 (m, 2H), 7.14~7.24 (m, 4H), 6.02 (s, 2H), 5.92 (s, 1H), 4.45 (s, 1H), 4.33 (s, 1H), 3.75 (s, 2H), 2.99 (d, J = 4.8 Hz, 3H), 2.87 (s, 3H), 1.95~2.04 (m, 2H). | 643 |
| 188 | 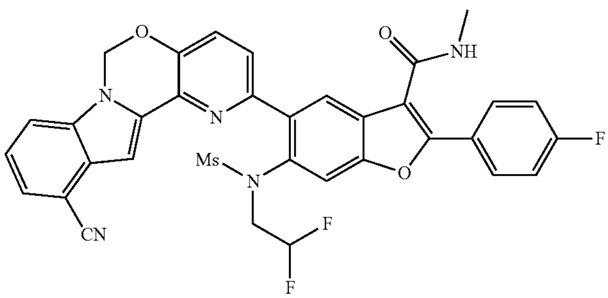 [SMILES: CNC(=O)c1c(-c2ccc(F)cc2)oc2cc(N(CC(F)F)S(C)(=O)=O)c(-c3ccc4c(n3)-c3cc5c(C#N)cccc5n3CO4)cc12] | ¹H-NMR (CDCl₃, 400 MHz) δ 8.03 (s, 1H), 7.93~7.97 (m, 2H), 7.73 (s, 1H), 7.52~7.60 (m, 4H), 7.30~7.36 (m, 2H), 7.20~7.22 (m, 2H), 5.84~6.21 (m, 4H), 3.98~4.21 (m, 2H), 2.98 (d, J = 4.8 Hz, 3H), 2.97 (s, 3H). | 672 |
| 189 | 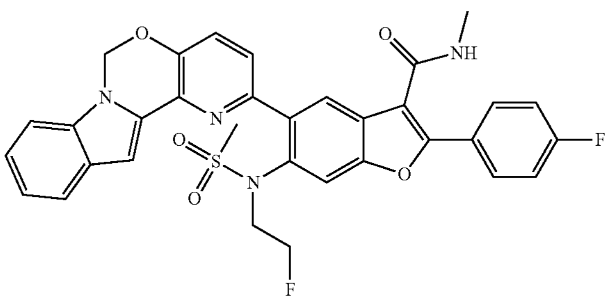 [SMILES: CNC(=O)c1c(-c2ccc(F)cc2)oc2cc(N(CCF)S(C)(=O)=O)c(-c3ccc4c(n3)-c3cc5ccccc5n3CO4)cc12] | ¹H-NMR (CDCl₃, 400 MHz) δ 8.03 (s, 1H), 7.99~7.97 (m, 2H), 7.70~7.68 (m, 2H), 7.58 (d, J = 8 Hz, 1H), 7.50 (d, J = 8 Hz, 1H), 7.23~7.28 (m, 2H), 7.24~7.13 (m, 4H), 6.01 (s, 2H), 5.92 (s, 1H), 4.65 (d, J = 72 Hz, 2H), 4.23~3.74 (m, 2H), 3.07~2.97 (m, 6H). | 629 |
| 190 | 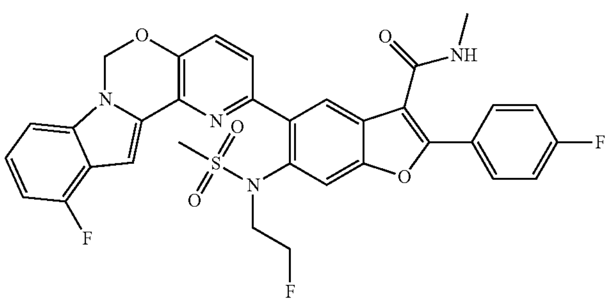 [SMILES: CNC(=O)c1c(-c2ccc(F)cc2)oc2cc(N(CCF)S(C)(=O)=O)c(-c3ccc4c(n3)-c3cc5c(F)cccc5n3CO4)cc12] | ¹H-NMR (CDCl₃, 400 MHz) δ 8.04 (s, 1H), 8.00~7.96 (m, 2H), 7.69 (s, 1H), 7.61 (d, J = 4.4 Hz, 1H), 7.51 (d, J = 8.8 Hz, 1H), 7.22 (m, 4H), 7.13 (d, J = 4.4 Hz, 1H), 6.87~6.82 (m, 1H), 6.01 (s, 2H), 5.90 (s, 1H), 4.67 (d, J = 4.8 Hz, 2H), 4.21~3.75 (m, 2H), 3.01~2.99 (m, 6H). | 647 |
| 191 | 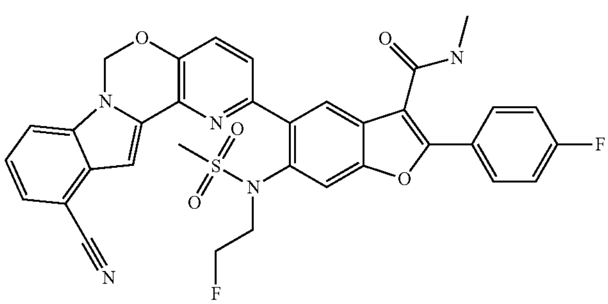 [SMILES: CNC(=O)c1c(-c2ccc(F)cc2)oc2cc(N(CCF)S(C)(=O)=O)c(-c3ccc4c(n3)-c3cc5c(C#N)cccc5n3CO4)cc12] | ¹H-NMR (CDCl₃, 400 MHz) δ 8.05 (s, 1H), 8.00~7.96 (m, 2H), 7.67 (d, J = 8.0 Hz, 2H), 7.57~7.52 (m, 3H), 7.36~7.34 (m, 2H), 7.23 (d, J = 8 Hz, 2H), 6.06 (s, 2H), 5.89 (s, 1H), 4.70 (d, J = 8 Hz, 2H), 4.57~4.53 (m, 2H), 4.25~4.12 (m, 1H), 3.77~3.63 (m, 1H), 3.04 (s, 1H), 3.01 (s, 1H), 3.00 (s, 1H). | 654 |

| Compound No | Structure | NMR | MS (M + H)+ |
|---|---|---|---|
| 192 | 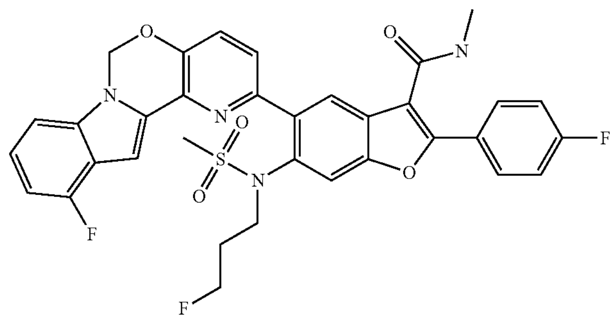 [SMILES: CNC(=O)c1c(-c2ccc(F)cc2)oc2cc(N(CCCF)S(C)(=O)=O)c(-c3ccc4c(n3)-c3cc5c(F)cccc5n3CO4)cc12] | ¹H-NMR (CDCl₃, 400 MHz) δ 7.89~7.92 (m, 3H), 7.63 (s, 1H), 7.42~7.49 (m, 2H), 7.12~7.16 (m, 4H), 7.05 (d, J = 8.4 Hz, 1H), 6.79 (d, J = 8.0 Hz, 1H), 5.94 (s, 2H), 5.79 (s, 1H), 4.26~4.38 (m, 2H), 3.69 (s, 2H), 2.93 (d, J = 4.8 Hz, 3H), 2.89 (s, 3H), 1.88~2.98 (m, 2H). | 661 |
| 193 | 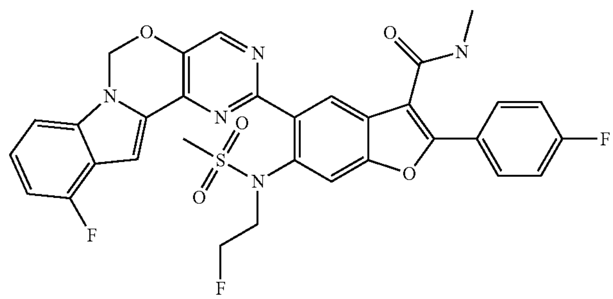 [SMILES: CNC(=O)c1c(-c2ccc(F)cc2)oc2cc(N(CCF)S(C)(=O)=O)c(-c3ncc4c(n3)-c3cc5c(F)cccc5n3CO4)cc12] | ¹H-NMR (CDCl₃, 400 MHz) δ 8.65 (s, 1H), 8.48 (s, 1H), 8.02~8.06 (m, 2H), 7.75 (s, 1H), 7.48 (s, 1H), 7.13~7.32 (m, 4H), 6.87~6.91 (m, 1H), 6.07 (s, 3H), 4.63~4.78 (m, 2H), 4.48 (s, 1H), 4.02~4.10 (m, 1H), 3.05 (d, J = 4.4 Hz, 3H), 2.97 (s, 3H). | 648 |
| 194 | 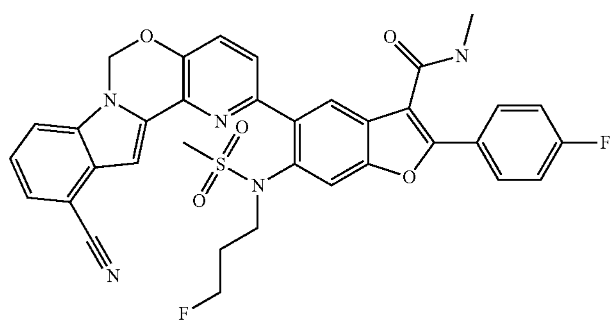 [SMILES: CNC(=O)c1c(-c2ccc(F)cc2)oc2cc(N(CCCF)S(C)(=O)=O)c(-c3ccc4c(n3)-c3cc5c(C#N)cccc5n3CO4)cc12] | ¹H-NMR (CDCl₃, 400 MHz) δ 7.94~8.80 (m, 3H), 7.61~7.67 (m, 2H), 7.51~7.57 (m, 3H), 7.30~7.35 (m, 2H), 7.19~7.23 (m, 2H), 6.05 (s, 2H), 5.90 (brs, 1H), 4.31~4.43 (m, 2H), 3.73 (t, J = 7.2 Hz, 2H), 2.99 (d, J = 4.4 Hz, 3H), 2.91 (s, 3H), 1.93~2.05 (m, 2H). | 668 |
| 195 | 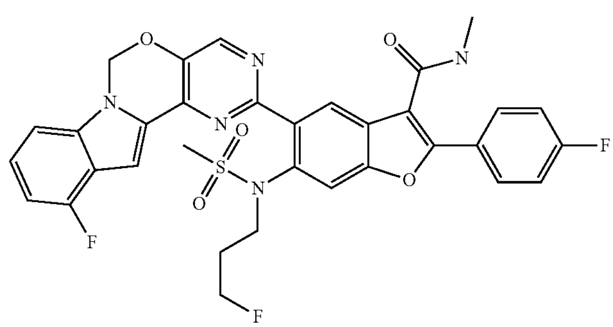 [SMILES: CNC(=O)c1c(-c2ccc(F)cc2)oc2cc(N(CCCF)S(C)(=O)=O)c(-c3ncc4c(n3)-c3cc5c(F)cccc5n3CO4)cc12] | ¹H-NMR (CDCl₃, 400 MHz) δ 8.64 (s, 1H), 8.40 (s, 1H), 7.99~8.03 (m, 2H), 7.76 (s, 1H), 7.49 (s, 1H), 7.13~7.33 (s, 4H), 6.87~6.92 (m, 1H), 6.07 (s, 2H), 6.00 (s, 1H), 4.57~4.60 (m, 1H), 4.45~4.48 (m, 1H), 3.97 (br s, 1H), 3.72 (br s, 1H), 3.04 (d, J = 4.8 Hz, 3H), 2.93 (s, 3H), 2.07~2.17 (m, 2H). | 662 |
| 196 | 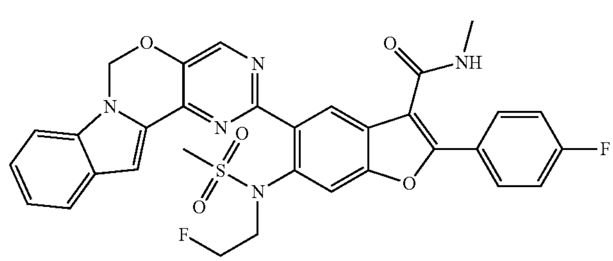 [SMILES: CNC(=O)c1c(-c2ccc(F)cc2)oc2cc(N(CCF)S(C)(=O)=O)c(-c3ncc4c(n3)-c3cc5ccccc5n3CO4)cc12] | ¹H-NMR (DMSO-d6, 400 MHz) δ 8.78 (s, 1H), 8.59 (s, 1H), 8.20 (s, 1H), 7.97~8.00 (m, 2H), 7.91 (s, 1H), 7.77 (s, 1H), 7.76 (s, 1H), 7.35~7.42 (m, 3H), 7.30~7.34 (m, 1H) 7.13~7.17 (m, 1H), 6.29 (s, 2H), 4.77 (br s, 1H), 4.65 (br s, 1H), 4.23 (br s, 1H), 3.98 (br s, 1H), 2.92 (s, 3H), 2.81 (d, J = 4.8 Hz, 3H). | 630 |

| Compound No | Structure | NMR | MS (M + H)+ |
|---|---|---|---|
| 197 | 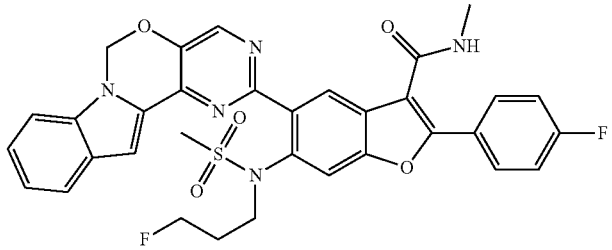 [SMILES: CNC(=O)c1c(-c2ccc(F)cc2)oc2cc(N(CCCF)S(C)(=O)=O)c(-c3ncc4c(n3)-c3cc5ccccc5n3CO4)cc12] | $^1$H-NMR (DMSO-d6, 400 MHz) δ 8.77 (s, 1H), 8.58 (s, 1H), 8.20 (s, 1H), 7.97~8.00 (m, 3H), 7.65~7.72 (m, 2H), 7.37~7.41 (m, 2H), 7.30~7.33 (m, 2H), 7.12~7.16 (m, 1H), 6.29 (s, 2H), 4.57 (br s, 1H), 4.45 (br s, 1H), 3.87 (br s, 1H), 3.72 (br s, 1H), 2.90 (s, 3H), 2.80 (d, J = 4.8 Hz, 3H), 1.94~2.04 (m, 2H). | 644 |
| 198 | 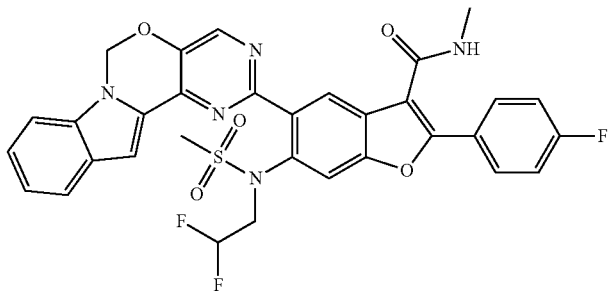 [SMILES: CNC(=O)c1c(-c2ccc(F)cc2)oc2cc(N(CC(F)F)S(C)(=O)=O)c(-c3ncc4c(n3)-c3cc5ccccc5n3CO4)cc12] | $^1$H-NMR (DMSO-d6, 400 MHz) δ 8.79 (s, 1H), 8.60 (s, 1H), 8.20 (s, 1H), 7.97~8.00 (m, 2H), 7.91 (s, 1H), 7.73 (d, J = 8.4 Hz, 1H), 7.67 (d, J = 8.4 Hz, 1H), 7.32~7.42 (m, 4H), 7.13~7.17 (m, 1H), 6.32~6.56 (m, 1H), 6.30~6.31 (m, 2H), 4.30~4.40 (m, 1H), 4.06~4.11 (m, 1H), 2.95 (s, 3H), 2.81 (d, J = 4.8 Hz, 3H). | 648 |
| 199 | 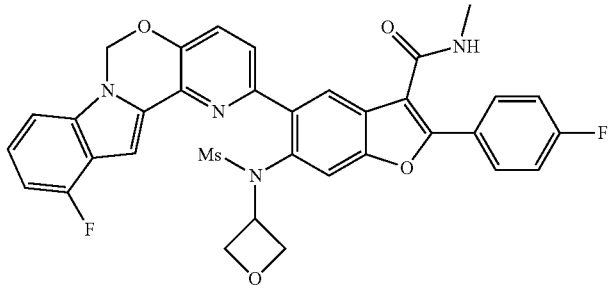 [SMILES: CNC(=O)c1c(-c2ccc(F)cc2)oc2cc(N(C3COC3)S(C)(=O)=O)c(-c3ccc4c(n3)-c3cc5c(F)cccc5n3CO4)cc12] | $^1$H-NMR (CDCl$_3$, 400 MHz) δ 8.01 (s, 1H), 7.87~7.91 (m, 2H), 7.65 (s, 1H), 7.43 (s, 2H), 7.25 (s, 1H), 7.14~7.17 (m, 3H), 7.06 (d, J = 8.4 Hz, 1H), 6.78~6.80 (m, 1H), 5.94 (s, 2H), 5.82 (s, 1H), 5.06~5.13 (m, 1H), 4.92~4.97 (m, 1H), 4.78~4.82 (m, 1H), 4.69~4.72 (m, 1H), 4.58~4.62 (m, 1H), 2.94 (d, J = 5.2 Hz, 3H), 2.55 (s, 3H). | 657 |
| 200 | 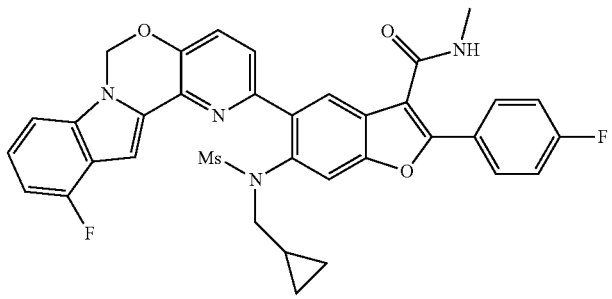 [SMILES: CNC(=O)c1c(-c2ccc(F)cc2)oc2cc(N(CC3CC3)S(C)(=O)=O)c(-c3ccc4c(n3)-c3cc5c(F)cccc5n3CO4)cc12] | $^1$H-NMR (CDCl$_3$, 400 MHz) δ 7.95 (s, 1H), 7.91~7.94 (m, 2H), 7.70 (s, 1H), 7.53 (d, J = 8.4 Hz, 1H), 7.42 (d, J = 8.4 Hz, 1H), 7.12~7.17 (m, 4H), 7.04 (d, J = 8.0 Hz, 1H), 6.78 (t, J = 8.0 Hz, 1H), 5.90~5.93 (m, 3H), 3.54 (s, 1H), 3.35 (s, 1H), 2.94 (d, J = 5.2 Hz, 3H), 2.82 (s, 3H), 0.96~1.03 (m, 1H), 0.38~0.44 (m, 2H), 0.17~0.21 (m, 2H). | 655 |
| 201 | 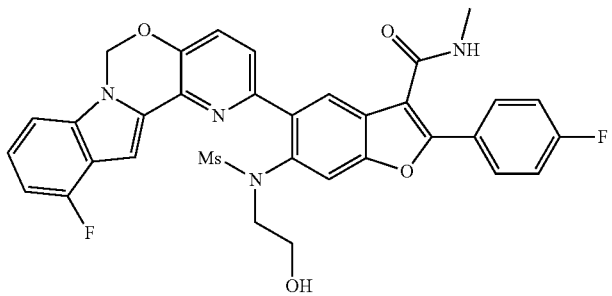 [SMILES: CNC(=O)c1c(-c2ccc(F)cc2)oc2cc(N(CCO)S(C)(=O)=O)c(-c3ccc4c(n3)-c3cc5c(F)cccc5n3CO4)cc12] | $^1$H-NMR (CDCl$_3$, 400 MHz) δ 7.93 (t, J = 8.8 Hz, 2H), 7.56 (t, J = 6.0 Hz, 2H), 7.44 (d, J = 8.4 Hz, 1H), 7.19~7.22 (m, 3H), 7.09 (d, J = 7.6 Hz, 1H), 6.82 (t, J = 8.0 Hz, 1H), 6.54 (t, J = 6.0 Hz, 1H), 5.91~6.05 (m, 2H), 5.81 (s, 1H), 3.94 (s, 2H), 3.68~3.85 (m, 2H), 2.97 (d, J = 4.8 Hz, 3H), 2.66 (s, 3H). | 645 |

-continued

| Compound No | Structure | NMR | MS (M + H)+ |
|---|---|---|---|
| 202 | (Enantiomer 1, peak 1 on SFC) | 1H-NMR (CDCl3, 400 MHz) δ 7.91 (s, 3H), 7.53~7.62 (m, 3H), 7.39~7.42 (m, 1H), 7.20~7.25 (m, 2H), 7.06 (d, J = 8.0 Hz, 2H), 6.82 (d, J = 6.0 Hz, 1H), 6.01 (brs, 1H), 5.89~5.96 (m, 2H), 4.26 (s, 1H), 3.49~3.93 (m, 3H), 2.96 (s, 3H), 2.70 (d, J = 10.8 Hz, 2H), 2.55 (d, J = 10.8 Hz, 1H) 1.23 (s, 3H). | 659 |
| 203 | (Enantiomer 2, peak 2 on SFC) | 1H-NMR (CDCl3, 400 MHz) δ 7.91 (s, 3H), 7.53~7.62 (m, 3H), 7.39~7.42 (m, 1H), 7.20~7.25 (m, 2H), 7.06 (d, J = 8.0 Hz, 2H), 6.82 (d, J = 6.0 Hz, 1H), 6.01 (brs, 1H), 5.89~5.96 (m, 2H), 4.26 (s, 1H), 3.49~3.93 (m, 3H), 2.96 (s, 3H), 2.70 (d, J = 10.8 Hz, 2H), 2.55 (d, J = 10.8 Hz, 1H) 1.23 (s, 3H). | 659 |
| 204 | 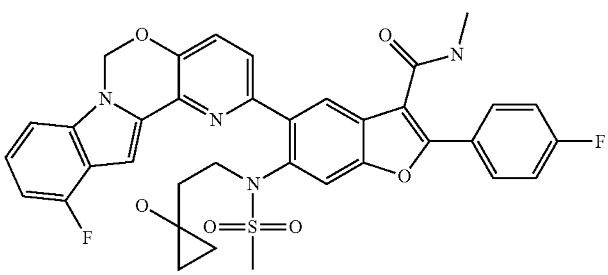 [SMILES: CNC(=O)c1c(-c2ccc(F)cc2)oc2cc(N(CCC3(O)CC3)S(C)(=O)=O)c(-c3ccc4c(n3)-c3cc5c(F)cccc5n3CO4)cc12] | 1H-NMR (CDCl3, 400 MHz) δ 7.93~7.96 (m, 3H), 7.31 (s, 1H), 7.47~7.51 (m, 2H), 7.19~7.26 (m, 4H), 7.12 (d, J = 8.0 Hz, 1H), 6.85 (t, J = 8.8 Hz, 1H), 6.01 (s, 2H), 5.91 (brs, 1H), 3.89~3.95 (m, 2H), 3.25 (s, 1H), 2.97 (d, J = 4.8 Hz, 3H), 2.81 (s, 3H), 1.96~2.00 (m, 1H), 1.74~1.78 (m, 1H), 0.74~0.83 (m, 2H), 0.38~0.51 (m, 2H). | 685 |

Example 74

Preparation of Compound 205

Step 1—Synthesis of 5-bromo-6-(N-(4-chlorobenzyl)methylsulfonamido)-2-(4-fluorophenyl)-N-methylbenzofuran-3-carboxamide

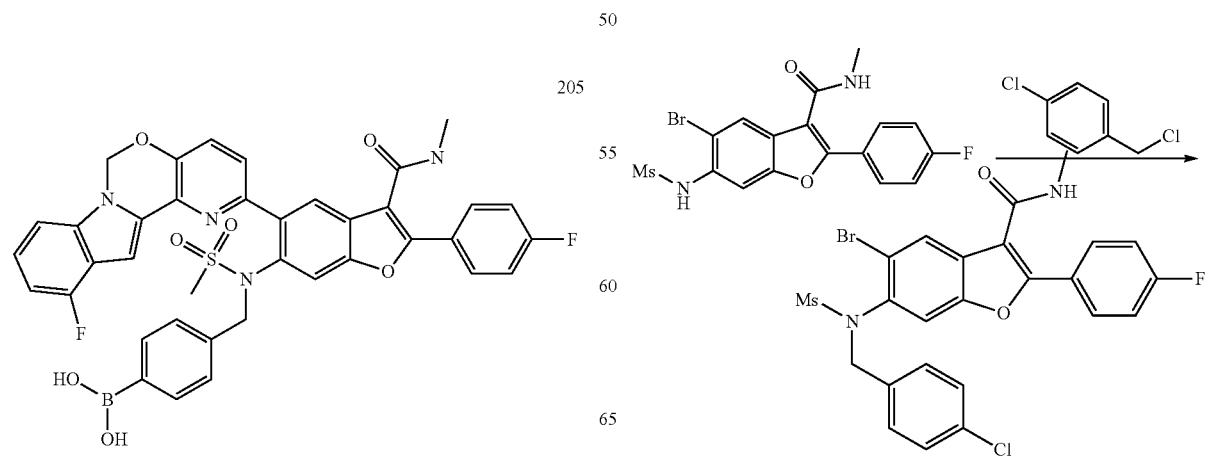

313

A solution of 5-bromo-2-(4-fluorophenyl)-N-methyl-6-(methylsulfonamido)benzofuran-3-carboxamide (0.55 g, 1.25 mmol), 1-chloro-4-(chloromethyl)benzene (0.24 g, 1.5 mmol), K$_2$CO$_3$ (0.35 g, 2.5 mmol) and KI (0.25 g, 0.15 mmol) in DMF (10 mL) was stirred at 80° C. for 2 hours. The mixture was concentrated in vacuo and the resulting residue was washed by H$_2$O and filtered to provide the white solid 5-bromo-6-(N-(4-chlorobenzyl)methylsulfonamido)-2-(4-fluorophenyl)-N-methylbenzofuran-3-carboxamide without further purification. $^1$H-NMR (CDCl$_3$, 400 MHz) δ 8.14 (s, 1H), 7.81~7.84 (m, 2H), 7.15~7.25 (m, 7H), 5.79 (br s, 1H), 5.15 (d, J=7.4 Hz, 1H), 4.55 (d, J=7.4 Hz, 1H), 3.10 (s, 3H), 2.96 (d, J=4.8 Hz, 3H). MS (M+H)$^+$: 565/567.

Step 2—Synthesis of 6-(N-(4-chlorobenzyl)methylsulfonamido)-2-(4-fluorophenyl)-N-methyl-5-(4,4,5,5-tetramethyl-1,3,2-dioxaborolan-2-yl)benzofuran-3-carboxamide

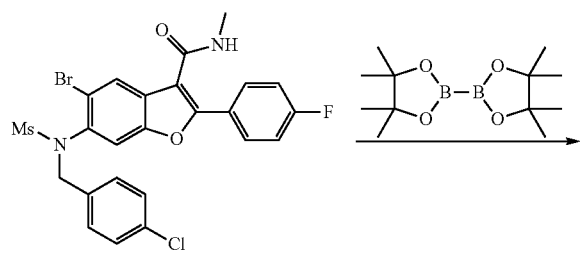

-continued

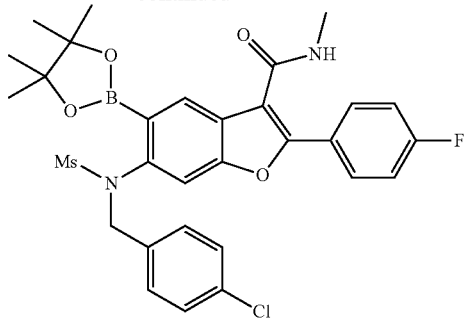

To a solution of 5-bromo-6-(N-(4-chlorobenzyl)methylsulfonamido)-2-(4-fluorophenyl)-N-methylbenzofuran-3-carboxamide (0.71 g, 1.25 mmol), (Bpin)$_2$ (0.95 g, 3.75 mmol) and KOAc (0.37 g, 3.75 mmol) in dioxane/H$_2$O (25 mL/3 mL) was added Pd(dppf)Cl$_2$ (0.14 g, 0.19 mmol) under N$_2$. The mixture was stirred at 100° C. under reflux for 8 hours. Then it was filtered and extracted with EtOAc. The combined organic phases was washed with brine, dried over Na$_2$SO$_4$ and concentrated in vacuo. The resulting residue was purified using flash gel chromatography (petroleum ether: EtOAc=4:1) to provide 6-(N-(4-chlorobenzyl)methylsulfonamido)-2-(4-fluorophenyl)-N-methyl-5-(4,4,5,5-tetramethyl-1,3,2-dioxaborolan-2-yl)benzofuran-3-carboxamide. $^1$H-NMR (CDCl$_3$, 400 MHz) δ 8.27 (s, 1H), 7.85~7.88 (m, 2H), 7.19 (br s, 5H), 7.13 (t, J=8.0 Hz, 2H), 5.95 (s, 1H), 4.81~5.08 (m, 2H), 2.97~2.99 (m, 6H), 1.39 (s, 12H). MS (M+H)$^+$: 613.

Step 3—Synthesis of 6-(N-(4-chlorobenzyl)methylsulfonamido)-5-(11-fluoro-6H-pyrido[2',3':5,6][1,3]oxazino[3,4-a]indol-2-yl)-2-(4-fluorophenyl)-N-methylbenzofuran-3-carboxamide

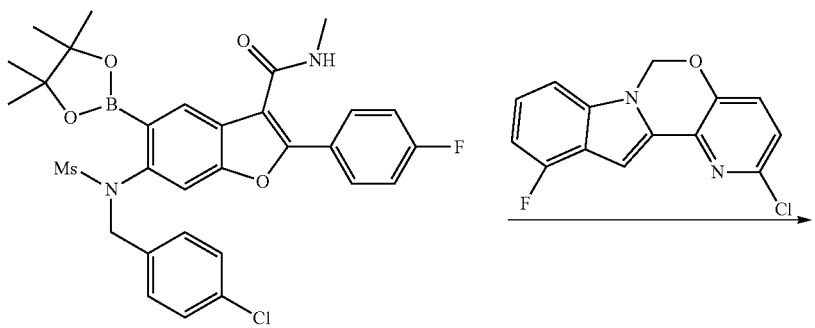

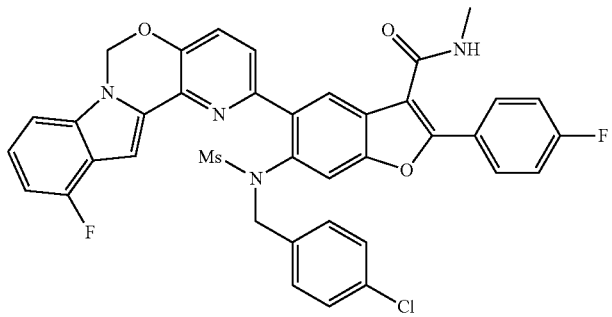

To a solution of 6-(N-(4-chlorobenzyl)methylsulfonamido)-2-(4-fluorophenyl)-N-methyl-5-(4,4,5,5-tetramethyl-1,3,2-dioxaborolan-2-yl)benzofuran-3-carboxamide (0.15 g, 0.25 mmol), 2-chloro-11-fluoro-6H-pyrido[2',3':5,6][1,3]oxazino[3,4-a]indole (0.09 g, 0.33 mmol) and $K_3PO_4 \cdot 3H_2O$ (0.15 g, 0.56 mmol) in dioxane/$H_2O$ (6 mL/12 drops) was added $Pd_2(dba)_3$ (12 mg, 0.013 mmol) and X-Phos (12 mg, 0.026 mmol) under $N_2$. The mixture was stirred at 100° C. under reflux for 2 hours. Then it was filtered and extracted with EtOAc. The combined organic phases was washed with brine, dried over $Na_2SO_4$ and concentrated in vacuo. The resulting residue was purified using flash gel chromatography (petroleum ether:EtOAc=2:1) to provide 6-(N-(4-chlorobenzyl)methylsulfonamido)-5-(11-fluoro-6H-pyrido[2',3':5,6][1,3]oxazino[3,4-a]indol-2-yl)-2-(4-fluorophenyl)-N-methylbenzofuran-3-carboxamide. $^1$H-NMR (CDCl$_3$, 400 MHz) δ 7.90 (s, 1H), 7.82~7.86 (m, 2H), 7.39 (s, 2H), 7.04~7.19 (m, 10H), 6.76~6.80 (m, 1H), 5.95 (s, 2H), 5.86 (s, 1H), 4.66~4.78 (m, 2H), 2.89 (d, J=4.0 Hz, 3H), 2.74 (s, 3H). MS (M+H)$^+$: 725.

Step 4—Synthesis of 5-(11-fluoro-6H-pyrido[2',3':5,6][1,3]oxazino[3,4-a]indol-2-yl)-2-(4-fluorophenyl)-N-methyl-6-(N-(4-(4,4,5,5-tetramethyl-1,3,2-dioxaborolan-2-yl)benzyl)methylsulfonamido)benzofuran-3-carboxamide

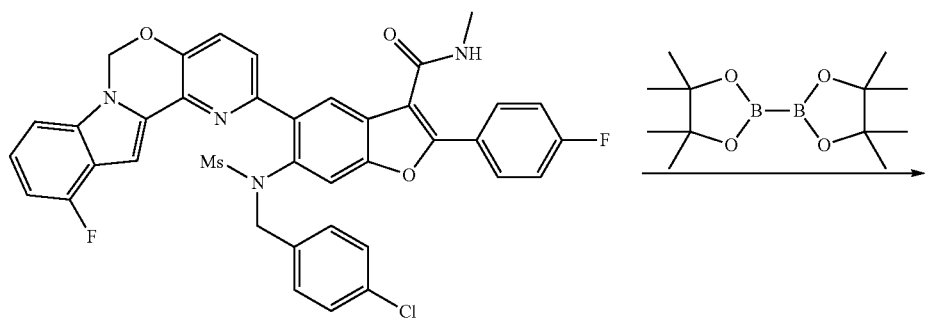

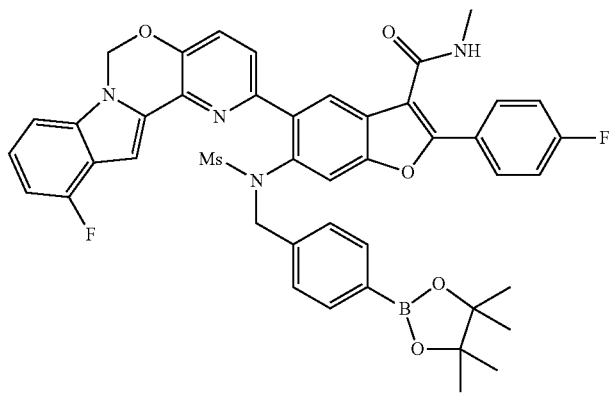

To a solution of 6-(N-(4-chlorobenzyl)methylsulfonamido)-5-(11-fluoro-6H-pyrido[2',3':5,6][1,3]oxazino[3,4-a]indol-2-yl)-2-(4-fluorophenyl)-N-methylbenzofuran-3-carboxamide (0.12 g, 0.17 mmol), (Bpin)₂ (0.11 g, 0.42 mmol) and KOAc (0.049 g, 0.5 mmol) in dioxane/H₂O (6 mL/12 d) was added Pd₂(dba)₃ (0.016 g, 0.02 mmol) and X-Phos (0.016 g, 0.03 mmol) under N₂. The mixture was stirred at 110° C. under reflux for 2 hours. Then it was filtered and extracted with EtOAc. The combined organic phases was washed with brine, dried over Na₂SO₄ and concentrated in vacuo. The resulting residue was purified using flash gel chromatography (petroleum ether:EtOAc=1:1) to provide 5-(11-fluoro-6H-pyrido[2',3':5,6][1,3]oxazino[3,4-a]indol-2-yl)-2-(4-fluorophenyl)-N-methyl-6-(N-(4-(4,4,5,5-tetramethyl-1,3,2-dioxaborolan-2-yl)benzyl)methylsulfonamido)benzofuran-3-carboxamide. ¹H-NMR (CDCl₃, 400 MHz) δ 7.91~7.96 (m, 3H), 7.66~7.68 (m, 2H), 7.46~7.47 (m, 2H), 7.27 (s, 1H), 7.15~7.21 (m, 6H), 7.09~7.11 (m, 1H), 6.77~6.87 (m, 1H), 6.01 (s, 2H), 5.89 (s, 1H), 4.67~4.88 (m, 2H), 2.97 (d, J=4.0 Hz, 3H), 2.81 (s, 3H), 1.28 (s, 12H). MS (M+H)⁺: 817.

Step 5—Synthesis of (4-((N-(5-(11-fluoro-6H-pyrido[2',3':5,6][1,3]oxazino[3,4-a]indol-2-yl)-2-(4-fluorophenyl)-3-(methylcarbamoyl)benzofuran-6-yl)methylsulfonamido)methyl)phenyl) boronic acid (Compound 205)

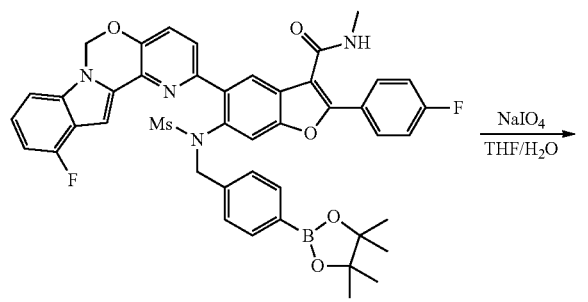

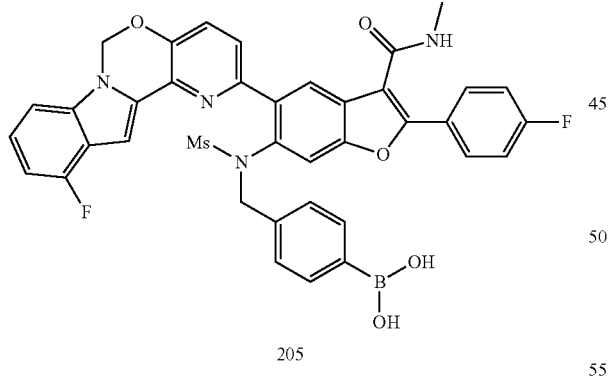

205

A solution of 5-(11-fluoro-6H-pyrido[2',3':5,6][1,3]oxazino[3,4-a]indol-2-yl)-2-(4-fluorophenyl)-N-methyl-6-(N-(4-(4,4,5,5-tetramethyl-1,3,2-dioxaborolan-2-yl)benzyl)methylsulfonamido)benzofuran-3-carboxamide (0.12 g, 0.15 mmol) and NaIO₄ (0.16 g, 0.74 mmol) in THF/H₂O (12 mL/4 mL) was stirred at room temperature for 24 hours. The mixture was filtered and extracted by EtOAc. The combined organic phases was washed with brine, dried over Na₂SO₄ and concentrated in vacuo. The resulting residue was purified using prep-HPLC to provide Compound 205. ¹H-NMR (Methanol-d4, 400 MHz) δ 8.00 (s, 2H), 7.77~7.79 (m, 2H), 7.53~7.66 (m, 1H), 7.51~7.52 (m, 1H), 7.22~7.44 (m, 6H), 7.11~7.14 (m, 1H), 6.99~7.01 (m, 1H), 6.91~6.93 (m, 1H), 6.82~6.86 (m, 1H), 6.14 (s, 2H), 4.84~4.86 (m, 1H), 4.50~4.58 (m, 1H), 3.17~3.20 (m, 3H), 2.93 (s, 3H). MS (M+H)⁺: 735.

Example 75

Preparation of Compound 206

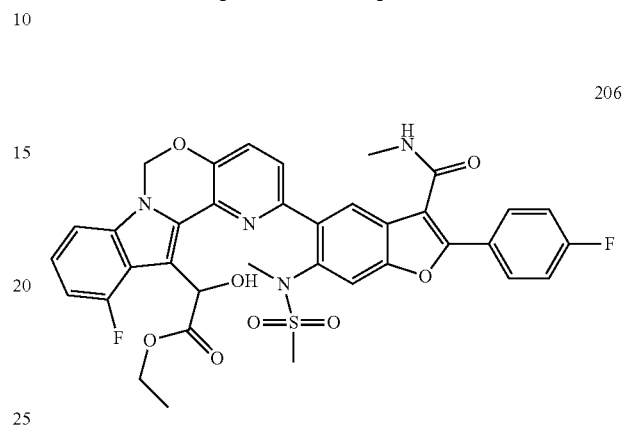

206

A mixture of 5-(11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (500 mg, 0.814 mmol) and ethyl glyoxalate (323 µl, 1.627 mmol) was heated at 115° C. for 3 hours in a sealed tube. The reaction mixture was cooled to room temperature, concentrated under vacuum then applied onto 2-EP column (30 mm×250 mm) eluted with 30% IPA/CO₂. This resulted in 108 mg (18.5%) of ethyl 2-(11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indol-12-yl)-2-hydroxyacetate (Compound 206) as a white solid. LC-MS (ES, m/z) C₃₆H₃₀F₂N₄O₈S: 716. Found: 717 [M+H]⁺.

Example 76

Preparation of Compound 207

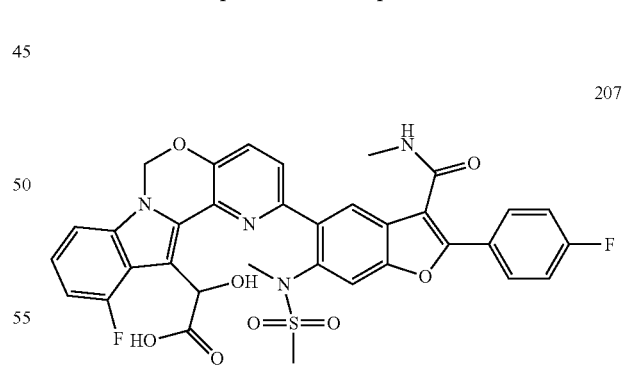

207

A mixture of ethyl 2-(11-fluoro-2-(2-(4-fluorophenyl)-3-(methylcarbamoyl)-6-(N-methylmethylsulfonamido)benzofuran-5-yl)-6H-pyrido[2',3':5,6][1,3]oxazino[3,4-a]indol-12-yl)-2-hydroxyacetate (233 mg, 0.325 mmol) and lithium hydroxide (54.5 mg, 2.276 mmol) in THF (1 ml), water (0.5 ml) and MeOH (0.5 ml) was stirred at room temperature over night, then concentrated under vacuum. The resulting residue was purified using EP column (30 mm×250 mm), 60% IPA/CO₂. This resulted in 128 mg (57.2%) of 2-(11-fluoro-2-(2-

(4-fluorophenyl)-3-(methylcarbamoyl)-6-(N-methylmethylsulfonamido)benzofuran-5-yl)-6H-pyrido[2',3':5,6][1,3]oxazino[3,4-a]indol-12-yl)-2-hydroxyacetic acid (Compound 207) as a white solid. LC-MS (ES, m/z) $C_{34}H_{26}F_2N_4O_8S$: 688. Found: 689 [M+H]$^+$.

Example 77

Preparation of Compound 208

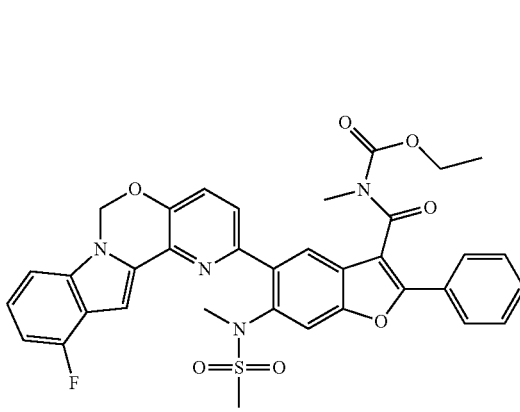

To a solution of 5-(11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (100 mg, 0.163 mmol) in THF (2 mL) at −78° C. under $N_2$ added n-butyllithium (0.203 ml, 0.325 mmol). After 10 mins, ethyl chloroformate (61.8 mg, 0.569 mmol) was added to the reaction mixture. And the reaction mixture was warmed to room temperature and stirred overnight under $N_2$. The reaction mixture was quenched with 5 ml water extracted with 3×10 mL ethyl acetate. The organic layers were combined, washed with 2×5 mL of saturated brine, dried over anhydrous sodium sulfate and concentrated under vacuum. Silica gel chromatography eluted with ethyl acetate/hexane (20-100%) resulted in 38 mg (34%) of Ethyl (5-(11-fluoro-6H-pyrido[2',3':5,6][1,3]oxazino[3,4-a]indol-2-yl)-2-(4-fluorophenyl)-6-(N-methylmethylsulfonamido)benzofuran-3-carbonyl)(methyl)carbamate (Compound 208) as a white solid. LC-MS (ES, m/z) $C_{35}H_{28}F_2N_4O_7S$: 686. Found: 687 [M+H]$^+$.

Example 78

Preparation of Compound 209

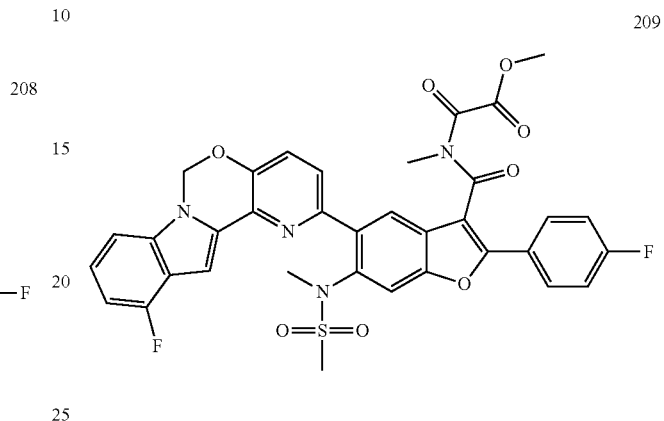

A mixture of 5-(11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (260 mg, 0.423 mmol) and methyl oxalyl chloride (311 mg, 2.54 mmol) in $CCl_4$ (6 ml) was heated under reflux for 5 hours. The reaction was concentrated under vacuum. The resulting residue was purified using silica gel column eluted with ethyl acetate/hexane 20-100%. This resulted in 58 mg (17.6%) of methyl 2-(5-(11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamido)-2-oxoacetate (Compound 209) as a white solid. LC-MS (ES, m/z) $C_{35}H_{26}F_2N_4O_8S$: 700. Found: 701 [M+H]$^+$.

Example 79

Preparation of Compound 210

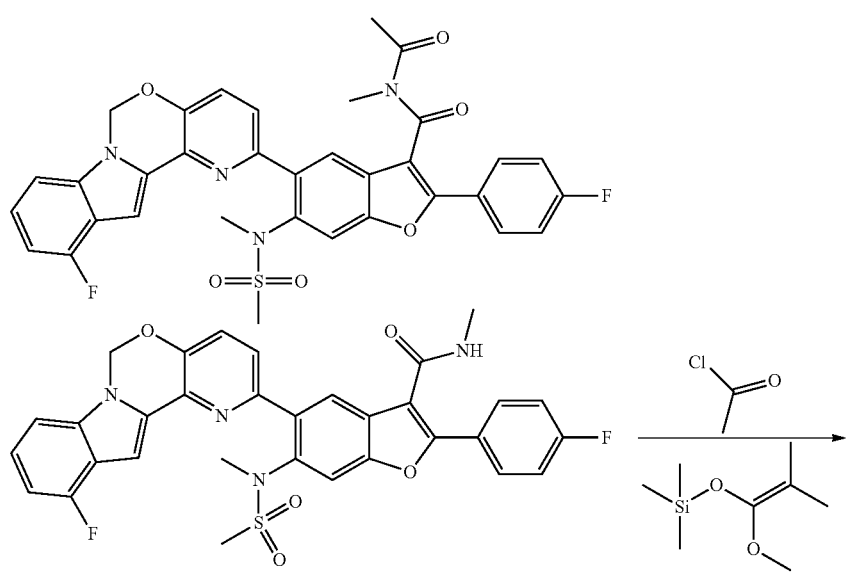

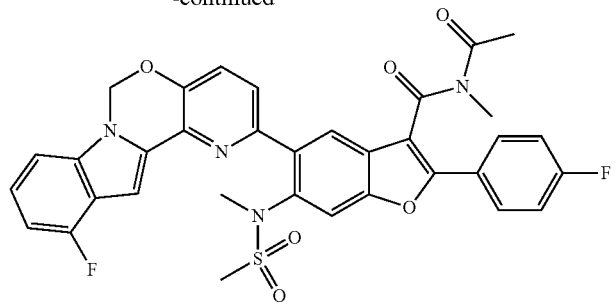

To a solution of 5-(11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (500 mg, 0.81 mmol) in dichloromethane (2 ml) was added acetyl chloride (174 μl, 2.44 mmol) and ((1-methoxy-2-methylprop-1-en-1-yl)oxy)trimethylsilane (495 μl, 2.44 mmol). The resulting mixture was stirred at room temperature overnight. Concentrated in vacuo and added Et$_3$N (5 ml). Silica gel chromatography (eluted with 0-5% MeOH/dichloromethane) to provide N-acetyl-5-(11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (500 mg, yield: 94%) MS (M+H)$^+$: 657.

Example 80

Preparation of Compound 211

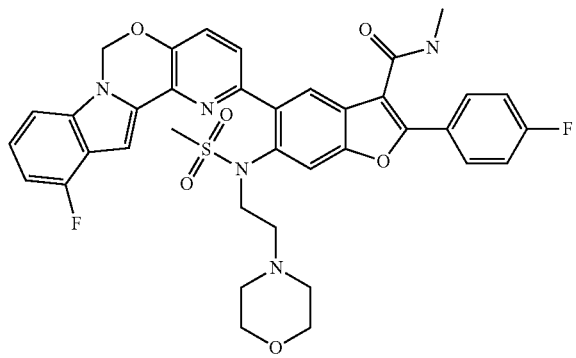

Step 1—Synthesis of 5-(11-fluoro-6H-pyrido[2',3':5,6][1,3]oxazino[3,4-a]indol-2-yl)-2-(4-fluorophenyl)-N-methyl-6-(methylsulfonamido)benzofuran-3-carboxamide

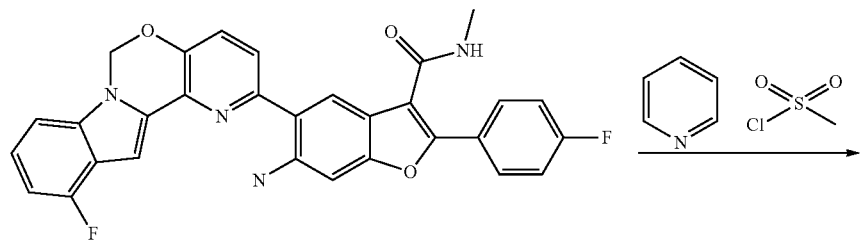

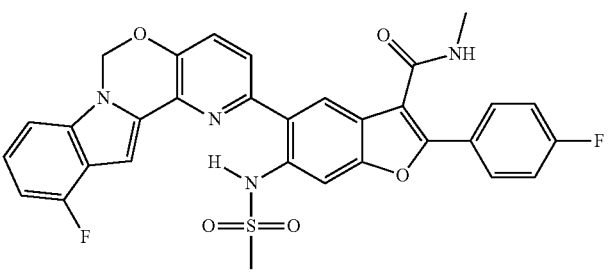

323

To a mixture of 6-amino-5-(11-fluoro-6H-pyrido[2',3':5,6][1,3]oxazino[3,4-a]indol-2-yl)-2-(4-fluorophenyl)-N-methylbenzofuran-3-carboxamide (1000 mg, 1.914 mmol) and pyridine (1.548 mL, 19.14 mmol) in dichloromethane (30 mL), methylsulfonyl chloride (0.741 mL, 9.57 mmol) was added dropwise at 0° C. The mixture was allowed to room temperature and stirred overnight. The reaction mixture was quenched with NaHCO₃ and 20 mL dichloromethane was added. Solid crushed out, the mixture was filtered and washed with water. The crude solid was dried under vacuum and gave the crude product 5-(11-fluoro-6H-pyrido[2',3':5,6][1,3]oxazino[3,4-a]indol-2-yl)-2-(4-fluorophenyl)-N-methyl-6-(methylsulfonamido)benzofuran-3-carboxamide (1100 mg, 96% yield).

Step 2—Synthesis of gave 5-(11-fluoro-6H-pyrido[2',3':5,6][1,3]oxazino[3,4-a]indol-2-yl)-2-(4-fluorophenyl)-N-methyl-6-(N-(2-morpholinoethyl)methylsulfonamido)benzofuran-3-carboxamide

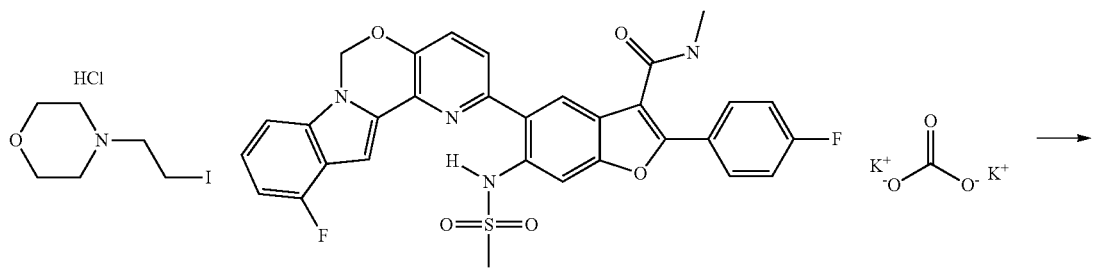

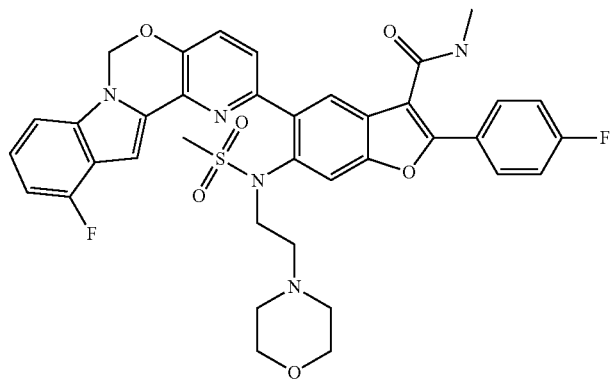

To a microwave tube was added 5-(11-fluoro-6H-pyrido[2',3':5,6][1,3]oxazino[3,4-a]indol-2-yl)-2-(4-fluorophenyl)-N-methyl-6-(methylsulfonamido)benzofuran-3-carboxamide (100 mg, 0.167 mmol), 4-(2-iodoethyl)morpholin-4-ium chloride (139 mg, 0.500 mmol), K$_2$CO$_3$ (57.5 mg, 0.416 mmol) and DMF (4 mL). The mixture was heated at 150° C. for 1 h. The reaction was cooled down and the DMF solution was loaded to the C18 column directly through a filter, and purified using ISCO (0 to 100% water/acetonitrile) and gave 5-(11-fluoro-6H-pyrido[2',3':5,6][1,3]oxazino[3,4-a]indol-2-yl)-2-(4-fluorophenyl)-N-methyl-6-(N-(2-morpholinoethyl)methylsulfonamido)benzofuran-3-carboxamide (Compound 211, 25 mg, 21% yield). MS (M+H)$^+$: 714.

Example 81

Preparation of Compound 2

2

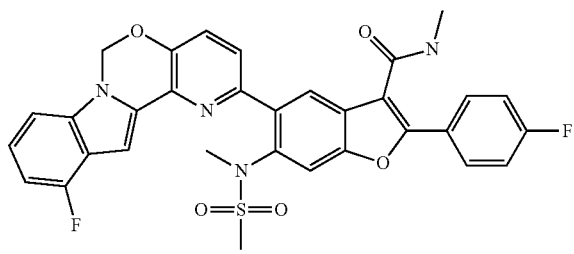

Step 1—Synthesis of ethyl 3-(4-fluorophenyl)-3-oxopropanoate

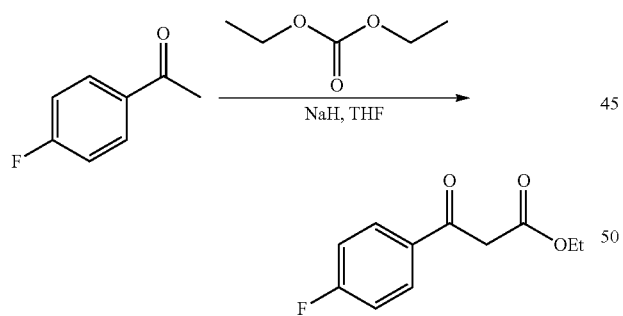

Diethyl carbonate (130 g, 1.1 mol) was dissolved in a suspension of NaH (60% in oil, 50.2 g, 1.3 mol) in anhydrous tetrahydrofuran (1.5 L), and then 1-(4-fluorophenyl)ethanone (150 g, 1.09 mol) was added dropwise at 70° C. The resulting mixture was stirred at 70° C. for 3 hours. After the reaction mixture was cooled to room temperature and poured into HCl (1 N). The mixture was extracted with EtOAc, the organic phase was dried with anhydrous NaSO$_4$ and concentrated in vacuo. The resulting residue was purified using column chromatography (eluted with petroleum ether/EtOAc=50/1) to provide ethyl 3-(4-fluorophenyl)-3-oxopropanoate (217 g, yield: 95%). $^1$H-NMR (CDCl$_3$, 400 MHz) δ 7.92~7.97 (m, 2H), 7.07~7.13 (m, 2H), 4.14~4.20 (m, 2H), 3.93 (s, 2H), 1.22 (d, J=7.2 Hz, 3H). MS (M+H)$^+$: 211.

Step 2—Synthesis of ethyl 5-bromo-2-(4-fluorophenyl)benzofuran-3-carboxylate

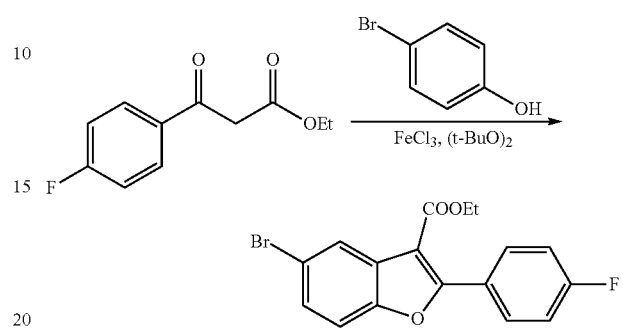

A solution of ethyl 3-(4-fluorophenyl)-3-oxopropanoate (130 g, 0.6 mol), 4-bromophenol (311 g, 1.8 mol) and FeCl$_3$.6H$_2$O (19.5 g, 0.09 mol) in DCE (700 mL) was heated to reflux, and then 2-(tert-butylperoxy)-2-methylpropane (193 g, 1.32 mol) was added dropwise under nitrogen. After 6 hours of refluxing, the mixture was cooled to RT, quenched with saturated NaHSO$_3$ and extracted with dichloromethane. The organic phases were washed with water, brine and dried over Na$_2$SO$_4$, filtered and concentrated in vacuo. The resulting residue was purified using column chromatography (petroleum ether/dichloromethane=15/1) to provide the crude product, which was crystallized from cold MeOH to provide ethyl 5-bromo-2-(4-fluorophenyl)benzofuran-3-carboxylate (37 g, yield: 14.3%) as solid. $^1$H-NMR (CDCl$_3$, 400 MHz) δ 8.12 (s, 1H), 7.97~8.01 (m, 2H), 7.37 (d, J=4.0 Hz, 1H), 7.32 (d, J=8.0 Hz, 1H), 7.11 (t, J=8.0 Hz, 2H), 4.32~4.38 (m, 2H), 1.36 (t, J=8.0 Hz, 3H). MS (M+H)$^+$: 363/365.

Step 3—Synthesis of ethyl 5-bromo-2-(4-fluorophenyl)-6-nitrobenzofuran-3-carboxylate

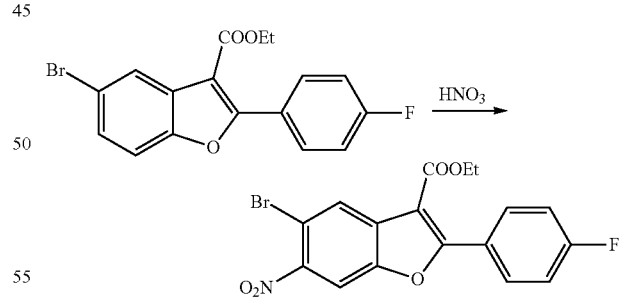

To a solution of ethyl 5-bromo-2-(4-fluorophenyl)benzofuran-3-carboxylate (50 g, 137.6 mmol) in CHCl$_3$ (500 mL), fuming HNO$_3$ (50 mL) was added dropwise at −15° C. and the mixture was stirred for 0.5 hour. The reaction mixture was poured into ice water and extracted with CH$_2$Cl$_2$. The organic layer was washed with a.q. sat. NaHCO$_3$ and brine, after removed the most of solvent, the resulting residue was crystallized with petroleum ether/dichloromethane=20/1 to provide product of ethyl 5-bromo-2-(4-fluorophenyl)-6-nitrobenzofuran-3-carboxylate (35 g, yield: 66%). $^1$H-NMR (CDCl₃, 400 MHz) δ 8.36 (s, 1H), 8.02~8.04 (m, 3H), 7.13~7.18 (m, 2H), 4.36~4.41 (m, 2H), 1.37 (t, J=4.0 Hz, 3H). MS (M+H)⁺: 408/410.

Step 4—Synthesis of ethyl 6-amino-5-bromo-2-(4-fluorophenyl)benzofuran-3-carboxylate

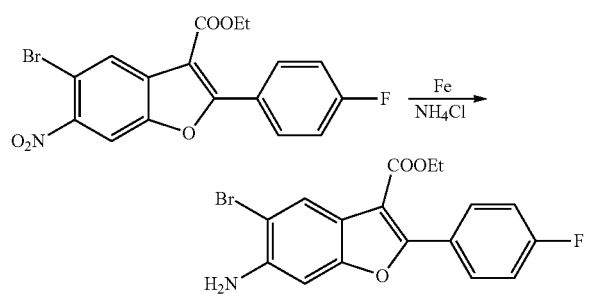

A mixture of ethyl 5-bromo-2-(4-fluorophenyl)-6-nitrobenzofuran-3-carboxylate (52 g, 127 mmol), iron filings (21.3 g, 382.2 mmol) and NH₄Cl (41 g, 764.4 mmol) in MeOH/THF/H₂O (2/2/1, 500 mL) was stirred at reflux for 3 hour. After filtered and concentrated, the resulting residue was purified using column chromatography (petroleum ether/EtOAc/dichloromethane=20:1:20) to provide ethyl 6-amino-5-bromo-2-(4-fluorophenyl)benzofuran-3-carboxylate (40 g, yield: 82%). ¹H-NMR (CDCl₃, 400 MHz) δ 8.01 (s, 1H), 7.94~7.98 (m, 2H), 7.08 (t, J=8.0 Hz, 2H), 6.83 (s, 1H), 4.32~4.36 (m, 2H), 4.18 (s, 2H), 1.35 (t, J=8.0 Hz, 3H). MS (M+H)⁺: 378/380.

Step 5—Synthesis of 5-Bromo-2-(4-fluoro-phenyl)-6-methanesulfonylamino-benzofuran-3-carboxylic acid ethyl ester

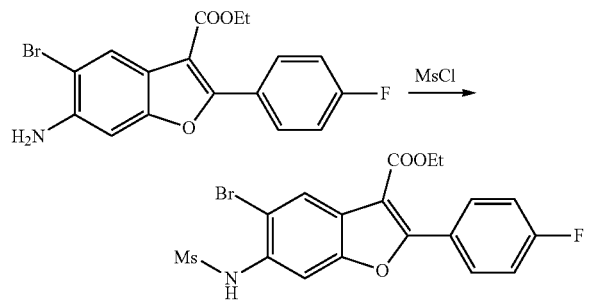

MsCl (31.7 g, 277.5 mmol) was added to a solution of ethyl 6-amino-5-bromo-2-(4-fluorophenyl)benzofuran-3-carboxylate (35 g, 92.5 mmol) and pyridine (60 mL) in dichloromethane (300 mL) at 0° C. After stirred overnight at room temperature, the mixture was diluted with water and extracted with dichloromethane. The organic layer was washed with brine, dried over Na₂SO₄, filtered and concentrated in vacuo, the resulting residue was purified using crystallized with EtOAc to provide the pure product of ethyl 5-bromo-2-(4-fluorophenyl)-6-(methylsulfonamido)benzofuran-3-carboxylate (35 g, yield: 82%). ¹H-NMR (CDCl₃, 400 MHz) δ 8.27 (s, 1H), 8.01~8.05 (m, 2H), 7.87 (s, 1H), 7.15~7.19 (m, 2H), 6.87 (s, 1H), 4.38~4.43 (m, 2H), 3.00 (s, 3H), 1.40 (t, J=40 Hz, 3H). MS (M+H)⁺: 456/458.

Step 6—Synthesis of 5-Bromo-2-(4-fluoro-phenyl)-6-methanesulfonylamino-benzofuran-3-carboxylic acid

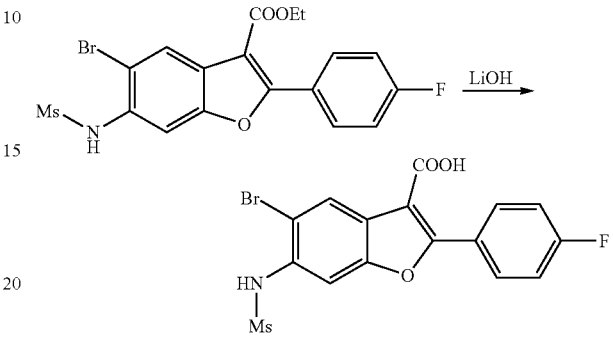

To a solution of ethyl 5-bromo-2-(4-fluorophenyl)-6-(methylsulfonamido)benzofuran-3-carboxylate (53 g, 0.23 mol) in dioxane/H₂O (5/1, 600 mL) was added LiOH.H₂O (25 g, 1.17 mol), and the mixture was stirred at 100° C. for 3 hours. After concentrated, the resulting residue was dissolved in H₂O, 1 N HCl was added until pH reached 3, and the mixture was extracted with EtOAc. The organic layer was washed with brine, dried over Na₂SO₄ and filtered. The solvent was removed to provide the product of 5-bromo-2-(4-fluorophenyl)-6-(methylsulfonamido)benzofuran-3-carboxylic acid (48 g, yield: 96%). ¹H-NMR (DMSO-d₆, 400 MHz) δ 13.49 (s, 1H), 9.67 (s, 1H), 8.30 (s, 1H), 8.12~8.17 (m, 2H), 7.87 (s, 1H), 7.45~7.50 (m, 2H), 3.16 (s, 3H). MS (M+H)⁺: 428/430.

Step 7—Synthesis of 5-Bromo-2-(4-fluoro-phenyl)-6-methanesulfonylamino-benzofuran-3-carboxylic acid methylamide

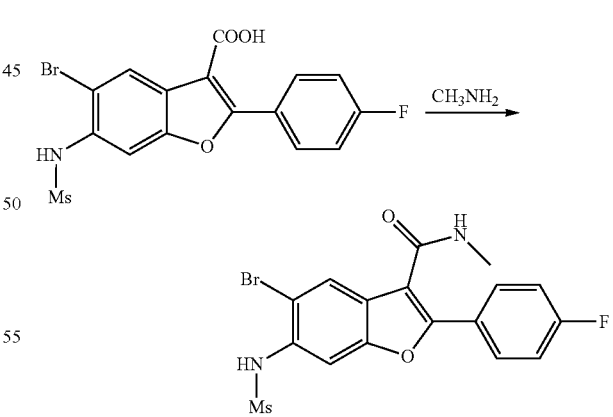

A solution of 5-bromo-2-(4-fluorophenyl)-6-(methylsulfonamido)benzofuran-3-carboxylic acid (33 g, 77 mmol), HOBT (15.6 g, 115.5 mmol) and EDCI (22.2 g, 115.5 mmol) in DMF (250 mL) was stirred at room temperature. After 2 hours, Et₃N (50 mL) and CH₃NH₂ (HCl salt, 17.7 g, 231 mmol) was added to the mixture, and the mixture was stirred overnight. After the solvent was removed, H₂O was added and the mixture was extracted with ethyl acetate. The combined organic layer was washed with H$_2$O, brine and concentrated in vacuo. The resulting residue was washed with EtOAc to provide the product of 5-bromo-2-(4-fluorophenyl)-N-methyl-6-(methylsulfonamido)benzofuran-3-carboxamide (32 g, yield: 94%). $^1$H-NMR (DMSO-d$_6$, 400 MHz) δ 9.55 (br s, 1H), 8.46~8.48 (m, 1H), 8.12~8.17 (m, 2H), 7.96 (s, 1H), 7.87 (s, 1H), 7.45~7.50 (m, 2H), 3.16 (s, 3H), 2.93 (d, J=8.4 Hz, 3H). MS (M+H)$^+$: 441/443.

Step 8—Synthesis of 5-bromo-2-(4-fluorophenyl)-N-methyl-6-(N-methylmethylsulfonamido)benzofuran-3-carboxamide

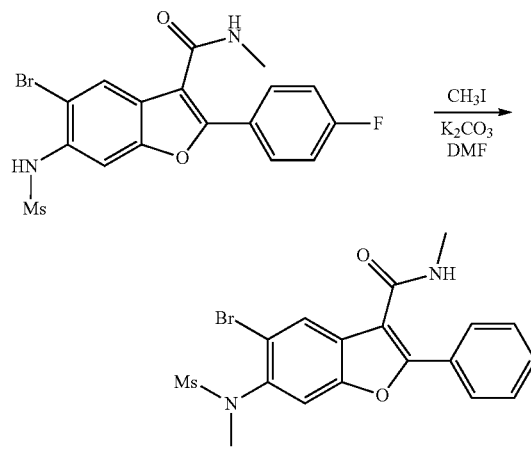

CH$_3$I (31.6 g, 223 mmol) was added to a mixture of 5-bromo-2-(4-fluorophenyl)-N-methyl-6-(methylsulfonamido)benzofuran-3-carboxamide (32 g, 74 mmol), K$_2$CO$_3$ (25.6 g, 186 mmol) and KI (246 mg, 1.5 mmol) in DMF (150 mL) under N$_2$ protection. The mixture was stirred at 80~90° C. overnight. After concentrated in vacuo, the resulting residue was washed with water (200 mL) and EtOAc (200 mL) to provide the product of 5-bromo-2-(4-fluorophenyl)-N-methyl-6-(N-methylmethylsulfonamido)benzofuran-3-carboxamide (31.5 g, 94%). $^1$H-NMR (CDCl$_3$, 400 MHz) δ 8.16 (s, 1H), 7.88~7.92 (m, 2H), 7.70 (s, 1H), 7.18~7.23 (m, 2H), 5.78 (br s, 1H), 3.34 (s, 3H), 3.09 (s, 3H), 3.00 (d, J=4.8 Hz, 3H). MS (M+H)$^+$: 455/457.

Step 9—Synthesis of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide

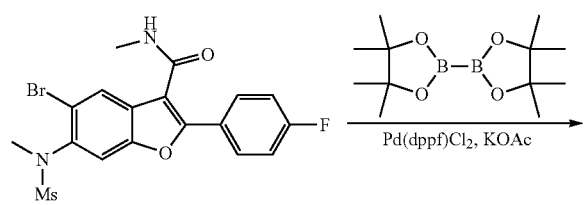

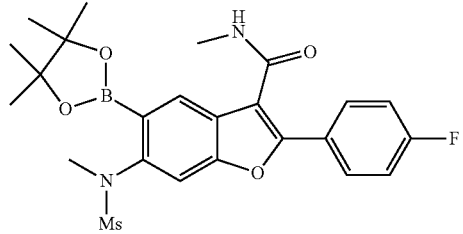

To a degassed solution of 5-bromo-2-(4-fluorophenyl)-N-methyl-6-(N-methylmethylsulfonamido)benzofuran-3-carboxamide (1.0 g, 2.2 mmol) and pinacol diborane (2.79 g, 11.0 mmol) in 1,4-Dioxane (25 mL) was added KOAc (647 mg, 6.6 mmol) under N$_2$ and stirred for 4 hours at room temperature. Then Pd(dppf)Cl$_2$ (60 mg) was added, and the mixture was stirred for another 30 minutes. Then the mixture was put into a pre-heated oil-bath at 130° C. and stirred for another 1 hour under N$_2$. The reaction mixture was cooled to room temperature and concentrated and extracted with EtOAc. The organic layers were washed with brine, dried over Na$_2$SO$_4$. After concentrated, the crude product of the boronic ester was purified using column chromatography (petroleum ether/EtOAc=5/1 to 2/1) to obtain 2-(4-fluorophenyl)-N-methyl-6-(N-methylmethylsulfonamido)-5-(4,4,5,5-tetramethyl-1,3,2-dioxaborolan-2-yl)benzofuran-3-carboxamide as white solid (700 mg, yield: 64%). $^1$H-NMR (CDCl$_3$, 400 MHz) δ 8.17 (s, 1H), 7.87~7.91 (m, 2H), 7.52 (s, 1H), 7.11 (t, J=7.6 Hz, 2H), 5.81 (d, J=2.8 Hz, 1H), 3.30 (s, 3H), 2.97 (d, J=5.2 Hz, 3H), 2.90 (s, 3H), 1.31 (s, 12H). MS (M+H)$^+$: 503.

Step 10—Synthesis of tert-butyl 4-fluoro-1H-indole-1-carboxylate

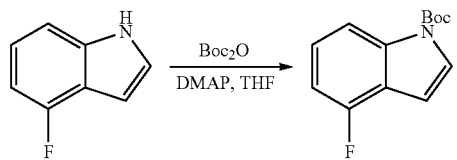 [SMILES: "Boc2O" ; Fc1cccc2[nH]ccc12 ; CC(C)(C)OC(=O)n1ccc2c(F)cccc21]

To a solution of 4-fluoro-1H-indole (5 g, 0.11 mol) and DMAP (150 mg, 3% Wt) in THF (50 mL) was added (Boc)$_2$O (8.5 g, 0.04 mol) dropwise. The mixture was stirred at room temperature for 2 hours. The organic solvent was removed in vacuo, and the resulting residue was purified using column chromatography (pure petroleum ether) to provide tert-butyl 4-fluoro-1H-indole-1-carboxylate (8.3 g, yield: 96%). $^1$H-NMR (CDCl$_3$, 400 MHz) δ 7.92 (d, J=8.4 Hz, 1H), 7.55 (d, J=3.6 Hz, 1H), 7.23 (m, 1H), 6.90 (m, 1H), 6.66 (d, J=3.6 Hz, 1H), 1.67 (s, 9H). MS (M+H)$^+$: 236.

Step 11—Synthesis of (1-(tert-butoxycarbonyl)-4-fluoro-1H-indol-2-yl)boronic acid

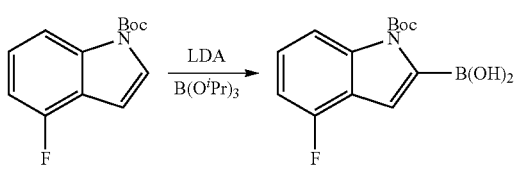 [SMILES: CC(C)(C)OC(=O)n1ccc2c(F)cccc21 ; CC(C)(C)OC(=O)n1c(B(O)O)cc2c(F)cccc21 ; "B(OiPr)3"]

To a solution of diisopropylamine (7.5 mL, 0.11 mol) in THF (35 mL) at 0° C. was added n-BuLi (21 mL, 0.055 mol) dropwise. The mixture was stirred at 0° C. for 40 minutes. Then the mixture was cooled to −78° C. Tert-butyl 4-fluoro-1H-indole-1-carboxylate (5 g, 0.02 mol) in THF (13 mL) was added dropwise slowly. After addition, the mixture was stirred at −78° C. for 2 hours. Then triisopropyl borate (3.29 g, 0.03 mol) was added. The mixture was stirred at −78° C. for another 40 minutes. The reaction was monitored using TLC. When the reaction was completed, the mixture was adjusted to pH=6 with 1 N HCl. After extracted with EtOAc (25 mL×3), the combined organic layers were washed with brine (50 mL), dried over Na$_2$SO$_4$, filtered and concentrated in vacuo. The obtained solid was recrystallized with EtOAc and petroleum ether to provide (1-(tert-butoxycarbonyl)-4-fluoro-1H-indol-2-yl)boronic acid (4.5 g, yield: 76.7%, which might be unstable at high temp. work up, store in fridge). $^1$H-NMR (CDCl$_3$, 400 MHz) δ 7.77 (d, J=8.4 Hz, 1H), 7.57 (s, 1H), 7.44 (s, 2H), 7.24 (m, 1H), 6.90 (m, 1H), 1.66 (s, 9H). MS (M+H)$^+$: 280.

Step 12—Synthesis of 6-chloro-2-iodopyridin-3-ol

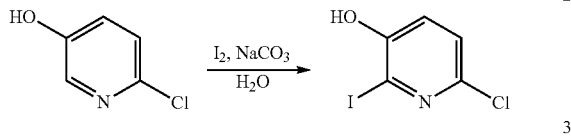

6-chloropyridin-3-ol (5.0 g, 38.6 mmol) was dissolved in water (50 mL) and placed under an N$_2$ atmosphere. Na$_2$CO$_3$ (8.2 g, 77.4 mmol) was added followed by iodine (9.8 g, 38.8 mmol). The reaction mixture was stirred at room temperature for 2 hours. The mixture was poured into 1M Na$_2$S$_2$O$_3$ and extracted with EtOAc. The combined organic phases were washed with brine, dried over Na$_2$SO$_4$ and concentrated to provide the product of 6-chloro-2-iodopyridin-3-ol (7.0 g, yield: 70.9%). $^1$H-NMR (CDCl$_3$, 400 MHz) δ 7.17 (d, J=8.4 Hz, 1H), 7.06 (d, J=8.4 Hz, 1H). MS (M+H)$^+$: 256/258.

Step 13—Synthesis of 6-chloro-2-(4-fluoro-1H-indol-2-yl)pyridin-3-ol

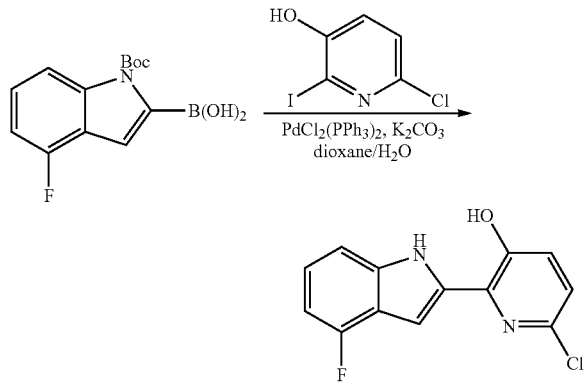

A mixture of (1-(tert-butoxycarbonyl)-4-fluoro-1H-indol-2-yl)boronic acid (5 g, 18.0 mmol), 6-chloro-2-iodopyridin-3-ol (3.82 g, 15.0 mol) and NaHCO$_3$ (3.78 g, 45.0 mol) in 1,4-dioxane (76 mL) and water (7 mL) was stirred at room temperature for 15 minutes. Then Pd(PPh$_3$)$_2$Cl$_2$ (527 mg, 0.75 mmol) was added under nitrogen atmosphere, and the mixture was heated at 100° C. under N$_2$ for 16 hours. The reaction mixture was cooled to room temperature, diluted with EtOAc (50 mL), filtered and concentrated in vacuo. The resulting residue was diluted with H$_2$O (60 mL) and EtOAc (30 mL), and the layer was separated, the aqueous layer was extracted with EtOAc (3*30 mL). The combined organic layers were washed with brine (50 mL), dried over Na$_2$SO$_4$, filtered and concentrated in vacuo. The resulting residue was purified using column chromatography (petroleum ether/EtOAc=20/1~3/1) to provide 6-chloro-2-(4-fluoro-1H-indol-2-yl)pyridin-3-ol (3 g, yield: 76.5%). $^1$H-NMR (MeOD, 400 MHz) δ 7.36 (s, 1H), 7.23~7.27 (m, 2H), 7.03~7.11 (m, 2H), 6.63~6.68 (m, 1H). MS (M+H)$^+$: 263/265.

Step 14—Synthesis of 2-chloro-11-fluoro-6H-pyrido[2',3':5,6][1,3]oxazino[3,4-a]indole

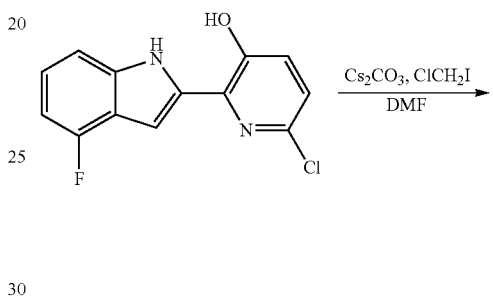

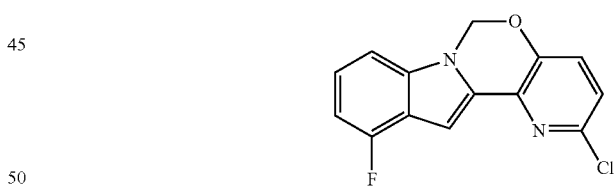

A solution of 6-chloro-2-(4-fluoro-1H-indol-2-yl)pyridin-3-ol (2 g, 7.6 mmol) and Cs$_2$CO$_3$ (7.46 g, 22.89 mmol) in DMF (100 mL) was stirred at 100° C. (internal temperature) for 15 min, and then chloroiodomethane (2.85 g, 15.3 mmol) in DMF (2 mL) was added dropwise. After the reaction was completed, the mixture was filtered and concentrated in vacuo. The resulting residue was diluted with water (50 mL) and extracted with ethyl acetate (30 mL×3). The organic layer was washed with brine, dried over Na$_2$SO$_4$ and concentrated in vacuo. The resulting residue was purified using column chromatography (petroleum ether:EA=10:1) to provide 2-chloro-11-fluoro-6H-pyrido[2',3':5,6][1,3]oxazino[3,4-a]indole (1.8 g, yield: 86.1%). $^1$H-NMR (DMSO-d$_6$, 400 MHz) δ 7.64 (d, J=8.8 Hz, 1H), 7.39~7.46 (m, 2H), 7.21~7.25 (m, 1H), 7.06 (s, 1H), 6.88~6.92 (m, 1H), 6.18 (s, 2H). MS (M+H)$^+$: 275/277.

Step 15—Synthesis of 5-(11-fluoro-6H-pyrido[2',3': 5,6][1,3]oxazino[3,4-a]indol-2-yl)-2-(4-fluorophenyl)-N-methyl-6-(N-methylmethylsulfonamido)benzofuran-3-carboxamide

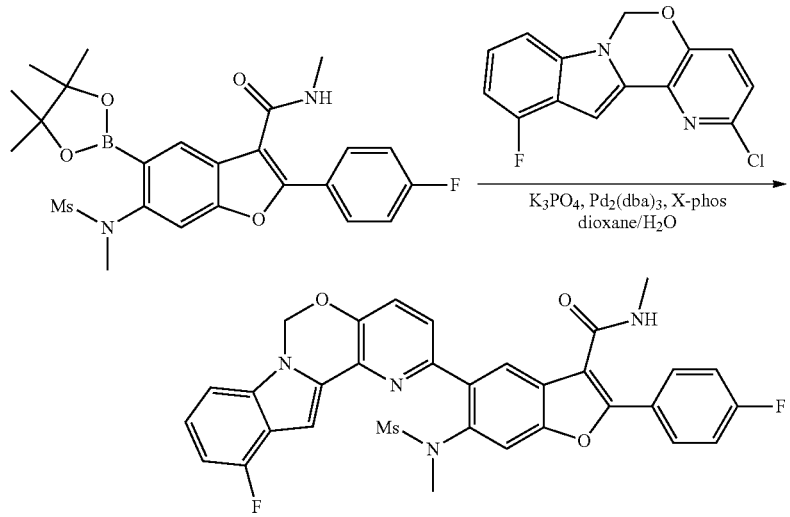

To a degassed solution of 2-(4-fluorophenyl)-N-methyl-6-(N-methylmethylsulfonamido)-5-(4,4,5,5-tetramethyl-1,3,2-dioxaborolan-2-yl)benzofuran-3-carboxamide (100 mg, 0.199 mmol), 2-chloro-11-fluoro-6H-pyrido[2',3':5,6][1,3]oxazino[3,4-a]indole (56 mg, 0.199 mmol) and $K_3PO_4 \cdot 3H_2O$ (159 mg, 0.597 mmol) in dioxane/$H_2O$ (0.8 mL/0.2 mL) was added $Pd_2(dba)_3$ (9 mg, 0.01 mmol) and X-Phos (9 mg, 0.02 mmol) under $N_2$. The mixture was heated at 80° C. for 1 hour. The mixture was then diluted with water (30 mL) and extracted with EtOAc (15 mL×3). The organic layer was washed with brine (20 mL), dried over $Na_2SO_4$ and concentrated in vacuo. The resulting residue was purified using prep-TLC (petroleum ether/EtOAc=1:1.5) to provide the pure product of 5-(11-fluoro-6H-pyrido[2',3':5,6][1,3]oxazino[3,4-a]indol-2-yl)-2-(4-fluorophenyl)-N-methyl-6-(N-methylmethylsulfonamido)benzofuran-3-carboxamide (60 mg, 48.8%). $^1$H-NMR (CDCl$_3$, 400 MHz) δ: 7.99 (s, 1H), 7.93~7.96 (m, 2H), 7.65 (s, 1H), 7.45~7.50 (m, 2H), 7.17~7.21 (m, 4H), 7.10 (d, J=8.0 Hz, 1H), 6.81~6.85 (m, 1H), 5.98 (s, 3H), 3.35 (s, 3H), 2.98 (d, J=4.8 Hz, 3H), 2.72 (s, 3H). MS (M+H)$^+$: 615.

Example 82

Measuring Compound Inhibitory Potency

Measurement of inhibition by compounds was performed using the HCV replicon system. Several different replicons encoding different HCV genotypes or mutations were used. In addition, potency measurements were made using different formats of the replicon assay, including different ways of measurements and different plating formats. See Jan M. Vrolijk et al., *A replicons-based bioassay for the measurement of interferons in patients with chronic hepatitis C*, 110 J. VIROLOGICAL METHODS 201 (2003); Steven S. Carroll et al., *Inhibition of Hepatitis C Virus RNA Replication by 2'-Modified Nucleoside Analogs*, 278(14) J. BIOLOGICAL CHEMISTRY 11979 (2003). However, the underlying principles are common to all of these determinations, and are outlined below.

Stable neomycin phosphotransferase encoding replicons-harboring cell lines were used, so all cell lines were maintained under G418 selection prior to the assay. Potency was determined using a cell ELISA assay with an antibody to the replicons encoded NS3/4a protease. See Caterina Trozzi et al., *In Vitro Selection and Characterization of Hepatitis C Virus Serine Protease Variants Resistant to an Active-Site Peptide Inhibitor*, 77(6) J. Virol. 3669 (2003). To initiate an assay, replicon cells were plated in the presence of a dilution series of test compound in the absence of G418. Typically, the assays were performed in a 96-well plate formate for manual operation, or a 384-well plate format for automated assay. Replicon cells and compound were incubated for 96 hours. At the end of the assay, cells were washed free of media and compound, and the cells were then lysed. RNA was quantified indirectly through detection of replicon-encoded NS3/4A protein levels, through an ELISA-based assay with an antibody specific for NS3/4A. IC$_{50}$ determinations were calculated as a percentage of a DMSO control by fitting the data to a four-parameter fit function and the data obtained is provided in the table below.

Data for selected compounds of the present invention was obtained for genotypes 1a and 1b using this method and is provided in the table below:

| Compound# | 1a IC$_{50}$ (nM) | 1b IC$_{50}$ (nM) |
| --- | --- | --- |
| 1 | 2.4 | 4.8 |
| 2 | 1.6 | 2.7 |
| 3 | 2.0 | 3.7 |
| 4 | 0.7 | 1.3 |
| 5 | 1.0 | 2.0 |
| 6 | 1.5 | 2.3 |
| 7 | 2.4 | 1.6 |
| 8 | 1.6 | 2.1 |
| 9 | 1.1 | 1.9 |
| 10 | 1.6 | 2.4 |
| 11 | 2.1 | 1.8 |
| 12 | 1.6 | 1.7 |
| 13 | 2.0 | 2.2 |
| 14 | 3.0 | 6.2 |
| 15 | 9.1 | 9.9 |
| 16 | 2.1 | 2.3 |
| 17 | 4.0 | 3.9 |
| 18 | 9.2 | 5.4 |

| Compound# | 1a IC$_{50}$ (nM) | 1b IC$_{50}$ (nM) |
|---|---|---|
| 19 | 19 | 21 |
| 20 | 6.7 | 6.9 |
| 21 | 14 | 13 |
| 22 | 3.5 | 1.9 |
| 23 | 0.9 | 1.2 |
| 24 | 3.0 | 5.1 |
| 25 | 1.0 | 1.8 |
| 26 | 1.1 | 1.2 |
| 27 | 2.9 | 6.1 |
| 28 | 2.1 | 4.5 |
| 29 | 4.8 | 8.0 |
| 30 | 1.0 | 2.1 |
| 31 | 7.2 | 6.5 |
| 32 | 5.7 | 19 |
| 33 | 0.9 | 1.2 |
| 34 | 1.4 | 3.3 |
| 35 | 2.5 | 4.7 |
| 36 | 1.7 | 7.1 |
| 37 | 3.4 | 5.9 |
| 38 | 3.2 | 5.8 |
| 39 | 2.4 | 1.8 |
| 40 | 2.0 | 2.2 |
| 41 | 2.4 | 5.0 |
| 42 | 3.1 | 4.5 |
| 43 | 2.4 | 3.9 |
| 44 | 2.8 | 2.4 |
| 45 | 9.2 | 11 |
| 46 | 1.5 | 2.1 |
| 47 | 1.2 | 1.8 |
| 48 | 2.2 | 2.6 |
| 49 | 0.6 | 1.7 |
| 50 | 15 | 4.6 |
| 51 | 17 | 33 |
| 52 | 1.7 | 2.7 |
| 53 | 8.0 | 7.9 |
| 54 | 69 | 39 |
| 55 | 57 | 49 |
| 56 | 13 | 12 |
| 57 | 11 | 13 |
| 58 | 13 | 8.7 |
| 59 | 2.5 | 4.2 |
| 60 | 69 | 31 |
| 61 | 6.5 | 11 |
| 62 | 12 | 3.4 |
| 63 | 92 | 83 |
| 64 | 71 | 44 |
| 65 | 11 | 19 |
| 66 | 49 | 59 |
| 67 | 9.2 | 10 |
| 68 | 60 | 19 |
| 69 | 57 | 45 |
| 70 | 71 | 18 |
| 71 | 13 | 4.5 |
| 72 | 52 | 9 |
| 73 | 625 | 36 |
| 74 | 15 | 25 |
| 75 | 2.8 | 2.6 |
| 76 | 4.5 | 5.8 |
| 77 | 10 | 11 |
| 78 | 5.7 | 3.5 |
| 79 | 10 | 11 |
| 80 | 18 | 15 |
| 81 | 36 | 22 |
| 82 | 15 | 11 |
| 83 | 15 | 12 |
| 84 | 26 | 16 |
| 85 | 13 | 7.7 |
| 86 | 17 | 12 |
| 87 | 3 | 3.3 |
| 88 | 2.7 | 2.6 |
| 89 | 1.1 | 0.9 |
| 90 | 5.5 | 2.4 |
| 91 | 3.3 | 7.4 |
| 92 | 4.2 | 6.5 |
| 93 | 4.4 | 6.0 |
| 94 | 2.3 | 5.6 |
| 95 | 3.2 | 5.3 |
| 96 | 4.1 | 5.1 |
| 97 | 2.9 | 4.4 |
| 98 | 3.9 | 6.3 |
| 99 | 1.9 | 4.6 |
| 100 | 3.3 | 3.6 |
| 101 | 5.8 | 8.7 |
| 102 | 3.9 | 4.3 |
| 103 | 3.3 | 6.9 |
| 104 | 2.4 | 4.8 |
| 105 | 1.4 | 0.9 |
| 106 | 5.5 | 2.4 |
| 107 | 1.5 | 0.7 |
| 108 | 14 | 2.4 |
| 109 | 2.0 | 2.1 |
| 110 | 3.0 | 4.8 |
| 111 | 4.5 | 4.3 |
| 112 | 20 | 23 |
| 113 | 32 | 29 |
| 114 | 7.3 | 18 |
| 115 | 8.9 | 19 |
| 116 | 53 | 9.4 |
| 117 | 74 | 7.5 |
| 118 | 19 | 4.0 |
| 119 | 17 | 5.1 |
| 120 | 4.3 | 2.1 |
| 121 | 3.0 | 7.5 |
| 122 | 5.1 | 5.2 |
| 123 | 3.4 | 3.6 |
| 124 | 19 | 4.5 |
| 125 | 5.1 | 3.4 |
| 126 | 2.7 | 1.4 |
| 127 | 3.5 | 1.6 |
| 128 | 2.6 | 0.9 |
| 129 | 1.7 | 2.1 |
| 130 | 3.0 | 3.0 |
| 131 | 79 | 50 |
| 132 | 4.8 | 7.9 |
| 133 | 2.6 | 3.2 |
| 134 | 4.0 | 2.9 |
| 135 | 2.4 | 2.4 |
| 136 | 3.5 | 2.9 |
| 137 | 44 | 7.9 |
| 138 | 62 | 19 |
| 139 | 1.9 | 1.9 |
| 140 | 7.9 | 5.9 |
| 141 | 2.4 | 2.4 |
| 142 | 4.1 | 4.0 |
| 143 | 15 | 8.0 |
| 144 | 2.9 | 1.9 |
| 145 | 5.3 | 2.7 |
| 146 | 225 | 37 |
| 147 | 9.0 | 6.9 |
| 148 | 2.8 | 4.6 |
| 149 | 1.2 | 2.2 |
| 150 | 38 | 30 |
| 151 | 4.3 | 5.9 |
| 152 | 14 | 15 |
| 153 | 2.5 | 4.9 |
| 154 | 2.7 | 2.2 |
| 155 | 7.0 | 17 |
| 156 | 2.3 | 2.9 |
| 157 | 7.6 | 11 |
| 158 | 42 | 24 |
| 159 | 11 | 22 |
| 160 | 19 | 16 |
| 161 | 32 | 54 |
| 162 | 29 | 18 |
| 163 | 1.1 | 2.2 |
| 164 | 1.7 | 1.0 |
| 165 | 27 | 9.7 |
| 166 | 69 | 27 |
| 167 | 21 | 17 |
| 168 | 3.3 | 2.8 |
| 169 | 14 | 5.0 |
| 170 | 54 | 13 |

-continued

| Compound# | 1a IC$_{50}$ (nM) | 1b IC$_{50}$ (nM) |
|---|---|---|
| 171 | 12 | 4.7 |
| 172 | 2.2 | 2.1 |
| 173 | 8.4 | 2.1 |
| 174 | 13 | 4.7 |
| 175 | 5.3 | 3.1 |
| 176 | 7.9 | 8.8 |
| 177 | 4.6 | 4.0 |
| 178 | 133 | 28 |
| 179 | 32 | 7.4 |
| 180 | 3.0 | 5.3 |
| 181 | 13 | 14 |
| 182 | 24 | 23 |
| 183 | 2.0 | 7.1 |
| 184 | 8.4 | 6.5 |
| 185 | 7.9 | 16 |
| 186 | 4.4 | 7.6 |
| 187 | 7.5 | 9.4 |
| 188 | 3.8 | 3.7 |
| 189 | 2.9 | 4.4 |
| 190 | 2.8 | 3.8 |
| 191 | 1.7 | 2.2 |
| 192 | 4.6 | 7.1 |
| 193 | 1.3 | 1.7 |
| 194 | 1.9 | 2.3 |
| 195 | 2.1 | 4.1 |
| 196 | 1.8 | 3.6 |
| 197 | 2.6 | 4.4 |
| 198 | 2.0 | 5.6 |
| 199 | 4.7 | 5.9 |
| 200 | 14 | 22 |
| 201 | 2.6 | 5.5 |
| 202 | 2.8 | 8.8 |
| 203 | 2.9 | 8.9 |
| 204 | 8.1 | 19 |
| 205 | 14 | 15 |
| 206 | 15 | 23 |
| 207 | 3.3 | 2.1 |
| 208 | 42 | 122 |
| 209 | 0.6 | 2.6 |
| 210 | 2.1 | 4.2 |
| 211 | 6.5 | 12 |

Uses of the Tetracyclic Heterocycle Compounds

The Tetracyclic Heterocycle Compounds are useful in human and veterinary medicine for treating or preventing a viral infection in a patient. In one embodiment, the Tetracyclic Heterocycle Compounds can be inhibitors of viral replication. In another embodiment, the Tetracyclic Heterocycle Compounds can be inhibitors of HCV replication. Accordingly, the Tetracyclic Heterocycle Compounds are useful for treating viral infections, such as HCV. In accordance with the invention, the Tetracyclic Heterocycle Compounds can be administered to a patient in need of treatment or prevention of a viral infection.

Accordingly, in one embodiment, the invention provides methods for treating a viral infection in a patient comprising administering to the patient an effective amount of at least one Tetracyclic Heterocycle Compound or a pharmaceutically acceptable salt thereof.

Treatment or Prevention of a Flaviviridae Virus

The Tetracyclic Heterocycle Compounds can be useful for treating or preventing a viral infection caused by the Flaviviridae family of viruses. Examples of Flaviviridae aredengue fever, Japanese encephalitis, Kyasanur Forest disease, Murray Valley encephalitis, St. Louis encephalitis, Tick-borne encephalitis, West Nile encephalitis, yellow fever and Hepatitis C Virus (HCV) infection.

In one embodiment, the Flaviviridae infection being treated is hepatitis C virus infection.

Treatment or Prevention of HCV Infection

The Tetracyclic Heterocycle Compounds are useful in the inhibition of HCV (e.g., HCV NS5B), the treatment of HCV infection and/or reduction of the likelihood or severity of symptoms of HCV infection and the inhibition of HCV viral replication and/or HCV viral production in a cell-based system. For example, the Tetracyclic Heterocycle Compounds are useful in treating infection by HCV after suspected past exposure to HCV by such means as blood transfusion, exchange of body fluids, bites, accidental needle stick, or exposure to patient blood during surgery or other medical procedures.

In one embodiment, the hepatitis C infection is acute hepatitis C. In another embodiment, the hepatitis C infection is chronic hepatitis C.

Accordingly, in one embodiment, the invention provides methods for treating HCV infection in a patient, the methods comprising administering to the patient an effective amount of at least one Tetracyclic Heterocycle Compound or a pharmaceutically acceptable salt thereof. In a specific embodiment, the amount administered is effective to treat or prevent infection by HCV in the patient. In another specific embodiment, the amount administered is effective to inhibit HCV viral replication and/or viral production in the patient.

The Tetracyclic Heterocycle Compounds are also useful in the preparation and execution of screening assays for antiviral compounds. For example the Tetracyclic Heterocycle Compounds are useful for identifying resistant HCV replicon cell lines harboring mutations within NS5A, which are excellent screening tools for more powerful antiviral compounds. Furthermore, the Tetracyclic Heterocycle Compounds are useful in establishing or determining the binding site of other antivirals to the HCV replicase.

The compositions and combinations of the present invention can be useful for treating a patient suffering from infection related to any HCV genotype. HCV types and subtypes may differ in their antigenicity, level of viremia, severity of disease produced, and response to interferon therapy as described in Holland et al., Pathology, 30(2):192-195 (1998). The nomenclature set forth in Simmonds et al., J Gen Virol, 74(Pt11):2391-2399 (1993) is widely used and classifies isolates into six major genotypes, 1 through 6, with two or more related subtypes, e.g., 1a and 1b. Additional genotypes 7-10 and 11 have been proposed, however the phylogenetic basis on which this classification is based has been questioned, and thus types 7, 8, 9 and 11 isolates have been reassigned as type 6, and type 10 isolates as type 3 (see Lamballerie et al., J Gen Virol, 78(Pt1):45-51 (1997)). The major genotypes have been defined as having sequence similarities of between 55 and 72% (mean 64.5%), and subtypes within types as having 75%-86% similarity (mean 80%) when sequenced in the NS-5 region (see Simmonds et al., J Gen Virol, 75(Pt 5):1053-1061 (1994)).

Combination Therapy

In another embodiment, the present methods for treating or preventing HCV infection can further comprise the administration of one or more additional therapeutic agents which are not Tetracyclic Heterocycle Compounds.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a patient, the method comprising administering to the patient: (i) at least one Tetracyclic Heterocycle Compound, or a pharmaceutically acceptable salt thereof, and (ii) at least one additional therapeutic agent that is other than a Tetracyclic Heterocycle Compound, wherein the amounts administered are together effective to treat or prevent a viral infection.

When administering a combination therapy of the invention to a patient, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Tetracyclic Heterocycle Compound and an additional therapeutic agent may be present in fixed amounts (dosage amounts) in a single dosage unit (e.g., a capsule, a tablet and the like).

In one embodiment, the at least one Tetracyclic Heterocycle Compound is administered during a time when the additional therapeutic agent(s) exert their prophylactic or therapeutic effect, or vice versa.

In another embodiment, the at least one Tetracyclic Heterocycle Compound and the additional therapeutic agent(s) are administered in doses commonly employed when such agents are used as monotherapy for treating a viral infection.

In another embodiment, the at least one Tetracyclic Heterocycle Compound and the additional therapeutic agent(s) are administered in doses lower than the doses commonly employed when such agents are used as monotherapy for treating a viral infection.

In still another embodiment, the at least one Tetracyclic Heterocycle Compound and the additional therapeutic agent(s) act synergistically and are administered in doses lower than the doses commonly employed when such agents are used as monotherapy for treating a viral infection.

In one embodiment, the at least one Tetracyclic Heterocycle Compound and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that can be treated or prevented using the combination therapy methods of the present invention include, but are not limited to, those listed above.

In one embodiment, the viral infection is HCV infection.

The at least one Tetracyclic Heterocycle Compound and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Tetracyclic Heterocycle Compound and the additional therapeutic agent(s) may inhibit the resistance of a viral infection to these agents.

Non-limiting examples of additional therapeutic agents useful in the present compositions and methods include an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a virion production inhibitor, a viral entry inhibitor, a viral assembly inhibitor, an antibody therapy (monoclonal or polyclonal), and any agent useful for treating an RNA-dependent polymerase-related disorder.

In one embodiment, the additional therapeutic agent is a viral protease inhibitor.

In another embodiment, the additional therapeutic agent is a viral replication inhibitor.

In another embodiment, the additional therapeutic agent is an HCV NS3 protease inhibitor.

In still another embodiment, the additional therapeutic agent is an HCV NS5B polymerase inhibitor.

In another embodiment, the additional therapeutic agent is a nucleoside inhibitor.

In another embodiment, the additional therapeutic agent is an interferon.

In yet another embodiment, the additional therapeutic agent is an HCV replicase inhibitor.

In another embodiment, the additional therapeutic agent is an antisense agent.

In another embodiment, the additional therapeutic agent is a therapeutic vaccine.

In a further embodiment, the additional therapeutic agent is a virion production inhibitor.

In another embodiment, the additional therapeutic agent is an antibody therapy.

In another embodiment, the additional therapeutic agent is an HCV NS2 inhibitor.

In still another embodiment, the additional therapeutic agent is an HCV NS4A inhibitor.

In another embodiment, the additional therapeutic agent is an HCV NS4B inhibitor.

In another embodiment, the additional therapeutic agent is an HCV NS5A inhibitor In yet another embodiment, the additional therapeutic agent is an HCV NS3 helicase inhibitor.

In another embodiment, the additional therapeutic agent is an HCV IRES inhibitor.

In another embodiment, the additional therapeutic agent is an HCV p7 inhibitor.

In a further embodiment, the additional therapeutic agent is an HCV entry inhibitor.

In another embodiment, the additional therapeutic agent is an HCV assembly inhibitor.

In one embodiment, the additional therapeutic agents comprise a viral protease inhibitor and a viral polymerase inhibitor.

In still another embodiment, the additional therapeutic agents comprise a viral protease inhibitor and an immunomodulatory agent.

In yet another embodiment, the additional therapeutic agents comprise a polymerase inhibitor and an immunomodulatory agent.

In another embodiment, the additional therapeutic agents comprise a viral protease inhibitor and a nucleoside.

In another embodiment, the additional therapeutic agents comprise an immunomodulatory agent and a nucleoside.

In one embodiment, the additional therapeutic agents comprise an HCV protease inhibitor and an HCV polymerase inhibitor.

In another embodiment, the additional therapeutic agents comprise a nucleoside and an HCV NS5A inhibitor.

In another embodiment, the additional therapeutic agents comprise a viral protease inhibitor, an immunomodulatory agent and a nucleoside.

In a further embodiment, the additional therapeutic agents comprise a viral protease inhibitor, a viral polymerase inhibitor and an immunomodulatory agent.

In another embodiment, the additional therapeutic agent is ribavirin.

HCV polymerase inhibitors useful in the present compositions and methods include, but are not limited to, VP-19744 (Wyeth/ViroPharma), PSI-7851 (Pharmasset), RG7128 (Roche/Pharmasset), GS-7977 (Gilead), PSI-938 (Pharmasset), PSI-879 (Pharmasset), PSI-661 (Pharmasset), PF-868554/filibuvir (Pfizer), VCH-759/VX-759 (ViroChem Pharma/Vertex), HCV-371 (Wyeth/VirroPharma), HCV-796 (Wyeth/ViroPharma), IDX-184 (Idenix), IDX-375 (Idenix), NM-283 (Idenix/Novartis), GL-60667 (Genelabs), JTK-109 (Japan Tobacco), PSI-6130 (Pharmasset), R1479 (Roche), R-1626 (Roche), R-7128 (Roche), MK-0608 (Isis/Merck), INX-8014 (Inhibitex), INX-8018 (Inhibitex), INX-189 (Inhibitex), GS 9190 (Gilead), A-848837 (Abbott), ABT-333 (Abbott), ABT-072 (Abbott), A-837093 (Abbott), BI-207127 (Boehringer-Ingelheim), BILB-1941 (Boehringer-Ingelheim), MK-3281 (Merck), VCH-222/VX-222 (ViroChem/Vertex), VCH-916 (ViroChem), VCH-716(ViroChem), GSK-71185 (Glaxo SmithKline), ANA598 (Anadys), GSK-625433 (Glaxo SmithKline), XTL-2125 (XTL Biopharmaceuticals), and those disclosed in Ni et al., *Current Opinion in Drug Discovery and Development*, 7(4):446 (2004); Tan et al., *Nature Reviews*, 1:867 (2002); and Beaulieu et al., *Current Opinion in Investigational Drugs*, 5:838 (2004).

Other HCV polymerase inhibitors useful in the present compositions and methods include, but are not limited to, those disclosed in International Publication Nos. WO 08/082,484, WO 08/082,488, WO 08/083,351, WO 08/136,815, WO 09/032,116, WO 09/032,123, WO 09/032,124 and WO 09/032,125.

Interferons useful in the present compositions and methods include, but are not limited to, interferon alfa-2a, interferon alfa-2b, interferon alfacon-1 and petroleum etherG-interferon alpha conjugates. "PEG-interferon alpha conjugates" are interferon alpha molecules covalently attached to a petroleum etherG molecule. Illustrative petroleum etherG-interferon alpha conjugates include interferon alpha-2a (Roferon™, Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name petroleum etherG-Intron™ from Schering-Plough Corporation), interferon alpha-2b-XL (e.g., as sold under the trade name petroleum etherG-Intron™), interferon alpha-2c (Berofor Alpha™, Boehringer Ingelheim, Ingelheim, Germany), petroleum etherG-interferon lambda (Bristol-Myers Squibb and ZymoGenetics), interferon alfa-2b alpha fusion polypeptides, interferon fused with the human blood protein albumin (Albuferon™, Human Genome Sciences), Omega Interferon (Intarcia), Locteron controlled release interferon (Biolex/OctoPlus), Biomed-510 (omega interferon), Peg-IL-29 (Zymo-Genetics), Locteron CR (Octoplus), R-7025 (Roche), IFN-α-2b-XL (Flamel Technologies), belerofon (Nautilus) and consensus interferon as defined by determination of a consensus sequence of naturally occurring interferon alphas (Infergen™, Amgen, Thousand Oaks, Calif.).

Antibody therapy agents useful in the present compositions and methods include, but are not limited to, antibodies specific to IL-10 (such as those disclosed in US Patent Publication No. US2005/0101770, humanized 12G8, a humanized monoclonal antibody against human IL-10, plasmids containing the nucleic acids encoding the humanized 12G8 light and heavy chains were deposited with the American Type Culture Collection (ATCC) as deposit numbers PTA-5923 and PTA-5922, respectively), and the like).

Examples of viral protease inhibitors useful in the present compositions and methods include, but are not limited to, an HCV protease inhibitor.

HCV protease inhibitors useful in the present compositions and methods include, but are not limited to, those disclosed in U.S. Pat. Nos. 7,494,988, 7,485,625, 7,449,447, 7,442,695, 7,425,576, 7,342,041, 7,253,160, 7,244,721, 7,205,330, 7,192,957, 7,186,747, 7,173,057, 7,169,760, 7,012,066, 6,914,122, 6,911,428, 6,894,072, 6,846,802, 6,838,475, 6,800,434, 6,767,991, 5,017,380, 4,933,443, 4,812,561 and 4,634,697; U.S. Patent Publication Nos. US20020068702, US20020160962, US20050119168, US20050176648, US20050209164, US20050249702 and US20070042968; and International Publication Nos. WO 03/006490, WO 03/087092, WO 04/092161 and WO 08/124,148.

Additional HCV protease inhibitors useful in the present compositions and methods include, but are not limited to, VX-950 (Telaprevir, Vertex), VX-500 (Vertex), VX-813 (Vertex), VBY-376 (Virobay), BI-201335 (Boehringer Ingelheim), TMC-435 (Medivir/Tibotec), ABT-450 (Abbott/Enanta), TMC-435350 (Medivir), RG7227 (Danoprevir, InterMune/Roche), ethyl acetate-058 (Abbott/Enanta), ethyl acetate-063 (Abbott/Enanta), GS-9256 (Gilead), IDX-320 (Idenix), ACH-1625 (Achillion), ACH-2684 (Achillion), GS-9132 (Gilead/Achillion), ACH-1095 (Gilead/Achillon), IDX-136 (Idenix), IDX-316 (Idenix), ITMN-8356 (InterMune), ITMN-8347 (InterMune), ITMN-8096 (InterMune), ITMN-7587 (InterMune), BMS-650032 (Bristol-Myers Squibb), VX-985 (Vertex) and PHX1766 (Phenomix).

Further examples of HCV protease inhibitors useful in the present compositions and methods include, but are not limited to, those disclosed in Landro et al., *Biochemistry*, 36(31): 9340-9348 (1997); Ingallinella et al., *Biochemistry*, 37(25): 8906-8914 (1998); Llinas-Brunet et al., *Bioorg Med Chem Lett*, 8(13):1713-1718 (1998); Martin et al., *Biochemistry*, 37(33):11459-11468 (1998); Dimasi et al., *J Virol*, 71(10): 7461-7469 (1997); Martin et al., *Protein Eng*, 10(5):607-614 (1997); Elzouki et al., *J Hepat*, 27(1):42-48 (1997); *BioWorld Today*, 9(217):4 (Nov. 10, 1998); U.S. Patent Publication Nos. US2005/0249702 and US 2007/0274951; and International Publication Nos. WO 98/14181, WO 98/17679, WO 98/17679, WO 98/22496 and WO 99/07734 and WO 05/087731.

Further examples of HCV protease inhibitors useful in the present compositions and methods include, but are not limited to, the following compounds:

343
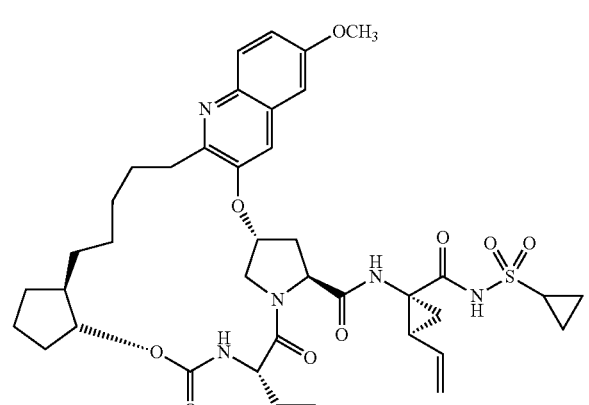
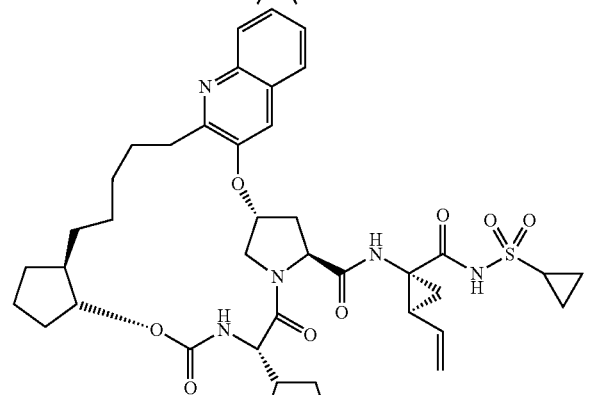
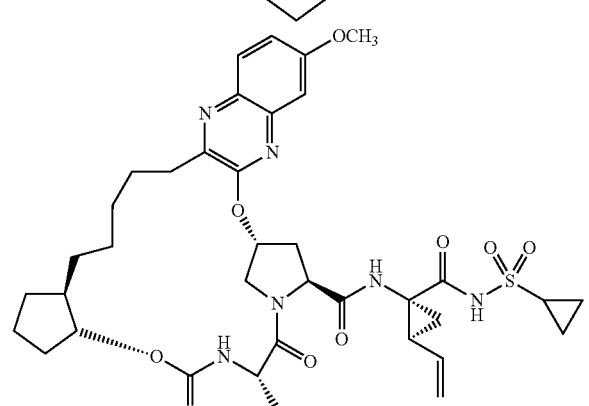
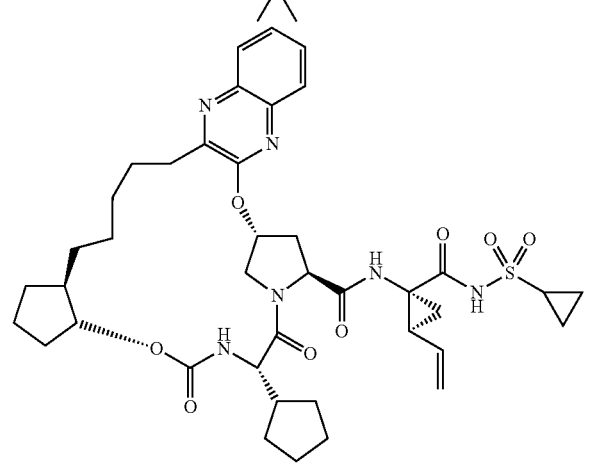
344
-continued
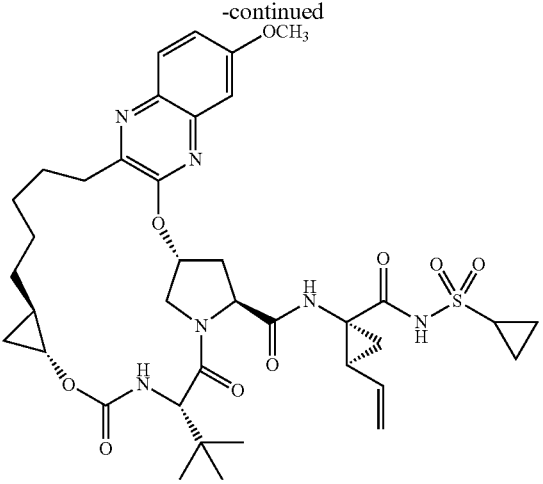
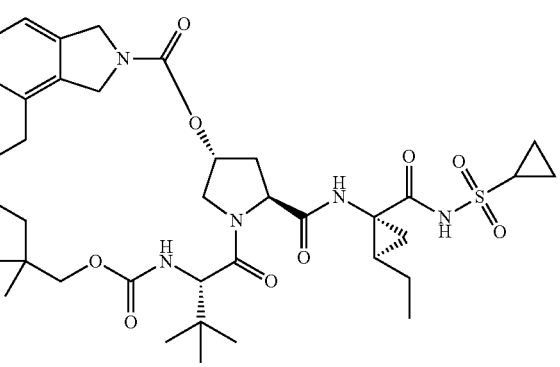
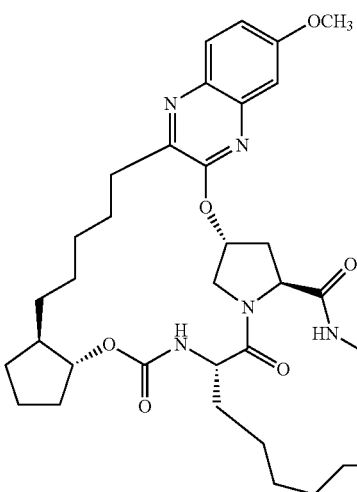

345
-continued
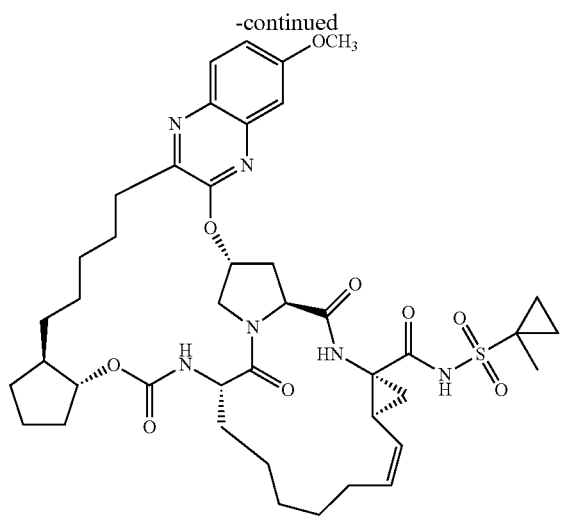
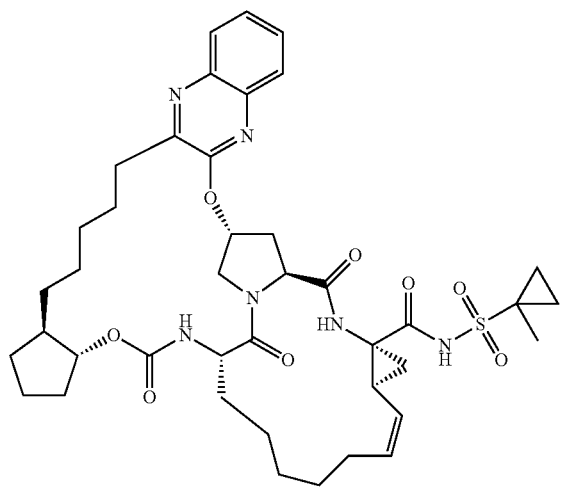
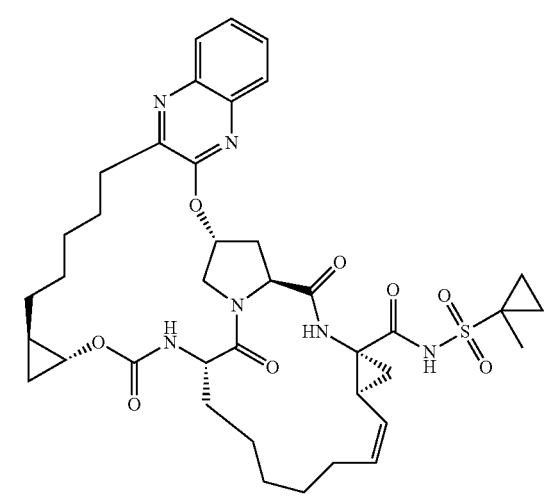
346
-continued
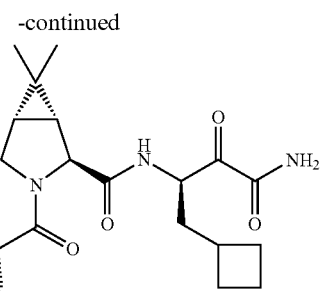
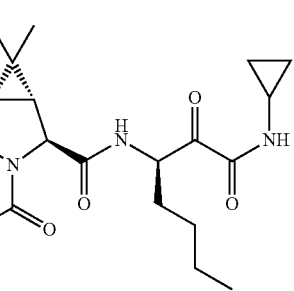
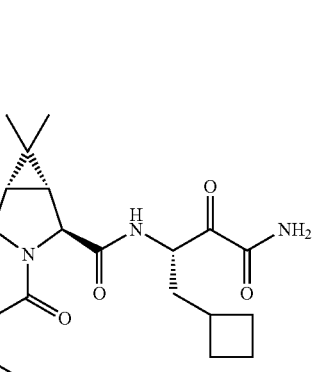
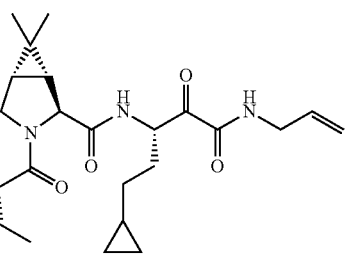

347
-continued
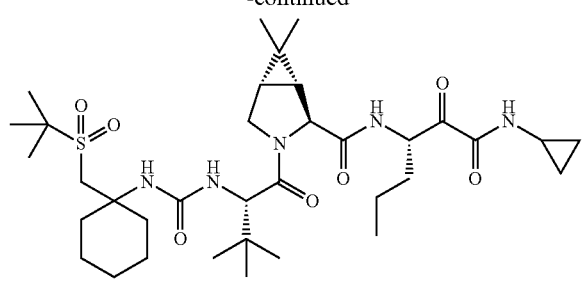
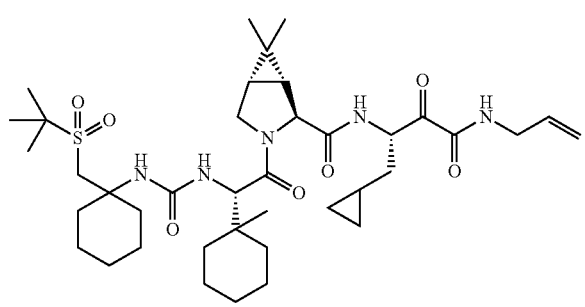
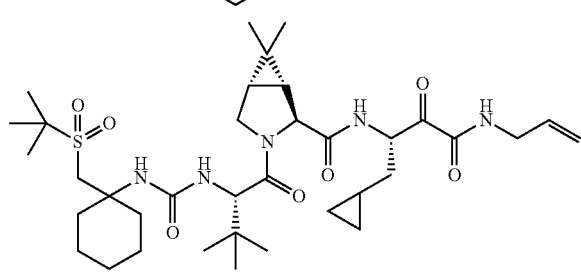
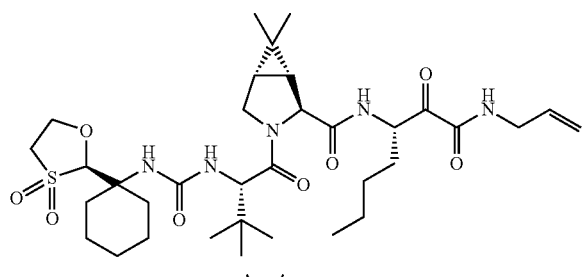
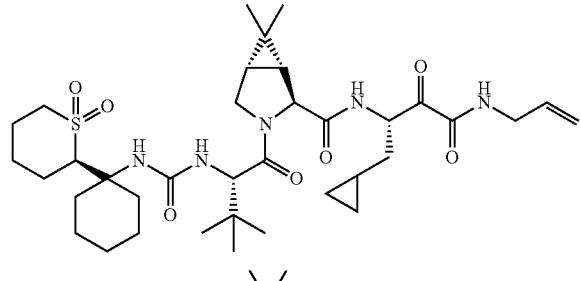
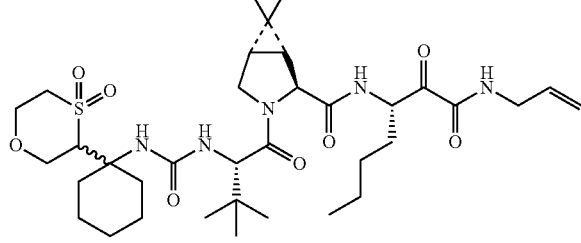
348
-continued
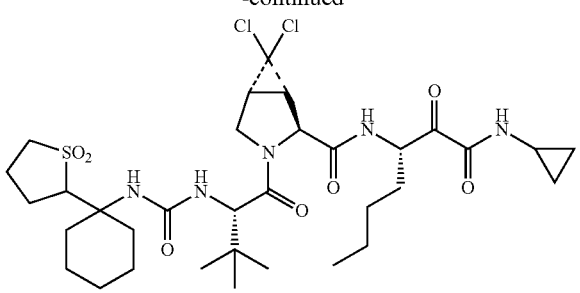
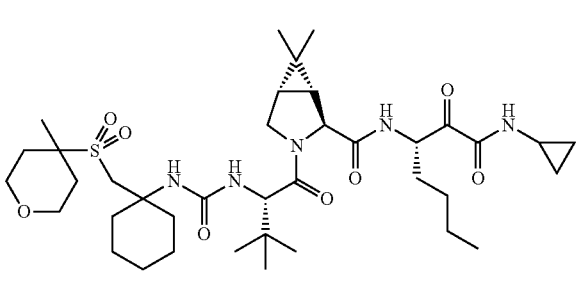
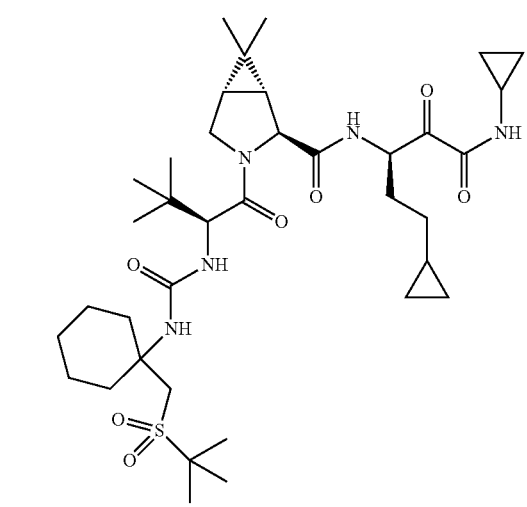
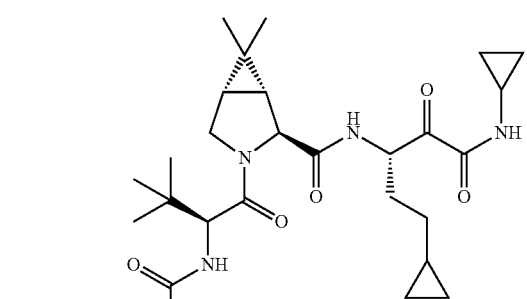
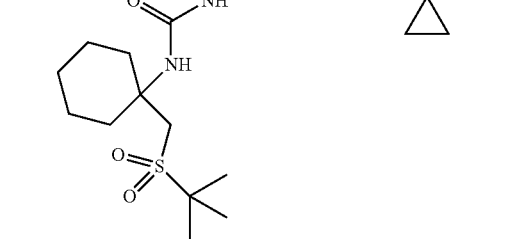

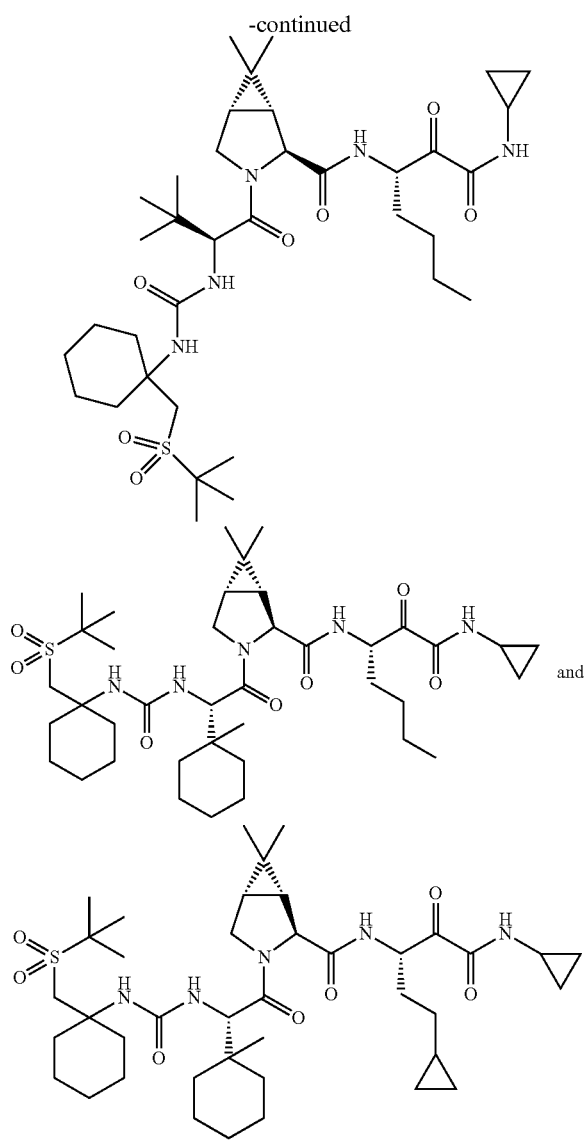

and pharmaceutically acceptable salts thereof.

Viral replication inhibitors useful in the present compositions and methods include, but are not limited to, HCV replicase inhibitors, IRES inhibitors, NS4A inhibitors, NS3 helicase inhibitors, NS5A inhibitors, NS5B inhibitors, ribavirin, AZD-2836 (Astra Zeneca), viramidine, A-831 (Arrow Therapeutics), EDP-239 (Enanta), ACH-2928 (Achillion), GS-5885 (Gilead); an antisense agent or a therapeutic vaccine.

Viral entry inhibitors useful as second additional therapeutic agents in the present compositions and methods include, but are not limited to, PRO-206 (Progenics), REP-9C (REPI-Cor), SP-30 (Samaritan Pharmaceuticals) and ITX-5061 (iTherx).

HCV NS4A inhibitors useful in the useful in the present compositions and methods include, but are not limited to, those disclosed in U.S. Pat. Nos. 7,476,686 and 7,273,885; U.S. Patent Publication No. US20090022688; and International Publication Nos. WO 2006/019831 and WO 2006/019832. Additional HCV NS4A inhibitors useful as second additional therapeutic agents in the present compositions and methods include, but are not limited to, AZD2836 (Astra Zeneca), ACH-1095 (Achillion) and ACH-806 (Achillion).

HCV NS5A inhibitors useful in the present compositions and methods include, but are not limited to, ACH-2928 (Achillon), AZD-7295 (Astra Zeneca), A-832 (Arrow Therpeutics), PPI-461 (Presidio), PPI-1301 (Presidio), GS-5885 (Gilead) and BMS-790052 (Bristol-Myers Squibb).

HCV replicase inhibitors useful in the present compositions and methods include, but are not limited to, those disclosed in U.S. Patent Publication No. US20090081636.

Therapeutic vaccines useful in the present compositions and methods include, but are not limited to, IC41 (Intercell Novartis), CSL123 (Chiron/CSL), GI 5005 (Globeimmune), TG-4040 (Transgene), GNI-103 (GENimmune), Hepavaxx C (ViRex Medical), ChronVac-C (Inovio/Tripep), PeviPROTM (Pevion Biotect), HCV/MF59 (Chiron/Novartis), MBL-HCV1 (MassBiologics), GI-5005 (GlobeImmune), CT-011 (CureTech/Teva) and Civacir (NABI).

Examples of further additional therapeutic agents useful in the present compositions and methods include, but are not limited to, Ritonavir (Abbott), TT033 (Benitec/Tacere Bio/Pfizer), Sirna-034 (Sirna Therapeutics), GNI-104 (GENimmune), GI-5005 (GlobeImmune), IDX-102 (Idenix), Levovirin™ (ICN Pharmaceuticals, Costa Mesa, Calif.); Humax (Genmab), ITX-2155 (Ithrex/Novartis), PRO206 (Progenics), HepaCide-I (NanoVirocides), MX3235 (Migenix), SCY-635 (Scynexis); KPE02003002 (Kemin Pharma), Lenocta (VioQuest Pharmaceuticals), IET—Interferon Enhancing Therapy (Transition Therapeutics), Zadaxin (SciClone Pharma), VP50406™ (Viropharma, Incorporated, Exton, Pa.); Taribavirin (Valeant Pharmaceuticals); Nitazoxanide (Romark); Debio 025 (Debiopharm); GS-9450 (Gilead); PF-4878691 (Pfizer); ANA773 (Anadys); SCV-07 (SciClone Pharmaceuticals); NIM-881 (Novartis); ISIS14803™ (ISIS Pharmaceuticals, Carlsbad, Calif.); Heptazyme™ (Ribozyme Pharmaceuticals, Boulder, Colo.); Thymosin™ (SciClone Pharmaceuticals, San Mateo, Calif.); Maxamine™ (Maxim Pharmaceuticals, San Diego, Calif.); NKB-122 (JenKen Bioscience Inc., North Carolina); Alinia (Romark Laboratories), INFORM-1 (a combination of R7128 and ITMN-191); and mycophenolate mofetil (Hoffman-LaRoche, Nutley, N.J.).

The doses and dosage regimen of the other agents used in the combination therapies of the present invention for the treatment or prevention of HCV infection can be determined by the attending clinician, taking into consideration the approved doses and dosage regimen in the package insert; the age, sex and general health of the patient; and the type and severity of the viral infection or related disease or disorder. When administered in combination, the Tetracyclic Heterocycle Compound(s) and the other agent(s) can be administered simultaneously (i.e., in the same composition or in separate compositions one right after the other) or sequentially. This particularly useful when the components of the combination are given on different dosing schedules, e.g., one component is administered once daily and another component is administered every six hours, or when the preferred pharmaceutical compositions are different, e.g., one is a tablet and one is a capsule. A kit comprising the separate dosage forms is therefore advantageous.

Generally, a total daily dosage of the at least one Tetracyclic Heterocycle Compound(s) alone, or when administered as combination therapy, can range from about 1 to about 2500 mg per day, although variations will necessarily occur depending on the target of therapy, the patient and the route of administration. In one embodiment, the dosage is from about 10 to about 1000 mg/day, administered in a single dose or in 2-4 divided doses. In another embodiment, the dosage is from about 1 to about 500 mg/day, administered in a single dose or in 2-4 divided doses. In still another embodiment, the dosage is from about 1 to about 100 mg/day, administered in a single dose or in 2-4 divided doses. In yet another embodiment, the dosage is from about 1 to about 50 mg/day, administered in a single dose or in 2-4 divided doses. In another embodiment, the dosage is from about 500 to about 1500 mg/day, administered in a single dose or in 2-4 divided doses. In still another embodiment, the dosage is from about 500 to about 1000 mg/day, administered in a single dose or in 2-4 divided doses. In yet another embodiment, the dosage is from about 100 to about 500 mg/day, administered in a single dose or in 2-4 divided doses.

In one embodiment, when the additional therapeutic agent is INTRON-A interferon alpha 2b (commercially available from Schering-Plough Corp.), this agent is administered by subcutaneous injection at 3MIU(12 mcg)/0.5 mL/TIW for 24 weeks or 48 weeks for first time treatment.

In another embodiment, when the additional therapeutic agent is petroleum etherG-INTRON interferon alpha 2b pegylated (commercially available from Schering-Plough Corp.), this agent is administered by subcutaneous injection at 1.5 mcg/kg/week, within a range of 40 to 150 mcg/week, for at least 24 weeks.

In another embodiment, when the additional therapeutic agent is ROFERON A interferon alpha 2a (commercially available from Hoffmann-La Roche), this agent is administered by subcutaneous or intramuscular injection at 3MIU (11.1 mcg/mL)/TIW for at least 48 to 52 weeks, or alternatively 6MIU/TIW for 12 weeks followed by 3MIU/TIW for 36 weeks.

In still another embodiment, when the additional therapeutic agent is petroleum etherGASUS interferon alpha 2a pegylated (commercially available from Hoffmann-La Roche), this agent is administered by subcutaneous injection at 180 mcg/1 mL or 180 mcg/0.5 mL, once a week for at least 24 weeks.

In yet another embodiment, when the additional therapeutic agent is INFERGEN interferon alphacon-1 (commercially available from Amgen), this agent is administered by subcutaneous injection at 9 mcg/TIW is 24 weeks for first time treatment and up to 15 mcg/TIW for 24 weeks for non-responsive or relapse treatment.

In a further embodiment, when the additional therapeutic agent is Ribavirin (commercially available as REBETOL ribavirin from Schering-Plough or COPEGUS ribavirin from Hoffmann-La Roche), this agent is administered at a daily dosage of from about 600 to about 1400 mg/day for at least 24 weeks.

In one embodiment, one or more compounds of the present invention are administered with one or more additional therapeutic agents selected from: an interferon, an immunomodulator, a viral replication inhibitor, an antisense agent, a therapeutic vaccine, a viral polymerase inhibitor, a nucleoside inhibitor, a viral protease inhibitor, a viral helicase inhibitor, a viral polymerase inhibitor a virion production inhibitor, a viral entry inhibitor, a viral assembly inhibitor, an antibody therapy (monoclonal or polyclonal), and any agent useful for treating an RNA-dependent polymerase-related disorder.

In another embodiment, one or more compounds of the present invention are administered with one or more additional therapeutic agents selected from an HCV protease inhibitor, an HCV polymerase inhibitor, an HCV replication inhibitor, a nucleoside, an interferon, a pegylated interferon and ribavirin. The combination therapies can include any combination of these additional therapeutic agents.

In another embodiment, one or more compounds of the present invention are administered with one additional therapeutic agent selected from an HCV protease inhibitor, an interferon, a pegylated interferon and ribavirin.

In still another embodiment, one or more compounds of the present invention are administered with two additional therapeutic agents selected from an HCV protease inhibitor, an HCV replication inhibitor, a nucleoside, an interferon, a pegylated interferon and ribavirin.

In another embodiment, one or more compounds of the present invention are administered with an HCV protease inhibitor and ribavirin. In another specific embodiment, one or more compounds of the present invention are administered with a pegylated interferon and ribavirin.

In another embodiment, one or more compounds of the present invention are administered with three additional therapeutic agents selected from an HCV protease inhibitor, an HCV replication inhibitor, a nucleoside, an interferon, a pegylated interferon and ribavirin.

In one embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and a viral replication inhibitor. In another embodiment, one or more compounds of the present invention are administered with one or more additional therapeutic agents selected from an HCV polymerase inhibitor, a viral protease inhibitor, an interferon, and ribavirin.

In one embodiment, one or more compounds of the present invention are administered with one additional therapeutic agent selected from an HCV polymerase inhibitor, a viral protease inhibitor, an interferon, and a viral replication inhibitor. In another embodiment, one or more compounds of the present invention are administered with ribavirin.

In one embodiment, one or more compounds of the present invention are administered with two additional therapeutic agents selected from an HCV polymerase inhibitor, a viral protease inhibitor, an interferon, and a viral replication inhibitor.

In another embodiment, one or more compounds of the present invention are administered with ribavirin, interferon and another therapeutic agent.

In another embodiment, one or more compounds of the present invention are administered with ribavirin, interferon and another therapeutic agent, wherein the additional therapeutic agent is selected from an HCV polymerase inhibitor, a viral protease inhibitor, and a viral replication inhibitor.

In still another embodiment, one or more compounds of the present invention are administered with ribavirin, interferon and a viral protease inhibitor.

In another embodiment, one or more compounds of the present invention are administered with ribavirin, interferon and an HCV protease inhibitor.

In another embodiment, one or more compounds of the present invention are administered with ribavirin, interferon and boceprevir or telaprevir.

In a further embodiment, one or more compounds of the present invention are administered with ribavirin, interferon and an HCV polymerase inhibitor.

In another embodiment, one or more compounds of the present invention are administered with pegylated-interferon alpha and ribavirin.

Compositions and Administration

Due to their activity, the Tetracyclic Heterocycle Compounds are useful in veterinary and human medicine. As described above, the Tetracyclic Heterocycle Compounds are useful for treating or preventing HCV infection in a patient in need thereof.

When administered to a patient, the Tetracyclic Heterocycle Compounds can be administered as a component of a composition that comprises a pharmaceutically acceptable carrier or vehicle. The present invention provides pharmaceutical compositions comprising an effective amount of at least one Tetracyclic Heterocycle Compound and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules can be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Tetracyclic Heterocycle Compounds are administered orally.

In another embodiment, the one or more Tetracyclic Heterocycle Compounds are administered intravenously.

In one embodiment, a pharmaceutical preparation comprising at least one Tetracyclic Heterocycle Compound is in unit dosage form. In such form, the preparation is subdivided into unit doses containing effective amounts of the active components.

Compositions can be prepared according to conventional mixing, granulating or coating methods, respectively, and the present compositions can contain, in one embodiment, from about 0.1% to about 99% of the Tetracyclic Heterocycle Compound(s) by weight or volume. In various embodiments, the present compositions can contain, in one embodiment, from about 1% to about 70% or from about 5% to about 60% of the Tetracyclic Heterocycle Compound(s) by weight or volume.

The quantity of Tetracyclic Heterocycle Compound in a unit dose of preparation may be varied or adjusted from about 1 mg to about 2500 mg. In various embodiment, the quantity is from about 10 mg to about 1000 mg, 1 mg to about 500 mg, 1 mg to about 100 mg, and 1 mg to about 100 mg.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The amount and frequency of administration of the Tetracyclic Heterocycle Compounds will be regulated according to the judgment of the attending clinician considering such factors as age, condition and size of the patient as well as severity of the symptoms being treated. Generally, a total daily dosage of the Tetracyclic Heterocycle Compounds range from about 0.1 to about 2000 mg per day, although variations will necessarily occur depending on the target of therapy, the patient and the route of administration. In one embodiment, the dosage is from about 1 to about 200 mg/day, administered in a single dose or in 2-4 divided doses. In another embodiment, the dosage is from about 10 to about 2000 mg/day, administered in a single dose or in 2-4 divided doses. In another embodiment, the dosage is from about 100 to about 2000 mg/day, administered in a single dose or in 2-4 divided doses. In still another embodiment, the dosage is from about 500 to about 2000 mg/day, administered in a single dose or in 2-4 divided doses.

The compositions of the invention can further comprise one or more additional therapeutic agents, selected from those listed above herein. Accordingly, in one embodiment, the present invention provides compositions comprising: (i) at least one Tetracyclic Heterocycle Compound or a pharmaceutically acceptable salt thereof; (ii) one or more additional therapeutic agents that are not a Tetracyclic Heterocycle Compound; and (iii) a pharmaceutically acceptable carrier, wherein the amounts in the composition are together effective to treat HCV infection.

In one embodiment, the present invention provides compositions comprising a Compound of Formula (I) and a pharmaceutically acceptable carrier.

In another embodiment, the present invention provides compositions comprising a Compound of Formula (I), a pharmaceutically acceptable carrier, and a second therapeutic agent selected from the group consisting of HCV antiviral agents, immunomodulators, and anti-infective agents.

In another embodiment, the present invention provides compositions comprising a Compound of Formula (I), a pharmaceutically acceptable carrier, and wto additional therapeutic agents, each of which are independently selected from the group consisting of HCV antiviral agents, immunomodulators, and anti-infective agents.

Kits

In one aspect, the present invention provides a kit comprising a therapeutically effective amount of at least one Tetracyclic Heterocycle Compound, or a pharmaceutically acceptable salt, solvate, ester or prodrug of said compound and a pharmaceutically acceptable carrier, vehicle or diluent.

In another aspect the present invention provides a kit comprising an amount of at least one Tetracyclic Heterocycle Compound, or a pharmaceutically acceptable salt, solvate, ester or prodrug of said compound and an amount of at least one additional therapeutic agent listed above, wherein the amounts of the two or more active ingredients result in a desired therapeutic effect. In one embodiment, the one or more Tetracyclic Heterocycle Compounds and the one or more additional therapeutic agents are provided in the same container. In one embodiment, the one or more Tetracyclic Heterocycle Compounds and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

The invention claimed is:
1. A compound having the formula:

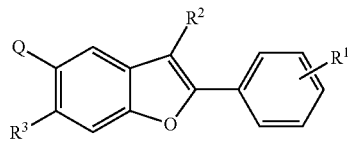

(I)

or a pharmaceutically acceptable salt thereof,
wherein:
Q is:

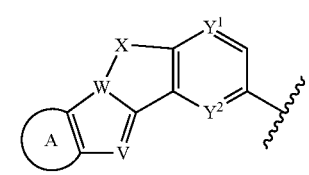

(Q1)

and
$Y^1$ is CH and $Y^2$ is N,
$Y^1$ is N and $Y^2$ is CH, or
$Y^1$ is N and $Y^2$ is N; or Q is:

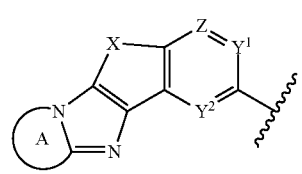

(Q2)

and
Z is N, $Y^1$ is CH and $Y^2$ is CH;
A is phenyl, 5 or 6-membered heteroaryl, 5 to 7-membered monocyclic cycloalkyl or 5 to 7-membered heterocycloalkyl, each of which can be optionally substituted with up to four $R^5$ groups;
V is N or —C($R^4$)—;
W is N or —CH—;
X is —(CH$R^8$)$_n$—O— or —C(O)—O—,
$R^1$ represents up to 4 optional ring substituents, which can be the same or different, and are independently selected from halo, $C_1$-$C_6$ alkyl, $C_1$-$C_6$ haloalkyl, phenyl, 3 to 7-membered monocyclic cycloalkyl, —O—($C_1$-$C_6$ alkyl), —O—($C_1$-$C_6$ haloalkyl) and —CN;
$R^2$ is —C(O)N($R^6$)($R^7$) or —C(O)O—($C_1$-$C_6$ alkyl);
$R^3$ is H, 4- to 6-membered heterocycloalkyl, 5 or 6-membered heteroaryl, —N($R^{11}$)$_2$, halo, —CN, —N($R^{11}$)$_2$, —C(O)O—($C_1$-$C_6$ alkyl) or —N($R^9$)—S(O)$_n$—$R^{10}$, wherein said 5 or 6-membered heterocycloalkyl can optionally have one of its ring carbon atoms replaced with a carbonyl group;
$R^4$ is selected from H, halo, $C_1$-$C_6$ alkyl, 3 to 7-membered monocyclic cycloalkyl, $C_1$-$C_6$ haloalkyl, —O—($C_1$-$C_6$ alkyl), —C(OH)—C(O)O$R^{11}$ and —O—($C_1$-$C_6$ haloalkyl);
each occurrence of $R^5$ is independently selected from H, halo, $C_1$-$C_6$ alkyl, $C_1$-$C_6$ haloalkyl, —O—($C_1$-$C_6$alkyl), —O—($C_1$C$_6$ haloalkyl) and —CN, wherein said $C_1$-$C_6$alkyl group can be optionally substituted with —OH or —N($R^{11}$)$_2$;
$R^6$ and $R^7$ are each independently selected from hydrogen, —C(O)$R^{11}$, —C(O)O$R^{11}$, —C(O)C(O)O$R^{11}$, $C_1$-$C_6$ alkyl, $C_1$-$C_6$ hydroxyalkyl, phenyl, 3 to 7-membered monocyclic cycloalkyl, 3 to 7-membered monocyclic heterocycloalkyl and 5 or 6-membered monocyclic heteroaryl;
each occurrence of $R^8$ is independently selected from H, halo, —OH, $C_1$-$C_6$ alkyl, $C_1$-$C_6$ hydroxyalkyl, phenyl, 5 or 6-membered monocyclic heteroaryl, —N($R^{11}$)$_2$, $C_1$-$C_6$ haloalkyl, —($C_1$-$C_3$ alkylene)$_p$-(3 to 7-membered monocyclic cycloalkyl), —($C_1$-$C_3$ alkylene)$_p$—O—($C_1$-$C_6$ alkyl), —($C_1$-$C_3$ alkylene)$_p$—N($R^{11}$)$_2$, —($C_1$-$C_3$ alkylene)—NHC(O)—($C_1$-$C_6$ alkyl), —($C_1$-$C_3$ alkylene)—OC(O)($C_1$-$C_6$ alkyl)NHC(O)O—($C_1$-$C_6$ alkyl), —($C_1$-$C_3$ alkylene)—OC(O)—(3 to 7-membered monocyclic heterocycloalkyl), —($C_1$-$C_3$ alkylene)—NHC(O)(3 to 7-membered monocyclic heterocycloalkyl), —CH(O—($C_1$-$C_6$ alkyl))$_2$, —O—($C_1$-$C_6$ haloalkyl), —C(O)O$R^{11}$, —C(O)N($R^{11}$)$_2$, —CH$_2$OC(O)CH(NH$_2$)—($C_1$-$C_6$ alkyl), —NHS(O)$_2$—($C_1$-$C_6$ alkyl), —CH$_2$NHCH($R^{11}$)C(O)O$R^{11}$, —N$R^{11}$—($C_1$-$C_3$ alkylene)—N($R^{11}$)$_2$, —N$R^{11}$—($C_1$-$C_3$ alkylene)-(3 to 7-membered monocyclic heterocycloalkyl), —N$R^{11}$—($C_1$-$C_6$ hydroxyalkyl) and —CN;

$R^9$ is selected from H, $C_1$-$C_6$ alkyl, $C_1$-$C_6$ haloalkyl, $C_1$-$C_6$ hydroxyalkyl, benzyl, —($C_1$-$C_3$ alkylene)-(3 to 7-membered monocyclic cycloalkyl) and 3 to 7-membered monocyclic cycloalkyl, wherein said $C_1$-$C_6$ alkyl group can be optionally substituted with a group selected from —N($R^{11}$)$_2$, —O$R^{11}$, —COOH, —C(O)N($R^{11}$)$_2$, —S(O)$_2$N($R^{11}$)$_2$ and 3 to 7-membered monocyclic heterocycloalkyl and wherein the phenyl moiety of said benzyl group can be optionally substituted with a boronic acid group;

$R^{10}$ is selected from H, $C_1$-$C_6$ alkyl, $C_1$-$C_6$ haloalkyl, phenyl, 3 to 7-membered monocyclic cycloalkyl, 3 to 7-membered monocyclic heterocycloalkyl and 5 or 6-membered monocyclic heteroaryl, wherein said $C_1$-$C_6$ alkyl group can be optionally substituted with a group selected from —N($R^{11}$)$_2$, —O$R^{11}$, —COOH, —C(O)N($R^{11}$)$_2$, and —S(O)$_2$N($R^{11}$)$_2$;

each occurrence of $R^{11}$ is independently selected from H, $C_1$-$C_6$ alkyl, and 3 to 7-membered monocyclic cycloalkyl;

each occurrence of n is 1, 2 or 3; and each occurrence of p is 0 or 1.

2. The compound of claim 1, wherein $R^2$ is —C(O)NH—($C_1$-$C_6$ alkyl).

3. The compound of claim 1, wherein $R^3$ is —N($R^9$)—S(O)$_n$—$R^{10}$ and $R^9$ and $R^{10}$ are each independently $C_1$-$C_6$ alkyl.

4. The compound of claim 1, wherein each occurrence of $R^1$ is halo.

5. The compound of claim 1, wherein Q is Q1, A is phenyl, W is N, $Y^1$ is CH and $Y^2$ is N.

6. A compound having the formula:

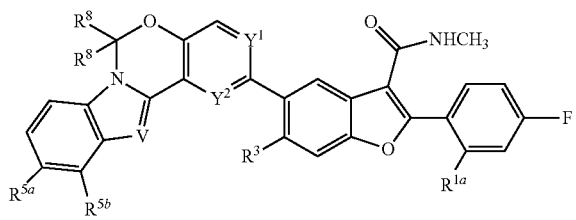

(Ib)

or a pharmaceutically acceptable salt thereof, wherein:

V is N or —CH—;
$Y^1$ is N;
$Y^2$ is N or —CH—;
$R^{1a}$ is H or F;
$R^3$ is —N(CH$_3$)S(O)$_2$CH$_3$ or:

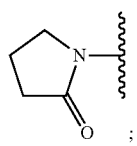 [SMILES: *N1CCCC1=O]

$R^{5a}$ and $R^{5b}$ are each independently H or F; and each occurrence of $R^8$ is H, or both $R^8$ groups, together with the common carbon atom to which they are attached, join to form a 4 to 6-membered monocyclic heterocycloalkyl group.

7. The compound of claim 1, being any one of

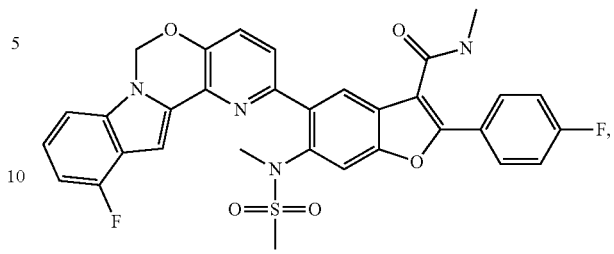

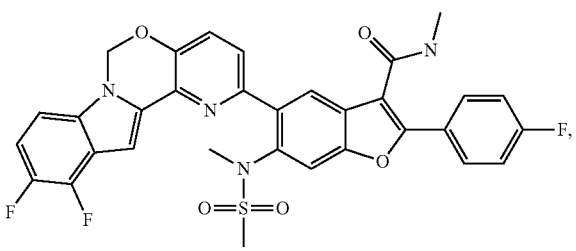

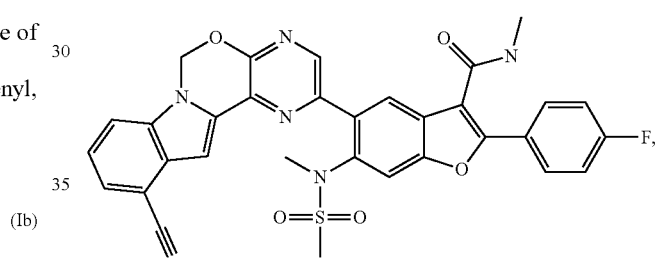

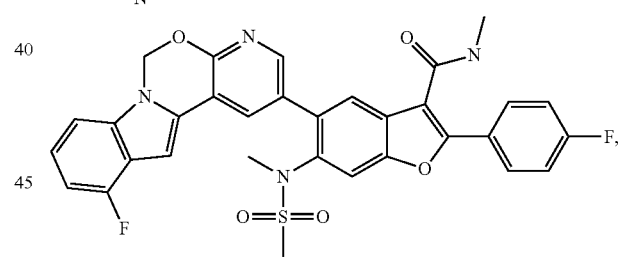

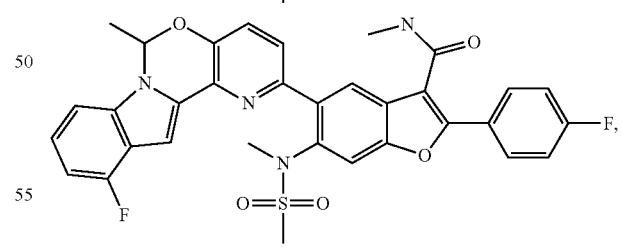

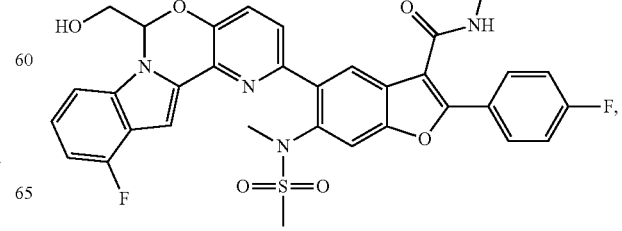

-continued
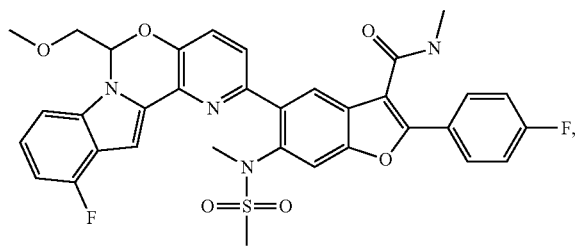
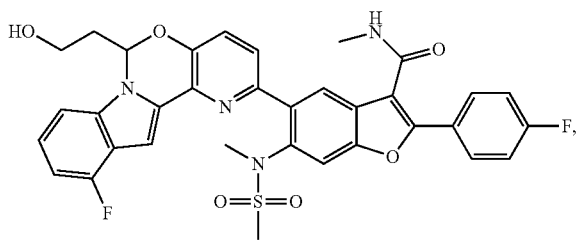
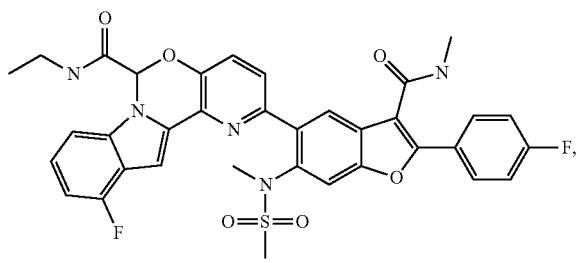
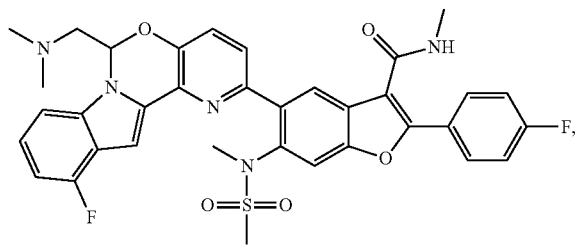
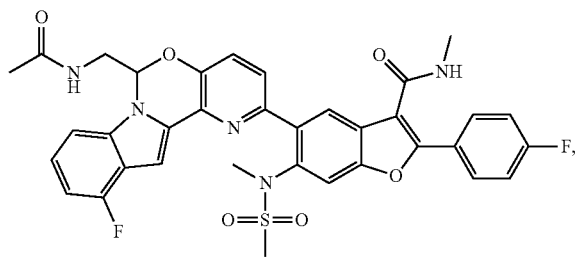
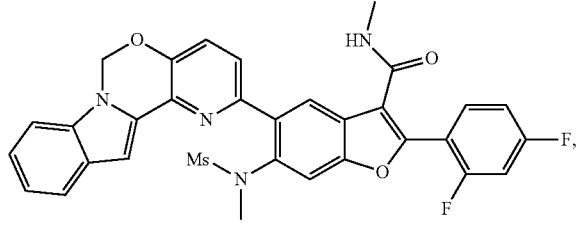
or a pharmaceutically acceptable salt thereof.
8. The compound of claim 1, being
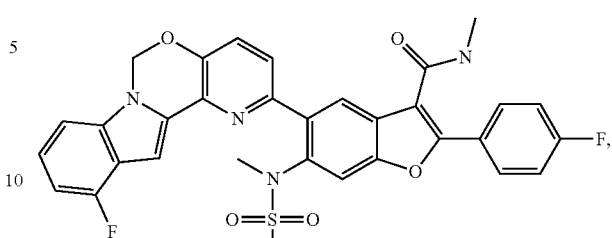
or a pharmaceutically acceptable salt thereof.
9. The compound of claim 6, being any one of
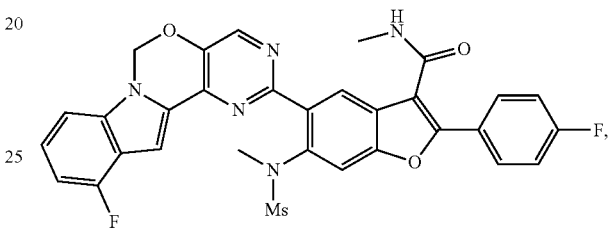
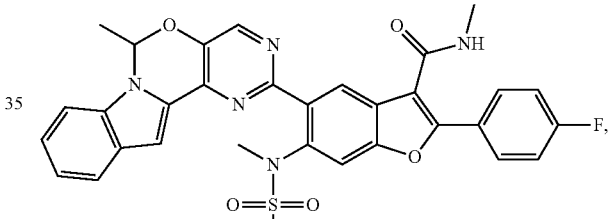
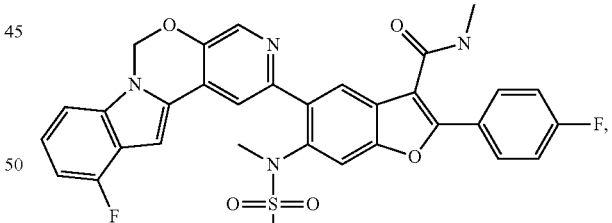
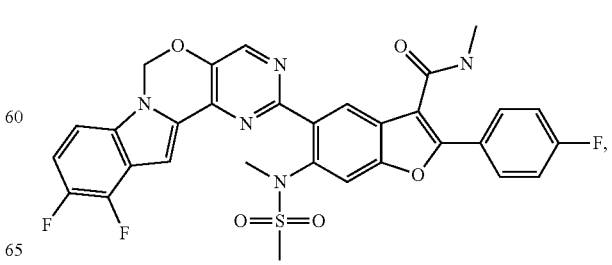

-continued

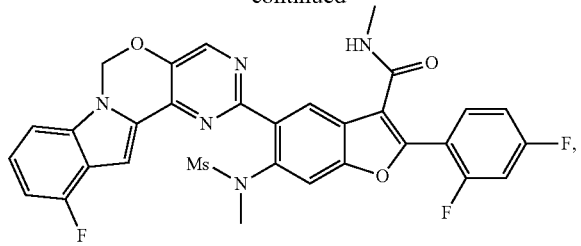

or a pharmaceutically acceptable salt thereof.

10. A compound being any one of

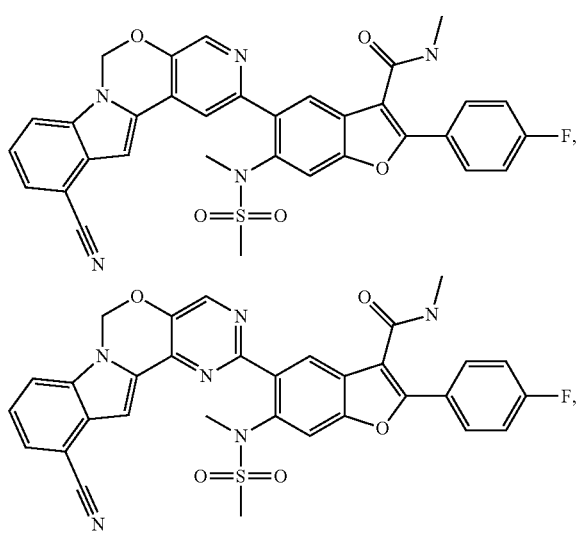

-continued

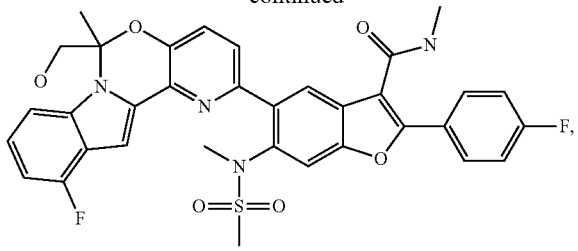

or a pharmaceutically acceptable salt thereof.

11. A pharmaceutical composition comprising (i) a pharmaceutically acceptable carrier and (ii) an effective amount of the compound of claim 1 or a pharmaceutically acceptable salt thereof.

12. The pharmaceutical composition of claim 11, further comprising an additional therapeutic agent selected from the group consisting of HCV antiviral agents, immunomodulators, and anti-infective agents.

13. The pharmaceutical composition of claim 12, wherein the additional therapeutic agent is selected from the group consisting of HCV NS3 and NS3/4A protease inhibitors, HCV NS5A inhibitors and HCV NS5B polymerase inhibitors.

14. A method of treating a patient infected with HCV, the method comprising administering to the patient the compound of claim 1, or a pharmaceutically acceptable salt thereof, in an amount effective to treat HCV infection in the patient.

15. The method of claim 14, further comprising administering to said patient an effective amount of at least one additional therapeutic agent selected from the group consisting of HCV NS3 and NS3/4A protease inhibitors, HCV NS5A inhibitors and HCV NS5B polymerase inhibitors.

* * * * *